(12) United States Patent
Morris et al.

(10) Patent No.: US 7,645,441 B2
(45) Date of Patent: Jan. 12, 2010

(54) COMPOSITIONS AND METHODS IN CANCER ASSOCIATED WITH ALTERED EXPRESSION OF PRLR

(75) Inventors: David W. Morris, Davis, CA (US); Eric K. Engelhard, Davis, CA (US)

(73) Assignee: Sagres Discovery Inc., Emeryville, CA (US)

( * ) Notice: Subject to any disclaimer, the term of this patent is extended or adjusted under 35 U.S.C. 154(b) by 1268 days.

(21) Appl. No.: 10/105,948

(22) Filed: Mar. 20, 2002

(65) Prior Publication Data

US 2003/0064383 A1   Apr. 3, 2003

Related U.S. Application Data

(63) Continuation-in-part of application No. 09/747,377, filed on Dec. 22, 2000, now abandoned, and a continuation-in-part of application No. 09/798,586, filed on Mar. 2, 2001, now abandoned, and a continuation-in-part of application No. 10/052,482, filed on Nov. 8, 2001.

(51) Int. Cl.
```
A61K 49/00    (2006.01)
A61K 31/00    (2006.01)
A61K 38/00    (2006.01)
A61K 38/28    (2006.01)
A01N 61/00    (2006.01)
A01N 37/18    (2006.01)
A01N 43/04    (2006.01)
G01N 31/00    (2006.01)
G01N 33/48    (2006.01)
G01N 1/00     (2006.01)
C12Q 1/00     (2006.01)
C12Q 1/68     (2006.01)
```
(52) U.S. Cl. .................. 424/9.2; 424/9.1; 514/1; 514/2; 514/4; 514/42; 514/43; 514/44; 436/8; 436/63; 436/64; 436/86; 436/174; 435/4; 435/6; 435/7.1; 435/7.21; 435/7.23

(58) Field of Classification Search ............... 424/9.1, 424/9.2; 514/1, 2, 4, 42, 43, 44; 436/8, 63, 436/64, 86, 174; 435/4, 6, 7.1, 7.21, 7.23
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,469,863 A | 9/1984 | Ts'o et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,567 A | 3/1989 | Cabilly et al. |
| 4,992,378 A | 2/1991 | Kelly et al. |
| 5,034,506 A | 7/1991 | Summerton et al. |
| 5,124,246 A | 6/1992 | Urdea et al. |
| 5,216,141 A | 6/1993 | Benner |
| 5,235,033 A | 8/1993 | Summerton et al. |
| 5,359,100 A | 10/1994 | Urdea et al. |
| 5,386,023 A | 1/1995 | Sanghvi et al. |
| 5,445,934 A | 8/1995 | Fodor et al. |
| 5,545,730 A | 8/1996 | Urdea et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,670 A | 11/1996 | Urdea et al. |
| 5,580,731 A | 12/1996 | Chang et al. |
| 5,591,584 A | 1/1997 | Chang et al. |
| 5,594,117 A | 1/1997 | Urdea et al. |
| 5,594,118 A | 1/1997 | Urdea et al. |
| 5,597,909 A | 1/1997 | Urdea et al. |
| 5,602,240 A | 2/1997 | De Mesmaeker et al. |
| 5,624,802 A | 4/1997 | Urdea et al. |
| 5,625,126 A | 4/1997 | Lonberg et al. |
| 5,633,425 A | 5/1997 | Lonberg et al. |
| 5,635,352 A | 6/1997 | Urdea et al. |
| 5,637,684 A | 6/1997 | Cook et al. |
| 5,644,048 A | 7/1997 | Yau |
| 5,661,016 A | 8/1997 | Lonberg et al. |
| 5,681,697 A | 10/1997 | Urdea et al. |
| 5,681,702 A | 10/1997 | Collins et al. |

(Continued)

FOREIGN PATENT DOCUMENTS

WO    WO 87/05330    9/1987

(Continued)

OTHER PUBLICATIONS

GenCore database alignment between Applicants' SEQ ID No. 5 and SEQ ID No. 6 with U.S. Patent No. 6812339 (filed Sep. 10, 2001) 7 sheets.*

(Continued)

*Primary Examiner*—Alana M Harris
(74) *Attorney, Agent, or Firm*—Lisa E. Alexander; David Gay

(57) ABSTRACT

The present invention relates to novel sequences for use in diagnosis and treatment of carcinomas, especially breast cancers. In addition, the present invention describes the use of novel compositions for use in screening methods. The invention provides compositions and methods associated with altered expression of PRLR in cancer.

10 Claims, 1 Drawing Sheet

U.S. PATENT DOCUMENTS

| | | | |
|---|---|---|---|
| 5,700,637 | A | 12/1997 | Southern |
| 5,759,776 | A | 6/1998 | Smith et al. |
| 5,776,683 | A | 7/1998 | Smith et al. |
| 5,928,870 | A | 7/1999 | Lapidus et al. |
| 6,074,825 | A | 6/2000 | Rundell et al. |
| 6,153,441 | A | 11/2000 | Appelbaum et al. |
| 6,812,339 | B1* | 11/2004 | Venter et al. ............. 536/24.31 |
| 2003/0099974 | A1* | 5/2003 | Lillie et al. ..................... 435/6 |
| 2004/0072264 | A1* | 4/2004 | Morris et al. .............. 435/7.23 |

FOREIGN PATENT DOCUMENTS

| | | |
|---|---|---|
| WO | WO 90/10448 | 9/1990 |
| WO | WO 91/04753 | 4/1991 |
| WO | WO 93/22443 | 11/1993 |
| WO | WO 95/25116 | 9/1995 |
| WO | WO 95/35505 | 12/1995 |
| WO | WO 97/27212 | 7/1997 |
| WO | WO 97/27213 | 7/1997 |
| WO | WO 01/94629 | 12/2001 |
| WO | WO 02/46467 | 6/2002 |
| WO | WO 02/059377 | 8/2002 |
| WO | WO 03/035837 A2 * | 11/2002 |
| WO | WO 03/008583 | 1/2003 |
| WO | WO 03/039484 | 5/2003 |

OTHER PUBLICATIONS

GenCore nucleic acid databases. Applicants' SEQ ID No. 5 and 6 aligned with U.S. Publication Application's seqeunce 13,880 (effective filing date Jul. 18, 2001), 6 sheets.*

International Search Report mailed on Jul. 26, 2004, for PCT patent application No. PCT/US02/38582, filed on Dec. 2, 2002, 8 pages.

International Partial Search Report mailed on Jan. 26, 2006 for PCT patent application No. PCT/US0307470, filed on Mar. 12, 2003, (7 pages).

Boutin, J.M., et al. "Identification of a CDNA Encoding A Long Form of Prolactin Receptor In Human Hepatoma and Breast Cancer Cells," *Molec. Endocrinology*, 3(9):1455-1461 (1989).

Database EMBL 'Online!, "Human Prolactin (PRL) Receptor mRNA, Complete CDs.," (Nov. 1990); retrieved on May 1, 2006 from EBI accession No. EM PRO:HSPRLR.

Peirce, et al., "Quantification of prolactin receptor mRNA in multiple human tissues and cancer cell lines by real time RT-PCR," *J. of Endocrinology*, vol. 171, No. 1, pp. R1-R4, XP002361681 ISSN: 0022-0795 (Oct. 2001).

Database EMBL 'Online!, "M. musculus mRNA for prolactin receptor," retrieved on May 1, 2006 from EBI accession No. EM_PRO:MMPRLR.

International Search Report mailed on Dec. 1, 2003, for PCT patent application No. PCT/US02/33835 filed on Oct. 22, 2002, 4 pages.

Allen, J. D. and Berns, A. (1996). "Complementation Tagging of Cooperating Oncogenes in Knockout Mice," *Cancer Biology* 7:299-306.

Altschul, S. F. and Gish, W. (1996). "Local Alignment Statistics" *In Methods in Enzymology* vol. 266, Academic Press, Inc., pp. 460-480.

Altschul, S. F. et al. (1990). "Basic Local Alignment Search Tool," *J. Mol. Biol.* 215:403-410.

Aplin, J. D. and Wriston, Jr., J. C. (1981). "Preparation, Properties, and Applications of Carbohydrate Conjugates of Proteins and Lipids," *CRC Crit. Rev. Biochem.* pp. 259-306.

Arenberg, D. A. et al. (2001). "The Murine CC Chemokine, 6C-Kine, Inhibits Tumor Growth and Angiogenesis in a Human Lung Cancer SCID Mouse Model," *Cancer Immunol. Immunother* 49:587-592.

Ausubel, F. M. et al., eds. (1992). *Short Protocols in Molecular Biology*. Greene Publishing Associates and John Wiley & Sons, pp. iii-xviii (Table of Contents Only).

Bai, J. et al. (1999). "Sequence Comparison of JSRV with Endogenous Proviruses: Envelope Genotypes and a Novel ORF With Similarity to a G-Protein-Coupled Receptor," *Virology* 258:333-343.

Beaucage, S. L. and Iyer, R. P. (1993). "The Functionalization of Oligonucleotides Via Phosphoramidite Derivatives," *Tetrahedron* 49(10):1925-1963.

Boerner, P. et al. (1991). "Production of Antigen-Specific Human Monoclonal Antibodies from in Vitro-Primed Human Splenocytes," *J. Immunol.* 147(1):86-95.

Bolli. M. et al. (1994). "α-Bicyclo-DNA: Synthesis, Characterization, and Pairing Properties of α-DNA-Analogues with Restricted Conformational Flexibility in the Sugar-Phosphate Backbone," Chapter 7 *In Carbohydrate Modifications in Antisense Research*, ACS Symposium Series 580, Shanghvi, Y. S and Cook, P. D, eds, American Chemical Society, Washington, pp. 100-117.

Brill, W. et al. (1989). "Synthesis of Oligodeoxynucleoside Phosphoridithioates via Thioamidites," *J. Am. Chem. Soc.* 111:2321-2322.

Brower, V. (1998). "Naked DNA Vaccines Come of Age," *Nature Biotechnology* 16:1304-1305.

Carlsson, C. et al. (1996). "Screening for Genetic Mutations," *Nature* 380:207 (1 page total).

Cole, S.P.C., et al. (1985). "The EBV-Hybridoma Technique and Its Application to Human Lung Cancer," *In Monoclonal Antibodies and Cancer Therapy*, Reisfeld, R. A. and Sell, S., ed., Alan R. Liss, New York, p. 77-96 (Includes Table of Contents).

Creighton, T. E., ed. (1983). "Posttranslational Covalent Modifications of Polypeptide Chains," Chapter 2.4 *In Proteins: Structure and Molecular Properties*. W. H. Freeman & Co., San Francisco pp. 78-86 (Includes Table of Contents).

David, G. S. and Reisfeld, R. A. (1974). "Protein Iodination with Solid State Lactoperoxidase," *Biochemistry* 13(5):1014-1021.

De Mesmaeker, A. et al. (1994). "Comparison of Rigid and Flexible Backbones in Antisense Oligonucleotides," *Bioorganic & Medicinal Chem. Lett.* 4(3):395-398.

De Mesmaeker, A. et al. (1994). "Novel Backbone Replacements for Oligonucleotides," Chapter 2 *In Carbohydrate Modifications in Antisense Research*, ACS Symposium Series 580, Shanghvi, Y. S. and Cook, P. D, eds, American Chemical Society, Washington, pp. 24-39.

Dempcy, R. O. et al. (1995). "Synthesis of a Thymidyl Pentamer of Deoxyribonucleic Guanidine and Binding Studies with DNA Homopolynucleotides," *Proc. Natl Acad. Sci. USA* 92:6097-6101.

Desbois, C. et al. (1996). "Exclusion of Int-6 from PML Nuclear Bodies by Binding to the HTLV-1 Tax Oncoprotein," *Science* 273:951-953.

Devereux et al. (1984). "A Comprehensive Set of Sequence Analysis Programs for the VAX," *Nuc. Acid. Res.* 12(1):387-395.

Doudney, K. et al. (2001). "Comparative Physical and Transcript Maps of~ 1 Mb around *looptail*, a Gene for Severe Neural Tube Defects on Distal Mouse Chromosome 1 and Human Chromosome 1q22-q23," *Genomics* 72(2):180-192.

Eckstein. F., ed. (1991). *Oligonucleotides and Analogues: A Practical Approach*, Oxford University Press, vii-xvii. (Table of Contents Only).

Edge, A. S. B. et al. (1981). "Deglycosylation of Glycoproteins by Trifluoromerathneusulfonic Acid," *Anal. Biochem.* 118:131-137.

Egholm, M. (1993). "PNA Hybridizes to Complementary Oligonucleotides Obeying the Watson-Crick Hydrogenbonding," *Nature* 365:566-568.

Elgholm, M. et al. (1992). "Peptide Nucleic Acids (PNA). Oligonucleotide Analogues with an Achiral Peptide Backbone," *J. Am. Chem. Soc.* 114:1895-1897.

Erny, K. M. et al. (1996). "Involvement of the *Tp1-21cot* Oncogene in MMTV Turmorigenesis," *Oncogene* 13:2015-2020.

Evan, G. I. et al. (1985). "Isolation of Monoclonal Antibodies Specific for Human c-myc Proto-Oncogene Product," *Biology* 5(12):3610-3616.

Fan, L. et al. (2000). "Cutting Edge: Ectopic Expression of the Chemokine TCA4/SLC is Sufficient to Trigger Lymphoid Neogenesis," *J. Immunol.* 164(8):3955-3959.

Feng, D. F. & Doolittle, R. F. (1987). "Progressive Sequence Alignment as a Prerequisite to Correct Phylogenetic Trees," *J. Mol. Evol.* 25:351-360.

Field, J. et al. (1988). "Purification of a RAS-Responsive Adenylyl Cyclase Complex from *Saccharomyces cerevisiae* by Use of a Epitope Addition Method," *Mol Cell. Biol.* 8(5):2159-2165.

Fishwild, D. M. et al. (1996). "High-Avidity Human IgGk Monoclonal Antibodies from a Novel Strain of Minilocus Transgienic Mice," *Nature Biotechnology* 14:845-851.

Gallahan, D. and Callahan, R. (1987). "Mammary Tumorigenesis in Feral Mice: Identification of a New *int* Locus in Mouse Mammary Tumor Virus (Czech II)-Induced Mammary Tumors," *J. Virol.* 61(1):66-74.

Gao, X. and Jeffs, W. P. (1994). "Unusual Conformation of a 3'-thioformacetal Linkage in a DNA Duplex," *J. Biomolecular NMR* 4:17-34.

Germer, S. et al. (2000). "High-Throughput SNP Allele-Frequency Determination in Pooled DNA Samples by Kinetic PCR," *Genome Res.* 10:258-266.

Goding, J. W. (1986). "Production of Monoclonal Antibodies," Chapter 3 *In Monoclonal Antibodies: Principles and Practice*, Academic Press, Inc. 2nd edition, pp. 59-103.

Hansen, G. M. et al. (2000). "Genetic Profile of Insertion Mutations in Mouse Leukemias and Lymphomas," *Genome Res.* 10(2):237-243.

Heid, C. A et al. (1996). "Real Time Quantitative PCR," *Genome Research* 6:986-994.

Herdewjn, P. et al. (1994). "Hexopyranosyl-Like Oligonucleotides," Chapter 6 *In Carbohydrate Modifications in Antisense Research*. Shanghvi, Y. S and Cook, P. D, eds, ACS Symposium Series 580, American Chemical Society, Washington, pp. 80-99.

Higgins, D. G. and Sharp, P. M. (1989). "Fast and Sensitive Multiple Sequence Alignments on a Microcomputer," *CABIOS* 5(2):151-153.

Hoogenboom, H. R. and Winter, G. (1992). "By-Passing Immunisation Human Antibodies from Synthetic Repertoires of Germline $V_H$ Gene Segments Rearranged in Vitro," *J. Mol. Biol.* 227:381-388.

Hopp, T. P. et al. (1988). "A Short Polypeptide Marker Sequence Useful for Recombinant Protein Identification and Purification," *Biotechnology* 6:1204-1210.

Horn, T. et al. (1996). "Oligonucleotides with Alternating Anionic and Cationic Phosphoramidate Linkages: Synthesis and Hybridization of Stereo-Uniform Isomers," *Tetrahedron Letters* 37(6):743-746.

Hwang, H. C. et al. (2002). "Identification of Oncognes Collaborating with $p27^{Kip1}$ Loss by Insertional Mutagenesis and High-Throughput Insertion Site Analysis," *Proc. Natl Acad. Sci. USA* 99(17):11293-11298 (Includes supporting information).

Jenkins, G. N. and Turner, N. J. (1995). "The Biosynthesis of Carbocyclic Nucleosides," *Chem. Soc. Rev.* pp. 169-176.

Jones, P. T. et al. (1986). "Replacing the Complementarity-Determining Regions in a Human Antibody with Those from a Mouse," *Nature* 321:522-525.

Jonkers, J. and Berns, A. (1996). "Retroviral Insertional Mutagenesis as a Strategy to Identify Cancer Genes," *Biochim. Biophys. Acta* 1287:29-57.

Joosten, M. et al. (2000). "Phenotyping of Evi 1, Evi 11/Cb2, and Evi 12 Transformed Leukemias Isolated from a Novel Panel of Cas-Br-M Murine Leukemia Virus-Infected Mice," *J. Virology* 268:308-318.

Jung, M. P. et al. (1994). "Hybridization of Alternating Cationic/Anionic Oligonucleotides to RNA Segments," *Nucleosides & Nucleotides* 13(6&7):1597-1605.

Karlin, S. et al. (1993). "Applications and Statistics for Multiple High-Scoring Segments in Molecular Sequences," *Proc. Natl Acad. Sci. USA* 90:5873-5787.

Köhler, G. and Milstein, C. (1975). "Continuous Cultures of Fused Cells Secreting Antibody of Predefined Specificity," *Nature* 256:495-497.

Kohno, T. et al. (2000). "Identification of Genes Associated with the Progression of Adult T-Cell Leukemia (ATL)," *Jpn J. Cancer Res.* 91:1103-1110.

Lee, F. S. et al. (1995). "Insertional Mutagenesis Identifies a Member of the *Wnt* gene family as a Candidate Oncogene in the Mammary Eptithelium of *int-2l/Fgf-3* Transgenic Mice," *Proc. Natl. Acad. Sci. USA* 92:2268-2272.

Lee, S. Wong et al. (1999). "Cloning of Mouse Sepiapterin Reductase Gene and Characterization of its Promoter Region," *Biochimica and Biophysica Acta* 1445(1):165-171.

Letsinger, R. L. et al. (1986). "Effects of Pendant Groups at Phosphorus on Binding Properties of d-ApA Analogues," *Nucl. Acids. Res* 14(8):3487-3499.

Letsinger, R. L. et al. (1988). "Cationic Oligonucleotides," *J. Am. Chem. Soc.* 110:4470-4471.

Letsinger, R.L. and Mungall, W. S. (1970). "Phosphoramidate Analogs of Oligonucleotides," *J. Org. Chem* 35(11):3800-3803.

Li, J. et al. (1999). "Leukaemia Disease Genes: Large-Scale Cloning and Pathway Predictions," *Nature Genetics* 23:348-353.

Lockhart, D. J. et al. (1996). "Expression Monitoring by Hybridization High-Density Oligonucleotide Arrays," Nature Biotechnology, 14:1675-1680.

Lonberg, N. and Huszar, D. (1995). "Human Antibodies from Transgenic Mice," *Intern. Rev. Immunol.* 13:65-93.

Longberg, N. et al. (1994). "Antigen-Specific Human Antibodies from Mice Comprising Four Distinct Genetic Modifications," *Nature* 368:856-859.

Lund, A. H. et al. (2002). "Genome-Wide Retroviral Insertional Tagging of Genes Involved in Cancer in Cdkn2a-Deficient Mice," *Nature Genetics Advance Online Publication* pp. 1-6.

Lutz-Freyermuth, C. et al. (1990). "Quantitative Determination That One of Two Potential RNA-Binding Domains of the A Protein Component of the U1 Small Nuclear Ribonucleoprotein Complex Binds with High Affinity to Stem-Loop II of U1 RNA," *Proc. Natl Acad. Sci. USA* 87:6393-6397.

MacArthur, C. A. et al. (1995). "*Fgf-8*, Activated by Proviral Insertion, Cooperates with the *Wnt-1* Transgene in Murine Mammary Tumorigenesis," *J. Virol.* 69(4):2501-2507.

Maddry, J. A. et al. (1994). "Synthesis of Nonionic Oligonucleotide Analogues," Chapter 3 *In Carbohydrate Modifications in Antisense Research*, ACS Symposium Series 580, Shanghvi, Y. S and Cook, P. D, eds, American Chemical Society, Washington, pp. 40-51.

Mag, M. et al. (1991). "Synthesis and Selective Cleavage of an Oligodeoynucleotide Containing a Bridged Internucleotide 5'-Phosphorotiate Linkage," *Nucleic Acids Res.* 19(7):1437-1441.

Marchetti, A. et al. (1995). "*Int-6*, a Highly Conserved, Widely Expressed Gene, is Mutated by Mouse Mammary Tumor Virus in Mammary Preneoplasia," *J. Virol.* 69(3):1932-1938.

Marks, J. D. et al. (1991). "By-Passing Immunization, Human Antibodies from V-Gene Libraries Displayed on Phage," J. Mol. Biol. 222:581-597.

Marks, J. D. et al. (1992). "By-Passing Immunization: Building High Affinity Human Antibodies by Chain Shuffling," *Bio/Technology* 10:779-783.

Martin, G. A. et al. (1992). "GAP Domains Responsible for Ras p21-Dependent Inhibition of Muscarinic Atrial K+ Channel Currents," *Science* 255:192-194.

Meier, C. and Engels, J.W. (1992). "Peptide Nucleic Acids (PNAs)—Unusual Properties of Nonionic Oligonucleotide Analogues," *Angew Chem. Int. Ed. Engl.* 31(8):1008-1010.

Mikkers, H. et al. (2002). "High-Throughput Retroviral Tagging to Identify Components of Specific Signaling Pathways in Cancer," *Nature Genetics Advance Online Publication*, pp. 1-7.

Moore, A. S. (2001). "The Role of Chemoattraction in Cancer Metastases," *BioEssays* 23(8):674-676.

Morris, D. W. et al. (1986). "Transfer, by Selective Breeding, of the Pathogenic *Mtv-2* Endogenous Provirus from the GR strain to a Wild Mouse Line Free of Endogenous and Exogenous Mouse Mammary Tumor Virus," *J. Virol.* 58(2):247-252.

Morris, D. W. et al. (1990). "Insertion Mutation of the *Int-1* and *Int-2* Loci by Mouse Mammary Tumor Virus in Premalignant and Malignant Neoplasms from the GR Mouse Strain," *J. Virol.* 64(4):1794-1802.

Morrison, S. L. (1994). "Success in Specification," *Nature* 368:812-813.

Müller, A. et al. (2001). "Involvement of Chemokine Receptors in Breast Cancer Metastasis," *Nature* 410:50-56.

Needleman, S. B. and Wunsch, C. D. (1970). "A General Method Applicable to the Search for Similiarities in the Amino Acid Sequence of Two Proteins," *J. Mol. Biol.* 48:443-453.

Neuberger, M. (1996). "Generating High-Avidity Human Mabs in Mice," *Nature Biotechnology* 14:826 (1 page total).

Nusse, R. and Varmus, H. E. (1982). "Many Tumors Induced by the Mouse Mammary Tumor Virus Contain a Provirus Integrated in the Same Region of the Host Genome," *Cell* 31:99-109.

Nygren, H. (1982). "Conjugation of Horseradish Peroxidase to Fab Fragments with Different Homobifunctional and Heterobifunctional Cross-Linking Reagents," *The J. Histochem. and Cytochem.* 30(5):407-412.

Paborsky, L. R. et al. (1990). "Mammalian Cell Transient Expression of Tissue Factor for the Production of Antigen," *Protein Engineering* 3(6):547-553.

Pain, D. and Surolia, A. (1981). "Preparation of Protein A-Peroxidase Monoconjugate Using A.Heterobifunctional Reagent, and its Use in Enzyme Immunoassays," *J. Immunol. Meth.* 40:219-230.

Palmarini, M. et al. (1999). "Jaagsiekte Sheep Retrovirus is Necessary and Sufficient to Induce a Contagious Lung Cancer in Sheep," *J. Virol.* 73(8):6964-6972.

Pauwels, R. et al. (1986). "Biological Activity of New 2-5A Analogues," *Chemica Scripta* 26:141-145.

Pearson, W. R. and Lipman, D. J. (1988). "Improved Tools for Biological Sequence Comparison," *Proc. Natl Acad. Sci. USA* 85:2444-2448.

Peters, G. et al. (1983). "Tumorigenesis by Mouse Mammary Turmor Virus: Evidence for a Common Region for Provirus Integration in Mammary Tumors," *Cell* 33:369-377.

Peters, G. et al. (1989). "The Mouse Homolog of the *Hst/k-FGF* Gene is Adjacent to *int-2* and is Activated by Proviral Insertion in Some Virally Induced Mammary Tumors," *Proc. Natl. Acad. Sci. USA* 86:5678-5682.

Pierce (1994). "Cross-Linking," *Pierce Catalog and Handbook* pp. 155-200.

Presta, L. G. (1992). "Antibody Engineering", *Current Opinion in Structural Biology* 2:593-596.

Rawls, R. L. (1997). "Optimistic About Antisense," *C & E. News* pp. 35-40.

Riechmann, L. et al. (1988). "Reshaping Human Antibodies for Therapy," *Nature* 332:323-327.

Roelink, H. et al. (1990). "*Wnt-3*, a Gene Activated by Proviral Insertion in Mouse Mammary Tumors is Homologous to *int-1/Wnt-1* and is Normally Expressed in Mouse Embryos and Adult Brain," *Proc. Natl. Acad. Sci USA* 87:4519-4523.

Sambrook, J. et al., eds. (1989). *Molecular Cloning, a Laboratory Manual*, Second Edition. Cold Spring Harbor Laboratory Press. pp. xi-xxxviii. (Table of Contents Only).

Scopes, R. K.,ed. (1982). *Protein Purification: Principles and Practice*. Springer-Verlag:New York, Heidelberg, Berlin, pp. xi-xiii.

Shiramizu, B. et al. (1994). "Identification of a Common Clonal Human Immunodeficiency Virus Integration Site in Human Immunodeficiency Virus-Associated Lymphomas," *Cancer Res.* 54:2069-2072.

Smith, T. F. and Waterman, M. S. (1981). "Comparison of Biosequences," *Adv. Appl. Math.* 2:482-489.

Sojar, H. T. and Bahl, O. P. (1987). "A Chemical Method for the Deglycosylation of Proteins," *Archives of Biochemistry and Biophysics* 52-57.

Sorensen, A. B. et al. (1993). "Amplification and Sequence Analysis of DNA Flanking Integrated Proviruses by a Simple Two-Step Polymerase Chain Reaction Method," *Journal of Virology* 67(12):7118-7124.

Sorensen, A. B. et al. (1996). "Sequence Tags of Provirus Integration Sites in DNAs of Tumors Induced by the Murine Retrovirus SL3-3," *Journal of Virology* 70(6):4063-4070.

Sorensen, A. B. et al. (2000). "Sintl, a Common Integration Site in SL3-3-Induced T-Cell Lymphomas, Harbors a Putative Proto-Oncogene with Homology to the Septin Gene Family," *J. Virology* 74(5):2161-2168.

Sprinzl, M. et al. (1977). "Enzymatic Incorporation of ATP and CTP Analogues Into the 3' End of tRNA," *Eur. J. Biochem* 81:579-589.

Stein, C. A. and Cohen, J. S. (1988). "Oligodeoxynucleotides as Inhibitors of Gene Expression: A Review," *Cancer Res.* 48:2659-2668.

Sternsdorf, T. et al. (1997). "Nuclear Dots: Actors on Many Stages," *Immunobiology* 198:307-331.

Suzuki, T. et al. (2002). "New Genes Involved in Cancer Identified by Retroviral Tagging," *Nature Genetics Advance Online Publication* pp. 1-9.

Suzuki, T. et al. (2002). "Web Note A, CIS Definition, Retroviral Tagging in the Post-Genome Era Identifies New Genes Involved in Cancer". (1 page total).

Thotalcura, N. R. and Bahl, O. P. (1987). "Enzymathic Deglycosylation of Glycoproteins," *In Methods in Enzymology*, Academic Press, Inc., vol. 138 pp. 350-359.

Tijssen (1993). "Overview of Principles of Hybridization and the strategy of nucleic acid assays," Chapter 2 *In Laboratory Techniques in Biochemistry and Molecular Biology*, Hybridization with Nucleic Acid Probes Van der Vliet, P. C., ed. Elsevier, Amsterdam, London, New York, and Tokyo, vol. 24 pp. 20-78.

Van der Krol, A. R et al. (1988). "Modulation of Eurkaryotic Gene Expression by Complementary RNA or DNA Sequences," *BioTechniques* 6(10):958-976.

Varmus, H. E. (1983). "Using Retroviruses as Insertional Mutagens to Identify Cellular Oncogenes," *In Oncogenes and Retroviruses: Evaluation of Basic Findings and Clinical Potential*. Alan R. Liss, Inc., New York. pp. 23-35.

Vaughn, J. et al. (2000). "Genomic Structure and Expression of Human *KCNJ9* (Kir3.3/GIRK3)," *Biochem. Biophys. Res. Commun* 274(2):302-309.

Verhoeyen, M. et al. (1988). "Reshaping Human Antibodies: Grafting an Antilysozyme Activity," *Science* 239:1534-1536.

von Kiedrowski, G. et al. (1991). "Parabolic Growth of a Self-Replicating Hexadeoxynucleotide Bearing a 3'-5'-Phosphoamidate Linkage," *Angew. Chem. Int. Ed. Engl* 30(4):423-426.

Washington University. (2002). "Washington University BLAST Archives" located at <http://blast.wustl.edu> visited on Dec. 15, 2002, three pages.

Wolford, J. K. (2001). "Analysis of Linkage Disequilibrium Between Polymorphisms in the *KCNJ9* Gene with Type 2 Diabetes Mellitus in Pima Indians," *Mol. Genet. Metab* 73(1):97-103.

Zhang, W-X and Yang, S. Y. (2000). "Cloning and Characterization of a New Member of the T-Box Gene Family," *Genomics* 70(1):41-48.

Zlokarnik, G. et al. (1998). "Quantitation of Transcription and Clonal Selection of Single Living Cells with β-Lactamase as Reporter," *Science* 279:84-88.

Campbell, A. M. (1984). "The Production and Characterization of Rodent and Human Hybridomas," Chapter 1 *In Monoclonal Antibody Technology*. Burdon, R. H and van Knippenberg, P. H., eds, Elsevier, pp. 1-32.

Database GenCore on STN, Accession No. U52152, Schoots et al. "Cloning of Four Inwardly Rectifying Potassium Channels from Human," Direction Submission Mar. 25, 1996 amino Acid and Nucleic acid Sequences.

Database GenCore on STN, on Accession No. AF275818, Yang et al. Jul. 23, 2000. "A Family of Novel PR- Domain (PRDM) Genes as Candidate Tumor Supressors".

Hunter, W. M. and Greenwood, F. C. (1962). "Preparation of Iodine-131 Labelled Human Growth Hormone of High Specific Activity," *Nature* 194:495-496.

Jiang, G-L et al. (2000). "The Yin-Yang of PR-Domain Family Genes in Tumorigenesis," *Histol. Histopathol.* 15(1):109-117.

Sawai, H. et al. (1984). "Synthesis and Properties of Oligoadenylic Acids Containing 2'-5' Phosphoramide Linkage," *Chem. Lett.* pp. 805-808.

Schoots, O. et al. (1999). "Co-Expression of Human Kir3 Subunits Can Yield Channels with Different Functional Properties," *Cell Signal* 11(12):871-883.

Skinner, R. H. et al. (1991). "Use of the Glu-Glu-Phe C-Terminal Epitope for Rapid Purification of the Catalytic Domain of Normal and Mutant *Ras* GTPase-Activating Proteins," *J. Biol. Chem.* 266(22):14163-14166.

Genbank Accession No. M31661 (Jan. 8, 1995).

Genbank Accession No. X73372 (Jun. 29, 1993).

Database GeneCore Accession No. U78076, created on May 14, 1999, last visited on Oct. 24, 2004. Lee et al. "Cloning of Mouse Sepiapterin Reductase Gene and Characterization of its promoter Region," Gene Sequence, *Biochim Biophys Acta* (1999). vol. 1445, No. 1 pp. 165-171. MPSRCH Search Report 2004, 1 page.

International Search Report mailed on Nov. 10, 2004 for PCT patent application No. PCT/US02/41414 filed Dec. 26, 2002, 8 pages.

\* cited by examiner

COMPOSITIONS AND METHODS IN CANCER ASSOCIATED WITH ALTERED EXPRESSION OF PRLR

The present application is a continuing application of U.S. Ser. Nos. 09/747,377, filed Dec. 22, 2000, 09/798,586, filed Mar. 2, 2001 and 10/052,482, filed Nov. 8, 2001, all of which are expressly incorporated herein by reference.

FIELD OF THE INVENTION

The present invention relates to novel sequences for use in diagnosis and treatment of cancer, especially carcinomas including breast cancer, as well as the use of the novel compositions in screening methods.

BACKGROUND OF THE INVENTION

Oncogenes are genes that can cause cancer. Carcinogenesis can occur by a wide variety of mechanisms, including infection of cells by viruses containing oncogenes, activation of protooncogenes in the host genome, and mutations of protooncogenes and tumor suppressor genes. There are a number of viruses known to be involved in human cancer as well as in animal cancer. Of particular interest here are viruses that do not contain oncogenes themselves; these are slow-transforming retroviruses. They induce tumors by integrating into the host genome and affecting neighboring protooncogenes in a variety of ways, including promoter insertion, enhancer insertion, and/or truncation of a protooncogene or tumor suppressor gene. The analysis of sequences at or near the insertion sites led to the identification of a number of new protooncogenes.

With respect to lymphoma and leukemia, murine leukemia retrovirus (MuLV), such as SL3-3 or Akv, is a potent inducer of tumors when inoculated into susceptible newborn mice, or when carried in the germline. A number of sequences have been identified as relevant in the induction of lymphoma and leukemia by analyzing the insertion sites; see Sorensen et al., J. of Virology 74:2161 (2000); Hansen et al., Genome Res. 10(2):237-43 (2000); Sorensen et al., J. Virology 70:4063 (1996); Sorensen et al. J. Virology 67:7118 (1993); Joosten et al., Virology 268:308 (2000); and Li et al., Nature Genetics 23:348 (1999); all of which are expressly incorporated by reference herein.

Breast cancer is one of the most significant diseases that affects women. At the current rate, American women have a 1 in 8 risk of developing breast cancer by age 95 (American Cancer Society, 1992). Treatment of breast cancer at later stages is often futile and disfiguring, making early detection a high priority in medical management of the disease.

PRLR is a prolactin receptor. The PRLR is a member of a larger family, known as the cytokine class-1 receptor super-family, which currently has more than 20 different members. PRLRs are widely distributed throughout the body. A number of disease states, including the growth of different forms of cancer as well as various autoimmune diseases, appear to be related to an overproduction of PRL, which may act in an endocrine, autocrine, or paracrine manner, or via an increased sensitivity to the hormone.

The first step in the mechanism of action of PRL is the binding to a cell surface receptor. The PRLR contains no intrinsic tyrosine kinase cytoplasmic domain but associates with a cytoplasmic tyrosine kinase, JAK2. Dimerization of the receptor induces tyrosine phosphorylation and activation of the JAK kinase followed by phosphorylation of the receptor. Other receptor-associated kinases of the Src family have also been shown to be activated by PRL. One pathway of signaling involves phosphorylation of cytoplasmic Stat proteins, which themselves dimerize and translocate to nucleus and bind to specific promoter elements on PRL-responsive genes. In addition, the Ras/Raf/MAP kinase pathway is also activated by PRL and may be involved in the proliferative effects of the hormone.

Accordingly, it is an object of the invention to provide sequences involved in cancer and in particular in oncogenesis and breast cancer.

SUMMARY OF THE INVENTION

In accordance with the objects outlined above, the present invention provides methods for screening for compositions which modulate carcinomas, especially breast cancer. Also provided herein are methods of inhibiting proliferation of a cell, preferably a breast cancer cell. Methods of treatment of carcinomas, including diagnosis, are also provided herein.

In one aspect, a method of screening drug candidates comprises providing a cell that expresses a carcinoma associated (CA) gene or fragments thereof, such as PRLR. Preferred embodiments of CA genes are genes which are differentially expressed in cancer cells, preferably lymphatic, breast, prostate or epithelial cells, compared to other cells. Preferred embodiments of CA genes used in the methods herein include, but are not limited to the nucleic acids selected from Table 1. The method further includes adding a drug candidate to the cell and determining the effect of the drug candidate on the expression of the CA gene.

In one embodiment, the method of screening drug candidates includes comparing the level of expression in the absence of the drug candidate to the level of expression in the presence of the drug candidate.

Also provided herein is a method of screening for a bioactive agent capable of binding to a CA protein (CAP), the method comprising combining the CAP and a candidate bioactive agent, and determining the binding of the candidate agent to the CAP.

Further provided herein is a method for screening for a bioactive agent capable of modulating the activity of a CAP. In one embodiment, the method comprises combining the CAP and a candidate bioactive agent, and determining the effect of the candidate agent on the bioactivity of the CAP.

Also provided is a method of evaluating the effect of a candidate carcinoma drug comprising administering the drug to a patient and removing a cell sample from the patient. The expression profile of the cell is then determined. This method may further comprise comparing the expression profile of the patient to an expression profile of a healthy individual.

In a further aspect, a method for inhibiting the activity of an CA protein is provided. In one embodiment, the method comprises administering to a patient an inhibitor of a CA protein preferably selected from the group consisting of the sequences outlined in Table 1 or their complements.

A method of neutralizing the effect of a CA protein, preferably a protein encoded by a nucleic acid selected from the group of sequences outlined in Table 1, is also provided. Preferably, the method comprises contacting an agent specific for said protein with said protein in an amount sufficient to effect neutralization.

Moreover, provided herein is a biochip comprising a nucleic acid segment which encodes a CA protein, preferably selected from the sequences outlined in Table 1.

Also provided herein is a method for diagnosing or determining the propensity to carcinomas, especially breast cancer by sequencing at least one carcinoma or breast cancer gene of an individual. In yet another aspect of the invention, a method is provided for determining carcinoma including breast cancer gene copy number in an individual.

Novel sequences are also provided herein. Other aspects of the invention will become apparent to the skilled artisan by the following description of the invention.

DETAILED DESCRIPTION OF THE INVENTION

Figure 1:
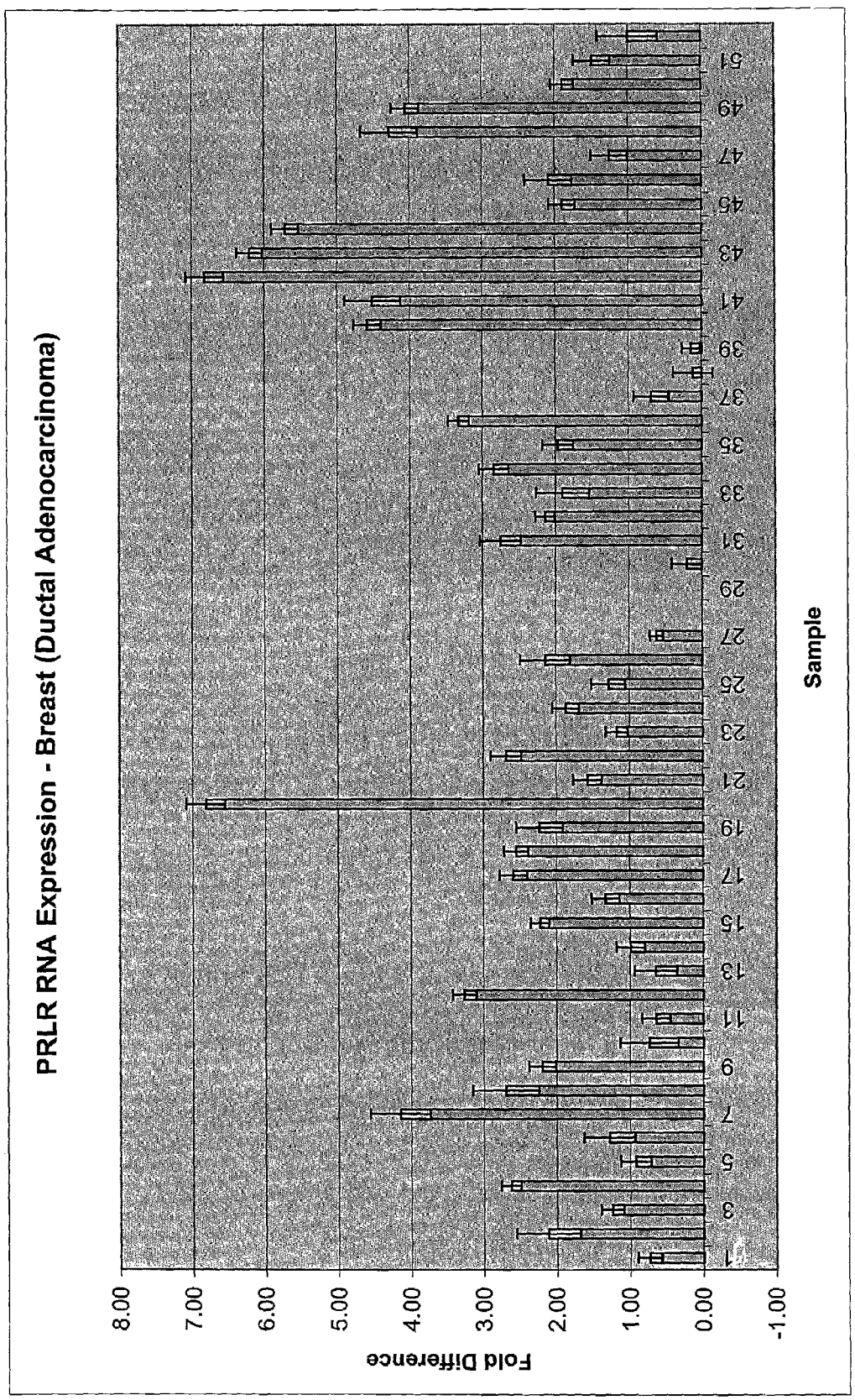
FIG. 1 depicts mRNA expression of PRLR in breast cancer tissue compared with expression in normal tissue. Samples 1-50 are breast cancer samples. Samples 51 and 52 are normal tissue. Bars represent the mean of expression level. Error bars represent standard deviation.

The present invention is directed to a number of sequences associated with carcinomas, especially lymphoma, breast cancer or prostate cancer. The relatively tight linkage between clonally-integrated proviruses and protooncogenes forms "provirus tagging", in which slow-transforming retroviruses that act by an insertion mutation mechanism are used to isolate protooncogenes. In some models, uninfected animals have low cancer rates, and infected animals have high cancer rates. It is known that many of the retroviruses involved do not carry transduced host protooncogenes or pathogenic trans-acting viral genes, and thus the cancer incidence must therefor be a direct consequence of proviral integration effects into host protooncogenes. Since proviral integration is random, rare integrants will "activate" host protooncogenes that provide a selective growth advantage, and these rare events result in new proviruses at clonal stoichiometries in tumors.

The use of oncogenic retroviruses, whose sequences insert into the genome of the host organism resulting in carcinoma, allows the identification of host sequences involved in carcinoma. These sequences may then be used in a number of different ways, including diagnosis, prognosis, screening for modulators (including both agonists and antagonists), antibody generation (for immunotherapy and imaging), etc. However, as will be appreciated by those in the art, oncogenes that are identified in one type of cancer such as breast cancer have a strong likelihood of being involved in other types of cancers as well. Thus, while the sequences outlined herein are initially identified as correlated with breast cancer, they can also be found in other types of cancers as well, outlined below.

Accordingly, the present invention provides nucleic acid and protein sequences that are associated with carcinoma, herein termed "carcinoma associated" or "CA" sequences. In a preferred embodiment, the present invention provides nucleic acid and protein sequences that are associated with carcinomas which originate in mammary tissue, which are known as breast cancer sequences or "BA".

Suitable cancers which can be diagnosed or screened for using the methods of the present invention include cancers classified by site or by histological type. Cancers classified by site include cancer of the oral cavity and pharynx (lip, tongue, salivary gland, floor of mouth, gum and other mouth, nasopharynx, tonsil, oropharynx, hypopharynx, other oral-pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, nos; ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); cancers of the lymphomas (hodgkin's disease and non-hodgkin's lymphoma), multiple myeloma, and leukemias (lymphocytic leukemia; myeloid leukemia; monocytic leukemia; and other leukemias).

Other cancers, classified by histological type, that may be associated with the sequences of the invention include, but are not limited to, Neoplasm, malignant; Carcinoma, NOS; Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Branchiolo-alveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/ squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant;

Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

In addition, the genes may be involved in other diseases, such as but not limited to diseases associated with aging or neurodegenerative diseases.

Association in this context means that the nucleotide or protein sequences are either differentially expressed, activated, inactivated or altered in carcinomas as compared to normal tissue. As outlined below, CA sequences include those that are up-regulated (i.e. expressed at a higher level), as well as those that are down-regulated (i.e. expressed at a lower level), in carcinomas. CA sequences also include sequences which have been altered (i.e., truncated sequences or sequences with substitutions, deletions or insertions, including point mutations) and show either the same expression profile or an altered profile. In a preferred embodiment, the CA sequences are from humans; however, as will be appreciated by those in the art, CA sequences from other organisms may be useful in animal models of disease and drug evaluation; thus, other CA sequences are provided, from vertebrates, including mammals, including rodents (rats, mice, hamsters, guinea pigs, etc.), primates, farm animals (including sheep, goats, pigs, cows, horses, etc). In some cases, prokaryotic CA sequences may be useful. CA sequences from other organisms may be obtained using the techniques outlined below.

CA sequences can include both nucleic acid and amino acid sequences. In a preferred embodiment, the CA sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an CA protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, the CA sequences are nucleic acids. As will be appreciated by those in the art and is more fully outlined below, CA sequences are useful in a variety of applications, including diagnostic applications, which will detect naturally occurring nucleic acids, as well as screening applications; for example, biochips comprising nucleic acid probes to the CA sequences can be generated. In the broadest sense, then, by "nucleic acid" or "oligonucleotide" or grammatical equivalents herein means at least two nucleotides covalently linked together. A nucleic acid of the present invention will generally contain phosphodiester bonds, although in some cases, as outlined below (for example in antisense applications or when a candidate agent is a nucleic acid), nucleic acid analogs may be used that have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365: 566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp169-176). Several nucleic acid analogs are described in Rawls, C&E News Jun. 2, 1997 page 35. All of these references are hereby expressly incorporated by reference. These modifications of the ribose-phosphate backbone may be done for a variety of reasons, for example to increase the stability and half-life of such molecules in physiological environments for use in anti-sense applications or as probes on a biochip.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. As will be appreciated by those in the art, the depiction of a single strand "Watson" also defines the sequence of the other strand "Crick"; thus the sequences described herein also includes the complement of the sequence. The nucleic acid may be DNA, both genomic and CDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

An CA sequence can be initially identified by substantial nucleic acid and/or amino acid sequence homology to the CA sequences outlined herein. Such homology can be based upon the overall nucleic acid or amino acid sequence, and is generally determined as outlined below, using either homology programs or hybridization conditions.

The CA sequences of the invention were initially identified as described herein; basically, infection of mice with murine leukemia viruses (MLV) resulted in lymphoma. The sequences were subsequently validated by determining expression levels of the gene product, i.e. mRNA, in breast cancer samples.

The CA sequences outlined herein comprise the insertion sites for the virus. In general, the retrovirus can cause carcinomas in three basic ways: first of all, by inserting upstream of a normally silent host gene and activating it (e.g. promoter insertion); secondly, by truncating a host gene that leads to oncogenesis; or by enhancing the transcription of a neighboring gene. For example, retrovirus enhancers, including SL3-3, are known to act on genes up to approximately 200 kilobases of the insertion site.

In a preferred embodiment, CA sequences are those that are up-regulated in carcinomas; that is, the expression of these genes is higher in carcinoma tissue as compared to normal tissue of the same differentiation stage. "Up-regulation" as used herein means at least about 50%, more preferably at least about 100%, more preferably at least about 150%, more preferably, at least about 200%, with from 300 to at least 1000% being especially preferred.

In a preferred embodiment, CA sequences are those that are down-regulated in carcinomas; that is, the expression of these genes is lower in carcinoma tissue as compared to normal I tissue of the same differentiation stage. "Downregulation" as used herein means at least about 50%, more preferably at least about 100%, more preferably at least about 150%, more preferably, at least about 200%, with from 300 to at least 1000% being especially preferred.

In a preferred embodiment, CA sequences are those that are altered but show either the same expression profile or an altered profile as compared to normal lymphoid tissue of the same differentiation stage. "Altered CA sequences" as used herein refers to sequences which are truncated, contain insertions or contain point mutations.

CA proteins of the present invention may be classified as secreted proteins, transmembrane proteins or intracellular proteins.

In a preferred embodiment the CA protein is an intracellular protein. Intracellular proteins may be found in the cytoplasm and/or in the nucleus. Intracellular proteins are involved in all aspects of cellular function and replication (including, for example, signaling pathways); aberrant expression of such proteins results in unregulated or disregulated cellular processes. For example, many intracellular proteins have enzymatic activity such as protein kinase activity, protein phosphatase activity, protease activity, nucleotide cyclase activity, polymerase activity and the like. Intracellular proteins also serve as docking proteins that are involved in organizing complexes of proteins, or targeting proteins to various subcellular localizations, and are involved in maintaining the structural integrity of organelles.

An increasingly appreciated concept in characterizing intracellular proteins is the presence in the proteins of one or more motifs for which defined functions have been attributed. In addition to the highly conserved sequences found in the enzymatic domain of proteins, highly conserved sequences have been identified in proteins that are involved in protein-protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopeptide repeats and WD domains to name only a few, have been shown to mediate protein-protein interactions. Some of these may also be involved in binding to phospholipids or other second messengers. As will be appreciated by one of ordinary skill in the art, these motifs can be identified on the basis of primary sequence; thus, an analysis of the sequence of proteins may provide insight into both the enzymatic potential of the molecule and/or molecules with which the protein may associate.

In a preferred embodiment, the CA sequences are transmembrane proteins. Transmembrane proteins are molecules that span the phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles. For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains. Many important cell surface receptors are classified as "seven transmembrane domain" proteins, as they contain 7 membrane spanning regions. Important transmembrane protein receptors include, but are not limited to insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc.

Characteristics of transmembrane domains include approximately 20 consecutive hydrophobic amino acids that may be followed by charged amino acids. Therefore, upon analysis of the amino acid sequence of a particular protein, the localization and number of transmembrane domains within the protein may be predicted.

The extracellular domains of transmembrane proteins are diverse; however, conserved motifs are found repeatedly among various extracellular domains. Conserved structure and/or functions have been ascribed to different extracellular motifs. For example, cytokine receptors are characterized by a cluster of cysteines and a WSXWS (W=tryptophan, S=serine, X=any amino acid) motif. Immunoglobulin-like domains are highly conserved. Mucin-like domains may be involved in cell adhesion and leucine-rich repeats participate in protein-protein interactions.

Many extracellular domains are involved in binding to other molecules. In one aspect, extracellular domains are receptors. Factors that bind the receptor domain include circulating ligands, which may be peptides, proteins, or small molecules such as adenosine and the like. For example, growth factors such as EGF, FGF and PDGF are circulating growth factors that bind to their cognate receptors to initiate a variety of cellular responses. Other factors include cytokines, mitogenic factors, neurotrophic factors and the like. Extracellular domains also bind to cell-associated molecules. In this respect, they mediate cell-cell interactions. Cell-associated ligands can be tethered to the cell for example via a glycosylphosphatidylinositol (GPI) anchor, or may themselves be transmembrane proteins. Extracellular domains also associate with the extracellular matrix and contribute to the maintenance of the cell structure.

CA proteins that are transmembrane are particularly preferred in the present invention as they are good targets for immunotherapeutics, as are described herein. In addition, as outlined below, transmembrane proteins can be also useful in imaging modalities.

It will also be appreciated by those in the art that a transmembrane protein can be made soluble by removing transmembrane sequences, for example through recombinant methods. Furthermore, transmembrane proteins that have been made soluble can be made to be secreted through recombinant means by adding an appropriate signal sequence.

In a preferred embodiment, the CA proteins are secreted proteins; the secretion of which can be either constitutive or regulated. These proteins have a signal peptide or signal sequence that targets the molecule to the secretory pathway. Secreted proteins are involved in numerous physiological events; by virtue of their circulating nature, they serve to transmit signals to various other cell types. The secreted protein may function in an autocrine manner (acting on the cell that secreted the factor), a paracrine manner (acting on cells in close proximity to the cell that secreted the factor) or an endocrine manner (acting on cells at a distance). Thus secreted molecules find use in modulating or altering numerous aspects of physiology. CA proteins that are secreted proteins are particularly preferred in the present invention as they serve as good targets for diagnostic markers, for example for blood tests.

An CA sequence is initially identified by substantial nucleic acid and/or amino acid sequence homology to the CA sequences outlined herein. Such homology can be based upon the overall nucleic acid or amino acid sequence, and is generally determined as outlined below, using either homology programs or hybridization conditions.

As used herein, a nucleic acid is a "CA nucleic acid" if the overall homology of the nucleic acid sequence to one of the nucleic acids of Table 1 is preferably greater than about 75%, more preferably greater than about 80%, even more preferably greater than about 85% and most preferably greater than 90%. In some embodiments the homology will be as high as about 93 to 95 or 98%. In a preferred embodiment, the sequences which are used to determine sequence identity or similarity are selected from those of the nucleic acids of Table 1. In another embodiment, the sequences are naturally occurring allelic variants of the sequences of the nucleic acids of Table 1. In another embodiment, the sequences are sequence variants as further described herein.

Homology in this context means sequence similarity or identity, with identity being preferred. A preferred comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., Methods in Enzymology, 266: 460-480 (1996); http:blast.wustl]. WU-BLAST-2 uses several search parameters, most of which are set to the default values. The adjustable parameters are set with the following values: overlap span =1, overlap fraction =0.125, word threshold (T) =11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the nucleic acids of Table 1. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleotides than those of the nucleic acids of Table 1, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the nucleic acid homology is determined through hybridization studies. Thus, for example, nucleic acids which hybridize under high stringency to the nucleic acids identified in the figures, or their complements, are considered CA sequences. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assaysz" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, the CA nucleic acid sequences of the invention are fragments of larger genes, i.e. they are nucleic acid segments. Alternatively, the CA nucleic acid sequences can serve as indicators of oncogene position, for example, the CA sequence may be an enhancer that activates a protooncogene. "Genes" in this context includes coding regions, non-coding regions, and mixtures of coding and non-coding regions. Accordingly, as will be appreciated by those in the art, using the sequences provided herein, additional sequences of the CA genes can be obtained, using techniques well known in the art for cloning either longer sequences or the full length sequences; see Maniatis et al., and Ausubel, et al., supra, hereby expressly incorporated by reference. In general, this is done using PCR, for example, kinetic PCR.

Once the CA nucleic acid is identified, it can be cloned and, if necessary, its constituent parts recombined to form the entire CA nucleic acid. Once isolated from its natural source, e.g., contained within a plasmid or other vector or excised therefrom as a linear nucleic acid segment, the recombinant CA nucleic acid can be further used as a probe to identify and isolate other CA nucleic acids, for example additional coding regions. It can also be used as a "precursor" nucleic acid to make modified or variant CA nucleic acids and proteins.

The CA nucleic acids of the present invention are used in several ways. In a first embodiment, nucleic acid probes to the CA nucleic acids are made and attached to biochips to be used in screening and diagnostic methods, as outlined below, or for administration, for example for gene therapy and/or antisense applications. Alternatively, the CA nucleic acids that include coding regions of CA proteins can be put into expression vectors for the expression of CA proteins, again either for screening purposes or for administration to a patient.

In a preferred embodiment, nucleic acid probes to CA nucleic acids (both the nucleic acid sequences outlined in the figures and/or the complements thereof) are made. The nucleic acid probes attached to the biochip are designed to be substantially complementary to the CA nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, etc. In general, the substrates allow optical detection and do not appreciably fluoresce.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 9525116; WO 9535505; U.S. Pat. Nos. 5,700,637 and 5,445,934; and references cited within, all of which are expressly incorporated by reference; these methods of attachment form the basis of the Affymetrix GeneChip technology.

In addition to the solid-phase technology represented by biochip arrays, gene expression can also be quantified using liquid-phase arrays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR® Greene I, is an example of an intercalating dye, that preferentially binds to dsDNA resulting in a concomitant increase in the fluorescent signal. Sequence specific probes, such as used with TaqMan® technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signaling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, and an array of probeprimer reactions can simultaneously quantify the expression of multiple gene products of interest. See Germer, S., et al., Genome Res. 10:258-266 (2000); Heid, C. A., et al., Genome Res. 6,986-994 (1996).

In a preferred embodiment, CA nucleic acids encoding CA proteins are used to make a variety of expression vectors to express CA proteins which can then be used in screening assays, as described below. The expression vectors may be either self-replicating extrachromosomal vectors or vectors which integrate into a host genome. Generally, these expression vectors include transcriptional and translational regulatory nucleic acid operably linked to the nucleic acid encoding the CA protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence.

For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the CA protein; for example, transcriptional and translational regulatory nucleic acid sequences from Bacillus are preferably used to express the CA protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The CA proteins of the present invention are produced by culturing a host cell transformed with an expression vector containing nucleic acid encoding an CA protein, under the appropriate conditions to induce or cause expression of the CA protein. The conditions appropriate for CA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect, plant and animal cells, including mammalian cells. Of particular interest are *Drosophila melanogaster* cells, *Saccharomyces cerevisiae* and other yeasts, *E. coli* Bacillus subtilis, Sf9 cells, C129 cells, 293 cells, Neurospora, BHK, CHO, COS, HeLa cells, THP1 cell line (a macrophage cell line) and human cells and cell lines.

In a preferred embodiment, the CA proteins are expressed in mammalian cells. Mammalian expression systems are also known in the art, and include retroviral systems. A preferred expression vector system is a retroviral vector system such as is generally described in PCTUS9701019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, CA proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the CA protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, CA proteins are produced in insect cells. Expression vectors for the transformation of insect cells, and in particular, baculovirus-based expression vectors, are well known in the art.

In a preferred embodiment, CA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica*.

The CA protein may also be made as a fusion protein, using techniques well known in the art. Thus, for example, for the creation of monoclonal antibodies. If the desired epitope is small, the CA protein may be fused to a carrier protein to form an immunogen. Alternatively, the CA protein may be made as a fusion protein to increase expression, or for other reasons. For example, when the CA protein is an CA peptide, the nucleic acid encoding the peptide may be linked to other nucleic acid for expression purposes.

In one embodiment, the CA nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the CA nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Accordingly, the present invention also provides CA protein sequences. An CA protein of the present invention may be identified in several ways. "Protein" in this sense includes proteins, polypeptides, and peptides. As will be appreciated by those in the art, the nucleic acid sequences of the invention can be used to generate protein sequences. There are a variety of ways to do this, including cloning the entire gene and verifying its frame and amino acid sequence, or by comparing it to known sequences to search for homology to provide a frame, assuming the CA protein has homology to some protein in the database being used. Generally, the nucleic acid sequences are input into a program that will search all three frames for homology. This is done in a preferred embodiment using the following NCBI Advanced BLAST parameters. The program is blastx or blastn. The database is nr. The input data is as "Sequence in FASTA format". The organism list is "none". The "expect" is 10; the filter is default. The "descriptions" is 500, the "alignments" is 500, and the "alignment view" is pairwise. The "query Genetic Codes" is standard (1). The matrix is BLOSUM62; gap existence cost is 11, per residue gap cost is 1; and the lambda ratio is 0.85 default. This results in the generation of a putative protein sequence.

Also included within one embodiment of CA proteins are amino acid variants of the naturally occurring sequences, as determined herein. Preferably, the variants are preferably greater than about 75% homologous to the wild-type sequence, more preferably greater than about 80%, even more preferably greater than about 85% and most preferably greater than 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies.

CA proteins of the present invention may be shorter or longer than the wild type amino acid sequences. Thus, in a preferred embodiment, included within the definition of CA proteins are portions or fragments of the wild type sequences herein. In addition, as outlined above, the CA nucleic acids of the invention may be used to obtain additional coding regions, and thus additional protein sequence, using techniques known in the art.

In a preferred embodiment, the CA proteins are derivative or variant CA proteins as compared to the wild-type sequence. That is, as outlined more fully below, the derivative CA peptide will contain at least one amino acid substitution, deletion or insertion, with amino acid substitutions being particularly preferred. The amino acid substitution, insertion or deletion may occur at any residue within the CA peptide.

Also included in an embodiment of CA proteins of the present invention are amino acid sequence variants. These variants fall into one or more of three classes: substitutional, insertional or deletional variants. These variants ordinarily are prepared by site specific mutagenesis of nucleotides in the DNA encoding the CA protein, using cassette or PCR mutagenesis or other techniques well known in the art, to produce DNA encoding the variant, and thereafter expressing the DNA in recombinant cell culture as outlined above. However, variant CA protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the CA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed CA variants screened for the optimal combination of desired activity. Techniques for making substitution mutations at predetermined sites in DNA having a known sequence are well known, for example, M13 primer mutagenesis and LAR mutagenesis. Screening of the mutants is done using assays of CA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the CA protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the CA proteins as needed. Alternatively, the variant may be designed such that the biological activity of the CA protein is altered. For example, glycosylation sites may be altered or removed, dominant negative mutations created, etc.

Covalent modifications of CA polypeptides are included within the scope of this invention, for example for use in screening. One type of covalent modification includes reacting targeted amino acid residues of an CA polypeptide with an organic derivatizing agent that is capable of reacting with selected side chains or the N- or C-terminal residues of an CA polypeptide. Derivatization with bifunctional agents is useful, for instance, for crosslinking CA polypeptides to a water-insoluble support matrix or surface for use in the method for purifying anti-CA antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the a-amino groups of lysine, arginine, and histidine side chains [T. E. Creighton, Proteins: Structure and Molecular Properties, W. H. Freeman & Co., San Francisco, pp. 79-86 (1983)], acetylation of the N-terminal amine, and amidation of any C-terminal carboxyl group.

Another type of covalent modification of the CA polypeptide included within the scope of this invention comprises altering the native glycosylation pattern of the polypeptide. "Altering the native glycosylation pattern" is intended for purposes herein to mean deleting one or more carbohydrate moieties found in native sequence CA polypeptide, and/or adding one or more glycosylation sites that are not present in the native sequence CA polypeptide.

Addition of glycosylation sites to CA polypeptides may be accomplished by altering the amino acid sequence thereof. The alteration may be made, for example, by the addition of, or substitution by, one or more serine or threonine residues to the native sequence CA polypeptide (for O-linked glycosylation sites). The CA amino acid sequence may optionally be altered through changes at the DNA level, particularly by mutating the DNA encoding the CA polypeptide at preselected bases such that codons are generated that will translate into the desired amino acids.

Another means of increasing the number of carbohydrate moieties on the CA polypeptide is by chemical or enzymatic coupling of glycosides to the polypeptide. Such methods are described in the art, e.g., in WO 87/05330 published Sep. 11, 1987, and in Aplin and Wriston, LA Crit. Rev. Biochem., pp. 259-306 (1981).

Removal of carbohydrate moieties present on the CA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131(1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of CA comprises linking the CA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

CA polypeptides of the present invention may also be modified in a way to form chimeric molecules comprising an CA polypeptide fused to another, heterologous polypeptide or amino acid sequence. In one embodiment, such a chimeric molecule comprises a fusion of an CA polypeptide with a tag polypeptide which provides an epitope to which an anti-tag antibody can selectively bind. The epitope tag is generally placed at the amino- or carboxyl-terminus of the CA polypeptide, although internal fusions may also be tolerated in some instances. The presence of such epitope-tagged forms of an CA polypeptide can be detected using an antibody against the tag polypeptide. Also, provision of the epitope tag enables the CA polypeptide to be readily purified by affinity purification using an anti-tag antibody or another type of affinity matrix that binds to the epitope tag. In an alternative embodiment, the chimeric molecule may comprise a fusion of an CA polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3c7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

Also included with the definition of CA protein in one embodiment are other CA proteins of the CA family, and CA proteins from other organisms, which are cloned and expressed as outlined below. Thus, probe or degenerate polymerase chain reaction (PCR) primer sequences may be used to find other related CA proteins from humans or other organisms. As will be appreciated by those in the art, particularly useful probe and/or PCR primer sequences include the unique areas of the CA nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, CA proteins can be made that are longer than those encoded by the nucleic acids of the figures, for example, by the elucidation of additional sequences, the addition of epitope or purification tags, the addition of other fusion sequences, etc.

CA proteins may also be identified as being encoded by CA nucleic acids. Thus, CA proteins are encoded by nucleic acids that will hybridize to the sequences of the sequence listings, or their complements, as outlined herein.

In a preferred embodiment, the invention provides CA antibodies. In a preferred embodiment, when the CA protein is to be used to generate antibodies, for example for immunotherapy, the CA protein should share at least one epitope or determinant with the full length protein. By "epitope" or "determinant" herein is meant a portion of a protein which will generate and/or bind an antibody or T-cell receptor in the context of MHC. Thus, in most instances, antibodies made to a smaller CA protein will be able to bind to the full length protein. In a preferred embodiment, the epitope is unique; that is, antibodies generated to a unique epitope show little or no cross-reactivity.

In one embodiment, the term "antibody" includes antibody fragments, as are known in the art, including Fab, Fab$_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of Table 1, or fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens. In the present case, one of the binding specificities is for a protein encoded by a nucleic acid of Table 1, or a fragment thereof, the other one is for any other antigen, and preferably for a cell-surface protein or receptor or receptor subunit, preferably one that is tumor specific.

In a preferred embodiment, the antibodies to CA are capable of reducing or eliminating the biological function of CA, as is described below. That is, the addition of anti-CA antibodies (either polyclonal or preferably monoclonal) to CA (or cells containing CA) may reduce or eliminate the CA activity. Generally, at least a 25% decrease in activity is preferred, with at least about 50% being particularly preferred and about a 95-100% decrease being especially preferred.

In a preferred embodiment the antibodies to the CA proteins are humanized antibodies. Humanized forms of non-human (e.g., murine) antibodies are chimeric molecules of immunoglobulins, immunoglobulin chains or fragments thereof (such as Fv, Fab, Fab', F(ab')$_2$ or other antigen binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework residues (FR) regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies [Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., BioTechnology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

By immunotherapy is meant treatment of a carcinoma with an antibody raised against an CA protein. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen.

In a preferred embodiment, oncogenes which encode secreted growth factors may be inhibited by raising antibodies against CA proteins that are secreted proteins as described above. Without being bound by theory, antibodies used for treatment, bind and prevent the secreted protein from binding to its receptor, thereby inactivating the secreted CA protein.

In another preferred embodiment, the CA protein to which antibodies are raised is a transmembrane protein. Without being bound by theory, antibodies used for treatment, bind the extracellular domain of the CA protein and prevent it from binding to other proteins, such as circulating ligands or cell-associated molecules. The antibody may cause down-regulation of the transmembrane CA protein. As will be appreciated by one of ordinary skill in the art, the antibody may be a competitive, non-competitive or uncompetitive inhibitor of protein binding to the extracellular domain of the CA protein. The antibody is also an antagonist of the CA protein. Further, the antibody prevents activation of the transmembrane CA protein. In one aspect, when the antibody prevents the binding of other molecules to the CA protein, the antibody prevents growth of the cell. The antibody may also sensitize the cell to cytotoxic agents, including, but not limited to TNF-$\alpha$, TNF-$\beta$, IL-1, INF-$\gamma$ and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity. Thus, carcinomas may be treated by administering to a patient antibodies directed against the transmembrane CA protein.

In another preferred embodiment, the antibody is conjugated to a therapeutic moiety. In one aspect the therapeutic moiety is a small molecule that modulates the activity of the CA protein. In another aspect the therapeutic moiety modulates the activity of molecules associated with or in close proximity to the CA protein. The therapeutic moiety may inhibit enzymatic activity such as protease or protein kinase activity associated with carcinoma.

In a preferred embodiment, the therapeutic moiety may also be a cytotoxic agent. In this method, targeting the cytotoxic agent to tumor tissue or cells, results in a reduction in the number of afflicted cells, thereby reducing symptoms associated with carcinomas, including iymphoma or breast cancer. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against CA proteins, or binding of a radionuclide to a chelating agent that has been covalently attached to the antibody. Targeting the therapeutic moiety to transmembrane CA proteins not only serves to increase the local concentration of therapeutic moiety in the carcinoma of interest, i.e., lymphoma or breast cancer, but also serves to reduce deleterious side effects that may be associated with the therapeutic moiety.

In another preferred embodiment, the CA protein against which the antibodies are raised is an intracellular protein. In this case, the antibody may be conjugated to a protein which facilitates entry into the cell. In one case, the antibody enters the cell by endocytosis. In another embodiment, a nucleic acid encoding the antibody is administered to the individual or cell. Moreover, wherein the CA protein can be targeted within a cell, i.e., the nucleus, an antibody thereto contains a signal for that target localization, i.e., a nuclear localization signal.

The CA antibodies of the invention specifically bind to CA proteins. By "specifically bind" herein is meant that the antibodies bind to the protein with a binding constant in the range of at least $10^{-4}$-$10^{-6}$ $M^{-1}$, with a preferred range being $10^{-7}$-$10^{-9}$ $M^{-1}$.

In a preferred embodiment, the CA protein is purified or isolated after expression. CA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the CA protein may be purified using a standard anti-CA antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the CA protein. In some instances no purification will be necessary.

Once expressed and purified if necessary, the CA proteins and nucleic acids are useful in a number of applications.

In one aspect, the expression levels of genes are determined for different cellular states in the carcinoma phenotype; that is, the expression levels of genes in normal tissue and in carcinoma tissue (and in some cases, for varying severities of lymphoma or breast cancer that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or carcinoma tissue.

"Differential expression," or grammatical equivalents as used herein, refers to both qualitative as well as quantitative differences in the genes temporal and/or cellular expression patterns within and among the cells. Thus, a differentially expressed gene can qualitatively have its expression altered, including an activation or inactivation, in, for example, normal versus carcinoma tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or down-regulated, resulting in a decreased amount of transcript. The degree to which expression differs need only be large enough to quantify via standard characterization techniques as outlined below, such as by use of Affymetrix GeneChip® expression arrays, Lockhart, Nature Biotechnology, 14:1675-1680 (1996), hereby expressly incorporated by reference.

Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the CA protein and standard immunoassays (ELISAs, etc.) or other techniques, including mass spectroscopy assays, 2D gel electrophoresis assays, etc. Thus, the proteins corresponding to CA genes, i.e. those identified as being important in a particular carcinoma phenotype, i.e., breast cancer or lymphoma, can be evaluated in a diagnostic test specific for that carcinoma.

In a preferred embodiment, gene expression monitoring is done and a number of genes, i.e. an expression profile, is monitored simultaneously, although multiple protein expression monitoring can be done as well. Similarly, these assays may be done on an individual basis as well.

In this embodiment, the CA nucleic acid probes may be attached to biochips as outlined herein for the detection and quantification of CA sequences in a particular cell. The assays are done as is known in the art. As will be appreciated by those in the art, any number of different CA sequences may be used as probes, with single sequence assays being used in some cases, and a plurality of the sequences described herein being used in other embodiments. In addition, while solid-phase assays are described, any number of solution based assays may be done as well.

In a preferred embodiment, both solid and solution based assays may be used to detect CA sequences that are up-regulated or down-regulated in carcinomas as compared to normal tissue. In instances where the CA sequence has been altered but shows the same expression profile or an altered expression profile, the protein will be detected as outlined herein.

In a preferred embodiment nucleic acids encoding the CA protein are detected. Although DNA or RNA encoding the CA protein may be detected, of particular interest are methods wherein the mRNA encoding a CA protein is detected. The presence of mRNA in a sample is an indication that the CA gene, such as PRLR has been transcribed to form the mRNA, and suggests that the protein is expressed. Probes to detect the mRNA can be any nucleotidedeoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a CA protein is detected by binding the digoxygenin with an anti-digoxygenin secondary antibody and developed with nitro blue tetrazolium and 5-bromo-4-chloro-3-indoyl phosphate.

In a preferred embodiment, any of the three classes of proteins as described herein (secreted, transmembrane or intracellular proteins) are used in diagnostic assays. The CA proteins, antibodies, nucleic acids, modified proteins and cells containing CA sequences are used in diagnostic assays. This can be done on an individual gene or corresponding polypeptide level, or as sets of assays.

As described and defined herein, CA proteins find use as markers of carcinomas, including breast cancer or lymphomas such as, but not limited to, Hodgkin's and non-Hodgkin lymphoma. Detection of these proteins in putative carcinoma tissue or patients allows for a determination or diagnosis of the type of carcinoma. Numerous methods known to those of ordinary skill in the art find use in detecting carcinomas. In one embodiment, antibodies are used to detect CA proteins. A preferred method separates proteins from a sample or patient by electrophoresis on a gel (typically a denaturing and reducing protein gel, but may be any other type of gel including isoelectric focusing gels and the like). Following separation of proteins, the CA protein is detected by immunoblotting with antibodies raised against the CA protein. Methods of immunoblotting are well known to those of ordinary skill in the art.

In another preferred method, antibodies to the CA protein find use in in situ imaging techniques. In this method cells are contacted with from one to many antibodies to the CA protein(s). Following washing to remove non-specific antibody binding, the presence of the antibody or antibodies is detected. In one embodiment the antibody is detected by incubating with a secondary antibody that contains a detectable label. In another method the primary antibody to the CA protein(s) contains a detectable label. In another preferred embodiment each one of multiple primary antibodies contains a distinct and detectable label. This method finds particular use in simultaneous screening for a plurality of CA proteins. As will be appreciated by one of ordinary skill in the art, numerous other histological imaging techniques are useful in the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing carcinomas from blood samples. As previously described, certain CA proteins are secretedcirculating molecules. Blood samples, therefore, are useful as samples to be probed or tested for the presence of secreted CA proteins. Antibodies can be used to detect the CA proteins by any of the previously described immunoassay techniques including ELISA, immunoblotting (Western blotting), immunoprecipitation, BIACORE technology and the like, as will be appreciated by one of ordinary skill in the art.

In a preferred embodiment, in situ hybridization of labeled CA nucleic acid probes to tissue arrays is done. For example, arrays of tissue samples, including CA tissue and/or normal tissue, are made. In situ hybridization as is known in the art can then be done.

It is understood that when comparing the expression fingerprints between an individual and a standard, the skilled artisan can make a diagnosis as well as a prognosis. It is further understood that the genes which indicate the diagnosis may differ from those which indicate the prognosis.

In a preferred embodiment, the CA proteins, antibodies, nucleic acids, modified proteins and cells containing CA sequences are used in prognosis assays. As above, gene expression profiles can be generated that correlate to carcinoma, especially breast cancer or lymphoma, severity, in terms of long term prognosis. Again, this may be done on either a protein or gene level, with the use of genes being preferred. As above, the CA probes are attached to biochips for the detection and quantification of CA sequences in a tissue or patient. The assays proceed as outlined for diagnosis.

In a preferred embodiment, any of the CA sequences as described herein are used in drug screening assays. The CA proteins, antibodies, nucleic acids, modified proteins and cells containing CA sequences are used in drug screening assays or by evaluating the effect of drug candidates on a "gene expression profile" or expression profile of polypeptides. In one embodiment, the expression profiles are used, preferably in conjunction with high throughput screening techniques to allow monitoring for expression profile genes after treatment with a candidate agent, Zlokarnik, et al., Science 279, 84-8 (1998), Heid, et al., Genome Res., 6:986-994 (1996).

In a preferred embodiment, the CA proteins, antibodies, nucleic acids, modified proteins and cells containing the native or modified CA proteins are used in screening assays. That is, the present invention provides novel methods for screening for compositions which modulate the carcinoma phenotype. As above, this can be done by screening for modulators of gene expression or for modulators of protein activity. Similarly, this may be done on an individual gene or protein level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokarnik, supra.

Having identified the CA genes herein, a variety of assays to evaluate the effects of agents on gene expression may be executed. In a preferred embodiment, assays may be run on an individual gene or protein level. That is, having identified a particular gene as aberrantly regulated in carcinoma, candidate bioactive agents may be screened to modulate the genes response. "Modulation" thus includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. Thus, if a gene exhibits a 4 fold increase in tumor compared to normal tissue, a decrease of about four fold is desired; a 10 fold decrease in tumor compared to normal tissue gives a 10 fold increase in expression for a candidate agent is desired, etc. Alternatively, where the CA sequence has been altered but shows the same expression profile or an altered expression profile, the protein will be detected as outlined herein.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the CA protein and standard immunoassays. Alternatively, binding and bioactivity assays with the protein may be done as outlined below.

In a preferred embodiment, gene expression monitoring is done and a number of genes, i.e. an expression profile, is monitored simultaneously, although multiple protein expression monitoring can be done as well.

In this embodiment, the CA nucleic acid probes are attached to biochips as outlined herein for the detection and quantification of CA sequences in a particular cell. The assays are further described below.

Generally, in a preferred embodiment, a candidate bioactive agent is added to the cells prior to analysis. Moreover, screens are provided to identify a candidate bioactive agent which modulates a particular type of carcinoma, modulates CA proteins, binds to a CA protein, or interferes between the binding of a CA protein and an antibody.

The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the carcinoma phenotype, binding to and/or modulating the bioactivity of an CA protein, or the expression of a CA sequence, including both nucleic acid sequences and protein sequences. In a particularly preferred embodiment, the candidate agent suppresses a CA phenotype, for example to a normal tissue fingerprint. Similarly, the candidate agent preferably suppresses a severe CA phenotype. Generally a plurality of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of an CA protein. By "neutralize" is meant that activity of a protein is either inhibited or counter acted against so as to have substantially no effect on a cell.

Candidate agents encompass numerous chemical classes, though typically they are organic or inorganic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids, as defined above.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In assays for altering the expression profile of one or more CA genes, after the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occurring as needed, as will be appreciated by those in the art. For example, an in vitro transcription with labels covalently attached to the nucleosides is done. Generally, the nucleic acids are labeled with a label as defined herein, with biotin-FITC or PE, cy3 and cy5 being particularly preferred.

In a preferred embodiment, the target sequence is labeled with, for example, a fluorescent, chemiluminescent, chemical, or radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data is analyzed to determine the expression levels, and changes in expression levels as between states, of individual genes, forming a gene expression profile.

In a preferred embodiment, as for the diagnosis and prognosis applications, having identified the differentially expressed gene(s) or mutated gene(s) important in any one state, screens can be run to alter the expression of the genes individually. That is, screening for modulation of regulation of expression of a single gene can be done. Thus, for example, particularly in the case of target genes whose presence or absence is unique between two states, screening is done for modulators of the target gene expression.

In addition, screens can be done for novel genes that are induced in response to a candidate agent. After identifying a candidate agent based upon its ability to suppress a CA expression pattern leading to a normal expression pattern, or modulate a single CA gene expression profile so as to mimic the expression of the gene from normal tissue, a screen as described above can be performed to identify genes that are specifically modulated in response to the agent. Comparing expression profiles between normal tissue and agent treated CA tissue reveals genes that are not expressed in normal tissue or CA tissue, but are expressed in agent treated tissue. These agent specific sequences can be identified and used by any of the methods described herein for CA genes or proteins. In particular these sequences and the proteins they encode find use in marking or identifying agent treated cells. In addition, antibodies can be raised against the agent induced proteins and used to target novel therapeutics to the treated CA tissue sample.

Thus, in one embodiment, a candidate agent is administered to a population of CA cells, that thus has an associated CA expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US9701019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, CA tissue may be screened for agents that reduce or suppress the CA phenotype. A change in at least one gene of the expression profile indicates that the agent has an effect on CA activity. By defining such a signature for the CA phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular differentially expressed gene as important in a particular state, screening of modulators of either the expression of the gene or the gene product itself can be done. The gene products of differentially expressed genes are sometimes referred to herein as "CA proteins" or an "CAP". The CAP may be a fragment, or alternatively, be the full length protein to the fragment encoded by the nucleic acids of Table 1. Preferably, the CAP is a fragment. In another embodiment, the sequences are sequence variants as further described herein.

Preferably, the CAP is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In one embodiment, the c-terminus of the fragment is kept as a free acid and the n-terminus is a free amine to aid in coupling, i.e., to cysteine.

In one embodiment the CA proteins are conjugated to an immunogenic agent as discussed herein. In one embodiment the CA protein is conjugated to BSA.

In a preferred embodiment, screening is done to alter the biological function of the expression product of the CA gene, such as PRLR. Again, having identified the importance of a gene in a particular state, screening for agents that bind and/or modulate the biological activity of the gene product can be run as is more fully outlined below.

In a preferred embodiment, screens are designed to first find candidate agents that can bind to CA proteins, and then these agents may be used in assays that evaluate the ability of the candidate agent to modulate the CAP activity and the carcinoma phenotype. Thus, as will be appreciated by those in the art, there are a number of different assays which may be run; binding assays and activity assays.

In a preferred embodiment, binding assays are done. In general, purified or isolated gene product is used; that is, the gene products of one or more CA nucleic acids are made. In general, this is done as is known in the art. For example, antibodies are generated to the protein gene products, and standard immunoassays are run to determine the amount of protein present. Alternatively, cells comprising the CA proteins can be used in the assays.

Thus, in a preferred embodiment, the methods comprise combining a CA protein and a candidate bioactive agent, and determining the binding of the candidate agent to the CA protein. Preferred embodiments utilize the human or mouse CA protein, although other mammalian proteins may also be used, for example for the development of animal models of human disease. In some embodiments, as outlined herein, variant or derivative CA proteins may be used.

Generally, in a preferred embodiment of the methods herein, the CA protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the CA protein is bound to the support, and a candidate bioactive agent is added to the assay. Alternatively, the candidate agent is bound to the support and the CA protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the CA protein may be done in a number of ways. In a preferred embodiment, the candidate bioactive agent is labeled, and binding determined directly. For example, this may be done by attaching all or a portion of the CA protein to a solid support, adding a labeled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. CA protein), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the CA protein and thus is capable of binding to, and potentially modulating, the activity of the CA protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the CA protein with a higher affinity. Thus, if the candidate bioactive agent is labeled, the presence of the label on the support, coupled with a lack of competitor binding, may indicate that the candidate agent is capable of binding to the CA protein.

In a preferred embodiment, the methods comprise differential screening to identity bioactive agents that are capable of modulating the activity of the CA proteins. In this embodiment, the methods comprise combining a CA protein and a competitor in a first sample. A second sample comprises a candidate bioactive agent, a CA protein and a competitor. The binding of the competitor is determined for both samples, and a change, or difference in binding between the two samples indicates the presence of an agent capable of binding to the CA protein and potentially modulating its activity. That is, if the binding of the competitor is different in the second sample relative to the first sample, the agent is capable of binding to the CA protein.

Alternatively, a preferred embodiment utilizes differential screening to identify drug candidates that bind to the native CA protein, but cannot bind to modified CA proteins. The structure of the CA protein may be modeled, and used in rational drug design to synthesize agents that interact with that site. Drug candidates that affect CA bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of CA proteins may also be done. In a preferred embodiment, methods for screening for a bioactive agent capable of modulating the activity of CA proteins comprise the steps of adding a candidate bioactive agent to a sample of CA proteins, as above, and determining an alteration in the biological activity of CA proteins. "Modulating the activity of an CA protein" includes an increase in activity, a decrease in activity, or a change in the type or kind of activity present. Thus, in this embodiment, the candidate agent should both bind to CA proteins (although this may not be necessary), and alter its biological or biochemical activity as defined herein. The methods include both in vitro screening methods, as are generally outlined above, and in vivo screening of cells for alterations in the presence, distribution, activity or amount of CA proteins.

Thus, in this embodiment, the methods comprise combining a CA sample and a candidate bioactive agent, and evaluating the effect on CA activity. By "CA activity" or grammatical equivalents herein is meant one of the CA protein's biological activities, including, but not limited to, its role in tumorigenesis, including cell division, preferably in lymphatic tissue, cell proliferation, tumor growth and transformation of cells. In one embodiment, CA activity includes activation of or by a protein encoded by a nucleic acid of Table 1. An inhibitor of CA activity is the inhibition of any one or more CA activities.

In a preferred embodiment, the activity of the CA protein is increased; in another preferred embodiment, the activity of the CA protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of a CA protein. The methods comprise adding a candidate bioactive agent, as defined above, to a cell comprising CA proteins. Preferred cell types include almost any cell. The cells contain a recombinant nucleic acid that encodes a CA protein. In a preferred embodiment, a library of candidate agents are tested on a plurality of cells.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

In this way, bioactive agents are identified. Compounds with pharmacological activity are able to enhance or interfere with the activity of the CA protein.

In one embodiment, a method of inhibiting carcinoma cancer cell division, is provided. The method comprises administration of a carcinoma cancer inhibitor.

In a preferred embodiment, a method of inhibiting lymphoma carcinoma cell division is provided comprising administration of a lymphoma carcinoma inhibitor.

In a preferred embodiment, a method of inhibiting breast cancer carcinoma cell division is provided comprising administration of a breast cancer carcinoma inhibitor.

In another embodiment, a method of inhibiting tumor growth is provided. The method comprises administration of a carcinoma cancer inhibitor. In a particularly preferred embodiment, a method of inhibiting tumor growth in lymphatic tissue is provided comprising administration of a lymphoma inhibitor.

In another embodiment, a method of inhibiting tumor growth is provided. The method comprises administration of a carcinoma cancer inhibitor. In a particularly preferred embodiment, a method of inhibiting tumor growth in mammary tissue is provided comprising administration of a breast cancer inhibitor.

In a further embodiment, methods of treating cells or individuals with cancer are provided. The method comprises administration of a carcinoma cancer inhibitor. In one embodiment the carcinoma is a breast cancer carcinoma. In an alternative embodiment, the carcinoma is a lymphoma carcinoma.

In one embodiment, a carcinoma cancer inhibitor is an antibody as discussed above. In another embodiment, the carcinoma cancer inhibitor is an antisense molecule. Antisense molecules as used herein include antisense or sense oligonucleotides comprising a singe-stranded nucleic acid sequence (either RNA or DNA) capable of binding to target mRNA (sense) or DNA (antisense) sequences for carcinoma cancer molecules. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules may be introduced into a cell containing the target nucleotide sequence by formation of a conjugate with a ligand binding molecule, as described in WO 9104753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1-100% wgt/vol. The agents may be administered alone or in combination with other treatments, i.e., radiation.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the various CA sequences are important in carcinomas. Accordingly, disorders based on mutant or variant CA genes may be determined. In one embodiment, the invention provides methods for identifying cells containing variant CA genes comprising determining all or part of the sequence of at least one endogenous CA genes in a cell. As will be appreciated by those in the art, this may be done using any number of sequencing techniques. In a preferred embodiment, the invention provides methods of identifying the CA genotype of an individual comprising determining all or part of the sequence of at least one CA gene, such as PRLR of the individual. This is generally done in at least one tissue of the individual, and may include the evaluation of a number of tissues or different samples of the same tissue. The method may include comparing the sequence of the sequenced CA gene to a known CA gene, such as PRLR, i.e., a wild-type gene. As will be appreciated by those in the art, alterations in the sequence of some oncogenes can be an indication of either the presence of the disease, or propensity to develop the disease, or prognosis evaluations.

The sequence of all or part of the CA gene, such as PRLR, can then be compared to the sequence of a known CA gene to determine if any differences exist. This can be done using any number of known homology programs, such as Besffit, etc. In a preferred embodiment, the presence of a difference in the sequence between the CA gene, such as PRLR of the patient and the known CA gene is indicative of a disease state or a propensity for a disease state, as outlined herein.

In a preferred embodiment, the CA genes are used as probes to determine the number of copies of the CA gene, such as PRLR in the genome. For example, some cancers exhibit chromosomal deletions or insertions, resulting in an alteration in the copy number of a gene.

In another preferred embodiment CA genes are used as probes to determine the chromosomal location of the CA genes. Information such as chromosomal location finds use in providing a diagnosis or prognosis in particular when chromosomal abnormalities such as translocations, and the like are identified in CA gene, such as PRLR, loci.

Thus, in one embodiment, methods of modulating CA in cells or organisms are provided. In one embodiment, the methods comprise administering to a cell an anti-CA antibody that reduces or eliminates the biological activity of an endogenous CA protein. Alternatively, the methods comprise administering to a cell or organism a recombinant nucleic acid encoding a CA protein. As will be appreciated by those in the art, this may be accomplished in any number of ways. In a preferred embodiment, for example when the CA sequence is down-regulated in carcinoma, the activity of the CA gene is increased by increasing the amount of CA in the cell, for example by overexpressing the endogenous CA or by administering a gene encoding the CA sequence, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, for example when the CA sequence is up-regulated in carcinoma, the activity of the endogenous CA gene is decreased, for example by the administration of a CA antisense nucleic acid.

In one embodiment, the CA proteins of the present invention may be used to generate polyclonal and monoclonal antibodies to CA proteins, which are useful as described herein. Similarly, the CA proteins can be coupled, using standard technology, to affinity chromatography columns. These columns may then be used to purify CA antibodies. In a preferred embodiment, the antibodies are generated to epitopes unique to a CA protein; that is, the antibodies show little or no cross-reactivity to other proteins. These antibodies find use in a number of applications. For example, the CA antibodies may be coupled to standard affinity chromatography columns and used to purify CA proteins. The antibodies may also be used as blocking polypeptides, as outlined above, since they will specifically bind to the CA protein.

In one embodiment, a therapeutically effective dose of a CA or modulator thereof is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for CA degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the CA proteins and modulators of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the CA proteins and modulators may be directly applied as a solution or spray.

The pharmaceutical compositions of the present invention comprise a CA protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, CA proteins and modulators are administered as therapeutic agents, and can be formulated as outlined above. Similarly, CA genes (including both the full-length sequence, partial sequences, or regulatory sequences of the CA coding regions) can be administered in gene therapy applications, as is known in the art. These CA genes can include antisense applications, either as gene therapy (i.e. for incorporation into the genome) or as antisense compositions, as will be appreciated by those in the art.

In a preferred embodiment, CA genes, such as PRLR, are administered as DNA vaccines, either single genes or combinations of CA genes. Naked DNA vaccines are generally known in the art. Brower, Nature Biotechnology, 16:1304-1305 (1998).

In one embodiment, CA genes of the present invention are used as DNA vaccines. Methods for the use of genes as DNA vaccines are well known to one of ordinary skill in the art, and include placing a CA gene or portion of a CA gene under the control of a promoter for expression in a patient with carcinoma. The CA gene used for DNA vaccines can encode full-length CA proteins, but more preferably encodes portions of the CA proteins including peptides derived from the CA protein. In a preferred embodiment a patient is immunized with a DNA vaccine comprising a plurality of nucleotide sequences derived from a CA gene. Similarly, it is possible to immunize a patient with a plurality of CA genes or portions thereof as defined herein. Without being bound by theory, expression of the polypeptide encoded by the DNA vaccine, cytotoxic T-cells, helper T-cells and antibodies are induced which recognize and destroy or eliminate cells expressing CA proteins.

In a preferred embodiment, the DNA vaccines include a gene encoding an adjuvant molecule with the DNA vaccine. Such adjuvant molecules include cytokines that increase the immunogenic response to the CA polypeptide encoded by the DNA vaccine. Additional or alternative adjuvants are known to those of ordinary skill in the art and find use in the invention.

In another preferred embodiment CA genes find use in generating animal models of carcinomas, particularly breast cancer or lymphoma carcinomas. As is appreciated by one of ordinary skill in the art, when the CA gene identified is repressed or diminished in CA tissue, gene therapy technology wherein antisense RNA directed to the CA gene will also diminish or repress expression of the gene. An animal generated as such serves as an animal model of CA that finds use in screening bioactive drug candidates. Similarly, gene knockout technology, for example as a result of homologous recombination with an appropriate gene targeting vector, will result in the absence of the CA protein. When desired, tissue-specific expression or knockout of the CA protein may be necessary.

It is also possible that the CA protein is overexpressed in carcinoma. As such, transgenic animals can be generated that overexpress the CA protein. Depending on the desired expression level, promoters of various strengths can be employed to express the transgene. Also, the number of copies of the integrated transgene can be determined and compared for a determination of the expression level of the transgene. Animals generated by such methods find use as animal models of CA and are additionally useful in screening for bioactive molecules to treat carcinoma.

The CA nucleic acid sequences of the invention are depicted in Table 1. The sequences in each Table include genomic sequence, mRNA and coding sequences for both mouse and human. NA indicates a gene that has been identified, but for which there has not been a name ascribed. The different sequences are assigned the following SEQ ID Nos:

TABLE 1

| (mouse gene: Prlr; human gene PRLR) |
| --- |

Mouse genomic sequence (SEQ ID NO:1)

Mouse mRNA sequence (SEQ ID NO:2)

Mouse coding sequence (SEQ ID NO:3)

Human genomic sequence (SEQ ID NO:4)

Human mRNA sequence (SEQ ID NO:5)

Human coding sequence (SEQ ID NO:6)

MOUSE NOMENCLATURE
ICSGNM   Prlr
Celera   mCG18319

HUMAN NOMENCLATURE
HGNC     PRLR
Celera   hCG37101

MOUSE SEQUENCE - GENOMIC
TCAGAATTTGACTGTCCTAAAGAACCTTCTTCCGCTGTGCGAGTCTGGGCAGGCAGAACATTCAGGAGAAACCACAGGGAAACAGGTCTGTTTT
TAAAATTTCCTTTTCATGCTCTGTTTCCCTTTTACCTCCTCTCCCTGTTCTTTCCATATCTACTGTCATTTTGCTACCCAGAAAACCTAGTGATT
CCTCCCAGCTGACAGGGCTGAGCTTGTGTTTCCACGGAGTCCAGGTTCATGGCAGGCCTGTTGAATATGGCCCTGGAATGACGTGCTTTCCTGC
TCTTTATTTATCAGAGCCTATGACTCATAGGGCCTAGTGGACTACGCTTCCAAAAAGCATTAGTTTTTGTTATTTTCCAGTTAGCATACAAACT
GTTTCAGAATGACAGTCTCAGACAGACAGCCAAACAGACAGACAGAGAGATAATTTTACTTTGTTTAATTTTACCCTTGTCCCTCTTCACCCTT
CCTGCTAATCTTCCTTCACACAAACAATTCCTCTTCTGTTTTCCATGTCATATAGATATGTACACTCCCCCCACACACACATACCCCACACACAC
TCACACAGACCCCTTTTACTTTCATATCAACCATTCTTTTCTATTGGGGAAGGTAGGGTAGGTATGCCCCACGGTGAGCACATAGAAGTCAGGA
GATCACTCTCCAGAGTTCTCTCCTGCCACCCTGTGGGATCCAGGGTTCAAACCTAGGTCATCAGGCCTGGACCAAAGGGCCTCTTACCACTGAC
CCATCTCACCAGCCTTATCAGGTTTTTTCCCCTTCAATCTGGCATATGATAGAAAACTTGTAGTATTTCTTGTTCAAAATCTGGCTTCTTTGAT
TTATTTGCCTCTCTAGTTCCATCTAGCATACAAACTATTTCAGAATGACACTCTTAGGTAGATAGATAGATAGATAGATAGATAGATAGATAGA
TAGATGATGCATACATACATACATACATACATACATACATACATAGATACAGATAGACAGAGACATTTCATTTCTACACTTAAATACATCTC
TGCTATGTCTATGCACCACATTTGCTCTATTCAGTCATCTGCTAATAGACACCCATGCTGGTTCCATATCCCTACTACTATAAATAGTGCTACA
TGAACATGAATGTACAAGTCATCTGTCTAAAATGCTGCCTCAGATTGCTTCAGGTATATACTTAGGAATGGTACAGTTTGGTCATATAGTCATT
CTTTTTTGTTTCTGATGAACCTCCATGCTAACTTCTATATGGCTACTCTGGTTACATACTCTACAGTAGCGTATGAACATCTGTTCCCCTACAT
ATCTGCTCCAGAACTTATTGGATTTTTTTTGAGGTTGTTTTCAGCCATTGTGTATACAGTGGGATGGAATCTCAGTTCTGTTTGTTGGTTGGT
CTGTTGTTTAGAGACAGGGTCTTCCATAGCTTAGTGTACAGTATGTAGACTGTGGACCAGGCTAGTCTCAAACTCTCCCTGATGTTCCTGCTTA
TTTTTCCTAATTGTTATGATCACACATGTATGCCAACAAACCTGGCTTCATTGCAGCTTTCTGAAGTTTTATTTTTAGATTTATTTGTTTTATT
TTTATATGTTTGCCTATATGTGTGTACATGTACATGTGTGGGCCACATATGTGTGGTCCTTGCAGAGGTCAGAAGAGGGTGTCAGATCTCCT
GGAACTGGAGTTACAGATGGTTGTGAACCATATCTGAAAACTATACCCGAATCTTCCACAAGAGTATGTATGCTCATAACTGCTAAGACACCTC
CACAACCTCAATGTAGCTTCAATTTACATTTTCCTATGGCTAATGTTCCTATGAACAATTTTATATTTTATATGTATTTATTGGCTAATTCACT
TCTTTTGAGAACTGCCTTTTTAATTTATCTGTCCATTCATTGATTGACTTTGTCTTTTGTAATTTTGAGTCAGGGTTAAAGTTTTTGAATTCT
TTCTATATTCTAGATATATAAAGATTAATAGTTGGCAGGAATTTTTCTCCCAAAGATCTGAACGTTAATGCTTTCCCTCAAGGTTCACTTTAG
CTGTCTTGCTTAAAGCTTGATAAAAAAAACTAAAGTCCTTTCCAATCAGACACGTGTGAGCAAGTTTTCCCTGAGCCACAAGCTGCAGTGCAGGA
AACTATCTGGATCAAAAACGTGTTCTCGTGATTTCCATTAAGGGATTGTCTCTTGTTCCCTGTCCCCTAAGCGAGTGCTGATAACAGTCCTCCA
TACCTTAGCACGTAAGTCAATCATTAACAATGGGCTGTACTTTTCACTGGGTTGTAAAGAATAAGAAGTCAGAGCTACAGAAATCTCCTTTCTT
GAGGTAGGCAGTGGAAGGAAGAGTGTCACTTGCCTGTAAACCTCATAACAATATGTAGCAGGCTGCAGCCCAACACGCAGGGGACGTGTCCGA
ACAGAGGAGAGTCACAGGTAAGGAATACGGGTCCATTTCTGTTTCTCTATCCATTCTGATTCTCTCTTCTCACCTTTCCAATCTGTGGACTAAA
AATGAACAGGGTCAAGGTGTGATTACAGTATCAGTGGTAGAAAGAGGTTTCTATGGACTGACCTGTGTTTTAACAAGAGATGGGCATTAGATGT
TAGTTAATTCACAATCTCCGTCTGACTCCTTCAAGACTGATTTCTTACAAACATCTGACTTCTTCAAGACTCGGAGTTCCAGAGAGAAAATGTA
TGTCAGTTACAGGAGCAAAGATCAGCGCAACAGCAGTGGTCACATGACAGGCCAGTCCTTGGGGAGGATAAAGATGAATTAGTGTGGACTTGGG
AACATCTCCAGATCCTACTCAAAGGCAAAAGGAGGTTAGATGGTAAATTTGAAAGAATTGCTACAAAATGCGCCAAAGGAATTATGCTT
ATTTCTCTTTTTTTGACAGACTTTGGGGGTTTTTGGTGTTTTGTTTGGTTTGGTTTGGTTTGGTTTGGTTTGGTTTGGTTTGGTTTGGTTGGT
TGTTTTTTTGCAATGATTTGTTTTAAAATAAATTTGTCTTCTTTAGAAAGCTTCCAGATACTCACTTTCCTTTCTCAACGACTTTCTTCTGCTA
TTACATGTGGCATTCTTGTGACACATTTATGACGACGAACCAACGTTAGCATGCTATCTACTTAAGCTCTTACACTATCTACATTAACATTGAG
TATTTGTCTCAGATATTTTATGGGTTTTAAGAAATGCATAATGACACATCACTGACTTGTACAAAATAGTCCCATGATCCTAAAAGTCCCATG
TTCTACCTAGTTCTCTTTCCCCACTCCCCTACCAAGCCCCTCAAAACACTCACCATTTTTCCTGACTCCATGCCTTTACCCGGTCTAAAGGGT
CGCCTGGTTGCAATGAAGTAGAACGTGGTCTTTTCGGATTGGTTTGAATTAGTAGTGTGCTTTTGAGTTTTTTCTGCATCTTTCTGTGGCTCAG
TAGCACATCCCTCTTTGTCGCTGAGTAACATATGACTATGTGACTAAACTACAGCAAATGTATCCAGTTGGGCAAATGTTTTAGCATGGTAGAA
AGTGGAAACGATAAAGGTGGGGGGAGTTTAGAAAGTGGCAGTCATATAAACGTGATGAGAAGCAAGAGAACACGAAGTAGAAAAACTAGCTAGA
AAGCTAAACACAGATGCCTCAGTTGAAATAAAAATTTTTTTAAAAGCTCTGGTTCTAGGGTGGCGCCAGCTCTTTTCTAAGCATATAGATTATG
CTGGGAGACACATTACCTTCAACCCAAGAGCCTACACATGGTAGGCACCCCATAACATTTTTGAAGCCCCCAAACTCCAAGACTTTTCCAAAA
AGAGGCTTCCCCAAGACACCAGCTTATTGGCTCAGAAGCCATATCAGGGAAGCTGTAGCTGCTTGGTCAGATGAGCCTTTGCATGCCATAGGAT
AAGAAAATATTCCCTTGATAACCTTTGTTTGACCGTGGCTTATGGAAGCTATGAGTATAAGCAAAGAACTCATGTTTCAACCTAATCACAGAT
TAGCCCAAACAATTTCCATGTAACAACAACAAAGGCTATGAGAAGATGAGCCAGCTATGCCTTCAAATGTTCACCACATTCTAGAGCAGAGAAC
AGTCATGTACCATTATCAGTAGCCCATGCAATGATGTAGGAGCCCAGTCCAAGGTGATGCAGCTTACAGTATGGCTGTGTAGTTGTCCAGGGAA
ACTGATGGGCCAGCTGGGGCTTGCAGAACCTAAAGAGACCTGCAAGTAGCAATTTGCTAACTCAGTGGGGCTACCATGCAAAAAAAGCTGATCA
CCCAGGCTAGTCAATGTATTGGTTCAAAATCATCAACTGCTTAAAACCAGGTTCTCTGCCAGAGCATTGATTGTATTCCTTAATGCCCAGAT
TCCTTTCTTACTGTGTGATGAAATGGGGAATTAGCCAGACATGAAGATAGGACCTTGTGATTCAGAGCTTTTCATGTCCTCTACTAAGTTAACT
TACACACTCAGCACAGGCTAAAAAATACCTGAGGATTTTCTACACAAGACAAATCTGGGAACTGCTTTGCCCAAAGGCTATTCTGTAGAGTGGA
GCTCATCCAAAGACTTACAACTTACTGCTTGTCTCGGTTTATGCTTACACAACAAGAGGGCTTGACCATCATTGTAGACAGTTTAGAATGGATG
GTGGATTTGGAGGCATCGGAATGACAATGTGTAGCTCTCATACCACTCAAAGCTCCTGGATGGGAATACTTGAAGAAGGAGATGTCTATGTG
AAGACTGATTCTGTGCAGCACATCTGCCGACCTAGAGATCTTCAAGCCACAGGGCAATAGAAACATCTCAAGCAACTTCCGTGTAATGAGAAATG
AGCAGAGGAGAATCAGACTCTGATTCCAACACAGCATCAGCTGGGGAAGCAGCTGCCTCTATGCATCAGCTTCTAGCCACTTCTGCTTGTCGG
CTTGTCTCTAGAGCATATCCTGAACATAAAGTGCCTGAGACAGGAACAAGCAGTACCTAGGCTAAAGCCACAATGACACAGAACTTACCTTGCT
TGTGCAAAGCACCAGACTCACTTTCAGAACCTGGGGCAAGTCTAGATCCCCAATTTTGAAAAGCATTTTGATGATTTCATATATCTATAGGATG
GATTTTTTTGTCATTTTCATGTGAGACACATGTGTCTCCCCCTTCTCCTGCTGGAATTTTTCTCAACTGGTGTCCCATGTTCTCTTTTTCTGTGT

TABLE 1-continued (mouse gene: Prlr; human gene PRLR)

```
GTATGGTGCCAGATAATTGACTCCAAATTTTTCTGGGAGAAATGTGCATCTATATCTCAAGACTTTGTTTTCAAGGAACTAACCAAATAGGATG
TCCATCTTACTTCCTTGTTTATTTGTATTTTCTTTTTATGTCTAGAAGAAATTAGTCATGAAAAATCTAAGACCAAGTCCAACATTTGGTAGTAG
GGGAGAGGAAGAGAAGGCAAGGTACTGTGTCCTGGGAATGTGACTGATTTTCCAGACAAACCTTCTCGTCTTCTTGTCCACATTTTCTCGTGAT
TTGTTTCAGAACCCTTCCTGACCTCACTCTTTTGACCTTATTTCATGCTCTTCTCTCCACCTGCCTGATAGTACTCAGCTGCAGACACAGGACA
CATTTATGCATCTCTCATCAGTATAGGGCTCAGGATTATCCCCAAGGGATATGGCGTGGGTGCAAAGATGAGAGCACAAGGCAGAGAATGTCA
CGAGATGGACACAATCTCTTCCATAGAAGCCCTCATTTTAGGATATTAAAGGACAGAGACACTATGGCAGAAAATTGTACAATGTCCTTGGCAT
TATAAAGTTAAACTCTGGGCCCTTTGACCATCCATATGTTCTCTCCATGTAGGTTAATCAACCACAAATTATATAACAGGATAGGGGTTGGAAA
TACAAAGGTGGATGAAGTAGCCCTTGTTCCCAAAGAGCTAATGGGTGAGACTGGCTCATGGGTCCATGATGGTGGCAAAAAGTACGGTGACCTG
GGACCACATCACAGAAACTTGTAATGAGGTCAGCTCAAGAGGCCCTGGGATCACATTGTGATATACGATAGAGCTCCTAAGTACCAAACTGAAA
GATGAAGCTGAGAGGAAGATGTCTGCGGAGAGCATTACACTGGAAAGAGAAACCCCAGAGAGCAGAGAACAGAAGCCACAGAAGTAATACAGTGG
TAGCTGGAAGACTGCAGGTCAAATAAAGGAAATTGTGATGTTTGTCCTGGGGAGAAGTGATACCTGAAACAGAAACAGGGCTAGCCCCTCTGGA
TGGACTTAAGCCATGCAAGAAGATAGAGACTAAGGAAAACCATCAGAGCATTGCAGATAGATGAGGCATGAAGGGAGATTTGCATTTGAGGAAG
GAAAAGTCTGGATGAATGTGAAGAATAGTTTAAAGGAGACAAAACAGAAGACTTGGAAAACACGTGGGAGGCTGTTGACATGAGGTGGCTTAG
AAACAGTGTTCCTAGGAAGTCTCGTTCTACACCTGTCACCTCAGGGTTCCTGATGACCCGTGAGCAAGACTTTCTAGAAAGAGCCGGTTCATTA
ATCACGTCACTTCTGTGGTATTAATAAAGCAACTATCATGGCTTTATTTTGTATCGACAACACTATCATGTAAATATTCCTTACTGATAAGGGC
CAGTCTCCCTCAGCATTTGTCAGCCACTAGGCTCAGGGAGCCAGCTACCTTGCATTTCTTCACTGCCTCTGTAAAGAGAAGTTTTCTCTTTGAT
TATGAGTAGATACACAACTGCCTTGATGCTTGTTCTAGCACAGCGGAAGAGGATAACTACCAGGGAAACTCGCCAATCACAAGGAAATCCGAGT
GTTTCTCTCGTACCCCAGTGTTGTCAGTTAGGTTTCATTTCAAAGTCAAGATTGTTCAAGCCAAGATACAATTGGTTTTAAATGCTGTCTTTAA
AGAAGGAATATGTTAGAGAAAATTGCTTGACACTCATTAGTGTGAAGCATGAGGGCAGCACTTCATGGCTGTGACTCAGTCTAAAAATTTCATC
ATCTCTACTAGTTTGCCAGGGTGGCCATAGCGAAGCTAGCCAACTGGGGGATCTCAAATGACAGAAAGATATTGCAGTTGGGAGGCCAGGAAA
CAGAAATCAAGGTGATCAAGGTAGCAAAAGTGGCTGTCTTCGAAGTCAGTGAGGAAGAATCTGTTCCTTGTCTTTCTCTTCACTACTAATGGG
AATCGGTTGCACTCCTTGGCTCATAGAACACCCTTGCCTCTTTTTTAATGCTGACATGGTTCTCTCTCTACTCTCTCTCTCTCTCTCTCTCT
CTCTCTCTCTCTCTGTGTGAGGGGAGATTTATCTTTGTCAGTATGAACCCATATGTCTAGACCGAGCCATCCCATTTTAATAAGTTAGAC
TGAAGCAAAGCCCATCATAATGGGCTCCTCTCAGCTGCGTCCCTCTGCGATGACCTTTTTTCCAAATAAGATCCAATTCTGAGATGTCAAGTGT
TCTTATGTTTCAACATAAGAATTTGTTGTACATTGACAGATACAATTCAGTCCAAATACCACCTAATATGATTTCAAAATTAAATAAGTTATCT
TCTATTTAAAAAAAATAAAACCTTGAAGATCCTCCAGTTTCTGAGTTCTTCTTCTGTTTCTTTCTTGAGAGACTTGAAGTTCTTCTCATACAGA
TTTTTCACTTCTTTGGATAGAGTTACCCTAAGATATTTTATATTGTGAATATTATGAAGGGTGTTGTTTCCCTAATTTCTTTCTCAGCCT
GTTTATCCTTTGCGTAGATGAAAGCTACTGGTTGGTTTGAGTTAATTTTATATCCAGCCACTTTGCTGAAGTTGTTTATCAGCTGGAGAAGCTC
TCAGGTTGAATTTCTGGAGTCGTTTATGTATACTATCATATCATCTCCAAATAGTGATACCTTGACTTCTTTGCCAATTTGTATCCACTTGATC
TCCTTTTGTTGTCTTATAGTTCTAGCTAGAACTTTGAGTACTATATTGAATAGATAGGGAGAGAGTGGGCAGCCTTGTCTTGTCCCTAGTTTTA
GTGGGATTGCTTCAAGTATCTCTCCATTTAACTTGATATTGGCTGATATTGGTTTGCTGTGTATTGCTTTATTATATTTAAGTATGAACCTTGAAT
ACCTGATACTTCCACCACTTTTAACATGAAAGGGTGTTGTATTTTGTCAAATGCCTTTTCAGCATCCAATAAGATGTCGATGTGATTTTTTTC
TTTCAGTTTATTTATATAGTGGATTGTATTAATGGATTTTCATAGTGAAACAACCTTCCATGCCTGGGATGAAGCCTACTTGATCATGGTGAAT
GTGGTTGATCGCTTTGATCTGTTCTTGGATTTGTTTTGTAAGAATTTTATTGAGTATTTTTGCCTCAATGTTCATAGGGAAATTATTCTGAAGT
TCTCTTTTTTGGTTGGGTCTTTGTATAGTTTAGGTATTAGGATTAATTTTGCTCATAAAATGAATTAGGCAGTATTCTTAATGTTTCTATTT
TATGGAATAGTTTGAGGAGTGCTGGTATTAGCTCTTCTTCTGCACTAAAGCCATCTGGCCCTGGGCTCTTTTATTGGGGTGGGGGGATTTTAA
TTACTTCTATTTACTTAGGGGATATGGGTCTCTTTAGATAATTTACCTGCTCTTGATTTAACTTTGGTTCATGATTCTAGTTTTGTTGATTCTT
TTATCTCTTTGTTTCTATTTGGTTGACTCAGCCCTGAGTTTGACTATTTCCTGTCATCAACTCCTTTGGGGTGTGTTTGCTTCTTTGTTGTTGT
TGTTGTTCTAGGACTTTCAGGTGTACTGTTATGTTGCTAGAGGAGAATCTGTCCAATTTCTTTACCAGGGCACTTAGTTTTTTTCAGCACTGCT
TTCATTGTGTCCCATAAGTTTAGGTATGCTGTGTCATCATTTTCATAGAATTCCAGGAAGTCTTTAATATCTTTCTTTATTTCTTCCCTGACCA
AGTTACCATTGAGTAGAGAGTTGTTCAGTTTCCAGGTGTATGTGGGTTTTCTGTTGTTTTTGTTGTTACTAAAGTCTATCCTTAGTCTGTGGTG
ATCTGATGGGATGCATGGGACTATTTCAATCTTCTTATAAAGGTTGAGGTTTGTTTTGTGACTAATTATATGGCCAATTTTGAAGAGGGTTCCA
TGAGGTGCTGAGAAGAAATTGTATTCTTTTGTTTTCGAGTGAAATGTTCTGTATATATCTGTTAAATCCATTTGGTTCATAACCTCTATTAATT
TCATTGTGTCTCTGTTTAGTTTCTGTTTCAGTGACCTGTCCATTAGTGAGAGTGGAGTGTTGAAGTCTCCCACTATTATTGTGAGGGGTTCAAT
GTATGTTTTGAGCTTTAGTAAAGTTTCTTTTATGAATGTGGGTGCCAGGATAGGAGAGTATGATGAGATACAACTGATTTTCAGTTGTCACTGA
GAGTTTGTAGTTTGGGTGAGCTAGGGCAAAATCTATGAAGTGAAGGCATTATGTCCTCCTGAAGAACCCAGAGAATGAGTTTTTCAACATTTGA
GCCTTGTTCCTATGGGCCTGGATAGGACCACCATATGTGAGTCTTAGAATGTCATTTCAACGTGCCCTGGATGGGATGAACACATGCTGCCTAGG
GGAGTAGCTGACGTGCATCAAAGTGTTTACTCGACCCAGATCACATCAGAATCAACCCTTGTAAAAATAAATAAGGTATGTTGATTTTTGTGC
AGATGGTTAAACAAATCTGATGGGGCAAAATGAGTTCTAGGAATAAGGGATATCAGAGGGCAAAGCTGCTGAAGATAGCAAGAGCTGCACCTGG
ACAATTTTGGGGCATAGTCCCTGGCAGCTGTGAGTGGCTGTTCTAGGGGACTGCAGTGCCAAGAAGAAATACTTGCCTGCCAAAGAGAGAAGC
TGACTCAAGGGGCAAAGTCAAGCTGAGCTGAATTCTAGGGGAAACGTAGAAGAGCAATCATCCAGAGAGGGGCTCTGATAGAGCTCCCTGGCCA
CTGTCTGCTCTTTTCAGAAGTCTGGACTCCCTGACCTCCAAGGCCTCCTCCAAGGTATGGAGTTCTCTCCCCTCTTGGATGTTTCTATCTCCTTTC
ACTGATGCTCAGGGAGACTTGTGACTTGAGCTGGAAAATACTGCTCTGGGAGGGAAGAACGGTCTGTTGTCCTAAAGCAGTGTGACCTTGGAAA
TGTAGCTAAACTTTTCTGGACTCGATGTCTTTCTTTGTTTTCTGAGATTCTTGGAGTTCTGAAATCATGGGCTCTTCTGGGTGAAATGGATCT
TAGAAACCTAGCCCAGTTTTGTGGCTGAAGAAACTAATGCTGAATTGAGAGATTTCATTATTGTCAGGAAACTAATCTATTAAAGGCAGGGTAC
ATAAAACTTGAAGATCTTCCTTCTCACCAAGAACCAATTCCACAAGAGCCCTTGGTGTCACAGGCCTACATTTGTTCCTCCTGAGAATCCTCTG
AAGTACAGTCTTCTACCTGCCTCAGACTTGTGCAAACTGGTTTCCCCAATGCCTTCCTGCTGCTGAATAAAAAGTCAGAACCTTACATGTCAGA
CACATTTCCTGCCACCTCCATTTACCCTCCTGCAGTTCCCTCTTTCTAACTGGCTTCAAGCTGAGTAGAAGCAAGGATCTGATTGTTGTGAGTG
GGCAGGTTCATCAGAGGGTACAGATAGACCAACAAAAGACTTATTCCAAGCAATATCCAGTTTCCCAAAGGAAACTCCTATCCAATGGATGAA
AGATAATTATTATGTAAGGATTGTTTTATGATTTGATGAATTTAAATGATCCGTTGTGAATAGAATGCAGGGATATGGCACAGGTTGA
TGGGAGCTAACTGGATGTTCTGCAGTGATTGGATTCTCCTGGATCAATATCCTCCTCCTCCCGCCCTCCCTGTCTTATCTTTGGCTTAGAGAGC
CAGGTGCATCCAAGTACAGGATTCCTGATCAGCATCAGCACCTCTCAAAATCTAAGAGAAAAGTTGGCTCCTCTGGGTAAACTGAAGCCTTAGC
AAGGTACTGATGCCTCCTCGGGTGACTATGTTACACCTTCCAAAGTGATTTGGCTTTTATGTCCCAGTTAGATGGTTTGGTGTCAGCAGCATA
TTGTAGCTTACATTGAGGATAAGTTAAGTTATTGGTCCCACCCCCACTTTTTTTTTTTTTTTTTGAAACAAGGTCTCTCACTGAACC
TGGACCAATTTGCCAAGAGTACCAAATCAAGCCATAAGCAGTCTCCTGTTTCCGCATCCCCAGCCCTAGGATCAAAGGCATGTGCTACTAACAC
CTGGGCTTATAGATGGATGCTGCAGATGTAGAACTCAGGTCCTTTTGCTTAGTGCAGCAGACACATTACAGACAAATCTGTCTCCCCAGCCCTC
ATTTTGTTCATTCAAATATCATCCAAATTTATCTGTGATAGTATAAATGAGTGAGTTGCCATTCCCCTTCTCACACTAAGCCTTTGAAATTCAG
GATGAATTTCATACTAACAGTGTGCCCTTCAATAATACAGATATATTTCCGATGAGTCTGCTGCCATCCAGGATAACACATTTTGTGCAGGAAT
ATGTGCTTTGAGCCCTGTGGTGTCTAAGGTGTATCTTTCAACCCAGATCTTTGACGTGTTAGAGAGCAGTGACATGGTTGGAGTCACGCATTCT
GTTTCAGGGATTCTGAGCAGAAACGAGCCAGGAAATAGTGACCGTTCCCTGGCTAACCATTCCTCCCCAGAAGCATCAATGTTCCAGTCCCAGG
CAGCTTTCCAGACTGCCCTAATCCCTTGACATGCCTCCAATGCTAGTTCCCAGCAGTAAGCATGTAAGACACCTGCCTTCCCTTGGTAGAGTTC
CAGTGTTAATTATTAACAAACAAATCCACGGTGCACCACAGCAAGATGTCACTGTAAGGCTACCAAGTTTCCTAGAACATGTCCAAAAGGACTT
TGTTCCCACTGGGTTCCTAGTCTGAGTCCAGACCAGTGTATACACAAACAATGGGGGTGGTATTTTTATTAGAAGAACTTCAAGCTACCAATCC
TGGAGACACACTTGGAAGCTTTCTCTAGGAAAATGTCTGTTCCTATTTGACCCTCAACCAGACAGGTGTCTGGGAAGAAGAAATCACACTAC
CTAAGAGGGAACTGCAGTAACCATCCATCACCTCTGGCATATTTATAGATAAATTCACCTATTGTGTATGCAGCAACTGTAATGGAGGATAAGCTT
TCAGGAGATTTGATTTACTAATGACATAGACACAAAGGAGTGGCATTCACACACCCTGGATATTAGAGTGGAGGGGATGTGGGAACTTTGTCCC
ATTCTAGAATATGCATGAGGCCTCTGAAGTACAGACAAGGATGGAGCCCAGAGTGCAAAACTAACAAGAAGAGGGGCAGATTGCTTCCTACCCA
```

TABLE 1-continued (mouse gene: Prlr; human gene PRLR)

```
AGGAGAGCTGGATATCCAAAGCTCACTTCTGTAAAGCCTTTCTAGGAGTTCCTTCAAATTTTGTTTATGTGAAACAAAGCTTTTCCTAATGATG
TAATGTGGCTTTGGCCTAAGTCACATCAAAGTACTGTCATCTTAAACTAGGGGTTAATTGTCGGGTAGTTACTATCTGTATGGCCCTGGCACAC
TCGACAGCTACTCCATTTCCGCAAGTGCAGAGCCCTGTGACTCACTGGGGACGGGCATGAGCGTTCTTGCCTTACTAGGAAGATTGAATAAGCA
CAGTCAAGGTGCTTAGCCATCTATTACAGCAGCACCATAAGTCCTGCCTTTGTTCAGGTAGCATCATGGCCTGAAGACAGGTCCAGGTAGGGTC
ATTCTCCCAGGCAGAGACAATATCCAGGTGTCTATGTAATGATACGGGTACCAGGATCTTGCCAAATCTGACCATCCTAGTCCACCCAGACTGT
TGGTATGGTTTTATCTTCTAACTTAAAACAAATGCTCTTTTGGAGGAAAAACTTTTAATTAGCTGATAATCTGATGATTATCAGGACTTCAATG
TCATCACCAGCACTAAAAGACCAAAGTCTTATGAGCAAGGGCATACAAACATACATGTCTTAGGACTCAGTCCATATAGTCAGATGGCCAGTTG
TTATCTAGATTTTAACACTCTTGGCTTACTTGTCTATTACAAATACTATGGAATTCAGGTCATTTGGAGACTGCCATCTTTCAGTTCAGAAAAA
TTATTTTGAAAATCCTTCAGTTCAGAAGAAATTGAGGTTCTTCAAAACCCATGTTTCTTGCTGTTTGCAGCCACTAATTATTCCATAACCCTGA
GGTTGCAACACTGTTCAGTAATGGGCTGTGAACCTAAAACAAAGTTATCATATGCTAATATGAATGTCTATGGCCAATCCCAGGCCAAGTAATC
CACTTATTCCCTGTGGCTTTTCCTCCAATATCAATGCAAGAGGAGTAGGGAACACACCTGCATCCTGAAGACCCTGTTTGCTATGGCCTGGAGC
TCCTTGGACCTGGTGAAATTAAATGAAAACAATATGATGATATCCTCTAGAGGGAGACCTGGGTCTGAAATCAGGATGCTCTCTGGTCATAGGA
GGCATGGTGTGGGCTTGTAAGCTTGAGTAGAGGACATGAAGCTTAAGACCAGGGCCTTTTATTACAAGCCTTTTATTGGTGATGTACCTCTAAC
AAGGTACATTTGGCAACTAAAAGTGTGTCCAGGGAAAAGCTGCTAAGAATCAGACTGAGGAGCCTAGAAACTCTGAGGAGAAGTTAGGGTGCTT
CCCCCAGAGAAACTGGATGCCAATCTATTGTTTGAAAAGCCAGTCCTATAGAACAGGTCTTCTTTGTTCCAAATAATAAAAACAGGAGCTAGGTC
AAGGAAACTGTTGCAAGTTATTCTCTTACTTCTACACGCATCATGCATGCTGTCACACACACACACACACACACACACACACACACATATATAT
ATATATATATATATATATATATATATATATATATATATATATGCACACACATGCATACACATACAAATGTGTATGTGCATGCACATGTAC
AAACAAATGAATAAATAGGCAAATAATTGTAAAGAAAATACTTGAAGTCAGACAGTGGAATTGAATGAAGATTCCAAGACAGAGACCCTGGGTC
CTTTAAGCTGCCTGCTCTCTAAGGTGATGCTTTTCTTGGCATATGATGGAGAACAGGGGTACCAGCCATGGAATTGATGGGGCACTAAAGAGCC
TGTTAGAGAGATGCTAAGAGGCTCATTTGTGGATTTAAGTGATGAACAAACAAAGTGGGTTTATGGTTTTGGTGTTCTGCAAACTGTGATTTT
CGACTTAGGCCATCCCACATATTAAAAATAAAACTAAAAATAAAATCAGGCTCCATGGGCTTTACCCATCCCATCTTAGCATGTCTGTTATTGT
TGTCCTTGCTCCATTCACGTTTAGCCAGGCATGTTGGTGAGCCTTTAAGTACAATTTGTGTTCTAATGAAAGGAAAATTAAATGCACATACATTTTTATTAT
CCTGATCCTCTGCCTCTGACAATCTTTCTGCCTCTCTTCCACAATGATCCCTGAGCCTTGGGTATAGGAGTGGTCTTGTAGATTGGGACTGGGA
TCCTCCATCCATTTGGATTGGTTGTGTTTGCTGGGAGGGTTTCACTGTCTGTTGCATAGAAAGGTTTCTTCAATGAGGGGAAAACTCAGGGGT
GAGCACGACACTTCTCTGTGAGTGTAAGGACTCTAGTTAGGAACTATGCCAGCTTAGCAAAGTGCTGCTTGCAGTTTCTCCATGACGTCACTGG
CCCTTCCTAGTTGGCTGGGTTCCCAATACCAGGTGTGATTTTCCTCTTGTCAAGTGGGTCTTAGGTCCAATTAGAGAACTGTTGGTTACTACTA
AGGTATGTGTGCCAGTACTACTGAACCCTTTGTATTACCATGACATATTGGTTATAATGATAAACCATATGTGTTATATGTGTGTAATATACATG
CAATATATATGCTATTTATGTGTAGTATATATATATATATTTATGTGTATTATATATATATTTATGTGTTTCACATATATGTATGTGTGAGTGTAT
GTGTGTGTATGTGTGTGTGTTCCAGTTCATGGCTGTCATAGACCTACTGGCTGCTTCTCTCCTTTGGAAGCTTGCATGGTGCATTCTCTA
ACCATGAAATCTAATCCTCAAGGAACAGGCTTTCAGGTCAATTCCCGTTTGGGAGCCTCTGTCACTGCGTCTGAACTACTTGGTGTCTTCAGCA
TTAAGAACAGAATGCTAGGAAGGTGTGTTGTAAGTAGTTTGTTTGGTATTTTGTTTTGTTTTGTTTTGTTTTGTTGCTAAGCCAATGGGTCACAAT
AAGCAGAATGGTGATGTGGCTAAGAACATGGGCTGTGGAGGCTAAGGCCATAAGGTTCAAATGCCAAGTCTTCTCTTATTGGAGTCTGAGAATG
TGGGGCAGTTACATAATTTACTTATGACTGTGCTTTGGTGTGGAGATAGAAATGATAATGTTTGCCCCTGCTGTTATCACTAGGTTTTAATCAC
AACTATCTTTGACTCACAATGAACACTCAGTACATGCTGGAAATGATTCTCATAGAAGGAATATTACCTTTTATTTCTTAAGCCAATGTGAGAA
CTTAAAAGGCACCAGCTTGCAAACACAGAGACTATGTCTCTTTTGCATTGTGTTCTAATGAAAGGAAAATTAAATGCACATACATTTTTATTAT
AATTAGGACACAGTTCAAAAGTGATAAGCCCTGTTGGTCTAGGGAATGACTACTCCTATGACATAAAGGAAAATGAAATCAAGTCCAGTATAGA
TTTTTGGCCATGAAGCTCAGAGAGTAAGTAAGATTTCTGGAATTCCTATCATTCTATGTGGCTCTATGGCTTATTCCCCAAGAGAGGCAAACAA
TTAAGGCCCTGTGCAGAGGTGCTTCCACCCTGGTGTACACAGTGAAGTAGTAACAGCTGATGGACGACCTCATTAGCCCTCCCCTAAGCCTTTC
TGTCTCATCATGAGTCTCAGCTATGTGACCACGGGAAACAGGAGAGAAAAAGATACAATGGGGACCCACGTGTCTCTCCTTAAGTACTGCTTATG
ATATTGAGGTTGGGGGTCTCTGAGCCATTTATTCCTCCTCTGGTTCTTTGGACCACTTGGGCATTGGAGCTCTACACCCCTGGCAGATCAAGGCA
CATTCTGTGCTCTTGGGAGCCTTCCTGATCCTATATGGAATGACTTAGATCAATGGGAGGACAGCAGCAGACTCCTGCAGTCAGTCAAAGTGG
TTTCCACTCCTAGGAGGAACACACCAGTTTGTTTCTGTGTGAAATACAGAAATATGACAGCTTTGTCGCAACGCTAAGCAAACCATTGTGTGGC
AGAACAAGCTTCTTTTTCACGTCAGAGGTTGACACACTGGCCCCACAGACAACACCAACTGTTCCCTTTGGAAACAGAATGGTGGCAAGAATGA
GCAGTTATGTGGACATCATCATTCTGGATCATCTCTAAGATCAACATTATTTTAGAATGCTGACAATGATATGTTTTGTGGGCATGCTCCAGGG
GAGGATTCAGTACATGGAAAATACATGCTAATCATCCACACATAACTGAGGGAATCATAAAGAGTGGATGATGCCCTGAGGGAATGTGTATTAT
TTACAGAGATATCTCCATGTCAAGACCCAATGCATCAGATCCATGGGAAATCGGCAAAGCCTTCTCTGGTCTGAGTATGACTGTTGACAGTGTG
TGCAAGCACGGGTGTTCACTAACAATTTACCAGTTTGTGCAAAAGCTGACAACTGCAGCTTCCTCCCCTGCAGGTGTGTACTGCCTGAGATAGCT
CAACCTTCTTTGGAGACTAGCTAACCAACCCCCTGTCTCGTAGATAACAAAACCCCCTTACGTTTCAGACTGCCTCAGTAACTGATCTCCTCCAT
GCAAAGAAGCATAGCCCATCCAAACGCAGCTACACGTGTCTGTGTCTCTCCTTTCTTCATTCCCTCACTGCTCAGTCAGGTCACCTCCAAGCTG
CACATGGAACACAGAACATCCCCATCACCTTGGGCCAAGCGTCTGGCATATGCTTCCAATCTTCAAGTTTTGAGTGGAGAGAAAATGTGGGCT
GGAATCTACAAATGTGAGCTGGAAGCCATTCCTCATGATAACCCTCGCTCTTTCTTGCCTTTTTCTTTTCTGTGTTTTTTTTCTTCATTTATTG
CTTATGACACTAGCAACGCAACCTATTGGAATAAAAATGTGGCTTCCCAGAACATTGTCTAACTTACTTCTCAAAGAAAGGGACCATTTCTGT
TGATAGTAAGACTTGGCTTGAAAGGGCCAGTTAACCCTGGCCCCAGTTTGTCTTGATCAACATCTCTAAGGCGTCCTATATTTGATCTAGCACC
TACAGAAAGAGTAGCTACGCTCAGAAGAAAAATATCTCTACAAAAGATTCACTTGTATGAAATATTTTATACACTAATCTAGCTGAATCGGT
CTCTTTCTGGTAGAAAATACAGTATCCAAATATATAGGGAGTAATTATGATAGGTAAGCCTGATAAAGAAGACCTCAGATCATGTGACCAGA
TAAGCCTAGCAATTGTCTGAAGACTTCAAACTACCCCTTAGGACTACTGAAAGGATGCCTGAAGAAAAACATCTAGAAACAAGTTTTGTGTGGA
CCAAACAAGGAGCAACAGAGAATTTTTGCACACAGGGAGTCTATGTAACTGCCCCAGTCATTTCTCCTAAATCTTTTTCTGCTAGAAAGACCTT
TGGTCTGGTCCCACTCATCATTTTAAAAAGACTTACAGGATTGAAATGATTTTAGCCTCTTCTTTCCTTCTTTACAGAAATGAGTTCTGAG
ACGAGAAGACTTGGGTGGTTAAGTCTGATGCTGTTAAATATATCAGGGGTTGAAAAGGGCTTAGAAGTGTAACATTCAGCTGGGCATGGTGGCA
CACGCCTTTAATCCCAGCACTCCGGGGGCAGAAGCAGGCAGATTTCTGAGTTCGAGGCCAGCCTGGTCTACAAAGTGAGTTCTAGGACAGCCA
GGGCTATACAGAGAAACCCTGTCTCGAAAAACCAAAAAGAACCCAAACAAACAAACAAACAAAAATGTAACATTCTGATTGATGCATGT
CCCTTGAAATGTTTCTGAGCTTTACTATGCATTAAATAACTTGAAATGAATGCAAGCATGCACAGTGCTTCTTTCTGTCTTACTGAATTTAAGG
ATGCCAAACAATTCTCTCATTTTTCCTTTGCTGGAAGGTGTGGCTCACCATTCTATTAGACAAAATTGTAGCTGACCTCTAATACCTAATTAGT
GCAAAACAATGCTACAATTATTGGGCATGACTTTTGACACGTTTTGGCTGCTAATGCAACCACTCCTAGTTAAATAGATTGGCAATGAATGTTCA
ATGCAAACTTTGTCAATGAGGCCAGCCTACTACTAGATATCCAACCATACAGGTAATGGCTGAACAGATCTTCATTCCTACAAAACCTCA
AGAATTATCCATTTTGCAACTTAAGTATATGCTGTTCATTACTTTTGTACAAGCTTGCTCTCTCTCTCCCTCCACCCCCCCCCTCTCTCT
CTCTCTCTCTCGTGTGTGTGTGTGTGTGTGTTTAATGGCTTACGAATCCACATAGGATTCTTGTACATATTCATTTTGGTTATTT
ATTCCCCCTTAATTAATCCCCCTTCATCTCCATGTCTCTCCCTGCCTGCTGGACCTAACCCTCTTTTGCTATATTCTTTACCCACTGTCC
TTCTTTTACATCTTTATTTCAATCATGTGGACCCGTTTCTCATTACCTAGGCTTTATCCATACTCACTTCTACTTAGAGACACATGTTTAACAG
TGAAAGGATAAGATTGCCATCTGAAAAAGGGTGTGGGGATATGGCGTGTTTATTTTTCTGAGTCTAATTTCTTGAGTTCTTTGTATATATTGGA
CATTAGCCCTCTATCAGATGTAGGATTGGTAACAATCTTTTCCCAATCTGTTGGTTGTCATTTTGTCCTATGACAGTGTCCTTTGCCTTACAGA
AGCTTTGCAATTTTATGAAGTCCTGTTTGCTCAATTATTGATCTTAGACATAAGGCATTTATGTGCATGTGTTTGTGGTATGTAATGTGTTGGAGAGC
AATGCTTCTCCCATTTCTTGGGACTTTTTTTTTTTTTGGAGAGCAGTTGCCTAGATGTTCATCAGCAGGTGATAGAAAATGTGGTGCATAC
CTACAGTAGGTTATTCAACAATAAAGATAAGCAAAATTACAAATTTTATAGGAAAATTGATGGAACATCTCTCTGTCTCTGTCTCTCT
CTCTCTCCCTGGTGGTGGGCATATAAAATGCAGTAGCCACTTCAGAAAACGGTCTGACAGACATCACTCAAGAGCCTCAGACAAAAGGTTGTCA
TGTGAGCAAGGGAGTCCACTATTGCCTATATATTTCTCTACGTTGGTAACAGATATAGTATGTAAAAGTGTTTGTAGCAGTACTATAACACTAT
GCATAGGTAAAAACAGCTCAATGTCTATCAACAAATAAGGAAAAAAATGTGCTAAGTAATATGATGGAATAGTACTCAACTGCAGAAAAAGAA
```

TABLE 1-continued (mouse gene: Prlr; human gene PRLR)

```
TGAAGTAGATGACATAGTGATGCAGTGTAGAACACAGATAAGGATCAACAGTATTATGCTAGGCTAAAAGTCACTTATTTGTTGTCTATAGGAT
AGAACCTGAATAGGTAAATCCAAAGAGAGAAATGCTAGAGTAGTGTTTCCAGGGGCTGAGAGAAGACTAAACTGAGTGTAGATGGATTATATGT
CTTCTGCTGCTGCTCCTTCCATGTCTGGCTGACGACAGATGTTTTGACAATGGATGAGAAGCTGATGAATAATTTTTTTAAAAAAATACTGAAC
TTTACGTTTTAAAAGGGTAACTGTTATATGAGTACTCTCAATTTTAAAGGAAAAAAAGCAATGTTTAAAAGTGGGCCAATGTTGGAAGTCAACT
GTGAGAAGTTAAGAGCAGATTCACAAATAAGCACTGGAATTGGGCCTTGATTTGGGGGAATATTAAGAATATAACTAGAAGACGTTGTAAGAAA
AGTTTGGATGAGTCAGAAAATAGGGAGACCGGCTAGAGAGATGTCTCAGTGTTTAAGAGCACTGATTGTTCTTCCAAAGGTCCTGAGTTCAAGG
TCCCAGCAACCACATGGTGCCTCACGACCATCTGTAATGAGAACCAATGCCCTCTTCTGGTGTTTCTGAAAAGAGTGACAGTGTACTTGCATAA
AATAAATAAATAAATAAATCTATTTAAGAAAATAGGGGGACAATTGTGTGTTAGCAAAATACAGTAGAGACTAGACTAAGGTTCATTAAAACAC
AGGCCAATAAAGATGAGGCCACATGTATGTGTTCAGGACACATATACTGTAATACGTAAAATACATTAAAAAGTTCAGACTTCTTCAGGCTCGT
GAAAAACACACTGTGAATGCTTTAACCCTCATTGTCTGATCGTAACCCATTCCTAGTCATCTCCCTTTCCTTTCCAGCTAGTTTGCATCTTACG
TCCGCGTGTGTACATGTGCAGCTTCTATATAGGCCGCCACAGCTGATTCCTGTTTGTCCTTTTCCCAATTTTTTATTTGGTATTTTCTTCATTT
ACATTTCAAATACTATCCCGAAAGTCCCCTGTACCCTTCCCTCCCCCTCCTCTACCCATCTACTCCCACTTCTTGGCCCTGGTGTTCACCTGTA
CTGGGGCATATAAAGTTTGCAAGACCAAGGGGCCTCTCTTCCCAATGATGGCCAACTAGGCCATCTTCTGCTGCATATGCAGCTAGTACTTGGA
TGGAAGGCCACAACTGACTCTTAAAGACTGTATGTAACACCAAATATTAGAGCAATTGTCTTCACTTAGTAGCATTTCTGAGGGTTTAAGTCCC
TTTCATTTGGATTCTCAGTTTCCATGTGCAATGAATTTTTTTACAGGTGAGCAAGAAAAGTATGGAAGGAAGCCTAAGAAAGGCCGCAATGAGA
CTTTAAAAAATGATGCCAATTTTAGAACGCATCTTCTCTTTCAGACTTGGAAAATTAACTTTTATTACTGCCCTATGCAAACTAAATTTAAAT
AAGCTTTGGATTATACCCCGTGCGTATGAGCGGACGTTATGACATTGATTGACAACGTCAGATCTACCCTCAACCCTCTGAGAGTATGATTCAC
ACATACCTGGGATCAGAAAAGAAGTGTTTTCCAGACTAGGCAAGTCACTAGAGCTCTGGTGGTACTCAGGGTAGATTTCTTCCCCATAATTCCT
AGCTAAAGATGAAAGATACAGACAAATGACCCATCCTAGGAGAATTTACAAGGGTAGTGGTAAGCAGGTAGGTTTCAGAACAGCTCATGAAACA
ATTCTGCAGCAGGAGTCAAGGAGTCCCAAAGAAGTGGCCTATATGGGACAGCAAGGAGAGACTCAAAAAAAAAAAAAAAAGGAGGAAAAAAAAAC
CCTATGTGGGGCTCAGCAGTGAAGAGCACTGAGTGCTCTTTCAGAGATCCTGAGTTCAATTCCCAGCAACCACATGGTGGCTCACAACCATCTG
TAATGAGATCTGATGCCCTCTTCTGGTGTGTCTGAAGACAGCTACAGTATACTCATATACATAAATCTTTTAAAAAAAAAGTCCTATGTAAAAG
GCATAATGGTAGATGTTGCAAGAAAGCAGTGTGTGTATTGGTATCTGGCAGGAGGCTCAGGAATGTTCACATCACAGTCGTTAGGAAAGGAAAG
CAAGGGACCCCTTATTGTAGGATATATGGACAATTTAATCATGGGGTTTTTTCCCCAATAATAAAATTTTCAGCAGGAAAAAAAAATAACAG
TAAACAGTAAGCTACGTGTAACATAAGGATGAAAGATTTCAAAACCCGTCTTTTACAAAATGCACAGCAACAGCTTCTTTTGTGACAGCATCAT
CAGTCCCCGTGGTTTGCAGCCGGATGTAACAAGCCCTTTTGAAGAGCTAAGAGGGCAGAAAGTTTCTGTTGCCAAATATATAAGAGAAGCAGGA
AGCACTTAGCCTCGGACCAGGAAGGGCATCCTTGCAGGAGACCCTGCAGGTCTGTGCAGTTCATTGCCCiAATGTTCCCTTAAATAAAGAGCCA
CAGACTTCAGGAGTGTGTTCCCCCCTGAGTGATTCTGCAAGAGTTGTTTGCCCTCCAGCACTGGGCTGTGCTGAAAGAGTTTAGTTTCCCAGGG
AACAAGATCTGGGTCTAAGGCAAGGCAAGCAGCATCCTATGCCCAAACCAGTAACTCCGTTTTCTCAGCCTGCCAATCACATTGGAGCTTCCAG
ACCATCANNNNNNNNNNNNNNNNNNNNNGCCTCAAGTCTCCAGTCCCCATCATGATAGTGAGACCCAGAGGAAAGGGAACACCTGTTGCCACCAT
TTTGAAGGGACAGTGGTGACCCATAAAGAGGGTGCTCTAAAGGAGACAGGACAATTCAAGGACTTGGATAAAATATCAAACTGACAGTGGTGAG
CAACTGTCAGGTTCTAGGACCAGTTTAATCCTGACTGGGCAGAGGATAGGGGCCATCCACACAACCCTCGGAGGGAGCGTTCTATAGAACCGGC
TGCCTTGGTCAGCTTAGGGCAACCAGCATTAAGGCAGCAGGAGGAGGGATATAACCCAGGCTCACCTCTCCCAACCCCTACACAGGGTTCCTTC
CTGCCAAGGCTCTCTACACCCTTTAGTTTACAGTGGAAATCAGAAGGCAGTAGGACTCAGGTGCAGACCCATATAATTCAGAACAGGAAACAGGAA
ATGTGGAAGAAGGAGGGGCTAAGGGAGAGCACAAACATTGGCCAGCTGCAGCCCGGCCCCAATTGGGACTGCAGACTTGGGTAGATGGATGGTT
GCCACATCCTGCTCTGAGCCTTTTGAGTGACTCTGAGATAGAGCGCCTCTGTGGAGTTCCACAGAGCAGGCACACAGGCTGAAATCATGAGGTT
TGTATTTTACCTCCTTGCCGGTTTGCAAGTCTTGAAGCTCACTCCTCTAAGCTGATGGCAGCCCTCATGCAAAGCAACTCTGATTGCTGTGTCT
GGGGTTCAATACACACACACACACACACACACACACACACACACACTCAGGTGCACGTGCATACACACAAAGACAGAACAGTTTGCTTGCAA
CATTGTCATAGCTTAGTGAACAGTATAGCATTGTTCTGGCTCAAGAAGCCCTGGTTCTTCAAAGCTCCTACTTAGATGAAATTATTTGCATCAC
AAACAAAAATTGTTTTGCATTTTTTAGATAATGAAGGATCGTTTAAATATATAAATTAAGGGCTATTTAGAAAAAATAGGTGTCTTTGTGAGAC
TGGCTTAATTCACTTACCATGATCATATTCAGTTATGGTCATTTTAAATACAAATCATGTGTGTTCCAATGACGTGAGATTACAGTGAACTATC
TAGGGAAACTAACAGGAGTGGAGTAGGGACAGGAGAGGAAGAGAAACGATGGGTGATGGGCACATATGCTCAAAACCATAATGTACTGGGGCTG
GAGAGATAGCTCAGCGGTTAAGAGCACTGACTGCTCTTCCAGAGGTTCTGAGTTCAATTCCCAGCAAACACATGGTGGCCCACAACCATCTGTA
ATGGGATCGGATGCCCGCTTCTGGTGTGTCTCAAGACAGTGACAGTGTACTCACATACATAAAATAAATGCATCTTTTTTAAAAAATCATTAT
ATACTTGCATGGAAATGACCCTATGTAACCGAGTTTCATTTAGTTGTTTTTCAATTGTTAGAGAAAGACTAAATTTTCTCTAAGATAGCCATAT
GAAGACAGTTGATCACTCTATGTCCCAGAAGCCCATCTGGAACTTAGCATTTTGAGCAAACCATAAATTTGATGAAATACCTCCTATTCAAGGC
GGCAAGCATTCATTTGCCTCACATTTCTAAGTCTGCCCCTGTGACTGCCTTAGCTCCTTCTTCCCAAATTCTCCAGTTACCTGGCCCTTAGGGG
TGGTAGCGAAATCTCCTTCCTGACAGCTTCCTTGGCCAGGTGCTTCTGTGTGGAGTCAGTGCCCCAGGCCGCCAGCTGTTCAAGTGTTTGGGCAT
ATGCACACACAGGAACGACTTGGGCAACACCCTTTGCCTTGTTCGGGATGTTCTTCTTGCAGACCCTTGCCCAGACATAGGGAGTGCCTGTGA
AGTGCTCCAGAATAAATCGGAATGTCCCACTGAAGCCAGACACCGTGGTCTTCATGTTAATGTGTAAGTAGAGTAGTGATCATTTATTTATTCT
TTTGATTCCCTTTTGCAGAGTTTTTATTGCCCTGTCTGAGATATTGGAGTTTTCTGCTACAGTAAATTTAGCAGGATTTCTCCAAGGTGACTTTA
GCGCCAGTGAAGGACTTATTGTGCCTCTTCAAGTGGTTCTATCACTCTGTTGTGCTAGGGGTAAAATGAGGTGCCAGGTGGATTCAGGACAAG
CAGACACAAGCAAGCTAGGAAACCTGGCACTCGATCCCCTCTGCGGTGCTTAGGCAAGCCTTCTCGGCTACTGAATTTTGAACTTTCACAAGAA
CAGATCGGCTGTTTGTTCAATGTTTATTACTCCTGCCACAACGCATGGCATGAGGTTGGCGCGGCCTGTTTATTTCTTTGTGTATATGGA
TATGTGTTTGTGGGTGTACATGAATGGGTGGTATGTGTACACACGTGTGCATGGGGAGACATGCCCAGGGCTATTTAAATCTTCTGCCCTTTTC
CTTCACTTCCCTCCTGTTCCTTCTTAAGAACAAGCATTGCTTCACTCTAAATTTTATTTTCTCCTCTAGAAAAAACTGTTATCATTCAACTCA
ACATGTTTTCCACTGAAACTTCTTCCCATATTAATTTTTAGGTTTTCATGTTCTCGTTTTATTCGTACTTATTGGCCGCTATTTTCAAATTAATA
GAGTCCAATGTCATATTTCTGTATATTGCATCCCTGTTGCCCATCTATGCTTCTCCTCCAGACTATTTCTTCCTGTGCTTATTCGCTTAGTGAA
AGTACATTGCCAGGCTAGAAAGGTGGTTTGTTGGCTAACAGTGTTCTCTGCACAAGCCTGGGAACCCGAGCTTGGTTCCTCATATCCAAGAAAG
GAGAAAGCAACTCTGAAAGTTGTCCTCTACTTTTTCATGTGCACCGTAGCCCATGCCACCCACACCCACAAATACACACCACACACACATA
CACAAAATAATAATAATAATTTTAAATATATCAACTGACTTACAAACATTTGTTTTTTTTTCCCGATGACATTTGTGATGTTAACGCATAA
TTTGATTCTAATTTAGTTGTAAGCATATTCTATTTTGACTCTTTGAAGTTTTTTGAAATTCAGTATCTAGCTGTGGTGGTGAGCTTTCCACATC
AACTTATCATAACCAAGAATCACTGGGAAAGAATATTTCAGTTGGAAAAATTATTTGGATCAGAGTGATCTGTGGTCAGGTCCACGAGAAAATG
TCTTGGTTGCTAATTGGTGTTGGGGGACTCACTGTGAGTAGCACCATTCACTCAGGGGACAGTGAGCTGTCAAGGCAAGAGAAAACGGAA
AGACCTCAAGCAAGCAGGCCGCATGGCTATTTGTTCATGCCTGCTTGTGACTGTAGACATTATGTGATGAGCTGCCTTGAGAGTCTGCTTCAGT
TTCTCCTCAGTGACAGACGGTAACCTGGAATTGTAAGACAATAAACTCTTTCCTCCCCATAAGCTGCTGCTTCTTGGATGCTTTCTTGCTACAAC
AGAAATTAAACCAAGGCATCAGCTTATATTCTGCCTGAGTGCGTATCCCAGGTGCCCAGAAGTGTTGGCTGTTGTACTCTGCACATTTCAATGG
AGTATCAGTCAGGTTATGATGTCCTTCCTAATTTTTTAGCAAATGTGGTTTATTTTATTTTTTCAATTTTTATTATTAACTTTTATTAATTAT
TCCATTCATTTACCTCTCAAATGATATCCCCCTTCTTGGTTACCCCTCCCCAGCCCCATCCACCTTCTGTTTATTTTAATTAATTAATTAATTA
ATTAATTAACCAGTACAGAAAAAGTCCACTGAAAAATCCATGTCCTGGGCCCAAAATACAAATAAATCAAAAGGAGTAGAGTCCTGCTGCT
ACATTTCTTCGTGAGTAGTTATAACTTCCCTGAGATTTTTTATACCAGGGTTTGTTTCCTCCTGGTTTCTCCTCAGTGACGTCATCCTGAGGT
TAGTGGTTACTGTCACTGTCTCTATCCTCATCTTGACTCCATAATATTCTTCCTCTTTCGATCCAGACCCTCAGGGTTTAAGAGTAGCTTCAAG
CTGAGAAAAGGTCAATTTTCTCCAAAAAAGCTTCCATCTCCCACTGAAAATGCCATCTCAGAGTGAAGTACACTCATTCTGAAATGTCAGGGC
CAATTGGATGGTCATCAGAAAGCTTGGCCTGGTTGATATCTTTATCAGCACAAACCTGAAATGCACAGTCCTCAAAGGGCGGCCTCTTTGTG
CTCATCCGAAAGTGATGGAAGGAAGGCAATACAAAAGGGGCTGAACTCTGGTCACCAGAAGTCAGAAACCATGCAAACAACCAGTAATGAATAG
TGAATTCTAGAATTCAAATTAGCAGATGTTTTAAAGAGACAAGCTTTCAATTTTCATTTTAAACATGAGCAAAACCTGTGTTCTGAAAGAAAG
ATTTAGAGAAGAGAAAAAGCAAAAAGAATATCTAACATATTGCATGACCCACCACTCCCACAATGTGCTCCTGGTAAACTTGAATCACATCTTT
```

TABLE 1-continued (mouse gene: Prlr; human gene PRLR)

```
TCTCCATCCCGATAATTCTCTAACTCTCAAGGAGAGGCCTGAGTTAACTCTCTGAAATTCCATATCTTAGGCACTGGATCTTCGTGATTATCAG
GATGTGCTGTCTTTATCACTTTGAAGTGAAGACAACTGCTGTCCTGATCAATGACTTTGAATTTAACTTATTCTTTTTCCGTCTTGCTCCCTAA
AGCCTTTGGTGGACAGTTTTGTTCCTTGGTTCTTGGGCTTCCCCTTCCTAAGAGTTTTGTTTGCATGTCTATTCAGATGCTAAAATATTGTGTT
AACATCCATGGTGATTATTTTAATGTTTGTTCTTTCAGTTTGGGCAGTTTGGCATTTGGGAATTATACGTACTTTGACACTATTAAATTAGATG
AATATAGAATTGTATCCTTATGATGAATAAACCTTTTATAATTACTAAACTCATGGTTTATAAATAACAAAACTCCCTGCATCTTTTGTCTTTA
TCTGATATTAGGTGTAGCTGCATCAGCTTTCTTTTGGCTAATGTTTTGATGGTGATATCTTTTTGTATTGCTTTATTTTCAGTCTCCTACTTTC
TTTTGGATTATTTAATCCATTTACAGTTAATGTACTTACTGGATTTTAAATTTTACATCTCCCTCTCACAATTTCTTTTACTTCTATAACTTAT
ATTCTTTTATATTCTTCTTGACTTTTTAAAAATGTTAATCAATGCCAATGTTTTACTATTCTCTTTGTTCTATTTACTGTCCCGTTAATACTGT
CTACTGTGATTCTCCAAGTCATTACCCAAGGATTATATGTTCTTTCTTTGACCTGTTACAGTTTACTTTAAGTTAGTCTTTCTTTTATTTTGTA
TCCACCCTGGGAATTCCTCCTGGGGAATGATGTTATGCTAGGGTACAAGCTACCATTGAGTCACCACCCTACCCTGTTAATTATAATGAATAAT
GTAACTAACTAGCTTGCAACAGCTTAATGTCATTGCAAATATTTCTCAGCTTTCCATTATTATTATTATATACTTTCATATATATATATATATATA
TATATGTTACAAGATTGTTAAAGTTACAAGATATTGTTGTATTAAATGATCAATGAATGTTAAAATTTACCAAATATTTACTCTGGTTTTTTTT
TCTTATTTTATTTATGTGAGTAAATTGTAGCTGTGTTCAGACACACCTAAAGAGGATAGCAGATTTTATTACAGATGGCTGTGAGCCACCATGT
GATTACTGGGAATTGAACTGAGGACTTCTGGCACAGCAGTCAGTGCTGTCTTAACCACTGAGCCATCTCTCCAGCCCTACTCTGATTATTTTATT
CCTTCTGGTGTTAGTATCATCCTTCTGTGATCATGCTTTTTACTTTTTTATTTTTCATTTAGAATCATGTTTTCTGAGTTTTGGTAATGGCACT
CCACTGTGGGAATGTGAAATTTGGGTCATTGCCATCTAAAACTCAGTCACTTTGGCAGCATGGCTCAGTTGAATGGCCTCAAATCCCAGGACAC
TTATTTCATTATGTATCTGTCTCTGCTCCAACAATTGTCCAGAGATACTGACCAGTAACAAATCTCCCAAGACAAAAAGAAGAAAAAAACCAC
CCAGGCCATTATCAAATCACCTCACTTCATTGTTTTTTCCTCCAGGATCTTAACTGCTCAGATCAAATGGACCATTTAAAGAGCTAGAAATG
ATAGATAGATAGATAGATAGATAGATAGATAGATAGATAGATAGATAGATAGATAATAGGTAGATAGATGATAGGTATAGATAGATAAAAG
ATTAATATTTGATAGATAAATAGATAAAAGATAGGTAGGTAGGTAGAGAGGTAGATAGATGATAGGTAGGTAGGTAGGTAGGTAGATAGATAGA
TAGATAGATAGATAGATAGATGATAGGTAGGTAGGTAGAGAGATAGATAGATAGATGATAGGTAGGTAGATAGATAGGTAGATAGATAGATAGA
TAGATAGATAGATAGATAGAAGTAGTTGGTGGTAGCAGTGATGATAAGAAGATAAAAAGCAACTTTATGTTGCCTTAGAAGTAGAATTT
GTCTTCCCATATAAAACTATATACAACACTGAATCTATTATAAAACATCCTTGAACATTATGTCATGTGGACAGACAATACTCTGTATACACAA
AAGGCAATACATTCTTTATCATCTATTTAATGGTCAGTATTAGTAACCAAGTTTAATCACAACCTTCTAGATAATACTACTGAGATGCCAATGA
CTGCTTTCAATATATAAGCCTGAATTATGAACGCTCTATAATGCAGCCATTACTTTTTGAAATTTTTAATATTTTTATTGGATATTTTCTTTAT
TTATATTTCAAATGTTTTCCCCTTTCCAGGTCTCCCCTTTGGAAACTCCCTATCCTACCCTCCCTCCCCCTGCCTCTATGAGGGTGCTCCTCCA
CCCACCTACCCACATACCGACTCCAACCTTCCCATCCTGGTATTCCCTTACACTGGGGCATGGAAGACTCTCAGGCCCAAGAAGGGCCTCTGCC
ACATATGCGACTGGAGCAATGGGTCACTCCATGTGTACTCTTTGGTTGGTGGTCCAGTCCCAGGGAGCTCCAGGGGTTCTGGCCAGTTGACCCT
GCTGCCCCCCCACTCCACGGGGTTGCAAACCCCCCCCCCCCTCAGCTCCTTCAGTCCCTTCTCCAACTCCTCCATCTGGGACACTGCACTCA
GTCCAATTATTGACTGTGAGCATCCGCCTCTATATTTGTCAGGGTCTGGCAGAGCCTCTCAGGAGACATATCAGGCTCCTATCAGCAAGCACTT
CTTGGCTTCGGCAATAGTGACTGGGTTTGGTGGCTGCATATGGGATGGAGCCCCAGGTGGGGCAGTCTCTGGATGGCCTTTCCTTCAATCTCTG
CTCCACCCTTTGTCTCCAAATTTCCTCCGGTAATTTGTTCTCCCTTCTAAGAAGCACTGAAGCATCCACACTTTGATTTTCCTTCTTGGGCTTC
ATATGGTCTGTTCATTTTACCTTGGGTATTCCAAACTTTTGGGCTAATATCCACTTATCAATGAGTACACACTATGTGTGTTCTTTTGTGGCTG
AGTTACCTTACTCAGGATGATATTTTCAAATTCCATCAATTTGCCTGGGAATTTCATGAAGTCATTGTTTTTAATAGCTAGATAATATTCTATT
GTGTAAATGTACCATATTTTTCTGTATCCATTACTTTTATGTATCACAACTTGGATTTTAAACAGGTTTAATTTAAGGATCTTTAAAAATAAGA
TGGGGTTAAGATTGCAAGCCTATAATCACATGTATCTGGGAAGCTGAAGCTAGACAGTTGGAAGTTCAAGAATTCCTGGGATACATAATTAGCT
CAAGGTCAGCCAGAGCAACTGACTGATACCTTATCTCATATAAAAGTTAAAAAGAGGTGTGGACATGTATATCTGTGATTGAATGTTTCATAT
CCTAGGTGCACTTTCCAGTACTAAGAAAGAGAAAGAAAGAGAGAAAGAAAGAAAGAGAGAGAGAGAGGGAGGGAAGGATGGAGGGAGGAAGGAA
GGAAGGAAGGAAGGAAGGAAGGAAGGAAGGAGGAGAAGAAGAAGAAGAAGAAGAAGAAGGAGGAGGAGGAGGAGGAAGGAGGAGGAGGAGGAG
GAGGAGGAGGAGGATGATGAGGATGATGAGGATAACAACAACAACAACAAGAACAAGAAGGAGGAGGAGAAGAGGGGGAAGAGGAGGNNNNN
NNNNNNNNNNNNNNNCTTATGTCTGTACATACGAAATACTAAAGCTTTATCTAATATTTTTCTTCAAGATTACAACAAGAACATTGAACACTAA
TACAGAGAACATCTGCAGTGATGTGATTTGAGGAAAATGAACCCAAAGGCTCACTTATCCAGGCACTTTGAATCACTTTCTTAACTCTGGCCAC
TTAATGAATGTGGGGAAAAGGAAAGAAGTTGAGAAAATTTGAGATAAGACTGTTGGAAAGCAATATGTTCTATAGTTATTGTCATGAATTATTT
TCCCCAAGAGTTTCTTTTATGGATATTGTCCTCCATATAACCCAGGCTCATCACACAGGGCAGTTTATCCAAAGCAGAGCTAACTGTGGTTGGAA
ATTTTGCAAATATTGTAAAGTCTTGAGAAGCCTAAAACACATACAGAACAATGTGGAATTAACTTCTGTGAGGCAGGACCATAAAGCCTTGAAC
AACAATTCATATTTATTTAGAGAAACTAGGCTAAAGCAAAGCAAACAAACAAAAGAATTCACTGAGGGAAGTCCAAAGCGTATTTTGTTCCACC
TCCTACCTCAGCCTTGGTAAACAGAGCTCTAAATTTCTATTTACAATGATTACATAAATATTATATGGTGACATTTCTGACTGTGAACCACCAT
ACACTCAAGTATGTAAAGAAAGTGTACACACAGGAATCAATGTGTTCCAAGAAGATGCTTGAATAATTGTCTAACAAAATTTATCCCAGGAGAC
AGACTATGCCAAGTTATAGTACGAAAGTTATAGTATCTGCATTGTACAATAGCACAGGAGAGCAATGTTACTACACCCCAAGTTTTTCTTTT
ATGGTAATAATAATTTGTTCTTTAACATTTAAATCATTTATGAGTTGTAGATTCAAAGCATACATTGTGATTTCTCTTCTGTGTTCATTACAGG
ACAACACTGTCCTATTTTTGTCTCCTCTGTTGTTATTATGTTTACATAAAAATCTTTCAAGACAAAATAGTTATGTTCTACATACTCTCTTGCC
CTTAGCTTCCGTAACTTTTGCCATAAGAATTAGTCTTTTCTGCCCACACTGTATTCTTACCAACATGTGACTTTGAGTACCATAACTGAACTTG
AGGCATACTATATTTTCAAAGGGCATTATACATTTTTCAGCACAGGGTATTAGCCCATTGGGATACAGTGAAAAAAAGTCTTTAAAAACTTGC
TACAGGTTTGAGTTGCAATGTATGCTTTGAACTACAACTCATAAAGAATCTAAATGCTAAAGAACAAATTATTATTACCATAAAAGAAAAACT
TTTGGGGTGAAGTAATGTTGCTCTCTCCTGTGCTATTGTATAATGCAGAGAACTTGTAAGAAAGTGAGCCACTTGGTAGTTCAAGAAGGATGTT
AGAGAGAATCTTAATTATATAGCTATGTGAGTCCAGAAGTGTGTAATTAGTATATTATTCCATATGTGCTCTTGAGCTTTTAATTTCAAGAACT
GTATGTTGGAATGATTTTGCCAGAGCAAGTTAATGACTGAAGGAAGGAAGGAAGGAAGGAAGGAAGGAGGGAAGGAAGGAAGGAAGAAGGAAGGAA
GGAAGGAAGGGAAGAAAGGAAGATGTGACTTACTAGAAGTTGATAGTAGAATTCTCACTGGACTCTAAGAGTTTAAATTTATTACAGGTTCTT
CCTCCTAGCCTCATGCTCTTAGAAATAAGACTCAGATTCAAAATATATTTTCATATACTTTGGCCATGTGGCTAGGCTCTTCTCTGACTAAAAT
CATAACTTAAAACCAACCCATTGATTTTCATCTACATACTGCACACATACCACATGTTACTTGTGCTATGTGCCTGTCTCCTCCACATCTTCCTGG
GTGGAACTCTTGTCTGGCTCTATCCCAGAATTCTTTCTCCTCCCAGATGTCCCACCTCCCATTTCCTGCCTAAGCCATAGGCCATAAGCCTTTT
AATTGACAGGTGATGCACCCATACAGTACACAAGATAGTCTCTACAGCCTAAGTTTTGACATTGTTTCCTAATGTAGAAATTATTAGGAGCTA
ATTTCTGAAAAGTTTTAAAAAGTTATGTAGACTGTCCATTAACTAACGTTTCAGAAAATTGTACACAGAGAACTCTTATTTCCTTTTGCCTAGT
AAATTACCTCTCTACATAAGAGCGTTAAACCAGATATGTATGTCATTGATAATCATATATTTTTTCCGCTCTTTACATCCATCATTCCATTAGAAA
ACTTTATGGCTTTTTGGCTCCATTTTCACCGTCTTACTGCCTCTAATCCTAATACCTTTTTGAATGGAGAACTGTTAGATCTTTACAGGCAGTT
CAAATATCCAGAAATGAGACCAAAGTGGACTATAGGATGATTTCCAGAAGTTAGATAGAAACCAGGATTCCTTAGAAATTTGTAAAGCCAGTTC
CTATTTACCAAAAGGATTCACTTCTCTTGTCCCTGGCACAACGGACATAGAGCTCCACCGACATGTGCCTGTGGTTGCATTTCAAAGCCCATGC
CATCCTCCAGGCTCCTTCAGCCCCTACTGAAATATACTTGTTACACATTTCAAAGGCTATGCCAACCTCCCCAGACATCCATCCTCCTTATACC
TATTTGTTCTCTTTTTCAACATGAATGATTTTCCCCTTACCCTGGCTATTTTCCCTATACTTTCCCTCTATCTCCTGCTCTCCTCTTTACTCTCT
CACTCTATGGGCTATTCTACATTCTCATAGATGCACTGGCCATGTCCAGTCTGCTTTGATTCTCTCTACTCTCTGATTCACAATAAAAC
CTTCTCCTCACCTGTACCATGGAGAGGACATTTCAATTGTTTCCTTACTGTTTCCCTTGCAAAAGGAAGATCACCCCAAATTTGGTGCCAATT
CTTCTACTAGTAAGCAATCCATAAATATTCAATTAGTGCATATATAGACAAATGGACTTCTCCTCCAAATTAATAAAACTTAAAATATAACAAG
TTAAGAAGGCATGTAACATGAGGAGCTGTAAAGAATTCAGATAGCCTTCTTTGGTATTTTAATGGAAATCTGTGACTCAATTTACATGTGGAAG
TTCTAGTACACACATGCTTCATTTAGTTAAATACGTATACAGGTGGAAGTTACTATATCTCTTGCCCTTTGCCTTGCAAATTCCACTCAATCAA
TGCCAAGAACTGAACTAAGAAGACATGTTCACCTCTCTTTCCCTTCACGTTCAATGTGACTCAGTTGTGACCCTGAAAGGACAGTACATTCCAT
CTGTCTCACACCTGCCTGGTGTCTGGGATCCATCTCTGGGATTGACAGCATCTGTGTCCTCTGATTTCTACTCTTTAGAAAAAAAAATCAATG
CCCACATCATATTGGTAACCTTTCAAAAAGCTCAAGAAGAGTGACAAGAAAGCAAAATTGCTCCCAGGGAGCTTCAATTGCTGGTGAAAGGCTG
```

TABLE 1-continued (mouse gene: Prlr; human gene PRLR)

```
ATCCAATAAGACCTCCTGGCAGAAAGCACAGACATTCCAGGTCATTCCAAATGCCTGTGACAATATGTCAGTACACTGTCTGACTGCGTGTGTA
GTAGTGACTCTTAACATGGTTATTTACTAACCACGTGTTGCCATGGAAACAAGGTAAAGCAACATGCTCTTGAGACACAGAGACTTAGCATGTT
AGAGAGGTGGTGCCTAAATCCCATTCTACAGCCAGTAGGCTGTTCACACAGGCAGACCACACCCCTCTAGGCCTCCTATTCTTCCTTGGGACAT
GAGAACCCTGTAGCCACTCATCCTCAAGCATGGTATCCGCTCTCCTCTTGTATTTGAGAAGCATAACATTCTGAGGCTAAAGGGCGGAGCCAG
CCATCTTCTTGACCGGTTGGGCTTACAATTATGTACTTGACAATCTCCAACATGTTTGAATCAGAGAGGAATACAGTAAAATTCATTCATATGA
TGCTCTGGTACTCCTGCTTATTGAAATAGAAAAAACAGACATACATACTTAGACTCTCAACGTTTGCAGGAAAAGAAGTTGAAAATATGTTCAA
GAGTTCAGATGGCTTCTTTGATTCGTGGTAAGTTTGAGTTCTATGGATTTGGGTTACTCGAACTCTGATTGGTCTCTGGAGTACATGTAGACGT
TAAGATGCTATATGCTCTGAGAGAACAGTGAGCTGAGAGGGAAGCCTATAAAGTAGTGACACTCAGATATAGAAACATTTTCATATGATAGTAG
TAATGGTGCCAGCACTTCTTCCACCAATGTCACTGACAAGCTTCTTGTTACTGGAAGGAGAAAAAGTCATCAGACCTTATGAAAAAAGGTGCT
AGGAATACATGCGCAGGGATTTTCTTATGTGCAAGATTCACTGAGCTCTTTCTTATGACCATATAACCCATCTACATAAAAATATTATTAGGTG
CTAAATCCACAGCAACTCAAGCTTTGGAGCCTTGGAAATTGGCTTTAGGAAAAGAGATCACCTGGCAAGCTCCATGTCTCCCTTTCTCACAGG
ATTTTTGGAATAGGATTAGGGTCAACAGTGATTTTAAGTCTCACAAAGAAAACAAAAATCGATTTCTTGCAAAACTATCGCTGTGCAAGTTTG
GTTTTCCAGCATAGATCCGGGCTGCCAAGAATGCTGGCTCCAGCTAGGTCTTCATTAGCCAAGTCAGGGGATAGTCAGGGCATTCATCCAGGTG
ACCTGAGCCAACCCCACCCACTCAGAAAACCAAGACAAGTTTGCCTGGTAGAGCAAGGGCCTCACTGGCTGCAGGCTGTGACTCCATGTGTCG
TGACTGACACCACAACCAGGTATGTCATGAGAAAACTTTGACAAGCTGGATGGCAGCTCGTCGTTCCTTGGATTTCTTCCTTAACTTTGCTTT
CTGTGGCTAACAACTGCCATTGAATATAAGGTTATGTAGGAAGAATTTTAAGTATGCCTTAAGAAGTTAGGATTGTGTCCTTTTGTAAAAATGA
TAACCCTACAGAGGTCCCTTTCATAGCATTAACCTGTGGTCGTGTAAATGGGTACTCAGCCTTAGAGCCCATCTCTTTAGAAAGCAAATCATTA
TGCAATCAGACAACTTTAAAGTTGGAATGAAGTTACCACTATCTCAATTAGGAGTAAGGGGAAGGTATAGTCTGTAGGAGTTATGCGACTTTTG
AGGGTAACACAGGTAGCTGGGCATGCAACCAAGCATACAATACTGGCTGCGCTCTCATTCAACGTATCAAGAGTCTTCTCTGATATGTGACACA
AGCAAATAGAAAACTCATAGCCTCCAAAGAAAGATCTTAGATTCATCAGGTATGTTTGTATGCATATGTGTGCATGTGTGTGTGTGTGGAGA
GAGAGAGAGAGAGAGAGAGAGAGACAGAGAGACAGAGAGACAGAGAGACAGAGAGACAAAGACATTGAGGCAGAAAGAGAGAGATAGATGAAGC
AGAAAGAGAGATAGAGATATAGAGACACAGAAACAGAGAGACAGAGAGACACAGAGACAAAGGAAATAGTAATACCTTGGGTTTCTGGCTATAT
AGTCTCTCTCTCAATTTCTTGTCATTGTAGCCTGAAAACATCTAAAAATCACAGGAACAGGGATGACTGTGCCTCAGCAAAACTGTTAATAA
ATATAAAAATGTGAATTTACAGCAGTTTCATGTGCTATGAAAATTTATTATGTTTTGAGGGGTTCTTTTCTACAACATAAAACCCATTCTTGGC
TCTTAGTGGACCGGATTTTGCCTAGGACAATAGTTTATCTGGCATAGGGTAATAGAACCAGCCCAGGAGAGAATGAGCTGTGGACTCTGTCCTT
CACTCGGGCTCTCTGACCTTGTAGCTGACTCCACAAGCCCCCTTTTCCTTTTCAAGGGTTCTGTCACCCTACACTGTGAAATTAGTCACTGTGT
GTCTCTTCCCAAAACATTCCTTATTTCTTAAAGTCAGTATAATTACAAGGCTTGTTTAGAGCACGGTCATAAACGTCATAGTGAGGACTGGAGC
AAATGTTGCTTTGAACATAACTCTGTGACTTCAACTAGGTGGCTATGGTAAAAAAGGAAGTACTTCCGTTTGCCCATAAACAACTGTCTTAAGG
AATTTGCTACATTCCTTGAGTCAGCTGGATCTCTGGACAGGCCTGGTTGTTTAGCTTACTAACAGCCAATCTTTCTTTCCGACTGGCCCTGAGT
ATGTGTGTCAGTAGGACAGAAGGCCCTCTGGGTGAGAGCAAGCAAATGAAGACCACTGTTTTAACTCAGATACAGGCGGTGGGGGTAAGTCTCA
GCCAAGACAGAAACGCTTTTCCCTCAGCTGTGGTGTGAGTGTTTCCTTTGCAAACTTTGTTGAAATGTTATTGATGTTGTGATAGTGTTGGTAG
ATTTAGTGTCTAACTGGTGGTGAACTGGGTCATGAGGTCTCTTGCCTTATGATTGTCTGCAGTGTGGAGAATGGGTAAGTTAGCATGGGAGGAG
TTCGCCAAGAAAGGGAAGGCTCTCTCTACATCCTTTCTCTGGCCCCTACCCTCTCTGTGTCACATAGGTTTACCTTCCTTTCTACACCAGATGA
CACAAAGTTTGAAAAACTTCAGAACCATTAGACAAGTAAAAACTTTCCCAGTCTCCCCCAGGTTTCTATAATAGTTGATAAAATTGGCTATGAC
TTGTTTTGTTTATGTTGGTGTTGTGTTTGGCATATGTTTTGGTTCTTTGACCCTCAGACCCAAAGAGAGAGGTGGTTTTCTCAAGGCCAGGATA
AAGGCACAAAAGACTTTGGCTCAGAGCCACCACAGAAGAACTGTGAGAGAGTCCCAGGAACCCATAATCCAGGCGTCTTCCATATATGAAGTCTCC
AAAATCAACTAATATTGCTTACACTAATATTGATACCATTCAACATGACAACTTCTTAAAATCACTGACAGTGATGCAGTGTGGGGCCTATTAA
ATATAGTTATCAAAACTTTGAGTTGCAAGTGGCAGAAACCAAATGCAAGATGAGACATATAAGGAAACGGCCACATCAGCTTTAACTTTGGAAC
CAGCCATAAGCATGCCACTGCTTACGCATCTCTTCCCTCTCTGCTTTCTTTGCGTTGCACATCATGCATCATGTGGAGAGACACAAGCTCTA
GCCTTCTGAGGCGCTTAGAATCCTGATAGCTCACAGTCTCAAAAAGGAAGAGATTTTATCTCCACATCTATCTCAGTAGACAAGATTTTCTGTC
CTTGTTTCAGACATTGCTCACTGTCAGACCCACCAATGGAATGGAAAAGACCCTTTTTGGGGTGGATTTTTAGATTCCCAGTGATCAGCATGGA
GCAAACAATGGGAAGTTGTGTGTGAAGGAAGGGGGGGGTAGATGCAAGGCTAAAAGCAGTGCCTGCACCAACTGATTCCTGTATCTAATAAAA
ATGTGGCTTTTAAAAACAGTAAGCATCGTAGAACCCACCCCATGAGTGTTGGATGATTCTGGATAATTCTTTCCTCTCTCATTCCTGAGCCGT
CAGTCTTCCCTGGTGAAGACCTGAAATAGTACAAAAGACGATGAATGGGTTGATACTATTGTGAGAGTTTGGTATAAAACTCAGCTCTCTTTTT
GCTCGCTACACTCTTTGATTTCTACCTTTTGTTTCTACCAAGAATGATATACCAAGGAGACATTTACTAGCTGTGAATTCCTGGACTGTGGAGT
TCACAGCACCCAAAGCTGTAGGAAAAAAAAATGTATTCTTTAGAAACTACCTAGTCCTAAGTATTCTGTAAAGAGAGCACTAAGCAGGCTGCAG
TGGCTGTGGCTCCTGCAGAGTCTTACTTCCACACAGTGACAGGGGTATGTGCATTCATCGTCCCCTGCTCTTAGAAGTTGGAATGCAAATCCCT
TGAAGCCAGGGCCAGAGTCACTGTTCCACAGGGGACTGCCTTCCCTCACAATACAGGACCATCACTTTTAGCACAACCCACAGGTCTTCTGAAT
ACTCAAAAGCATGAAGCTAACAGACAGAGCCTTATATGGTGCTAAGGACAGAGTCAAGTACAGTGTTAGTAGACACCTATAATCCCAACACAG
ACACCTGAGGCTTTTCCTTTAGAAGAGATGGGAAGCCAGGGGTGTGGAAAATTAAGGTTTTGTTCCTGCTCCCTTCTCCACTCCTCCTCCTCCC
TCTTCTTTTGGTGTTTTTGCTGGATACTGTGTTCCATGATGCAGTTTAAACTACCCCTAAATTCAAAATCCTCTTGCTTCAGCCTTCAAAGTAC
TAGGGCTATTGTCATATACTGCCATTCGCCAGCCTGTCAGTTCAGCTGTTTGACTTTTAACTGGCACATACCATTATATGTATTCATTGAGTAC
ACATGTTATTTGGAAAGGTATAGACTATAGAATAACTGGCTCTACAGTGTATTGCCTCAGTTCTGTGGTAAGAATGTCTTATATTAATTGCCAC
TGTGGTTATACCATGAACATATTCCCCTCTTACAACTGAAATCTTGTTCCCTGTAATCAACATTTTCCTACCAACCCCATAGCCTGGCCTGCAC
ACTCTTAGTCCTCTTGCTCTATACGAGTAGTAGTTTTAGGTTCTACATAGAAATGAGGTCATGTATTTGTCTTCCAGTGTCTGGCTTATTTCAC
ATAACACTCTGGAGTCATTCTTGTTATCCAAGTCTTTCTGTAACTGAAAAGTATCTCACTGGGCCTGTGTACCACAATTTTTATTAGCCATGCAG
CCATGATGAATAATCAAGCTACATTTTTGATACAGCAAATATTATTGCAACCAACATGGATATCTCTTTGCCATATTGACTTATTATTTTT
TTATACACAACTAGTAGTGAGATAGCTGGGTGATGTGATGTGTCTACTTTTAGGTGTCTGAGGAAACTCCATAGTGTTTTTCCTAGTGGTTGTA
CTAATTTACATTTCTACCAGCAATGTGCAAGAGTCCCTTTTCTCTTGTATCCTTGGCAACACTTATAAATTTATCTTTTCAGAGTAGTGGTTC
TAGCAATGAGGTTGTATCTCATTGGCATTTTGACTTCCAGTTTCTCAATAAACATGATGTTAACATTTTAAATGCACATAATAGGCACGATTG
TTTTTTTCTTTTGAGAAATGGGCATTCTATTATTTTATCCATTTTGAGCCATACCCTTGTTATTAGATTGCTTTGTTCTGTATGTATTTTGAGCA
TTAAGCCCTCCTCTGATGTATAATTAGTAATTAGAATTCCTTCTATCCTTTCATTGTTCACTGGCACATTTTGAAGAGATGTGCTGTGACCTAG
TGCTGGCTTTGAAAGCATCACCCTGCCTGTTCTATTGGAGACATACAGTCTTCAGAGGCACACAGAGAGACAGGAGAGCAATGAGGAGCTTGGT
GTGATCTCCAGGGTAAAGACCTCATTTTAGGCCAGGTTGGTGCTCTAGATAAAGGTAAGAGGAAGCTGCATTCGCTCATCTATTTAAAGACAG
AGGAAGCAGGTTTCGCCAGTTTGAACTGCCAAGTGTATGGAAAGAGATGAGAAAGTCAAGGATGACCATCAAGGCTTTTTGTTCTGAGAAACT
GGAGTAAAAATAAACATTTGTAGTTTACTTTGTTCTTGACTCACATGAAAGGGAAGTATATTTCTGTGACAGTTAAAATAAGTACATGGGTACT
TTGAAGTATGGTTTTAAAACTGTCTTAAACTAAAGCCATGAACTTTTATTGTTCTGCCTATGCAAGCAATGTAAAAAAAATGCATGCATATGTA
TTTTTCAGAATACTAAGATATAATATATAATAATACACACACACATATATAGACTGTTTGCAAAACAATGAATTCTTTTC
TGTATCATTTTTATAAATGATTATGTGTCCAGGAATCAGAGTAAAGTTTTGGAGATGCATGTAGCAAGGGTTTCCTTATTAATTTCATAATTTA
ACACATTGAGCTAATTGGTTTGCTCACAAGGGCCATAGCTGTTAGTCACTGTACCTTTATTCAAGAGGAGAGCAGCTAAAGCTGGATGGTGCAG
TAAGATGAACCTTGGTCCTGCAGTCTGTGCATGGAACTGACCCCTCTCAGCATCAGACTCTCCAGCCATTCCTTTCATTACTTTGGACCTCGGT
CCCACATCTTATAAGTGAAGGTAACAGAAGCCAGTGTCACACAGTGCAACAGATGCAAGACGTCTGCACTCCAGGTGTCCCCGATTACTAATGC
CTGGGAGCAGTTTAGTTAAACAAATATTTGGTTCCAGCTGTATTCTAATTTATGTACTTGTTCATGTTCTTCTTTGCTATAAATGATTGCTGAC
CTTATTAACTATGGCCCTTGTGAGTGAAGATTGAAACCAATGAGCTTAATGTGTTAAAACTGTGAAATTAATAAGGAACTTTTGTTACATGTGT
CTCCAAAAAGCTTTATTCTGTTTCCTGGGCACACAACGATCTGAGCATCAGAAATGAGCAGAATAAAGCTAGACACTGTAAATCTATCATTGCT
CCTGAGAAAACTTAATTAAAAATATACTCCAATGTCTTTTTCATATTTGAAAGGTACAACCTCAGATTATTAATTTATTATGGTATTTTACTTT
GAGACAGGATCTTATGTAGCCCAGGTTGGCCTGGAACTCATTATGTAGCCAAGAGTGATCCTGATTCACCTACCACCAACTCACACTTGCTAGG
```

TABLE 1-continued (mouse gene: Prlr; human gene PRLR)

```
ATTATAGGCATATGTCTCCATGATCCATAGCAGATCCTTTAAAATAATGGCAATGAATAAATAAGTATATAAGCAGTGAAGAAACAGGATGACA
GTGTGAGACTAGATAACCAGATAACCCTAAACTCTAGACACTGGTATGTCTGTGTACCCTAAATTATTTAGGCTTGTGGTGCAAGACGTCAGAA
TCCTTCTTTCCTCAGATGAGAACATTGATGTCTTCATGTCTAACGTGTCTGTTTGCATTCAATGAGATTATGAATATCTCCCTGGGAACTGTTG
GCTCTATTAGTAGGGAATATATATTCACATGTTTTATTTTAAACATTGCTGTTCAGTTTTGGAAGACTGTAGCTATTTGAAGCTATCCATGCAC
TCTATTAGAAGTGGGAATTTATTTTTAATTATCAATTAAGAAGTCATCCATTGTATGTGACTGGCTTTGAACAAAAATAATAATAATTAAAGC
ACACACACACTGTGTAGACAGACATTGTTACAATGCCAGTAAAGGGAACAACCACAGCACATATGGCATGAATGTTGCTTGAGACCTGAGTATA
ATCCTTAGGTCTTGAGCAGAATGAGACAGCTGACTTCCTGTAGCCGGAAGAAGAATGAGTGCTTGCTGTGTACAATGCTCAGGAAGGGCTGACA
GAGACACAGGCGAGCAGCGGAGGTGGGGAAGACAATTACAAAGGAAGCAACGAAATCTGAACAAATCAGAGACTCTCTAGAAGATAACCCAGGT
CTCTGTACGAATAATCAGTCTGTCAACCACTTCCTCTACCTGCTCTCTCTATATATTTTTATTAGATATTTTCTTTATTTATATTTCAAATGCT
ACCCCAAAAAATTCCCTATACCCTCCCCCCCCCCCTGCCCTGCTCCCCTACCCACCCACTCCCACTTCTTGGCCCTGGCATTCCCCTGTACTGAG
GCATATAAAGTTTGCAAGACCAAGGGGCCTCTCTTCCGAGTGATGGCCGACTAGGCCATCTTCTGCTACATATGCAGCTAGAGACAGGAGCTCT
TGAATTGGAGGACTCTCTGCTAATTGTCTTGTCTATACCTGATAGCCACCCTTCACTAAGCACTCTCTGAAAGTCAGACTTTATATACACAATC
TTCTCCTCTCACCTTTAGTACTATGTCGTTATCTCCATATTCAAATGAAGGAAACTAAAGCCAAACATTTTTCCTAAAAGACAAACAGCAAGTT
TATGGAAGACGTGTAACCTAAGGCTGGGATTTTCCAGGAGCAGCTCCCATGCCTTCTTCAGGACCCTGGCTTGCCTCCATTAGCAAATGTACAC
ATCACGTGAGCATGTAGACCCCAACTGGCTTCTCCACTGTGTGCCCCGCTACCTTAGGAGTGAGAAAGTAATGATACTTGCAAACAAAGCATCC
ACGTGTTACATTATCTCCCACACACACTACAAACCACACACACTACAAATACTTAAAACCAGCCCTCAGGCTTAATTAACAAGAAGTAAACTAT
ACAATTTTCCAAATGATATCTGGACTCATGTACAGTGAGCTCATATATTCATTTATTCCCAGAGCTGTATAACTTCAAAATTAAACTAATTAAT
TCCTTGTATTGTCAAGCAAAACATTGACAATTTTTTCCTGTGACCGCCTGTTCCTAGCATGCTTTGTTCTTAAATGTGTAATGATATAAAGTCTT
AGGTGATTGTTTTTGAGTTGCGTTGACTTTCATGCTAATTATCTGAGTGATGGACAATGTGTTCCATCTCCTAACTCACATGGCCTAATAGACG
TGTCAATCTAACACAGTCATGGCATGAGTGCCAGCTGTTTTTGAAACATCGATCTGTCATCTCACAAGATGAGCCTCCCAATTTTCCTTAGTGT
ACTTAGTCATGTGTAACTAGGTCTTAAAGTACCCTAAGTTTCCTTGAGGCACAGACACATGCAATTATTTTCATCGTAAGTCTTGCCTGGATGA
AATAATTGAACATGAAAAGTTGCTGCACCCCAGTGAATCCAGTTTATAAAAGCGTGTGTGATGAATGAGATAGGGCAGATTCGAGTGATCGTTA
TGGAGAAAAGGCCATTCAGATTAAGCAAACTGACTCCTTCAGTGTGTGGGTGCCACAGAAGGCATTCATACCAGAAGGCTGGAAATAGTAATTT
TTCCACCTTCCCTTGATGTTTATGATTTGTGCATTTCTCCAAAACATCTTCCTATTAGGATGAACTCAGTCACAGGATGATAGCAAACTGCGTG
CACCAATGTGTCCATGTCTCTGGCTACTTTATAACAAACCACCCTGGACTTCATGGTGCAAAGCAATGATCATTTTATTATACTCATGAATTAT
GTAGGTCAGGAAATCAGACACAGCCCAGCAGTGACTCCTCTGTCTGTTGTGTAATGTCTAGGGTCTCAGCTGTGAACAGTCAAAGACTTGGGAA
CTCGAATCACTCTTAGTGTCTGTCGAGGATGATGTCAAGAAGCTGGGCTTCTTGGCAAAGGCTTTTTTGAACGTATGCTTTTCTGCAGGGCTCGC
CTCTGAGGCCTCTGAACTCTGAAGAGGACCTGCAAGATCACGTGGATCTTAGAGCAGATGCACCTGAAGCATCGTGCACGTGCACATAAGCG
GGCCTTCTCTAGTCTAATTTTGGCATCCTTGCAGCAATGGTTCACCTGGATCAGGGAAGCACTTGACTTACTTCTTAATGGGTGAAGAACAAGA
ACATGTTACTAGAAGTTTATTCAAATTGACTGGCCGTGATTACTGGTCAGCAACAGCTGCTGTGGAACTGTTGCAGGGGCAAAGGCAGTGTTTA
GGGTCACATAGTAATTTAAATATCACCTCTCAGGTAGGACCTACATCACTTCTGCCTGCATTTTAAGGCTTGTGGAGCCACGCCTAGATTCATC
ACGCAAGGGTGGTGTCAACTGTGTACTCAGAAGGAAAAGAGAACTACCAATATTGATGAATGGTGATGGTTATGACCACTTAAAAATACTGCCT
CCATGATGAAATGTGGATGTTTCTTTCAAAGCTAGTTTTTGTAATTAATTTGAATCAGTTCATACGTGCTTCTGCCATCCACCAAATATGCTTG
ATGGGCAATGCACGTAACATAAGATGCTGGATCCGGGTGTGTATACAGCCCCCATGAAAGGCAGGAAATCACTTGAAATTTCGGTGTATGGCCT
TTTCAATTATTTCTGTCTTTATCTCCCGCAGTCATTTACTATAGTTTGCACACCCTACTGTTAGTCAAAACCCTGATGTCATAGTCATCACATC
GGTACCCTTTTGTAATCTGTGATATTGTATAGAGTGTGTAGCTATAATTAATATGGAATTGCAGGTAGATACTATTAATTGAAGTGTCCCGATT
AATTTAATTATTTCTTAAATCATTTCAAACAACAGTTATCTTACATCAAACTCTGATAGATAGAATGGTTCGTTCTTACTTTCATTTAAAATGT
ATATAGATATTTAAAGTACAAGTAGTGGATAAATCCAGGTATAAAGCAGCTTATTTTTCGAAAGCAGAGCCTGTGGCTATACTTCAACAATAAA
AAGAGCTAAAACCAGTGTGAGACCTGCTGGGGACCAGTTTATATTTTGTCTATAATGAGAAAATCATAGTAACAAATTGTCAAACAATCCTGA
TGCCCTATGAGAAACAATGGAGAAAAGGCAAGCTCTGGGACAGGCTCAGAGGTGACAGGGTGGATTTAATTTACTTGTAGTTTGACATCAGGGA
TGCATCTGTGCATCTGTACATGTAACAACTTTAAATGCCCACCCTTCCTTTCCACCTTGCTACATCTGGTACTGTAGAACACTGCATACTAGCT
GGCCTGGGGACTCTGAGGATTCCCCTGTCTCTGTATCCCATCTTGCTGTAGTAATGCTAGGATTACAGACTAGGAATGTAATCGTGTGTGTTTT
TATGTTTGGCTTCTCATGGGTCCTAGGATCCATTCTTCAGAGTTGTAAAGCAAGGGCTTTGAACATTGAGCCATCTCCCAGCCTTGGGGAAATG
TCTTCACAGGTAGCTCTGGCTATGTAGAAAATTGCTGGCAAGCTTAGTTAATACAGGCACTAAATTGTGCTGCAGAATGCTCCAGTGAAACTCT
CTATGGATAACTTGGTAAAAGATCAAGGCACTTCAGTTAAACAATTTACCTAATTACCTATTTAAAGGCATCTAAAAAGAGATAGAACCAAATG
AACCCATTGGAAGCATAGACTAGAAATGCAGTAATATCATGAACATGTGTTTAAATAAATGTGTACATGGCAAAAGCCATACAGCAGCATGGCT
AAGCTTCTTCATCAACATGTATTCAAAATTATGAGAAAACCTATCTCAAAAGTTACATGAGACAACTACTTGTCCAGTTTTCTGTCCTGGCACA
TCTATGTTGAATAAAACCTGTCAGTATAGGCTTATGATCAGATCGTAAATTTGCTAAAACAGGTACCTCTTCCCTAGGTCTGTCAAACATGGT
CAATCAGTTACAGCTTAGGGCTTAAATCTCATCTAAGGCTGAGTCAGAAGAAGTTAACATAGGTTCTATCAAAACCACACACAATGCTGGAGAT
AAACATTGTAACAATGACTTTGCCTACTATGATAATGAAATGTCAGGTCTTTTGAGGTCTCAGTCAGATGTAAAACAGACTAGATACTGATTGT
GCTAACAGAAATTTACTGAGGAACTCAGCATTTGTCTCTCAGGAATCTTAGCTACATTGTGGCAGACAATGATTATCAGGTTCATTTACTTAGT
GCTTTGCGGTCCAAAGCACACACCTCTCATAGCCCAATGCTATATTTCTTGTACCCTCCCAATGGTTGAAGGCTGTCATGGTCACTGTTCTAT
AGTAGTGAAGACAATGTGACCAAGGCAACTATTATATGAAAGAAATCATTTAATTGGGAGCTTGCATACAGCTTTATAAGTTTAATCCATGA
TTATCATGGTGGGAAGCATGGCAGCAGGCATAGCAGGCATGGTACTGAAGAAGAAGTTAAGAATAAGTGGGCCTAGCATGGACTTTTGAAACCT
CAAAGCCTCCCTCAAGTGACATACTTCCTTCAACAAGGCCATATCTTCTAATCCTTGAAGTCTTTTCAAAGAGTTCCACTCTGTGTTGACTAAG
CATTCAAGTATACGAGCCAATGGAAGCCATTCCTATTCAAACCACCACAAAGGCTAATCCTCTCTCAAAAACAAAAAAGATTATGTATATGT
ACATTTTCATAAATATGTCTTACATATTTAAAACTCTGCATGTAGATATAATTCTAAGACTTCCTAAACATGCAGAGGGTCTATAATACACTTT
GGCTAGCTTGTGTTCAAATGACATTTTGTTGTTGTTTAAAGCTAGGAATTGCCTTCTTGGAAATATCAAATCCCTACAGAACTATTAATGA
AAAATAACTATCTCTTTTAAAGTAATTTTTTTAAAAAAAAAAGCTTCTCTTAGAAAAGAAAGGGAACTTTTTCTGGGGTGCATCTGTAAAATTT
TCTTCAGTCCTCAAAACAGTCCTTTACCAATGAAAACTCCACAGCAGCAAAAGATAAGGTTGAGCTCACAGGACTGGTCAACCATAGGGATTCTA
TCACAACTCTGTGCTGCCTGCATCAAAGCCCCAAGACCCTCCAGCCTCTSSSSTCAGCCTCAGTTCTTTGCGCGCGCCCGACTGGCAGCAGTAA
CGACGCTGTAACAGGATCCTTCTGCACACGTTTATTGGGAGAGCTTGATTGCAGAGGCGAAGAGACCCTGAGCCCAGAACTGGTGCTGCTTTTA
TAGGCCTAGGAGAGGCGTGTCTCATACCCGGATTGGTTATGCACTACGCCTCATTTGCATGTTCCTCATCTGATTGGCTACTCTCTCTCTCT
CTCTCTCTCTCTCTCTCTGTACCTCACAGAGCCTCATTATCATCCCATCATTTGCATGTCTCACATCTGATTGGTTATACTCTCAAAGCCT
CATTATTATGCCCAGGCCAGGCAGTGTCTTTGCAAAAAACTTTACTGCATATGACATTGGTTGTTTGTCCAAACTTATGCGTGGTGGCCAG
CAGTAGTCAGTGCCACTCTGCAACGGCACATGNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNATATGTTT
GCGTGCAGCTTCTACCTCATTTAAAACTTGCTAAGACCACATGTATCTGATCTACATATATTCCCTGTTATATCACAGATGCTAGGTGTGATAT
AGCACACAGTTGATACCATCCCTTCTCAATAGTTACTGCTAGCCAATTCCCATTGAATGCCTATGGCAATTGACTATTTTGTTAATAGAGTTGG
ACTCTGTCAATCAGTTGAAAAAGTCACTTCGTAACTTTTCCACTATGCTAAAGGTCATGGCAAAGTTGTACCAGGACTTATGAAGGTTCTTTGT
TAGTCTGTTCACAGTAGCAGCACTAGAGAAATCTTATGCAGTTGTTATGAACAGTTGTACTTAAAAATCAAAGAAAAACTAGATTAATTTGAG
GAAGTCTCTCTTCACCAACAGAGTTTAAATGCCCTCCACATTAAGTGGATGTTTTTAAGTTTTCCATGCAAGAATTCAAGTTTCTAACTCTCAC
```

TABLE 1-continued (mouse gene: Prlr; human gene PRLR)

```
TGGACAAGCTGTCTTATTCCCAACTCTTCCTTAGGATCTTCTTTTTGATTATATTACCATAAATGTTTATTCAACATGTGTGATACTCATGACT
ACTTACCATTGAGAGAGTAAGTGGCAGCCTAGCCAGTCCAGGGCAGCCATGTTTCCTTACACTGATGAGCGATGCCCTTAATCACCTAAATTCC
AAAACTATTACACTTCCCATGCAGCATTGAGCATCAAACCATTCCTTATAATAACCTCAGAGGTCTGGGCCCTTTAGCTCCCTCAGTGACAA
AGCAATGACACTAAGCACTGTACAGGACCGATCTGGCTTTCAAACTAAAAACAACTATAGACAGTAGAAACAATGGCCATCATCACTTTTCTTT
CCTCTTAGGTGAAGGAACCAGAGGCTGATAAAACTTAAACCCCTACAATAGAAATTAAATAAAACAAATTTAGTGAGTCACTATGGCCCAGGAA
AGGCAATAAGTGGTTAAAAGGTAAACTGCTGTCACGATGCTTTCATTACACAGAGATTTTAGGGACATGACATGAATTTTGGCACAGAAAATCG
TGTGTAAATATCACGTGGGCTATGGTGAAAGGCTTAACTATTTATTTTCCTACCTCAGTATTAATTACCTGAGTCACATATATAAGAATGGGTG
AATAAATAGATAGATAGATAGATAGATAGATAGATAGATAGATAGATGAGTTCTTTTTTGTATAGTTTATAAAGAAGTTCCTAACT
AAAAACAAGTTCCAAAGTACTGTGCTCTTTTATGGACTTTCAATCAGTCTGTAAAGCTTTTGTAGGGCCTATCATGAGCCAGGCTCGGGCAGT
TAGGAAAATGCAAATTTAATAAAGGCTTTGGCCATTAGGAGCGTGTGTGTCTTTCTAAGTTACGTCTATGCAACAACAATGCTGTCTGTACAGT
AGAGTAGAGGGCTCAGAGAAAGCAATGGAAATTCACAGAAAGAGGTGAAAGCCCTTGTAATTCATATACCCCAGAGAGGAACTTAAAGAGTGTG
TTTAGTAGGAATAGGCACCTGCCAAAGAATCTATGAACCCCAAGATATCCAAACTTCTTATAGTCCTGGAAGGAGTTTCTTCTGAGTTGGCTCA
GTTGTGCACTGACCGCTGTTTCCTGCTACATCTTCTCAGAGCAAATAGGAAAGGAAAAATGCTTCTGCTCTGTATTGTATGCTCCTTTCATTAA
ATCACCCTCGGGACAACTGAGTGTTCCAGAAATAGGTGTTGGTTAAAAAAAAAAAAAAAAAAAAAAAAAAAAACAAAAAAACAGGTATTTCTGTGCA
ATCAGAAAGTGCCTCTGCTTTGTTACCAGCATAAAGCATTCATGAAATCAATTTTCAGCACCCACTGGATAGGGCTGATGTGCGAACTAGCTTT
GCGTAGCCCATCGTCTTCTTTCCGAGATGATTTGACAGGACTGGCATTTTATCATGAATACAAAGAGGATGAGCATATTCTCCTAATATATTCA
TTACTTCCCTCTCCGAACTGGTAAATAATATACATATGGTAATTTGAGAGACATAGTGTTCCCCATTGCTCCTTTTTATTCCTGGAACTCTGGC
TGTCTTTGTAAATGCTGCAAAAATCAAAGGCAAAATTACCTCAAAATTTGATTTTGGAGTCCTTCTAGTCTCACTTTCTGGTGCCCACACAAGA
GCTATTGCTTATTTTCTGTTCTGACCTGTATTATTCAATAGCATCACCCCTTCTGCTTGCAATCTTATTGTAGAACCTTCTAGAGTGACTCAAA
GAAGCCATCTATTTATTCATTAACAAGCACCTATTAAGTACCTACTCTGTCCCAGACACTGTGCTAAATGTTCAAAAGAATAAGGACCATGAAA
GCCTATGGCCCAGGCCCATTCTTGTTTTCTCGAGTTTTGTAATCATTTCTCACACAATTATAAAAATCCATGGCATCGTAGAAAGATAGGAAAG
ACTGTGGAGTGGATGCCGTAAACAGAACTAAATGAATAATGAATGACAAGCTGAGAAAATGTGAGTGTTTGCCAGAGCATGTGAGTCTAATTAG
CAGGCATAAACTGATATGCTAAACCAAAACGTGATGAGATTTTAGATCCAAAAGAGCCATTTTTATAGACTGGACCTGAAAGAATTGGATTTTT
AGATGGGAGTATGAAGGCAGATCTGAAGGGCAGTTTTCTTAGAACTAAGTGAAAACGAGATGTTTTACTCTGCACGGACTTGATTGACTTGCCA
TGGCTTGAACGATCAGAATACAAGTCAATTGTGATCAGTAATTTCTTCACTTGTATACTTAAAAGTGTTCATTGACCTACTGCGTTAGATGAAT
TGGTCTTTGCTGAAAGCAAAGGAAATTAAAGGTCTGCTCTTCTTGAATTTGTGTTCAGATGAATGGACAATGGGAGTAAATCAGTGTATGGAAG
CCCCAGCTAGATAGGCACCGAGACGTAGGCTGCAAAGAAGACAAATGGGTGGAAGATGTCTCTATAAATATACATGGTTGTTAGGGCAAACTGA
CCATGCACATTGGNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNTCCCATTCCACATCAAATGTGTTCCATGGCTGCAATCAAGTCCATGCTCAAC
AGTACATGAAGATATGACAGTCTGGTTTCCATTTATATAATTGTTTTGTTGCCTTCTTTATTCTTACTGGATGAGGTCTTATTGTGCTGTCCTG
ATTGACCTGAACTCTGGGTTTCAACAGTCCTGATACCCTCAGCCTTCAGAGCAAGGTGCCTCCCAGTTCTGCCTTATTTTACTCTCTCTCTCTC
TCTCTCTCTCTCTCTCTCTCTCTCTCTCTCTCTCTTTACTAACTATGAATTCACACCAACAGTTTCTAGAATCTCTTTTAAAGCATACCT
GATAATGATGCTGATATTGGTTAAAATAATGTAACAAATGCTTCTTTTATTACTTTATATGAATTACCTGTCATTTAATGCTCTGAGATGGTGT
GGGGATATAGGGCGCTGTTATCGTTCCATTTTATAGATGAGAAACTGAGTACACAGAGATAAAGTAACTCACTTATTTCCATAAAGCAAGTAA
GTGGTGCCACTAGAGTATAAAATCAAACAACATAGTTAGAAACACTATCCTTATCTGTCTTTAGTGTTTATTTCTTCACAGCTCCATCATCTTC
ATAGACACACACACACCCTACTTAAAACCTGCATGTCCATAATTTCCACAAGCAAGCACCTTGAGCTGAAACATTCGGGGCTGTTTTAAAGTAA
ATTTTGCTATTATTCCTTTGGCAGAATTTAAATTCTGAAGGAGATTTTCAAGTGATTTCCTCTCAGGCTTCATTTAGAGGCATTGAATAAAGTA
ATAGCACCTTTGAGAATGCACCTTAGCATCTTAGTGTTGGGCACCTGTAATGATAGCACGTGGGAGTCTGAAGCAGGAGGATTTCGAGTGGCC
AGGCAGGGGAAAGAGAGAGGGGGAGAGAGGAAGAGAGAGAAAGAAAGATTCCTACTCTGGCAGACTAACTGTTTCTTTAACTATCACTATTAAA
TACACTAAATTATTCTTCAGCTCCTCCTTCACTGTGGATCCATGCCTTTAAAACAAGCACCGTTGTCCCCTTTGCCTGTGCATCCTGAGTCTCT
ATACACCTTTAGCATTCTGACCCAGGATTCTCAATTGATTGCCACTAAAACCCCAGATATGGGTACAAATCTGAGCAAATTCATCTCAATATGC
ATTAGCATAATTAGAATTATCTAGGGATGTCAGATCATCTTAAGCACCTACTTATTTGAACACTTAAGTATAATTAGCACTTGTGAA
AGGTCTCTGGTTTTCAAGTGTCTTGCAAGACTCTTGTTTTTTTTTTTTTTTTTTAGTAAGCTTCTAAAAGCTGCTTGTCTTTAGGTGTTCAGT
GAACGGGAAAGATAAACATTTGAGGCTTGCCCTTTTCCTCTTTCTGACTAAATGCGGGTCATAAAGTAGAGCCACGGATCAGCAAGCCCCATC
ACACAGATGAACACAGATAGCCCTTGCCCTCATGGAAGGGATCATGTAGAGTCCTCTCTATTCCAAAAGAACTTCACAATCTCCATAACTACGT
TTGGCATTTCACATCTGTCTTGTCCTTTTGTGACATGTGGATTAGCAGACAGTGTCCTCGGGCTCTCATGATGAATGTAGGGTAATACAGCAGCC
CAGAGCCATGGCACCTAAGTATGACTTGGATGTGATCCCACTTGGATATGATCCCTAAGGGACAGGATAAGGACACTAGATCAAATTTGGATCA
AAGAAGAATTGGAAATCAAAGAGTTGAGAATAACACCCAGCCCTGCATCTGCATCTGTTTAATTAGTCTTTTCTCCATCCATTTAAATGTGTC
AAAAATGTGTAAAGATCCATTCAAATAGAAAAATAGTAATTTTTCATGGAGTGAGGGCAGGAAATAAATGTCAGATTCCCAGTAGTAAATAAAT
ATAATTTTTAGACATATAATTAGCTTTCCTCAATCTCAGTGTCTTCATCCTAAAAGGGCTTACTTTTGGTAAAGGGGAATTAAACCTGAATTGT
TCAGTTGGAGTCCAGTGAAAGAGCAGCAGGCAAAAGAACATCACAGCTGCTACAGATCCCACTTTCTCAGGAATGAACAGCTGDDTTTGAATGGT
GTCTACGTTATCCAAAATGCCACAAAACAATTGATGATAAAACTGGTGGATGGACATATAGTCTGAATGTTTCTCAAAGCTCTTAGTACTCAAA
GAACTTAAGAAAAGGGGAATAAGGAGGTTTGCCTAGAGTAGAGTGTTTCGGGCAGAATAAAGAACCCCTTTTATCTCATTTATTAAGTTGAACA
GAACAAATAAGAAGCTATCCATCTCTATAAAAATCAAATACAGTTAGTTCCTTAATGAGTTGCGTCTTTTGCTCCTAACTGTAATACATACAA
TAGTGTATTATTTCCTTTTACCCAGATAGATTTCCTGAAACCATAATATTCAGAGGCAGAGACTAAAGGTTAATTTAAAAAAAAAAAACCCTC
AGGGGTAAATTATTACTATTAGAGGAGAAAGTTATATTTTTAAAGCTTATAGTATTATTTTTCCAAATTAATTTTTAAAATAGTATTTTCATGT
ATTCTTGAAATGTAAGTATATTCTAGATTACGTAAATAATTGATAATGGACTACCAAGAAAAAGTATACATGTAATATTCAATATACAAATTA
GCTTCAGTAAATCTCTCTTTTGAGTCATTATTTCCACTAAAATGTCTCTTACATTGAAATTATTCTATGAAATATGAAATTTAGAATATAATGG
ACACCTTCTTTTGTTACTTAATCATGACGTAACGCTTTGCTCTTTTCATATTTGAAGTCAGAAACGCCTTTAACATCCTAGGAAAGCCATG
TGGATGTCATGATCTGGCTTTCTTTGTCGGATAATATACTAGATTATTTTCTTCTTCTGAACATCTTAAACCTCCTAGATGAGTTTTTCCTTC
AATTTTAAATGCTTTTGAAGCAGGACTTCATTTTGTTTCGAGCATTTCTTGGAATTACATAGAGTTGAGTAAATATGAATATGCCAGCATCCTTC
TAAATGGACTACCTTTAAACTGTTTCAAAAGTAAACCATGCATCAAAAGTCAACTCGGAAGACCTGTGTTCTCTCATACCCCTACACCTACCCT
GCCCCTGTGGGTTTTTTTTTCTTGGTAATAACAATAAGTGCTTTAGGATTTCTATGTTAGGATGTATAAACAGAACACTATGACCAAAAGCAAC
TTGGGAATGAAAGGGTAGCAATAATTACAGGTCTACATATCACAATATATCACTGTAGGAAGTCAGGGCAGGAACTCAAACAGTGCAGGAAC
CTAGAAGAATACGCTGATGCAGGAGCCATAGAGAAGTGCTGCTCAGTGGCATGCTCCCCATGGCTTGTTCTACCTGCCTTCTTAGAACACCTAG
GACCATCAGCCCAGCCATCACACCATCCACATGGGCTAGGCCCTCCCACATCAATCACTAATCAAGAAAATGCACTACACAAACTTGCTCATGA
GCCTAGCTCCTGTAGACATTTTCTCAATTGAGAATTCATCTTCCCAAATGAAATGACTCTGGCTTGTGTCAGGCTGTTATAAAACTCACCAGC
ACATACAGCGACCCAAAACTTCATAGGTACTTTGAAATAAGTGAATCTCCAATCATGCTGCTATCCTTTTAAGAATTTGTAACTATCCCTGCAA
ACTGTTGTGGGCTATGTCATGGTCTCTAAATGCCACCCTCTTACATCCTAAGCAGAATGAAGCATGAAATAGGAACTAAGGTGTGGCACAATGC
AGACAACTTTCCTCTGGGCTCTCCTTACAGGACACTTCTCAGCCATGAATCTTACTGGCCTCTACCTTTCACATAACCAGGGAAACCAAAACAT
ACATCCATTTTTAATCTTGTCCTCTTCCCCACACATTCTCAATCTTTTCTCACTGTTCCTCCTCACAAAAGAGCAAGCATAGGAACAAATGA
GAAAGTTTCTGACTGCCATTGACTCTGGGAAAATATTAGTCTTGTGCTGATTGTTGCAGTGATTGCATATATAACATGAAATTTACTATCTTAAT
CATTTCAAGTGCATGGTTAAGTACAATCACACCATTATGACAATCCCCAGTATATTTAAATTTTTATCACACAGAACTGAAACACCTTATCTCT
ATGCTACACTAACCAGTCCTTTCAAAAAATTCCAAGTCGTAAGTCTAAGATTAGGCAAGACATAGCCTTTGTGCTCTTAAACACTTTTCCAAAA
TATATTCATTTTAAATTTGTATGTATAAAAATGAATAGCTATTTTAGCATACAGAATTAAATCAGTCATTTTAATGATTCTACTGATTGGCTTC
CAGGAGCATCTGTGTGTCTTCTCATTAAAGTAACCAATGCATTACAACTGTCATTGCTCTGTGACTCTTCTTCTCTTGCTTTGCTATTTAATGT
```

TABLE 1-continued (mouse gene: Prlr; human gene PRLR)

```
TTCTTTGAAGTCAAAGAGTAGCTCTTCATGATATGCATCCAAGTGTGCACTTAAATCATAGAACTTATTCTTAGCAAGGAAGTATGTAGTGAAG
CACCTGGTCAAATGGGAAGACAGCCTTGAGAAAGACAATGTTTTTCCTGCTGAATTTCTAGGAATAGCCAACAAAGTGGGAGTCCTGATAGGTG
AGACCAGCAGTGTGCTCTTTCATAACCTCTTTCAATTACTCTCAACTCTTCTTTATTTTTGGATCCTATGTAAAATTTTCTATAAAGAAAAGAG
GTTATACATATGTTTTGAAACAAAACATCTTGGATCTCGAGGAACGTTTTGTCTCATTATTGAGATTCATTGGAAGCCTGTCATTGAATGAAAAG
ATATCATTGAAAACATGTGGCCTTTAAACCAACCACCGACTCTCTCCAAGCCTCTTTTCTTTATGACTAGAATGAGAATAACGGTGTATATCTG
CATCTTCTAACACCTGAGAAGATTTAAAAGCAGTGAGCAGTGTGCTGCCAGCCTCCTCACCCTGCTGCCTAACAAGGTCCCTCCCACATGAGCA
GAGCAATCCAGGAAGCAGGTGACAGAGGATGAGGTAGTCCAGAGCAGAGACAGGAATATAACAGAAACTGGATCTATCTGGCTCTGGATACTAG
ATCTAGGTTGGACGTAATGACATTGGGAGCTGTGACTGATGGGTTCTCAACCAGATGCCACCTTTCTCAGTGTCTAGAGGAGTGGTATCTAACA
ATGACTAAGATGGTTTCCCAAGAGAATTTGATACTGAAATCTCACTCCCTCTCCCTCTCCTTCTCCCTTTTCCATCCCTTTTCTTCTCCCTCTC
CCCATCATCCTCCTCCCTCTTCCTCCACCTTCCTTTCCATTCCTAGTGATCAAATTCAGAGCCATCCACATGTTCGAATATTAGTTAGGCGCGC
TTTCTAGCACTGCGGTACATCATCAGCCCTGGAAAGACTTATTGCCATGAATGAATCGTTACTGGCATGTACGTGATCAAGGCAGAGCCACCAT
GGTCCATGGGTTCTGTTAAATACCTCACTCTGAACATGACAAAACCTCGATATAACAACATTAACAGCTTAACACGTCACTCGTGCTGACCTTG
AGAAACTCTACTTTTAGAGACTTTCTGACATAGGTGCCTCTCCCCATCATTGATTTCCTCTTCGTCTGGTAACCTGGAAATTCTTCAGGTTACT
TTTGTTCTGGTTCTCTTCTTTGTTCCTTTGTCCCTCTCTTCATCCTTCTTCATAACTTTTTCCTTTCACTGACTTCACTAAGACAAGATTCTT
TTGTTTTCTTCACTAACTAGTAAATTGCTTCTTTCCCAACTCTTACTCTTAAAAGCAACAGAATAGAGCTCTCTAAGGGAAAATAACATAAAGC
TTGAAACCACATAAAACTGCATTTGTATTTGTGTAGACATGCATGGATTGTTCTTTAGGCCAGTAGATTCAGAGACAAAACAAACAAAAACCA
TCCCCCAGTGTTACAGATAGTTAGGGGGACTGGACTGTGTAACATCAATCCCAAGAAATACCTTAAGTAAGTACTCCCAGGTTCTTTAGAATGA
AAAATCTAGGAGGTGTCTTAGTTCTATTGCTGAGAAGAGACACTATAACAAGGCAAGTCTTATTAAAAAAAAAAAGCATTTAATTGGGGCTG
GCTCACAGTTTCAGAGGTTTAGTCCATCCATTATCATCATGACAGAAAGCACTCAGGCAGACACGATACTGGAGAAGTAACTCAGAGTTCTACA
TCTAGATCCTGCATGCAGCAGGGAGAGAGAGAGACACAGGACCTGGCTTGGGCTTTTAAAACGCCAAACCACACCCTCAGTGATTAATTTTCTCCAAC
CAGGCTATACCTACTCCAACCAGGCCACACCTACTCCAACAAGGCCACACCTACTCCAACAAAGCCACATGTCCTAATGCTACTCCCTAAGCAT
TCAAGCATATGATCCTATGGGAGATGTTCTTATCCAAACCATCAGAGATGGTATCAGATGCCCTATAAAGGAGTAGGGCTTTCAGGCCAAACTT
ACTTTGAAAGGTTCTCAAATGATTATGAGACAACGGGTTTGGGCAACATAAACAGGTTGTTTTTATAAATTTCAACCACTGGCTTGCTATCT
TATCACTCAACCTTTTACCAATGAGCAGATTTCAACCAAAACAACATTTTTTTTTGATTAGTTGAGTGAAATCTCAATTCATTGCATCTCAATT
TATTGTCAGACTTTAAATCAAGTGGGCAATTATTTATTCCCATCAAGGCAGCCTTTTGCTATCCTGTAGCCAAAATAATAAATACTGGTTGTTA
GTTTTATATTCAACCTTGTTCCTCAGTGTTTTAAATTATTCTGATACAGCTTTGGATGGAGAGTGAATAAAAAGAGGCATGGTCTCTGGAGCCC
CAGATCTTCTCATAAAGACCCAAGAATAAAGTGGTCTAAACAACCCTTACACACTTGCTCACTCACTCAACAACTCTTTGGAAAACTCACCCAA
TCCCAGCTCCGTCTCTTGATTTACTCTTTATTCTCATGACTGAAGAACTCAGCTGTTTATGTTTTAATAAAAAATGGTTTAAAAGACCAAGCAG
AATCCATGGGGACTGTTTCTGAGATATCCAGCTTACTGGCATATTCTAATGTCTACTTGGCAATAACTGAAAGTGTGGCCTTTGTATTCCAAG
TAACTCTGTCTTTGAGTAGTTTGCAGATTTATCACTTGTTGGTCTACAGCCTTTAAGTTAGGGATCATATCCAAAGCTGCCTGGTTTTATAGGA
AAAGCCTAGTTGTTTCCAAAAGCAAGGCCAATTAATAGAGCATTCAGAATTTGAGATCTATTTCCATGGAGGAAATGATCTTAAAGTGAAGT
TAATTAGGAGTGCAGAGAGCCAGAGATGATAAATTCAGAATTGCATAATAGATTTGTATACTAAAGGGGCCTGTGTCATCTCCAGTCCTAAAGA
GACCGGCTGCTGAAGAATGAGACTCAGAAAAATGGGTGGGTTATATCGCCTCCAGCTTTCCATGTCACATGCACATGTCACATGGCCTTTCATG
ACCTATATTAAAGTTCTCCAGAGAAAGAGAACCAGTGGGTTATTCTGTAAATATGTGTGTAGGTTTATATATGCATGTATATATAAATGAAGGG
AGATTTTTTTATGGCAAGGGATTGAAGTGATGATATTAAGTTTAAATTCAGTCTGGAGACCTAGGAATGACAATGATGTAACTCATTCTACATC
TCAACTGAGAGATTCCTGGTGGTATAACTTTTACTTAGAGGCCAAAACCTAAGGTACAGAGTAGAGACTGGGGGAGTCTAGTGACCTGAAAACC
AAGAGCTCTCATGTCCAGAGTCAGGACAAAATGAATCTCACATCCACCGACTTTTAGTTTTTCTGTTCTGACTCTTAAAGGATTGGATAGTAC
TCACCTAAAACAACAACAAAAAAGAAAAAGAAGAGAAAAGAAAACAGGAAAAACCATTCTCCTTTTGAGTCAAACTCTATTCTCTTCCAGTAA
TACTGTCAGAGATACATCAGAAATAGTATCTTACCAGCTATCAAGATACCTTTTACCCTAGTCAAGCAGACTAGGCTACACAAAATTGAAGCCT
TTATGTCCCTGTCCATGAAGACAGGCTTAGCTGGATAATACCCAAGTCCTCTATTATAGCATCTTGCCAGCTATCAAAGTGCCTCTTAGCCTA
TCAAGCAGTCTGGGCCATGCAAAATCACGAAGCCTCAGTATCCCCATCTGCAGGAGACAGGCTTAGCTGAATAACACCTAAGTTCTCAATTAT
ATACCAGTGCTCTATGAATGCAAAAATAAGGCTTGGAACACTCTGCCTTGACCAGTTTAAGCATCAACAGAAGCTGATCGCTGGACATGCCTTC
AATCACAACTTACACATTAACTTATTAAATTTACTAGCTAATTCCAATTTGTTTTCTATTTTGAATGGCAAAAATTTTCAACTGGGTCTCTACT
TGATTTTATCAAGAAATTGATGGTTCTGTTTGGTATAAAAGTATTTTGGTTCTTTTTCCAGAATATGGTCATCATTACTAGAGATATAAATTGA
GCTAAATAGGAGTAAAGTATCATGTCTGTGATTTCATTTAAAAATAAAGATAAAATAAAATGTGGCTAGATCACATAAGATGCTGTTTGGGCTG
GCAACATTTCTCATTAAAAACTATATTCTGAAAAAAGGTATCAGGGACCTAGGGGAGACAGATATGGGTAACATTGACTGTTCTGGGCGTGGAG
GTTCAATTTATTTATTTGCCTTTTCACCCTCTGTAGTGTGTGTGTGAGTGAGTGTGTGTGTGTGTGTGTGTGTGTGTGTGTGTGTGTGTGTGTG
TGTGTGTTAGTGAAGTGGAATCAATTTCCTGAAGCCTTGAGAGATTTAAATCTCTTCACTGAGAGTGTCTCTTCAACTGCATGCAAGCATGAAT
GAATATTAAGGGTAAGGTACTATGACTGCCCTCTTGGTTCATCTTTCCATTGCTACTGCACAAGTCCCAGAATTTTGAATATCGTTGGGTCACC
ATTTGTCCTATAGGCTTCTGTAACCTCCTTAATCATTTGTATATAATCTAGTGTGTGTTCATTACACAGATTCAAAGCTTATGTTGGAGTGTAT
CTGTAGATAGATTGGGCTTTCTCATATTCTTCCCTCTACCCTCCTTGTTTTATATCCTCACAACATCTTTTCTTTTCCTTTTTTGTTTGTTTC
TTGTTTGTACATATGAATTTAAAACTGTGAATTTATCTGTCTTTACTATATCTGGCTTGTTTTGCTTGACACCATGACCTGTGTTTCCATCCATT
TTCCTGAAAATGATAATACTTAAATTTTTATGGCTGAATTAAACTCCATTGTGGATTATTCTATGCTTTATCAATTTACCTATTGAAAAGTA
CTTATACTGCTTTTATAACTCGGCTATTCCTTAATCATTTTTCTAATTCTTTCTAATAGACATCCTATTAAATAAAACTGAACAAGGTATTGTA
CCAATGAACTCAGAACACATTTACTGGCTTTACATAGAACATTACAACTTTTCCTTTGGAAGGAAAATAGATGCTGCCCTCGAGTAGGGTGCAC
ACTATGTTCATATCAATTAACATTGGTGAAAACATTACAATTCAATTGGTCATCAGTAAGTCAGAGTTGCTTATAGAACACATGTTTATAACC
CTATATCCCGCTCTGATAGAAAATAACCGGTTAGCTTCTTAAGGTTGATATAGTAAAGTTGCCACAATTAGGTGGCTAAAAAATACAGAAACTTA
TTTTCTCCAGGTTCCAGAGTCGAACAACTTAGAATCTAGGTTTATTTGGTACTGTGCTCAATTGAAACCCTAGATAGAACCCATTCTTGTTTC
TCCTGAACTTTTCATGAGAACCAACTGCCTTGTCATTTCTCAGCTGAAAGCTGCATCCTCCAATCTTCATCTTCATATGTGATCTCTCCTGTGT
CTATGACTTATAAGCACACCATGAGATTAAGGGCACACCCTATTTCAGGATGACTTCATCTCTACTCATTACACTTTTTCCAAACAAGGCTGTG
TTCTGAACATAGAAGGGCTTCACCATCTCTTTTTGGAAGAAGCAACTCAAACCACGAGGCCATCCAACAAATGACACTGTGAGATGGATTCCA
TTTGAATCTTTTATCATAGCTATAGTTCCTAATTTTACAAAATGAAGGGCTAAAGTTTACTTCCTGCCATGCCTGGGAAATAATATTCAGACA
ACATGTTCCAGGACAATGTCTAGGATCTTTAGAAACACATACTCTGTGCTATATGGCTGTTCTACAGAAGCCACCTGAGAGTCACAATAGAGAC
ATCGGATGTAAGCTTCTTCTGAAAAGAATTAATGATGCTTCTATAGCTTCCTTGTTATACCACGCCCACTCCTACCTAAAGTCCTTCCACTC
CATCTGAATCACTGAAAGCTTTAAATCTAACTGTGTTGATGCTGCAGCAGGAAAGCCACAAACCAAATCAGGACAAACCAACAACCCAATCAGA
AGTATTTTATACAATTATTATGTTGGAGGTTGTGGTCTTTTCTTACTTGAGTTTTTCTGCAATGAGGGAGAAATAGTGAGGACCTTTTGTATCT
CTAGGTAAATATTTAAATCTGCCAGAAGAGCCAGTTACCCAACAGGTAGTCAGCTCACAGGTCAGTGCTCATTGGAAGATGTTCAGAGCCAGAAA
CCAATCCCASCCAGGGATCCTATGCAAATCTAGCAAGACCTTGGCTTTCATCTTCTATTTCCTGAAACAAGCACCCAAGTGTTAACTGGCTTGTG
AAATACCTTGGGTAAGTCTCTTGTGTGTTAAGATTCTGGCTGATTTACATCTGCCAAAAAGGGGTATTTGTTATTTCTTGATGAGGCCCAGGC
CCTCTGCACTAACATGTATGTTTTCGATTTTCATTCCCAACCTGATGCTTGACACTTACATGCTTTCTAGGGTGAATGAAAGAAACTGAGAAT
CAGGTTTCTCTGTCATTAGCACAGAATCAGCTAAGAAAGAACTAGGATAAAGATGGAAGAAGGGGAAATGAATATCATAAGACTAAGGAAAAAC
CTTTAATATGAATTACAATGATTAAGGATTAGCATTAGAAAGTATGTGGGTTTGCAAAGCTACTGGAATCTTTTTAGACTTTAGAGCTCTCAC
CTTTCTTGAAGTCACTTGAGTTTGCCATCTTGAGATCTTGACTATTATGTAAAACCTCTAACTGTGTTAGGTCAAACAAGAGTGTAAGAGGTGT
GAGAAGGTTGCATGATTGCTTGTGACTCTTTTGTTGCCAGCTAATGTGATGAGTGTGGAACCAGAGCAGAGAATAGAATGAATGGAACAATCACC
ATATTTGCTGAATAAATGTCTTTGTCCATTTTTTGTTGCCATTCCTGTACTTTATGAAGCAAATTAGTTCACTTCCTACAAGTCTGGACATGGG
AAGTCCAAAGCTGAAAGGCAGCATATGGTGAGAACTATCCCACTAGTAAAGATGCCCTGAGAACCCCCAAGCCCAAGTCAGCACAGGACAGCA
TATGTCAGAACAACCACGCTGACTTGTGTGTCTCTTCCTCAGATTACGAATTCCACTACTCATTATGCAGACATCCCTCTCATACCTCATCGACT
```

TABLE 1-continued (mouse gene: Prlr; human gene PRLR)

```
CTTAATTATTCCCAAAGGTCCAAGCTCCAATCAACACTAACAGGTGGTTTGTGGGTTATGAGAGGACAAACACGGGAAGAACCTAGTGAGGCAT
TTCAACCCCAAGGATGAAGTTGGCCATCACCCTGGTTTCTTCAATAAACTGAGCAAATGAGTAACAGTAAGAAAGGAATAGTACCCTGATGCCT
AAAGTCTCAACACCAGCATCTAGAAAGGAGTGCACACGACCCCACCCCTTATCTTCCTTGCCAGTTTCTGCTTTTTATTCAGTAACCATTGACC
CTGCCACCATTCATCACCAGAAGTCACAGAGTTGCAAGGTTATGTCCTCAGTCAACTCAGCTTTGATTTGTCCCCTTGGGTCCTCACTTAGTAA
AGAAAAGAGAACAAGGCAATACTGGTAATAACCAAAACTGAGGCAGATATGGTTTGGCTTGAGAGGTGGACTTGATAAGAGGAGAACCATTTAT
CACTTGGATGCCAACTTCTCATTTGTCAAATGTTTGATGGGTTTAGTCATGAAGTCTCCAGGCCAGGAGGACTACATGTTAAATAGCTTCTTAC
TTATTGTCATCTATTCAAAACAGGTCGGCTAAGCATGGACAATGGGTGTTACGATATCTTCAAGTAAGCTGTAGACTGACAGGCTAGTTCATTT
TTTACTATCTATTGTTATAAATTCATGGATTTTTGGGGGGACATTCTCATTGTGCCCATCAAATGCCTTGATCCCACTCATGCTCATGCTACTC
TGCTACCCACCGCAGCCTCTTTTCTTGGTCTGTATTGTCTTCCCTAATGCAGCCTTTTAGAAAATACCTTCATTGTGATAAAGTGTACATGCTT
AAAGCTCATGTTTAAAATGTATACTTCAGTGGGTTTTATGTAGATACAGAGTTATAAAACTGTCATAACAATCTAATTTTAGCACATATCACCA
AGTTAAAATGTGTATGTTAGCAGGCATAGCTCATCCCCCTACTCTCTCCACTCCCGTTAGCATACAATACTCAGTCTGTGGCAATCTCTAAGTC
ACTTTGCTTGCTATTGCAATTTTTTCATAAGTTCCTACCACTGCCTAGATCATAAAATATTTCCCCTATATTTTTCTACAGTAAATTGAACAT
TGAAGTTACATATTAAAGTCTTGATCCATTTTGAATTGATTTTTTTTTTTTTTCGAGACAGGGTTTCTCTCTGTAGCCCTGGCTGTCCTGGACC
TCACTCTGTAGACCAGGCTGGCCTTGAAATCCGCCTGCCTCTGCCTCCCAAGTGCTGGGATTAAAGGCATGCGCCACCACTGCCCTGTTTTGAA
TTGATTTTTTGCAAAATGGGAGATACAGATTTAATTTCATTCTTCACAATGTAAATACCAGTTTTGCCAGCACAATTTATTAGGAAGGCTGTCT
TTTTATTGCCAGCTTTGTCAAAGATTAGATGACTGGAGCTGTGTGGGTTGATCTCAGGTCCTTAATTTCACTGGTCTATAGGCTTGTTCAGTAC
TTTGCTATGATATCAATAGCAAAGTAAATTCTATTAGTGTTTATGAAGAGTGAGTGTTTATGAAGAGTGAGTGTTTGCAATATTCCTTAATGG
TAACAGCATGAATAAGATTCCGATGTCTATATCTGTGGTTTTCAACTATCTAATCGACGGCACTTAAATGATCCTTTGCTTCCCATTGTAATA
AAACATATCTAAAATGTACAGATGAGTTTGGTTTTGTTTATGTGGGATCCAACTCCTGACTTTGTGTGCTCAGCTGACGTGTCTGTAACGGAAT
GTTCTGCCAGTCTCCAGTGCTGTCTACCAGGACCAGCTAGCCACCTAATGCTGTCTGTAATTTTAACTTCATCTTCTCACAGGCTGAGTATAAA
TGAGGAGACACAGTAGGAGATATACGGAGCAAAGAGGCTTTTAAAGGTCTTAGGATTCTTCCAGAATCACTATTCAGGATGGTCTTCCTTAAGA
ATGGCAAAACCCTGCATGTTTATCATTTGTATGTGGACAGTTCAAAGTTCAGGAGGCCTCTTGTGGATGTTTCTTGTCTTCGGAGTATTAAATA
ATACTTAACTGTCTTCTGTTCTCATCATCGAATGAATATGACTTTGTTCTTATTTCCTAGGACTATGCTGTCAGTGATTATGAATAAGATCATT
AATGTGTATTCGTTACTTCAGTTTCTTGTGTATTGTGTACCAAAAGAAAGAACAACAACCCAAAAAGTTGGTTAGAATTAGAGACTACTGCCT
TGTCATAAAGATGTACATGCTATATTTATACAACTTTCAGATGGAGCCCCTCTGTTGGCCCATGCTGACTACATATAACACATCAGGTTCGTCA
GCATCTTATTCCTGGGATACAACTACAACAACATGCTCAAAGAAAAAGAAACCTTGGTTTTTTTGTTTTTTGGGTTTCTTTCTTTTTTTCATAA
AAGTGATTGAGTGAGTTGTATCATTAAGCAATGATGTCACTAGAACTCATAAGGGGAAATCAGAAAGGCGAACCTGGAAACGTCTCGAAGTAAA
AACCAGGAACCCCCAGCACAGTGAGTGCACGGACTCATTGCTGTCAGCTGAGGAATTGCTCTTGTGTCCCTGCTACTGGAGCTCTGACTTGGTG
ATGTAAGATGGCCATCCCCCTCACCACTCATCCATCAGCAGCACTTTTAAATTTACCTTGGAAACAAAAGAGCAAACTGAAGTACAGTGCGTGT
CATATGATGAGTTCAACTACCTCTTCGAAAGGCAACATCAGAGAGTGAGATCAACAACTAGACTAAGAAGGAGAAGTCACTGTTGTTGACACAA
GCTATTAATTTACTGCTCTGAAATGATCGTTAACTGTTTTGCTCCAAGAGAGAAATCTGTTCAAGGGACAGAGAGAAATATTGTTTAGATGG
TCCCTAATGAGACAGAAGTAGTAGGGAAATAGAAATGGATTTCCCCACTAGCACTGCTCCCTAAACAGGCTCCCTTATTAACCAGCATAAAGGA
TGGAAACATTTTGGCTACATAACCCTACATAATCCTAACCCTTGGATACTAAGACGAGAAAGTATTTACTCTCTGATACTTCCAGGTAAAGAGG
GGATGTTCTCAGTTCAGATCACCAGAACCATAACGGTTCTCTTAGTTAATTAGAAGAGTATGTTCTCTCCTGGTGTACGGCATTTAGTGACTTC
CAACTTTTAAAAATGTAACTTTTTATAAACCTCCTCGCGAGGATTTAAAACAGGACACAGGTGACATTTAAGAATGATTTTAATACTGCAAT
CAATGAGGAATTAATTTTCTTCGAGGTGAGAGTTTCCTGCGTCTGGAAACGGAATCTAGTCCTTCACACCCCATCAAGCTTGCACTGGAGCACAG
ACCTGTAGTCTCAGCCTCACATATTTAAAAAAAAAAAAAACAATTCCGGATTTTATGTGGAGGTCTTGATCCACTTGGACTTAAGCTTTGTA
CAAAGAAATAAGAATGGATTGATTTGCATTCTTCTACATGCTAACCACCAGTTGAAAATGCTATCTTTTTTTCCACTGGATAGTTTTAGCTTCT
TTGTCAAAGATCACGTGACCAAAGTGGTGGGGTTCATTTTGGGGTCTTCAATTCTATTCCATTGATCTACCTGCCTATCTCTGCACCAGTACCA
TGCAGTTTTTATCACTATTGCTCTGTAATACAGCTTAAGGTCAGGGATGGTGATTCCCCAGAAGTTTTTTTATTGTTGAGAATAGTTTTGCTA
TCCTGGGTTTTTGTTATTCCAATTAATTTGCAAATTGCTCTGTCTAACTCTATGAAGAATTGAGTTAGAATTTTAATGTGTGAGTCTCAGCCT
CACAAATTTTTTAAAAAACAATTCCTAGAGTTTTCTAGAATATATATATATATATTTATCACTTAGATGCTAGGTTTTTTTCTTTTTTTTCTT
TTTTTTATTAGATATTTATTTCATTTACATTTCCAATGCTATCCCAAAGACTCCCCCACCCGCTCCCCCACCCCACCCACTTCCTTGGCCC
TGGCAAGTCTGTTTTGTTCTTTCTGGTTTTTCTGCTCTCTTCATATTAGTAGCATGGCCCTGGTTTGCGAATGCTCCACACTTGACCTGAGAAG
TGGACTTACACTGGTCTCTTAGCTAAAATAAACAGAAAGCCATTCCGTTCGGGTCCACTGCTGGTGGTCACCTCATTACCATGCCCAAACCATG
GCCACTCCAGTTAAGATGATCACTGGCCAACTTCCAAAGAACCACATTTGTGCTGCAGTTATTCATTGGACTGGAACAACCTCCTCCCCGCCCC
ACCCCCACCCCCACCTCTCTCTCTCTCTCTCTACCCTCTCTCTCTCTGATTTTAAATTGTTTGTATAGCTACTTTCTTGCTTA
CAAAATCCAACTCTGAATTGTAATATTCCATGTTGGTCAATCAAGGCTCCCTGTTTTGTTTGTTTGTTTGTTTTATATCATCAGTAGTAC
TCTCTATTTATTTTATATCATTCTCAAAAATATTTAAAGTAACTCGCTTCCAATATGTCTGTAATAACCAATACCAGAACTGTAAATAGGTTAT
GACAATAAGAAAACATATAACCCTTTTGGTATTTCCCTGTTACAGAGCACATACATCCCTCCATTAGAGTCACTACCCTTTGAGAATACCAACC
TTTCTAGATGCTCCTGGTAAAGCTAGCATGTGGGAAACATTGCTCAAAAATGCCAGGGTACCTCTGATAAAACACAGGCTGGTAAGACTTTCTT
GAGTAGCAGTGTGATAGTCTACCTGTGTTCTCAACTTTGGTTTCCAAAGAAATTCCCATCATAATCTAGTGAAACTCCTAGCAGTGGAGGGTAT
GGAGCCTGAAGTTGCCTCTTCCTCTAGCCAGGTAGAACTCCCAGTGAAGGGATTAGGATAACCCACCCACAAAACCTTGGGCCCAAAATTTATC
CTGCCTATAAGAAGTGCAGGGACAAAGATGGAGCAGAGACTGAGGGAATTCTCAACCAACGACTGGCTGGCTTGAAATCCATTCCGTGGGCAAA
AACCAATCCCTGATACTACTAATGGTCAGAACCTGTTATGCTTGCAGACAGGAACCTAGCATGGCTGTCCTCTGAAAGGCTCCACCTAGTGCTG
ACTGAAACGGATGCAGAGACCCAGAGCCAAAAGTTAGAACTGAGCAATCTTATGGAAGAGTTGGGGGAGAACTAAGGGCCTCGAAGGGAATAG
GAACTCCACAGGAAGACAACAGAGTCAACTAACCCTGGACCCTCAGGGGCTCCCAGAGAATTAATCACCAACCAATGAGCAAGCTTGGGTTGCAC
CTAGGTCCCCTGAACATCCTTAGCAGGTGTGCAGCTTGGTCTTCATGAGAGTCTTCCATCAACTAAAACAGGGCTGTCTTTGTCTCTGTTGCC
TATCTGTTGATCCTGTTTCCCTAGCTGGCTGCCTTGTATGGCCTCATTGGAGGAGAGAATGTGCCTTGTCCTGAAATGGTTTGATGTGTCAGGT
GGGCCTCACTGTTCTCAGAGGAAGGGACAGAGGAAGGAGGGAGGAGCTGGTGAGGAAGGTCAGGGAGAAAGGGCTGGGATCAGAATGTA
AAGGGAATAAATAAATAAATTAGTGGAAAATGTTTATCAAGAATAGTGTACAGCACACAATTAAAAAAAAAAAGAGCCATGAATTTAAAAAA
GCAATGGGTTATGTGATAGGGATTGAAGGAAGGAAAAGGGAGGAAGAAATGTAATCATAGTATAATTATAAAATGCTAAAATTTATTTAAA
TGTAAAAAAACAGTAGGGGAAATCAAAAGTGTCAAAAGCAGAAGGAGAGATGGGCATGTTGTCATGAATCCATACAAAGAATAGGAGACATAT
GAATTCAAGAATTTAGGTTGGATGTGAGTAGTTGGAAAGAACATGAATTTTCCCCAGCAGATTATTGCAAAAATATCCAAACATTGGAGCAAA
AGTTCTAAGTGCAGATTAAATTGTAAGTTTCTCCAATATTCTAGAACCAGATGATTCCAAATACTGCCTTCTTATGAGTTCTGTTTATCCAACC
CAAGTAAGATCCGTGCATCTTTGCAAAGTTCTTGTCACATCTATAGTGACAATGAGCATACTTTTATCAGAATGGCCCTTATCTTCCTGGGTTG
CCATAATGATTAGAAAGTTATTCTGCTCAGTTAAAAATTTATTCTAGTTCTGGCCAGTAACAGAAAAGTAGAAAGTCCAGCAAGATGTTTCATT
AAAGTTTACTCAACCCAAGTTGGCTGCCACATAATTTTCCACTGGTTTCAGAACAGTAATTTGGGTGGATTCCTTGAAAGCTCAAATTTTGGAT
AATTAATTCTCAGGGTGTCTGTGTTGGAAAGCAAAGGGTAGAGTCTAACAAGAAGCAACTAGGTCATCACTCATGAAAGCTTTCTTTAGAAAAGC
AAGTTCTGCCTGCATTATTGTCCACTCTCTGGTGTGAGCCCTCTCCTCTTTCTTGTTTTCTCTGATATGCAGTAAGTTGAACTTCCTCTTTCTA
CCTTTGGGTGATAAAGCCATAGGGCTCTCACCAGCTGTGAGAAAGAGTATTTTATCCTTGGACTTCCCAGTCTCTAGAACTATAAAATATAAGG
CAGGGGGTCCACTCTGTTCTCTCAGGCCTTTGAATATATTTTCTTTGGTGGCCATGGCCATTTTGAATGAACTCAGGACAACACATAGATTCTT
GAGAAGAACATGTTGTCTTCCTACCTTTGGCTCCCCCTTGTCTTCTATGTTTTCTTCATCTTTTCCTTTCCTCTGACAAGTTGCATCTAGCTC
TCATAATTCTTTAATATAACATTTAATTTAAAAACTGTTTGGAAGAACTCATACATTAGTCCTGTATTTACATCTCCTTTCTCTCCCCTCAAT
CCTTCCTCCATCTGAGGTCCATTACCTCTTCTTCTATAATTATAGTTACACAAAATTGTGTTTGTATACAACCTCCTGAGTTCGTTTAGTGTTT
CTTTTATGTACATATGTTTAGGTCTTGGTAGTTGGGATTGGATAACCTATTACAGAACACCTTGCTGGGGAAGTCTGACTTTCCCTACACAGCC
ATTGACTGTGTATAGTTCTTCATCTAGAGATGGAGCCTTGTGAAATTTTTCCTACCCACATTGGCATGTAGACTGACCTTGTCATTATCTAGAC
```

TABLE 1-continued (mouse gene: Prlr; human gene PRLR)

```
CTTATTTAGATAGCCACACTGTTGATGTTTCATGAGAGCAGCATCCCTGGCATGTCTAGAAGATACTATCTAGCAGCAGGTATTTTGGTCTTCT
GGCTCATACAATCATTCCATCTCATCTGCAATAATCAAACCTCAGGTCTAAAGATTGTATTGTAGATGTGCCAGTTGGGGCTGAACACCTCACA
GTCACTCATCACTGAATTTTGACCAACTGTGGATCCCTGTAATAGCCTCTTGGATGGCATCTTTCATGAGGGTTGAGAGCTAGCTACACTTGTC
TGTGAGTATAAAACAACACAAACCATTGTCATGACCCTTGGTTGCCTTGATTGCCTCCAAGAACTTGAAGGTAAGACCCTACTTCTTAAGTCCA
AACATACTTCAGATGAGGATATGGTGGCATCAAGCTGGGACTGACCTGAATGCCCCATTTCTGAGGACAAACTCTCATAGTACTAGAAGTAATA
TGCAAATTGCTAAGGAAGAAAAGAAATAAATATTCCTTCCCAGCTAGAAGGCCTATAAACCACAGCAATGACCAGCCTGCCAAGGGACCTACAG
TGGGGTAATAGTGAAACTATTATCTTGGAGTCATCAACAGCCATCTAATTAGACTTAAAGTCCACTTACTAGAAGGAAACTCATACCTGATACT
GGAAGCCTAATGAACACATGGCTAGACCTCATAAGAGAACCTACTATGATTTTTTTTCTAAATCAATAAATTATATAATTATTTTCTAAGTGAA
TAATTACTTTATTAGTTCTTTAAGAATATCAAACATGCACACCATATATCATGTCATTCCTCCCTCTTCCCCTTAACACTGTGGTTCTCAACCT
GAGGGTCAAATGACTCTTTCAAAGGGGTCACCTAAGACCACTGGAAAATGTGACTATTTACTGTATGAACCATAACAGAAGCAAAATTACAATT
GTTAAGTAACAACAGAAATAACTTTATGATTGGGGGTCACAACAACAGGAGGAATTGTTTTAAGGTTCACAGCATTAGGAAGGTTGAGACCCAC
TGTCTTAACCCTCACAGTTCTACTCATCCACTCCCCATCCACTTTCAACTTCAAGTTCACCTTTTACTTTTATAACCCAACTAATGCAATTTCT
GCCGCCCATGTACTCAAGGGGAGAGACCATACACTGAAGCATGCTCCACCTATCAAAGGCCACACCTTTAATAAAAACCGGCTGTCCTTGACCC
CGCAGCCAGAAACTATGAATAGCTCTTCAGGCTGTGATGGGAGTTCATGAAGACCTCGTCTTTGCTGGAATGCTGACCAGCTGGATCTTAAAGCA
CATCTCTGAGCTGCTGGGAGCTCAGGAGTGGGGTGGTCATGCTTCTCCAGAAGGCACTGTTTTTCTCTGGTCTTCCTTGACCTCTGGCCCTTA
CAATCCTTCTTTGCTGGTTCCTGGAACTGGGAGAAGCATATAGCTGCTGCTTTTAAAACTCTAAAAGGCAAGAAAATTCAGTTAAAACAATGG
AGAACTTTGGTTGAAGCCAGGATAGGTTTATTTCTGCCTCTACAGAATCATAAAACATCATACACCTGACAGGAGTGGGAATGTGTAATTGAAG
ACGGCGAGTAACTATTTATCATAAGCTAAAATTTAATATAAAGCTACTCAATGTCTTTAATATCCCATCCTAAAGGGCTAAGCACTATGTAGTGC
TAGATCCTTGAGTAGAGAACAATAAACAGAGAAGACAGTTGACGTACATGAGAATCCTCAGATATTACCCAAATACGTTTCAGATAATCAATAA
CTGTTGGCTGAGTGAATATGTACATGAACAAATGAGCAACCTACTAGAGCTCATTTTCCATGATGACTTTTTACAGTTTTTCTCCAATATGTTA
CGTACATTTTAATCATTTTTTAAAATTAACTCTCTATTAAGAAGCTTGGTACTTATGAAGATTAGACAAATCGTGTGTTCAAGTGCTCATGCT
CAGAAATAGCGTCTGGCAGTCAACAAATGTTAACTAGTGATTTTCTTCTTTTTCTAGTTATTCTTTAAAAATAGGATTATGCTGATGCCCTCA
GGCTCACTAATCTCAAAGTCATTTCCCTAATCCACTAATGAAAAGAGATCTGGAGTTGCAATCAGTTCCTACTCTGTGCCTTTAACTAGGCCAC
CCACACCAACCCCTTGGTGCTGGCACCAATAAAATATATGCAAAATCCTAAATATTTTTTCACTTCTTCCTCTGTACTGTTTAGTTAGCCCCAA
ACTTTGGGCCAAATCTACCATGTCCAGTCAGCACTTGTCTACTCCCTGTTGGACCTGATGTCTGAACTGAATTTACCTCATTTGATTCTGTTCT
TTCTCCTTCTCTCTTAATCAGCCCAGTGAAGGTTTTGTAATTTCCTTTTGGTTCCAACAAGGCTCACTCCATTAACCCAAGTTTTGGGATTTGC
CTCTGCCACATATGGATCAAAATTTCAAACTGCAGTTGGCATGAGTGTTGAAACTTATCCCTCAAAACTAGGAGATAGGTCTGATGTTCTTTG
TGTTTCTGTATTTCAGGAACAGAAGGGGGGAAAAAGAATTTCACCAAGCTCAGATTTCCTTCTTTTATTTCTCTGTTAGTGCTCTATGTGACTG
GCTGCCCCACTGAATCTGTTGGCTCTGCCTCAGTCTGTGGTTCTCAGACCCAGCTACTCACCAAGATTATGCCACAAATGATTTCTTGGATGCA
TGTATGTGTTCTTCCTTCAAGGGCTTGTGTTTTCAGGTTGCTATGAGTGACTAGACCTGTTGCCAGAATGCATGAATCCTCTCTGATTTTCTGA
GTATATCCGAAAATTTATTGAGCTAATATCAATAGATAAGGCACAGCTTTGGTAAATTCATCAGTTACAATGACACCAGCAGCTCTGAGATAGAC
AAGAAATACTTGCTGTCTTTTTCACCTCTGACTAGTGGGAGCTTGCCATGCAGAATCTCGTCTGTTAGTTACATAAAAGACCAAAACTGTGAGCT
CTGTGCTCCTGAAAAGATAAAATTCTGGACTTGCTTGCTTCATGACACACTATGCAGACCGTGTCTCCTTTTATATTGAGAGGCAAATATTGA
ACATAGGACTCCATGTGGAACCTAATAAAGGCACTAACAAAATTACACTTTCCACTCTGTGTTTTATGCCATACTCCTAACATTGTGGCCAAAC
TGGTCTTCAACGCTTTTACTCAATTTACTCAAGTGTGTGGGTGGGGGGGGGGGTCATTGTTTCCTGAATGGTTGAATTTTAAAAACAAATT
TACTCAATGTATTTTATCATATTTCTCCCTCCCCATTCCTCCCAATAACCCTCTTTCCTAACCAACCTACTTCACTTTTTTCTTGCTTAAAAAA
AAAAAAAAAAAAGGTACATTTTGTGTGGTCCACCTCTTCCTGAGCATGGGGCCTTCCCTGGACTGTGGTCGATATGCCCAGTGTCATTGCATTCA
TCGAAAAGAAGTGATGTTTCCTTTCCCTCAATGACTGTCATTTGCAAATATTGTTTTCGTGTGGGTGGTACACTGTACCCATTTTTCTTTCCCC
ATACACTGATTTTGTCCTGTTCGAACTTGAGGTCTTGTGCGTGCTAGCACCATCTCTGTGAATAGCCATGAGCATCACTCTGTTATGTCTGAG
AAACGCTGTTTCCTTGAAGTCGCCCACCACCTCTGGCTTTTAAATTCTGCCTCTACATCAATTCCTGAGCCTTGAGGAGAGAGGTGTTATGCAG
AGATTCCATTTAGGACTGAGTGCTTTAATATTTCTCACTTTCTGCAGGTTGTCCACTTGCGGGTCTCTGAGTTAATTGCCATCTACTGAAAGAA
GTTCTCTGATGAGAGTTCTGTAATACAGTGAGCTGTGGATATAACAGTCATTTATTTTGTTAGAGGGAGTTATTCTGTTGCTATGTTCATTTAGG
CTTTCCCCTAGGCCCATCATCTAGTCACAGCTTTTGAACCTCATTAACAGCTGTGACATGTTGTTCCATCTCATAGAGTAACCCAGAAACCTTAC
CAAACGAGTAGTTGGTTACGCCAATAGCACCTATGCTACTATTGCATCACTGAGTGTATCTTGAAGACAGATTGCTACTACAGCTCTCAGGGAA
CATAGCTGGATGAGACTTAAAACTGCTTTTCTTCTCCAGTAGCTTGTATTATATCATCACCCAGCACGATGAATGCTAGTCGTAATAGGTCAAA
CTTCTAGTTGAGTACCAGGTTGGTTTCTCCATGTTCAATACCATAAGTGTGTGGTGTCTTCAGTAATAATCTTAGCATCATATTGTGGTAGG
TACTCAATATCATTGGCAATACTTTGTAATATTTAAGGGTGGTCTGTGGAACTGTTTTTGCCAATGACTCAAAAAGATATAACACTCCCAGGT
ATAGGTTTTATGGTAACATATGATGTCCAGTTGAGACATTGTCTCCCCCATCCTATGATAACTCCATTTAAATTCCATTTATATACGACATATAT
TTTAGGAAGCATCTACAGGAATAGGCTTCTGTATGGCTTTTCAAAAGACCCTTAGGGTAAGTTGTCCCTTCCCATGGTCCCTTCTCTACTCTGT
CCACCTATCACCCTCTCCATTTAATCCTCCTATTCTAATTTCCCTTTTATTGTGTGGTAACAATATAGTTATTTCCCATTCATGGTCCCTAGAA
GATCACCTCCTCCTTCATCCTAGCTCTCTACTTTCTGTTTAACCTTGGTTATTCTGATATTGAAACACATATATCTAAAAGCTAACACTGGCAT
ATGAGGGAAAACATTCAATATTTGTCTTTCTGAGTCTCAGTTCCATCACTCTGGGTGATTGTTCTAGGGCCATCCATTTGCCTGCAGATTTAA
TAATTTCATTTTTCTTGAAAGCCAGATAAAATTTTATTGTATAAATGTACCTCATTTACATTATCCAATTTACCAGACGGTAGACTTCAAGGCC
TTTTCCAATTTCTGGCCATTATGAATAGAACAGCTATGAGCAGGGGGCCCTTTTGTATATGAACAAGAGTTTTATAGATGGATCTTGAGATAGA
TCAATTTTTGGCTTTTGAAGGAACTTCCGTACTGACTTCCATGGTGGCTATATAAATTTGCACTCCTTCCACAATGAATAAGTGTTCTTCTTTC
TCCACATCCTTGCCAGCATCTGCTGCGTTGTTTTATTTATCTTGCACTGGAATAAGATGAATTCTCAAAGTAGTTTTTATCTGC
ATTTCTCTAGTGATTAAATATATTGGAAAATCTTGTTTCTCACTCAGTTGTGTATTATCTTTTCAGAACTCTACTTCTGTATCCCATGTTTAA
TTGGGATATTTGCTTTATTAATGTTGAGGGTTTTTTTTTTTTACTTCTTTGTATATTGAGATACTTATCCTCTGTAAGATAGATAATTAGTA
AAGATTTTTTCCTATTCTGTAGCTGATGCTTTACTCAAATAATGTTGTCTAGCATGTAGAAACTTTTTAACTTCATGAGGTTCCACCTATTAAC
TGTTGGTTTTAAACCTTGTGCTATCAGATCCAGGGCCAGAAAGTCTTTTCCTGTGTCAATGAGTTCAAGCCTATTCCTTAAGTTCTCTTCTGT
CATTTTCACTGTATTTTGTCTTATGTTGACGCCTTTGGTCCATTTGGAGCTGAGTTTTGTCAGAGCAATAGATATAGATTATAGGTCTGTTTTT
TTTTCTTCAGCATGTAGTTTGTATGCAGTTTGACTAGATGCTGTCTTTTTCCAGTGTGTGTTTTTAGGCTTCTTTGTAAAAAAAAAAAAATAAG
AAGAAAGAGGGAAAAGAAAAAGAAAAGCTTTTCATGGTGTGTATATTTATTCGTGCATTTTCAATGTCTCTGATTTTATGCCAATGCTATGCTA
TTTTTATTGCTGTAGTTCTGTAATTAATATCTAGAGAACCTACAAAAAATGACATATATGTGCATGACATACCAACATTAAATCAAGA
TTAATAAAACAACTTAAACAGACTCATAACCCTTAGTGAAATGCAAGAGTAATTAAAAATCTCCCACGTAAATGAACTCCAATGCCAAATGGAT
TCAGTGTAGAATTCTACCAGACCTTCAATGAAGAACTAACACCAATACTCCTCAAATTATTCCATGAAACAGAAACTGAGGGAAATTTCTCAAT
GCTGTTTCTATCAGGATCATACAGTCACAGATAAGCTTGCTCTTTAAGAGAGCAATGAATGAGACTATGCAGTGTTATTGTGGGCAGGGCTG
AGAAATAAGAAATCTGTCACAACTCATCAACGTGAAAAAGAAATAGAAGAATGAATTTCTCTGGGGCTCAGTGAAAGGCTGAACCATGGAGG
AATAATATGGCTGGAGAGACAGACCACCACTAAAACTAAGTCACAGGAAAGGTAGTTGTGGAAGGAAAGAGGGCCCTTGCATGCCCATTTCCCA
TTCTCTACCTCATGCCCCATGCCTCTACCTCTGCCTCCATCTCCAGAAGGTTGATTCTTCCAGAAGTCACTCTTCTGAAAGGCAAGAGAGCCTA
GCAGTCAGAACCATCAAACCCAGAACAGAAAAAGAATAAGCATGGAATCAAGGATTGACCGGGATTAAGTGGCATGCCAGTCATCTGATACATA
TTGAATGAATAATAGAGGTGCAAATGATGAGAGCCCAAGACCCAGCATGCAGTAAAGGCTTTAGCGGCTGCTGAAACTACATTCCCTTGCTT
CTCTGTCTCCGAGTCTCTCGTCAGTACTGTGGTGGTATTTCAGACTGTCCACTTCAGTGCAGCCTCTGACCTGTGTCTTGTTGCCTCTGTGACT
TTCTCCACCCTCAGCTAATACCTCTTCATTTCCAACAAGAATAGAGAGTGTTGATGGGAACAGGGAGGAGCATGGGTGTTCCGAACAGAGTTA
GGACATTATCAAAGAGAGCTCAAATAATTTCCAGAACCTAAAACACATTCTAGAATATTTAAGAGATTCTTTTTCTTTATCTTTTTTCTTTTTT
AAAGAAAATTTGGTGCCACTGCACCCTATGGAGAAATTTGGTGACTTACTTCTAGGAAGCTTGCCCCAGACATCTGTGTCATAAGCTGTGAGT
TCACCAGACGCCTCGTTACCAAACGTCTTGTGGATGAACATCTTTTCTATTCAAATAGCTTTCATCCTATTATGGGCTTTGATTGAAGACACAA
```

TABLE 1-continued (mouse gene: Prlr; human gene PRLR)

```
TCCAGCTATCTAGTCAGAGCAGCAATGTTGACACTGCAGTGACTGCTGTGCATGAGTGTTTCAGAGTTATGAGGACACTGGTGGCCACCATGGGCCT
CCTGCTGGTCACCTTCTCCTCCTTAGCTGCATTAGCAAGAACATCCAGCACTAGCTTCCTCAAGGGATCATTCCTAGTACTCTGGAATCTGAAT
GCTAAGAAATTATTTGAAAGCCTTTTTGGCTGGTTCCACTAGCCAGTTGGCTCTCAGATGGAATTGTGAAACTAAATTGGACAATAGCTATGAA
TTTATGTTCATAAATAAAAGACATTTTAGGGGAGGGGATGTCTTGCTTCCTTTTTTGCGTGTGTATGTGATCCATGTGCATATATGTGTATATG
GCCCTTGTTTATGCATGTAGAGGCTAAAGATTNNNNNNNNNNNNNNNNNNNNNTTTAAGTAAATCCTCCTAATCTAGCTATATTTGGCTGGCCTA
GGTGGCCAGCTTGCTACAGGGGTCCTGTCTCTACAGCCCATGTTTGCTGGGATCTGGGATCATAGGTAGGCCACCATGGTTCCCCAGGATGTAC
ATGAGTGCTGGAGATCTGAAATCCAGTCTCACAGTCACATGGCAGGTGCTTTATCCACTAAACAGTCATCCTAGCCCTAAAAACCAGGTTTATA
AGGCAGTTTATGCCATATAGACACCTGGTTTGCATTCAAATGTTGAAAGAGTTCCTTTCTATCTAAGATCAGCATCTCCAACTCTTATCTACTT
TGCATCTCTTAAACCCTAACCAATGGGAAACAAGAGTCTGGAATTTCATCCAAAAGCCTAGAGTCAGAAATGCTAGATGGGATAAGATTGAGGC
TGTGACACCTGGTGTAAGTACATCCCAGAAGACAAAAGCCCTCATCCGACATTTTACTGAGTCTTCCACTTCTCACTCTAAAAAGCCTTCTCCT
GCCAAAGGATGTTTGAACCACTGATGAAGGATCTAACTTGAGCTTCACATAAAAGTGAGTCTCACTCAGACAAGTTCATATCTGTATTCCTCAG
TAAATCCCACCTAGGGCCTCCAATATATTCCTTATCATTTAATTCCAGTTGGGACAGCTGGTGAAAGTGATCTATGCACTATAGATTAGATACT
GAATTAATATTAATTTCATGACACACACACATATATACATATATATATTACATATATATGTCAATGGTTTTGTATACACACACACACACACACA
CACACACACACACACATATATATGATGAATGCCCCATTCTTAGGAGATAAACTCAAATAATTAGGGACAAAAAAGAGGCATCGTAACTATGAC
TTACTCTCTGATGACCTGGGGAAAATGTAATTTTTGTTACATAAAAGATATAGGATGGTGAATAACATATTAATAATTCGTGTGTTTGTGTGCA
ATACGTGGGATTTATTTTTACAACTTTTTTTTTCCAAGATTGACATGACTTCATAATGAAGTTGCAAAAACAAGTAAGTCCAGCTTTTCTAATGC
TCATCTATGCTCTGCAACACAGGAAGCTAGAAATGCTCTCTCCTGATTTGTCCTGTTTGAGTTAAAATGAGTCATCTTCTCTTTCAGCTAAAGA
ACGCTTCTCTGTGGAGGTGAGCATCGCAGATGTTTTGCACATGAACCTCGAAGGTAAGGAGGGTTTTACCGAGTGCCCACATAATTGCCTCCCA
TTGTCCCTCTCATACAGACAAGGGCAGGGACGTGGCTATCTTGATTCTCAAAGAGCATCATCTCAAACCATCAATACTCACACAGAGCAGTCCA
CTATCCTCAAAAGGGGGGGGGGGATCTTCAATCTCTGTTTCAGAAAACCTGATGCTCGTCTCCTTTTCTTGTTTTTCTCAAAAGCTTTTCATGG
TTGAAATCCCCTAGCTGTGCAATTAGATTTTTATTTCCTCTTTATACTTGTCTGTACTTGGGAGGATTTTTTTGACAATGTCTGGGTTACTTTT
ATAATCAGAAAGAGAAAGATTGCATCTTCTTTTATTTTTTCAACCAGCTCAATACCAATTCTGCTATCACTTCCTGAGACATCTCTCGGCCTCT
TTAATATTGTCACTACTTGGGCTCGATCCGTGCCAGCCTATATGACAATACTTATATGTGGTGGGCTCTCAGTTTTCCTCACCTACTAATACCA
AGGGAGCCCTGGGAGCCAGAACCTGCCAGCAAATAGGTCATGGAGAAATCACCCACACAAAGATTGCCTCTGCATATACCACAGTCAAAGATCT
AGGCTACTTAAGAAGATAGCAGATTGCTTTTGGTCTTTGAGACCTTTCCTTCCTGCTCTTCAAGAGAAAGTGAAAAACTCATTAAGATAGAAA
CTGACTATTATTATTAGCTGAAGAAAAATCTAAGTGAAACGTTCCTAAGATTTCTTTGAGCCACCTTGTGATGGATGAATAGTGATTCTCCTTT
AAGGGCCATCTTTCACTCCAGTGAAGGCTGGCCTGTCCCATGGATCAAAGATGTCAAAGATTGTCAAGACCTTCTGAGTCAAAGATCTTTTTG
TCACAAAGACTGCTCTCTGGTAGTATATTCAGCAACATTGGAATAGAATACCACTCCAAACCCAGCTTCAACAACCAACAGTGTCTAGATGTTG
CTTAAGGTCCTGGGAAGGACAAAACCACCCACCCTGGGTAGTGACAGTAATGTGTTCAGACACTGCCTCATGTCTCCTAAGTGAAACAAAAATC
CCTTCTATCAAAAAGCACTTCTCTAAGTTACCTAAGCCCTGCCAAGACCTTCTGTTTTTTTCATTTAAGTGGTTGAAATTCATAGTGTTACAG
AGTGGAAACAGGAAATGTCTACAAAAAGAATGCCATAAACACTTTGGGTATAAGAAATCTCTGTGGCATTAATGTCATTTTCTAGACAATCCAT
TAACATAAGGACTGGTGCGTCAATCCAGCAAGAGTTCTATGCATTTCTTCCTACTTTCTTGGCTTCTAACCCTTGAGTTCACATGGTACTTGAA
GGATAGAGACAGATTGAGAGTCAAAACATTATGCTAAGTTCTTTAGTAATCTTTTGCCATGTGGATTAGGAAGCATAGACAACTGGAGTCTGAA
CTATGTTGCAAACACAAGAGAAATTTGCCTGCAAATTACTTTTTTTTTTACTTTTATGTGTACTTATTTATTAACCACATGTTTGTGTAAAAAC
GTTACCTCTGACTGACTTTTCAAATCTTTTAAACATCGAGGCATAGATCCTTAACTAAAATTCATCTTTTCCACTCCAAACAGTACACAGCAGG
TGAAGTTTTGGTAACAGAGAGATGTTCCAGTGGTTGGAACAGGAGATTGAGGCTCCAATATCACATCCCAGTACACACACATAGATATCTACTG
TGCTTGCTCATCTCTAAGTACCCTTGGGGCCTTTCATCCCTCTGGTTGACCTTCTTCCCTAGCATCTACCCTAGTCTCATGTCCTCCACCCTTT
ACCCAACCTGGGATGTGGTATGCAAAGATTATACTCATGCCAGTGGATATCTGTGAAAACACAGGCAGAAACTTGAAGGCAGTTAAGACAAGTC
AAGACACACAGCAACACAGCTCTTCTTCAACATGAGAAGAACATCTAGAAACAAATGTTNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNCTCCAGCTTTTC
AATTATGATCCACTAGTTGTAATCACTTCAGAGCATGGCAAAGCAAAGCACCGCCCTACCTGGCACCCATACATCCTTTTACAAGAACTCTGGCA
TCGTCCAGGCTCTGCCCATTCCATGTCTTCTGCAGCTCCTGTCCATACACTTGTGACTTTAAATCTTGACAGATCTGTGAGATATAAAGACACA
GAATGATCCAAGAGCACTGTGGAGGAGTTGTCATTCACTAGGTGTCTTTTGATGCTCATCTAAAGGTCTTCACCCATTATCTTTGTATACATCA
CATGTTTCTGCCACCATCCAATTCTTGCCACTTGGGCTTCTACTTTGACTAAAATATGGTATCATTCAAATCTGTGTGCTAATCTTGGCATAT
AGACATGTAGCTCGCTGATACATTTCTTGCTTAGTATGTGTGATACTCTGGGCTCACTCTCCAACAGAAGCAGAACAGAAAGACTTGGAGTGT
TGCCTATGAGGGTTAATACCTTAGCTTATGCATCATATTTGCTTATGAGTTGGACTTTCTTGTCCACCTGGGAAGACTTTGAACTTGGAACTCA
ATGGAGACTTAGTTTTGTTTTTGTTTTTGTTTTTGTTTTTGTTTTGTTTTGTTATGAGAAGCTGAGTGCACTGACCCTCATTCACTATGCCACTA
GCCCCAAATACCAATTTAAATATAAGACTCGTTGAAATTAAATATTAAAAATTCAGTTCCTCACTTATATTGAATCCACTCCCAATGTTCTATAG
CTGCACATGCTTAGTGGTCATGTTATTGGGCAGGGAATATCAAGAATACTTCCATTACAACATAAGTTTCTATAAGAACAAGCTGACCATCCCA
GTGAGGAGCTCTGGGAAAGTGATAAAGCTCAAACAGACAGGCTCAGCAGTGAGGGAGAGAGATGACAGAACAGGATTCTAAAAAGAAAGTGAAA
GGACCAGTCAACGTACTTCAACTAGGTCAACAATTATATCACTGATACCCAACCATGAACAAATGTACAACTACTCTACCACAAAACACTAGGA
AACAAAGAAGTAACCATCTTTGATGGTCTTTGAGACCCATTTTCTCCCCTGTCTAGTCTTTGGAGTCTGTGAACTCATTGTGAAACAAGAAA
CTTTTCTTCTGAATCCAGAGGCAAGAAGATCCTAAGCTGTGCTCACACATTGAAGCCAATGAACTCCCAGTCAATCGAGAAAGCAACACTCTGG
TAGCCATATACAAAAGCCTATTTAGAGCTAGGATTATTCAAACAAAGAAAACAATACAAGGCAAAGGTACCATCTCTCTGGGGACTTTTGACT
CTATAACAAGTCCAAGGAACACAGGGGTTTCCAGGACAATTATTGTCCCTGTAATGGAGCAGATAGTGTGGTCATGGCCTCCTGCTGACAGCAG
TGGCTTATCCTTACCTAGCACATTGTCAACAAATAGATTACTTCCACAAAGTCACTCATCTTAGTCTCTCCTCACAGAGTCACCGAGGGAAGAA
GAGCAGATGTGGCCCTCTGTACTTTACATACAAAAGAGTGAAGGCACAGAAGAGAATGAGACAAGCCATAGTTAGCAAGGTTGGTGAAATTCA
GGACCAACAATAGAAACAGCCACCTAACCTGTCTGCAGTTCACAACTCCTCTCTGGAGATACAAGTCACTTAGCACCTGTTCAGGTCCCTA
AGTCTGTCATCTCCAAGGCTATGACCTCCTCATAGATAATGCTGCAAACTCAGCTTGTCACTCCATCCCTGTACAGAGTCCCCAGCAAGCTCAC
TGATGGTACCTCATCTACTCAAACTGCTGTAAGAGGGGACAGGAGCAATTGTTACTAATTCTGTTGCTGCCCTTCTCAGAAGACCCCTTCTTTC
AAGCAAAAACATACCTAGTAATTGCAGAAAAAATCAGTGTTTGTCTCAGTGTATACATAGGTCTACCGTCTATCTTCCTGGCAAAAGTCAGG
TGGAAAATGCTACCCCCAAAATACTCTGTCTGCCTTGAGATACTCTTAATCATGGCAGATTTTATTTCTCTAGAAAACTGAGTTAGAATGTTT
CCATTCATATGACTTTCAATAGCCTGTAACCAAATATGATATATTCTCACACTTGAATGAACTCATCATTCATGATGTCTAATAGTCATTTGCA
TTCTTGGCTACATGAAAGATTGGATTCGATATTTTCCTTTAGCATGCAAAGATATGCAGAGTGATATAGCTTTTATGTCTGATAAACTGTAAA
CACAAAATCCACCACTGACTAAAACAGTGAAGAGGAAGTAAGATCTAAGGCTGTTTAGATAAAATAATATTGAAGATGGCACAAAAATTAAAA
TGCTCACTTTAAATGTTTCCCAACTAGCTGACACATCCAGCATTGTTTGGCTTGGAAACTTGACAAAGAGCAAAGAGTGAACGAATAAAGGGCA
GATACACATACAGAAAAGCCAAGTTAGCCAGGCTATGCACACTCTAAAAGAACAGCACTGTACTGGCTGGTTTTATGTGTCAACTTGACAGCTG
GAGTTATCACAGAGAAAGGAGCTTCAGTAGAGGAACTGCCTCCATGAGATCCAACTGTAAGGCATTTTAGTGATCAAGGGGGAAAGGCCCCTTG
TGGGTGGGACCATCTCTGGGCTTGTTAGTTTTGGGTAGTCTTGGTTCTATAAGAGAGCAGGCTGAGCAAGCCAGTAATGAACACCCTCCATGG
CCTCTGCATCAGCTCCTGCTTCCTGACCTGCTTGAGTTCCAGCCCTGACTTCCTTGGTGACAAACAGCAGTATGGAAGTGTAAGCCGAATAAAC
CCTTTCCTCCCCAACTTGCTTCTTGGTCATGATATTTGTGCAGGAATAGAAACCCTGACTAAGACAGGCACCAACTCCACAGCACCCTGGAACC
TCAGCCTGTTGACTCTGTAGAGCACAGGAGGGAGAATGTGCCTAATCTCAGTAGGAAGTCTTACTAGCTATGCAATCTCAGGGCAAAAACTTCC
AGGAGGAGAAATTGTGTTGCTAGTTTTTGCCCACACTGGTCAGTTGGACTGTTGAACACACTTTCAACATTTGCATTTGAACCAGAGGAAAGC
TTTACCATCCCTCTAAGGCTCCAACTAGGCGTGCAATCTTTGCCATTCCCATGCATCTGAGGAGTTGGTCTTTGACATGGCTGTAAACATGTCA
AACAATACATATTCACTCAGAATTTCATCTGTTCTTGACACACTCAAGACTTACGTGTGGCTCTTCATACCTAGCAATGCACCCCTTGCCTTCC
ATTACAGCAGAACCCCAGTGTTTCTCAGTCGGCATCAACCTTTCTCTTCATCTAAGCCATTACACGTTACAGTTAGACTACTGAGCTAGCTATG
TCAAGTTTTGCTATCTGCCCAAGGCAAATGGGCCACGCTCTGGAGATTCTACTTCCTCCCAGGGCTGAGTAAGTCCAGACTCTAAGCTTCTTCT
```

TABLE 1-continued (mouse gene: Prlr; human gene PRLR)

```
GCATCTTTTTGTGGCATGACCCCAGAGAGGATACTTGGAGCAGCAAGCCATAGCATGCCTGGCTAAAGGTGGATTAAACACTGGGCATGTAGCA
CTTTCCTAAGAAATTCTGGGAAAATCAGTTTTAGGTTTGATTTAGCAGGTCATGATAACTTCAAGGAACCAGCGTCAGGATGAACGGTAGAAGG
GGGGCTCCTCTCCCTCTTTCTTTCAGCAGAGAGGGAATTTTCTGCTATGCCTTCATCACTAGAATTTAGTGGGATGGCCATTCCTAAGGCTGCA
GTCTGGACAAAAAAAAAAAAAAGATTACAATGGCCCTGATTAGCATAGCCTGTTACTTCCTCATCCCCTGGGGCTGGATGCCTGATGCCTGACT
GGACTCTGCATAAAAACAAAGGGAGAAGTAGTTGTTGGAGAAGAAACTTATGGTATCTGCCAGGCTCATTGGGTGGATAGGACTGTGTCAAAGA
CAAGACAAGGACGTTTGTTCTCACCAGAGAGGCACCCTCCACAGGGAAGCAGCGTCATCTCCTCAACAAGGTCAGATCATTTATGACAATAGGC
ATGACACCTACAGAGCATTTTTTTCCTACACTTGTCATTTATGTGCTTTACTGGAGACTCTTTGAGAGATGGTATGTGTACACTAAAGGAGTTC
TTTCTGACAAAATTTATTTTATGTCCTGTTCTTACATCTAACTATACATAGCTAGATGAAAAGATGGGTGGATGAATGCATGGATGGATGAGTG
AGTGGGTGANNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNATGATGGATGATGGTTGGGTGGATGGGTGGGTGATGGGTGG
ATGGATGGGTGGATGGCTGGCTGGGTGGATGGCTGGGTGGATGGCTGGGTGAATGGCTGGGTGGATGGCTGGGTGGATGAGTTGATGAGTAGAT
GGGTGGTTGGATGGGTGTATGGATGGGTGGATGGATGGATGGATGACTGGATGGGTGGATTGATGGGTGTGTGGATGGGTAGGTGGATGGATGA
ATAGTTGAACATTTAAATCACTAACATGGGTCAATCTACCTGTTTTCTAACCTGCCCCACTACACTCACAGCTGGATCTTTATATATTCACTCC
TTTCCATTCCCACCCAACAAGTCTACAATGAAAGTATTCACTCTATTCCCTGAACTAGCCTTGGGTCTGGTTGTTACCTCTCTGACTGGTTGGT
ACCTTTTCTGCCCAGAAGGTTGCTTCTGAAGAAGAACAAGATGGAAAAGGGAAGAAGGGGAAAGCAAGTAATTATCTTGGTAGATATAGTTGCCC
AGATGTTTGAATGCAGAAGTAAGTCTGAAAGAACATCTTGTTCATGAGTGATAAAGTGTGACTCAGAAAAGTAGAGACAGGTTGTGCTCCTAAG
GGGAGCACAGAGAGGAGGGTTGACTTTGGGACTGGTTCTGAGCATTATGAGGTGGGAGAGATGTGTAGGCTTTCTGTGTTCCTGGCCCAGTCTG
TGAACCTACAATTACTACTATCCTTTAGACTTCCAGCTCCTAGTGCTTTGTATTACAAGTCTGTTGAGCCAGAGGAAAATTTACACAGAGAATC
TCACACCAGGAGCCCTGCTGAAGTTTCTTCTGAATAAGATGGCCTGGTCCTTCTCGGGGCCCCTGAAGAAGATATTTTCTGCAAAACTGCCATT
CACCTACTTGTCAGAAGCTGAATGGCAAATAATGGGTTCCTGGATGTTTAAATGCACTCAGACACAGTAATGCAATTAGGGAAAGTAGGAGGA
AGTCTCGAAAACAACTGAGCAGCCAGTGGGCATGAGAGCTGTTGAAATCCTTCACTCTAGCTTGAGAGATAGGTACATGTTCAGCTACAAAAAT
GGTTCATGGAGGTTGGTTCTCAGCCACTGCTTTACTCATTGCCAGAGACACAGAGGTCCGATACTCTATGGTAGCCTCTGTTCACACCACTGAA
TGTCAGGTTTTCCTTAGCGAGCTGGTTTTGTTGCATTAATGATGGTGTTCAAATCTGCCTCCTCAGTTGCAATAGCAGTCACTTTTTATTTCGT
TACATTAGAAAAGTAGTCATTACCCACTTTAGAATAATATTCCCTCCCAGAGGGATTCACCATTTCTGTGTTAGCATGAATCTGTTTCGTATCC
ACTGTCTGAGCACCCGTGCAAAGACATTTGTGAGACATTAGGATCAGGCATGTCTACTTCCTGTATCTAATTATTCCTGCACTTCACCTCTGGA
AGTCATTGAAATTTTAATCACATTATGTCAAGGCTTAAATAATATTCCACTGTTGTCTATGCTATGATCTGGTTAAGCAGCCCTTTAGGATCTG
GTGTTTAGATTGTTTTCTAATAATTTGGGCTTTATAAATAACACTACAGAGGTGGACTCTCTTTATTCTAATGTTTTGTGCACCTAGGTTCACT
CAGGTTAAAGTTCTGAAGTGTATTTTCTGATTCAATGTGTATCCGTATTCTTGAGACTTAACATATGAGAAAAGTTAAACCAATGTACACTCAA
ACCACAAATCCAAATGTATTTATACACTCAGTAATACCATTCTGAAACCTCCAGGGTTGAAAAAAAAAAAAAAAAAAAAAAAAAAAGAGTAAAA
ATAAAATATTTTATATGAAAATATTTTGAAAATTAAAATTCCATTAAAATAAACATTGTCATACTATCTATTTTTAAATGACACAAGTAGAAGA
TGTCAGCTTCTTTGATGAAATATTGTGGTGTTAATAGCCTTTTTAAAGTCCCAAATCCTTGCTAACTTACCTCTCTAAGTTCGGCAGACACTCA
GACACTCAACAGGTTATTTCCTGAGAACCATTTACTGAATACCCATAGAGTATAGAGCTTTGTTTTAAATTTGAGGATTAACACACACATAC
ACAAAGAATTAATCAATGAGCTTCTAGTCTAGCCTGAAGAGCTACTAGAGTGGGGAATTGCATAAACATAAGTCAAATCATTATCAGGACTAC
CCTGTACAACAGCTTTGTGAGACCTAAAGTGTCTGCTGGATGGGAGATGGGACAGAGAATCAGGAGGTATCTGGTCTTTCCATTGGATGACCAT
GAACCTATCTTTGCTGCTTCTAAAAATACTCATATTTTCTAGTAGCCAGAGTTCTGGATGGAAAGAGAGAGACATCATTTTGGGCAAAGACTTATT
TTAACAGTCTATATGGTAGGATTAATAAGATCCCAATGTTAAGTATCATCTACCATTGCTCTAGAAATCAATAGAGCTTTGTGGTGAATTAAAT
ACAAAAGGAGGGGCTGACTATACAACTGTTTGGAACCATAGTAGGACGCAGAGATTTTAGGGAAGTGTGAGGGAAAATAAGGAGGGGGGGGGGC
GCAAATATTGCCACTGTTGGAAGAACAAGACAAGGAATTTTGCCAAGTATCTAACGTGTGGTGGCCAGAGAACCCTTCAGCTTTGTCAAACTAC
AAAATCCTTGCTCTTTTTAATGCTTGGAGTGACAAGGGTCTGAGTGTAGTTTCCAGATGGGTGCCTGGTGAGAACGAAGGCCACCTACTGGAAG
CTGTGACACTTCAATACTCACCCTTCATTCTGTTCATGTGTAAGCTCTACCATGGACTCAGAACAGTGGTGCTGAAGCTGGAAACCCTTCCCTT
GAACTGTGCAGGGTATAAACTGCCCATGACCTGCTTCTCTTCTCATTTTAATCTGATGGATACCCAGGTTCCCATGTGCTTGGCACATGAGCCT
ACAGTTTTAAAGAACAAGTGGGGAGTGTAATGCCATCTTTTAGACCATAAAGGGCATGCAGAGGTTTTTTCCCAAACACCCAGGTATGTGTGAG
CCCTGCCACTTAAGGACACCTAAGAAAAGCATCTCAGGCTATTATAGTTTCAAATAAATTGACCATTGATAGAACTAAGAGTATCATCAAAGCG
ACCAATTTTTCTCCCAAATCACATTGGTTTGATAATATTAAATCAATTTCTGTTTCTAAAACTCAGCTGACAGCCTTTGGACTACACTGGTGCC
TGCCAGGCTATGGACTGAAATCCTTATGGGTGATTCCCAAGTAGAGTCTTTGTGGAAAACAGGAAAATTGAACTAACCTTTGAGTATTGACATC
CCAAACTATTATCCCTTTCATAGTTTCAGAGAGTAGTCGTTATAAGGCATGGTGCTGATTAGATGTTATGGAAACAGGCAGTCATTTTATTCTT
ATAAAGCAAAGAGTAACAATGATTTGCTGGGGATTGCCTGGTCATTGTTATGGTAGAAAGGTGTAGATGTTTACCTAGGCCTGTTCTACTTC
ATTGACCTGGGAAAACTACTAGTCAAATGGAAAGTGGGGCCCCCGATTTGCTTGATAAATAGCAGTGTAATGGAGGACCTAAGAAATACAGAGAT
ACAGAGAAGTATTCCTTCCATAACTTAGAGCCACACTTGAGTTTACGACATTAAGCATGCTCTGTTTTTTTCTAATTGATAGTTTCTTTTGA
CATGTTTTTATTTACTCTTTGAATTTTTCATATAATATATTTTGATCACATTCCCTCTCCCATATCCTCCCAACCAATCTATCTATCTATAT
CTATCTATCTATCTATCTACCTATCTACCTATCTATCCATCTATCCATCTATCTCTATCTCTATCTCTATCTCTCAAAATAA
AAAATAAAAAAACAAAATCAAATCCAGTTTTCCTTGGCCACAAATGAGATCCAGAAAGCAAACCAAATAGACATTTTGATGAAGTACATGTAATGAAAGC
AAAGCTCAGCTAAGCAGCTCAACTCTCTGGAACACAAATGAGATCCAGAAAGCAAACCAAATAGACATTTTGATGAAGTACATGTAATGAAAGC
CATTTATCTATAAGACAGGTGGAAAATTCCTTTGGTCCTCCCTCACAACTTATTGTCATCATTTAAATGACTTCAACTTTCTAAATTTTTATTT
TCATGTTAGCTTTCCAACTTTGCAGATCAAAAGCAGCGATGGAATGAAATGGATCTGTTTAGGCCTACTAGAAGAGAGTTAGTAGCAAAAACAG
CTATTAACTATTAAATTAAAATTTTTAGGGAGCAAAAACAATGAAGGATAGAAAGGTCGGGAGAAGAAAAAAGACTAACAAGAAAATAGC
TAGGCACTGAGGATCCTTGTGTCCTAGGTATCTGATTTAAGGGTCTTTGGTCTGTATTTACTCTCGGTATAGCATCCTGTGACCATGCCACTCA
CTATAACTGATATGTTCACAAATGATATCAGTGTTCTGATTAACAAGTCATAGAAGTAAATAATATTTACATTTGTATCCAATTCATTAAAATA
TTTTTTTATCTGAGAACATGCTTTACATAGCTAGATACATAGCTACCCTGTGATGTGTTTTTCATTGAAAAATCACATTTTTTAAAAATCATTTT
ATTTCATTTGAAGATTGTACACTCAGATTTGTTTGCTGCTGAAATTCTCACACATTCCTTCAATTATTATTTCCAATTATATTTTCTTATGTAATTT
GGCTATTAGCCAGATGCCCTGGAGCCAAATCTCATTGTATGTTTTAGTACATCTGTTGGCGCCAAATCTCATTGTATGTTTTAGTACATTTGTT
GCTGAGTTCAGTTTAATGCACATGAAATGGTATTGGAGGAATGCACAAGACCTTAGTCACTTGAAGTGCATCTTAATAGGAAGAAAGAATTCCC
TGATTCAAGGGTACATGTTATTGCTCCTCTCCTTACCCCCGTGGATCTGAGACTGTGAGAAGGGGTGAAAATATTATGTTCTTTATGGTTTTCT
ATAAGTGAGTCAGTCCGAGTTTGTAACTTAGTGGTAGATTGCTCACTTCAAAATCCTGACGCTCTAGGTTCAAACCCTGGCACTACAAACAAGG
GAGAAAATGGTAAAGCAACCAGTCATTCAGCAAGTGTTACTGCACCGGTGAATGTGTGCAAAGTGACAACGCGAATGGTATAGAAGCTGAACAA
AATGACTTTGATAATAGTGTTCACAGTGACACTGAATCAGCACACCAGACATCAAAGGTTTACTTACTCATAGGTACTTGATTGAATACTG
TAGTTATCACCCAAAGTAAGCAGTAATAGCCAGCCATTTCCAGATTATTCATAGATTAGTCAGGCTAAGTAAAACCAAGCATTTCCGATACTCA
GTCTAGCTACAAAGCTTACTGGATTGTTACTTCTCAGCCCTATAAAGTTCAGTAGGTTCTGAGTGGAATTCTAGAGCTTCCCTTCTGT
TCCATGATCTCTTGGGTCCACAAACTACTACAGGCCAGGAGAGAGAAAGGAATGTGCAGACAAGGATGTGGAGGGGCAGAGTGTATTTATGAA
AGAGCTTTAAAGGTCAAGACTAGACCAAAAAAAAAAAAAAAAATGTAGCCTTTCTCCCCATTCTCCAATGCCACAGCTCAATCATCTGACCCCA
TGTAACCATAAAAGGAACAGTTAGAAGAACTTTAGCTGTAGAGAAAGGAAGAATAGACCCAAACTGTGGCAGGTTCTGGATCCTTTTCCTTC
TCTTGTGAGGGACTCTCAATATCCTCACTGAAGTGGTAAAGAAAGTACAACTTAGAAAGAAGAGATAATTTTGACATATTCTTGGGTGAATT
TCTTGTTGGACTTACTAGTTTTCTCAGATGTAGGTACAGCTCATCCTCAGTGCTCTAAAGATATTCCCATCAGACACCTGGCTATTTTCCCATT
GATGCTCAAAGGAGGCCATGGGTTACTCAAGGCCACACAGTCACTGTGAAAGGGAAGAACTGGACCTCCTCACACTCCTCAGGCTTAGAGAT
GAACCTGGACCAGATTTTCTCAAGTCTTTGGTTTCCTTTCAGTGCATTTTGGAGTTTTTGGATTCAAAAACTCCAAAAATCTCAAACAGGCAGC
CAGGGAGTCAGTAAACCGATAATTAATCTTTTTATTTTCGTTTTCAATTTTCCATTTACTTCCAAGCTTGTTTCAAGAAATTAAGAAACACAC
AAAAATAGATAAGCTTGTTACCAACAGTAATTTGTGTGTGCTCATGTTTTAAAAGGAATCTAAGGTTCTTTTCTGTTTAATTAAACCGCATGCA
```

TABLE 1-continued (mouse gene: Prlr; human gene PRLR)

```
CACATACACATACAGCTCTGTAAAACAGAATTTTCTTCTAACAATCTGGCAAAACATATGTCTCCTCCTACTACAGTGGCCTCTTGGTAGTGAC
AGCTTGCCATAGAAACAAACTACAGTGAGATTTCTGTGACTTGAAACAACATTCATTTTTTTAAAAAAACTCTTTTTTATAAGAGGCAGCAGGCT
GACTCTGGTGCTGCTGAGATTATCTGGGCTCCTCTGGGCTCTGGAGAACTTTTTGCCTTCTTGTTTTGCCACCCAATTGAGGATTATTATCTT
ATACTAAATAGCTCCATAACTTAGAAAAGAAAACCTCAGCCACGTCCTGTGACTGTTTCTGGATGGATGGATGCAGCCAAAGTATCACCCAGTC
ACCACCACCTTTCAAATGGATGAGTCTAAAGTAACTGGATTGCAGTGTGTTCCCTTTCCAACATAATGACTCAGTATGCCTTATAATTATACAT
GCTTCCCCATGACTCGGAATAAGAAAATATTTGGGGACAATAATCCACTTAGCCTGTCCCACCACCACCTGACCTTCATTCATCGAAGTCTCAA
ATGTGGCATTTCTCAGAGAAAGCAGCCTCTCTTTCTCTTTTTCTCTGTTTACCTCTAAATGGAGCTCTCTAAATTCAGCTCCAATGTCAGTCAC
AGAATTACATTTTTCAAATGTCCCTTCCTGGGCCCTACATCCAGAGACATATGACATTAGGAGATAGTGTATACAGAAAGTCTCTAAAGACAA
GGCCCAGGGAATGTCTACTACTATAAAAGAAGAACTACTATTGGCCTCACACAGTACCCAGCATTAGAGCCACCTTTGGGAAGTTGGTTTGAGC
ATAGAGACCCTTATCAAAACAAGGGAAAACAGCCTTGGAGAAGTCACAGTCTGTGGTAGCAAGGTCACCTTACCTGTTCCCTGCTCTCATACCA
GGTACATTTTGTATGTCTAAGATGGGGCTCCTTAAAGGTAGGATCAGTGGTCCTCTGTAGATATATAAAGTAGAAAGCATGCGATAAATATACA
AATTCTGGTGTTCAACTCCTAAGATCTTCTTCACCCACTAGCTATGTGATCTTGGGCAGTTCATAGAACATGTCTGAGCTGCAGCACCCTTATC
TGTGAGATGAGAATAATAAGGGAGATAGGGTCCTAGTGGCCTTTAATTAATAAAGATACTGAGGAAGCCATATAAAGCACAAAGATTACAAGTT
CAAAGCTTGCCTTGGACACAGGGTAAGTTGGAGATCAACATAGTCAACTTGGCAGGACTATCTCAAATATAGTTGGAAAGTGGAGTGGAGTTAT
ACCTAGTAATAAAGGGCTTTCTTAGCATGTGAAGCCCTAGGTTAAAACCTTACTACCAGGGGGAGGAGGAAGAGAAAAAGAAGAAGGGGAAGGT
AGGGGAAGAGGTATAGGGAGAGAGGAGGAGGAGCAGAAAAAGAAGAGGAAGAGACAGAAAAGGAGGAAGGTAGGGTTGGGTTCAGACTCAACCC
CACTCTTGTATATTATGTATACATAACCTATACACATCTTCCTGTACACTTTAAATCATTCCAAGATTATTTATGATGCCTAATATAAGCTAAA
TGATACATTCAGTTATCATACTACCCTATTTAGAGAATGACAAAGAGTCATATTTGGTTACAATGCAAATGCTTTCCAAATGCATTCAGTCTGG
AGTTGATGAAACTACAGATGCAGAAGCTGTGGATGTGGAGCGCCCAACCATCTTCCGAAGCTCAGGGGACACAGTATAGGAATGGAAACTCTCC
CACACTGGGAGTGTGAATCGTGGTTTGAAAGCACTGCAGCCTGTGGAGCTAGCTGTGAAACATTCTATCCAAACATGTTGCCTTTGCACTGT
TATTTATTGATGGATGATCTCATGAGTAACTGGTTCCTCTGGACCTCAGGCCAACATGGATTTTCTAACATCTGTCCAAACTCTGCCCTGGACA
GGGAGAATTAACATTTACCCAATTCCTATTCTTTCCTTTAAGCAAAAAAAAAAAAGCTGATTAAAAACAAAGCTCTGCAGTAAAAAGAGGCAGC
AGGGACTCTAAGTTGAGTGAGTTAGTGTAATAGGAGATGGGTGTGATGCCTCACCTTTGGGTAAGCATCTACATGTTAAAATCACCCTAGTGC
AGAAGTGAATACAGCACTGAACTGTAATTTGCTACATCTAGCTTTGAAGATAGAACTCCCTGGGACACTACTCTGATGTTGGACCAACCTGTGC
CAGCTCCCATTTGGACCGCACTGTCTCTGCTAGTTAACTCTACATCTTACGAATGCAGCTGTCTGCATACACAGCACATGGCCGTACACAGCA
CAGCTTCCTCTCAGGAACCTCTTCAGTTTTTGAAACAGGAAGAGAATGGGGTATGCAAACTCAGAAGTGAATGTTTTAAAGTGTCTCCATAGCT
ATTGCTAGTAGCTTTCACACAACCATGATGATCTAGCTAAACACTGAGCAGTTATCCAAATGGCAGCCAACTTAGGATGGTGCACAGGGAGGA
CAGATCTTCTGGAAATTTTAATTGAGGATAAATTACCACCCTGTGGTGTAAGCATCTTTGCGCTAGATTCATTTTAATAAAAGAAATGCAGATC
CCTTATTCCTAGCTGGAGTTATTGCTCTGAAAGCCAACGTACAACAATCTTAATCTTCAGCATGGTGTGAAACAGCTAATCCCTTCTGTTCTTC
TCTTCCCCCTGGGAAGATTATGTCTTTTGTTTTCAAAATTAAATGCTAGCATTCTGTATTGGAAAGAAAAGTCAGACTCCTGAGAATCAAGGGG
CACATGTGAGGTTCTTACCCAGTTATTTCACCCTCTGGCCATTTAGTACTGGGGGCAATTGAGGTGATCCAGTGAGCAGAGGAGCCCAAAGGAT
GTACCTAGCAGTGCATAACACTTAATAGATAAATTTATTTAATATTAGTTTACAAATTATGGAGGCTTTTTTACATTTGGGAGACAGAAATGTT
AGAAATGGATTTAGGTTAGTGGAAGAATGTATGGCTGGCAGTACACTCAGTGCTATAGTAAAGAACCATTGTTGGTGAGCTTTATGTGTGCAG
GGCTTTCTTATGAGGGTCTTGAGTGCTACCAGAGGGAGAGTCTGGTTTTTACCCTGATAAGTTCTCTGTTCTCTGCCACATTGCCCTACAACGT
TAAATGTACAGGTAGCAAGCGCTAAGTGGATTCAGTGAGTTTGGTTTGGTTTGGTTTGGTTTGGTTTGGTTTGGTTTGGTTTGGTTTGGTTTGG
TTTGGTTTGGTTTGGTTTTTAAAAAAGCACATGAATTGAAAGGAATAGTGTTAGGGAGGGTTGGTGATAAATTGGTGGGGAGGAAAAGG
GGGCATCTTTGATCAAAATGTATTGTATATGTATATGAAATTCTCAAACAGCTTTTAAAGTTGTCCAAAAACCAAAAACAAACCCTAACAGTAGA
ATTAATGTAGAAATTACAGTATCACATTCAGCAAAATATAAATGAAATAAAACAAAAATAAATTATGTGAAACTACATACAACAACCAGAATGT
ATCATCAACAAGGTAGAATGACAGAAACTGGATACGCACATTCATTAAATGCTTATCAGGAAGTTGGGAAGTACTGTT
GGGCATGGGTAGAGATCAGGAGGAGGCACTGGTTGGATTTCTGGGCTACTCTTTGTGATCTTTTGCAACTTAGGTGGAAGCATAGAGCTATTC
ACTTGATGATAACTTATTGCAAATACCTAAGATTTATTCTTCTTCAAGTAAGTCTTAAATTGTCTTTGTCCATCAAAGACAAGGTTTATAAGA
GCTAAAAAGATCCTTAGACATTCTGCCGAGCTTACTGGGAACAATTCTAGGGTTAAGGAGACTGAGTCAAATAGAGAGACCACAGTGACAAAAG
AAAAAAAAAGCAGCATGGAGAGAAACTGGAAGTATCTCCTAGCACCAAAGGATGGAAACAAATCCCACATCATGGGAGAGTTAAGCCTTCC
TTCAGACTTTTATAATTGATAATCTCAGTGGTGGGTGGGCCAAAGCATGCAGAGAAGTATAAGCAGAAAGGACTACATCAGAAAAGCTAACATC
AGGCAGTGATCTGGTGAGAGTTCAGATCTGTCCTATTTACCTCTTGAAGGTAATACTGTCTCCTATTATTTGGGATGCTTTCCACAATGTGGAT
GGGAGGGAATACTGTAGGCCATTGGACCCTGCCTAGTTTTCCATCTAGGAAGGAGTCATTCTAGGTTCCCAAAAGAATGAGCCGGACTATAGAT
TGCAAACTCAGCTGTTGACCTCAATGGAAGAGGGTTGGTTTAATGGAGGACAGCAATAAAGAGGGGCTTCTGGAAGGAGTGGGTCTAAGTAGGA
CCACTGTTGATGCACAAGGCATACCTAGGGGAAAATGGTTAGTTTTCTTGGCAT

MOUSE SEQUENCE - mRNA
ATGTCATCTGCACTTGCTTACATGCTGCTTGTCCTCAGCATCAGCCTCCTGAATGGACAGTCACCACCTGGAAAACCTGAAATCCACAAATGTC
GTTCCCCTGACAAGGAAACATTCACCTGCTGGTGGAATCCTGGGTCAGATGGAGGACTCCCCACCAATTATTCATTGACATACAGCAAAGAAGG
AGAGAAAAACACCTATGAATGTCCAGACTACAAAACCAGTGGCCCCAATTCCTGTTTCTTTAGCAAGCAGTACACTTCCATATGGAAATATAC
ATCATCACAGTAAATGCCACGAACGAAATGGGAAGCAGTACCTCGGATCCACTTTATGTGGATGTGACTTACATTGTTGAACCAGAGCCTCCTC
GGAACCTGACTTTAGAAGTGAAACAACTAAAAGACAAAAAAACATATCTGTGGGTAAAATGGTTGCCACCTACCATAACTGATGTAAAAACTGG
TTGGTTTACAATGGAATATGAAATTCGATTAAAGTCTGAAGAAGCAGATGAGTGGGAGATCCACTTCACAGGTCATCAAACACAATTTAAGGTT
TTTGACTTATATCCAGGACAAAAGTATCTTGTCCAGATCTCGTCAAGCTGAGACCATGGATACTGGAGTAGATGGGGCCAGGAGAAATCTATTG
AAATACCAAATGACTTCACCTTGAAAGACAACTGTGTGGATCATTGTGGCCGTTCTCTCTGCTGTCATCGTTTGATTATGGTCTGGGCAGT
GGCTTTGAAGGGTTATAGCATGATGACCTGCATCTTTCCACCAGTTCCGGGGCCAAAAATAAAGGGATTTGATACTCATCTGCTAGAGAAGGGC
AAGTCTGAAGAACTGCTGAGTGCCTTGGGGTGCCAAGACTTTCCCCCCACTTCTGACTGTGAGGACTTGCTGGTGGAGTTCTTGGAAGTGGATG
ACAATGAGGACGAGCGGCTAATGCCATCCCATTCCAAAGAGTATCCGGTCAAGGTGTTAAACCCACACCTAGATCCTGACAGTGACTCTGG
TCATGGAAGCTATGACAGCCATTCTCTTTGTCGAAAGTGTGAGGAGCCCCAGGCCTACCCCCTGCGTTCCACATCCCTGAGATCACTGAG
AAGCCAGAGAATCCTGAGGCAAATATTCCTCCACCCCAAATCCCCAAATAACACCCCAATTGTCATACAGATACATCCAAATCTACAACAT
GGCCTTTACCACCTGGCCAACACACGCAGATCTCCTTACCACAGCATTGCCGATGTGTCGAAGCTAGCTGGAAGTCCTGGAGATACACTGGA
CTCTTTCTTGGACAAAGCAGAGGAAAATGTTCTAAAGTTGTCTGAAGATGCTGGAGTGGAAGAAGTGGCTGTGCAAGGAGGGCCAAAAGCTTC
CCTTCTGACAAACAAAACACATCTTGGCCACCACTCCAGGAGAAAGGCCCCATTGTCTATGCTAAACCCCCAGATTACGTGGAGATTCACAAAG
TCAACAAACACGGAGTGCTATCATTACTCCCCAAGCAGAGAGAAAACCACCAGACAGAAAACCCTGGGGTTCCTGAAACCAGTAAGGAGTATGC
CAAGGTATCTGGGGTCACGGATAACAACATCCTGGTTGTAGTGCCAGACTCACGAGCCCAGAACACAGCGTTGTTCGAGGAATCAGCCAAGAAG
GTTCCACCATCGCTTGAACAGAACCAATCTGAGAAAAGATCTGGCCAGCTTACTGCAACCTCAAGCAACTGCAGACTCCAACTGGGCAGGCTGG
ATTACCTGGATCTACTGCACTCCTTTCACTGAGAGC

MOUSE SEQUENCE - CODING
ATGTCATCTGCACTTGCTTACATGCTGCTTGTCCTCAGCATCAGCCTCCTGAATGGACAGTCACCACCTGGAAAACCTGAAATCCACAAATGTC
GTTCCCCTGACAAGGAAACATTCACCTGCTGGTGGAATCCTGGGTCAGATGGAGGACTCCCCACCAATTATTCATTGACATACAGCAAAGG
AGAGAAAAACACCTATGAATGTCCAGACTACAAAACCAGTGGCCCCAATTCCTGTTTCTTTAGCAAGCAGTACACTTCCATATGGAAATATAC
ATCATCACAGTAAATGCCACGAACGAAATGGGAAGCAGTACCTCGGATCCACTTTATGTGGATGTGACTTACATTGTTGAACCAGAGCCTCCTC
GGAACCTGACTTTAGAAGTGAAACAACTAAAAGACAAAAAAACATATCTGTGGGTAAAATGGTTGCCACCTACCATAACTGATGTAAAAACTGG
```

TABLE 1-continued (mouse gene: Prlr; human gene PRLR)

```
TTGGTTTACAATGGAATATGAAATTCGATTAAAGTCTGAAGAAGCAGATGAGTGGGAGATCCACTTCACAGGTCATCAAACACAATTTAAGGTT
TTTGACTTATATCCAGGACAAAAGTATCTTGTCCAGACTCGCTGCAAGCCAGACCATGGATACTGGAGTAGATGGGGCCAGGAGAAATCTATTG
AAATACCAAATGACTTCACCTTGAAAGACACAACTGTGTGGATCATTGTGGCCGTTCTCTCTGCTGTCATCTGTTTGATTATGGTCTGGGCAGT
GGCTTTGAAGGGTTATAGCATGATGACCTGCATCTTTCCACCAGTTCCGGGGCCAAAAATAAAAGGATTTGATACTCATCTGCTAGAGAAGGGC
AAGTCTGAAGAACTGCTGAGTGCCTTGGGGTGCCAAGACTTTCCCCCCACTTCTGACTGTGAGGACTTGCTGGTGGAGTTCTTGGAAGTGGATG
ACAATGAGGACGAGCGGCTAATGCCATCCCATTCCAAAGAGTATCCGGGTCAAGGTGTTAAACCCACACACCTAGATCCTGACAGTGACTCTGG
TCATGGAAGCTATGACAGCCATTCTCTTTTGTCTGAAAAGTGTGAGGAGCCCCAGGCCTACCCCCCTGCGTTCCACATCCCTGAGATCACTGAG
AAGCCAGAGAATCCTGAGGCAAATATTCCTCCCACCCCAAATCCCCAAAATAACACCCCCAATTGTCATACAGATACATCCAAATCTACAACAT
GGCCTTTACCACCTGGCCAACACACGCGCAGATCTCCTTACCACAGCATTGCCGATGTGTGCAAGCTAGCTGGAAGTCCTGGAGATACACTGGA
CTCTTTCTTGGACAAAGCAGAGGAAAATGTTCTAAAGTTGTCTGAAGATGCTGGAGAGGAAGAAGTGGCTGTGCAAGAAGGGGCCAAAAGCTTC
CCTTCTGACAAACAAAACACATCTTGGCCACCACTCCAGGAGAAAGGCCCCATTGTCTATGCTAAACCCCCAGATTACGTGGAGATTCACAAAG
TCAACAAAGACGGAGTGCTATCATTACTCCCCAAGCAGAGAAAACCACCAGACAGAAAACCCTGGGGTTCCTGAAACAGTAAGGAGTATGC
CAAGGTATCTGGGGTCACGGATAACAACATCCTGGTGTTAGTGCCAGACTCACGAGCCCAGAACACAGCGTTGTTCGAGGAATCAGCCAAGAAG
GTTCCACCATCGCTTGAACAGAACCAATCTGAGAAAGATCTGGCCAGCTTTACTGCAACCTCAAGCAACTGCAGACTCCAACTGGGCAGGCTGG
ATTACCTGGATCCTACGTGCTTCATGCACTCCTTTCACTGA

HUMAN SEQUENCE - GENOMIC
CTTCCCCAGGGACACATATTGAATAGGCCTGCAATGGGGCCTTGGAATTTGCATTTTAATGGCCACCTCATGTTATTCTGATGCACAGCTATGT
TTGAGAATTATGGCTCTAAAGCAAAGCTCTCCAAGAAAGAAGTACATACCTAGGTATACAAGATGATCCAGTGAGTTGAAGTATGAAAATAATA
TAGTAGTTATTTGGGGTATTTTTTCTAAGAAAGAAACTAATCTTTACTGGTATTTAGATTGACAATAGTGCCTTCACTGAGTTCTCAAATTAGC
TCAACACAAGTTCTGGAAACTACACAAGATAATCTCCAGAATCAAAAAGAGTTCAGCAAACACACGGGGGTTGCCATGGTACCTCCACTGCTTG
ATTGCCATTTATGTGCTACAGGTTTTCATCAATGCAGTTTATTTTTATAAAAGCAAGACCTTTAGAATATGCAACTTGACAAAATAGGGAGTGAG
TATGAAAATGTCTGGTACCACACAGAAGTTTCTTGTTTAATTCATGACGAAGTAGTAAAAAGTTGTTGGATTTAAAAATGAGTTGTCCATTTC
CTTTTACAAAACGATAATTGTTCCCAAAGTGTAAATCTCAAATGCATGATGCTGAGTGAAAGAATGCTACATACTGTACAATTCTACTTACATG
GCAGCCTGGAAAAGGGAAACTATAAGGATAGAGAACAGATTAATGGTTGCCAGGGGACAGGGTAGGGACAGGGTTTGGCTACGCAGAAGCATGA
GCGTATTTTGAGGGGCCGGGCTGCGGGGCGGTGGGGTGTGCGGGAGTAATGAAACCATTCTACATCTACATTGTGATGGTTATGTGACTTTTTG
CATTTGTCAAAGCTCCTAGAGATATACACTAATGAGTATGAATTTTATAGCAAGTTACACCCTAAAAACATTCACTTAAAAAAAGTAAGTTTT
GCTGAACAAAAAGAAAATTTCTACCACCTTTCATGCAGTATATTTTTCAGCCATAATAGGTGTAAAACTAAAAACTGAAAATAAACTAAACTTA
GAACCAGATCTGCATATCACTGTGTCTCAAAGTGTTAAGCCAACATCTTTTTTTTTTAAAAAAGCATACTTAATCACATTATTCTCATTAAAA
TTTTGATAATTAATAATTTCAGAACTAAATGGTTTATACCATTAAAAATAAAATTATTTATTTATTTTTAAATAATTTTGACTTTTATTTTA
GATTCGGAGTACGTGTGCAGGTTTGTTACATGGATGTATTGCATGACTCGAGGTTTGGGTGTATGAATGACTCACGTCATCCAATGAGCGCAGT
ACCGAATAGGTAGTTTCAGTCCTTGCCCCGCTCCTTCCCTTCCCTTCTAGAATTCCTCATTGTCTATTGTTCCTATCTTTACGTCCATGCATA
CTCAAAGTTTAGCTCCCACTTATAATAGAGAACATGAGGTATTTGGTTTTCTGTTCCTGCATTAATTTGCTTAGGATAATGGCCTCCAGCTGCA
TCCATCTTACTGCCAAGTACATGATTTGGGGTTTTTATGGCTGTGTAGTATTCCATGGTCAAATTTTTGTTTCATCTTATTTCATTCTTTTAAA
ATTTCTACTTTCATTCATTTATAAATACAGTAGTACATATATATAAATTTATGACTAAAAATACATATGTATTTGGAAAGGCATGCTAAAAATGAT
TTTACTGCTAAGATGATAAACAGAAAACTTTGGAGGTCACTTCTCTAGAAAATAACTCTTCAAAATTTAATGTACGTAGGAACTACCTAGGGAT
CTTGTTAAAATATAAAGTCTGATGCAGCAGGAAGTCTCTCACCAGATCAAATGCTGGCACCTTGATCTTGGACTTCCCAGTCTCCAGGACTGTG
AGAAATAAATTTATGTTCTTTATAAATTAAAGAAAAAATACAAAGTCTGATTCACAAAGTAGGGATGGGGTCTGAGATCTTGCATTTCTAATAA
GATTATGATTAATCTAATAAGTTGAAATCATTTGTTTTGGTTTAAACTAATTTACCAAGTCAATTCATTCTAATTACCTTCCGGGTTCACTCATAG
ACTAGGCCTAGGGTTAAAATGATAATTAGTATGATGCCAGTGCACCTGGCCCTAAGACTATACTTTGAATAGCAGGACTCAGACCACAGTAGCC
CGAAGCATCTATGCAGCTATTATAGAGACTAACAACTGCTGCATTTGATTCAGCAGACTCAGTTTTCCCTCTTTGGGTTTGGGAGACATGAAT
TCTTATCAGTCAATAGGCCAGCTCTCTTAGCATCTTCCCATGGAGCAAATGATTCCCATTCCCATGCTCATAAAAGCTGATTTTACTTAGGTCA
CTGCTTATCCACCAGCGTGGGTTTCCTTAGAAGGAAGGACACATTGTCTAATAATGACGTGACATGATTTCCAATTTCATCCATGTCCCTACAA
AATGTCAACTCATATCAGCCTCACAATGACCTTTGGAGGTAGAACAAAGCAGATGTATTATATAAACCCATTTGCAAGTGCTACATGACAGAAGCA
AGCACAGTGCTTTCTTTCAGAGTTGGAGTGATCAGGCAAGCTTTAAGAAGAAAAGTACCATGGAGTCTGAAGATCAAGAATGGGTAAGGTTTTT
AGATGAAGGGTGGGAAATAACATTCCAAGAAGAGAGGATGGATTCAAACACACTGTAGATATGTATTGAGCTACTACTACTCTAAAGCCCAATG
AAATCAGCAGGAGTAAAGATGTTCTAACTTTATTCTGTGGGAACATCTAAATGTTCATATATAGAATGATTACATAAATTATTGTGCAAAAAGATTATAA
CATGAAAGCATTTGAGTTTGATGTAGGCAAGACTGGTGAAGATGAGTCCAGCCAGGGGGGCTATTGAAGAGGAAGAAGTAAAAAATGATGAAGG
CACAAATTGAGGCAATAACAGTGGAAGGGACAAAAATATTTAAGGACTTCATTCCTTTTTTTTTTTTTATTATACTTTAAGTTTTAGGGTACA
TGTGCACATTGTGCAGGTTAGTTACATATGTATACATGTGCCATGCTGGTGCGCTGCACCCACTAACTCGTCATCTAGCATTAAGTATATCTCC
CGATGCTATCCCTCCCCCCTCCCCCCACCCCACAACAGTCCCCAGAGTGTGATATTCCCCTTCCTGTGTCCATGTGATCTCATTGTTCAGTTCC
CACCTATGAGTGAGAATATGCGGTGTTTGGTTTTTTGTTCTTGCGATAGTTTACTGAGAATGATGATTTCCAATTTCATCCATGTCCCTACAAA
GGACATGAACTCATCATTTTTTATGGCTGCATAGTATTCCATGGTGTATATGTGCCACATTTTCTTAATCCAGAAGGACTTCATTCCTAATTGG
ATGTAGAGTGTAACAGAGAACACTGACAGTTGAAGCCATAAAAAAAAATAATAAGCTTTTATATCTCAAGGCCCATAAACAAGTGCATGCC
CTTTGACCTAGTTGGGCCTCACCTGGTGTTTTAGACAAAGGAAATTAATTCCCAAAGGCAACTTTTTTTTCTACACTTCCCATAAGTATGTTTA
TTACAGCATTATTTATAGAGTAAAAATTTGGGAACAATCTAAATGTTCATAATATTGTGCAAAAAGATTATAA
TGATAAGATTACATTAAAAAATTGAAGGATACTTTTAAAAAGATATAAATAGATATATTTCCTGGATGGGAAGAATTAATGCCCTAACAATATC
AATTTTTTCTCAAATTAATATATAAATGTAATGTAATGCCAAAAAAAGATTTTGAATTGAACAAATTGACCCTAAAATTTTATGAAAAATAAAT
ATAGTGGACTTATCAAGACAATTTCAAAGGAAAGTGACAGTGTGCTTTGCACTAACAGGTATTGTACTGTTTTTACAGTTACAGTAAACAAAA
GTCTATATTTTTGGCATATAAATAGGCATCTCAAAGAAACAGGATGGTGTCCCGAATTCATAAATATATATCAAAATGTAACACATGATATG
TGACACTAGAAATCAGTGGAGAAATTATGAATTTTTCTATAAGGAGTAAAATTAAAAATAAAATTCAGGAGAAATTAACTGTCTACCTTATGT
AATAGTTAAAGATCTATTAAAAAAAAAACAATTTAACAGAGTTAATTGCAAAGAAGCAATACAAAAAACCCAAAAGCTGTAACAGAAATAATT
GACAGATTTGAGTACATGAAAATTAAAAACTTTTGTGCAATGAAACAGTCCATAAACAATATCAAAGGAAGCCTGACAGGCACAAATGTTTGCT
ATACATTGAACAAAGTGTTAGTATGTTTAATAATAAAAGATGCAAAATTAATTTTAAAAAATTGTGGAGGCCAGGCACGGTGGCTCACGC
TGTAATCCCAGCACTTTGGGAGGCTGAGGTTGGTGGATCATGAGGTCAGGAGATTGAGACCATCCTGGCTAACACGGTGAAACCCCGTCTCTAC
TAAAAATACAAAAAATTAGCCGGGTGTGGTGGCAGGCGCCTGTAGTCCCAGCTACTCAGGAGGCTGAGGCAGGAGAATAGCGTGAACCTGGGAG
GCAGAGCTTGCAGTGAGCCGAGATTGCACCACTGCACTCCAGCCTGGGCAACAGTGCAAGATTCCATCTGAGAAAAAAATATATATATACG
GGCCAGGTGTGGTGGCTCACACCTGTAATCCCAGCACTTTGGGAGGCCGAGGTGGGCGGATCAGGAGGTCAGGAGTTCAAGACCAGCCAGGCCA
ACATGTGAAACCCTGTCTCTATTAAAAACAGAAAAATTGCTGGTCGTGGTGGTGGGCACCTGTAATCCCAGCTGCTCAGGAGGCTGAGGCAGG
AAAATTGCTTGAACCTGGAAAGTGGAGATTGCAGTGAACCGAGATCATGCCACTGCACTCCAGCCCAGGTGACAGTGCAAGACTCCATCTCAAA
AGAAAAACAGGCATAAGATTGAACAGCCACAACATAAGAGAAAAAGTCAAAATATAATAAGCACATGAACTCAACCTTGAAGGCAATCAGAACA
CTGTGAATTAGAACAATGAGCTATCATATTTTGCTTATCAGACTAGCAAGATAAGATTGATAAAGTCCAGTGCTAGCAAAAATGTGAGTAA
ACATCCTTGGTAAGAGTGGACACTGAAACATTTGTGTAAAAAATTGGAGTATATATGAAAATTTAAAATGTTCCTACCCTGTGGCTCAGTAA
TCTCATTTCTAGGGCTTCTCCAACAACATATTTGGAGAGCAATTTGGTAGCTATCAAAATTTTAATGTTCATTCTCTTTGAGCCAACCAAGTC
ATTTATTTTTTATTTTATTTATTTATTTATTTATTTATCTATTTATTTTTTTGAGACACAGTCTCAATCTGTTGCCCATGCTGGAGTGCCATGGCACT
ATCTCGGCTCCCTGCAACCTCTGCCTCCCAGGTTCAAGCGATCCTCTGGCCTCAGCCTCCCTAGCAGCTGGGACTACAGGCGTGCACCACCACT
CCTGGCTAATTTTTGTATTTTTAGTAGAGAGAGGGTTTCACCATGTTGGGCAAGCTGGTGTGGAACTCCTGACCTCAGGTGATCTGCCTGCCTT
```

TABLE 1-continued (mouse gene: Prlr; human gene PRLR)

```
GGCCTTCCAAAGTGTTGGGATTACAGGCAGACGCGAGCCAACCTGCCTGCCAATCAGGCCATTCTAAGTATCTATCCTAAAGTCCATGCAAAGA
CAATCCTAGCAGCACTTCTTAAAATAAAAAGCTGGAATTACTAAAGACCTAACAATGGAAGAATGGTAGAATATATTACAAACTATGTAACCAT
TAAAAAAAAATGGAGTAAATCTATACATAGTTACCTGGAATATGTGATTTCATTAAGTTTAAAAAAGAAAAGTCACAGAAATTATTGCATTTTG
AATTTTTAAAATATTTGCATGTGCATACAGAGACATGACTATATACACATGTAAAAAGGAGGCAACCACCAATACGTCAATGGTGGTTACCTC
TGAGACAGGATTAGATGAAGGAAGGAGGATGTGTGATTTGGAAGTACTATATTTTACTGTATAGATAAAGATGTAGATTTCTTTTTAACAGTGC
TAGGATTTGGGGTAGTTTTTTAATCTTTGGATATTTTTAGCAGTTTTCTATTTTTTTCTAAAGAAAGAAACATAGTTCTCCCACATATGGACA
TGCCATTCTTCTGAGGATGCTTAAGTTGACCCCAGGAGGAGCCCTAGCTGCTGTTCCCCATTAGAGGCCCCTTTTCAGCAGGAAGTAGCCAGAA
AGAGTCCTTGCCCAAAACCCCCTAACAGCAGTTAGTGTGATATCGCCACAGGGAGGAATGTGGCATGAGTTATCAAGAAATTATTTTAGGCAGA
TAGAGAGTAAAAGGGGTCCTTGGGAAGTTTTCATTTTTTAAAGTATCTCCAGAAAAGTTTCTTGTAAAACCCCGGCTTTTAGAGCCAGGCGGGC
AACCTTTGATATGCAAACCTAGGCCATTAGAAACTGGGTTCACCCAAACATGCCGATTCCAGGGACCTTCTTGCCCTTGCCCCACATGTTCCTG
GCAACATGGCCGCCCCCACATATCCCTATTTGTGTAGAACATCATGCGCCCCGCATTTGCATATTAAAAGGCTAGAGTGGGAGGGCCAGCTCT
TTCATGGGCTACGTGAATTACGTGCCTAGTCAAACCAATCCCTGAGCCCTAGGCAAATCAAACACCGCCTCCTCCAGCCTCTGCTTATATACC
TGGCTGGTATCCGCAGCAAGTGGGGACTTACTCTTTTGGCTTTGGAGCGCCCCCCTCCCTCTGTCTCTGTACAGGGAAGCTTCTTCTTTCTTCC
TTCTCCCTTTCCTTCTTGACCCTTCTTGCCTATTAACCTCTCCACTCTCTTAAAACAAAAAAAAAAAAAAAAAAAAGAAATGTGGTTCTCAAAG
AAGACAAATGAAGTAGCAATGATAAAACTCCTTCCCTATTTGAGAAGGAGGAGAGAGAAAAGGAGCCACGGCAGAAACCAACAGAGGAATGCCA
CAGACAGAGGGGAGGCTCCCGCCAGAGGATGGCAGAGGCCTGGAAGCCAAGGCGTGAGAACTTCAAGAGGAGGAAGTGAACCGAAGCCCAGTGC
TGCAGAGAGGCCTGGAGGGCCCTCCCAGAGAGCAGCCAGTGAGTGGTAGTGATGAAAGCCAGGTGCAAAGAATTCAAGGGAGCCATTTTCCACC
CTGCCTGTGCATTTTTGTAAAAACAGAGAAGTCAGAGCCCCATTCTAAACCTCCTGCATTAGAAGCTCTGCAAGTGACACCCAGACACAGTACA
TTTTAAACACTCAGGTGATTCTTGTTCACAGCCAAGGTTGAGAACCAGTGAGTTAAGGCACTGAGAGGGAAGTAAGTAAGGAAAGCTGGTGTGC
GTAAGTCATTCTTTCACTAAGTTTGGCAGGTAAAGAAATGAGTGAATTAAACTGTAAAGCCATCAAAAGGGTCAAAGAAGATGTAGAAGTTGTA
GGTTGAGATAAAGAAGCCTATGGGCAGAAAAGATTAAATATGCAAGAAAGGTAGAGGAAAGGGGAAGGAAAGAAAGGAACTTGATGTTTCTAG
ACTTTGTTAGATGGCACACATTTTTACATATGCCATCACATCTATTATTATTTGACTGGATTTTTGAGGCACATGCTACTGTGTCCAATTTACA
GTGAGAAACCAAGAATAGCAAGGACCTAACCCAGTGCCAGTGCTGGGCTCTTCCTCGCATCAGGCTGAGAAGCAAGGTCTTGGAGGAAGTAAA
CGGATATGGAGTCCAGGACTCAGGTAGGGAGTCAGCTTGCAAAGGACGAACACGTCCGCTAAGACAGAGATGCAGAAATGAACTAGAGGAGGAC
ATCAGTAAAGAAGCTGTGAAGCTGGAGCACATCAGTGCATAGAGAGAAGGAGATAGTCAAAGAACCACTGTGGGGCAGAAAAGGAAAATATAGT
GGCTCACTGCGGATTTCATCATCTCAGGAAAGCTGGGGCAAGGTAACTCACTGACAATGAGTACCCGTGGCTTTGTGACAGTGCCTGTGTGCTA
CACAACAGAGCAGAAAGCCAGCCCTGCCCTTCTTACCAGTGAGGTATGGATTGACCACGCAACGACCAGTCTGTAAGCCAGGAGTACAGACGAG
CCAAGCTGCCTGCAGCTGAGTGGGAACCACAAGGAGGAAAAGCCAAGTCCCTGCCTTCTAAGAGCTGACAGTCTGGAGTTACCCAGAGTGATCT
TCTATTTCACTAACTGTTAAAATAGTCTGATTAGAACAACTATTGTAGAATTGAGTGACCCTTTGCTTTGCAAAGGTCATATAGAAATATTCTG
CCACTGAGGATCTCATGTCGCCCAGTGGTTCTGAAAATAAATAGAAGTTGCGTACCTTCATGGACACCCATGAATGAAAGTAAATATACCCTAA
TCATCACAGGAAGCATGTGCGGTCTGCACGTGAAAGATGCATCTCCCATCAACAGAACCAGGTGGAGTCTATGTTTTAATAAGGACGTGT
TATTGATCGGGAAGTATTAGGTTATTATGCCTAGGTAGTTGCTTCTGGGATTCCAGTCCAAAAGGATCACCAAAGCATCATGGGATTTTCAATG
GCTTCCTGTGGCTTGGCAAATGCTCACTGCTAACTGTGATTTCCCAGTTATCCAGAGTAGCAGTCAAATCAAAGGGGAAAGCCTCATGTTTCAA
TAACTTAAAACAAAACAAAAAAAAAAAACGGCCAGGCGCAGTGGCTCACGCCTGTAATCCCAGCACTTCAGGAGGCCAAGGTGGGTGGATCATGA
GGTCAGGAAATCAAGACCATCCTGGCTAACACGGGTGAAACCTCATCTCTACTAAAAATACAAAAAACTAGCCGGACATGGTGGCACGCGCCTGT
AGTCCCACCTACTCGGGAGGCTGAAGCAGGACAATTGCTTGAATCCAGGAGGCAGAGGTTCCAGTGAGCCGAGATGGGGTCACTGCAATCCAGC
CTGAGCGACAGAGCGAGACTCTGTCTCAAAAAAACAAACAAAAACAAACAAAAAAAAAAACTCAGTAACCTTGGTTTAAAGTATTTCCTTGGTG
GCCCTCTGGGTTGTGTAACAATCGGATGCATTAATTATTATGGCATCAAATGACACCAGCAACATACATAGTCAGAAATAACTATTTGATTCAG
GCAGGTGCTATTATTTGTTTCAGCACTGTTAAATGTGGGGTTTTGTTTTGCAAGAGAAAAGGCGGTTGTGTGTGGTTTCAAGAAGAAGAAAA
GTCAGAACAACATGCAGCCCATTAGAAAGATAAATTCTTTATTTGTTGGAAAACAACAGAAGTGGGGCTATTTAGGCACCGCCAATGTTTATTA
TATTCATATGGCAGAGAATAAACACAGCACACTAGAGTTTGCGCTTTGGGTATTAAAAAAAAAAAAAAGCAAACCTTCTTAGGTCACTGACT
ATCTTCTTTTGCTCCTTTCTATCTGACTCCTCAGGCAAGGTGCAATTCAAATCCCTGGAGAACCTCTCAAATATAGCTGCTGTTCAATGTTACT
CAGAAATAAGGAAAGAAATTTGACACGGAGACACTCCACATCTTGGCTGCCTGGAAAAATATCATCTTTGAGGTCATTCAACTCACTAAGTCAT
TTTTTATTATTGTTTTGTCTGTCTATTTTCTGGTACAGTCTCAATGAAAGATATGTGGCCCTAATCATGCAAAACCGATCTGGGGGGAATCAGTT
GTTTCTTCAGGTCTTCGCAGGATTCCAGCTCCCCAACTACCTCCGTGCCCTTCTAAAACTGGCAGGCTCTGGACGTTTGCATGCTGAAGAAA
ATCACTGTTTTGCCTCCAGCAAGGAACATAAATGTTGCAACACTGACTCCTCCTCTCATGAAGAAAGAGTGAACAAGTGCACCGAGTTGAGCTT
CTTCTCACAGAGCCACCGGGCTGGGGACCGGGGAGCGGAGGCTGAAATCCCAGACGCCGGTTTTCTGGGCTGGGCTTTCTGCCTTACTCACTC
CTTCTCCCTCTTTTCTGGATTTTACCGACCGTTCGCGAAACAGCTTTCCACACAATGGAGCTTCATGTCCTCGTGCAGGAAGTACTCATCGACTG
ATGTGGCAGACTTTGCTCCCTGGCAAAAGTAGATACCCATGGCGAGCTGAGGCCGCCTCCGACGGCGCGCGGCAGGGCTGCGCGGGCGGCCGC
TCTCCGGGATGCGGGTTCGAGGCCCGCGTGCTGAAGGGGAGAGCGGGGCCACCGGCGCGGGCTCCTGGAGAGAACGCCAGCCAGGAGCCAGAGT
CGGCAGCCGGCGGGAAGCCCGGGATCCGCCCGCCTCCCGCCCGGATGTCCCTTCTCAGAGGGGCTAAAAAATACTCTTAAGGTGCTTTGCCTC
CACCACTGCCCCCAACCCCAGCTTTTACAAACTGCACTCGGCTCGCATTCCTTTGTCAAAGGCATCTTCACCTGTATCCTTGAGCATGAGTT
TCGGCGTTGATTGTGGGATTCTCAGAATGCAAATTATTTGCGTCAAAATAAAAAGAAAAGAAAAAAAGAGCGGGAGGGAGGGGAAGGGGCCAGAC
AGGTGATGTGATGAAAGCCGGACTCGAGACTCTCCCATCAGCAGCAGCCGCCGCCGCAGCAGCCTCGCGGGCATCCGGCGGGAAAGTTTAGGG
TTAGCAATGCTGACCTGAAAGGTGTTGCTCCTCCCAAAAGTCAGCGGGGGTAGGGGCAGATGAGCAGCCTCCGGGCCAGAAGCCGGAGCTGGAC
GGAGGCACCTAGGCAGAGGAATTGCAGCCCGGGAGGGAAGCTGGAGGAGAGCCCGCTGGAGAAGGGAGGGAGGAAGGGAGGAGGGAGTTGGTTAA
AGTCAGGCAAACTCAGGTAACTGGAGGGCCGGCCCGAGTGCTACGGCAGGGGAAGGCAAGGGCTGGAGTTCTGGCTCTTTGAGTAGAAAACTAT
CCTTTTAGTGACCTCTACCTGTATCCTGGGGAAGCAACCCACACTGCCCTGAAAACAAGCAACGTAGGGGATTCTATGACTGGACTTGAAATG
GTTGCAAAACATTATTATTAGTCTGGAGGGATCACTTTGTCTTCATTTGTCAAGTTGACCGGGCAACATTTCCCACCTGAAATCGTGCTTCACT
TGACCAGGGAAGTGCTGCTAATCCCAATCCTGACCATCAGCTGTGCAAACTTGGGCAAGAACTTACCCTCTCTGGGCTTCGATTTTTTTTCTG
CAAAGTTTAGGGAATTAATTAATTATATATATATATTATAGAAATATATATAATATATATATAAATGTTTAATGAGGTGGAAGTGCTGAATAGT
GCAAGAGAGGAGCAGATGAAAATATTAATTTCAGTGGTTCTTAAAAATTAGGGGTGATAGGTCCTTTTGAGAATTAGCTGTGAGTCCTCTTCCT
GGGGGAAAATGCATATGGCATGTACATAAAATTTTACATGCAATCCCTGAGGGTTTGTGGATACTCCCTGAAAGCCATGCCTGAATCCCAGGTG
ACAATCCTTATTCCTCCTGTATCAAGACCACCCAGCCAACTCTGCTGGTTGGGCTGACTGTGGGAGTAATCCACAGCCTTCTTGG
GGGTCTGGAGTCAGCCACGCTGCTGAAGGAGACAGCTCCCCTGTCATGGGTGAGCTCCCCACATGCTCTCTCCAGAGCTCTACCAGCCTCTGAC
TCCAGGGGACCCCTCCTCACAACCCTTTTTAATGACTCTCCTAAGGCGACAGTCCTTACCCCTAGAATTTTCAGTCCCACCAACCCTGGAGAGC
CATCTAAAGAGGATCGCTGTCTGAATCAGAGTGCTCTTCAGGTCACCTAGCTGGATGGCAGGGAGGCCAAGGCTTTGTTTGGAAATGAAGCAGT
CTTTGCTCCCTGAGGCATAGTATGAGTAGGCAGCCATATTCTTTTGAACCTCTGTACTTTGCCTTTAGAGGACTAAGGACTCACATCTCTGGGG
ACCCTGGGTGTTCCACTAGCAGTGCCAGCAAGGCACATCAGAAAACACACGCCTTTGGAGCTCAACAGACTGGGCTTCAGATCTTGACTCCC
ACACTGAGCAAGCCTCTGAGTTTTCCTGAGCTTCACTTTTCCTGTCAGCACAATGAAAATAATGCTGCTTTTTTTTTTTTTTTTGCATGGTT
GTTGGGAGAATGGAAATACTATGAATCATGCCTAGCCCATAGTCAATGATAAACTTTTTCTTAATATTAATGTGGCACCATAAATAAGTGTTCA
ATAGTCTCATGCTTTTAAGAACACTTACTCTCTCTCCTAGGGCTTACATTAGTAGAAGAATGAGTAAAATTAGTTCTGGTCTAGTTATG
CACAAAAAGGAGTGGTGGCCTCAGAATACAGAGTCAGACTGGCTGTTCGAATTGTGCAGTGTCAAGGAGGACACTATGTATTGCCGGCAAGTAA
AGTATGTCCAGACCGGCGTGGATACTTGACCTGTCTCTCAGTTCTCTTTTGACCCATAATCTTGAGTACAAAACAGCTAGTGCTGTGCCTGCAG
CTAAAAACAGCCAGGCATGGAAAGAAGTGTTGTGGCTGGGTCCATCTTCAGAAACTGTAGAGAGAAATATCTCCATTGTCATCTTTCACAGTTT
GGCACAGATGTAGCCAACTCAGCATGTACTCTCTCTCCATGGGGTCCTGGTGCCTCCATTGCAAGTGGTCAGATGATGTAGCAATGAAGAAGG
AAACATCGGAAACTTAAAAGGGAAATTGGATATCCACAGAGTAGCCAAAGATCTATCAGTATACTTTGGTGAGGTATTCCTGCATGCAAAGATAG
```

TABLE 1-continued (mouse gene: Prlr; human gene PRLR)

```
CAATATTCATGCCTACTATTTACTGAGCCTTTAAGATGTGCTAAGCACTTTCACACATTGCCTCAATTAATTCTCATAGCAAGATTGCAGAGTA
TGAGTTATCATTTAAAGCTTTACCAGTAAAGAAACTGAAACATGGAAATGTACATACACCCCCCAACCCCACCCCCACATCCGCCTAGCTCAG
GAAAGGCAGAACCAGGATCCAAGCCCAGGTCTGTCTGACTTTGGCACCCACTCTTTTTCCACTACCCAGTGCTCCCAAGCTCCCAATATCAGG
CACTTGCATCAGCCAACCGGATTAAGATTCTTCTAAAAGGCAGGAATAGCCAAATCTAGTGGGTGCTTTTAAGTGGTGTGAACATGTGCTTGGC
TTGTGATACATATTAACGGGTAGCAACAACAAGATCACCTATGGGAGGATAATATTCCTGACCCTTCCCAAGCCCAGCCATTAGACTCAAGATT
GGCAATATCCAACATTAGCAGGTGAGGCTGGCGCTCTGTCACTGACTTCCTTGGTAATCCTTTTAGTTAAACAGAGCTCTGGAATGTTCATTCT
CTACCACCTTTAGAATCAGAACACCACTTACCTTTACCTCCCTGTGCTGAGCACGTTTTCATTCATTTATTCGACAAGCATTTGCTGAGCTCTG
TTTTGTGCTGGGCACTTGATGACACAGTGGGGAATGAGACACACAGGATCCCAGCCCTTGTGGAGCTTCTATGCCAGAGAGAGTGACAGAAAAC
AGTCGGGTGAACAAATACATAAATAAAATCATTTCAGATACTGATAAATGCTATGAAGAAAATAGAGGCTGAAGGCTACAGAGGGACAGGGCGT
GGGAGCAACTTTCAACAGGGAAGTCAGAGAAGACTGCCATACAAAGGATACCCTTGAACTTAAACCCGCATTTTCAAAAAGGGAGCCAGCCCTG
TGAAAGTCTAGGGAAAGGGCTACCTTAGCAGAACTCTCAAGAGAAAGTTCTTAAATTGGAGTAAATGAAGCAGTAAAGCTTAAAGTCTGAAGAT
GGGCCCTTTAGAAGTTGACTTGTATATAGGGGGAATTATTATTTGAATGCCTACTATACTATTCTAAGCTGTGCTGTATACTCTGTTTATCTTC
CCAATGATCTGGTGAGTTAGCTATTTTTGTTTTTATTTTACAGTTGAAGAAACCAAGAGTCATCAAGGTTAAGGAGCTAGTCCAAGGTTATGGA
GCTAGTCCAAGGTTATGAAGCTGGTATTTGAATCCCTTAGTCTATTTCACTCCAAAGCCCACAACTACTTGCTAACACAGCATGTGGGCTTTGA
GATAATGTCTTTTGGAGAAAGTAAGGAAGCCGATAGAAGGAGAATATCAAAAGTAAATTAAGTAGCTGAATGCTGACAACGATTTGTATTTGAT
GTCCCAAATTCCAGTTAGTGCACCTACAACTGAACTGTCCAATACAGTAGCCACTAGCCACATGTGCCTATTGAGCACTTGAAATGTGGCTATT
TCATATTGAGATGTACTGTAAATGTACAACGCACCCCAGATTTTTAAGACCTAGTATTCCCCCAAAAAAGTAAACTGTCTTGGCCAGGTGTGGT
GGCTCATGCCTGTAATCCAAGCACTTTAGGAGGCCAAGGCGGGTGGATTGCCTGAGCTCAGGAATTCGAGACCAGCCTGGGGAACACGGTGAAA
CCCCGTCTCTATTAAAAATGCAAAAATTAGGCAGGCATGGTGGTGGGTGCCTGCAATCCCAGCTACTTGGGAGGCTGAGGCAGGAAAGTCTCTT
GAACCCGGGAGGCGGAGGTTGCAGTGAGCCAAGATTGCGCCATTGCACTCCAGCCTGGGTGAAAGAGTGAGACTCCGTCTCAAACAAAAACAAA
AACAAAAGTAAACTGTCTCAATTTTTATATTGATTGTGTGTTGAAATGATAATATTTTAGGTATACTAGTTTAAATAAAATATATTAAAATTAA
TTTAACCTTTTCCTTTAATGTGGCTTAATAGAAATGTTTAAATTACATATGTGACTCACATGATATTTCCGTTGAACAGCACTGATCTGATCTAGACT
AATAAGTTGACAAATACATGATAGGACCTTTTTCCCCCTTCTTCCAAACGTGACTTCTTCCTCTGTTCTTGTGTCAGGCTCCTTCTCATCTGCC
CCCATATTCAGTTATTTGGTGAAGCACGAGAGAAAAGAGGTCCCTCTTCCTTCTCCCCCACCCTCATGCTGCTGGTTAGCAGGTGATCATTTGA
AGTCCACTATACCATGTCACTTTGGGATCTGATAAAATAGACTCAGTGATTATATTCATCACCAAGACCAATCCTCTCACTCAGGTAAATCTCA
AGAGGCTTTCAAACGTCCTACAATGAAAGGGTCATTTTAAATCTGGATTTAAAGTTTTACCTTTAAATCACTTCCTAGTACATTGTCTTTGTAG
TTTTGGGCACTTTTGTAAAATCAGACGAGGAGACAACTAGAGCTTCATGTTTTTGTGCAAAGACTCATTAAATAAGTAATCTCATGCAGTAATAAA
TGTTTCTCCCTGTCCTCTTGCTTAAAACAGCATGAACAAAAGTAGTCCCAGTTGCCAGAAGGGCTACTCCAGGGGCATCACAAAAGACCACCT
TTGGTTTCTTTCTTTTGTCCACTAGCTAAAGTGGCCCTCAAATATGTCAATGAAATAAAGATATATTTTTTTCCTGCAGTTTCATTTATTTCA
AAAAAAAGAGCAGTCAGATTCTGGTATTGCTGGAGAAAGCCTCTGAAGAGCAAAGACCTGGATTCTGCTTTTGTGTACTCTACTGGTTTGCATG
TTACCCTCTCTCTCCCTTTTTCCCCCAACTTTCTCCCTTACTTCCGTAGTAAGTTTGGTGTTGATGAGATAATGCCACAAAAAATGCTAATG
GTGAAATGTGCTGTACAAATTGGCCATGGTTATGATTGATAACCTGAATACAAATGGCATCTCTAGACATGTGCCTGCAGGGAGGAGTTGCCTT
TATGTAGCTGGAGCAAAACATTATGTAAGATTCTCTTGGAATAACATTTGTTCATTTCCACTTGAAATCCAAATCTGGGGGAAATGGCAGTAAA
GAAGCTGACAAGAATGAATCTTAGTGTATCTGTCACTGGTAGACTGAGTTCTTTCTCTAGTCTGTATAGGTTCCAGAGAGAGAACACCCAATTG
AAAAAGGACAAGCTGGTTTTATTCACTGGCCAGAAATGGAAAATGAAGACCTCTTGCTCTAAAAAAGTCACCTTCTCCCTAGCTGTGGGAACT
GCAGGATTGTGATGAGTTAGATGTGGGGCGGGAGCTATGTAAACACATGCAGGGAGAAAGTACAGAGGCACAGACACAGATAAACATGTTTCT
CCATGCGTCCTATGGAGAGAAAATGGCGGCAGTTTTCTTCTAGGGATGGGGAGCCCAGCATTGTAACGCTATGTTAATGACCTAAACGGAACAA
GGGGTAGCCAGTTCTGGTTTGCACTGGTTTCCTGCAGGCCTCTTGTATTTGGCAAAGGATCACCAAGCTCCTGCGACATCCCAGGCCATCTGGA
GTTCTTTAAGCAAGAGTATCTATAGATAAAGAAACTAGGGAAGATAACAATTTAAGAAAATAATGACTTTCCCAGCTATTTCTCTAGGGCTGC
CCTGGTAATATTTCTACATCAACAGCAACACATATTTTTCAGCATTGTGTAAGCCAGGAAATCTATGCTAGACTCCACGGGGAAAATAGAAGAA
TAAAACATGGTTCTTGCTCTGGAGGAGCATAGTTCCTAGTTGGGAAGGTGGACAGAAACATAAAAGACCAGTAGCATGTAAAGAACATTTTCTA
AGTGTTACATAAATGATGCAAACAAAGTTTTGCAATTCTGGAGGGCAGCATGCCCATAACCTCTAAGGTATATTAAGAAAGACAAAGTAGAAAA
TGGGCATTGAGGGCTGGAAGCCTAAAGACACAAGGAGGAAGGAGAGACCACCTCACATAGAAAAAAATGCACAGTGGTGTGGCAGTGGAAAT
GTACATGGGTTCGGGGGTGCGTGATGTGGAAAAGAACAGTTGGCTTAATCCAGTGGCTCCAGATCTGAGCTTTACATCAGAATCACCTGAGAAG
CTTTTAAAAATTACAAATGCCTCAGCCCCACTCCAGAGCTTCCATTTAATTAGTTTAAGACTGGGGACTGGTCTCAGTGGTGTTTCTGATTGAT
TTTGTTTTGTTTTTGTTTCTGTCTCAATTTCCCAGAATATTCTAATGTCAAGTCAGAGTTGAGAATCACTGAGCAAAAACCAAGATTTTTATAT
CATAGTCATGGGACATAAAATGAAAGAAGTAATCTTTTAAAGGAGATTAAATGGACAACCAAGAGTGTGACCTTTAATTTGTAGAAACTGTATA
TACATGCACATTTGTATGTAGTCTTTTAAATTCACAGATAATTCCTCGTGGTGATTCTGTCTACTTGGATGATGTGGCTGAAAGCCTTTGTAAC
CAGCTGCCTACTCTTGTCCTCTGTGTACTTTGGGGGTGTCCTATAGTGGATCCTAGCTAAGTGGGGCACAATGGGCATCTCACAGGAGCTTGTT
TCTACCAGGCTTTTTGTAATCATTGCCAAGGGCTTTATTATCATGCCTAATAGTGCCCACAGTAGCTATTTTATAAGCATCTGCAATCTTCCCT
CACCCTCTCCAACTTTACAAATTGAGAAATGGAGTTTAATTACTTGCCTTGGGCCAGGAGACTAGCTGGTGGTGATGAAGGTGAAATGAGAATTCTCA
GGGAGGTGAAATTAGAATTTCCAGCTACTGAATTCCACATACCTTATTAAACTCCCAAAGTGAGTCTACCCACTCTCCTGTTGGTGTTAGAATG
TTATTTCTTACATGAATGAATCAGTGTCACAGATCAGTAGGTGAACATGACTGGTTTCCCTAAGCTGCCAACACTGTGATTATCTGAGTGTCAA
TGACCCATAGGCAGTCACAGTGGTCCCGAGAGCCCCGTCCCTGATGCCTGGGAGCTCTCAGTCTAGTGAAGTTTGGCCTTGCATATTTATAGTT
TATCCACTCTAACATCTGGGAAGTGAAGACTCTGGTTGCTATTCCACTGCTCCTAGCCCCACACTTTACGGCTGTTCTGATTTCCCTTCTCTGA
AGCTCTTGTTCACTGAAAGGATATCAGTTTTTGCTACACCCCTGAAAAAAAAGAGGAGAAGCCCAGCATTTTAAACAGTGCTTTTTTTTTTC
TTTTGGATGGAGTCTTGCTCTGTCTCCAGGCTGGAGTGCAGTGGCGCGATCTCGGCTCACCGCAACCTCTGCCTCCCGGGTTCAAGCTAGTCTC
CTGCCTCAGCCTCCCGAGTAGCTGGGACTACAGGCACGCGCCACCAAGCCCGGCTAATTTTTGTATTTTTAGTAGAGATGGGGTTTCACCATGT
TGGCCAGGATGGTCTCGATCTCTTGACCTCCTGATCTGCCCGCCTTGGCCTCCCAAAGTGCTGGGATTACAGGCATGAGCCATTGCACCCGGCC
AACAGCTACATTTTAAAGAATCCTTTATATGTGTTGGGAGCTTCTGGGTTCACTGCCCACGGTGAGACTAGGGGTGGGGACGGACGTTCTTCTG
AAGGACAGTGCGGGGAAAAAGCCAGAGTCTTGGCAATACAGCCTCTTTAGACAAAAAGATAGGTCAATTTGTACCATTCCCAAATGGTTGGGTT
TTCTTTTCTCTGTCTCAAAATCCATTACTGATTTAAAACAATTTCCAAAAGCTTTAGCAATAGCAAAAGCAAGCCTCTTAAACAGTGTTGCTC
CACACTGATTGCACGTGAGAATCACCTAGGGAGCTTTAGAAACAACTATAGACTCACTGAATCAATATTCTGGGAAGGGGCCTGGACATTCGTA
TTTATTTACAGTTCTCCAGGTTTATAATGTGCATCCAGGGCTAAGAGCTACTATCTGGTCAGCTATGATCCAAATCTTAATTACTTATTTGTATT
TCTTCTTTTGCCTTGTTTTAGAGTCTCATGGCCCAGAAAACCATCAAACTATATTTTTGTTGAGTAGCAATTTCATCATTCTGTTCTTTAAAAA
ACATGATTTGAGCATAATTTAAGTTTGCTACTTCTATAGAGAGACCTCACACTCAGTAGCCTCATCACTAAAATTTTCTGTGTGCAATTTAGA
AATCACATTGCCAGAAGCTTGCTAATTAATTATGAGACTGAAAGATAAAGGTTAAGCTTTCCTGCCACCTATATATTAGATTTCCCAATTGCTA
TGTTAATCTTTAGTTAACCAAGACTTGCTTTCTTGTCTCAGCCATTTTAAAGCCAATTAACTCTGTTCCTGTTCACACCCTTATTAAAAATATA
ATTACAGCAGTAGTCTCCAGGGACTGTCATTGGGTAGGCTTTACAAGGTAAATTAGCCAAGAAATAACTAGGCTGTGTAACACCCTCTCAGAC
CCTGGGAAATCATTTTGGTTGCAGAAGCTACTTAGTATCAGATAGGCTGGGGTACTCATAAATTTGGATTTGGAAAAAGCCAATTCCAAGTCAT
CCTAAATGTGGAAGAATCTGTGATTTTGAGAATGATTCTGGAATCAGTTATCCAGGGTCCAGCCAAGTCTGATACACCGATCCTCAGAAGGTTG
TATTAATAACAAAAAGAACCAGGTTTTTGTTATTAGATTTGATGGAAGAGGCTGGGGGACAGAAGGTGATGTAGCATTTTGTTTTCTGGGGTGC
TGAGATTGTGGGATTAGGAGAAAATAGAAAAAAGATTGCAGGGGAGAACGATGGACAGAGGCCTCCTGTTAGTCAACTATCATGGGCATCAGA
AATTTCTTTATTCACTCAACTAATGTTTATGGAGGTTCTGCTTTGTTCCAAGGACCCATTATAGGAGCTGGAGATAGAAGGATGAAGTTCCTACT
CTAGTGTAGTTTAGATTCCAGTAAGAGGGAAACAGATATCCACACTAAAAACAAACAATAAATAAAACCCAATAAATTAGTCAGTACTATGAAAA
AAATGCAATGAACTGAAGGGAATAGAGTTTGCTGAAGGCTGCTTTCAATAGCTTGTACAAGTTGCACTGTCTGAGGAGGTGCCCTTCAAGCTAG
CACATCAATACTAAAAGAAAAGCATGCCGAGAGCTGGCAGAAAGAAGGCTTCAGGCAGAAAGAACAACAGCAAAAGTCCTAAGACTGGAAAAG
```

TABLE 1-continued (mouse gene: Prlr; human gene PRLR)

```
GTCTGAGTTGTTCAGGAAACAGAAAGGAGACCATTGTGGCTGGACCCGAGGTAAGAAGCAATGAGGGAAAGGTGGGAAAAGAGCAAGGAGGGCC
CGAGGTCATGGGATGGAGTTAGGCTGTTAAGTGCTTTGAGAGCCTAACATCCTAACTCATTGGGAGGTTTTCAGCAGGGTAGGAACATGGTTGG
CATTGCCTTTGAGAGCTCTTCCCAGCTTCTGTGTGGAGAATGGCTTGAAGACTGAAAGCAGAGGGTTTGTAGGAGGCTGATCGGAAGTACAAGC
AAGAGGGGAGGGTGGATCATGCCAAGGTGACAGCAAGCAAGGTGGAAGAGGTGTTGGATTCAGGATGGAATTTGGAGGTATGGCCAGCATGGCT
TTCAGATGGAGGGGACCAGCGAAAGTGCTGGAAAACCTAGTCCTGCTCAAGATGATTGTTCCTGCCCTACCCTTGTTTTAGACCCCTTGTTTTG
AACTAAAACAGAATAATATCTAGTGCTATTTAAAAACATTAGGAATTTTAACCTTAACTTGTTTAAGCAGACAAAACAAATCCCTGCCTGGGG
AGAAACTTCTGTTTGCTGCTTTTGCCTCTTAACCATAAAAATTTCATCCTGTCTCGTAAGACTATTCTGATGGCTTTTGTTGTTTTGATTACT
GTGCTTTTCGTAAGTGCTGGAAAGGTCACATTCGCATTACTAGTTTATCTCTTTTCGAGTGTTTTGACACTTTGGCTGTGTTTACCAAGGCCT
TCCTGCTGTCAGACATTTACATGGGGCTTTCTACAGTTGATCAGTTTCTCCATATAAGTGCTAATATAATCGCAAGCATTTAGTGGGCACTGAC
TGTATGCAAGGCCTTGTTTAAGAATTTCATGTTTTAACTCATTTAGTCCTTCCAGCCACCCTTTATAATAAAAAGTGTGTACTCTTATTATCA
TTTTATAGATGAGGAAACTGAGGCAAAAAAAGAGGTTAAGTCATATGCCCAAGATCATACAGCTGGTAAGTAGTAAAGCCAGGTTTTGAACTGA
ATCCATCTGTACAGCTCTGGGTTCCTAGTAACTATGTTGTGCCACTTTTCTATGTAATTGAAGCTGCCACCTTCAGAAGTAGACTTGTTTCTCC
TGCAAAAACCCCAAGGTACCACTAGGAGACACTAAAACTGGGCCGGGCTTCCGGGAGTTGGACTGGTGGGGAGATGGCATAATCTAGAGGCTGA
ATGATCCAACCCCCCTCCAGGAAGGCCTCACATCTAAACCACCTGCCATCTGCCAAGGTGGGAGGATAAACCACCCCCCACCCCGCAGCCAACA
GGGCACTGGCTGGTGAAAGTTGCCAATACCAGAGGAGTCTTGATGAAATGCCCTCTCTTTTCCTCAAACTCTTTCTGCCTACTATTCATAGTAT
CTGTGTTGTACCCACCCACCTGCCACTTATCAAAGACTGAAGAAACCAAAGTTATTCAACAAGCCATGAAGCAAATTCTAATTGCTCCCCACGG
CCATCTGAGGCTGGCCTTTGGAAACTTAAAAAAAAAAAATTAAAAAAGAGAGTCATATTAATTTATTTGTTACCACATTATTTGCTTTAAAAT
TCTGGTGGCTTCTTTCCAGTGTTTTATTAGTAGAAGCGAAATAAGCCTAGGAAACACAATATTTCATTCTGTCTTCTCTGCTTTTCACTGCATA
TCTACCTTCAAAAATGTCTTCTCTCAAGTTACTTGGTTTCTCAATAACTAGCGTGAAAGTAACAGACCTTCCTTCCTTCCTAATGATAGTAACA
ACAAGGGATTTACAGAATTGAAGTTTATATAAGGAAATGCATTAAGATTTTAACTTAAGTAAGTGAACTATTCAGCAATGGCTATAAAGACAGT
AATTGTGATGATTTGTCTTCTATATTATATGTTTAAACTAGTTATATATTTTAATTATATAAGATGCAATTTTTTGCTCCAGTTTCCATAGGG
TAATTTTCAACAGAGATTAACATGCGTTCATTGGAAGTGTTGAATTTACCTAATCAATATCAATTTGTTTATTCAACTTTAATTTTCAAAAA
AATGTTATTTTAAAATATTATATGATATGTGTCAGGTATTTCTTACGGTTGACTTCCAAATTTAAAACTGCAAAGAAAACAGAAATCCATACAT
ATAGTTGCAGTAAACATACTCAATTTTGGAAGATTGCAGTGGCAACATCAGTGAATTAAAGTTTGAAAGCTATTTCAAATCTTTGCATATTCT
CCAAATAACTCAGAATCCTACAAAAAGCTAAATATTTAAAAAAATTTATCTTCAAACCAATAATGTAAGTTTCTTCTTTATTGGGATGATTTTG
GTTAAATATTTAGCAGAAAGTAAGGGTGAATATATATTTGATATAGGTATGTCCTAAGCTAAAATCAAGTCATTTAAAGATCAGAGCAATTAAT
GGCAGTTATGTGATCACAGGAATCAGTCTATCTCCTCCCTCAGGGTTTGATTCAATGAGTTTTATTTTTCTCTTAGCAACTTTTCTTATTTTAC
TTTTCAAAGGACATCATTGAAACCATAATAGTGTTCATATCTGTGACTTTTAAATTTTTATTTATTTTTATGCATGGTTTAAAATTCATTTAGT
TCATTTAAAATTCAAAGATATAAAAGAGCATTCATAAAAATGTCCCCCTCTCCTGTCCTCCAGCCTTTACAAAAATATACCATATATATTAATA
TGGGCTAAATACCCTTTTAAAGTTATCTCACACGCAAGATGCTATGACTGTGTGAAGCCGGAGCCTACAGACTATTGCTGATCCCCAGTAGTA
GTAGCTGACTCTTTAGTGGCCCTGGAGCTTCCTTTCTAAACTCAAGTGTATATTTAATGTGGCTATTTAGGGATGAACAGCAGTATTTTCAG
AGAAAAGTATAGAAGAACAGATGAAATCACACAAGATGCACACATCTGGGTATTGGTGGGCATGTACTTTCAGCAGTGAGTTTACAAATAATCT
AGACAGAGTTAAGTATCAGGTTTAAGAGTCCTAGGATCTAAGCCTGCACGGGTTCAGTCTTCTGCAGGAACTTGGGAATGTTGGGGTTCACTTA
GGCCCCCAGTGTTGGCATGTACACCCACTTTCAGGAGGCTGGAGGTATAAGTTCCTCTCTGCATTTGTCTCAGGTCATCACAGGCCTCAGAAGT
TTCTCAACAGAAAAGGATTGCATGGGTTGGATGTCCAGAAGGATACGTGGGATTGAAACATCAGTCAGTGGAGCTAGAGGCTTGCTAAGACTTGG
GAAGAGGATGAGGGAAGGCAAAACCTGTCACCTAAAGGGGAATTCTAGAATGTACTTACTACACTCATGACATTACCCTACCACCTTCATTTAT
CACCTTGTGTCAAACATAGACTTCTTGGTCAAGACCACTATGCTGTAAGCTACCTGAGGGCAGGACTATGACTTATTCTCCTTTGTTTACCCTG
CCCCAGTGCCTAACAGTGTCTTTGGAATTGGAATGTTCAATAAGTGGGTTAAACTTTTGAAACTGAATATTTCAAATAATCACAGATAACAGAT
GGTTAAAAACCAAGTCCTTCTCAGCCTAACTAGTGCCAAACCAAATCATTTGTCCATGTCTCTAAAGAAATGAAAGTTTTCTAATTACCTATAT
AGGTCTGGACTCAAAACTATAAGGCAGCACACTGTCTTTGGTGTTGACCTATGTCCCAGGTTGTCCATGGTCATCACACACTAATGACCACTTG
TATGTATTTCATCTAGAGGATCACACAGAGTGGTATGCTAGGCCCAAGGAATAAGTTTACCTGCTTATTTCACTTCTCCACTGTCATCCTACTG
TGTTTCAGGAAGAATTTCTTTTACCTCTGCTTACTCTACTAAGATGCCCCACATAAGCCCCCAACTCCTTTTCTTGTCCCCCTCCCACTTTGTT
GTCTATTTTCTTCTGTCAGACCCCTTCCTCCTCCAAACTGAACCTTCCTGAGAATATACCAAAGAACTCAATAAACCATTCAGCCCACTATAGT
TCAATAAATGAGCACTTCCAGAATTTGCATTTTAATAGTGGTTCAACCTCAAGTCTCTGTTGGTGGAAATGTCACTGTGATCTAGGTGAGGGAA
ACATTTTGAGAGCCTGTGGGAACCTCCAATAGCACCCTTATAGTAGCTTCTTCTGGTGCCTGTGTAATACTACAATTTCCAGAAGCCTTGTTGAT
ATCCAGCTAAGTGAAAAGAAAGTCCTCAGTTCCAGAGTTCTTACTTCTATTTCTTTTTTTTTCTTTTCCCTTTTGTTTTTTTTTGAGACAGAG
TCTTTTTCTGTCACCCAGGCTGCAGTGCAGTGGCGCAATCTCGGCTCACTGCAACCTCTGCCTCCTGCGTTCAAGCGATTCTTCTTGCCTCAGCC
TCCTGAGTAGCTGGAACAGATGTGCGTCACCCAAGCCCAGCTAATTTTTTTTTTTTTTTTTTTTTTAGTAGAGACAGGATTTCACCATGTTG
ACCAAGCTGGTCTCGAACTCCTGCCTATCCACCTGCCTCAGCCTCCCAAAGTGCTGCAATTACAGGCATGCGCCACCGTGCCCGGCCCTTACTT
CTATTTCTAAATAGCAATGGATTCCACTCTTCCAAGGACCCAGAACTTGCCCTAGGGGTGAGGGTCTTTTGTACATCTTGCAACTGAGAACTTT
TGCTAGAATCAGACAGACAACATAGATCTCAGCTCTAATTTTCCAGGAGTGAAGCTGTGGAGCAAGTGAGTTACCTCTCTGTCTCACTTTTTCA
TCTGTACAATGAGGCTACTAAAACATACATTCCAGGGTTGCTGGGAGAAAAAGCAACAGGTATGTACAACATTTGGCACCAAGGAAGCAC
ACAATTCATGGGAGTAATTACTATCACCTCACCCAAGAGTTCATGATTTACTGGGGACACCAACACATGTACAGTCAACAGGGTAAAATGCTA
AGGGTGTGGGCAAGTGTTGAGTCTGAGCTCAGTAGAAATTTATGAGCCTCAAAGGCCTAAAACATCCTTGACCACTCAGTTCTATTTCACAC
CCTTCTTGTACTTCACCAACAAACCAGCAACATGCTTCTGGTTGGCAGCCCTTATAAAAGAATTTACCTTCTATAGTCAAGTCCAAAGCTCTTA
ACTGCTTACCACATGACAGCCAATAAGACAAGATATTTGGGGCAAGGAAGATGACTTTTTTTCAGGGAGCCAGCAATCCTAGAAGATGCAGACT
GATGTACTAAAGAACCATCTTAAGTTGATAGATTGTTAGGCTCCTTTTATGTTAGGGGAAGGGGGAATAGGTAGGGGGGTTAAGGTCCACAGTTG
ACTGGTGACCACAGGCATCTGGGCATCAGCAGGGATCTAGGAGGTTGCAAAACTTCTTTGTTCATGGTCAACTATTTTCCAGATTGACCTTGTT
TCTATAAATTTTTAAGATGGCATTGTTATTTGTGTGCATACTTTCTAATCTCCTCAGGGGTCTGTTTCAAAAGAGAGATGGTCATTAGTTCTGA
AGTTAAACTATAATCTAAATTCTTTCCATCATTAGCTTGGCCTATGTATAGGAATGAGCAAGAGGCTTAGCCTGTGAGGTTAGAAGCAAGATG
GAGTCAGCTATGTGATATTTCTCCCACTGTTACACATCTCTGAATACAAGAGGAATACATTTCTTCTTTTTGCTGTGTTTGCTTCAAGCCTGTA
CCACTGAGAAATTGGGTGATCCAGGGAAGTTTTACTTCTCTTGAACCTCAGGCTCTATCTTTGTAACAATGGAGAAATCAATGCCTGCATTCTA
GGCCCTTTTGAGGGTGGAGGAAGACAATGGTTGAGAAACTTCTCATCTATAGTTGATCCTCAATGCGTTTGCCCCTTTTCCTGTGGCACTGCTT
TGTATTTGGATGGTTCGAGCAGTGCGTCACACATGGAGGAAAGGCAATGGAATGATGACAAATAGTTTGTTGATTTGGTGCTTTGTACATTCAC
CCACAAATGGCACAGTTTCAGGGCCACTCGTCCTTGCCAAATACTATCTGAAGAGCTAGGTTATGAGCCTTTGGAACCCAGATCTGATAAGCATG
GAGGAAAACTCCTCAAGGGAGATGAAGCTAGGAGATTAGCAGAATATACTTTCTCCATTTGTCCCACATTTGATGCCAGCAGGCAAACCAGAGC
CAGCTGGGCAGTGTACAATTCCCAGAAATAAGGAAAGGGTAGAAGCACCTGTTTTTCCTCTAGCAAAACCAAGGCAAATGGAAAAGCTCAGAAA
TATATCAGCACCATTAGCAAGAGGCACAACGGGGAAGGCTGGAAATGTGCTGAGGAAATCAATTGCCGGTCAACGCATAGCTACCTGCTGGA
GAAGAGAGTCTGCAGACACACCTCAGCCTGGACAAAGGCTCCAGGACGCGGGAAGCTGTGCTCTGCAGGAACTGGGCCCCAGGCACTGAGGACTG
AAAACCAGCCCAACAAAGCATACCTGTTTCCATTTGTGAGAGATGAAATGATATGGGTTTGTGACTCACTAAACCACTTGGAAGGCCAAACAA
TTACAAAAGCAAGATGCCTGGCTTCTTCTAGCCACATGGAGGGGCCCTCAGACTTGAGTAGCTGTGTGCCACTTGTCTGGGGTGGCTGCACCAA
AAGGAACAGTGAGGTTTAGATGCTTGTTATTGTTCATTGTTCAGTTTTGGTTCTGCTTATTACTTCTAATTCCTCAAATATTATTGTGATTAG
TGGTATAGAAAGGAAACGTTCATTTGTGAGCAAAGTGTGTAATAAGAATTTAATAATGAAATTCCCAGAAAAAAAAACTCAGATAGCTAAAGAA
ACAGCAGTAACATGAGCTCCAAATATCTTGAGTTGTATTGTTAAGGTGAGAATCCATAATGTAAAGGGAATAATGTAAAGGGAATGCTTTGAAA
TCAAAGGCATAATCCAAGTGTGATAACCTAAAAGGTTGTGGATTTCTTTTAAAGTAGAAATTACATGTGGCTTTGGGAAATCATCAGCTGAAGC
ATAAGCTATGCTTATGGATTCTCGCTGTGTTGTCACTAAGACCGATTATATAAAGACTTGGCAAATCCATGTACAAATGTAAAACTTCCCACAA
TGGTATTTCATGGGGATCTCCTTTTACAAAGTGGTCGTTGATCAGGACATTTTTCACTGATATATTCCTTTGGAAGCAATGAATTTTAGATAGG
```

TABLE 1-continued (mouse gene: Prlr; human gene PRLR)

```
ATATGATTATTGTACAATGTGATAGGTAGCTCTGATTATTCAAGCAGCTAGGGCATTATTCAGTGGCAAAGCATTAAGCTACTCTGGAATCTTT
CTTCTGTGTAAGCAGGCAGCTGCTGTTGAGACTTTCTCTTTGTGGGTGAATTTGCCCAACCAATGGCAAGCATTCATTGGGAGTAGGGGAATGA
CGCTGATCACTGTTAATGACAGTTGAAAATGAAATGCTTTAATGAATCTCATACTTGGACTTGGCTGCTGAGCCAGAGCCCTGTACTTGAAGAG
CTTAATTATGATGCCTCAAAATTTAGATCTTGACCCTGAACTGCTATGACTTCCTCCCACCCTCAGTTTTGAGAGAAACTTTAAATTCGCTAGG
GGATTCAATGTTTTACATGCTTGGTTATGCAAAATGGGAACAGTAGTGTCCAAACAATGGAATAGGCTTCTATATTATTATTTTCATTTAGGCA
GTATAACTGACATGATTACCAAAGTCATGTTATAGTACATGTATACAAATTAATTTCATACCGGGGGACTTCATCGGGGGGAAAAAAGGGAAGT
CCCTATTTGTGAAAACTATGATTTTGGTTTCTTTCTGAGTAAAGCACTGCTAATCTCTTTGGTGTACAGGAAAGTATGGTATTATGTTCTAAAA
ATCAGAAGCCCCAGACCTTAATTTCAACTAATCTGATGACATCATTTTGTACTCAGAGTTTCATTTCCCAACAATTTCATGTTTCTTAGTAGGT
GGGGAACCCAGAATTGAAAGGCATCAAAAACAGCTAAATATAACCAAAAACCTGCTAACTCACCAGCTTTCTAAAATTCAGGAAGTATCTTTAA
CTTGATTGCTGAATCTCCAAAGACATGATGATCAGATGACTGGTTAATGGGTATTTTTCAGACTCTACATGATTATCAGAAATGGCTGCCCTG
GCCAATTGTATACCTACGAAGAGGTATTATGTAGAAGAACTTATATTCATCTACTTAATGTGGACCTCAAATATTAAGGATGTTCCTAATGTGT
CTAGACCGGAGTCAGCAATACTTTTCATAAAGAGCCAGATAGTAAATATTTCTAGGCTTTTTGGGCCATATAGCCTCTGTCACAATTCCTCAA
CTCTGCTCTTGTCACACAAAAGCAGCCATAGACAATGCATAGGTGAATGAATGTGGCTGTGTTTCAATAAAACTAGACTCTCTTAATGCCAAGT
ATTTGCTGGAATAACACAAATTAATTTATCCTCAAATCTGTTTAACCTATTAATATGTCAGTCAATATTACATTAATAATTTTATGAATCTGGTA
TCATATTATACATGAATTTATCTGAACATTTGGTTAATTCATGAATATTTACTCAATATTAATACTACATCATGAATCTGTTATCAAGTCATAT
ACAGATTTCTTAAAAAATTTCCCTTATTTAGCATACTTGTGAATAACATCAATAAGCAAGTATCTTAAGTTAACTATCAGGTTATATAGCAGAT
CCTCTCCCCCTTTTGTAACTCTTTCTGTTACAAGGGATTTTACATTATTATGGTATTGGGAAGTAAGTCTATTTATCCTGTCCCTATCTGTCTT
CGTATTAACCATATTCTGTTATAGCTTTTATCTTTGCAGACAGAAGTTCAAATCTTCATGATTTGTCCTTAAACAACCCCCACTTCCTCATC
CTCCTTGAACATTTTATGCCTCCATCACTGTCTCTTCAGGTCTTGTGAGTCCTTGAAGTGCAGTGACTAGGCTGGAACATGGTGTTCCAGGTTGG
TCACATCACCTCTTCCTAATGATGCCCCATTGTACCTTTTGACTATAGCAAGGAATAAACAAAGTCAGAAGTGTGAAAGTGGGGGAGAAATTGA
GAAAGTGCAGGGGATTTAGGGGAGAGAAAAATGGACTACAGGAAAAGAAAACATTGACTTTTGCAAAGTGCTCTAAACTGGCTACAAATGCATT
CCGTAATTCTTTAAACCTTAATTGTAACCGCAGTTAAGCTTTCCGGTGTGTTTGGAATAAGAACAAAACTAAAATCCTTCTTTGTATAGAAATTA
TCCTGCAGTAACTTAGAGCCAATATCTCTAGTTAGGATGAGCGCAGTGGCTCATGCCTGTAGTCCCAGCACTTTGGGAGGCTGAGGCAGGTGGA
TTGCTTGCACCCAAGTAGTTTGAGACCAGCCTGGGCAACATAGCGAAATGCTGTCTCTACAAAAAATTAAAAAATTAGACGAGCATGGTGTCA
CGCACCTGTTGTCCTAGCTACTTGGGGGCACTGAGGGGAGAGAATCACTTGAACCTGTAAGGTCAAGGCTGCAGTGAGTCATAATCACGCCACT
GCACTCCAGCCTGGATAACAGAGTTAGACCTGTCTCAAAAAAAAAGAGGAAGAGATCTCTGGTTAGAGTTTGTCTCTGATGGATACTAACCATG
CAAGTAGTTTACACAAACCACATTCTTTCTGTAGAATGAGGGAAGACTTGGATATAATTTAGCATAATGAGCTAAATAACTCTAGACTGAGCTTC
GCTGCCCAGACAGGACTCTACTTGTGATCTGGGAAGATCTACCCTTGCACTGAATTCTCCTCTTCTCTCCTGACTCTGTGAGAAAAGTTTGC
ATGAATTTACTGAGATTAGTTATAGAAGGAACTGTGTGTCATTGAAAGTCTTGTACAGAAGTTCACATTAAAATATATCATAGTCATCTTTGGG
AATGATTCTGCAAAATTCATAAAACAAACATCTCTGAAACCCTAAGGCACACTGTGCTGGAGGCTAAGGGAATAATAGTGAGCTGAGTGGTTTC
TGCCTACACAGAGCTTCTAATATATTGAGGAAAGAGATCTCAATCAAATTCAATTCATTTATAAGTATGGTAAGGACAACAAAGGAGAGACAC
ATTATTCTGTAGGAGAATAACCCTGTCAAAGTGATGACTGATTTAAGATCAAAATGGGAAGGTAAAATTTTCTCAGTACCTGCAAAGGCACTGA
GGTGGGAGGGAGCATGCCAATGTAGGGAAATGAAGAAACCCAGTGTGTATGAGCCAAGCTGAATAAAACATGAGAAGAAGCTGGACAATGAGAG
AGACCAGTCCCCAAGCTCTCAAGGAGCAAGAGGAAGCCTTTTCGGCATTGAAGTGGAGGGATGGCATGATCTCGTCGTAGTTTTTAAAAGAA
CCACTCAGGCTACTCTTTTGAGAATATTGTGGGAGGCCAGAGTAGATGCCTATAGACTTATACAGAGGTTAAGGCAGTTGATAAGAGTATAAAC
AATGATGGTAGCTTACCTCACATGCTTTTTAGATTATAGGCTAGAAGGTGGCCAAGCCCATATACCATCATGGCACAGTGAATACGTTTTCCT
TCTGGATCGTGGAAATGAATATTGTGCCACACAGCTTGATTGACACTCCCCAATGACTTTTAATACTGTGGGATCTCTGGCACATACTTCAGAA
GATGAGAAAGGAGTTTTAATTAACCTCTGTTTAGGAATTCCATAGACATAATTTTCATTAACATCTACTTGGTATTTCATCTCCATGAATTCTT
TCCAGTGATAAAGCTAGTTGGTTTATCCTCCAGGACTGCTCAGTTCTGAACAGTGGGTCTTAAGTACTCTTTGGATTTCTTTGAAGGCTTTTTT
TTATTTTTGTTGACTACCTCTCTACTCATTTTGCCCCAGAAAAATGTAGTCATTTCTTTGATAAGTGAAATCTAAGAAAGGCTTATTTCATTT
GGTACATTAAAGAGATGGAAGAAAGTAACTTTACATAAGAATATAAATGCCAGCTGTCCAGCATATTACAGAATAGATTTCTAAATTTGCTGAA
AGGTTAGGAAAATGGATTCTTATATAGGCTAAAATTTTTTATAATTTTTTTGGCATTCTAGAATGAAATAAAGAAAATCGGTATCATCTTGATC
TCATCACCCAGAAGAAAAAAAAAAACACTGATACATGGTAGAATTTTCCTCTCTCATTTTTAAAAAGAATCAGGAATAGATTGTATACATATT
TTTCAAATTCTTTCTACTTAGTGTTATATGATAGTCAATAATATATGTGTATGTAAGTAGCAATAAATCATTCCTGAAAACTTGTTTTTTAAGC
TTGTATAACATTCCGTCATATGGATGTACTGATTTTGCTAATTTGTTAAGTTTAAAATAATATTCATTTCATTTCTTTGACTACTAGGTATAA
TTAATTTTTTCATACACTCACTACCCTTCATACTTCTTTTATTGATTTCCTTTTTATGTTAATTATTAAGATTTCTATTTGACTCTCAACATTT
TCTTAATTTTTTTATCATTAATAGATGTAAAAAAATTCTTAATTTTAAAAAATAAACCCTTTTCATCTAAAGATAGCAATCTATTTTCCATA
ATACTTGTTATAAATATTTCCCCAGTTTGATGTTGGTCTTTTAATTTTGTTAAAGTATTTTGACAAATAAATAAGTTTTTGTGGCTTGAAGT
TTGTTCATTTTTTTCATTTGTGATTACAGTTTAGTTGTTGATTCAACACATCCTTATTGAGTGTTTTGTGTTCAGCACTAAGCGAGACACAAGA
GGTAAGACAGAAAAACAAGGTGCAGGTGGTTTTGCCACTTAGAGATTACAATTTAATGAGGGGATAGACAAACAAAACCAGGTCATTATAAAAT
AGTATACTACAAGCTATGCAAGAGGAAATACAGGTGGGAAGAAGTACCTGATCTGGACCTGGGGGATAAGGGAAGGCTTCTGGAAGGAAACAAC
CTTCTAGCTGAGAATGAAGGAAAATGGCAACATGAATTTAGAGAGGAGGAAACAGTATGTGTGAAAGTGTTGTTCAGTGCTCCTAAATGTTAAGG
TCCTCTTTTCCCCAGAACATGGAGTGTGTGTGTGTGTGTGTGTGTGTGTGCGCGCGCTGGGTGTGTGAAGGAGCAGGGCAGGGTGGTGGTCAAG
TGTGAGCAGGAGGCCACTGGGGAGGCTGCGGCAGTCCGAGAGAAAGACAATGATGTTGGGCAGAGGATGTGTTGAATAACTCATCCCTTTTCAC
TGGACAAGCAATGCCTCAGTGTATATTAAGTTCTTATTCATAGCATACCGTCTATTCCAGAATAATCTAATTAGTTTTATTGCTATATCAATTC
TTGGGCCAACACCACACTGGTTTTGAGTTTAAGTGAACCGTCTAAACTGGTAATGCATGCATTCCTCTCATCACTTTTCATTTTCAAAATTGATTT
ACCTATTCTTGCCAATGCGTCCTCCCAAGTAAACTCTAAAATAATTTCAAAAGTCACAAAAGCATACGTGTGTGTATATGCATGTGTGTAAATA
CATGTATATATGTGTATGTGTGTTTCTTCCAACCATTTTTCAGTTTTTGGAGAATAAGATGTTTTATTCAAGTTGCTGTCAGTAAATATTTTA
TATTACATGACTTCTCTATACACACACACACACACACACACACACACACACAATCTCCCATTGGTAATTTGATTGGGAATGTGTTAAATCAGGA
GAACAGACATTCTTTTTTAATATTGAGTCAGCCCATCAAGAAGCATTCAAGAAGTGTTTCCCACTTACTCATTTCTTTATACTTCTTTTAAGCCTT
TATAGTCTTACTCATATAGGTCCTGCATATTTATTGACGGGGTATTCTTTTTCTTTTATAATTTTAGCTTTTAATTATGAATGGATTTTCTT
CCATTATCTCCTCTCTGGTATTACTGGACTACAGGATAAATATTAATGATGTATATTTACTTTTTATCTGATTATTTAACTGATTATAATTAAT
TATAAGTGTTCATAGTTAATTATAAAAGTTTATAATCATGGTGTCTTTAAATAATGATAATTGTTCTCCTTCCAAAAATTGCATCTAATTTTTA
TTTGGTGTCTTACACGCATTGATCGTAACTTCTAATACTAAACAATGATAATAGTGAGCGTCCTGCTTAATATCAATTTCAAGAAGAACAC
CTCTTACATAACATTTTTAAAAGTGTGTTATGTGGAAGCTAATAAAATAAACTTGGGAAATGCGACAAATGAAAATTCTCTCTCCCAGGCATTC
TTAATTCATATTAACATATTAAGATGAGATCTGCAACAAAGAGATGAGTTCAACTGAGTTTAACCCAGTATTTCTAAAATGTATTTGACTATGG
AAGTATTTTCCCTCATTTAGAATTTTACATCAGTTATGACAGTCAAAATTATATTAATTTGATCTTCTTTCTTTTTTAGAAAAATAATTTC
ATACTTTCTTGCTTTTCTGTTTGATCTCTCTTTTGCCATATGGACATGATTTGGGTTTACTTTTAATTTTTTCAATAATTGAGAAGCTCGT
CACCCTTCTTTTTATTTCTACAAGTGGTTACACTTAAAGTTTCCAAGACATTTCTATCCATATCTTTATACTTAGCAAAGTCAAAGACATGACCA
TACAGTTTTCTAATCAACTTCAAAATGAAATGTTATCTTTGAATAACCCCATCAAAAGAAATTTAATCCATTTTTACTTCCTTCCAACCTTTCC
TCAGTATTGGTAAGAATAATTTAACATTTTTTATTCATGTTACTGTCAGTAAATATTTTATATTATATGACTTCTCTTTTGTGAATTATGTGAT
CTGTTCAGCAACATAATCCTTTCATACATTCCTGAGCACTGTCTGGTTTGTGTCATTGTTGTGTCCATAACTATTGCTCTTTTTATACCATGA
ATTTCTCATTTTTTTACTTTTTAATTTTAATATCTTAAGATTCGCCACCTTTTATCCCATTTATCCTTTTAGGGTGTATAATGTAGGTCATCTA
CATTTTGAAGTGCCTGATTCTGTTTACTATAGTGTCAGTTTTACCCCTTTACTGCCTTCAGTGGACAAATTAGTACTATTATTTCATTTCTGG
CTCCTCTACAACCCCTTTTAATCTAACCCAGCACTCTTTTCCTTCCTTACTTTTATCTCATAATGGCTACCTGTCCGTTTTCCACAGTATTTTC
TATTTCAGTTGAAGATGATAAACAGTTTTCTGACATTGACATTAAGATGATGTTTCAGTTTTCTTGTTAGACAATTTTGTTCACTGTCTAAGCT
ACTTATTTTTCATGATTACTCGTCTAGGAATAAAAATCAATCTACTTAGACCCAATATTTTTGAACACTGAGCATATGTAATGTGTTCTTAAAC
```

TABLE 1-continued (mouse gene: Prlr; human gene PRLR)

```
CTGTTCAATATGTACTGGGCTCTAAATGTCCTGGCCTACAGCTGGAGGGCAGAATGACATGTCCTAGTTCAATATCAGCCTCTAACAGGAATGC
TACTGATGTAGTTTTCTGCACTGAGATAGGATCTTCTTTTCTTCCATTGCCTATTCTCCTGGAGGCAAAATAGAGAACATAAAAAGTCATCATC
TTTGGTATGTTCTTCTTTAGGGGCTTTTTCTTTCTCCCAGCCCAACCCCCATAGTCCTTACTTGCTAGATGTGTGTTCCAGGATTCAGTTCACC
ACTGCCCAGTCTTCTAACATCCAATTTCATTGTTTTCTGAGAGTTGAGAATTTTCATACAGATATAGAAGGGATGCTGTGCTTGTTTGAAATGG
TTCTATTTGGCAGAGGATAGCCGAACAGTTTTTAGGCAAAGAATGAACTGTCTACTTACTTTCTTTGAAGAAGCCAACAATTTGGTTTTGTTGC
CAACAGCAAATAATATATTGGCTAATAATTGTGGTTTACAGTGACATGGGTAATGTTAGTCATAACATGTCTTCCAAGTTTCTGGCTATGGACT
AACTGTAGGTCTTGGAGTTTGGTATTATCTAGAATTTTCCTTCTCCCTCCTCCCCCACCTCTTATCTTTTAGCATAGTTGAAGATTGGAACTTC
TTCCCAGAAATCTAGCATCTTCATAAGTCCTTTCCGGTTTTAAGATTTTTATCTTATATTTTATATATATATTACATATATTTCCTGTGAATCT
TGGCTGAATTTCTCATTTAATAAAGTCCAAGTTAGTATGAATAAATAACATGTTTCCCGATTTTACACACATACAGAAATTCAAACACATAATG
AACTCTCTGGCAGCCTTTAGCATTTGTAAGTGCTCTCTCACCAGGAAAATCCTTTAATAGATAACCAAGTGTCCTGGGGAAGAAGGGTGTCAGG
AAACTTATTATATTTGTGTCACTTTCTTCAAAGGGTGATTAAGTATATGTCTCCAAACATGTGATGTTATCATCTTTGAGTATCACTTGAATTC
AAGTCAATATTTATTGAGACCCCATGTTGTATCAGGTGCCTTACTAGAAAGTCGACATATAGAGATGCATAAGACATGATCTTTTTCAGTGGGT
AATTTAAGGTCTTTCTTCTACTGCTAGCATTGTCATGTGTAAGGCTGGTGGGTTGAGTCTTTGGAATTTGTGAAGATTCTTCCAGGTTGTTTAA
AAAATCTTTTGATTCTCACAAATGTATTTTTTCTATTTCTTAGAATTATGTTCTTTATGGCTACCAGGAAATCCTTTGAAACTGGAATTAGATT
GCATTATTCCACTGGGGTAATAGGATTGGTAAGGTAGGAGTGTCTTTGAAGAATAATGCTAAATAACCCAGACACTAAGGCTGAATCTTCAGCA
CAGCTCTTAAGGCATCCTGTAAGTACCCTCTGCTGCTTATTAGAAATCCCAAAGCCCTGCTCCCTTAGGAAAGCGGCCCATCCCCATCCTCATC
ATAAGATGCAAGGCATAGCTAAACATCTCAACTTCTCACTTGAGTATTATATACTCTCAGGCCAGGATACTTTCCAACTCAAGAGTAAGATAAC
ATTACATTCTGATCTTCTTGTGTGTGTTTTATGTTTTTTTTTTGTATTTTTATTTATTTTTTTTTTGAGACAGAAATTTTACTCTTGTCAC
CCAGGCTGGAATACAACGGCGCAACATTCTGATCTTCTTTTGAGAGAAAAGTTTCACACAATTAGCCTTTGAAATACACATTCCTTTAAGTACC
ATGAAAACATTGTCCCATACAACAATATTTCTAAGAAACACACATGTCCCTCCCACAATGATTTTTCTTGTTACCACCAATAAAAATTAGAGC
TGTGTTGTTTTTGTTGTTGGGTTTGTTTTTGTTTTTGTTTTTGGTGACTACTGTGACCCTCAAAAAATCAATCCGACTTTCTCGATCTTGATT
TGCAACACCAAGGTTACCAAACAAAGAGAATGGTTCAATGAGGGAAAGCTCAACTACCTGCCCTAAATATTTAGTATAGCAATGCTGAGCTTTT
GGTAATGGCTCAAAATTCTCATGCTTTCCCACTAAATGAAAAGGGGAGCTTTGCTACTAGTAAACCATATTCAAGAAATAATTCTTATTAATAC
TTTGCTTCTTTCCTATGAATTATTGCTTTGTAATGGATGTTTGACAAGTTACTAGCAAAGCAGTCTTCGATGAGCACAGAGACCCATCAGATCT
GTATTAACACCTCCAACCACTGGAGTTTCATTAAGTAGGTTTCTCTACCCCTCTCCTTCAGGCCACAGATAGGAAGAATGACATTGGGTCCAAA
GTTCTGGCACAAAGAATGATGTCTGCCTTCCTGTGATGATTTCAAATTCAGGGTAATAATTCCAACTATCTTTCCCTGGCCATGATAGAAAGCT
CAAGAAATCTTGGTTCCTTGTCTCTTTTCTTCCATCCAGTTGGTCTTTCTAATTACACACTCAACACAATGTTCTGCTGAGCAAGACATCTGCT
GTAGCCACTATCACCCTTGGCATAACCAGATATTTAAAGGTACCTAAAGGAGTTTAGCTATATTTTGCCAAGATCCTAAGTTCTATGCATAAG
AATCCTATCCACTTCTCTATTGCCTATAGAAAGGACAGCTCAGTCTTTCTGAAAGAATTGTTCTCAAACAAGAAAGCATTGAGGTAACATGTC
AACAAGGTGGACTGGTAATTGGTGTTCCTTTCAGASCCAGTTGGAGGAAATGGCCAGCTCAGACATTCTCTTCTCCCAGTGTCCTATGGGAAC
AAGATTTACCCAGACACAGCTGACTATGAGAAGTCTTCAGGGATTTACAACCTGTCTAAGAACAAGGCCAATGGGGGACTCACTTTGCAACACG
TCCCTATTTGATTGTCAGAGGACAGATACTCTATTAACAAAGGAATTTGCACTGGTATTTTCAGGGACACATCAAGTAATTGCCACTTGAACGT
TTTTCCAGGCTTTCAAAGGAATGTAAGAATGGCCTAAGGCTAAATTACATTCATGTCTTTAGTGAGTCATTATATTACTGGCAATAAAGTATAT
TATTACTTTACTTTCAGATGCCCTCACATATTTTTTAAAGTAGAAAGGAGACATATTATGGTCACCATTCTTAAGAGACTTAACTAAAAGACA
CTAATTTAATCTTTTAGTTACTTAAAAATAGCTGTTGCTCACCCACTATGTGCCAGGCTCTAATACCAGGCACCAATATGAAAAGGTGAGTATTC
TCTGGTCTCCCTAAGCACAGTCTAGTGGAGGAGACAGACAAAATGCAGCCATGGCCAGAAGGGGGGAGCAGTTAATGAACAAGTAGGCAGAGAGT
AGGGAGGGGATTCTGAGAGACAGTACGGACGGACTGAGGGTAAGTTGTACATCCCTGATATTTGGGCAATTGCAAATAGTTTGATGACCAAAT
CACAAGGAGAAGAAGTGACAGCAAGCATGGCTGAAAATGTAGGTTGGTGTCAAATTGTAAAAAGCCTTGAATACTGTGCTGAACGGTTTGATCC
GTGAATCAGGTAGAGGACTTGACTCAGGTCTCTTGACTCAAAGGTCATGTTTTTCTCTGCTAGATTGCACTTATCCTTCCAAATGCTAGTGGA
CACCACACTGAATTGATCAAAGATCTCTCAATGGAAATATGTAAATTTCCTGTAAGAAGCAATTGTAGGTTCTCTTATTATCATCTCCATCT
CACAGATAAGGAAACTGAAGTATAAAGAACTTGAGTAACTTGTCCAAGGTCACACAGCTAGTTAGGTGATCCCAGACAATTTGGCTCCAGAGTC
ACTAGTCCTAACTACAACAATTTAGCCTCTCTTTATCTAGAGGTCTTTATGCATTTGTCTGCATTCTACTTACGTTGGTATTGGTGAGTAAAGA
TTCCCTTCCAGAATAGGTTTGATAAATTGCCAAGTCTGAAACTGAAAAATTAATATCCATGATAACAACAGGTTTGGGGTCAAGGAGTGAAAGG
AATTCATCCCATCCTGTCTCTAAATACTTTTTTCTTTACCAATTTATGGGAATTTGAGACCAGATATCTGGAACCAAGCAGCCTCACCCTATTA
AGGGAAAGAAAAAGAACAGAAGAAAAGAGGAGGAGAAGAAGAGAAGAGAACTAAAAGTATCTGCAAAAATATTAAAGGATTTGACCGAGA
TCTCTGAGATGCTCCAAAGATTGCAATTGTGCTTACTATCCAAGTTAATGGCTGTAAATCTAAGAGAATTATGATGTGCCTGGTAAATATTGGT
TGTTTTGTTTAAGTCTTCATGGAGAAAATGGAAAAGACATTGGCATGAGATGAAGTCACAGCAGGACAGACAGGTCCTGCAAGTGTTTCTT
TAGATGCATTGATATTCATAACATCCAAACAGGCCTTAAGGCTGTCTTCTTACTTTACACTTACCAAAGGGGTAAAATATCATTTTCCTTGGAC
ACACAAATAATAAACGTACTCTCACAACATCACTTGAATGTTGTGGTTTTGCAAATATACTATGTTTAAAAGCTATAGCCCTCAAATCCCTTA
CTAGACATCAATATTTGTTGGAATTTCAACATCAAAGATTATTGTGAAGGGGAGGGGAGGAGTTACTCCAAAGGCTAGAACCAGTGCATAT
ACCATAATAACAACTCTGCATGCATTATTGCTTCTAATCTTCATAATTTTGAGTACTATCTTTATTGTCACCATTTAATGAAGATGTTAAGGTT
CTGGGGGCTTAAGTGACTTGCCCAAAGTTACACAGCTTGGTAGAAACAGAATTTACCACAGAACTTGTGTGTTAAGCCAAATAATTTTCTAGTT
CCATACAACTAAAAATTGGAAGGAAAAAGTAGAGCCTTATGAATAGAGTCCTGAGCAAGAAGGATGAACAATCTGCAGATGAAGTACTCTGTAA
AGGAAAGATCTGGGTTTGAATTCTAACCCTGCCTCCGTTCATCTGTGTGATCTTCGCAAAGTCTGTTAACTCTTTAAACTGTTGGATATTTATA
AAATGGGACTGGTGCTATTTGGCCTGATATCTTACAGGGGAAGATTCAGTCAGGCCAGGCGTATGTAGGGTCTCTCTGACCTGGAAAGCCCTAT
ATAAAGACATGGTACCATTCTTAGTGTTAGGACTGAAACTACATCCCTAGTGTCCTGCTACACAATACCCAGAAACCCTAGGCTCTTC
CTTCAATCCCATACTCCTTCCTCAGCTGCCAGGACAGCTTGGTTAAGAAAAGCCTTGTTCTTGGGGAGTATATCCATGAAAGTATCTCTATTTC
GTTGCAGTTTCACATTAAGTAAAATTAGAGTGCCCTTCACGAAGAATATATAATTGAAACCCTCCCACTGACTGCTGGACAAAGCACTTGTCA
GTCAACAAACCAGGTAGATTGAGTCTGCCCTCAGAGTTTTTGTATTCTGAGAGTGACTAGCAACTTTCTCTCATCCTAGAGCAACAGGGCTTTC
AGAGGACAGGTTCTGGGGCACGGCTAGCCACGATAGAATTGGTTTGTGTCCAAAGTCATGATTATCAGGAGAGCTGCCATTTATCAA
CCACCTCTTTGATACTTGGTGTATAGGACAGGCGTGTTAACTATATTATTTCTAAACCACAAGATAAGTCTGTGAAGTATTTTTATCCCTGGTT
TACAAAGGAAGAAATGAGGCTCTGCGAGACATGCCAGAAAGAACATGCTCTACACAACCAACTGGTTACAATGTGCGGCTTTGTCCAGCACTAC
CTCTTCTTTCTTGGCAATCATCAGAGCCACTCAAGGCTTGGAGGACTGTGCTGGCAAAAAGAAATCTTGTATTTTCTAAAACTCACACCCACA
CTTTGGAGGGGACAAGATTGAGATCAACCCCATTTCCTACTCTTTCTTTATGACAGTTTATCAGAGCATTTTTCCTTATATTCACTCAGTCC
TGAGTTTCTATTTAGTTGTGATAATAGATACATTTTTGAATTTTTAATACCTTCGGGTGCAAATTTGGAATCTATGGAGGATAAGGGAGTAACA
AAATGTTATGGAAATTGAAATATATAAATTATTAATTTTCCCTCTCCTACAGATTTACAATCACTTTATTTGGGGATATCAAGTAGGTTATG
TGGTTACTGTAGTACTCATTTAATAATCAGATTTATTTAGAGAACTATAAAAGGTACAACTTAAGGGGAAATATATTTTAGATGATGTTTTT
TTTTCAATTTCCAATTTTTGAAGAATGACGTGTTTTTAAAAACTTTTAAAAGAATTTCTCCACATTTCACTCCCTTTAAGGTAAATTGATAGCT
GTGAAAATGGCACCTTGGAAACATTTCTGTCATAATCATAGGAGAGAGTGAGAATTATTAATATTCTCAGCCATGTAGCATCATAAAGTAGATC
ACAGCTGTTTCTTTCAGAAAATGTCATTTGATTTTCGATCAGATGTATGGTCCATCTCACAATCTAACCGCTTCCACATCTGGAATATCTTAAC
TGAAAATGTCCACAGCATTACACGGCCTGGCTCAGGGGAGAAAAGAACTAGGGCCTGCATCGAATTCTGTCTCTCACTCAGCTGATCTGCATT
CCTCCTATAGCATTTCCTTATAATTAAGAAGAGCTCATAGATTTGGGAACTGCATGAGCCTCTGTAACCTTCTGGTGAGGGTGAGAGCTCAGA
ACTGCATTTCTATGCATTTTTCCCTAGTCTTTCCTGCTTCGGAGGAGAAGCCTGCAAGAGCTTCCTGCCAAGGGACCCTGCTTTCTCAGCAGC
CGGATCCGGAGAGCCAGAAATCCATCTTCAGCTCCTTTGAACTTGGCTGTTGTTAATCATGCTGTGGTTGTCCTTTAAGAGCAAAGGCTTCACG
GAGAGCAGATCAGCTGGCTGTAGGGAGGGTTTCAGCTTCTCATTGTAGGCAGATCATCTGCTAACAGCTTACTGAGAGAAAGTTGAGGACATGT
GGCTGAAACACTGTCAGAGCTGCTGTGAACACAGTCCAAGTGAGCAATTTTATGACCCAAACCAAGCAGACACTAAGTGCTTTCTAGTGGTGGA
AAAGGAGCAGAGAGAAAAGAACAAAGACCAAGTGGTGGAAACAAAAAAAATATATATTTCTTTCAGCAGCTAACATATTTTTCTGTTTAGAAG
```

TABLE 1-continued (mouse gene: Prlr; human gene PRLR)

```
ATTGGTATCTCCTACTTAACCACAAACTACAACACATAAGATCAAATAAGATTAAATGTCCGGTTTGCTAAATAGCAGAGCGAAGAAACTAAGG
TCAAGATTTCAGACTCTTACATCTGAGGAAAGAGAGAGGCAAAGAGAAGATACTGGAAATGCCAATATCCAGTCAATGAAATAAACAGAGGCTA
CTGTAGGCATCCCCAGAAGCTTGCCTTTTGTCCAGTGCCATGGGAACCACAGAAGGCACTCAGCTTTGCAGCTTCACTCAGAATTGGGGCAATG
CTCCACAGAGTCAAGGGCATGTTATTATAAAGTGCTCCATTTGTTTACTTTGGCAAGTGGAAGATGACTTTGCTAAGCGATACTCTGCTGGGGC
TCAGGGCCAGCACTGCTGGAGTAGGAAAAGGGAGACTTCCTGGGCAAGGCTTCTCAATCTTCCTGCCAGCAGCATTGCAGTCGGAGCGGCACT
GAGGTGTCAACAAAAGGATGATGAACTGTGTCAGCAGTGTTAGCAAATGGCTGAAGTAGAACGGAGCTGCCCAGGATGCTGCCCTGTCGCTGGG
GAATCTGAGGGAGGCTGAAAGATATTGTAAAAGAGATTGAAGGGCTGGACTGGCTGGAGGAATGGTGCCATCGGCATCCATGCCACAATACTCC
AGGACTGCCCTGCCTTTGTCAGGACAGCCATCAGAGGCGGTTTTCCCTCTAACCAGGATGGGCATCACTCCTTGGGCTTGCCAGTCTTACCTCT
CCTCATGCAATTGCATGTCCAAGGCATGCCCTCAGGGGATGGTGCTGATCCAGGGTGGCAAACCCAAGTGGGGAGAAAATGCTGAATCTCATCC
TCTCAGAGATCTGCTGCAGTCAGCGACTATACTGAGGTGCATGATCTGAGCAGCAGTCGCTGGTTGGGGAGGCTTCTTTGTGGAGTGGGTCTCA
GCCACAGCCTGAGGGTCCTCTCTTGGGGATGCTACCAGTTAATTGGGTCATCTTCAGCCTCCACCCAAACTTAGGCCTGTAGGTCCATCAATTA
CTATATCAGCCTCAAGGACTGAACAGGTGGGAGGAAGGACTAGTGTGAGTGATGGAAGCAGCTGAGCTGAGGAGTGCTGGCACCTGTGCAAATC
CAGCAAGAATGACATCTGGCTGAGCTTCAGTCATTCACCTAAGCACCAATCGGGGGTCACTCCCAGATCTGAGCAATGAGGGAAACTTCCCAGG
GGGAACCCCGCACTTGGGTAGACCTGGGGGAGCAGCCAGAAGGGAAAGGGGTTGAACCTGTAGTTGATTAAGATTCAGAGAAAGAAAAAACAAAA
ACAGAAAACGATCATAGTTTCAGACACTCCCAATGAGCCTGTGACCTCCCCAAAATCCTATAGCCAAACACACGGGTGGATCTGGCCTCACTTT
CCCATTCTCCCACTTGTGACTTTTGATTCCACATCATAGCTAAGGTCCTCGGCAAATTGGATTAAACTTTGGATTTAAAAATAAAATAGAATTA
AAATAAAATAAAAAGTTGGGGACAGGAGAAAGTGGTTTCCAAGAACCTACACCTCTACCCCTGAAATGACTGAATATTGTGTTCCCCTCAAA
ATTCATATGTTGAAATCCTAACCCCAATATAATGGAGCCTTTGGGAGGCTTCATGAATGAGATTAGTGCGCTTACAAAAGGGTCCCAGAGAG
TCTCTCACCTTTTTCCACCATGTGAGGTTACAACAGGAAGTCAGCAGGTGTGCAGTCCAGAAAAGAGCCCTAACCAGAACCTGACCATGCTGGCA
ACCTGATCTCAGACTTCCAGCCTCCAGAACTGTGAGAAATTAAGTTATGTGGTTTATAAGCCACTCCGTCTAAAGCACTTTATTATAGCAGCCT
GAACTGATTAAGACACTCCTGAGAACGATTCCTTCGGGGAAGGTCTTGATTAGCCTTCACCTAGCCCAGTTTGCAAACACACTGGAGTGTCCTG
CCCATGGCAATGTTCATGTAGCAGCCTGGGAGACAGAGGAGGGGGATTCCTGCAGGAGCAATCTTCCCAAGGAGGCAGTTCCTACTAGCTAACT
TTCTTGTCCTGCTTGTGCTCATTGAAGGTCCAAACCTGTCCCCTGCCCTATGTTTGTTTTCCTCCTAATCCCCTGGCTGATGGAGTCAGGCTTT
GGAGAATTCCTTTAAGAGTCTTAGTTGGCCTTATGGATCCCAAAACACACCCTTCTCTATTGATGCCAGATTCTGAGCAGGCTGACAGTGCATG
CATGAGAACCTTTCATAAAATAGGACTATTTTTATTCCCTTTGCTTTTTCTTTGTGTTATTTCCCCTCTTCACTCCCTGTCCTTTTACCTTAC
CATATACATTTGTCACCTCCTTGCCTGGAAAGCCTAGTGTCACCTCCCTGCCTTTTCACAGCCTATAGGATTGAGTCCAAACTTGCCAGCTTGG
CCTTTCATGGAGTGCAGGTTTAGTACAGGACTGCTAAACACAGTTTCAGAATGAACCATTCTCCTGGCCTTTATCATTGCCAATATTTCTCTTT
ATTTTATTTTATTTTATTTTAGGGAGAGCCGATATTTCATAAGAGTTGATGGACTGCTTTGCCTGGAAACTTGAGAATTCATATTTTTAT
TCAAAATCGTTTTCATTTTTTTGCTTAGAGCCTGTTAAAGACTGAGGCCCTCTCTCGTCCCTTCTACTCCCAGCCAAACCCAATAGACACATG
TGAGCAAGTTGTCACCTGACCCGAAGCTCCAGCCCCTGGAACCAACTGAAACAAAATGTATCCTTGCATTTTCCAGCAAGGAATTGCCTTGCCT
ACAAAAATACTCTGTACTTTAATATGCAGATCAATTATTAACAGTAGGCTGTACCTTTCACCAGGTTGTAAAAGGATGACTGCGTAGAGCCACA
GCATTCTCCTTGTCAGTGTAGGAAATGCAGAGGAGGATGTTACCTCCGGCACTTGCCTCTAAGACACCTAATAAAGATGAGGAAGGCTCCAGCC
TGAAGCGTGGGTGAGGTGTCCAGCTGCCCAAAGGCGACAGGTGAGATACTCAGGTCCCCTTCCTCTTTTTGCTGTCAGTTCTGATTCTCTCCTT
TCAATCTTTCTCATCTGTGATTGGGAATGGCAGGGGTGGGGTGTGTTTGGGGCATCAGTGGTGGTAAAAATGGTCTTATGGGCAGGGCCATGTT
GAATAAGAGATGAGCATGGAGACGCGTATTAACTTAAAAGGCCAACACCGAGGCTCATTTGAGACCGTAGGAATTCCAGGGAGACAGTGTTGT
TCAGGCATGGGATCGAAGATCAGGAGGGCGGCTCAATAACACGCTGGCCCGGTCACATGACAGACCAGTCCTTGGAGTGAACTGGGAGACAAGG
AGGCTGCTTTGGCATGGAGCTGAGAACATCTCTAGATCGCACTGGAAGGCAGAGAGAGGCCAGACAGGGAACTCTGAAGAGCTGCCACAGCCTG
TGCCAGGGTGACATCAGGGTGAGTTGAGATGATTTTTTAACAAACTTCATTTTTTGCAGCAGTCTTAGGCTTACAGAAAAATTGAACAGAAAG
TACAGACAGTTCCCACATACCCGTTTTCCCCCACAGAGTTTCTCTATTAATAACATCTTATGTTCGTGTGATGTTTATCATGATGAACCGA
TGTTGATATATCATTATTAACTAACAAGTCCAGAGTTTACATTAGGGTTTACTTTTTGGGTCGTATGGTTCTATGATTTTAACAAATGTATAA
TGACCTGTATCTATCATTACAGTATCATACAGAATAGTTTCACTTCCCTAAAAATCACCCTCCCTTCCTTCCTGCAAATCTCTGACAACTGCTG
ATCTTTTTACTGTCTCTATACTTGTGTCTTTTCTGAAATGTCATGTAGTCAGAATCATGCAGAATGTAGTCTTTTCTGACTGCTTCTTTCACTT
AGCAATATGCTTTTAAGCTTCCTCCATGTTTTTCCAGGGCTTGGTAGCTTCTCTCCGTTTTAGCACTGAGTGATACTCCATTGTATGGATGTAC
TGTAGTCTGTTTATCCATTTGGGCAGATTTCCAGCAAGATAAGGCAGAAGCAATGGAAAGGGTGGATGAAGGGAAAACTGCAAGGAACACA
GGACAAGATAGAAGCAAGAGCAGGAAGGTTTTGGAGAAGTGGAAAAACAAGCTAGAGAGATAGGCACAGAGGCCTAACCTGGGGTAAGGCAGGG
CCTTGTAACCAACGCTCAGTGAGAGAGGCCAGCCCCTCACTGACCTGCACCAGGCTTTCCTGATTTTATAGACAGAGTGTCATGAGGTCATGAG
GGCAGGAACCATGTCAGCTTCATCCTGAGAGCCCAGCACTTTGTAGGCATCTAATAAATATTTATTACACCAATGAAACCTTCAAAGTCTCTTC
TAAAAAAGCAAGTTCTCCCAGACACCAGAAGACAAATGGCCTAGCAGCCCCTGAGCCAGTCATCTCGGGCAGTTGTGAGCTGGTTGCTTATTTG
AACCCTCCATGCCACGGGGCAGCATCAAGCTTGCCTGACACACACCTCCTGAGCCAGGAATTCACCACTTTGCCACCATCTCTGCCTGGCTTGG
GAGATGCTCCGTGGACAGAACCAGAGCCGTGCTGCAGGGAAGCAGAAAAACCAAAGGAGATGCATGCCAATCTAACATGCCAGTTTAAAAAAAG
GCATTCTTGCCTCAGAGTAAGAATCCAGCTCTCCATGCACTCGTCTTTCAACCCAATCACAAGGCATCAGAATTAGCCCATATGACCTCTATGG
GACAAGAAGAGCAAGCAGGGTGATTTGGGTGCTAAGAAATAGCTGTGAGAAGATGCGGCAGCGTGTGCCCTCCAGATGTTCGGAGAGAACAT
CTGTGCAACAATAGCAGTAGCTCCCATGCACTGATGTGAGAACCCAGCCTAAGGGGTACAGCAATCTGGTGGTAGGGGTAGCTCTCAGAGGG
TCTGACAATTCACCTAAAGATTGCAGGACCAATAGGAACCTGCCAGTCAGAAATTCCTAGCTCAGTGGTGCCCTCCAAGCAAGAGAGCTTATCA
GCCAGACCTGTGTCTTGGTGCAACATCACTGCTTAAAATCAAGTCCTCCCAAGGCATGGTGTCCATTTTACTTTCTCTGGATGAAATGAAGACA
GAGAATGAACCCAGTAAGATGATAGAGTGCTTTGCTTTGGATCTGTTCATATCTTACATCCGTGTTGTGCTCACATGAGTTACACAGTCAGTACA
AGGGTAGAGAGCTCTTGAGAATTTCTTACCTAAGGGAAAGAACTTGGGGCTGCTTTGCTCAAAGGCTATTTTCAGTGTGGGGCTTATCTAGA
GACATATATTTTGCTCCTTGTCCCCACTGCTGTTGCATAACTACGGGAGTTGAGGGTCACTATACACAGACACAGATGGTAGAGATGGGGCAG
TGGTTGGGCAAGGAATAGCTGCCTTGCCACTTCGAAGTCTCCTAAATGGCATCTCTGAAGAAGAAGGATATGTCCACAGGGAGAAGGGCCCAT
GGTGACTCTGTTGCTCCTAATGTGCCAGGCTCAGACTCTTCAAACCACAAGAAGTGGCCCAGCGAGTTCCATGTAACTGCAAATGCAAGCAGGA
AAAAACCACACTCAGATCTCAGCACAGCATCAGTCTTGGGGACAGCTGGCCTTTCCTAATGCAGCAGCATCTGGCTGCTTCTGCTGTACCTGGA
TGTCTTCAGGGCAGTTCTTCCACACAGGAGGACCCAAATAAAAGCAGAATTCCTACCATTAAGCTTTCCGTATCCAAAACTTTCTATGTGAAAG
ATACAGCATCTGTGTCTCACAAGAATCTGTTTTCTTGGGGCATCTGCTATTTGGCAGCTAACCAAAACAGAATTCCCATCTTATTTTCTTGTTC
ATTTGTGCTACATGGAAGGGACTGGTCCTGAATATTCAGGGCAACATCCAGCATTTGGTAGTAGTGGAGAGAAGAGAAGAGAAAGCTCTGAC
TGTGTTCCTCTGTCTGGGAATGTGACTCTCACACCTCCCAAATCCTCCCATTCACACTTTTTCTCCCTGACTTTCCAGAACCCTTTTTAGGCTT
AGCTCCTTTTATCTTACCCTACACGCTTTCTTTCTACCCACACTGGTGGGTACTTTTCAGCCATAGACATTGAGCACATTTAAATATGCTGGA
GTCCTTAGAGAATTAAGAGGTGGGGAGAGAGGAGGGCACAGAGCTGAGGATGGCACTAGCTCATTCACAAGGAGCCCTGAATTTCCAGGGACA
TTAAAGACAGATGCTCATGACAGACATAGAGCTCTGCCCTAATTGTTTGTAATGTTGAACTATGTGTCATTCGTTCACTCTATATATTCTCTC
AACATTGGAATTGAGCACCAATTATGTAACAGAGTAGGTCTTGGCAATACAAAGATGAATGAAACATACCCCTTGTCCCCAAGAAGTATGTGGA
CACGACAGGCACATGGACCAATGATGGTCATGTCAAGCGTGATGAAGTCCATGGTCCTGAGGGACACTTGGACCACGGCCTGCATGAGAGGCC
TGGAACCCAACTGGGCGGATCTAGAAAGAATTCCTCTGGACTTGATTCCTGAACTTGAAGGTAGAGATGGAAGGAGAAGAGTTCTGGGTAGCAT
GTTCCTGGCAGAAGAAGCCCACTGCAGAGCAAAGGCACTGAGGAAGCCTGGTGGTCACTGGAAAACTGGGATTCAAGTAGCTGAAATCGTAAG
GGTGCAGCCTAGGGAGAAGTGAGACCCGTGGTGGGGGGCAGAGCCAAATCTCTGTATCCAAACCTTTCTATATGAAAGATACAGTGTCTGTGTC
TCACAAGAATCTGTTTTCTTCGGGTGTCTGTTATTTGAGTGCTAACCAGAACAGAATTTCTAAAGATGGTCTTTGAGGCCAGGTAACAAGGCTG
AGGCTAAGAAGAACTATGGAAGGTCTGTTGGCAGGAGAGATGTATGATTAGATCTGCATTAGCAGAAGGAAAGTTCTGGCTGAAATCTGCAGAG
CAGTTTGGAGGGGACAAGACAGATGACATGGAGAACACTTAGGACGCTGTTATAATAAAATAGGCTAGAAATGATGTTCCTCAGAAGTCCCTTT
CTCCCTGCACACCTGGCCACCTCAGACCTCCTGTTCAAGGGGAAGGCAGGCTGGGAGAGAGGTTTCTTGAAAATAACACATCTGGGCCGGGCG
```

TABLE 1-continued (mouse gene: Prlr; human gene PRLR)

```
CGGTGGCTCACGCCTGTAATCCCAGCACTTTGGGAGGCCGAGGCGGGCGGATCACGAGGTCAGGAGATCGAGACCATCCCGGCTAAAACGGTGA
AACCCCGTCTCTACTAAAAATACAAAAAATTAGCCGGGCGTAGTGGCGGGCGCCTGTAGTCCCAGCTACTTGGGAGGCTGAGGCAGGAGAATGG
CGTGAACCCGGGAGGCGGAGCTTGCAGTGAGCCGAGATTGCGCCACTGCACTCCAGCCTGGGCGACAGAGCGAGACTCCGTCTCAAAAAAAAAA
AAAAAAAAAAAAAAAAAAAAAAAAAAAAGAAATAACACATCTGTTAATTGGATCATTTCTGTGTGGTCAATGTCTGTAGGGGCTTTGTTTTG
GTCATCATAGTATAAAATCCCCATTATGTAATATTTCCTCCTGATAAAAGCTCACTGTGTGTCTATACCCTACCAGCTTCCTTATAGTATTTGC
TCATTACCAGGTTCAAGGACCTGTCTGTGTGGCTCTTCCCCAGAGCCTCTGTTGGAAAGAAGATTTGTCTTTGGTTATAAGTAGATACACAGTG
GTCAAGATGCTCTAGCACAGTGCAGCAGAATAAGATGGGCTCAGTAGGGAAAGATCATTCACCCCTAAAGTGTACACTTATTCTTTTCTGATTA
TGATAGGATTATGTTGAAATTAAAAATTGTTTCAACGAAAAGCAACTGATTGCTTAGGCAAAGCAGAACTTTTTTTTTTTTTCCTGAGGCAA
AGTCTCAGTCTGTCACCCATGCTGGAGTGCAGTGGCACAATCTCACAATCTCGGCTCACTGCAACCTCCATCTCCCCAGTTCAGCGATTCTCC
TGCCTCAGACTTCCGAGTAGCTAGGATTACAGGCACCTGCCACTATGCCCAGCTAATTTTTGTATTTTTAGTAGAGACAGGGTTTTGCCACGTT
GGCCAGGCTGGTCTTGAACTCCTGACCTCAAGCGATCCACTCGCATCAGCCTTCCGAAGTGCTGGGATTACAGGTGTGAGCCACCATGCCCAGC
CAGAATTATTTTAGTACTGTAGTTAAGAGGGCACATTCTGGAGCAAACTGCCTGCTAAGTGTTCGCTGTGGGGCATTGGGGAAGAACTTAATC
TCTTTGTGCCTTGGTTTCCACATGTAAAATGGGATAATTATATTGTCCCCTGTACTGGTTTGCTGGGGCTGCCATAACAAAGTACCACAACTG
GGTGGCTTAAACAACAGAAATGTGTTGTCTCATAGTGCTGGAAGCCGACTCACTCAGAAGCATGGACTCCCTTACCTCCAAGTCCAAGGCAAT
GGGGCTCTCTCCCTCTTGCCTCTTGAATTCCTGCATCTCATTTCACTGGGTAAACAGGGAGGCTCCTGTGCTCCAGCAGGAAAACCCTGGACTG
GGAAGCAGGATGTCTACTCTGATCCTGCTGCCCAAAGCTGTGCGGCTTTAGACAAGTGGTTTGACCTTTCTGGGCTCAGTTTCCTTGATTTTC
ACTATTATTTGAAGGGCTTGGGGTCATGGAAATCATGAACTCTTCACACTGAGAGGAATCTTCATAATCCATTTTGTAGATAACGAACCTAAGG
CTGAAGAGGTCAGGGGCTTGCACCCAGTCATAGAGCTAAATGAGGTGTTTATGCAAAGAACCTAGAACTCCGGCGTCTTGACTCCCACCTGGGACACATT
TTATCAGTAATAGTGAACTCTCATCTGTTGATAGTGTTAGAATTCTCACATTTACTCCCCATAACAACTTTCTTTTTTTTTTTTAAACGGAGT
TTCTCTCTGTCACCCAGGCTGGAGTGCAGTGGCACGATCTCAGCTCACTACAACCTCTGCCTCCCGGGTTCAAGCTATTCTTCAGCCTCAGCCT
CCCTAGTAGCTGGGAATACAGGCATGCACCATGGCGCCTGGTTAATTTTTGTATTTTTAGTAAGGATGGGGTTTTGCCATGTTGGCCAGACTGG
TCTCAAACTCCTGACCTCAAGTGGTCCACCTGCCTCAACCTCCCAAAGTGCTGGGATTACAGGTGTAAGCCACCATGCCTGACCAGCACCCTTC
TGAAGTAGGTGCTTTCAGAAATCTGAAAGCATAGTGTCGGTTAGCAGGGTTGGATCTCTTCTGGTACTGTGGAGGAAGAATCTGTGCATGGCTG
TCTGCTAGCTTCTGGTGGTGTGCTGGTCATCCTTAGTGTTACTTGGCTTGCAGAAGCACCATCGATCTCTGCTTTCATCGTCGTGTGGTGCTGC
CCCTGCATGCATGTATCTGTGTCCAAATTTCCCCTTTTTATAAGAGCACCAATCATATTGAAATAGGGCTCACCCTCATAATCTCATCTCAACT
AATTATATCTGCAATAACCCTACTTCCAAAAAACACCACGTTCTGAGGTCCTGGGTGTTGGGATTTCAACGTATGAATTTGGGGTGGGAGGGCA
CAATTCAACCCAAACATTACCTAATAAAGTTTTCAACAGTAAGATGAGTTAACTCTCTGGAAAGCATTTAAAACAGTGTCTGACATTCAGAA
AGCTCTCAGTAAACGTTACATTATGCTGGGTATAAATAAAAAGCTCCCAGGACAGTGGACGGCATTGAGATTCCACCGGTTTGTATTAGTGTGG
CCTCGCCAGTAATTTACATCTTCTATCTTTTTGGTTGGTCAGGGCTTAAGCCATACCAGGTAAATATTTTGAATAATACTCCTAGCTAAAAGG
TGCAAGGAGTAGATACTGTGGGTTCTGATTTTTCTTTCCCGTTCTCCAAGCTGTGTACACAGAACCATGCAAGTCGCCCCAACCAGGGAAAAAC
AACTGCCATTTCTTTTAAAGGGAAACCAATGAAGGTCTTGTCCTGATGAGCTCACAAAGGCAAACTTCTTCCATGTCTGTCGCTCACTCAGTGGG
CTGAAGCAGAGCCTTCACGCTAAGCTTTGGAGACAAAGCTTCTTAGAGAATGTGCAACGTGGGCTGATCCCAGGCTGCCCAAGGAGCAGCTGAC
GAGTGTAAAAGTGTTTGCTCACCGATTAGAATCAGTCCTTTAAAAAATAAATAAGGTATGTTGATCTTTTATGTGATGATTAAACAAATCAGAT
GGCCCAAAATGAATTCCAGGTAAAGAGGAATAAAAATATCAGAAGGCAAGCTGCTGAAATTAGCAAGAGCTGAACTCGAAAAGCCCGACTTTCA
GGCACGGCTAGTTTCTTCCTAGCAAGTTCCTGACGGAGCTGGGTGGCTGCCCCAGGTGACTGCAGGTAGCAGGAGATTAAGGAGACAGCACCTGC
CTGACAAAAAAGGTTGCTGACACAATAGGCCAAAGTTAAATTGAGCTGCCAAGGGAAAATGATTGGGGATATGCAGTTAACAGTTGAGGGAGAT
ACCAGAAGAATTTGTGTCCACAGAGAGATTTTGATGGGGCTGACTTTGCCGCTGACCGACTCACCTCAGAAGCATGGACTCCCTTACCTCCAAG
TCCAAGGCAATGGGGCTCTCTCCCTCTTGCCTCTTGAATTCCTGCATCTCATTTCACTGGGTAAACAGGGAGGCTCCTGTGCTCCAGCAGGAAA
ACCCTGGACTGGGAAGCAGGATGTCTACTCTGATCCTGCTGCCCAAAGCTATGCGGCTTCGGCTCACCGCAACCTCTGCCTCCAGGGTTCAAGCT
ATTCTTCAGCCTCAGCCTCCCTAGTAGCCGGGAATACAGGCATGCACCATGGCGCCTGGTTAATTTTTGTATTTTTAGTAAAGATGGGGTTTCA
CCATGTTGGCCAGACTGGTCTCAAACTCCTGACCTCAAGTGGTCCACGTGCCTCAACCTCCCAAAGTGCTGGGATCACAGGTGTAAGCCACCAT
GCCTGACCAGCACCCTTCTGAAGTAGGCACTCTTATACCCATTTTACTGATCAGGAGACCGGCTTGCCCAGGATCCTGCAGCTACTGAATAGAG
GGGCCAGAACTTTGCTGGTTTGGTGCGGTTCCTGGTACACACCAGGCTGCCTCCAATCTCCCTTTGATAATCCTAGCCACATGCCACCGCGGGTG
CTCTAGTGTAGGCTGGCACCAACCCCACCCAGCAAGAGCCAGGATCTGCTTCTTGAGGGCAGGCAGGTTTATCACACAGCGGGGTGCAGAAGAG
TAGTATTCATCTTCCTAGTGTAACCACTTATAACTACTTTTCAGTGAATCAAATAGATTTTTAAGCAAGAACATTGTAAAAATCTGCTTAATCA
AGGGTGGAGCAAAATGAGTTAGCCAGGGCCACCCTAGCTCAGATGGGGTGGTAGCTGCCTCTGCTCCACAATGAGGTATTTACACTTGCTCCCC
ACCCTCTCCTTTGCCCCATTATCTTTTAGTTAAAGGGCCAGGTGCACCAGAACACAGGTGCCTTGAGTAGCACCAGCACCTCTCAGGGTCATAG
GGAAGAGCTGTTTCCTCTGGGTAAACTGAGGCCTCAATAAGGCATAAATGCCTTCTCTGGGTGAAGAAGATATGCCCTCTAAGATCTCTCCAGG
GTGAATCTAGAATAAGTTGTAGTCTAGATGGCTTGGCAGCACTAGCCAGTGTGACAGTAAGTCTTGATGAACATCAGTCAGCGTCATGCTGAGG
GACAACCTCGAGGAGAGGGAATGTGTACTTGTTACAACAGCACACCCAATAGAAATAGCATGTAAGCTACAAATGTAACTTTATATTTTCTAGC
AAAAAAAAAATTTTTAAAGAAACCAGTGCAATTCATTTTAATAGATCTTATTTGTTTCAATATATCCCAAATATTGTCCTTTCAATGTGTGAT
AATATAGTTATTAGTGAGATATTTTCCATTCCCTTTTTCATACAAAGTCTTTGATACTCAGTGTGTATTTCACTCTGACAGTGCACCTCAATGT
GGTGCAATAGGCGAGGGTCTATGTGGTACATCCCGTGCCCAGTGTGCACTTAAAGGCTGTAGATCCATATATGGCGACTGTCTCCTAGATAGAT
GAGCCCAGCAAGGCTCAGTGGGTGTTTTGAGGTCCATGGTCTCTCAGGTCCGTTCCACCCCGACATTGACGAATCAGAGAACACTAATATGG
TTGGGAACACTTTTATCTTGCTCCCCATAGTCTGAACAGAAAGAGACGCCACAGAATACAATCACGACTCTCTCCCTCCTACGGACTCCCTCCC
CACAAGCAATCAATGGGCTGGTCTCAGACAAAGACACCTAGTCAAGGCTGGTGAAAACTGCTCTATTTCCTAGTAGGCCTCCACCTGTAATTCT
CAGCAGTTTGTGTGTATAGATAGAATTCCTGCCTTCTACTAATGTGACTGTTCCTGCTCAGAGATCTAGAGTTAATTATTAGCAAATTCACAGT
GAACCAGAGCTAGGTCTTGCTGTAAGGCTCCTGTGTTTTTAGAAGTACGTTGCCATGGGGATTTTTGTCCCCACTGGGTTCCTCCTCAGGACC
CCAGACAGATAGATACACAAACCCTGGGCCCATAATTTTAGTTAGAAAAGGCCCAAGCCTAGAACCTCAGGGAACTCATTTGGAAGCTTTTTT
TTTTAGGAAACTTACCTTTCCTATTTGACATCTCAATCAAACAGGTGTTTGGGGAGAATAAAAGCATACTACCTTAGAAGGGACTGGGGTCATC
TGGCCAGACTTGTGGAATAAAGAGAATTTCATTCCTTGTATAAAATAACTCTAAATAATGGTAAGCTCTTAGGAGACTTGATCTACTGGCTACA
TATACCCACTATGAAATTAACACATTCTGGAATTTAGATGGAAGAATATGGAATTGGTCCTTCTCAGTGTATGGACGAAGCATCAGAAATGAA
GAGAAGGGCCAAGCCTAGAGAGCAAAACTAAAGACTCACTGGTCTGTGGGCTTCCTGCCCAAGGAGAGCTGAAAGCTAAAGGATGCTTCACAAT
GTCCTACAAGTTGTTTTTCTAAAGTCCTTCCAGCGGTTGAAACTGTGTTTATGCAAAACAAAACTTTCCTTTGTTGCTATAATCTAGAGGTGGA
CTTTGGCTTAAGTCATGCCAAAATATTATCATTCTAAACCAGTAACACCTATATTTGTTGAGCATTTACTATATGTGGCACTATGCTAAACT
TAACTACCCCTTTTCCTCATGTGTAACAGTCAGGTGACTTCACAGCTGCCTTGTGGATACTTGTGTTATTTGAAAGATTGCATAAACACATGTA
AAATGCTTAGAAGTCTACCACCTCATCTTACCTACAGCTTTGGTGAGTCCCTGCTTTGGCCAAGTAGAATCATTCCCTGTGAGGAGGGGAAGAG
GATAAGAAACAGGCAGAGTTGACCTTACAGGTAGACACAACAGGCAGGCGAGGGTCCATGTGGTGCAATGATCCCATGCACATGCCTGATTCAGTCA
TTCTAGTTGAGTAGGATTGTCTGGTTGGTTGTTATTATTTTGTTTTTTGTTTGTTTCTTTCTTTTGTTTTATAAGATGGAGTCTCACTCTGTCG
CCTAGGCTGGAGTGCAGTGGCTCAATCTCGGCTCACTGCTGCAACCTCTTCCTCCCGGGTCAAGCAATTCTCCTGCCTCAGCCTACCGAGTAG
CTGGGGCTACAGGGCATGCCACCACACCTGGCTAATGTTTTGTATTTTTAGTAGAAATGGGGTTTCACCGTGTTGCCCAGGCTGGTCTCAAACT
CCTGAGCTCAGGCAATCCTCCCACCTCAGCCTCCCAGAGTGCTAGGATTACAGACGTGAGCCACCGTGCCTGGCCAGTTTTTATCTTGAAAGCT
TAAGGGTCTCCCACTTAAATTCAAATACTCTTCTGAGGATAACCTTTTAATCAGCCAACTATCATGAATCTCAATTATCAGGAATTCCAGTTAT
```

TABLE 1-continued (mouse gene: Prlr; human gene PRLR)

```
TCCAATTATCAGGAATTCTTTATATCATCCCAGGAATCTAAAAGAGCAAGGTCTTATAGGTAAGGGCAAACTTTCTGATGCCTTGGAATTCAGA
CCCTAAGTAGAGATGGTCATTTGACATCTAGTCTGATCGACTGTAGAGTTACTTCTATACAAATAAATTCAAGTTATCACAGGGTTTCTTTCAG
TTGGGGACAATACTTTGAAAACTTTTAGGCTCTGAATGAATAACTTGGCAAAAGAAAATGTTAGGGTCCTTCAAATACCATACTTGTTGTGGTT
TTCTCACAGATACACCAGTCTATAACCCTGAGGTTTCAACACTCCACTCAGTTGTGGGCTTTTTATCTAAATCAAAACTATCACATGCCCACAT
GTGCATCTGCAGCCAACCACAAATGATCTAACAGGACCAGATTTCACTGGAGCTCTGTGACCCTTCTCCCAGTGTGAACTGAAGGGAAAAAAAC
CTGGAGCCTAAGGGACTCCCTTTTCCGTGTCCTGAAGACCACTGGCTTTGGTTAAGCCAATATGATGGGCTCATTGAGAGAGAGACTCAGGACC
TCGGATCATGCCACACTCTCTGGCCCCAGAAGGCATACCACAGGCTGCCAGCTTTGTTGGAGAACCTGAGACTTAAGGCCAGGATATATCAAGA
GCCCTGTACCCAGTTCTGTGATGTCTTAATACCTTTGACAAGAGACATTGGCAACTCACTGGGTGTCCATTGGGGGGCGACAAGGAAACAGACT
GATGAAACCAGAGAATGTGACAACTAATTACATGTTGTTTCCTGTAGAAGAGAAATTCTCAGAGGAACGTGGTGACTGTCTGTTCTTTAATGGA
CTGTCATATGAAAGCAGGAGAAGGAGATTCTTCCTTACTCCAAATGACAAAACTAGGAGCAGTGAAATGAGCTTATAAGGTGGCCGGGTTTTTC
TAGCAATTGGAGCTCTCTGCAGTGAGTGGACACTTGGCAGGGTAGTGCCTACTCCGCATTTGATGTGTTCACACCACGGCTAGAAGTAGGTGTC
GCAACTTCCAGTTGAAGAGGGAATTCTTTTCCTTGGGTGGGAGAGGGGCTAGAGAACGTCTCAGGTTGTTGCTAACTATGAGCATGGTTTTATA
ATTGTTTAAAAGTGGGTAAACAAGAAGAGTGTGTTTATGGTGTCTGTATTCCACAAACTATTATTTCCCACATTAACTGTTTCATATATGGAAA
ATCTGAGAAACAGGAATGCTAACAAGGTTGCAGTATAATTTAAAAATACTTCTGACAGATCATTGTATCCCAAAGGCAGTGCCCAGTGAGGTTA
AGAGCGTGGTTTGTGGAATCTGAGCCCACAGGGGTTTAAATCCTGCCTCTGCCCTTCTTAGATTCTGTGAACTTGGACAGATTCCCTCACTTAT
TTAAGACTTCACTTTTCAGCCCTTGAGATCCCACCTGCTCAATTATCTAAATGAAATCTATCACTGTGGAAAGAGCAAAGGCCTCCTGCTGTTG
AGCAAAATGTTTTCCAGTCCTTTGTTTCTGTGTGAAATAAAGCAGCTCCATCCCAGTGCTAAATGATCAACTGCATATGACAGAATGAGCTTAT
TTCATGCTCCCAGTAAATACAAGACCATAGACTACTCTGGATGGTAGTTTAAGTTTAAGATGAAATTGCTTCTTCTGATTGCCTTCTTCTTTAT
TGCTTCTTTCTCTGTTGTTCCTTCCTTCTCTGTTTATAACACTAACAGTCAAATCTATCTGTGTGGAAATCTATCTACTATATAGAACGCTAC
ATCACAATTTACAGAGGGGAAAATATTTTTGTCGGCAGTAACATTTCACTGGAAGAGGCACTATTTGGCCACCTAACTCTGGGATTAGGCTCA
GGTAGAATCAGTGCCTCAGTTTCTTTAGGTCAGCCATTATGAGTTGTTCCTTATTTGACCTAGCACATATATAGATGGTGGTTAAATTTAGCAA
AATTCTCTTCACAAAGGTTTCATTTGTCTGGAAGACTCTAAGTACTGATCTGGTCAGAGTACCATCAAAGCCCCTTGTTTGTCATGAGACCGTG
GACCAACATGTTAGTCTTTCTCATGTAAAAAAAAAATCATCAACAAATGCAGTGGGAGTTGGTAGTCATGAGTTTGAGGTAGTACAATATCCT
TAAAGTACACACTCAATCATGTGTGATAATTGGCCAACTCTACCTAACAACAGTTGAAGACCTCCAAACAGCTATCAGGACTACTGGAATCATG
TCTCCAGAAGAACCTGGAGAAACATTCACATTTGTGTGGACCAAGGAGGAAAGCAACCCAGACGACTTCTACTTAGAAGCACAGGCACATAGAG
CCTGTGTTATTGGCACAGGTATTTCTCTCCTAAGAGCCTTTTCTGCTTAAGAAGGCTTGAGGATCTATTCCCATTAATCATAAAAAAGGGATTT
GCTGGGCTAAATTATTTTAGCCTCCTCTTTATGCCTTACTTCACAAAGAATTGCAGTTAATCTGTAAATGAGTTCTGATGTTATGAAAATTGGA
TATGGCAAATTGTGTTATTAAGTCTATTAAGGGATGAAGAAGGACTCTTCTAAAAGAATAACGTAGTCTGAGTGGCAGCTCTCACTTAATAGAC
ATCTACCTAGAAATGTTTCTGAACTTAATGGACACATGTATAATTCAAAATTAATATAAGCACACAGCACCTCTCCCCATAACCTTATTGAAA
TTAAGGGTTCCAAATCATTCTTCTCTCCCTTTTACTTCACCTGCAACATGTGGCTCACCCTTCTTTAGACTAAGAGCTAAACTCTAATGCCTAG
TTAATGTAAAACAATGCCAGGATTATTAAGCATGATTCTGATAAGTTTTAACCCCTAATGAGATTATCCTTGGTTAAATAAATTGAATGGCTAG
TGGAATTCCAATGTAAAGTCAGCAGAGGTTAGCTGGTTGCTAGATATTTAACTATACATACCAGGAAGCTATGAGGACAAATTTCCATTTGCAC
AGAGCCTTGAGAATTGGCCATTTTAGGACTAAATGTGCTGCTCATTACTTTTACTCAAGGACATACTAATGACCAATATATGTTTAAATACCTA
CTATGTACAACTGCTTTCAAAAACACTTTCAATCTTGAATTGAGAAGGTAGGAGATCCATACCTGTATTAGGCCATCCTCACAGTGCTATAAAG
AAATATCTGAGACTGGGTAATTTATTAAAAAAAGAGGTGGATGAAGCTGGAAACCATCATTCTGAGCAAACTATCACAAGGACAGAACACCGCA
TGTTCTCACTCATAGGTGCGAATTGAACAATGAGAACACTTGGACACAGGGTGGGGAACCTCACACACCAGGGCCTGTCATGGGGTGGGAGAG
TGGGGAGGGATAGCATTAGGAGATATACCTAATGTAAATGACAAGTTAATGGGTGCAGCACACCAACATGGCACATGTATACACGTGTAACAAA
CCTGCACGTTGTGCAGATGTACCCTAGAATTTAAAGTATAATAAAAAAAAAAGTGGGGAAAAGAAAAGAAAAGAGGTTTAATTGGCTCACGGTT
CTGCAGGCTATACAGGAAGCATGATACTGGCATCTGTTCAGCTTCTGTGGAGGCCTCGGGAAACTTACAATCATGGCAGAAGGCAAAGGGCAA
CAGGTATGTCACATGGCCAAAGCAGGAGTGAGAGAGAGAACAAGGTGCCACACACTTTTAAACAACTACATCTCATGAGAAGTCACTCACTATC
ACGAAGAGAGCACCAAGGGAATGGTGCTAAACCAAGGTCCCCAACCCCCAGGCCACGGATCAGTATTGGTCCATGGCCTGTTAGAAACCAGGCC
ACACAGCAGGAGGTGAGTGGCGGGCAAGCAAAGCAAAGTTTCATTTGTATTTACAGCTGCTCCCCATCGTCATTACTGCCTGAGCTCAGCCTCC
TGTCAGATCAGCAGCAGCATTAGATTCTCATAGGAGTGCAAACGCTATTGTGAACTGCACATGTGAGGGATCTAGGTTGCACACTCCTTATGAG
ACTATAATGCGTGGTGATCGGTCATTGTCTCCCGTCACTCCCAAATGGGACCGCTAGTTGCAGGAAAGCAAGCTCAGGACTCCCACTGATTTT
ACATTATGGTGAGTTGTATAATTATTTCATTAAATATTACAAGGTAATAATAATAGAAATAAAGTGCACAATAAATGTAATGTCTTGAATCAT
CCCAAAACCACCCCCTCTCTGCCCCGTCCCAGTCCATGGAAAAATTGTCTTCCACAAAACCAATCCCTGGTGCCAAAAACTTTGGGAACTGTTG
TGCTAAACCACTCATAAGAAATCCAAACCCATGATCCATCCAGTCACCTCCCACCAGGCCCCACCTCCAACACTGGGGATTATAATCCAACATGAAAT
TTGGGTGGGGACACACATCCAAACTATATCAATACCTTCATAAAAGCAATTAAATAACTGTACAGTGTGATAGGCAATAAATGTCAAATGTCAT
ATGTATGAGGAACATAGAGAGGTGCTGTTATCAAGTCACTGTGTGACCCACTGAGCACTCGCAATGAGGCACAGGTAGTAATGTACCTGCTCAC
TTGCTTATTGTTGTCCCACCACGCTGAATTGGGAGCTTCATGAGAGCAGGGCCCATGTCGCATCTATTACCACAACTGCCTTATTCGCGTGGCC
TGTAGCTAGCAATCAGTAAAAAATTACAGCATGGATGAAGCTACAGAAAGAAAGTAAATACTGACAGGTGGGCAAAATTTTTAGATATGGATAT
TTAATGATGGGATGAACAGATGAATCAAGACAGGAAACAAGGCTTCGCGTGGCAAATATATCTTTCATTTGCCCAGCAAACATTTGCAGATCC
CTCACTATGTGCTAGACACTGTGGGCACATTTCTGTGTGGATTGTGTTTTTCTCTCTCAAAACTGGAGAGATTTTGAGATCAGCCTGTATGTA
GTGAGATGAAGAGGTATGTGGTTGAGATCAGGAGTAGTTGGGATTCTGTGAGGGATAGGGCTCCTTAGGTGTAGAGAGCCTTGAGACCTTTGTT
GTGAGGATAGTGAAAATCAACAAAAGAATTTATGTTAAGGAAGGTTAAAAAGTCACTCTAAAGGTCTCAGAAGTGCCTATGACATCATGAGGAG
ATGTCCATTCCTGAAAACTTTAGCCAGGTTACAAACACTTTAAGAAACCTATCTCAAACTTCAAGAAAAGTGAGATCTGTATTTACACAGAT
AGAAATTTCCAGGACTGGATTATATTTGCACTTTTTTGTTAAATTTTTACTTAACTAGTATATTAATATTGATAGTACTTTGTGACTTTTTCAT
AAATATAACTTTTAAAAAATATGGTATTTCTAAAAAGGTTTGGTGCATTGTTAAAATGTGGTTTTGATTTATTCACAGACAGAAATCTTCTCTA
ACAGACTATACTTCCATTTCATAATTCAGTGAGGTAATGGGACTCAGTTATACTAAATTTATCATAGAGCAAACTTTGCTAGTTTTCATCTGTT
CATTACATTTTATGTAATGGCAGACAGTGTAATAACTAATACCGTTAACCCAACCATCTCTTCCCTATAATGTTTCTATAGGAACATACAGTGT
ACATTTTGCAGTTCTCTACACGCAGACAAATTCTACCAGTGTGTATTCTGATTACAAGCTAGTTGCTTCATAGGCCATATGTCTATCTTCAGTC
CCTATGAATCATGTAAATTACAGAGCAAACTGCCGATACTCAGTATATGTATATGACACATAAGAGTCAAGTATACTCAGCTCCTAAGAGCAAG
TGAGAAGACAAAGAAGATCTACTGTGTGTAGAAATACTTCTTAAATCATCTTTCCTGAAGGCCTAGTTTGCAACTGAGTCGCAAAAATTTGGTT
TCAAAAAGTTAAGCTTGCAATAATAAAAAGATAACCCAGTTTAACAATGGGCAAAGTGATCTGAACAGACATTTCTCAAAAAATGATATAGAAA
TGGCCAGTAAGCACAAGAAAAGATACTCATCATCATTACTAATTAGGGAAATGCAAATCAGAACGACAATGAGTCACCTCTTCACAGTCACTAG
GATGGCTATGATTAAAAAAAAAAAAGACAGGCAATAACCAGTGTTGGCAAGGATGTGGACAATTTAGAACCCTCATACACTATTGGTAGACATG
CGAAATGAAATAGTCATTTCAGAAAACATTCTGGCAGTTCCTCAAAAGGTTGAACATAAAGTTACTAGGTGAACCAACAATTCCACTACTAGCT
ATATATCCGCCAAACTGAAAACAGATACTCAAGCAAATACTTGTCACATACTTTATAGCAGCCCTATTCACACTGTCCACATACTTGAAAAC
AATTCAAATATCCATCAATGGATAAATAGATAAACAAAACGTGTAATTTGTACAATCGAGGATTCAGCCATAGAAAAGAGTGAAGTACTGATA
CATACTAGAACATAGATGAACCTCAAAAATGTTATGGTAAGTAAAGGAAACCAGTCAAAAAAGACCCACATACTTTATGATTCCATGTGTATGAT
ATGTCCAGAATAGGGAATTCCATACAGACAAAAAGTAGATGAGTGTTTGCCAGGGGCTGGGGAGAGGTGGGGATGGGAATGACTGGCTGATGG
TTAGTTTCCTTAGGTGGTGAAAAAAAATGTTTTAAAATTGATTGTAGTAATGGATCCACAGCCTTGTGAATATACCAAAAACCACTGAACTGTGT
AGGGGTGGGTTGCCCCTCCACACCTGTGGGTGTTTCTCGTAAGGTGGAACGAGAGACTTAGGAAAGAAAAAGACACAGAGACAAAGTATAGAA
AAGAAATAAGGGGACCCGGGGAACCAGCGTTCAGCATATGGAGGATCCCGCCAGCCTCTGAGTTCCCTTAGTATTTATTGATCATTCGTGGGTG
TTTCTCGAAGAGGGGAGGTGTCAGGGTCACAAGACAATTGTGGGGAGAGGGTCAGCAGACAAACACGTGAACAAAGGTCTTTGCATCATAGAC
ACTGTAAAGGATTAAGTGCTGTGCTTTTAGATATGCATACACATAAACATCTCAATGCTTTACAAAGCAGTATTGCTGCCCGCAGGTCCCACCT
CCAGCCCTAAGGCAGTTTTTCCCTATCTCAGTAGATGGAGCATACAATCGGGTTTTATACCAAGACATTCCATTGCCCAGGGACAGGCAGGAGA
```

TABLE 1-continued (mouse gene: Prlr; human gene PRLR)

```
CAGATGCCTTCCTCTTGTCTCAACTGCAAGAGGCATGCCTTCCTCTTTATACTAATCCTCCTCAGCACAGACCCTTTACGGGTGTCGGGCTGGGG
GACGGTCAGGTCTTTCCCTTCCCACGAGGCCGTATTTCAGACTATCACATGGGGAGAAACCTTGGACAATACCTGGCTTTCCTAGGCAGAGGTC
CCTGCGGCCTTCCGCAGTTTTTGTGTCCCTGGGTACTTGAGATTAGGGAGTGGTGATGACTCTTAAGGAGCGTGCTGCCTTCAAGCATCTGTTT
AACAAAGCACATCTTGCACCGCCCTTAATCCATTTAACTCTGAGTTTGACACAGCACATGTTTCAGAGAGCACGGGGTTGGGGGTAAGGTTATA
GATTAACAGAATCTCAAGGCAGAAGAATTTTTCTTAGTACAGAACAAAATGGAGTCTCCTATGTCTACTTCTTTCTACACAGACACAGTAACAA
TCTGATCTCTCTTGCTTTTCCCCACAGAACTGTACACTGTAAAAGGGTGAGTTTGTGGTATGTAAATTTATCTGAATTTTTAAAATAAAAAAGA
AAGTTAAAAAATGTTAAACTTGGAATTAATGATGGTTTTTTTGAACCAGATTAGTAACTACTGAAATTAGTCCTTGATTTTTGGAAAAGCCTTT
AAAAAATGGTAAGTGGGAGAAGTTATAAACAAAGAGATGAATGAGTCACAGAAAATTGGGAGACAAATAGATGATAACAAGGGACAGTACAGAA
AGACTCAACTGAGTTTTATCAAATCACTCAGGCAGATAAACATGGGGGCTGCATGTGCATCCGTATGTGTGTATATGTTTATTTACATCTAATA
TACACACATGATATTACATGAAATATTTATAACATATAATAAATATATATTCATACTGGAAAAATTCTCAAAGAAATATACCACCAAATGTTAACA
ATAGCTGTCCCTGTTTAGTGGGATTTCAGGTGACTTAGATCCTTTCCCCCTTTGGCCTCTCAGTATCTTATAACTTTGTGTGCTAAGATCATTG
ATAGTTGAACAATAAGAAGAAGAAAGTGAGTGTGGAAGGATGTTGCTAGAGAAAGTGTATTCTTGATTATATGGAGGAAGTGGGGGCAGTTTGT
GAAGTCTTCCTTACGAATAGCATCCTATTTGAGAAGACCAGTCTTCACACTGGAAAAAATGCATAGAGCAAGGTGGGCATCACTTGCAGAACAG
TTTGGCACAGGACTACCTCTGAAATATTAAGGCTTAGGAGACTTGTTCTTAGAAACTCTTCAGGCAAAGTTTACAAAAGGCCTTTTCCTCCTTG
CTTAGCAGATTCTCCCAAGGCATCCACATCTACACTCTCCGTAAGTCACTATATACTGGACCTAGCACACATCTGTCTACCCATCATTGTATTA
GTCTGTCCTCACGCTGCTTATAAAGACATACCTGAGACTGGGCAATTTACAAAAGAAACAGGTGTAATGGACTTACAGTTCCATATGGCTGGGG
AAGCCTCACAATCGTGGTGGAAGACAAGGAGGAGCAAGTTGTGTCTTACATGAATGGCAGCAGGCAAAGAGAGAGAGCTTGTGCAGGGAAACTC
CTGCTTTCAAAACTATCAGATCTTGTGAGAATTATTCACTATTATGAGAACAGCATGGGAAATACCCGCCCCCATTATTTAATTATTTCCCACC
AGGTCCCTCCCACAACACGTGCGCATTATGGGGGCTACAAGATGAGATTTGGGTGGGGACACAGAGCCAAACCATATCAACTATCTATCTATCT
ATCCATCCATCTGTCCATCCATTTATCTTTAATTGGGATACGTCTACAAGCAACTCGATACCTAAAAGTATGGGAATTTCATTTGCTAAGTCAC
AAAATAACTTTTAAACCATCCTTATATTATACCTAACATGATCTGAGCACATAATATTGTCTAAGTCAGACCCATTCTTGCCTCTCTGAGCTTA
CACTCTTGTCAAGTGTGAGCCAGAAGGAGTTGGTCCAAGTAGAGACAAGTCTCACAGGCTTTGTGGTACTCAGGGTGGGGGTCTTACCCAACATT
TCCTCCCAGAAGCTGAAAGGCAGAGACAAGAAATTCATCCTGAAAGAGTTCACAAGGGTAAAGTCAAGGTGGCTGGTCCCCAGACAGGTCATAG
GAATAAGGTTCTGGTCATACAACAGGAGGCAAGGAGCCCAAGTAGAGGGACTTGGGTGTGGGGCAAGTGGGAGGGTTTCATTGAAAAACTAGGT
AGAAGACAGGGAGTAATGGTGGATAAGGCAAAGGACAGCATCTAATTCAGGCCTGTCATCAAGCTAGAGAATGTTCACAGCAGTGTTGTTTGAA
AGAGAAAGGCATGGAAAACACTTTGTTGTCTATCAGCAGGTGTGAATAATTTAATTGTGGTGTTTTCAAATAGTGAGATTTCCAGCAGAGGAAA
TTAATAAACCAGAGCTGCATGTGCTCGATGTAGAAAAAAACCCAAAGTGTCCAGACATGGTGGCTCACGCCTGTAATCCTAGCACTTTGGGAGGC
CGAGGCGGGTGGATTGCCTGAGCTCAGGAGTTCGAGACCAGCCTGGGCAACATGGTGAAACTCCGTCTCCACTAAAATACAAAAAATTAGCCGG
GCGTGGCGGCCTACGCCTGTAGTCCCAGCTACTTGGGAGGCTGAGGCAGGAGAATTGCTAGAACCTGGGAGGCAGAGGTTGCAGTGAGCCGAGA
TCGCGCCACTGCATTCTAGCTTGGGTGACAGAGTGAGACTCCGTCTCTTAGCAAAAAAAAAAAAAAAACCGAACACCCAGTGTTCTCACTCATAG
GTGGGAATTGAACAATGAGAACACTTGGACACAGGAAGGGGAACATCACACCGGGGCCTGTTGTGGGGTGGGGGAAGGAGGAGGAGGATACCA
TTAGGAGATATACCTAATGTAAATGATGAGTTAATGGATGCAGCACACCAACATGGCACATTCATACATATGTAATAAACATGCACGTTGTGCA
CACGTACCCTAGAACTTAAAGTATAATAAAAAAGTAAAAGAAAAGAAAAGAAACAACAACAAAAAAAACTACCCTTTAAAGGAATGCATAT
AAACAATAATTTATTTCTTTCACATTCATTTCACAGTTTGCTTACTGAAGCATCAGTGTGTCTTTCAATTGGATGTGATGTGTTTTGAAGACAT
AAGAGGCAGGAAAGTTTTGGTTGCCAAAAATAAAGAGAACAGGAGAAATTTAGCTTCTGACTGGATGGTCACTCTTGCCAGAGGCCTTGGA
GGAGGGCAAGGTTTTGCATTTTGTTTGCCATTTTTTCCTTAAATAAAGTGCCCTGGACTTCAGGTCAGTCTTGCCCCCTTGAGCTGCTAAATGA
TTCTGCCAGATTCTTTCAGCTGAGCTGTGCGGGGTCCTGAAGACCTGCTTTGACTTCCTCTGCACCAAACTGACTCACTCCCCAGGGAACAAGA
TCAAGGCTGAGGAAGAGAAAAAGCAGGGCATGAATGGACCCTATACCCAAAATAGTAATTCCATTTTCTCCACCTGCCATTCTACCATCACAGT
GAAGCTTTCTAAATTGTAAGAGGCTCTTGTAAAAATGAAGCCACTCCTGGGAGATGTTGAATTTTATCAGCCAACATGTATGTGGGTGTCCAT
GGAAAACAAGACCTTGGCAAATTATACCACAAATGGGCTGGGGCAAGTGGGAGGAGAGTGATAGGAGAACGTTTGAATCAGGACAAAACGAGTG
AACAATGTGGAGGCAAAGGGTGGGAACAAGATGTGCTTTGCCAACCAGACAAGTTTTTCAAGGCTAATTTTTCTAGAGACCATCTTAAGAACAA
TTGCAACACTAGACAAAAAGCACACAAACCAAAAAAAGAAAAAAATCTAAACCCAACAGCCTAAGTATCAGAAACCATCTTCTTATCCATATGG
TTAAAAAGTCAAAATGAATTTATTTCACAGAACCATTTCCTGGGCCGGAACTCATTTCTCCTTAAATAAATACTATAAAATTTTCCTC
AGAACAAATCAAGTCCCCTCTATAACCCCAGAAGACAAAGTACATCGGCAGTAAAAACAGACACAAAGTCTCCACTGTTGTCAGAGGTAGCATG
GCCTGGTGGGAGGACAGGGAGCTCATGCTGCCGCATCAGTCGGGAGGAGGGATTTGTCTTCTCCACAGGGCAGGATCCCTACAGGGAAACAGGAC
AAACTGAGAAGGGCTTGACAATGGAACTCTTTACAAAGGTGTCAGCAGAGTATTCAAAACCACAGGAGAATTGAGTGTCAGGGCTAGCAACTGT
ACGGTTCCAGAGCCAACCCATGTCGGAAGGGTCAGAGGGTGGGGACAGTCACCACAACCCCAGAAGGGAGAGTTCTGTAGAAAGGGCCATCTGGA
GGGAAGCAGTGACCTTCAGTCAGCCCAAGGTGACAGCCAGGCAGCAAGGAGATGAGTACCCTCAGCCTCACTCCTTCCCTTCCTCCAACCTCCT
ACCAAGCCTCCCTGTGGGTCAAGCTCATCCTGGGAGTCAGAAGGCAAGAGAGCCCCTAGATGCAGTCCACATAGTTCAGAGCAGGTTGCAGGTC
AGGAAGGGTGAAGACAGGAGAGGCAAAGGGAAGACATTGGGCAGGTCTTCCAGCTCACGGCCCTGTCATGCCTGCAGTCACTGTAGTACAGACT
GAATGTTCACTGTGTCTCGCTTTCAGCATTTAAGATGCCTCTGAGATAAAGAGCCTGCCTTGAGTCTCACGGGACATGCTCACATTTTCTGAAA
CCATGTAGCTTGCACTGTTAACCTCTTCCTCGGTTTAGAGGTTTTAGGGGCTCGTTTCACAAAGCTGCCCCAGCCCCTCATGTTAAACAACCTG
AGGGCTGTGACTGGGCAAAAATAAATAAATACATTTGCATTCAACATTGACAAAATACACACTTAAGTGAGACTTTTTTGCATCACAAAAAAA
TAAGTTTTTACTTTTTTCAAAAAGTAAAGGTTCTTTAAAAGATATCATCTAGAGTAGAATTAAGGGCTATTATTAGAAAATCACAGTGGTCCCT
AGGCAAGACATTTTGAGGGATGAACTTAAGCAGGCCCCAGACTCACGTCTTCCATGTCCTACAACCCAGGCATACCCCATCATCCCATACCTTC
AATTTATCCAAATACTTCCTGTTTCAGTTGGCAAATTCCACTGCCCCAAGCTTCCAAATGTCTTCCAATGCTGGCTTGCCTTCTTCCTAAATC
CCCTCCCCATAGTGTCCTGGACCCCATTAAAATGCCAGCAATGAAAGCATCTCCTTTCCCCTGTCTAGCACAGCCAGGTACATCTGTTCTGAGT
GGTCAGTGCCCAAAACAGCCCAGTTGCTAAACAGTTTGACCATCACCTATGCTCACACAGGAGTTACTGAGATGATGGTCCTCAACTGCAAATA
AAAAAACACAGGCCACTCTGTAGGAGCCATTAGCTCACAACTTGCTGGGCAGGCTCAAGTTTTAGGACTCAGCATGCTGAATAACACCTCTATC
CAATGGTAAATTTCTCTGGAAATGAATCCAAAAACCTCTCAGATGACAGATCTGGGACTTTCAAGTTGTTACATAGCAGCAAGGGTTGCTGTC
ATGATTTGTTTACTCTTTGATTCCCTGCTGTGGCTCATTTGAGATCTTGGAGTGTTTGCTGCAGTAATTATGGCAGGATTTTTCCAGAGTGGTT
TTAGCATCAGTGAAAGAATTAGTGTTCATTACTCCTTAATTCTATCACTCAACAAATTATAGGGGTAAAATTAGATCCTATTAAAAAAAAAAAA
AAACAGGGAAAAACAGCAAACAGAAACAAGCCGGAAAAGAGGAAACTAAATTCACCCTCTTAATACTGATAAGCAATTCTTCCCTACCACTAAT
TTTAAACCTTCATCAGAGACAGTACTTTGTCCGTTTGTTCAATACTTTATTCTTAGTGCCTATTACAGTGCCTGGTACATAGTTGGCCCTCAAT
ATATGTTTATTTAATGAACTGATTAAATAAACTAGACTCAGGCTCTGACCCTTGTGCTAAATCTGTGCTCACAATAGATGTTTAGGGCATATT
AAATTTTGAAGTCAGTTCATCTCTATGGAATTTATAGGCAAAGGGCTTTCTTTTTTTAGAGGTAGGTTCTTGTTCTGTCACCCAGACTAGAGT
GCATTTTGCATTTTGAGTCAGTGGTGTCTGCCAGTCAGACTAGAGTGCAGTGGTGTGATCATAGCTGACTGCAGCCTCAAACTTCTCGGCTCA
AACAATCCTCCCACCTCAGCTTCCTCACTAGCAGACTACAGGCACATGCCATTGCACCTGGCTAATTTTTAATTTTTATTTTTTATTTTTGTA
GAGACAGAGGTTTGCCACATTGCCCAGGCTGGTCTAAAACTCCTGGGCTCAAGCTATCCTCCTGCCTTTATTTCTATTTTGAAGCAAACAAAT
GATGCAAATGAATAAAGAGTCCTAGGAAGAAGTGTCCTCTGCTCTTGACTGTCCACTAACTCCAGACTTCATAGTGGCCCCCTTTGCTTAAGGC
ATATGATAAACTTCTAATGATGCTTGAATTATATTTCCACCAGCAGGATCAGTTATTTTCCTCAGACTCAAATTTTGCAATCAAAATGCACAGT
GTACACGGCTGCTTATATTGCAGCACATAGCATCTATTTTACCATTTCAATTTGATTTCTTACATGATGATTTGGGATGACAATAA
TGTGTTCTCAGTGAAGCCTCTTGACTAAACCAAAATTTGCATTTTTATAAACCTCCATGAAACAGCTTTACTTAGTAAGATTCTATAATGCTAT
ACTAAAGAAAATTACGTGGTAGCTTCAAAAGAAAATACTCCCTCCATCACAGAGACCGAGCCTCATATGAAAACAGTAAGCAGCACACAGGAAA
CTCATGCTGTAGATGAATTTGGAGAGCCACCTCAGGTTATTTGCATTATAGAATGCTAAACGCAGACTATGCAAGAAACCAGCCACCTAGAGAG
ATCTATATAGAAGTAGAGAAACTTCCATACCACCAGCAATTTTGGCTTTCCAATAAATATTGAGTGATGTCCAAAAGTCGTATAATTCAAAAG
TCTAGGGTAAGGAACAAGATAAAAGCTAACCCTTGTGGGTGTTGGTAAATCAATAATTAATTGGAGATCTTCCATGATATTTCCTCATAAGAAT
```

TABLE 1-continued (mouse gene: Prlr; human gene PRLR)

```
CATTGCTAAAATTGTTGTAATGACTACACAGACTCCCAAGATTGCAATAGTCAAACAACACAAACTGTTGAAGTCATGAAGGGATATGCAACAT
GGCTCCTTGGTTAACCTTTTGGTAGGGATCCAGTTTCCACCATCATGAAGTCCTGTTTTCAATATTAATTTACATCATTAGAATGCCTGCTGTT
CCATCAGCATTTTCTTGAGATTTCCTGGGCCATTCTCAGAAACCAGAGTTAGAATGCAGAAATTAATCATATTTCATTTTGACCTAACTATTAT
ACCCAGATATTTATAAGCCTGAAGTATATTTTTGCCTTACTGATAAACCAATAAGAAAGAACTTGAATATCTCATAAAATAAGGTCTTTCCGCA
AGCCACACATATCTAGATATGGATAATAGAGCTAAATAATCAGGTGTCGAGTCCAATACACTGTCAATCTATGTTTGACAAGCATCCAGTTCCT
TGCCTTGAGTCATTCAGTTCTTCGTTGTTCTTGCTGGAATGAAAGCCTATACAAAACCTAGCATTAATGAAGTTAATATGAAACTAATTAGCTG
CAATGCTACTGCGGGAAAACGGCCAATCATCATTTAATGAATGATTCTCAGTTAAGCACTTCAGAAAAGTATTTCCTCTGCCCCATAATCACCC
AGCTTCATGAAGATCCTGCTTTCCAGGTTTGAGGTGTGGGATCCAGATTCACTTATAACCTAATCAGGAAATGAACAGGATGATCTTGTACTGA
AGTCCTATATTAGTAATATATCAAATGAATAAAGAAAAATGTAAATAAAGTTAGAACTTGTAGTATCGTTTATCAACTCGCAGTATGTGAAAT
CCATGATGTACCTGCACCATAAATAAAACAAGATCTTCAAACTTCCCAGGGCTATTTAATTCTTCCATGATTTTTGTTCACAAAGAACAATCAT
TGCTCAGCCTATTCATTGCTCCTTTTGGAATGAAATACTTTTATTACTATTCACTTCAAAATATTTTTAAATTTCTGTTGTGATTGCTCCTTAG
ACCCACGGGTTTATTAAAGTATATTGCTTATTTTTAAATATTTAGGGATATTTTAGTTACTTGTCTGATATTGATTCCTAATTCAGTTTCTCT
GTGGTCAGAATGCATGTTCTGTATGACTTCAACCCTTTGAAATTTGCTGAAACAATGTTATGATTCAGGATATGGCCTTGGTGAATATTCCATG
AGTACTTAAAAGGAACATACATTCTACAGTTGTTGGCTGTAGTGTTTTATTATATAAACGTCAATTAAGTCATTTCTTAATCATGTTGAGAAAT
CATCTATGCCCTTACTAATTTTTTATTTTCATGTTTAACTAGATATGAGAATGGTGCGTTAACATCCTCTATGATTGTGTATTTGTCTATTTCT
GCTTTTAGTCTTGGAAGTTTTTGCTTTGTATATTTTGGGTCTATGTAATTAGATGAATGTAGATCTTTATTTTCCTGATGAATTGACCCTTTTA
TCATTATGACATGTCACTTTTTATATTTAATAGTATTTCTTGCATTAAGTTTTAATTTATCTGATATTATGTATAACTCTACCAACTTTCTTCA
GATTAGTGTTATGATGGTCTTTTTTTCCCATATCTTTATTTTCAACCTTCTTGGTCCTTATTAGAGTATTTAATCCATTTACATTTAGTGTAAT
TACTGGATTATTTGAATTTAAACCTACCATCTTAGTATTTCTTTTTCTGTTGTCTCACCTATTCTTTGTTTCTATTTTAATCCCTGCTTGCCTT
TATAAAAATTTTAAACAATGACAATTTTTAAAATATTTTCATTTATCTTCTTTGTTACCTTATTAATTAGGCCTCTGTTGTAATTCACCTAGTG
CTAACCCAGGGATTATAGCATCCATCTTTCACTCATTACAGTCTACTTAAGTTAACTTAGTCCTTTAGTTAGCATCATTTCTGTCTTCCATACT
ACTGTATGCGTTTTAATTCTACATATATTTAAAATTATAAGACATTTTTATTGTTGTTTTAAATAGTCAGTTTAAAAAATGTACCCTATATT
TACTGTTTTCAATGAACTTTCTTTTTTCCCACATTACATACTTCCATGAACACCTCCTTTTGGCCTATAGAACTCCTATTAATATTTCTTTTAG
TTCAGAGCTGCTGGTATGTATTTTCTCAGTTTTAGTCTGGGCTCACTTCTGTGATTCTCTCATCCCTTGGATTATTGACTTTCAAAACTCAGTC
ATATTGGCAGCCCCTAGCCCAGTGACACTGTCTCAAATCCCAGAACAATTTATTTAATGCCACATCTATTCTTGCTCCAAAAATTGGCAAATGC
CTCAAGAAGAAATGAAGAGAAGCCAGTATGAGACTCGCCTCAATCTACTTCCCTTTTCTGTGGGATCTTGAATCCCTCTCATTGACCAATATCT
TTAAAGAGTTAGATGATAGATAGATAGATAGATAGATAGATAGATAGATAGATAGACAAACAGATTGATGTTATTTTTAGCAG
CAGCATTAGTGTGAATAAGCTACTCCATTTTAGCTAGAGGTAGAAGTAATTTCTTCTTAGAGAAAAAGTTTGTATAGAATTGAATTTACCATCA
TAGCCATTCTTGAATGTCAGGCCAATTGAACTCCTAAGACTCTAGCATATACAAAAACAGAAACCACTATTTCTTATCATATGTTTAAGGGTG
TGTATTTGGAACCAATTTAGCCACAAACTTCCAGATGATGCTGACATACCAATAATTACTATTAAAAGCAATATAATACACAGGGAAAGCAAA
TATAGTCAATTGATATATGAGCTGTTGCTCTTATTGCAAGGATTGTAAGAGTTCTGCAGTGTGGCCATTATATGTGTGCCTCACAACTTGTATT
CATTGTAAGCTTCCTTTGAGAATTTTTATCTAAGAATAAGTCTACCCTCATTTTTTGTGGAGTATCAGAGCTTCTTCTCCTATTTGTCTTCAAG
ATTGAAAGGAGAATATTGAATGCTGATTCTCTGAACATCTGCAATAATGTATTCCAAGATATTGGCAAATCAGTCCAAAGGCTCAACCATCCC
AGCTAATTAAATTACCTGGTTAACTCTGTGGACTACCAAATCTAAATGGATGTAAGAGAGGAAGAAATTTGAAAAAAATAAAGATTACACAGTT
GAAAAAACAAGATATTCTCCAGTTATGAATTCTTTTCCCCAAGAGTGTCTTTTGTGTACATTGTTATTACAAAATCCAGTTGTCACATTAAACA
AGCCATGCTATCCAAAGCAGAGTTGATTGTGGCTGGAAATTTATTCCAATATTGAAAAGATGTGAAAGGGCTATAACACGTATCAGACAATCTA
GAATTGACCACTAGGGGACATGACCATGAAGCCTTAGACAATAATTCATATTTAGTTTGAAGTACTATTCTGAGGCAAAACAAACAAAAAGAA
TGATTATGGAGGACTCAATCTTAAAGTGTCTCCAAGCATGTCTTGTTCTGTCTCAAACCTTGGCCTCAACAATCAAAGCTCTGTATCATTATTT
GCAACACATGAATGCTAAATGGTATCATTTCTGACTATGGACCTATGTGTAGTTAAGTTGTGTGTAGGAATATGAGGATAGAAACTATTACTAT
CAACCAAATGGTAATATTGGACATGTTTCAAAGATTGTCTGAAAGAGCTTGTCCATGGAGACTAACCCCTTAACAAGTCCCAGGTTCTCCTCTC
CTAGAATGTGAATTCCACGTTCACCAGCAGAATTCAGTTCTGCTGAAATAGTCATGGAACAGTATTGTTTTAATTTCTCAAACTTTTCAACCAT
ATGTTTATAAAGGTTTATAAGACAAATAAGACTATCCCTGGCATATAATTCTTTCAGTAAATACTTCACATATTCTTCCATAAGAATTAGCCTC
TTCTGTAAACTCTGGAGCTACCCCAAGGTAAGATCGTACTACTGTAAATAAGCCCGAATCACTAGATTCCAAAGGCCAATGGTTACCCAGGCAT
TATTTGTTTATGACCTAAGAAAATAAGTCCATAGAAATAAATTGGCTTGAACAGAACCATCAAAAACCCCTTTCAATAGACATCTCAAATGAAA
TAGGTGGTTCTACTTCCTGAGAACACCTAAAGAACCTTTGTGTAAAAGAAGAAATCATTATTTCCATTCAGTAGCAATTTTTGAATGGTGTAAC
TTGCTATCTCCTTGCCTATTGGTACAATGCAGAGAAACTGTTCAAAGGTGAGCCATTCGGTAAAGAACGATAGAGTTAATCAGAGAGTCTCTGT
TATGCAGCTACATGGAATGCAGGTGTTCATTGCTGGTGTTTTTACCCGCTTTGAGTTCTTGTTTGTTTTGTTCCTATAGTAGGATGCTGCACT
GATTTGGGCAGGGCAAAGTGGTGGTTGATGGAAGAGCAGAACACCTGGGAAAGTCATCCAGAGTAATTTTTGATCCCAAGAAAAGATCAGCAGA
ATTCTCCTTGAGTCTCTAAGTCTTCACATTGTAGAACTGCTTAGGTAAAAACTAATTCAGGAAATGTGCAGTTATAAACTTTAATAAGTCACC
CATTAACTGACATTTTAAATGTAAATGTACTAAGGGGACTCTTTATTTCCCTCTCATTCGTAAGTGGACCATCCTCAACACAGAGACCCAAACC
AGAAACTTAGGAATCATCTTTGATTACTCTCTTTCAATCTTATCAAATCTTATTAGCAAATCTTATCCCTGAAATCTTTGTCCCTGAAATATAT
CTCAAGTCTTACCTGTCCTCACCAGTTCCACCGCTACCATCCTAATCCTGGCATCAACTCTGAACTGGACTGAGTCCTCCAGCAGCCTGGTTCC
ACTGCTTCTATTTTTTTTCCATTGTCTCTCTCCATTTCATTGTACACACAGTTGCCAAAATAATATTTTAAAATCTGTATCACTAATTTAAACG
CTTGTGGCTTTTCAGTGTACTTAGAAGAAAATCCACACTTGTAGACCCTGATGCATTCAGCCCCTACCTGCCTCCCCAGTCTTATACCAGACTC
CATTTCTCATATATTGCAGCCATGCTTGCCTTTTCAACATCTCAAGCAATCGAAGTGCTTTCTCGATTTGAGACTTTTTGTGCTTGCTATTTTC
ATTGCCCGGAATGCCTTTTCTGAAGAATCTCAAGCAGTTGACTTCCTCTGACTTTTTATGTATAAGCTTTACATGGTTCATATTCAGAGATCCCT
TCCCTGAGCACCCTTAGTAAACTGTTCTTGGCTTTGTTGGGTATTATTGGAACTTACCACTGCCTATAATTATTATGTTTGTCATCAGGTTTAC
TTGTTTCTTGCCTGTGTCCTCCACTAGATTGTAAGCCCCAGATATCAGCTAATTGGTTGTATAAGTTTCCATTCTTTATATAGTCTTTGAATAG
TAATCATGTACTTAGTAAAGCCACTAAGGCAAGTGGCCAAGGAGACGTGGACAGTTATTTATATCTAATCCAATCTGAAGAATTATTCCAAGCA
AAAATGACGTAGACTGACGCTTAAAATAGCTAAAAACTTATTTAGTTCTATCTCAAACCTCAGCTTCAATAAGCAGGCTTTCAGCCACATGTTT
TCAGTATATGAATTGCCAGAGCTTCCTACCAACTAGTCATATAGTGTGTCTACCTTAACCTGGTACCTTTACTTGGGTTGCATTTCATCAGCAG
CCAAGTCCATCTATTTGTCACAGTGTCTCTAGTACACTGCTTCTACATAGTCAGCAATCAGTGGATACTTGATGCCTGCATGCATGAATAAATG
AACTTCTCAGGAATGCTAGGGCCAGAGAAAGTTGATGTTTAAAAAGTTAGAAAATGTAGGCACTTGAGAAGGATTAAGAAATTAACATAAGCCT
TCTTTGAATTTATCATTGAAATCTATTATTCAATTTACATGTACAATTATTCCTTTAGTCAAATACATATACTTCCTCCCTGTAGC
ACTTACCATGTCTCTGACCCTTTGCCTTGCAAATTCCACTCTGATAATACCAGCAGTGAATAGAAATTTAAAAAGCCACTGTCCTCACTCCTTC
CACTCATGTTCTAATGTAAGCCTTTCTTTTATGCAGCCTGAATGCACAATTCACTTGTCATTATCTCGCATCCTAGCTGCTCCTCATGAAATGG
CATTCCTCTGGATTTGCTGAGTCCTAATGTTCAGGCAAAGTAAATCCCACATCATTCTGGCAGGCTTTCAGGAAGACTTAGGGACTCGTTGTCT
GCTAGTGCAAATAACAGCAAAGTGTGGTAGGACTTCCTCCTTAGTTCAGCGAAGAGCCAGGTCCTTGTCGCACGGCCATGAAAAATTAGGCTCA
CAGACGATTTCGAGGGGGAGAAAAATGAAATTTATTGGGCAAAAATGGGAAATTAGAAACAGGGGCCCTCTCCAAAGCCAGATCCCTGCTAG
AGTACTTCCCACCTCACAGGTTGAATCCCAGGTGCCACCCAGGAAGAGGAGGGGCCAGACTCCTCCCCTCTGCCAGCAGAGCAAACTTCTGTGG
CTCCACCCCAGTGTGTATTCCTCCCAGTGCGCAAGTCGGTTGGAGTTTTCTGGGAACCGCCTTCCCACCTGGCTGTCTCAAAAGGACTCCCAGT
TGCAGAGGTATGTGTGATTCAACAAGATCCACTGGCAGAAAATAGAGGCAAATTAACTCAAGGAGTCCATTGGAATATATCAACGTACTCCCT
TCCACTCACAAGGCAATGATTTCTAAAACAGTGAATCATTTTACTTACAAGGGGTCACAATGGAGACAGGATAGAGGGAAACTGCCCGGGAGCA
CAGGGACGAGGCATGTGGAGAGGTAGACCTTGGATCCAGTTCTGCAGCCAGTGAGCTGCTCACTCAGACCTGTTGCTCCCCTCCAGAGCCTCCC
TTTCTTCATCTGGGGTATGAAACAACTGGACCAGCTTATCTCTGAGATCCCGCTCAGCTCTGACCCTCCTGTTGGAGAAGGCTTGCATTCTGAG
ACTGCAGTCCCAAGTAGCAATCTCTTCGGAGGGCATGTATGTGATTACGTACTTAGTTGCTCACATAGTTTCATAAGAAATCCGGTAAAATTCA
TTCTTATGCTACTTTTGTATTCCCACTTATTTTGAATGGAAAATCCTTGTACATATTTCCTCAAATTATGGATAAAAAGTATACAAAATACACC
```

TABLE 1-continued (mouse gene: Prlr; human gene PRLR)

```
CTAGAGGCCAAGAAGCTCCTTTTGGTAGAAAGAATGTTGAGCCCTATGAATTTGAGCTACTCAAACTTTGTGGTTTGTTTTGGGAGCCAATCTT
GAATATAAAATATTTTTTGATCCAGCAGAAAGGTGAAATCACATTTGAAGTTTACAAAATAGTAATGCTAAGATAGATAGATTTTCTTGTGTGCC
ACACTTATGTTGTAACCAGAACTTAATTCACCATAATCATTGACAAGTCTTTTGTTACTGGAAAGGATAAGGGTTGGCAGGTCTTGTGACAAAT
GTTAGAATTTAATGCCCAGGATTTTTCTTGATGCACAGGACTCATTGGAAAAGCGGCAGCTATTTATTGTGACTATGAATCACGTCCACAGATG
AATATGATTAAGTGCTAAATCCATAGCAGCTGAAGTTTTTTAAAGCCTTGGAAAATTGGCTTTAAAAAATATCACCTGACAAACCTCAAGCTTT
TTCTGTCTCACAAGACTTTTGGAAAAGAACTAGGATCGACAGTGTTTTAAGGCTCACAAGGAAAAGAATCTAACACTTGTAAAATTATCTTCTG
TGCAAGTTTTATTTTCCAACGTGAATCTGGGCTGCCAAGCATACTGGCTCTAGCCAGATCTTCATTAGCCGATCCAAAAAGACAGTCGGGGCAT
TTATCCAGATAATGCAAGCCAACACTACCCTCTGAGAAACAAAAGTAACTTGCCTGATGAAGCAAGGAACCTCACCGATTATTCCAGATTAA
TGCATCTCCTTTTACTGGCACCATGATCAGATATTTTCAAGACAAAGTACTTGGCAAGTTGGAATCCAGCTGGGTCCTTTGATTTTTGAATTCA
CTTTGCTTCTGTGATTATGGCCACAGTTTTGAAAATAAAGTCATGTGGATAGAGTTGTGATTTTTAGGGATCAGGATGCCTCATAAAACAACAA
TGCTGTATTCTTTTGTAGAACAAGATCCTGCCTAGGCCTCTTTCCTAGTATTAATCTTTGGTCATGATGAATGTGCTCCCAACCATCCAACCTA
TCCCTTTGCAACCAGGCTTTTGTGAGATCAAATAATTTTTAGAGTTGAAATGAAGTTATTACCAGCTCTAAAATAAGGTACTACAGGAGGGAAG
TAAGGACCGACAAGAGTTAAATCACTTTCTAGGGTTGCGCAGGTAACTGGGAATGAAGCCAGGATGACAACTCTACTTGCTCTTTCATTGTATC
TTATGCTTCTCTGATGTCTTCCAAGGGATAGCAATATAATCATAGTCTTGAAAGAAAGATCTTTGTAGAGAAAAGGGTCAGCAGATTATGTTTG
TAATTGACTAGATAGAAGTAGTTTTGCTTTTGCAGGTTAAATGGCCTCTATAAAATGTAATTACCCAATGGGTTCTTCCTGCCCACTACACAAA
GACCACAGCTCTGCAGTAAAGAGTTTAACTGACACAAGGCCGGCCACGCCATGTGAGAGACAGAGTTATTACTCAAGTCAGTCTTATCGAAGGC
TTGTGGGCTAGTGGTTTTTCAAAGACAGTTTAGGGGAAGAGGTGGGGGTGGCTAGGAAATGGGTGCTTTCCACTGATTGGTTGAAGCGGAGAAG
AAATCGTAAGGGGTCAAAGCTGTCCTCTTGAGCTGATTCACTTATAGGTGGGGCCCTAAGGGTGATTTGGCAGGTCCGGGTGAAGCCATCTGGT
ACAAGTGGAGCCAACCATGTCAGACATGCAAAAAACCTGAAAACATATCTCAAAAGGCCAATCTGCAATAGTGATGTTATCTGCAGGAGTAATT
GGGGAATTTGCATATCTTGTGACCAGCCTACACCTTAGCAGAATTCAGGCTCCTCTCCTCCCCATAGACTGGGGCTCTCTCATGGCTTTACAAA
GGTGGTTGACTTTTGGGGAGGGGCTATTATCATTTAAACCATAACCTAAAAGTCTTCCAAAGTTATCTTGGCCTCAGCCCAGGAGTAATTAAGG
CAGCTTGACCACTAAAGGTAAGAGCAGAGATGGCTAAATACAGATCTCCTTCACTGCCATAATTTTCTCACTGATACAATTTTTGCAAAGGCATT
TTCACCCACTACCCAACTGTGTCATTGTAGCATGAAGGCAGCCATAGAAAGGAATAGGCATGACTGTTCCAGTGGAACTTTATGAATTAACACT
GAAATGAAATGTCATACAATTGTGACATGTCACAGAATATTTCATTTTTAATTGTTTTCAACTATTCAAAAATGTCAAAATCATTTTTAGCTT
GGTGGTGGACTGGATTTGGTCCAGAGCAGTAGTTTGCCTGCCTCTGTTATAGAGTAACACATCTGAGCCCATGAGAGAATTGATCCTGTACCTT
GGGTAATGCTCTTCCTCTCTGGCTCCTTTCTACACCTCAGTCACTTTTCCCCTGCAAGAGTTGTTGTCACATTAGACTGTAAAATTGGATCACTT
TTATATTTCATCTCTAACATGCCTTATTTAATAAAAGTCATTCTAGGTATGACTAAAGTTCCAGGGCTAACTTAGAAAAGGACTGAAGAGAAGA
ATTCTTCTGACAAATGCGGACCCAGCCACAAATGCCAGTGATATTGTCCCAAGTATTGGTGGCTTGGGTTGCACTTGATAACAGAGGGCAAAA
GAAAGTATAAATTTTGCTTGTTAACATAGCTTTAGTGGAAAATACAGAAAATGCCCCCAAACTCCATGCTAAGATCATGAACTAAACTGTTACA
ATGAAAGGAATTACTTGGGTTTCTATAAAAACAGCTGCCTCAAGGAATTTGCCACATTCCTTGGGTCTGCCTGAGCTCTGGTGGCCCACTGCTT
GGATAGGCCTGGTTTGTTTGCTAACTTAACATGCTTGCTTAACGGCCAAACATTCCCTTGAAATTCAAGGACTTTCTGTCCCGCTGACACTGTT
TATTTGTATCAGTAGAGTGGAGGGCTCTCTGGTGACACTCTAGTTTTTTCTGGGTTATAAGCAGATGCAGGTCTGTAGTTTTTCTGACTTGGAT
GGGGCCAATGGGTCTAAGCCAAGAGGGAAAATGCTTTTTTCTTTTTCGTGTTTATTTCCTTTTTTTTTTTTCCTATCTTGATTGGAGTACCCT
TAGAAGGAAAAGGAGAGCCATAATCGTTCTCTGGAGGCCAAAAGAAGGCCGAAGGATGCCAAAAATTGTCACAGTGGTGACTTTTGGCTGGAGC
CAGTGCAGAATGAGGGGCTATGAGTGTGCTCACTAGAACTGTAATCCAGATCTCTTCCAGGACCTGATTCGTATTGCTTTTTCCA
TGCTGTAGAACATGACACCCCACTCAATCACTTGTGCTGGTTCATTGTTACTTGTTATAGTAGTCATTGTTATCAAGACTTTTTGGTTGTAAGT
GTCAGAAACCTAACTCAAACAGAGCTAAGCAAAATAAATCTATAAATAAATATAATTAGCTCAAAAGTCTGAACTCACTGGATTGATCTTCAG
ACATAATTGCATGCAGTGTTCAAGCAGCAGCTACCATCTCTCCTTCCCTTCCTCTCTCTTATCTCTGCTTTCCTCTGTGTTAACATCCTGCTCT
GATAAGCTTTCTCCATGTGGAATGAAAGACGGGCTCCAGCCTTTCCCAGGCTCCTAAGTTCCTTGCAGCTCACGGTCCCAGAAGGAAAGAGATTG
TCTCCCAGCATCTGTCTCCATAAAAAGAAGCCACCGTCCTTGCTTGAGTCATGTTCTCACTCTTGGACTTAGCAGAGTCCAGAGGGCTTGAT
ACTCTCACTTGGATACTCTCAATACGTGCCAGCAAGGGGCACATATTCACCCTTCATTGGGCAAGGTAAGCCTGTTAACAGTCCCACTCGAATC
ATGGGGAGTAAGCAAAAGGAAGTTCTGAAAATGAAAGAATGTGGGACAGACATAAAACTCAAAGCTGTGCACTATGCTAGTAAATTATTCTTGT
GTACTTAATATGAATATGCTTTTATAAACAGTAAGCAAATCAGAAGCCACCCTGTGAATCATCAGTTATCTCTAGACATTTCTGGATTCCTTC
TTTATTCCCTGATAATCTTCTTTCCTTCCTTTCACTGCGTTGTAAGTGGAAATAACACAAGCCAAAAAGACCCTCTCCTGCTCTCAATACACAC
ATGGTCTAGTTCAGGAAGACAACATATAAACAGCAGGCATACGAGCAATTTCAGTAGACTGTGATGCCTGCCCAGGGTGCTCGTGGTCTACCTT
TCATGGACCAAAGACAACAGGAATAAGAGCATTCATCTTCCTCTGCTATTGTGAGAATATAGACAGTGCAAAGACTTGGATGCCAGTGCTAACA
TCCCTGCCTGACCTGACTTTGAGAAAAGGACCCGCCATTTTCAGAAGCCACCACAGGTTCTCTAAATACTCAAAGTGTGAGGCTAGCAGATAAAT
TTGGCTTATAGAGGGAGCTTCATACCATGGTTAGAACACAGCAAGAAAGGAACAAATTTTTAATGTATTAATTGAAAATCAGATTTCTCAGCTG
GGAAGAAGATATTAGCTGGAACACACACAAAAAGTATTTTTAAAGGTGCCCTTTTAAAGGCTGCCAAAACTCACCCAAAGTAGTATTCAAATA
TGAAGACAGATGTCTTTTCAAGACGGGAAATTTTAGTTCCGAGTATGAAAGAGAATTTTATTTATTTGTTTTTTCCCTTGCCTTTTCAGGCTTT
TCACTGACTTCGAGGGGATGAGGGTATGTGTGCTTAAAGTAGATGCCAGAGTGTCTTCTTGGAACTTCAGGTTTCCATGAGTAGAAGGAAGTGT
TGAATGAATGAGGACCCACGGCCCTGTCCAGTGTGGACATGCCATAACCCTGTGCTGAGCTTCCTCATCTGTGTTCTGGGCTTACATTGAATAT
GGCATAAGCAACCCCGAAGAGCCACAAAACTCTGCTCTGTTAAGGGAGGAGGGCAAGTCCTCCCTGGAAGGGGTTGTCTCATCAACCAGGAAAT
GGTGGTCAGGATGGATACAGTAGCATCTATACCTCAGCCCCCTTGAAGTATCCTGATGTCCACTCCCCACAAAATCTAGGCCTTCCATAGGAAG
TCAAGAGGATATTGTGCTGATATAAATTTGGACCACCAGTGAGTTTGCCCTCAGACCTGGTAAGAAGTGCATATTTCAGATATAAGATATTGCT
CTGGCCTCAGCTACATACAGTTTCCATAAAGGAAAACTTTGAAGGACTGCCTGCAGGAAAAGAATAGCCTCGTGTTGATGTATCTAGGGACAGA
ACTCTCAGGCAGGACAACAGCTTCCTCAAGCTCTTGTGACTACACTCTTTTTCCCAAGATATCTCATTGCATCTTTAATTTAGCTCCTAATTCAA
AGCCAAGCTCATGGACTGTTTCAAGCTCTGGACCATGAGCTTAGCTCTGAATTAGGAGCTAAATTAAGGATGCAACGAGACATCCTGGGAGAAA
TAGTATAGTCACAAGACTTGAGGAAGCTTTAGTGAAAAGCAGACCCACCCAGCATGTGTAATTCTTCCATGAGGTTTCATCTCACAGTCTGCAT
GTCTTGCAAGTGGGCTTAGGGCCACAGGGGCAGGAGCTCTTGGTACTCAGATGTTGTCTAGAAGTTTGGAGGAGAGAGATCCTTCCAACCTA
GGTCAAAAGGCAGAACTGGTAAAGGACTTGCAGCATGATAATTTGAGCACAATATCTGAGAGAGCAATCCATGGAAGTCATTTCAGGAAGGA
CATTGTAGACAACAGGAATAGCAAGTTCATAAGCCCTGACCTCAGGAACCTGCCCGGTACATTCAGGAGCATCAAGGAGACCATACTGGCCAAA
TGGCACAAGTGTGAGGAAAGTGTTGGTAGGAGGTGATTTCAGAGGGATGCCTGGAGGCCAGATCCTGGAGAGTCTTGTAGGTCATTGTATAACT
TTGACTTTTACTTTGAATGAGATGGTAAGCACTTATGAGCAGAAAGTGTATGATTTAACTTACGTTCTAAAAGAAGTATTCTGGCTCCTGTAT
TAAAAATAAACTGAAGGGCAAGGAGAGAGGTGGAGAGACCCATTGGGAGGCTAACGCAGACATTTATCCAGGCAAATATCACTTAGACCTCGGT
GGTGCAAGTAAGGAAAATGAGAGGAAATTGCATTTATAAAAATCTCATTTAAAGATAGAGTCAACAGGATTCATCATTGGATTGGATTGGAGTA
AATGAGAGAGAGGGAAATCAAGGATGATTCAAAGTGGTTTGTTTTTTTTTTGTTTTTTTTTTTATCTTGAGCAACTGGAGAGATGGAG
ACAACATTTTAAATTACTTTGTTCTTTGGTAACATGGCAGTAAACACTTATAAACTGTATTACAGGTGGCAATCAAATAAGCACCTGGCTG
ATTTGAAATATGGTTTAAAAAAAATTACAAAGTAAGGAAGATGAACTTGTATTGTTCTGCCCATGCAAACAATCTGTAAACTGTGCATTTA
TATATTTTTCAGTCATTAATATTTACAGCGGGAGAGAACTGTTTGTGAAATCATGAATTATCTTTTGTTGAATTTATTTTATTAATGAGTTA
GAAGTACCCTTTGTAAGCCATTGTACCTTTTTTCTAAAGGTGAGAGCCTAAAACTACCATGTTGCAATGGAATAAGCCCTGGTTCTAGCTTCACG
CCCTGGGAGTGACTTCTATTAGCTTTGGAATCTCCGGTAACTCCTTTAATCTTTGAATTCTCACTTTCTATGTCTTAAAGGTGATGGCTGCCC
ATTTCATCAACTGTGAAATGGCATCCAAGTCCCAGGTATCGTTAAGAACCAACGGCTTCCATTTTAAACAGAAGTTTTGTTAAACAAATATTTG
GTTTTACAAGGGTATTATAATTCATACCCTTATTCATTGTTCTTCCTTGCTCCCAATAGTCGATGGGTTTTTTTTTAGCTGTGGCTTATGTGA
TCAAAGAGGTGAAACAAGTTAGCTCAATTGGTTATATTCTGAAATTAATAAGGTGTTCTTTTTGCATGTGTATACAAATTAACTTCCCTCTGTT
TCTTGGCCACACACCTCACCTCAGCTTCACAAATGAGTAGAATTGATTACAACATGAATCAGACAAGAGAGTGTAGATCTATCACTGTTATTGA
GAAAGCAGTTCAAAAAACAAGCATTCCCGCATGTTAGTAACATGTTTTTATAAAAGCTGTAAATGTATATTTATTCATATGATTTAATATTTTT
```

TABLE 1-continued (mouse gene: Prlr; human gene PRLR)

```
TATCTTCAGTTTTTATTTTAAGTTCAGGGGTACATGTACAGGATGTGCAGGTTAGTTACACAGGTAAACATGTGCCGTGGTGGTTTGCTGCACA
GATCCTCCCATCATGTAGGTATTAAGCCCAGCATCCATTAGCTATTCTTCCTGGTGCCCACCCTCCCCTGAACCCCCTCCCCTGACAGGCTCA
GTGTGTGTTGGTCCCTGCAATGTGTCCACGCGTTCTCATCATTCAGCTCCCACTAATAAGTGAAAACATGTAGTGTTTGGTTTTCTGTTCCTGC
ATTAATTCGCTGGGGATAATGGCTTTCAGCTCCATCCATGTCCCTGAAGAAGACATGATCTCGTTTTTTTATGGCTGCATAGTATTCCATGGTG
TATACGTACCACATTTTCTTTATCCAGTCTATTATTAATGGGCATTTGGCTTGATTCCATGTATTTGCTATTCTGAATAGTGCTGCAATAAACA
TATGTGTGCATGTATCTTTATAATAGAATGGTTTATATTCCTTTGGGTATATACTCGGTAAGGGAATTGCTGGGTCAAGTGGTATTTCTGCCTC
TGGGTCTTTGAGGAATTGCCCACACTGTCTTCCATAGTGGTTGAACTAATTTACACTCCCACCAACAGCATAAAAGCCTTCCTTTTTCTCTGCAA
CCTCACTAGAGTCAGTAATATTTCTTCAAATATGAAGGACTTGACCTCAGATCCTTTATGATGATCATAAATACATAAATAGATAAGTTAAAAA
ATAGGAAGGACAGTGTGATACTAAATAACTACAAAATTAGAGATGTATCAAAAAGTATTTAGGCACTAAAATAGTTGAGAGATCATTTTCAGAG
CCTCCAAGAGTTTCTATGCCTTGAATTATTTGAGCATCCAGTGCAAGCTTTCAGAGTCCTTGCTTCCTTAAATATAAAACAAGAAGTCAGATAC
CTTTGCCTCTGACTTCTCAGAGGTCTTTGAGCTTGACAGTTCTATAATTCTATGAGTTTTCTACCTAGAAACTATTCCTTCCATTCAGTTAGGA
AATATATTCAAGTATATTTTATTTAATCTTAAACTTTGGAATCCCATTTGGTAAGCTGCTGTTATTTGAAGGTGTTGACGTATCCTCTGGGAT
CTGAGAAAATTATTATCAAAACCAATTAAAGGAATCATCTATTTTGTGCGATTGGTTTTGAAATCTGTCCAGTGGGCTCTTTCTGGAGGCAAGG
ATCCTGGTTACCAAGAGACTTTGCTGCAAATAAGGCAAACTGGGATGACATTTGGGGTTGGGATCCTTCTCAGGACCAAATGGGCACCCATCAT
CTTTGGGTCTAGAAGACTGCACTGGCATAAAGCAGCTGACTTCCTGTAGCCTTGCAGAAATAACAATGGGGTGTGTGTGTGTGTAGTGTG
TGTAGTGTGTGCAGTGTGTGTGTGTGTGTGTACAATGGTGGGGAACAGTTGGCAGAGCAATGAGCAAGAAATGGGAAACGACACTCAGAA
AAGCAGCAACCTACCCTGAGCAAATCAAAGAATTTCTTAGAATGCAACACTAGCTGTGTGTATGAATAATTGGCTTGCAAATCACTTCCTCTAT
TTGCTTGTTATATAATACCAATCATTTCAGTGTCACTGACGAAAGCCCAGAAGGGAATTACCATTACCAGCCAGTTTTACATATGGCTTTTGT
GAGGAATAAGGCCTTGAGGATGAGGGTCTAAATCTCTGGCCCACAGATCTGGACAGGCAGATTTCAAGCTGATCATTACATATCTTTTGAGAGA
GACAATCCCAGACGAATTGGCCTGGGGGGCAACATGAGAAGGCAAGACAAAAGAACATTGTAAAGACTTCACCTAGAATCCAAATTGTAGTTCT
CTCAGCAAGTTATCAAGAAGCAAATTAACTGCTAGATTTTGTAATCCAAAGATTATTTAATCTGTTTAGCTTTGTGTTGGAAGGATCGCTACTA
ATCATCTCTTTTATTAAAATATGATAATGATAGCCATCCTTTATTAAGTGCTTATGATATACCAGGCACTTTGTATACATGATTTGCCTTATTC
AGAATAACCCTGAAGGATCAATATTATTGTCTCCATATCAAAGAGAGGGAAACTAAGGCATACAAAAGTTATTTGCTCAAGGTCAAACAGCATG
GTAAGAGGAACTGCAATTTCATTCCAGGTCTTACGGATACCAAGTCCGATGCCTGCCAGCTTGCACCTGTTAAGTCATGTGATACTTAGGAAAT
GTACACATCACCCCAGTGCAGAGGCCTTTATCCACTTCCCTTCATTTTGCCTGGATTGTTGCTGTGAGTGAGAAATAAATGACATGAAATGATC
ATGTATATCACTGTCTTCAGAGGATGGTTAGTTCCTTGCTCTGGATTGTTTTTCTCTTTTGTTGGATATTTATTTTGACTTCTCTGCAAACTAA
AAATATGCATGCTCTAGTTTCTCTTGGGTACATAACTCCCAATATATTGTGAAGAATGAACATGGCCTACAAAGTTTAATTAAGAAGCAGTGAA
CTAGAGCTTACTTAGACAATACTTGTACTAGTGTGGGTTCATGTTGTCCATTTGTCTTTAGAGGTGTAGAACCTTGAAAGTCAGCTAATTAATC
ACTATTACTGTTGTGTACAGTATTGGCAATCTCCTATGCTAAAATTTTTTGTGATGATTTGAAGGTGGGAGGGGCAATATTTACTAAGTCTCT
CAACCTACATGGCAATATCTGAAACCTGCTTATAATGTAGTAATAGCTTAGGCACCACCTATTTCTGAAACATAAATCATCCCACAATATAAGC
CTCCCAGTTTTATTCATGCGTCTTACCATGTATAAATATCTTTTAACCATTTATTTCCTTGAGGGACAGTTATTTGTAGCATAAATCTGC
CTGGATAAAATAGTAAAAATTGCTATGCCCCAGTGAATTCAGTTTACAAAAGCTTACATACGTGAATGAGACATTGGAAATGTGGTTTATAGTT
AAGGAGAATGGATCACACGGATTATACCTGTATAACTTCCCTAGAAGGTTGATACCACTAAGATATTAACACCAAAAACTGAAAATAGTATTT
TTCATCTTACTTTGTTATGTACCCTTTGTGAATTTCTGAAAAACACCTTTCTATTATGATGGGATAAATTACGGTGTGGTAACAAACAAGCCCA
ACCTGTTTGTTCCGGTCAACTAGTTGCTTTATAACAAACCACCCCAAAATTTGTTTAAAACAGCTATCATTTGATTGTGCTCACAAGTTCTGTG
AGTTAGGAAATAAGACACAACACAGTGGTCTTATGTCTGTTGTGTAATGTCTGGGTTCTCAGCTGTGAACACTCAAATGGCTTGGAAACTGAAA
TCAGCTGGAGGCTTCCTTATTCATATGTTTGGTGCCTGGCTGGGATGACTCAGATTAGTTGGGGCTCTTGACAAAAGCACCTATACATGAACCC
TCTCAGGAGCCTTGGCTCTATGGTGGCTGGATTCTGAGAGGGAGCATGCAGAGAAAAGAATTCCAAGACAATGGATGCTCTAAGAGAAGCTACT
TGGCCTTTTCTGATCTAGTCTTGGTGGTCATGCAGCATCACTTTTGCCACCCAGATCAAAGGGGAAGAGGGAGACAGACTCCACCTGTGGATGGG
AGAGTGTCAAATTCACACAGAGTTGTATGCAAGCTATTCTTGGTCATCTTGCTCATCTATGAAATATACCCTCCTCCATGCATTGACTTACAA
CAAGGGTTTATTTCTTGCTCAAAGTCTGCTGTGAATCTAGGCAATTCTCCAGAGCAGCTGTTCTTTTGTTGGCTTAGCAATCCAAGCTGCTGCT
TCCATCTTACAGCTTTTCCATATCAACTCATGATTCCACAACCATTGCTACGAGGCAAGAGTAGTATGGAGGATCACACACTACTCTTAGAAAC
CACCAGCTGGAAGGGACTTATATCACTCCTGCTTACATTTGATGGCTCACATAGCCATCCCAAATTCAGTAGAGCAAGCATGGCCCTCCTGTG
TACCCAGAAAGGAAGGAGAGCTAGAAATATTGGTAAATAGCAATATTGTTTACCATAGCCTCAGAGATATTGCCTCGTGGTGAAACCCTATAAT
TCCCCTCAATTCTGATTTTTGCCCTTTATCAAATCATTTTATTCATTCCTTCATCCATCCAACAAAGATGTTTTATATGCCTACTATTAGCAAC
AATCAGTAGCTTGTTCCTGGAGGGAATGCAGCTGCTCCCCGCCAAAACACCCATATAATTCACTCTAGAAAACTAAAATTTCAGATGCTTTGTCA
TTGATTATTGTGGGGAGAAAATGTCTCTTTCAGCTCCGACTTTGTCTGTCTCCTCTAAGGCATGTGAAATAAGATTTTTTTTTCCTATTCTTA
CCTCCTATGGTCCCATTTTATGGTTTTCATGCACTACTGTCAGTCAAATATTTATCATATGTCTTTCAATATCTTTCCAATATTTATCATATAT
CTTTCCCCTTGTAGGCCTTAACTTTATGACCCACTATTAAGCACGCAGCTGTATTTCCAGAAAATGTAGATGGTTAATTCAATACTGCATGGC
AATTAACTGTCTTATAAATTAAATCATTTTAATCCATCTTAGAGTTATCATGCATAATTAGTCTGACAGCACAATTCTGTTTGTTGTTGTTTA
AAGGAAATTTAGATATCAAGGCTGCAAAGAATGCGTAAGTCTAGGCAGAAGGCTCTTATTTTCCAAAAGCAGAGCCCATCGTTGCATTTCAACA
ATGACCGCAACAAAAACCATCAGGAGCTGTTTGGGGCCTGTTTGTCTTTAGTCTTCAATTAGAAAAAAATGTGTTTCTGATGGAAAACCATAG
AACAATCCTCACTCTGTGGTAAGAAAGAATAAAGAGAAAGAAGTGGGCTCTATGATAGACTGAAGCAAGAATACTATTTTAGACTAGGTAGTGG
CCGGGCGTGGTGGCTCACGCCTGTAATCCTAGCACTTTGAGAGGCCAAGGTGGGCGTATCACCTGAGGTTGGGAGTTCGAGACCAGCCTGACCA
ACATGGAGAAACCCTGTCTCTACTAAAAATACAAAATTAGCTGGGCGTCGTGGCGCATGCCTGTAATCCCAGCTACTCAGGCGCACTGGCTCAC
GCCTGTACTTGGGAGGCTGAGGCAGGAGAATCGCTTGAGCCCAGGAGGCAGAGGTTGCAGTGAGCTGAGATTGCGCCATTGCACTCCAGCCTGG
GCAACAAGAGTGAAACTCTGTCTCAGAAAAAAAAAAAAGACTAGGTAGTTATCTTCCTGGGTGGTTTTGGCTATGTAGAAAATCACTCTTACTC
TCGATTAATTTATGTACCAAATCATGCTTTGAAATATCCCACTGAAAAGGTCTAAATTATTGATATCTTGGGTCAAGTTCTGACTTGAAGGCAA
ATAGTAGGAAATACAATGGCATTTATTGGAGGCACACACTACAAATATTGTAGTATCTTTAAGATGTGTTTAAATAAACAAGTAGATGATAAAA
CTATAAATTAGAGTCACTAAGACTCTCTAGCAGAGACCCTTACCTTTTGAAGTGCACCTTAAAATGGCAACAACACTTATCAGAAATTCCATAA
GAAGCTTAGTTGTCTGCTACTCTATTGCAGTATCATATGTGAGCTGCATGAAAACTGGATATTATTATTATCAAAGGTTATTATCAAATGGA
GCACAATTTTATTAATAACAATATTATTATTATCAAAGGTTTTAATTTGCTAAAACTATACAGCTTCCTTAGGTCTTCCAAACTAGGTCAGCCA
GTTAACCCTCAGATCTGGAGTACCACATTTGGCTGAGTCAGAAGAAATAAAGATGCTCTCAAAACCACAAACAAAACTGATAATAGACATTCTG
ATAACTTTAACTCCCACAGTAATAAATCTTGGGTCTTTTAAAGTTGGTCATGTCACACAGAGCTGCTTACTAATTATACTATAAAATAGTTACTA
AGCAACTCGACATTTTGATTTCCAAGAATTTCAGATAAAGATTATGAACTTTATTTATTTGGTGCTTTAGAGTCCAAGGCACTATTTTACAGCC
TAAAGCTGTATTTCTCAAGGCCATCTTCTTGCATTCTTCTAAAACTTAAGGGGGATCATCTGTCCTCAAAAATATAAGAAATTCTGTAAATGTG
TATTTTTGTGTATATATATTTGATATTTAAAATTCTGTATCTATATATACTTCCAAGACCCCTTAGAACTTACACGGTACCTGTAATTTGTT
TCTTTTTTATACTTAAGTACAAGTAATGTTAGTGATACATTTAAAACTAGGAATTACCTTGTTTGCAATATCAAATTTTTGTAAAATATTGAGT
TAAAAAAGTCTCCTAAAATTAAGATTTGAACTATTATAAATGGCTTCAAAGATCCTTTCGTTTCTAAGAGAAGGAAGGAATTAGGATTTATTGT
GCATGTATTTCATACCAGGTGCTCATCTACAGTTATTGAATCCTTGCAACAATCGTATCAGGTAAACGCTGTTATTCTTCTTACAGATGAAA
AATCTAAACCTTCTAAAATGAAAGTTTGTCCAAGTTAACATGACCAATTAGGAGAGCTTGGATTCCAACCCAAATCTGTTCAGTATCAAAGCTC
ACTCTCTTCCATCCTTGCCCCTTCTCAGCTCACATAGTAGCTTTCAGAAAACAGTAGCTATCTACCCCAGATAAAATTAAGCCTTTTTTCCTT
AGGAGAGGCTAGAAACTGAATCTTCTACCCCCTTTATTGGCATCACACAGGCACAAAAATCACCAATTCTCAAAAACCCTATACTCCCAAGTTC
AACCCAAATTGAATGGTTGGAATATTGTTGGTTTGTATGGAATAATTAACCCACATCTAAAATTAATTATACAAAGTGAAGTGGAGATTGAAG
CAGTTTTCTAGATAATTAAGGCAAAAATAACTGCAATTTTTTAAAAGACAGTTTGAAATATTTAGAAGGGTAGATTGCAAAATTATCCAACTT
AAGGTAGTCATATTCAGGGAGTTTAGCCAAAACACCTCTGAAGTTCATTGCCTTACAAATGAGTATAAAACTTAAACCTATGATTAATTCCCTG
TTGTTTTTTCTATCTGTATTATACATATAAATATATTTTATATATTGTCCTCCTGAGTTTCAAGAGCAATTTTCTTCTAATTCTTCTAATTTCT
```

TABLE 1-continued (mouse gene: Prlr; human gene PRLR)

```
TCTATGGATTCACCATAGTGAATCCACCGACACGTCTACCCTGTGACAATCTTGTTCTCCATTTGATTGCATGAAAAATACCATATGAATTTGA
CAAATCATTGGTTTTTTTGTTTGTTTTTCTCTTTTGCTGCATATCATTTGTTTGCTTCTTGAGCACTAGAATATATTTGTGCATGTATAAACC
AAGGCCTTTCTTCTGAAAATTAATAGTACTTTGAATCTCTTCTATATTCTGGTTCTTTTAAACTGTGGTTGTTTTAAGTTTGCCTCTCTTGTTT
TAGGATTTATTCTTTATTTTGAGGCCCTGATTTTTCACAAAACATTTTTCTCAACGAATCCTGAGAACACTGGACAATCATAGCTTTTAGCTAT
CATGAGTCCCATTACCCTTTGGCCTCCAGTTAAGCTCTGTCCTGCAAGACATAAATTGTCTGATTATCAACTCCTACTTTGAGTGAAAAATGGT
TGAATGAAATGAATATGCAGTTCATTTCAACAAAGCAAGAAATTTGCTGTTTAAAATTGTGGGGGATAATTCTTGAGATGGAAATATAGCCAGA
CCTCTGTGAATCTGAGAAGGCATTTCATGCTTCCAGAAATGAGGGGAGAAGTGGCAATGATATTGCTCATGAACAATTGGAAGCAATGATACTA
GAGTATGCAGCAAATCTCAGGGAGATTTCAGTGGTACAGTAACTGGCCTCACAAAAGTGGGATTTATTGCATTAAATCTTTGCTGTCCTTTCTG
GCTGGTTTGATATTTAAGAAATTATTAAACATAAAATTGTATGAGCAGTTACCTATGGTAGGACAAAATGGACTGACCTCTAATGGCTTGGTAG
ATGGGATAATTTTGGGAAGAGAGAGTGGAGCTCAGTTCAGCATCCTACTCTCCTCCTCAACATCATTTCCCATTCTTGGCCCTTGAGTTTAGAT
AGGAGTTGGGCATGTGTGTGTGTATGTGTGTGTGGTGAAGTGGGTAGATTCCTGTTCCCAACCCAATTAGATAACTCCACTTCCATCTAT
CTTCCTTGCATCTTCTCCAGCTCATTTGCAAAGAATGAAAGAAGCCTTGCTTCAAAAAGGTTTAGAGGGCTAAATAAGAGCACAAACTGGATT
TTCTGAAAACTGACCTGATTGCCTGGGTAATTAAACTGTCACTCCAGCAAAAGCATTTGTCTCCAAAAAGTACTGAGGTTGTCTTTCATCACTC
TAAGTCTAGACATTCTGAAACCTCCATCCTCTCCTGCAGAGAGAGGAATTAAGTCTCCACATTTCTAAACCATTGACAGTCTGTGGGGTGCCCC
ATTGTGTTCCTGACTTCCTATTCTCAGAAGGAGTTATAACGATGACAATGATGCATGCATGAGACATAGAGGTCCTCCCCAGCCCTCGGTTAGG
AAGTAAGGCAGCCACCCATGTACTGAACACAATAGTGCTTTGGAAAGAGCTCTGTTAAAAGTGAGTCTCAAAAATGTAAAGGCCTTTACGAGAG
GAACTTAATCTCCAGTGTGATAAAACGATGCACACATTACAAGGAGATGGATGTTATGAAAACAATAAGTACACCCAAGAGTACACGTACAAAT
CTGCATTGCAATTGATTTATTTGGATGCCTGTTTCTTCCTACACTATGAGCTCCTTGGGGCCATGAAATTCATTTGTTTTATCTATATATACTC
TCTTTGATATCCCCCACCCTGACAGCTAGTGCAGTCCTTTCTAAATAGTTGTTACTAAATATGTCAAATCAAATGCCTACAAGGACTGGTTGGT
AGAACCAGATTCTGGAAGTGACCAAGCAGGTCTAGCTTCATAAGAATGCCATCATCGTAGATTTGAGGGTCATGATGAAGTTGTACTAGGATTT
ATGGAGGTTCTTTGTCAACCAGTTCACACCACCAGTGACTTAAGGAAACTATATGTCGTCTATTGGGAACAGTCCTGCTTAAAGCAATTAGCAG
GGACAATTAATTTGGAGGGAAGTCTCTCCACTCAACAGCATTCAAATACCCTCTGCATTAGCCATGTTTTGAAAAACTCCAATTGCCTGAGT
CACTGATAGACAAACAGAAATGCAGACTATTTTGTATGCAGTTTTATAAAGAAGTTTCTAACCAGAGAAGAAAGGTGTTATTTTGAAATATTAA
GCTCTTAGTTGTTCTTTCATTTCAGTGAACATTTGTTGAGGGCCTGACATGAGCTAGGCACATGGCAAAGTTTTAGAGATGCAAAGGTAAATTA
AGACCCCTGTGTTAATTCTCATGCGGGCAAAGCAAGCACATTTTTTAAGTTGCAATAATGCAACAATGGTGGTGTGTACATAGTAGGGCAAAAG
CATAGAGAAAGCCATGGAAATCCTCAAGCCAAGTTCAAAGAGTCCTCTAATGTATGGCATACCACAACAAGGACCTTCAAAGGGTGCATTTGGT
AAGAAAAGGCAACCTCCAAAGATTCATCCAATCCTAAGGTTTCATAGAGTAGGGACTTCTTCCCTTAGCTGGAAAGGAAAGAAGTCATTTGGTG
TGCAGTAGACATAAATTAGGGGCCGTCCACTTTTTCTTGCAATGATTCATCTAATGGAGGAGCAGACCCTGGAGAGAAACATATCTCTTCTTGT
CTTCATTTTGTTCTTCTTTTATTAAATCACCCGCAGGACAACCGGATGCTCCAGCAATAGATTATAGAAAAACAGATGGGTATTTCTGTGCAG
TCAGAAGGCTCCTGTGCCCTTTTCCAGCATAAAACGTTTATGAAAATCAATTTTCAGTGCCTGCTGAACCAGGCTGATGTGAGAACTAGCTTTC
CACAGTTCATAATATTCACTCCAGGGATGATTTGACAGGGCTGATATTTTATCACGAATACAAAGGAGATGAGCACCATTCTCCTAATATATTCA
TTACTTGTCTCACCACCCTGGTAAATAATATGCATATGGTAATTTGAGAGACACAGTGTTCCCATTGCTCTTTTTATTCCCAGAACTCTGGCT
GTCTTTTCTAAATGCTGCAAATCAAAGGCAAAGTTACCTCACGCACCTGTAGTCCCAGCTACTCAAGAGACAGAGGCTCTAGACCAGGACTTGA
AGTTCAGCCTGGGCAACACAGTGAGACCCTATGTCTTTAAAAAAAATTGCCTAAAAATTTGGCCAGGTGCGGTGGCCCATGCCTGTAATTGGAG
GAACTTTGGGAGGCCAAGGTGGGCAGATCACTTGAGGCCAGGAGTTTGAGACCATCCTGGCCAACATGGCTAAACCCTGTCTCTACTAAAAATA
CAAAAAAAAAAAAAAAATTAGCCAGGCATGGTGGTGTGCACCTGTAATCCCAGCTACTTGGGAGGCTGAGGCATAAGAATCACTTGAACCTGGGA
GGCAGAGGTTGCAGTGAGCCGAGATTGTGCCACTGCTGTATTCCAGTCTGGGTGATAGAGCGAGACTCTGCCTCAAAAAAATTAAATTAAAATT
TAAAATAAAAAATTACTTAAAAATTTGATTTTACATTCCTCCTATTCTCACTTTCTGGTGCCCATACAACACATAAATTACATTCTTCTCTATG
TTTACCTGCATCTCTAGGGAACAAAGCCCCTTTCACTTGTTCTGTTCTATATAGAATGTTCTACAATACCCCAATAAAGATTCATTCATTTGTTC
ATTTACAAATATCTATTAAGCACCTACTGTGTGTCAAGCAGTATGCTAAATCTTAAGCATGAAACAAAAGAAAGATAAAAGTATCTGATTCAGG
GACTGGTTGTTCTGTTGTTCTGGGTTTTTTTTTTTTTTTTGGAAGCTTGTTGAAAATCTGTGGCATCATACAAACAAAAAGAATGCAAAA
CTGGTGCCTTAAATAGAAATGTATTAATAATGAGTGTTAGAGCTAAGAGAAGGCAAAATGTCTACAGAACACATGATTTCAATTAACAACAGTG
AGTAAACGAATGATCTGGAAAAAAATTTATGATCGGGCCCATGATTTTTTTTGTCGTTTTTTAAAAATTTTGTTTGTTTTTCTCATACTCATAT
TATTCTAAGGCCCATTGATTTTAGAAAGAAAATCTGTTTTATAAACTTAGCATATTAAAAG
```

HUMAN SEQUENCE - mRNA

```
GGAGGCTGAAATCCCCAGACGCCGGTTTTCTGGGCTGGGCTTTCTGCTTACTCACTCCTTCTCCCTCTTTCTGGATTTTACCGACCGTTCGCGA
AACAGCTTTCCACACAATGGAGCTTCATGTCCTCGTGCAGGAAGTACTCATCGACTGATGTGGCAGACTTTGCTCCCTGACAAAACTAAAGAAC
TCTCCTATTCATGGAGGCGGACACTGAGGATGCTTTCCACATGAACCCTGAAGTGAACTTCTGATACATTTCCTGCAGCAAGAGAAGGCAGCCA
ACATGAAGGAAAATGTGGCATCTGCAACCGTTTTCACTCTGCTACTTTTTCTCAACACCTGCCTTCTGAATGGACAGTTACCTCCTGGAAAACC
TGAGATCTTTAAATGTCGTTCTCCCAATAAGGAAACATTCACCTGCTGGTGGAGGCCTGGGACAGATGGAGGACTTCCTACCAATTATTCACTG
ACTTACCACAGGGAAGGAGAGACCATCATGCATGAATGTCCAGACTACATAACCGGTGGCCCCAACTCCTGCCACTTTGGCAAGCAGTACACCT
CCATGTGGAGGACATACATCATGATGGTCAATGCCACTAACCAGATGGGAAGCAGTTTCTCGGATGAACTTTATGTGGACGTGACTTACATAGT
TCAGCCAGACCCTCCTTTGGAGCTGGCTGTGGAAGTAAAACAGCCAGAAGACAGAAAACCCTACCTGTGGATTAAATGGTCTCCACCTACCCTG
ATTGACTTAAAAACTGGTTGGTTCACGCTCCTGTATGAAATTCGATTAAAACCCGAGAAAGCAGCTGAGTGGGAGATCCATTTTGCTGGGCAGC
AAACAGAGTTTAAGATTCTCAGCCTACATCCAGGACAGAAATACCTTGTCCAGGTTCGCTGCAAACCAGACCATGGATACTGGAGTGCATGGAG
TCCAGCGACCTTCATTCAGATACCTAGTGACTTCACCATGAATGATACAACCGTGTGGATCTCTGTGGCTGTCCTTTCTGCTGTCATCGTTTG
ATTATTGTCTGGGCAGTGGCTTTGAAGGGCTATAGCATGGTGACCTGCATCTTCCGCCAGTTCCTGGGCAAAAATAAAGGATTTGATGCTC
ATCTGTTGGAGAAGGGCAAGTCTGAAGAACTACTGAGTGCCTTGGGATGCCAAGACTTTCCTCCCACTTCTGACTATGAGGACTTGCTGGTGGA
GTATTTAGAAGTAGATGATAGTGAGGACCAGCATCTAATGTCAGTTCATTCAAAAGACACCAGTGGTCAAGGTATGAAACCCACATACCTGGAT
CCTGACACTGACTCAGGCCGGGGGAGCTGTGACAGCCCTTCCCTTTTGTCTGAAAAGTGTGAGGAACCCCAGGCCAATCCCTCCACATTCTATG
ATCCTGAGGTCATTGAGAAGCCAGAGAATCCTGAAACAACCCACACCTGGGACCCCCAGTGCATAAGCATGGAAGGCAAATCCCCTATTTTCA
TGCTGGTGGATCCAAATGTTCAACATGGCCCTTACCACAGCCCAGCAGCACAACCCCAGATCCTCTTACCACAATATTACTGATGTGTGTGAG
CTGGCTGGGCCCTGCAGGTGCACCGGCACTCTGTTGAATGAAGCAGGTAAAGATGGCTTTAAAATCCTCTCAAACCATTAAGTCTAGAGAAG
AGGGAAAGGCAACCCAGCAGGGAGGTAGAAAGCTTCCATTCTGAGACTGACCAGGATACGCCCTGGCTGCTGCCCCAGGAGAAACCCCCCTT
TGGCTCCGCTAAACCCTTGGATTATGTGGAGATTCACAAGGTCAACAAAGATGGTGCATTATCATTGCTACCAAAACAGAGAGAGAACAGCGGC
AAGCCCAAGAAGCCCGGGACTCCTGAGAACAATAAGGAGTATGCCAAGGTGTCCGGGGTCATGGATAACAACATCCTGGTGTTGGTGCCAGATC
CACATGCTAAAAACGTGGCTTGCTTTGAAGAATCAGCCAAAGAAGCCCCACCATCACTTGAACAGAATCAAGCTGAGAAAGCCCTGGCCAACTT
CACTGCAACATCAAGCAAGTGCAGGCTCCAGCTGGGTGGTTTGGGATTACTGGATGCCCATGTTTTACACACTCCTTTCACTGATAGCTTGAC
TAATGGAATGATTGTTAAAATGTGATTTTCTTCAGGTAACACTACAGAGTACGTGAAATGCTCAAGAATGTAGTCAGACTGACACTACTAAA
GCTCCCAGCTCCTTTCATGCTCCATTTTTAACCACTTGCCTCTTTCTCCAGCAGCTGATTCCAGAACAAATCATTATGTTTCCTAACTGTGATT
TGTAGATTTACTTTTTGCTGTTAGTTATAAAACTATGTGTCAATGAAATAAAAGCACACTGCTTATTTTTGGAGGACAATGCCAATAGGT
ATATCCTCTGGAAAAGGCTTTCATGTTTGGCATGGGACAGACGGAAATGAAATTGTCAAAATTGTTTTACCATAGAAAGATGACAAAGAAAAT
TTTCCACATAGGAAAATGCCATGAAAATTGCTTTTGAAAAACAACTGCATAACCTTTACACTCCTCGTCCATTTTATTAGGATTACCCAAATAT
AACCATTTAAAGAAAGAATGCATTCCAGAACAAATTGTTTACATAAGTTCCTATACCTTACTGACACATTGCTGATATGCAAGTAAGAAAT
```

HUMAN SEQUENCE - CODING

TABLE 1-continued (mouse gene: Prlr; human gene PRLR)

```
ATGAAGGAAAATGTGGCATCTGCAACCGTTTTCACTCTGCTACTTTTTCTCAACACCTGCCTTCTGAATGGACAGTTACCTCCTGGAAAACCTG
AGATCTTTAAATGTCGTTCTCCCAATAAGGAAACATTCACCTGCTGGTGGAGGCCTGGGACAGATGGAGGACTTCCTACCAATTATTCACTGAC
TTACCACAGGGAAGGAGAGACACTCATGCATGAATGTCCAGACTACATAACCGGTGGCCCCAACTCCTGCCACTTTGGCAAGCAGTACACCTCC
ATGTGGAGGACATACATCATGATGGTCAATGCCACTAACCAGATGGGAAGCAGTTTCTCGGATGAACTTTATGTGGACGTGACTTACATAGTTC
AGCCAGACCCTCCTTTGGAGCTGGCTGTGGAAGTAAAACAGCCAGAAGACAGAAAACCCTACCTGTGGATTAAATGGTCTCCACCTACCCTGAT
TGACTTAAAAACTGGTTGGTTCACGCTCCTGTATGAAATTCGATTAAAACCCGAGAAAGCAGCTGAGTGGGAGATCCATTTTGCTGGGCAGCAA
ACAGAGTTTAAGATTCTCAGCCTACATCCAGGACAGAAATACCTTGTCCAGGTTCGCTGCAAACCAGACCATGGATACTGGAGTGCATGGAGTC
CAGCGACCTTCATTCAGATACCTAGTGACTTCACCATGAATGATACAACCGTGTGGATCTCTGTGGCTGTCCTTTCTGCTGTCATCTGTTTGAT
TATTGTCTGGGCAGTGGCTTTGAAGGGCTATAGCATGGTGACCTGCATCTTTCCGCCAGTTCCTGGGCCAAAAATAAAAGGATTTGATGCTCAT
CTGTTGGAGAAGGGCAAGTCTGAAGAACTACTGAGTGCCTTGGGATGCCAAGACTTTCCTCCCACTTCTGACTATGAGGACTTGCTGGTGGAGT
ATTTAGAAGTAGATGATAGTGAGGACCAGCATCTAATGTCAGTCCATTCAAAAGAACACCCAAGTCAAGGTATGAAACCCACATACCTGGATCC
TGACACTGACTCAGGCCGGGGGAGCTGTGACAGCCCTTCCCTTTTGTCTGAAAAGTGTGAGGAACCCCAGGCCAATCCCTCCACATTCTATGAT
CCTGAGGTCATTGAGAAGCCAGAGAATCCTGAAACAACCCACACCTGGGACCCCCAGTGCATAAGCATGGAAGGCAAAATCCCCTATTTTCATG
CTGGTGGATCCAAATGTTCAACATGGCCCTTACCACAGCCCAGCCAGCACAACCCCAGATCCTCTTACCACAATATTACTGATGTGTGTGAGCT
GGCTGTGGGCCCTGCAGGTGCACCGGCCACTCTGTTGAATGAAGCAGGTAAAGATGCTTTAAAATCCTCTCAAACCATTAAGTCTAGAGAAGAG
GGAAAGGCAACCCAGCAGAGGGAGGTAGAAAGCTTCCATTCTGAGACTGACCAGGATACGCCCTGGCTGCTGCCCCAGGAGAAAACCCCCTTTG
GCTCCGCTAAACCCTTGGATTATGTGGAGATTCACAAGGTCAACAAAGATGGTGCATTATCATTGCTACCAAAACAGAGAGAGAACAGCGGCAA
GCCCAAGAAGCCCGGGACTCCTGAGAACAATAAGGAGTATGCCAAGGTGTCCGGGGTCATGGATAACAACATCCTGGTGTTGGTGCCAGATCCA
CATGCTAAAAACGTGGCTTGCTTTGAAGAATCAGCCAAAGAGGCCCCACCATCACTTGAACAGAATCAAGCTGAGAAAGCCCTGGCCAACTTCA
CTGCAACATCAAGCAAGTGCAGGCTCCAGCTGGGTGGTTTGGATTACCTGGATCCCGCATGTTTTACACACTCCTTTCACTGA
```

EXAMPLES

Example 1 mRNA Expression Analysis of PRLR in Breast Cancer Samples mRNA was prepared from breast cancer samples as by standard procedures as are known in the art. Gene expression was measures by quantitative PCR on the ABI 7900HT Sequence Detection System using the 5' nuclease (TaqMan) chemistry. This chemistry differs from standard PCR by the addition of a dual-labeled (reporter and quencher) fluorescent probe which anneals between the two PCR primers. The fluorescence of the reporter dye is quenched by the quencher being in close proximity. During thermal cycling, the 5' nuclease activity of Taq DNA polymerase cleaves the annealed probe and liberates the reporter and quencher dyes. An increase in fluorescence is seen, and the cycle number in which the fluorescence increases above background is related to the starting template concentration in a log-linear fashion.

For data analysis, expression level of the target gene was normalized with the expression level of a house keeping gene. The mean level of expression of the housekeeping gene was subtracted from the mean expression level of the target gene. Standard deviation was then determined. In addition, the expression level of the target gene in cancer tissue is compared with the expression level of the target gene in normal tissue.

As shown in FIG. 1, PRLR was up-regulated in approximately 21% of breast cancer samples examined.

We claim:

1. A method of evaluating the effect of a candidate anti-breast cancer drug comprising:
   (a) administering said drug to a breast cancer patient;
   (b) removing a breast cell sample from said patient; and
   (c) detecting alterations in said sample in the expression or activation of a gene comprising a nucleotide sequence at least 98% identical to SEQ ID NO:4
   wherein an alteration in the expression or activation of the gene is indicative of an effective breast cancer drug.

2. The method according to claim 1, wherein the nucleotide sequence encodes a prolactin receptor which induces tyrosine phosphorylation upon dimerization of the receptor.

3. The method according to claim 1, wherein the gene comprises the nucleotide sequence of SEQ ID NO:4.

4. The method according to claim 1, wherein the candidate cancer drug is selected from the group consisting of proteins, oligopeptides, small organic and inorganic molecules, polysaccharides and polynucleotides.

5. The method according to claim 1, wherein the candidate cancer drug is an organic compound having a molecular weight less than about 2,500 daltons.

6. a method of evaluating the effect of a candidate anti-prostate cancer drug comprising:
   (a) administering said drug to a prostate cancer patient;
   (b) removing a prostate cell sample from said patient; and
   (c) detecting alterations in said sample in the expression or activation of a gene comprising a nucleotide sequence at least 98% identical to SEQ ID NO:4
   wherein an alteration in the expression or activation of the gene is indicative of an effective prostate cancer drug.

7. The method according to claim 6, wherein the nucleotide sequence encodes a prolactin receptor which induces tyrosine phosphorylation upon dimerization of the receptor.

8. The method according to claim 6, wherein the gene comprises the nucleotide sequence of SEQ ID NO:4.

9. the method according to claim 6, wherein the candidate cancer drug is selected from the group consisting of proteins, oligopeptides, small organic and inorganic molecules, polysaccharides and polynucleotides.

10. The method according to claim 6, wherein the candidate cancer drug is an organic compound having a molecular weight less than about 2,500 daltons.

* * * * *

UNITED STATES PATENT AND TRADEMARK OFFICE
CERTIFICATE OF CORRECTION

PATENT NO. : 7,645,441 B2
APPLICATION NO. : 10/105948
DATED : January 12, 2010
INVENTOR(S) : Morris et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1937 days.

Signed and Sealed this

Twenty-first Day of December, 2010

David J. Kappos
*Director of the United States Patent and Trademark Office*

SEQUENCE LISTING

```
<160> NUMBER OF SEQ ID NOS: 7

<210> SEQ ID NO 1
<211> LENGTH: 96592
<212> TYPE: DNA
<213> ORGANISM: Mus Musculus
<220> FEATURE:
<221> NAME/KEY: misc_feature
<222> LOCATION: (1)...(96592)
<223> OTHER INFORMATION: n = A, T, C or G

<400> SEQUENCE: 1
tcagaatttg actgtcctaa agaaccttct tccgctgtgc gagtctgggc aggcagaaca      60
ttcaggagaa accacaggga aacaggtctg tttttaaaat ttcctttca tgctctgttt     120 cccttttacc tcctctcctg ttctttccat atctactgtc attttgctac ccagaaaacc    180
tagtgattcc tcccagctga cagggctgag cttgtgtttc cacggagtcc aggttcatgg    240
caggcctgtt gaatatggcc ctggaatgac gtgctttcct gctctttatt tatcagagcc    300
tatgactcat agggcctagt ggactacgct tccaaaaagc attagttttt gttattttcc    360
agttagcata caaactgttt cagaatgaca gtctcagaca gacagccaaa cagacagaca    420
```

```
gagagataat tttactttgt ttaattttac ccttgtccct cttcaccctt cctgctaatc    480
ttccttcaca caaacaattc ctcttctgtt tccatgtcat atagatatgt acactccccc    540
cacacacaca tacccacac acactcacac agacccctttt tactttcata tcaaccattc   600
ttttctattg gggaaggtag ggtaggtatg ccccacggtg agcacataga agtcaggaga    660
tcactctcca gagttctctc ctgccaccct gtgggatcca gggttcaaac ctaggtcatc    720
aggcctggac caaagggcct cttaccactg acccatctca ccagccttat tcaggttttt    780
tccccttcaa tctgcatatg atagaaaact tgtagtattt cttgttcaaa atctggcttc    840
tttgatttat ttgcctctct agttccatct agcatacaaa ctatttcaga atgacactct    900
taggtagata gatagataga tagatagata gatagataga tagatagatg catacataca    960
tacatacata catacataca tacatagata cagatagaca gagacatttc attttctaca   1020
cttaaataca tctctgctat gtctatgcac cacatttgct ctattcagtc atctgctaat   1080
agacacccat gctggttcca tatccctact actataaata gtgctacatg aacatgaatg   1140
tacaagtcat ctgtctaaaa tgctgcctca gattgcttca ggtatatact taggaatggt   1200
acagtttggt catatagtca ttcttttttg tttctgatga acctccatgc taacttctat   1260
atggctactc tggttacata ctctacagta gcgtatgaac atctgttccc ctacatatct   1320
gctccagaac ttattggatt ttttttttgag gttgttttca gccattgtgt atacagtggg   1380
atggaatctc agttctgttt gttggttggt ctgttgttta gagacagggt cttccatagc   1440
ttagtgtaca gtatgtagac tgtggaccag gctagtctca aactctccct gatgttcctg   1500
cttatttttc ctaattgtta tgatcacaca tgtatgccaa caaacctggc ttcattgcag   1560
ctttctgaag ttttatttt agatttattt gttttatttt tatatgtttg cctatatgtg    1620
tgtacatgta catgtgtggg ccacatatgt gtgtggtcct tgcagaggtc agaagagggt   1680
gtcagatctc ctggaactgg agttacagat ggttgtgaac catatctgaa aactataccc   1740
gaatcttcca caagagtatg tatgctcata actgctaaga cacctccaca acctcaatgt   1800
agcttcaatt tacattttcc tatggctaat gttcctatga acaatttat attttatatg    1860 tatttattgg ctaattcact tcttttgaga actgcctttt ttaatttatc tgtccattca   1920
ttgattgact ttgtcttttg taattttgag tcagggttaa agtttttgaa ttctttctat   1980
attctagata tataaagatt aatagttggc aggaatttt ctcccaaaga tcctgaacgt    2040
taatgctttc cctcaaggtt cactttagct gtcttgctta aagcttgata aaaaactaa    2100 agtcctttcc aatcagacac gtgtgagcaa gttttccctg agccacaagc tgcagtgcag   2160
gaaactatct ggatcaaaaa cgtgttctcg tgatttccat taagggattg tctcttgttc   2220
cctgtcccct aagcgagtgc tgataacagt cctccatacc ttagcacgta agtcaatcat   2280
taacaatggg ctgtactttt cactgggttg taaagaataa gaagtcagag ctacagaaat   2340
ctcctttctt gaggtaggca gtggaaggaa gagtgtcact tgcctgtaaa cctcataacc   2400
aatatgtagc aggctgcagc ccaacacgca ggggacgtgt ccgaacagag gagagtcaca   2460
ggtaaggaat acgggtccat ttctgtttct ctatccattc tgattctctc ttctcacctt   2520
tccaatctgt ggactaaaaa tgaacagggt caaggtgtga ttacagtatc agtggtagaa   2580
agaggtttct atggactgac ctgtgtttta acaagagatg gcattagat gttagttaat    2640 tcacaatctc cgtctgactc cttcaagact gatttcttac aaacatctga cttcttcaag   2700
actcggagtt ccagagagaa aatgtatgtc agttacagga gcaaagatca gcgcaacagc   2760
agtggtcaca tgacaggcca gtccttgggg aggataaaga tgaattagtg tggacttggg   2820
```

```
aacatctcca gatcctactc aaaggcaaaa ggaggttaga tggtaaattt gaaagaattg    2880
ctacaaactg cgccaaagga aaggaattat gcttatttct cttttttga cagactttgg    2940 gggttttttg gtgttttgtt tggtttggtt tggtttggtt tggtttggtt tggtttggtt    3000
tggttggttg ttttttgca atgatttgtt ttaaaataaa tttgtcttct ttagaaagct    3060
tccagatact cactttcctt tctcaacgac tttcttctgc tattacatgt ggcattcttg    3120
tgacacattt atgacgacga accaacgtta gcatgctatc tacttaagct cttacactat    3180
ctacattaac attgagtatt tgtctcagat attttatgg gttttaagaa atgcataatg     3240
acacatcact gacttgtaca aaatagtccc atgatcctaa aagtcccatg ttctacctag    3300
ttctctttcc ccactcccct accaagcccc tcaaaaccac tcaccatttt tcctgactcc    3360
atggctttac ccggtctaaa gggtcgcctg gttgcaatga agtagaacgt ggtcttttcg    3420
gattggtttg aattagtagt gtgcttttga gtttttctg catctttctg tggctcagta     3480
gcacatccct ctttgtcgct gagtaacata tgactatgtg actaaactac agcaaatgta    3540
tccagttggg caaatgtttt agcatggtag aaagtggaaa cgataaaggt gggggagtt     3600 tagaaagtgg cagtactata aacgtgatag aagcaagaag aacacgaagt agaaaaacta    3660
gctagaaagc taaacacaga tgcctcagtt gaaataaaaa ttttttaaa agctctggtt     3720 ctagggtggc gccagctctt ttctaagcat atagattatg ctgggagaca cattaccttc    3780
aacccaagag cctacacatg gtaggcaccc cataacattt ttgaagcccc caaactccaa    3840 gacttttttcc aaaaagaggc ttccccaaga caccagctta ttggctcaga agccatatca   3900
gggaagctgt agctgcttgg tcagatgagc ctttgcatgc cataggataa gaaaatattc    3960
ccttgataac ctttgtttga ccgtggctta tggaagctat gagtataagc aaagaactca    4020
tgtttcaacc taatcacaga agtagcccaa acaatttcca tgtaacaaca acaaaggcta    4080
tgagaagatg agccagctat gccttcaaat gttcaccaca ttctagagca gagaacagtc    4140
atgtaccatt atcagtagcc catgcaatga tgtaggagcc cagtccaagg tgatgcagct    4200
tacagtatgc ctgtgtagtt gtccagggaa actgatgggc cagctgggc ttgcagaacc     4260 taaagagacc tgcaagtagc aatttgctaa ctcagtgggg ctaccatgca aaaaagctg     4320 atcacccagg ctagtcaatg tattggttca aaatcatcaa ctgcttaaaa ccaggttctc    4380
tgccagagca tagcattgct attccttaat gcccagattc cttttcttact gtgtgatgaa   4440 atggggaatt agccagacat gaagatagga ccttgtgatt cagagctttt catgtcctct    4500
actaagttaa cttacacact cagcacaggc taaaaaatac ctgaggattt tctacacaag    4560
acaaatctgg gaactgcttt gcccaaaggc tattctgtag agtggagctc atccaaagac    4620
ttacaactta ctgcttgtct cggtttatgc ttacacaaca agagggcttg accatcattg    4680
tagacagttt agaatggatg gtggatttgg aggcatcgga ataagcaatg tgtagctctc    4740
tatcccactc aaagctcctg gatgggaata cttgaagaag gagatgtcta tgtgaagact    4800
gattctgtga gcacatctgc cgacctagag atcttcaagc cacagggcaa tagaaacatc    4860
tcaagcaact tccgtgtaat gagaaatgag cagaggagaa tcagactctg attccaacac    4920
agcatcagct ggggaagcag ctgcctctat gcatcagctt ctagccactt ctgcttgtct    4980
ggcttgtctc tagagcatat cctgaacata aagtgcctga cacaggaaca agcagtacct    5040
aggctaaagc cacaatgaca cagaacttac cttgcttgtg caaagcacca gactcacttt    5100
cagaacctgg ggcaagtcta gatccccaat tttgaaaagc attttgatga tttcatatat    5160
```

```
ctataggatg gatttttttg tcattttcat gtgagcacat gtgtctcccc cttctcctgc    5220 tggaatttt  ctcaactggt gtcccatgtt ctctttttct gtgtgtatgg tgccagataa    5280
ttgactccaa attttctgg  gagaaatgtg catctatatc tcaagacttt gttttcaagg    5340
aactaaccaa ataggatgtc catcttactt ccttgtttat ttgtattttc ttttatgtct    5400
agaagaaatt agtcatgaaa aatctaagac caagtccaac atttggtagt aggggagagg    5460
aagagaaggc aaggtactgt gtcctgggaa tgtgactgat tttccagaca aaccttctcg    5520
tcttcttgtc cacattttct cgtgatttgt ttcagaaccc ttcctgacct cactcttttg    5580
accttatttc atgctcttct ctccacctgc ctgatagtac tcagctgcag acacaggaca    5640
catttatgca tctctcatca gtatagggct caggattatc ccccaaggga tatggcgtgg    5700
gtgcaaagat gagagcacaa ggcagagaat gtcacgagat ggacacaatc tcttccatag    5760
aagccctcat ttttagggat attaaaggac agacactatg gcagaaaatt gtacaatgtc    5820
cttggcatta taaagttaaa ctctgggccc tttgaccatc catatgttct ctccatgtag    5880
gttaatcaac cacaaattat ataacaggat aggggttgga aatacaaagg tggatgaagt    5940
agcccttgtt cccaaagagc taatgggtga gactggctca tgggtccatg atggtggcaa    6000
aaagtacggt gacctgggac cacatcacag aaacttgtaa tgaggtcagc tcaagaggcc    6060
ctgggatcac attgtgatat acgatagagc tcctaagtac caaactgaaa gatgaagctg    6120
agaggaagat gtctgcggag agcattacac tggaaagaga agccccagag agcagagaac    6180
agaagcacag aagtaataca gtggtagctg aagactgca  ggtcaaataa aggaaattgt    6240
gatgtttgtc ctggggagaa gtgatacctg aaacagaaac agggctagcc cctctggatg    6300
gacttaagcc atgcaagaag atagagacta aggaaaacca tcagagcatt gcagatagat    6360
gaggcatgaa gggagatttg catttgagga aggaaaagtc tggatggaat gtgaagaata    6420
gtttaaagga gacaaaacag aagacttgga aaacacgtgg gaggctgttg acatgaggtg    6480
gcttagaaac agtgttccta ggaagtctcg ttctacacct gtcacctcag ggttcctgat    6540
gacccgtgag caagactttc tagaaagagc cggttcatta atcacgtcac ttctgtggta    6600
ttaataaagc aactatcatg gctttatttt gtatcgacaa cactatcatg taaatattcc    6660
ttactgataa gggccagtct ccctcagcat ttgtcagcca ctaggctcag ggagccagct    6720
accttgcatt tcttcactgc ctctgtaaag agaagttttc tctttgatta tgagtagata    6780
cacaactgcc ttgatgcttg ttctagcaca gcggaagagg ataactacca gggaaactcg    6840
ccaatcacaa ggaaatccga gtgtttctct cgtaccccag tgttgtcagt taggtttcat    6900
ttcaaagtca agattgttca agccaaagta caattggttt taaatgctgt ctttaaagaa    6960
ggaatatgtt agagaaaatt gcttgacact cattagtgtg aagcatgagg gcagcacttc    7020
atggctgtga ctcagtctaa aaatttcatc atctctacta gtttgccagg gtggccatag    7080
cgaagcctag ccaactgggg gatctcaaat gacagaaaga tattgcagtt gggaggccag    7140
gaaacagaaa tcaaggtgat caaggtagca aaagtggctg tcttctgaag tcagtgagga    7200
agaatctgtt ccttgtcttt ctcttcacta ctaatgggaa tcggttgcac tccttggctc    7260
atagaacacc cttgcctctt ttttaatgct gacatggttc tctctctcta ctctctctct    7320
ctctctctct ctctctctct ctctctctgt gtgtgagggg agatttatct ttgtcagtat    7380
gaacccatat gtctagaccg agccatccca ttttaataag ttagactgaa gcaaagccca    7440
tcataatggg ctcctctcag ctgcgtccct ctgcgatgac ctttttttcca aataagatcc    7500 aattctgaga tgtcaagtgt tcttatgttt caacataaga atttgttgta cattgacaga    7560
```

```
tacaattcag tccaaatacc acctaatatg atttcaaaat taaataagtt atcttctatt    7620
taaaaaaaat aaaaccttga agatcctcca gtttctgagt tcttcttctg tttctttctt    7680
gagagacttg aagttcttct catacagatt tttcacttct ttggatagag ttaccctaag    7740 atatttata ttatttgtga atattatgaa gggtgttgtt tccctaattt ctttctcagc     7800
ctgtttatcc tttgcgtaga tgaaagctac tggttggttt gagttaattt tatatccagc    7860
cactttgctg aagttgttta tcagctggag aagctctcag gttgaatttc tggagtcgtt    7920
tatgtatact atcatatcat ctccaaatag tgatacctttg acttctttgc caatttgtat   7980
ccacttgatc tcctttttgtt gtcttatagt tctagctaga actttgagta ctatattgaa   8040
tagataggga gagagtgggc agccttgtct tgtccctagt tttagtggga ttgcttcaag    8100
tatctctcca tttaacttga tattggctat tggtttgctg tgtattgctt ttattatatt    8160
taagtatgaa ccttgaatac ctgatacttc caccacttttt aacatgaaag ggtgttgtat   8220
tttgtcaaat gccttttcag catccaataa gatgtcgatg tgatttttttt tctttcagtt   8280 tatttatata gtggattgta ttaatggatt ttcatagtga aacaaccttc catgcctggg    8340
atgaagccta cttgatcatg gtgaatgtgg ttgatcgctt tgatctgttc ttggatttgt    8400
tttgtaagaa ttttattgag tatttttgcc tcaatgttca tagggaaatt attctgaagt    8460 tctcttttttt tggttgggtc tttgtatagt ttaggtatta gagtaatttt ggcttcataa   8520
aatgaattag gcagtattct taatgtttct attttatgga atagtttgag gagtgctggt    8580
attagctctt cttctgcact aaagccatct ggccctgggc tcttttattg gggtgggggg    8640 attttttaatt acttctatttt acttagggga tatgggtctc tttagataat ttacctgctc   8700
ttgatttaac tttggttcat gattctagtt ttgttgattc ttttatctct ttgtttctat    8760
ttggttgact cagccctgag tttgactatt tcctgtcatc aactcctttg gggtgtgttt    8820
gcttctttgt tgttgttgtt gttctaggac tttcaggtgt actgttatgt tgctagagga   8880
gaatctgtcc aatttctttta ccagggcact tagtttttttt cagcactgct ttcattgtgt   8940
cccataagtt taggtatgct gtgtcatcat tttcatagaa ttccaggaag tctttaatat    9000 cttttctttat ttcttccctg accaagttac cattgagtag agagttgttc agtttccagg   9060
tgtatgtggg ttttctgttg tttttgttgt tactaaagtc tatccttagt ctgtggtgat    9120
ctgatgggat gcatgggact atttcaatct tcttataaag gttgaggttt gttttgtgac    9180
taattatatg gccaatttttg aagagggttc catgaggtgc tgagaagaaa ttgtattctt    9240 ttgtttttcga gtgaaatgtt ctgtatatat ctgttaaatc catttggttc ataacctcta   9300
ttaatttcat tgtgtctctg tttagtttct gtttcagtga cctgtccatt agtgagagtg    9360
gagtgttgaa gtctcccact attattgtga ggggttcaat gtatgttttg agctttagta    9420
aagtttcttt tatgaatgtg ggtgccagga taggagagta tgatgagata caactgatttt   9480 tcagttgtca ctgagagttt gtagtttggg tgagctaggg caaaatctat gaagtgaagg    9540
cattatgtcc tcctgaagaa cccagagaat gagttttttca acatttgagc cttgttccta   9600
tgggcctgga taggaccacc atagtgagtc ttagaatgtc atttcaacgt gccctggatg    9660
ggatgaacac atgctgccta ggggagtagc tgacgtgcat caaagtgttt actcgaccca    9720
gatcacatca gaatcaaccc ttgtaaaaat aaataaggta tgttgatttt ttgtgcagat    9780
ggttaaacaa atctgatggg gcaaaatgag ttctaggaat aagggatatc agagggcaaa    9840
gctgctgaag atagcaagag ctgcacctgg acaattttgg ggcatagtcc ctggcagctg    9900
```

```
tgagtggctg ttctaggga ctgcagtgcc aagagaagaa tacttgcctg ccaaagagag    9960
aagctgactc aaggggggcaa agtcaagctg agctgaattc tagggaaacg tagaagagca  10020
atcatccaga gagggctct gatagagctc cctggccact gtctgctctt ttcagaagtc   10080
tggactccct gacctccaag gcctcctcaa ggtatggagt tctctccctc ttggatgttt   10140
ctatctcctt tcactgatgc tcagggagac ttgtgacttg agctggaaaa tactgctctg   10200
ggagggaaga acggtctgtt gtcctaaagc agtgtgacct tggaaatgta gctaaacttt   10260
tctggactcg atgtctttct ttgttttctg agattcttgg agttctggaa atcatgggct   10320
cttctgggtg aaatggatct tagaaaccta gcccagtttt gtggctgaag aaactaatgc   10380
tgaattgaga gatttcatta ttgtcaggaa actaatctat taaaggcagg gtacataaaa   10440
cttgaagatc ttccttctca ccaagaacca attccacaaa ggcccttggt gtcagaagcc   10500
tacatttgtt cctcctgaga atcctctgaa gtacagtctt ctacctgcct cagacttgtg   10560
caaactggtt tccccaatgg cttcctgctg ctgaataaaa agtcagaacc ttacatgtca   10620
gacacatttc ctgccacctc catttaccct cctgcagttc cctctttcta actggcttca   10680
agctgagtag aagcaaggat ctgattgttg tgagtgggca ggttcatcag agggtacaga   10740
tagaccaaca aaaagactta ttccaagcaa tatccagttt cccaaaggaa actcctatcc   10800
aatggatgaa agatattatt atgtaaggat tgttttatga tttgatatga atttaaatga   10860
tccgttgtga aatagaatgc agggatatgg cagcacaggt tggatgggag ctaactggat   10920
gttctgcagt gattggattc tcctggatca atatcctcct cctcccgccc tccctgtctt   10980
atctttggct tagagagcca ggtgcatcca agtacaggat tcctgatcag catcagcacc   11040
tctcaaaatc taagagaaaa gttggctcct ctgggtaaac tgaagcctta gcaaggtact   11100
gatgcctcct ctgggtgact atgttacacc ttccaaagtg atttggcttt tatgtcccag   11160
ttagatggtt tggtgtcagc agcatattgt agcttacatt gaggataagt taagttattg   11220
gtcccacccc ccactttttt tttttttttt ttttttgaa acaaggtctc tcactgaacc   11280
tggaccaatt tgccaagagt accaaatcaa gccataagca gtctcctgtt tccgcatccc   11340
cagccctagg atcaaaggca tgtgctacta acacctgggc ttatagatgg atgctgcaga   11400
tgtagaactc aggtccttt gcttagtgca gcagacacat tacagacaaa tctgtctccc   11460
cagccctcat tttgttcatt caaatatcat ccaaatttat ctgtgatagt ataaatgagt   11520
gagttgccat tccccttctc acactaagcc tttgaaattc aggatgaatt tcatactaac   11580
agtgtgccct tcaataatac agatatattt ccgatggagt ctgctgccat ccaggataac   11640
acatttgtgc aggaatatgt gctttgagcc ctgtggtgtc taaggtgtat ctttcaaccc   11700
agatctttga cgtgttagag agcagtgaca tggttggagt cacgcattct gtttcaggga   11760
ttctgagcag aaacgagcca ggaaatagtg accgttccct ggctaaccat tcctccccag   11820
aagcatcaat gttccagtcc caggcagctt tccagactgc cctaatccct tgacatgcct   11880
ccaatgctag ttcccagcag taagcatgta agacacctgc cttcccttgg tagagttcca   11940
gtgttaatta ttaacaaaca aatccacggt gcaccacagc aagatgtcac tgtaaggcta   12000
ccaagtttcc tagaacatgt ccaaaaggac tttgttccca ctgggttcct agtctgagtc   12060
cagaccagtg tatacacaaa caatgggggt ggtattttta ttagaagaac ttcaagctac   12120
caatcctgga gaacacactt ggaagctttc tctaggaaaa tgtctgttcc tatttgaccc   12180
tcaaccagac aggtgtctgg gaagaagaaa atcacactac ctaagaggga actgcagtaa   12240
ccatccatca cctctggcat atttatagat aaattcacct attgtatgca gcaactgtaa   12300
```

```
tggaggataa gctttcagga gatttgattt actaatgaca tagacacaaa ggagtggcat    12360
tcacacaccc tggatattag agtggagggg atgtgggaac tttgtcccat tctagaatat    12420
gcatgaggcc tctgaagtac agacaaggat ggagcccaga gtgcaaaact aacaagaaga    12480
ggggcagatt gcttcctacc caaggagagc tggatatcca aagctcactt ctgtaaagcc    12540
tttctaggag ttccttcaaa ttttgtttat gtgaaacaaa gcttttccta atgatgtaat    12600
gtggctttgg cctaagtcac atcaaagtac tgtcatctta aactaggggt taattgtcgg    12660
gtagttacta tctgtatggc cctggcacac tcgacagcta ctccatttcc gcaagtgcag    12720
agccctgtga ctcactgggg acgggcatga gcgttcttgc cttactagga agattgaata    12780
agcacagtca aggtgcttag ccatctatta cagcagcacc ataagtcctg cctttgttca    12840
ggtagcatca tggcctgaag acaggtccag gtagggtcat tctcccaggc agagacaata    12900
tccaggtgtc tatgtaatga tacgggtacc aggatcttgc caaatctgac catcctagtc    12960
cacccagact gttggtatgg ttttatcttc taacttaaaa caaatgctct tttggaggaa    13020
aaacttttaa ttagctgata atctgatgat tatcaggact tcaatgtcat caccagcact    13080
aaaagaccaa agtcttatga gcaagggcat acaaacatac atgtcttagg actcagtcca    13140
tatagtcaga tggccagttg ttatctagat tttaacactc ttggcttact tgtctattac    13200
aaatactatg gaattcaggt catttggaga ctgccatctt tcagttcaga aaaattattt    13260
tgaaaatcct tcagttcaga agaaattgag gttcttcaaa acccatgttt cttgctgttt    13320
gcagccacta attattccat aaccctgagg ttgcaacact gttcagtaat gggctgtgaa    13380
cctaaaacaa agttatcata tgctaatatg aatgtctatg ccaatccca ggccaagtaa     13440 tccacttatt ccctgtggct tttcctccaa tatcaatgca agaggagtag ggaacacacc    13500
tgcatcctga agaccctgtt tgctatggcc tggagctcct tggacctggt gaaattaaat    13560
gaaaacaata tgatgatatc ctctagaggg agacctgggt ctgaaatcag gatgctctct    13620
ggtcatagga ggcatggtgt gggcttgtaa gcttgagtag aggacatgaa gcttaagacc    13680
agggcctttt attacaagcc ttttattggt gatgtacctc taacaaggta catttggcaa    13740
ctaaaagtgt gtccagggaa aagctgctaa gaatcagact gaggagccta gaaactctga    13800
ggagaagtta gggtgcttcc cccagagaaa ctggatgcca atctattgtt tgaaagccag    13860
tcctatagaa caggtcttct ttgttccaaa taataaaaac aggagctagg tcaaggaaac    13920
tgttgcaagt tattctctta cttctacacg catcatgcat gctgtcacac acacacacac    13980
acacacacac acacacacat atatatatat atatatatat atatatatat atatatatat    14040
atatatatat atgcacacac atgcatacac atacaaatgt gtatgtgcat gcacatgtac    14100
aaacaaatga ataaataggc aaataattgt aaagaaaata gttgaagtca gagcagtgaa    14160
ttgaatgaag attccaagac agagaccctg ggtcctttaa gctgcctgct ctctaaggtg    14220
atgcttttct tggcatatga tggagaacag gggtaccagc catggaattg atggggcact    14280
aaagagcctg ttagagagat gctaagaggc tcatttgtgg atttttaagtg atgaacaaac    14340 aaagtgggtt tatggttttg gtgttctgca aactgtgatt ttcgacttag gccatcccac    14400
atattaaaaa taaaactaaa aataaaatca ggctccatgg gctttaccca tcccatctta    14460
gcatgtctgt tattgttgtc cttgctccat tcacgtttag ccaggcatgt tggtgagcct    14520
ttaagtacaa cttctgaaat tactagcaag cacaatctca cagcaaactc cctgatcctc    14580
tgcctctgac aatctttctg cctctcttcc acaatgatcc ctgagccttg ggtataggag    14640
```

```
tggtcttgta gattgggact gggatcctcc atccatttgg attggttgtg gtttgctggg    14700
agggtttcac tgtctgttgc atagaaaggt ttcttcaatg aggggaaaac tcaggggtga    14760
gcacgacact tctctgtgag tgtaaggact ctagttagga actatgccag cttagcaaag    14820
tgctgcttgc agtttctcca tgacgtcact ggcccttcct agttggctgg gttcccaata    14880
ccaggtgtga ttttcctctt gtcaagtggg tcttaggtcc aattagagaa ctgttggtta    14940
ctactaaggt atgtgtgcca gtactactga acccttgta ttaccatgac atattggtta    15000
taatgataac catatgtgtt atatgtgtgt aatatacatg caatatatat gctatttatg    15060
tgtagtatat atatatattt atgtgtatta tatatatatt tatgtgtttc acatatatgt    15120
atgtgtgagt gtatgtgtgt gtgtatgtgt gtgtgtgttc cagttcatgg ctgtcataga    15180
cctactggct gcttctctcc tttggaagct tgcatggtgc attctctaac catgaaatct    15240
aatcctcaag gaacaggctt tcaggtcaat tcccgtttgg gagcctctgt cactgcgtct    15300
gaactacttg tgtcttcag cattaagaac agaatgctag gaaggtgtgt tgtaagtagt    15360
ttgtggtatt ttgttttgtt ttgttttgtt ttgttgctaa gccaatgggt cacaataagc    15420
agaatggtga tgtggctaag aacatgggct gtggaggcta aggccataag gttcaaatgc    15480
caagtcttct cttattggag tctgagaatg tggggcagtt acataattta cttatgactg    15540
tgctttggtg tggagataga aatgataatg tttgccctg ctgttatcac taggttttaa    15600
tcacaactat ctttgactca caatgaacac tcagtacatg ctggaaatga ttctcataga    15660
aggaatatta ccttttatt cttaagccaa tgtgagaact taaaaggcac cagcttgcaa    15720
acacagagac tatgtctctt ttgcattgtg ttctaatgaa aggaaaatta aatgcacata    15780
cattttatt ataattagga cacagttcaa aagtgataag ccctgttggt ctagggaatg    15840
actactccta tgacataaag gaaaatgaaa tcaagtccag tatagatttt tggccatgaa    15900
gctcagagag taagtaagat ttctggaatt cctatcattc tatgtggctc tatggcttat    15960
tccccaagag aggcaaacaa ttaaggccct gtgcagaggt gcttccaccc tggtgtacac    16020
agtgaagtag taacagctga tggacgacct cattagccct cccctaagcc tttctgtctc    16080
atcatgagtc tcagctatgt gaccacggga aacaggagag aaaaagatac aatggggacc    16140
acgtgtctct ccttaagtac tgcttatgat attgaggttg ggggtctctg agccatttat    16200
tcctcctctg gttctttgga ccacttgggc attggactct acaccctgg cagatcaagg    16260
cacattctgt ggctcttggg agccttcctg atcctatatg gaatgactta gatcaatggg    16320
aggacagcag cagactcctg cagtcagtca aagtggtttc cactcctagg aggaacacac    16380
cagtttgttt ctgtgtgaaa tacagaaata tgacagcttt gtcgcaacgc taagcaaacc    16440
attgtgtggc agaacaagct tcttttttcac gtcagaggtt gacacactgg ccccacagac    16500
aacaccaact gttcccttg gaaacagaat ggtggcaaga atgagcagtt atgtggacat    16560
catcattctg gatcatctct aagatcaaca ttattttaga atgctgacaa tgatatgttt    16620
tgtgggcatg ctccagggga ggattcagta catggaaaat acatgctaat catccacaca    16680
taactgaggg aatcataaag agtggatgat gccctgaggg aatgtgtatt atttacagag    16740
atatctccat gtcaagaccc aatgcatcag atccatggga aatcggcaaa gccttctctg    16800
gtctgagtat gactgttgac agtgtgtgca agcacgggtg ttcactaaca atttaccagt    16860
ttgtgcaaaa gctagcaact gcagcttcct ccctgcaggt gtgtactgcc tgagatagct    16920
caaccttctt tggagactag ctaaccaacc ccctgtctcg tagataacaa aaccccttac    16980
gtttcagact gcctcagtaa ctgatctcct ccatgcaaag aagcatagcc catccaaacg    17040
```

-continued

```
cagctacacg tgtctgtgtc tgtcctttct tcattccctc actgctcagt caggtcacct  17100
ccaagctgca catggaacac agaacatccc catcaccttg ggcccaagcg tctggcatat  17160
gcttccaatc ttcaagtttt gagtggagag aaaatgtggg ctggaatcta caaatgtgag  17220
ctggaagcca ttcctcatga taaccctcgc tctttcttgc ctttttcttt tctgtgtttt  17280
ttttcttcat ttattgctta tgacactagc aacgcaacct attggaataa aaatgtgtgc  17340
ttcccagaac attgtctaac ttacttctca agaaaggga ccatttctgt tgatagtaag  17400
acttggcttg aaagggccag ttaaccctgg ccccagtttg tcttgatcaa catctctaag  17460
gcgtcctata tttgatctag cacctacaga aagagtagct acgctcagaa gaaaaaaata  17520
tctctacaaa agattcactt gtatgaaata ttttatacac taatctagct gaatcggtct  17580 cttttctggta gaaaatacag tatccaaata tagggagt aattatgata ggtaagcctg  17640
ataaagaaga cctcagatca tgtgtgacca gataagccta gcaattgtct gaagacttca  17700
aactacccct taggactact gaaaggatgc ctgaagaaaa acatctagaa acaagttttg  17760
tgtggaccaa acaaggagca acagagaatt tttgcacaca gggagtctat gtaactgccc  17820
cagtcatttc tcctaaatct ttttctgcta gaaagacctt tggtctggtc ccactcatca  17880
ttttaaaaag acttcagga ttgaaatgat tttagcctct tctttcttcc ttctttacag  17940
aaatgagttc tgagacgaga agacttgggt ggttaagtct gatgctgtta aatatatcag  18000
gggttgaaaa gggcttagaa gtgtaacatt cagctgggca tggtggcaca cgcctttaat  18060
cccagcactc cggggggcag aagcaggcag atttctgagt tcgaggccag cctggtctac  18120
aaagtgagtt ctaggacagc cagggctata cagagaaacc ctgtctcgaa aaaccaaaaa  18180
gaacccaaac aaacaaacaa acaaacaaaa atgtaacatt ctgattgatg gcatgtccct  18240
tgaaatgttt ctgagcttta ctatgcatta ataacttga aatgaatgca agcatgcaca  18300
gtgcttcttt ctgtcttact gaatttaagg atgccaaaca attctctcat ttttcctttg  18360
ctggaaggtg tggctcacca ttctattaga caaaattgta gctgacctct aatacctaat  18420
tagtgcaaaa caatgctaca attattgggc atgactttga cacgttttgg ctgctaatgc  18480
aaccactcct agttaaatag attggcaatg aagtttcaat gcaaactttg tcaatgaggc  18540
cagcctacta ctagatatcc aaccatatag acaggtaatg gctgaacaga tcttcattcc  18600
tacaaaacct caagaattat ccattttgca acttaagtat atgctgttca ttacttttgt  18660
acaagcttgc tctctctctc tccctccacc ccccccctct ctctctctct ctctctctcg  18720
tgtgtgtgtg tgtgtgtgtg tgtgttttaa tggcttacga atccacatag gattcttgta  18780
catattcatt ttggttattt attccccctt aattaatccc ccttcatctc catgtctctc  18840
cctgccctgc tggacctaac cctcttcttt gctatattct cttacccact gtccttcttt  18900
tacatcttta tttcaatcat gtggacccgt ttctcattac ctaggcttta tccatactca  18960
cttctactta gagacacatg tttaacagtg aaaggataag attgccatct gaaaagggt  19020 gtggggatat ggcgtgttta tttttctgag tctaatttct tgagttcttt gtatatattg  19080
gacattagcc ctctatcaga tgtaggattg gtaacaatct tttcccaatc tgttggttgt  19140
cattttgtcc tatgacagtg tcctttgcct tacagaagct ttgcaatttt atgaagtcct  19200
gtttgtcaat tattgatctt agagcataag gcatttatgt gcatgtgttt gtgtgtatgt  19260
gtttggaagc aatgcttctc ccatttcttg gagacttttt ttttttttttg gagagcagtt  19320 gcctagatgt tcatcagcag gtgaatagaa aatgtggtgc atacctacag taggattat  19380
```

```
tcaacaataa agataagcaa aattacaaat tttataggaa aattgatgga acatctctct   19440
ctgtctctgt ctctctctct ctctccctgg tggtgggcat ataaaatgca gtagccactt   19500
cagaaaacgg tctgacagac atcactcaag agcctcagac aaaaggttgt catgtgagca   19560
agggagtcca ctattgccta tatatttctc tacgttggta acagatatag tatgtaaaag   19620
tgtttgtagc agtactataa cactatgcat aggtaaaaaa cagctcaatg tctatcaaca   19680
aataaggaaa aaaaatgtgc taagtaatat gatggaatag tactcaactg cagaaaagaa   19740
tgaagtagat gacatagtga tgcagtgtag aacacagata aggatcaaca gtattatgct   19800
aggctaaaag tcacttattt gttgtctata ggatagaacc tgaataggta aatccaaaga   19860
gagaaatgct agagtagtgt ttccaggggc tgagagaaga ctaaactgag tgtagatgga   19920
ttatatgtct tctgctgctg ctccttccat gtctggctga cgacagatgt tttgacaatg   19980
gatgagaagc tgatgaataa tttttttaaa aaaatactga actttacgtt ttaaaagggt   20040
aactgttata tgagtactct caattttaaa ggaaaaaaag caatgtttaa aagtgggcca   20100
atgttggaag tcaactgtga gaagttaaga gcagattcac aaataagcac tggaattggg   20160
ccttgatttg ggggaatatt aagaatataa ctagaagacg ttgtaagaaa agtttggatg   20220
agtcagaaaa tagggagacc ggctagagag atgtctcagt gtttaagagc actgattgtt   20280
cttccaaagg tcctgagttc aaggtcccag caaccacatg gtgcctcacg accatctgta   20340
atgagaacca atgccctctt ctggtgtttc tgaaaagagt gacagtgtac ttgcataaaa   20400
taaataaata aataaatcta tttaagaaaa taggggaca attgtgtgtt agcaaaatac   20460
agtagagact agactaaggt tcattaaaac acaggccaat aaagatgagg ccacatgtat   20520
gtgttcagga cacatatact gtaatacgta aaatacatta aaaagttcag acttcttcag   20580
gctcgtgaaa aacacactgt gaatgcttta accctcattg tctgatcgta acccattcct   20640
agtcatctcc ctttcctttc cagctagttt gcatcttacg tccgcgtgtg tacatgtgca   20700
gcttctatat aggccgccac agctgattcc tgtttgtcct tttcccaatt ttttatttgg   20760
tattttcttc atttacattt caaatactat cccgaaagtc ccctgtaccc ttccctcccc   20820
ctcctctacc catctactcc cacttcttgg ccctggtgtt cacctgtact ggggcatata   20880
aagtttgcaa gaccaagggg cctctcttcc caatgatggc caactaggcc atcttctgct   20940
gcatatgcag ctagtacttg gatggaaggc cacaactgac tcttaaagac tgtatgtaac   21000
accaaatatt agagcaattg tcttcactta gtagcatttc tgagggttta agtccctttc   21060
atttggattc tcagtttcca tgtgcaatga atttttttac aggtgagcaa gaaaagtatg   21120
gaaggaagcc taagaaaggc cgcaatgaga ctttaaaaaa tgatgccaat tttagaacgc   21180
atcttctctt tcagacttgg aaaattaact tttattactg ccctatgcaa actaaattta   21240
aaataagctt tggattatac cccgtgcgta tgagcggacg ttatgacatt gattgacaac   21300
gtcagatcta ccctcaaccc tctgagagta tgattcacac atacctggga tcagaaagaa   21360
agtgttttcc agactaggca agtcactaga gctctggtgg tactcagggt agatttcttc   21420
cccataattc ctagctaaag atgaaagata cagacaaatg acccatccta ggagaattta   21480
caagggtagt ggtaagcagg taggtttcag aacagctcat gaaacaattc tgcagcagga   21540
gtcaaggagt cccaaagaag tggcctatat gggacagcaa ggagagactc aaaaaaaaaa   21600
aaaaaggagg aaaaaaaaac cctatgtggg gctcagcagt gaagagcact gagtgctctt   21660
tcagagatcc tgagttcaat tcccagcaac cacatggtgg ctcacaacca tctgtaatga   21720
gatctgatgc cctcttctgg tgtgtctgaa gacagctaca gtatactcat atacataaat   21780
```

```
cttttaaaaa aaaagtccta tgtaaaaggc ataatggtag atgttgcaag aaagcagtgt   21840
gtgtattggt atctggcagg aggctcagga atgttcacat cacagtcgtt aggaaaggaa   21900
agcaagggac cccttattgt aggatatatg gacaatttaa tcatggggtt ttttccccc    21960
aataataaaa ttttcagcag gaaaaaaaaa taacagtaaa cagtaagcta cgtgtaacat   22020
aaggatgaaa gatttcaaaa cccgtctttt acaaaatgca cagcaacagc ttcttttgtg   22080
acagcatcat cagtccccgt ggtttgcagc cggatgtaac aagccctttt gaagagctaa   22140
gagggcagaa agtttctgtt gccaaatata taagagaagc aggaagcact tagcctcgga   22200
ccaggaaggg catccttgca ggagaccctg caggtctgtg cagttcattg cccaatgctt   22260
cccttaaata aagagccaca gacttcagga gtgtgttccc ccctgagtga ttctgcaaga   22320
gttgtttgcc ctccagcact gggctgtgct gaaagagttt agtttcccag ggaacaagat   22380
ctgggtctaa ggcaaggcaa gcagcatcct atgcccaaac cagtaactcc gttttctcag   22440
cctgccaatc acattggagc ttccagacca tcannnnnnn nnnnnnnnnn nnngcctcaa   22500
gtctccagtc cccatcatga tagtgagacc cagaggaaag ggaacacctg ttgccaccat   22560
tttgaaggga cagtggtgac ccataaagag ggtgctctaa aggagacagg acaattcaag   22620
gacttggata aaatatcaaa ctgacagtgg tgagcaactg tcaggttcta ggaccagttt   22680
aatcctgact gggcagagga tagggccat ccacacaacc cctggaggga gcgttctata   22740
gaaccggctg ccttggtcag cttagggcaa ccagcattaa ggcagcagga ggagggatat   22800
aacccaggct cacctctccc aaccctaca cagggttcct tcctgccaag gctctctaca   22860
cctttagttt acagtggaaa tcagaaggca gtaggactca ggtgcagacc atataattca   22920
gaacaggaaa caggaaatgt ggaagaagga ggggctaagg gagagcacaa acattggcca   22980
gctgcagccc ggccccaatt gggactgcag acttgggtag atggatggtt gccacatcct   23040
gctctgagcc ttttgagtga ctctgagata gagcgcctct gtggagttcc acagagcagg   23100
cacacaggct gaaatcatga ggtttgtatt ttacctcctt gccggtttgc aagtcttgaa   23160
agctcactcc tctaagctga tggcagccct catgcaaagc aatctgattg ctgtgtctgg   23220
ggttcaatac acacacacac acacacacac acacacacac acacactcag gtgcacgtgc   23280
atacacacaa agacagaaca gtttgcttgc aacattgtca tagcttagtg aacagtatag   23340
cattgttctg gctcaagaag ccctggttct tcaaagctcc tacttagatg aaattatttg   23400
catcacaaac aaaaattgtt ttgcattttt tagataatga aggatcgttt aaatatataa   23460
attaagggct atttagaaaa aataggtgtc tttgtgagac tggcttaatt cacttaccat   23520
gatcatattc agttatggtc attttaaata caaatcatgt gtgttccaat gacgtgagat   23580
tacagtgaac tatctaggga aactaacagg agtggagtag ggacaggaga ggaagagaaa   23640
cgatgggtga tgggcacata tgctcaaaac cataatgtac tggggctgga gagatagctc   23700
agcggttaag agcactgact gctcttccag aggttctgag ttcaattccc agcaaacaca   23760
tggtggccca caaccatctg taatgggatc ggatgcccgc ttctggtgtg tctgaagaca   23820
gtgacagtgt actcacatac ataaaataaa tgcatctttt tttaaaaaat cattatatac   23880
ttgcatggaa atgaccctat gtaaccgagt ttcatttagt tgttttcaa ttgttagaga    23940
aagactaaat tttctctaag atagccatat gaagacagtt gatcactcta tgtcccagaa   24000
gcccatctgg aacttagcat tttgagcaaa ccataaattt gatgaaatac ctcctattca   24060
aggcggcaag cattcatttg cctcacattt ctaagtctgc ccctgtgact gccttagctc   24120
```

```
cttcttccca aattctccag ttacctggcc cttaggggtg gtagcgaaat ctccttcctg   24180
acagcttcct tggccaggtg cttctgtgtg gagtcagtgc ccaggccgcc agctgttcaa   24240
gtgtttgggc atatgcacac acaggaacga cttgggcaac ccctttgcc ttgtttcggg    24300
atgttcttct tgcagaccct tgcccagaca tagggagtgc ctgtgaagtg ctccagaata   24360
aatcggaatg tcccactgaa gccagacacc gtggtcttca tgttaatgtg taagtagagt   24420
agtgatcatt tatttattct ttgattccct tttgcagagt ttttattgcc ctgtctgaga   24480
tattggagtt ttctgctaca gtaaatttag caggatttct ccaaggtgac tttagcgcca   24540
gtgaaggact tattgtgcct cttcaagtgg ttctatcact ctgcttgtgc tagggtaaa    24600
atgaggtgcc aggtggattc aggacaagca gacacaagca agctaggaaa cctggcactc   24660
gatccctct gcggtgctta ggcaagcctt ctcggctact gaattttgaa ctttcacaag    24720
aacagatcgg ctgtttgttc aatggtttat tactcctgcc acaacaacgc atggcatgag   24780
gttgcgcgg cctgtttatt tctttgtgta tatggatatg tgtttgtggg tgtacatgaa    24840
tgggtggtat gtgtacacac gtgtgcatgg ggagacatgc ccagggctat ttaaatcttc   24900
tgcccttttc cttcacttcc ctcctgttcc ttcttaagaa caagcattgc ttcaccttt    24960
cacttaaatt tctcctctag aaaaaactgt tatcattcaa ctcaacatgt tttccactga   25020
aacttcttcc atattaattt ttaggttttc atgttctcgt tttattcgta cttattggcc   25080
gctattttca aattaataga gtccaatgtc atatttctgt atattgcatc cctgttgccc   25140
atctatgctt ctcctccaga ctatttcttc ctgtgcttat tcgcttagtg aaagtacatt   25200
gccaggctag aaaggtggtt tgttggctaa cagtgttctc tgcacaagcc tgggaacccg   25260
agcttggttc ctcatatcca agaaaggaga aaagcaactc tgaaagttgt cctctaactt   25320
tttcatgtgc accgtagccc atgtgcaccc acacccacaa atacacacca cacacacata   25380
cacaaaataa taataataat aattttaaat atatcaactg acttacaaac atttgttttt   25440
ttttcccgat gacatttgtg atgttaacgc ataatttgat tctaatttag ttgtaagcat   25500
attctatttt gactctttga agtttttga aattcagtat ctagctgtgg tggtgagctt    25560
tccacatcaa cttatcataa ccaagaatca ctgggaaaga atatttcagt tggaaaaatt   25620
atttggatca gagtgatctg tggtcaggtc cacgagaaaa tgtcttggtt gctaattggt   25680
gttggggac tcactgtgag tagcaccatt cactcatcag gggacagtga gctgtccaag    25740
gcaagagaaa acgagaagac ctcaagcaag caggccgcat ggctatttgt tcatgcctgc   25800
ttgtgactgt agacattatg tgatgagctg ccttgagagt ctgcttcagt ttctcctcag   25860
tgacagacgg taacctggaa ttgtaagaca ataaactctt tcctcccata agctgctgct   25920
tcttggatgc tttcttgcta caacagaaat taaaccaagg catcagctta tattctgcct   25980
gagtgcgtat cccaggtgcc cagaagtgtt ggctgttgta ctctgcacat ttcaatggag   26040
tatcagtcag gttatgatgt ccttcctaat tttttagcaa atgtggttta ttttattttt   26100
ttcaattttt attattaact tttattaatt attccattca tttacctctc aaatgatatc   26160
cccttcttg gttaccctc cccagcccca tccaccttct gtttatttta attaattaat    26220
taattaatta attaaccagt acagaaaaag tccactgaaa aatccatgtc ctgggcccca   26280
aaatacaaat aaaatcaaaa ggagtagagt cctgctgctc acatttcttc gtgagtagtt   26340
ataacttccc tgagattttt ttataccagg gtttgtttcc tcctggtttc tcctcagtga   26400
cgtcatcctg aggttagtgg ttactgtcac tgtctctatc ctcatcttga ctccataata   26460
ttcttcctct ttcgatccag accctcaggg tttaagagta gcttcaagct gagaaaaggt   26520
```

```
caatttctc caaaaaagct tccatctccc actgaaaatg gccatctcag agtgaagtac   26580
actcattctg aaatgtcagg gccaattgga tggtcatcag aaagcttggc ctggttgata   26640
tctttatcag cacaaacctg aaaatgcaca gtcctccaaa gggcggcctc tttgtgctca   26700
tccgaaagtg atggaaggaa ggcaatacaa aaggggctga actctggtca ccagaagtca   26760
gaaaccatgc aaacaaccag taatgaatag tgaattctag aattcaaatt agcagatgtt   26820
ttaaagagac aagctttcaa ttttcatttt aaacatgagc aaaacctgtg ttctgaaaga   26880
aaagatttag agaagagaaa aagcaaaaag aatatctaac atattgcatg acccaccact   26940
cccacaatgt gctcctggta aacttgaatc acatcttttc tccatcccga taattctcta   27000
actctcaagg agaggcctga gttaactctc tgaaattcca tatcttaggc actggatctt   27060
cgtgattatc aggatgtgct gtctttatca ctttgaagtg aagacaactg ctgtcctgat   27120
caatgacttt gaatttaact tattcttttt ccgtcttgct ccctaaagcc tttggtggac   27180
agttttgttc cttggttctt gggcttcccc ttcctaagag ttttgtttgc atgtctattc   27240
agatgctaaa atattgtgtt aacatccatg gtgattattt taatgtttgt tctttcagtt   27300
tgggcagttt ggcatttggg aattatacgt actttgacac tattaaatta gatgaatata   27360
gaattgtatc cttatgatga ataaaccttt tataattact aaactcatgg tttataaata   27420
acaaaactcc ctgcatcttt tgtctttatc tgatattagg tgtagctgca tcagctttct   27480
tttggctaat gttttgatgg tgatatcttt ttgtattgct ttattttcag tctcctactt   27540
tcttttggat tatttaatcc atttacagtt aatgtactta ctggatttta aattttacat   27600
ctccctctca caatttcttt tacttctata acttatattc ttttatattc ttcttgactt   27660
tttaaaaatg ttaatcaatg ccaatgtttt actattctct ttgttctatt tactgtcccg   27720
ttaatactgt ctactgtgat tctccaagtc attacccaag gattatatgt tctttctttg   27780
acctgttaca gtttacttta agttagtctt tcttttattt tgtatccacc ctgggaattc   27840
ctcctgggga atgatgttat gctagggtac aagctaccat tgagtcacca ccctaccctg   27900
ttaattataa tgaataatgt aactaactag cttgcaacag cttaatgtca ttgcaaatat   27960
ttctcagctt tccattatta ttattatata ctttcatata tatatatata tatatatgtt   28020
acaagattgt taaagttaca agatattgtt gtattaaatg atcaatgaat gttaaaattt   28080
accaaatatt tactctggtt tttttttctt attttattta tgtgagtaaa ttgtagctgt   28140
gttcagacac acctaaagag gatagcagat tttattacag atggctgtga gccaccatgt   28200
gattactggg aattgaactg aggacttctg gcacagcagt cagtgctctt aaccactgag   28260
ccatctctcc agccctactc tgattatttt tattccttct ggtgttagta tcatccttct   28320
gtgatcatgc ttttttacttt tttattttc atttagaatc atgttttctg agttttggta   28380
atggcactcc actgtgggaa tgtgaaattt gggtcattgc catctaaaac tcagtcactt   28440
tggcagcatg gctcagttga atggcctcaa atcccaggac acttatttca ttatgtatct   28500
gtctctgctc caacaattgt ccagagatac tgaccagtaa caaatctccc aagcaaaaa    28560 agaagaaaaa aaccacccag gccattatca aaatcacctc acttcattgt tttttcctc    28620 caggatctta actgctcaga tcaaatggac catttaaaga gctagaaatg atagatagat   28680
agatagatag atagatagat agatagatag atagatagat agatgataat aggtagatag   28740
atgataggta tagatagata aaagattaat atttgataga taaatagata aaagataggt   28800
aggtaggtag agaggtagat agatgatagg taggtaggta ggtaggtaga tagatagata   28860
```

```
gatagataga tagatagatg ataggtaggt aggtagagag atagatagat agatgatagg   28920
taggtagata gataggtaga tagatagata gatgatagat agatagatag gatagaagta   28980
gttggtggta gcagtgatga taagaagata aaaaagcaac tttatgttgc cttagaagta   29040
gaatttgtct tcccatataa aactatatac aacactgaat ctattataaa acatccttga   29100
acattatgtc atgtggacag acaatactct gtatacacaa aaggcaatac attctttatc   29160
atctatttaa tggtcagtat tagtaaccaa gtttaatcac aaccttctag ataatactac   29220
tgagatgcca atgactgctt tcaatatata agcctgaatt atgaacgctc tataatgcag   29280
ccattacttt ttgaaatttt taatattttt attggatatt tctttatttt atatttcaaa   29340
tgttttcccc tttccaggtc tcccctttgg aaactcccta tcctacccctc cctcccctg    29400 cctctatgag ggtgctcctc cacccaccta cccacatacc gactccaacc ttcccatcct   29460
ggtattccct tacactgggg catggaagac tctcaggccc aagaagggcc tctgccacat   29520
atgcgactgg agcaatgggt cactccatgt gtactctttg gttggtggtc cagtcccagg   29580
gagctccagg ggttctggcc agttgaccct gctgccccccc ccactccacg gggttgcaaa   29640 ccccccccc ccctcagctc cttcagtccc ttctccaact cctccatctg ggacactgca   29700
ctcagtccaa ttattgactg tgagcatccg cctctatatt tgtcagggtc tggcagagcc   29760
tctcaggaga catatcaggc tcctatcagc aagcacttct tggcttcggc aatagtgact   29820
gggtttggtg gctgcatatg ggatggagcc ccaggtgggg cagtctctgg atggcctttc   29880
cttcaatctc tgctccaccc tttgtctcca aatttcctcc ggtaatttgt tctcccttct   29940
aagaagcact gaagcatcca cactttgatt ttccttcttg ggcttcatat ggtctgttca   30000
ttttaccttg ggtattccaa acttttgggc taatatccac ttatcaatga gtacacacta   30060
tgtgtgttct tttgtggctg agttaccta ctcaggatga tattttcaaa ttccatcaat    30120
ttgcctggga atttcatgaa gtcattgttt taaatagcta gataatattc tattgtgtaa   30180
atgtaccata ttttctgtat ccattacttt tatgtatcac aacttggatt ttttttacagg  30240 tttaatttaa ggatctttaa aaataagatg gggttaagat tgcaagccta taatcacatg   30300
tatctgggaa gctgaagcta gacagttgga agttcaagaa ttcctgggat acataattag   30360
ctcaaggtca gccagagcaa ctgactgata cctatctca tataaaaagt taaaagagg     30420 tgtggacatg tatatctgtg attgaatgtt tcatatccta ggtgcacttt ccagtactaa   30480
gaaagagaaa gaaagagaga aagaaagaaa gagagagaga gagggaggga aggatggagg   30540
gaggaaggaa ggaaggaagg aaggaaggaa ggaaggaagg gagagagaag aagaagaaga   30600
agaagaagaa gaagaagaag gaggaggagg aggaggagga ggaggaggag gaggaggatg   30660
atgaggatga tgaggataac aacaacaaca acaagaacaa gaaggaggag gagaaggagg   30720
ggggaagagg aggnnnnnnnn nnnnnnnnnn nnncttatgt ctgtacatac gaaatactaa   30780
agctttatct aatattttc ttcaagatta caacaagaac attgaacact aatacagaga    30840
acatctgcag tgatgtgatt tgaggaaaat gaacccaaag gctcacttat ccaggcactt   30900
tgaatcactt tcttaactct ggccacttaa tgaatgtggg gaaaaggaaa gaagttgaga   30960
aaatttgaga taagactgtt ggaaagcaat atgttctata gttattgtca tgaattattt   31020
tccccaagag tttctttat ggatattgtc ctcatataac ccaggctcat cacacagggc    31080
agtttatcca aagcagagct aactgtggtt ggaaattttg caaatattgt aaagtcttga   31140
gaagcctaaa acacatacag aacaatgtgg aattaacttc tgtgaggcag gaccataaag   31200
ccttgaacaa caattcatat ttatttagag aaactaggct aaagcaaagc aaacaaacaa   31260
```

```
aagaattgac tgagggaagt ccaaagcgta ttttgttcca cctcctacct cagccttggt   31320
aaacagagct ctaaatttct atttacaatg attacataaa tattatatgg tgacatttct   31380
gactgtgaac caccatacac tcaagtatgt aaagaaagtg tacacacagg aatcaatgtg   31440
ttccaagaag atgcttgaat aattgtctaa caaaatttat cccaggagac agactatgcc   31500
aagttatagt acgaaagtta tagtatctgc attgtacaat agcacaggag agagcaatgt   31560
tactacaccc caagttttc ttttatggta ataataattt gttctttaac atttaaatca   31620
tttatgagtt gtagattcaa agcatacatt gtgatttctc ttctgtgttc attacaggac   31680
aacactgtcc tattttgtc tcctctgttg ttattatgtt tacataaaaa tctttcaaga   31740
caaaatagtt atgttctaca tactctcttg cccttagctt ccgtaactt tgccataaga   31800 attagtcttt tctgcccaca ctgtagttat accaacatgt gactttgagt accataactg   31860
aacttgaggc atactatatt ttcaaagggc attatacatt tttcagcaca gggtattagc   31920
ccattgggat acagtgaaaa aaagtctt aaaaacttgc tacaggtttg agttgcaatg   31980
tatgctttga atctacaact cataaagaat ctaaatgcta aagaacaaat tattattacc   32040
ataaaagaaa aacttttggg gtgaagtaat gttgctctct cctgtgctat tgtataatgc   32100
agagaacttg taagaaagtg agccacttgg tagttcaaga aggatgttag agagaatctt   32160
aattatatag ctatgtgagt ccagaagtgt gtaattagta tattattcca tatgtgctct   32220
tgagctttta atttcaagaa ctgtatgttg gaatgatttt gccagaggca agttaatgac   32280
tgaaggaagg aaggaaggaa ggaaggaggg aaggaaggaa ggaaggaagg aaggaaggaa   32340 ggaagggaa gaaggaaga tgtgacttac tagaagttga tagtagaatt ctcactggac   32400
tctaagagtt taaatttatt acaggttctt cctcctagcc tcatgctctt agaaataaga   32460
ctcagattca aaatatattt tcatatactt tggccatgtg gctaggctct tctctgacta   32520
aaatcataac ttaaaaccaa cccattgatt ttcatctaca tactgccaca taccacatgt   32580
tacttgtgct atgtgcctgt ctcctcacat cttcctgggt ggaactcttg tctggctcta   32640
tcccagaatt ctttctcctc ccagatgtcc cacctcccat ttcctgccta agccataggc   32700
cataagcctt ttaattgaca ggtgatgcac ccatacagta cacaagatag tctctctaca   32760
gctaagtttt gacattgttt cctaatgtag aaattattag gagctaattt ctgaaaagtt   32820
ttaaaaagtt atgtagactg tccattaact aacgtttcag aaaattgtac acagagaact   32880
cttatttcct tttgcctagt aaattacctc tctacataag agcgttaaac cagatatgta   32940
tgtcattgat aatcactata ttttttccgc tctttacatc cattccatta gaaaacttta   33000 tggcttttg gctccatttt caccagtctt actgcctcta atcctaatac cttttttgaat   33060 ggagaactgt tagatcttac aggcagttca aatatccaga aatgagacca agtggacta   33120 taggatgatt tccagaagtt agatagaaac caggattcct tagaaatttg taaagccagt   33180
tcctatttac caaaaggatt cacttctctt gtccctggca caacggacat agagctccac   33240
cgacatgtgc ctgtggttgc atttcaaagc ccatgccatc ctccaggctc cttcagcccc   33300
tactgaaata tacttgttac acatttcaaa ggctatgcca acctccccag acatccatcc   33360
tccttatacc tatttgttct cttttcaaca tgaatgattt tcccttacc ctggctattt   33420 tccctatact ttccctctat ctcctgctct cctctttact ctctcactct atgggctatt   33480
ctacattctc tcatagatgc actggccatg tccagtctgc tttgattctc tctactctct   33540
ctgattcaca ataaaaaacct tctcctcacc tgtaccatgg agaggacatt tcaattgttt   33600
```

```
ccttactgtt tcccttgcaa aaggaagatc accccaaaat ttggtgccaa ttcttctact   33660
agtaagcaat ccataaatat tcaattagtg cgtatataga caaatggact tctcctccaa   33720
attaataaaa cttaaaatat aacaagttaa gaaggcatgt aacatgagga gctgtaaaga   33780
attcagatag ccttctttgg tattttaatg gaaatctgtg actcaattta catgtggaag   33840
ttctagtaca cacatgcttc atttagttaa atacgtatac aggtggaagt tactatatct   33900
cttgcccttt gccttgcaaa ttccactcaa tcaatgccaa gaactgaact aagaagacat   33960
gttcacctct ctttcccttc acgttcaatg tgactcagtt gtgaccctga aaggacagta   34020
cattccatct gtctcacacc tgcctggtgt ctgggatcca tctctgggat tgacagcatc   34080
tgtgtcctct gatttctact ctttagaaaa aaaaaatcaa tgcccacatc atattggtaa   34140
cctttcaaaa agctcaagaa gagtgacaag aaagcaaaat tgctcccagg gagcttcaat   34200
tgctggtgaa aggctgatcc aataagacct cctggcagaa agcacagaca ttccaggtca   34260
ttccaaatgc ctgtgacaat atgtcagtac actgtctgac tgcgtgtgta gtagtgactc   34320
ttaacatggt tatttactaa ccacgtgttg ccatggaaac aaggtaaagc aacatgctct   34380
tgagacacag agacttagca tgttagagag gtggtgccta aatcccattc tacagccagt   34440
aggctgttca cacaggcaga ccacacccct ctaggcctcc tattcttcct tgggacatga   34500
gaaccctgta gccactcatc ctcaagacat ggtatccgct ctcctcttgt atttgagaag   34560
cataacattc tgaggctaaa gggcggagcc agccatcttc ttgaccggtt gggcttacaa   34620
ttatgtactt gacaatctcc aacatgtttg aatcagagag gaatacagta aaattcattc   34680
atatgatgct ctggtactcc tgcttattga aatagaaaaa acagacatac atacttagac   34740
tctcaacgtt tgcaggaaaa gaagttgaaa atatgttcaa gagttcagat ggcttctttg   34800
attcgtggta agtttgagtt ctatggattt gggttactcg aactctgatt ggtctctgga   34860
gtacatgtag acgttaagat gctatatgct ctgagagaac agtgagctga gagggaagcc   34920
tataaagtag tgacactcag atatagaaac attttcatat gatagtagta atggtgccag   34980
cacttcttcc accaatgtca ctgacaagct tcttgttact ggaaggagaa aaagtcatca   35040
gaccttatga aaaaaaggtg ctaggaatac atgcgcaggg attttcttat gtgcaagatt   35100
cactgagctc tttcttatga ccatataacc catctacata aaatattat taggtgctaa   35160 atccacagca actcaagctt tggagccttg gaaaattggc tttaggaaaa gagatcacct   35220
ggcaagctcc atgtctccct ttctcacagg atttttggaa taggattagg gtcaacagtg   35280 attttaagt ctcacaaaga aaacaaaaat cgatttcttg caaaactatc gctgtgcaag   35340
tttggttttc cagcatagat ccgggctgcc aagaatgctg gctccagcta ggtcttcatt   35400
agccaagtca ggggatagtc agggcattca tccaggtgac ctgagccaac cccacccact   35460
cagaaaacca agacaagttt gcctggtaga gcaaggggcc tcactggctg caggctgtga   35520
ctccatgtgt cgtgactgac accacaacca ggtatgtcat gagaaaaact ttgacaagct   35580
ggatggcagc tcgtcgttcc ttggatttct tccttaactt tgctttctgt ggctaacaac   35640
tgccattgaa tataaggtta tgtaggaaga attttaagta tgccttaaga agttaggatt   35700
gtgtcctttt gtaaaaatga taaccctaca gaggtcccctt tcatagcatt aacctgtggt   35760
cgtgtaaatg ggtactcagc cttagagccc atctctttag aaagcaaatc attatgcaat   35820
cagacaactt taaagttgga atgaagttac cactatctca attaggagta aggggagagt   35880
atagtctgta ggagttatgc gacttttgag ggtaacacag gtagctgggc atgcaaccaa   35940
gcatacaata ctggctgcgc tctcattcaa cgtatcaaga gtcttctctg atatgtgaca   36000
```

```
caagcaaata gaaaactcat agcctccaaa gaaagatctt agattcatca ggtatgtttg   36060
tatgcatatg tgtgcatgtg tgtgtgtgtg tggagagaga gagagagaga gagagagaga   36120
cagagagaca gagagacaga gagacagaga gacaaagaca ttgaggcaga aagagagaga   36180
tagatgaagc agaaagagag atagagatat agagacacag aaacagagag agacagagag   36240
acaaagacaa aggaaatagt aataccttgg gtttctggct atatagtctc tctctctcaa   36300
tttcttgtca ttgtagcctg aaaacatcta aaaatcacag gaacagggat gactgtgcct   36360
cagcaaaact gttaataaat ataaaaatgt gaatttacag cagtttcatg tgctatgaaa   36420
atttattatg ttttgagggg ttcttttcta caacataaaa cccattcttg gctcttagtg   36480
gaccggattt tgcctaggac aatagtttat ctggcatagg gtaatagaac cagcccagga   36540
gagaatgagc tgtggactct gtcctccact cgggctctct gaccttgtag ctgactccac   36600
aagccccctt ttccttttca agggttctgt caccctacac tgtgaaatta gtcactgtgt   36660
gtctcttccc aaaacattcc ttatttctta aagtcagtat aattacaagg cttgtttaga   36720
gcacggtcat aaacgtcata gtgaggactg gagcaaatgt tgctttgaac ataactctgt   36780
gacttcaact aggtggctat ggtaaaaaag gaagtacttc cgtttgccca taaacaactg   36840
tcttaaggaa tttgctacat tccttgagtc agctggatct ctggacaggc ctggttgttt   36900
agcttactaa cagccaatct ttcttttccga ctggccctga gtatgtgtgt cagtaggaca   36960
gaaggccctc tgggtgagag caagcaaatg aagaccactg ttttaactca gatacaggcg   37020
gtgggggtaa gtctcagcca agacagaaac gcttttccct cagctgtggt gtgagtgttt   37080
cctttgcaaa ctttgttgaa atgttattga tgttgtgata gtgttggtag atttagtgtc   37140
taactggtgg tgaactgggt catgaggtct cttgccttat gattgtctgc agtgtggaga   37200
atgggtaagt tagcatggga ggagttcgcc aagaaaggga aggctctctc tacatccttt   37260
ctctggcccc taccctctct gtgtcacata ggtttacctt cctttctaca ccagatgaca   37320
caaagtttga aaaacttcag aaccattaga caagtaaaaa cttttcccagt ctcccccagg   37380 tttctataat agttgataaa attggctatg acttgttttg tttatgttgg tgttgtgttt   37440
ggcatatgtt ttggttcctt gaccctcaga cccaaagaga gaggtggttt tctcaaggcc   37500
aggataaagg cacaaagact ttggctcaga gccaccacag aagaactgtg agagagtccc   37560
aggagccata atccaggcgt cttccatata tgaagtctcc aaaatcaact aatattgctt   37620
acactaatat tgataccatt caacatgaca acttcttaaa atcactgaca gtgatgcagt   37680
gtggggccta ttaaatatag ttatcaaaac tttgagttgc aagtggcaga aaccaaatgc   37740
aagatgagac atataaggaa acggccacat cagctttaac tttggaacca gccataagca   37800
tgccactgct tacgcatctc ttccctctct gcttttcttt gcgttgacat catgcatcat   37860
gtggagagac acacaagctc tagccttctg aggcgcttag aatcctgata gctcacagtc   37920 tcaaaagga agagatttta tctccacatc tatctcagta gacaagattt tctgtccttg   37980
tttcagacat tgctcactgt cagacccacc aatggaatgg aaaagaccct ttttggggtg   38040
gatttttaga ttcccagtga tcagcatgga gcaaacaatg ggaagttgtg tgtgaaggaa   38100 ggggggggt agatgcaagg ctaaaagcag tgcctgcacc aactgattcc tgtatctaat   38160
aaaaatgtgg cttttaaaaa cagtaagcat cgtagaaccc accccatgag tgttgaggtg   38220
attctggata attcttttcct ctctcattcc tgagccgtca gtcttccctg gtgaagacct   38280
gaaatagtac aaaaagacgat gaatgggttg atactattgt gagagtttgg tataaaactc   38340
```

```
agctctcttt tgctcgcta cactctttga tttctacctt tgtttctac caagaatgat    38400 ataccaagga gacatttact agctgtgaat tcctggactg tggagttcac agcacccaaa    38460
gctgtaggaa aaaaaaatgt attctttaga aactacctag tcctaagtat tctgtaaaga    38520
gagcactaag caggctgcag tggctgtggc tcctgcagag tcttacttcc acacagtgac    38580
aggggtatgt gcattcatcg tccctgctc ttagaagttg gaatgcaaat cccttgaagc    38640
cagggccaga gtcactgttc cacaggggac tgccttccct cacaatacag gaccatcact    38700
tttagcacaa cccacaggtc ttctgaatac tcaaaagcat gaagctaaca gacagagcct    38760
tatatggtgc taaggacaga gtcaagtaca gtgttagtta gacacctata atcccaacac    38820
agacacctga ggcttttcct ttagaagaga tgggaagcca ggggtgtgga aaattaaggt    38880
tttgttcctg ctcccttctc cactcctcct cctccctctt cttttggtgt ttttgctgga    38940
tactgtgttc catgatgcag tttaaactac ccctaaattc aaaatcctct tgcttcagcc    39000
ttcaaagtac tagggctatt gtcatatact gccattcgcc agcctgtcag ttcagctgtt    39060 tgactttta ctggcacata ccattatatg tattcattga gtacacatgt tatttggaaa    39120
ggtatagact atagaataac tggctctaca gtgtattgcc tcagttctgt ggtaagaatg    39180
tcttatatta attgccactg tggttatacc atgaacatat tcccctctta caactgaaat    39240
cttgttccct gtaatcaaca ttttcctacc aaccccatag cctggcctgc acactcttag    39300
tcctcttgct ctatacgagt agtagtttta ggttctacat agaaatgagg tcatgtatt    39360 gtcttccagt gtctggctta tttcacataa cactctggag tcattcttgt tatccaagtc    39420
tttctgtaac tgaaaagtat ctcactgggc ctgtgtacca catttttatt agccatgcag    39480
ccatgatgaa taatcaagct acatttttga tacagcaaat attattgcaa ccaacatggg    39540
atatctcttt gccatattga ctttatttat ttttttatac acaactagta gtgagatagc    39600
tgggtgatgt gatgtgtcta cttttaggtg tctgaggaaa ctccatagtg ttttccctag    39660
tggttgtact aatttacatt tctaccagca atgtgcaaga gtcccttttc tcttgtatcc    39720
ttggcaacac ttataaattt tatcttttca gagtagtggt tctagcaatg aggttgtatc    39780
tcattggcat tttgacttcc agtttctcaa taaacatgat gttaacattt ttaaatgcac    39840
ataataggca cgattgtttt tttctttga gaaatgggca ttctattatt tatccatttt    39900
gagccatacc cttgttatta gattgctttg ttctgtatgt attttgagca ttaagccctc    39960
ctctgatgta taattagtaa ttagaattcc ttctatcctt tcattgttca ctggcacatt    40020
ttgaagagat gtgctgtgac ctagtgctgg ctttgaaagc atcaccctgc ctgttctatt    40080
ggagacatac agtcttcaga ggcacacaga gagacaggag agcaatgagg agcttggtgt    40140
gatctccagg gtaaagacct ccattaggc caggttggtg ctctagataa aggtaagagg    40200
aagctgcatt cgctcatctc atttaaagac agaggaagca ggtttcgcca gtttgaactg    40260
ccaagttgta tggaaagaga tgagaaaagt caaggatacc atcaaggctt tttgttctga    40320
gaaactggag taaaaataaa catttgtagt ttactttgtt cttgactcac atgaaaggga    40380
agtatatttc tgtgacagtt aaaataagta catgggtact tgaagtatg gttttaaaac    40440 tgtcttaaac taaagccatg aacttttatt gttctgccta tgcaagcaat gtaaaaaaaa    40500
tgcatgcata tgtatttttc agaatactaa gatatataat aatataatac acacacacac    40560
acacacacat atatatatag actgtttgca aaacaatgaa ttcttttctg tatcatttta    40620
taaatgatta tgtgtccagg aatcagagta aagcttttg gagatgcatg tagcaagggt    40680
tccttattaa tttcataatt taacacattg agctaattgg tttgctcaca agggccatag    40740
```

```
ctgttagtca ctgtaccttt attcaagagg agagcagcta aagctggatg gtgcagtaag    40800
atgaaccttg gtcctgcagt ctgtgcatgg aactgacccc tctcagcatc agactctcca    40860
gccattcctt tcattacttt ggacctcggt cccacatctt ataagtgaag gtaacagaag    40920
ccagtgtcac agatgcaaaa acagcgtctg cactccaggt gtccccgatt actaatgacc    40980
tccactggga gcagtttagt taaacaaata tttggttcca gctgtattct aatttatgta    41040
cttgttcatg ttcttctttg ctataaatga ttgctgacct tattaactat ggcccttgtg    41100
agtgaagatt gaaaccaatg agcttaatgt gttaaaactg tgaaattaat aaggaacttt    41160
tgttacatgt gtctccaaaa agctttattc tgtttcctgg gcacacaacg atctgagcat    41220
cagaaatgag cagaataaag ctagacactg taaatctatc attgctcctg agaaaactta    41280
attaaaaata tactccaatg tctttttcat atttgaaagg tacaacctca gattattaat    41340
ttattatggt attttacttt gagacaggat cttatgtagc ccaggttggc ctggaactca    41400
ttatgtagcc aagagtgatc ctgattcacc taccaccaac tcacacttgc taggattata    41460
ggcatatgtc tccatgatcc atagcagatc ctttaaaata atggcaatga ataaataagt    41520
atataagcag tgaagaaaca ggatgacagt gtgagactag ataaccagat aaccctaaac    41580
tctagacact ggtatgtctg tgtaccctaa attatttagg cttgtggtgc aagacgtcag    41640
aatccttctt tcctcagatg agaacattga tgtcttcatg tctaacgtgt ctgtttgcat    41700
tcaatgagat tatgaatatc tccctgggaa ctgttggctc tattagtagg gaatatatat    41760
tcacatgttt tattttaaac attgctgttc agttttggaa gactgtagct atttgaagct    41820
atccatgcac tctattagaa gtgggaattt attttttaatt atcaattaag aagtcatcca    41880
ttgtatgtga ctggctttga acaaaaaata ataataatta aagcacacac acactgtgta    41940
gacagacatt gttacaatgc cagtaaaggg aacaaccaca gcacatatgg catgaatgtt    42000
gcttgagacc tgagtataat ccttaggtct tgagcagaat gagacagctg acttcctgta    42060
gccggaagaa gaatgagtgc ttgctgtgta caatgctcag gaagggctga cagagacaca    42120
ggcgagcagc ggaggtgggg aagacaatta caaaggaagc aacgaaatct gaacaaatca    42180
gagactctct agaagataac ccaggtctct gtacgaataa tcagtctgtc aaccacttcc    42240
tctacctgct ctctctatat attttttatta gatattttct ttatttatat ttcaaatgct    42300
accccaaaaa attccctata ccctcccccc cccctgccct gctcccctac ccacccactc    42360
ccacttcttg gccctggcat tcccctgtac tgaggcatat aaagtttgca agaccaaggg    42420
gcctctcttc cgagtgatgg ccgactaggc catcttctgc tacatatgca gctagagaca    42480
ggagctcttg aattggagga ctctctgcta attgtcttgt ctatacctga tagccaccct    42540
tcactaagca ctctctgaaa gtcagacttt atatacacaa tcttctcctc tcacctttag    42600
tactatgtcg ttatctccat attcaaatga aggaaactaa agccaaacat ttttcctaaa    42660
agacaaacag caagtttatg gaagacgtgt aacctaaggc tgggattttc caggagcagc    42720
tcccatgcct tcttcaagac cctggcttgc ctccattagc aaatgtacac atcacgtgag    42780
catgtagacc ccaactggct tctccactgt gtgccccgtc accttaggag tgagaaagta    42840
atgatacttg caaacaaagc atccacgtgt tacattatct cccacacaca ctacaaacca    42900
cacacactac aaatacttaa aaccagccct caggcttaat taacaagaag taaactatac    42960
aattttccaa atgatatctg gactcatgta cagtgagctc atatattcat ttattcccag    43020
agctgtataa cttcaaaatt aaactaatta attccttgta ttgtcaagca aaacattgac    43080
```

```
aatttttcc tgtgaccgcc tgttcctagc atgcttgttc ttaaatgtgt aatgatataa    43140
agtcttaggt gattgttttt gagttgcgtt gactttcatg ctaattatct gagtgatgga   43200
caatgtgttc catctcctaa ctcacatggc ctaatagacg tgtcaatcta acacagtcat   43260
ggcatgagtg ccagctgttt tgaaacatc gatctgtcat ctcacaagat gagcctccca   43320
attttcctta gtgtacttag tcatgtgtaa ctaggtctta aagtacccta agtttccttg   43380
aggcacagac acatgcaatt attttcatcg taagtcttgc ctggatgaaa taattgaaca   43440
tgaaaagttg ctgcacccca gtgaatccag tttataaaag cgtgtgtgat gaatgagata   43500
gggcagattc gagtgatcgt tatggagaaa aggccattca gattaagcaa actgactcct   43560
tcagtgtgtg ggtgccacag aaggcattca taccagaaag ctggaaatag taattttcc    43620
accttccctt gatgtttatg atttgtgcat ttctccaaaa catcttccta ttaggatgaa   43680
ctcagtcaca ggatgatagc aaactgcgtg caccaatgtg tccatgtctc tggctacttt   43740
ataacaaacc accctggact tcatggtgca agcaatgat cattttatta tactcatgaa    43800
ttatgtaggt caggaaatca gacacagccc agcagtgact cctctgtctg ttgtgtaatg   43860
tctagggtct cagctgtgaa cagtcaaaga cttgggaact cgaatcactc ttagtgtctg   43920
tcgaggatga tgtcaagaag ctgggcttct tggcaaaggc ttttttgaac gtatgctttc   43980
tgcagggctc gcctctgagg cctctgaact ctgaagagga ccatgcaaga tcacgtgaga   44040
tcttagagca gatgcacctg aagcatcgtg cacgtgcaca taagcgggcc ttctctagtc   44100
taattttggc atccttgcag caatggttca cctggatcag ggaagcactt gacttacttc   44160
ttaatgggtg aagaacaaga acatgttact agaagtttat tcaaattgac tggccgtgat   44220
tactggtcag caacagctgc tgtggaactg ttgcaggggc aaaggcagtg tttagggtca   44280
catagtaatt taaatatcac ctctcaggta ggacctacat cacttctgcc tgcatttaa    44340
ggcttgtgga gccacgccta gattcatcac gcaagggtgg tgtcaactgt gtactcagaa   44400
ggaaaagaga actaccaata ttgatgaatg gtgatggtta tgaccactta aaaatactgc   44460
ctccatgatg aaatgtggat gtttctttca aagctagttt ttgtaattat ttgaatcagt   44520
tcatacgtgt cttctgccat ccaccaaata tgcttgatgg gcaatgcacg taacataaga   44580
tgctggatcc gggtgtgtat acagccccca tgaaaggcag gaaatcactt gaaatttcgg   44640
tgtatggcct tttcaattat ttctgtcttt atctcccgca gtcatttact atagtttgca   44700
caccctactg ttagtcaaaa ccctgatgtc atagtcatca catcggtacc cttttgtaat   44760
ctgtgatatt gtatagagtg tgtagctata attaatatgg aattgcaggt agatactatt   44820
aattgaagtg tcccgattaa tttaattatt tcttaaatca tttcaaacaa gagttatctt   44880
acatcaaact ctgatagata gaatggttcg ttccttacttt catttaaaat gtatatagat   44940
attaaagta caagtagtgg ataaatccag gtataaagca gcttatttt cgaaagcaga     45000
gcctgtggct atacttcaac aataaaaaga gctaaaacca gtgtgagacc tgctgggga    45060
cagtttatat ttttgtctat aatgagaaaa tcatagtaac aaattgtcaa acaatcctga   45120
tgccctatga gaaacaatgg agaaaaggca agctctggga caggctcaga ggtgacaggg   45180
tggatttaat ttacttgtag tttgacatca gggatgcatc tgtgcatctg tacatgtaac   45240
aactttaaat gcccacccctt cctttccacc ttgctcacatc tggtactgta gaacactgca  45300
tactagctgg cctggggact ctgaggattc ccctgtctct gtatcccatc ttgctgtagt   45360
aatgctagga ttacagacta ggaatgtaat cgtgtgtgtt tttatgtttg gcttctcatg   45420
ggtcctagga tccattcttc agagttgtaa agcaagggct ttgaacattg agccatctcc   45480
```

```
cagccttggg gaaatgtctt cacaggtagc tctggctatg tagaaaattg ctggcaagct    45540
tagttaatac aggcactaaa ttgtgctgca gaatgctcca gtgaaactct ctatggataa    45600
cttggtaaaa gatcaaggca cttcagttaa acaatttacc taattaccta tttaaaggca    45660
tctaaaaaga gatagaacca aatgaaccca ttggaagcat agactagaaa tgcagtaata    45720
tcatgaacat gtgtttaaat aaatgtgtac atggcaaaag ccatacagca gcatggctaa    45780
gcttcttcat caacatgtat tcaaaattat gagaaaacct atctcaaaag ttacatgaga    45840
caactacttg tccagttttc tgtcctggca catctatgtt gaataaaacc tgtcagtata    45900
ggcttatgat cagagtcgta aatttgctaa aacaggtacc tcttccctag gtctgtcaaa    45960
catggtcaat cagttacagc ttagggctta aatctcatct aaggctgagt cagaagaagt    46020
taacataggt tctatcaaaa ccacacacaa tgctggagat aaacattgta acaatgactt    46080
tgcctactat gataatgaaa tgtcaggtct tttgaggtct cagtcagatg taaaacagac    46140
tagatactga ttgtgctaac agaaatttac tgaggaactc agcatttgtc tctcaggaat    46200
cttagctaca ttgtggcaga caatgattat caggttcatt tacttagtgc tttgcggtcc    46260
aaagcacaca cctctcatag cccaatgcta tatttcttgt accctcccag aactttgaag    46320
gctgtcatgg tcactgttct atagtagtga agagacaatg tgaccaaggc aactattata    46380
tgaaagaaat catttaattg ggagcttgca tacagctttta taagtttaat ccatgattat    46440
catggtggga agcatggcag caggcatagc aggcatggta ctgaagaaga agttaagaat    46500
aagtgggcct agcatggact tttgaaacct caaagcctcc ctcaagtgac atacttcctt    46560
caacaaggcc atatcttcta atccttgaag tcttttcaaa gagttccact ctgtgttgac    46620
taagcattca agtatacgag ccaatggaag ccattcctat tcaaaccacc acaaaggcta    46680
atcctctctc aaaaacaaaa aagattatgt atatgtgtac attttcataa atatgtctta    46740
catatttaaa actctgcatg tagatataat tctaagactt cctaaacatg cagagggtct    46800
ataatacact ttggctagct tgtgttcaaa tgacattttg ttgttgttgt ttaaagctag    46860
gaattgcctt cttggaaata tcaaatccct acagaactat taatgaaaaa taactatctc    46920
ttttaaagta attttttttaa aaaaaaagc ttctcttaga aagaaaggg aacttttttct    46980 ggggtgcatc tgtaaaattt tcttcagtcc tcaaaacagt cctttaccaa tgaaaactcc    47040
agacagcaaa agataaggtt gagctcacag gactggtcaa ccatagggat tctatcacaa    47100
ctctgtgctg cctgcatcaa agccccaaga ccctccagcc tctcccctca gcctcagttc    47160
ttgcgcgcgc ccgactggcc agcagtaacg acgctgtaac aggatccttc tgcacacgtt    47220
tattgggaga gcttgattgc agaggcgaag agaccctgag cccagaactg gtgctgcttt    47280
tataggccta ggagaggcgt gtctcatacc cggattggtt atgcactacg cctcatttgc    47340
atgttcctca tctgattggc tactctctct ctctctctct ctctctctct ctctctctgt    47400
acctcacaga gcctcattat catacctcat ttgcatgtct cacatctgat tggttatact    47460
ctcaaagcct cattattatg cccaggccag gcagtgtctt tgcaaaaaac tttactgcat    47520
atgtacacat tggttgtttg tccaaactta tgcgtggtgg ccagcagtag tcagtgccac    47580
tctgcaacgg cacatgnnnn nnnnnnnnnn nnnnnnnnnn nnnnnnnnnn nnnnnnnnnn    47640
nnnnnnnnnn nnnnnnnnnn nnnnnnnnnn nnnnnnnnnn nnnnnnnnnn nnnnnnnnnn    47700
nnnnnnnnnn nnnnnnnnnn nnnnnnnnnn nnnnnnnnnn nnnnnnnnnn nnnnnnnnnn    47760
nnnnnnnnnn nnnnnnnnnn nnnnnnnnnn nnnnnnnnnn nnnnnnnnnn nnnnnnnnnn    47820
```

```
nnnnnnnnnn nnnnnnnnnn nnnnnnnnnn nnnnnnnnnn nnnnnnnnnn nnnnnnnnnn    47880
nnnnnnnnnn nnnnnnnnnn nnnnnnnnnn nnnnnnnnnn nnnnnnnnnn nnnnnnnnnn    47940
nnnnnnnnnn nnnnnnnnnn nnnnnnnnnn nnnnnnnnnn nnnnnnnnnn nnnnnnnnnn    48000
nnnnnnnnnn nnnnnnnnnn nnnnnnnnnn nnnnnnnnnn nnnnnnnnnn nnnnnnnnnn    48060
nnnnnnnnnn nnnnnnnnnn nnnnnnnnnn nnnnnnnnnn nnnnnnnnnn nnnnnnnnnn    48120
nnnnnnnnnn nnnnnnnnnn nnnnnnnnnn nnnnnnnnnn nnnnnnnnnn nnnnnnnnnn    48180
nnnnnnnnnn nnnnnnnnnn nnnnnnnnnn nnnnatatgt ttgcgtgcag cttctacctc    48240
atttaaaact tgctaagacc acatgtatct gatctacata tattccctgt tatatcacag    48300
atgctaggtg tgatatagca cacagttgat accatccctt ctcaatagtt actgctagcc    48360
aattcccatt gaatgcctat ggcaattgac tattttgtta atagagttgg actctgtcaa    48420
tcagttgaaa aagtcacttc gtaacttttc cactatgcta aggtcatgg caaagttgta    48480 ccaggactta tgaaggttct tgttagtct gttcacagta gcagcactag agaaaatctt    48540
atgcagttgt tatgaacagt tgtacttaaa aatcaaagaa aaactagatt aatttgagga    48600
agtctctctt caccaacaga gtttaaatgc cctccacatt aagtggatgt ttttaagttt    48660
tccatgcaag aattcaagtt tctaactctc actggacaag ctgtcttatt cccaactctt    48720
ccttaggatc ttcttttga ttatattacc ataaatgttt attcaacatg tgtgatactc    48780
atgactactt accattgaga gagtaagtgg cagcctagcc agtccagggc agccatgttt    48840
ccttacactg atgagcgatg cccttaatca cctaaattcc aaaactatta cacttcccat    48900
gcagcattga gcatcaaacc attccttata ataatacctc agaggtctgg gcccctttagc    48960 tccctcagtg acaaagcaat gacactaagc actgtacagg accgatctgg ctttcaaact    49020 aaaacaact atagacagta gaaacaatgg ccatcatcac ttttctttcc tcttaggtga    49080
aggaaccaga ggctgataaa acttaaaccc ctacaataga aattaaataa aacaaattta    49140
gtgagtcact atggcccagg aaaggcaata agtggttaaa aggtaaactg ctgtcacgat    49200
gctttcatta cacagagatt ttagggacat gacatgaatt ttggcacaga aaatcgtgtg    49260
taaatatcac gtgggctatg gtgaaaggct taactattta ttttcctacc tcagtattaa    49320
ttacctgagt cacatatata agaatgggtg aataaataga tagatagata gatgatagata    49380 tagatagata gatgataga tagatgagtt cttttttgta tagtttataa agaagttcct    49440
aactaaaaac aagttccaaa gtactgtgct cttttatgga ctttcaatca gtctgtaaag    49500
cttttgtagg gcctatcatg agccaggctc ggggcagtta ggaaaatgca aatttaataa    49560
aggctttggc cattaggagc gtgtgtgtct ttctaagtta cgtctatgca acaacaatgc    49620
tgtctgtaca gtagagtaga gggctcagag aaagcaatgg aaattcacag aaagaggtga    49680
aagcccttgt aattcatata ccccagagag gaacttaaag agtgtgttta gtaggaatag    49740
gcacctgcca aagaatctat gaaccccaag atatccaaac ttcttatagt cctgaaagga    49800
gtttcttctg agttggctca gttgtgcact accgctgtt tcctgctaca tcttctcaga    49860
gcaaatagga aggaaaaat gcttctgctc tgtattgtat gctcctttca ttaaatcacc    49920
ctcgggacaa ctgagtgttc cagaataggt gttggttaa aaaaaaaaa aaaaaaaaa    49980 aaaccaaaaa aacaggtatt tctgtgcaat cagaaagtgc ctctgctttg ttaccagcat    50040
aaagcattca tgaaatcaat tttcagcacc cactggatag ggctgatgtg cgaactagct    50100
ttgcgtagcc catcgtcttc tttccgagat gatttgacag gactggcatt ttatcatgaa    50160
tacaaagagg atgagcatat tctcctaata tattcattac ttccctctcc gaactggtaa    50220
```

```
ataatataca tatggtaattt tgagagacat agtgttcccc attgctcctt tttattcctg   50280
gaactctggc tgtctttgta aatgctgcaa aaatcaaagg caaaattacc tcaaaatttg   50340
attttggagt ccttctagtc tcactttctg gtgcccacac aagagctatt gcttattttc   50400
tgttctgacc tgtattattc aatagcatca ccccttctgc ttgcaatctt attgtagaac   50460
cttctagagt gactcaaaga agccatctat ttattcatta acaagcacct attaagtacc   50520
tactctgtcc cagacactgt gctaaatgtt caaaagaata aggaccatgg aagcctatgg   50580
cccaggccca ttcttgtttt ctcgagtttt gtaatcattt ctcacacaat tataaaaatc   50640
catggcatcg tagaaagata ggaaagactg tggagtggat gccgtaaaca gaactaaatg   50700
aataatgaat gacaagctga gaaaatgtga gtgtttgcca gagcatgtga gtctaattag   50760
caggcataaa ctgatatgct aaaccaaaac gtgatgagat tttagatcca aaagagccat   50820
ttttatagac tggacctgaa agaattggat ttttagatgg gagtatgaag gcagatctga   50880
agggcagttt tcttagaact aagtgaaaac gagatgtttt actctgcacg gacttgattg   50940
acttgccatg gcttgaacga tcagaataca agtcaattgt gatcagtaat ttcttcactt   51000
gtatacttaa aagtgttcat tgacctactg cgttagatga attggtcttt gctgaaagca   51060
aaggaaatta aaggtctgct cttcttgaat ttgtgttcag atgaatggac aatgggagta   51120
aatcagtgta tggaagcccc agctagatag gcaccgagac gtaggctgca aagaagacaa   51180
atgggtggaa gatgtctcta taaatataca tggttgttag ggcaaactga ccatgcacat   51240
tggnnnnnnn nnnnnnnnnn nnnnnnnnnn nnnnnnnnnn nnnnnnnnnn nnnnnnnnnn   51300
nnnnnnnnnn nnnnnnnnnn nnnnnnnnnn nnnnnnnnnn nnnnnnnnnn nnnnnnnnnn   51360
nnnnnnnnnn nnnnnnnnnn nnnnnnnnnn nnnnnnnnnn nnnnnnnnnn nnnnnnnnnn   51420
nnnnnnnnnn nnnnnnnnnn nnnnnnnnnn nnnnnnnnnn tcccattcca catcaaatgt   51480
gttccatggc tgcaatcaag tccatgctca acagtacatg aagatatgac agtctggttt   51540
ccatttatat aattgttttg ttgccttctt tattcttact ggatgaggtc ttattgtgct   51600
gtcctgattg acctgaactc tgggtttcaa cagtcctgat accctcagcc ttcagagcaa   51660
ggtgcctccc agttctgcct tattttactc tctctctctc tctctctctc tctctctctc   51720
tctctctctc tctctctctt tactaactat gaattcacac caacagtttc tagaatctct   51780
tttaaagcat acctgataat gatgctgata ttggttaaaa taatgtaaca aatgcttctt   51840
ttattacttt atatgaatta cctgtcattt aatgctctga gatggtgtgg ggatataggg   51900
cgctgttatc gttccatttt atagatgaga aaactgagta cacagagata aagtaactca   51960
cttatttcca taaagcaagt aagtggtgcc actagagtat aaaatcaaac aacatagtta   52020
gaaacactat ccttatctgt ctttagtgtt tatttcttca cagctccatc atcttcatag   52080
acacacacac accctactta aaacctgcat gtccataatt tccacaagca agcaccttga   52140
gctgaaacat tcggggctgt tttaaagtaa attttgctat tattcctttg gcagaattta   52200
aattgtgaag gagattttca agtgatttcc tctcaggctt catttagagg cattgaataa   52260
agtaatagca cctttgagaa tgcaccttga catcttagtg ttgggcacct gtaatgatag   52320
caacgtggga gtctgaagca ggaggatttc gagtggccag gcaggggaaa gagagagggg   52380
ggagagagga agagagagaa gaaagattcc tactctggca gactaactgt ttcctttaact   52440
atcactatta aatacactaa attattcttc agctcctcct tcactgtgga tccatgcctt   52500
taaaacaagc accgttgtcc cctttgcctg tgcatcctga gtctctatac accttagca   52560
```

```
ttctgaccca ggattctcaa ttgattgcca ctaaaacccc agatatgggt acaaatctga   52620
gcaaattgat ctcaatatgc attagcataa ttagaattat ctagggatgt cagatcatct   52680
taagcaccta caaagtccta ttttgaacac ttaagtataa ttagcatttg tgaaaggtct   52740
ctggttttca agtgtcttgc aagactcttg tttttttttt tttttttttta gtaagcttct   52800 aaaagctgct tgtctttagg tgttcagtga acgggaaaga taaacatttg aggcttgccc   52860
ttttcctctt tctgactaaa tgcgggtcat aaagtagagc cacggataca gcaagcccca   52920
tcacacagat gaacacagat agcccttgcc ctcatggaag ggatcatgta gagtcctctc   52980
tattccaaaa gaacttcaca atctccataa ctacgtttgg catttcacat ctgtcttgtg   53040
cttttgtgac atgtggatta gcagacagtg cctcgggctc tcatgatgaa tgtagggtaa   53100
tacagcagcc cagagccatg gcacctaagt atgacttgga tgtgatccca cttggatatg   53160
atccctaagg gacaggataa ggacactaga tcaaatttgg atcaaagaag aattggaaat   53220
caaagagttg agaataacac ccagccctgc atctgcatct gtttaattag tcttttctcc   53280
atccatttta aatgtgtcaa aaatgtgtaa agatccattc aaatagaaaa atagtaattt   53340
ttcatggagt gagggcagga aataaatgtc agattcccag tagtaaataa atataatttt   53400
tagacatata attagctttc ctcaatctca gtgtcttcat cctaaagggg cttacttttg   53460
gtaaagggga aataaacctg aattgttcag ttggagtcca gtgaaagagc agcaggcaaa   53520
agaacatcac agctgctaca gatcccactt tctcaggaat gaacagctcc tttgaatggt   53580
gtctacgtta tccaaaatgc cacaaaacaa ttgatgataa aactggtgga tggacatata   53640
gtctgaatgt ttctcaaagc tcttagtact caaagaactt aagaaagggg gaataaggag   53700
gtttgcctag agtagagtgt ttcgggcaga ataaagaacc cctttatctt catttattaa   53760
gttgaacaga acaaataaga agctatccat ctctataaaa aatcaaatac agttagttcc   53820
ttaatgagtt gcgtcttttg ctcctaactg taatacatac aatagtgtat tatttccttt   53880
tacccagata gatttcctga aaccataata ttcagaggca gagaactaaa ggttaattta   53940
aaaaaaaaaa accctcaggg gtaaattatt actattagag gagaaagtta tattttaaa    54000 gcttatagta ttatttttcc aaattaattt ttaaaatagt atttcatgt attcttgaaa    54060 tgtaagtata ttctagatta cgtaaataat tgataatgga ctaccaagaa aaagtatac    54120 atgtaatatt caatatacaa attagcttca gtaaatctct cttttgagtc attatttcca   54180
ctaaaatgtc tcttcattg aaattattct atgaaatatg aaatttagaa tataatggac    54240
accttctttt gttacttaat catgacgtaa cgctttgtct ccttttcata tttgaagtgc   54300
agaaacgcct ttaacatcct aggaaagcca tgtggatgtc atgatctggc tttctttgtt   54360
cggataatat actagattat tttctttctt ctgaacatct taaactccta gatgagtttt   54420
tccttcaatt ttaaatgctt ttgaagcagg actcattttg tttcgagcat ttcttggaat   54480
tacatagagt tgagtaaata tgaatatgcc agcatccttc taaatggact acctttaaac   54540
tgtttcaaaa gtaaaccatg catcaaaagt caactcggaa gacctgtgtt ctctcatacc   54600
cctacaccta ccctgccccc tgtgggtttt tttttcttg gtaataacaa taagtgtctt    54660
agttaggatt tctattgcta taacaagaac actatgacca aaagcaactt gggaatgaaa   54720
gggtagcaat aagattacag gtctacatat cacaatatat cactgtagga agtcaggca    54780 ggaactcaaa cagtgcagga acctagaaga atacgctgat gcaggagcca tagagaagtg   54840
ctgctcagtg gcatgctccc catggcttgt tctacctgcc ttcttagaac acctaggacc   54900
atcagcccag ccatcacacc atccacatgg gctaggccct cccacatcaa tcactaatca   54960
```

```
agaaaatgca ctacacaaac ttgctcatga gcctagctcc tgtagacatt ttctcaattg   55020
agaattcatc ttcccaaatg aaaatgactc tagcttgtgt caggctgtta taaaactcac   55080
cagcacatac agcgacccaa aacttcatag gtactttgaa ataagtgaat ctccaatcat   55140
gctgctatcc ttttaagaat ttgtaactat ccctgcaaac tgttgtgggc tatgtcatgg   55200
tctctaaatg ccaccctctt acatcctaag cagaatgaag catgaaatag gaactaaggt   55260
gtggcacaat gcagacaact ttcctctggg ctctccttac aggacacttc tcagccatga   55320
atcttactgg cctctacctt tcacataacc agggaaacca aaacatacat ccatttttta   55380
atcttgtcct cttccccaca cattctcaat cttttctcac tgttcctccc tcacaaaaga   55440
gcaagcatag gaacaaatga gaaagtttct gactgccatt gactctggga aaatattagt   55500
cttgtgctga ttgttgcagt gatgtacata taacatgaaa tttactatct taatcatttc   55560
aagtgcatgg ttaagtacaa tcacaccatt atgacaatcc ccagtatatt taaattttta   55620
tcacacagaa ctgaaacacc ttatctctat gctacactaa ccagtccttt caaaaaattc   55680
caagtcgtaa gtctaagatt aggcaagaca tagcctttgt gctcttaaac acttttccaa   55740
aatatattca ttttaaattt gtatgtataa aaatgaatag ctattttagc atacagaatt   55800
aaatcagtca ttttaatgat tctactgatt ggcttccagg agcatctgtg tgtcttctca   55860
ttaaagtaac caatgcatta caactgtcat tgctctgtga ctcttcttct cttgctttgc   55920
tatttaatgt ttctttgaag tcaaagagta gctcttcatg atatgcatcc aagtgtgcac   55980
ttaaatcata gaacttattc ttagcaagga agtatgtagt gaagcacctg gtcaaatggg   56040
aagacagcct tgagaaagac aatgtttttc ctgctgaatt tctaggaata gccaacaaag   56100
tgggagtcct gataggtgag accagcagtg tgctctttca taacctcttt caattactct   56160
caactcttct ttattttttgg atcctatgta aaattttcta taaagaaaag aggttatact   56220
atgttttgaa acaaaacatc ttggatctcg aggaacgttt tgtctcatta ttgagattca   56280
ttggaagcct gtcattgaat gaaaagatat cattgaaaac atgtggcctt taaaccaacc   56340
accgactctc tccaagcctc ttttctttat gactagaatg agaataacgg tgtatatctg   56400
catcttctaa cacctgagaa gatttaaaag cagtgagcag tgtgctgcca gcctcctcac   56460
cctgctgcct aacaaggtcc ctcccacatg agcagagcaa tccaggaagc aggtgacaga   56520
ggatgaggta gtccagagca gagacaggaa tataacagaa actggatcta tctggctctg   56580
gatactagat ctaggttgga cgtaatgaca ttgggagctg tgactgatgg gttctcaacc   56640
agatgccacc tttctcagtg tctagaggag tggtatctaa caatgactaa gatggtttcc   56700
caagagaatt tgatactgaa atctcactcc ctctcccctct ccttctccct tttccatccc   56760
ttttcttctc cctctcccca tcatcctcct ccctcttcct ccaccttcct ttccattcct   56820
agtgatcaaa ttcagagcca tccacatgtt cgaatattag ttaggcgcgc tttctagcac   56880
tgcggtacat catcagccct ggaaagactt attgccatga atgaatcgtt actggcatgt   56940
acgtgatcaa ggcagagcca ccatggtcca tgggttctgt taaataccct actctgaaca   57000
tgacaaaacc tcgatataac aacattaaca gcttaacacg tcactcgtgc tgaccttgag   57060
aaactctact tttagagact ttctgacata ggtgcctctc cccatcattg atttcctctt   57120
cgtctggtaa cctggaaatt cttcaggtta cttttgttct ggttctcttc tttgttcctt   57180
tgtccctctc ttcatccctt cttcataact ttttcctttc actgacttca ctaagacaag   57240
attcttttgt tttcttcact aactagtaaa ttgcttcttt cccaactctt actcttaaaa   57300
```

```
gcaacagaat agagctctct aagggaaaat aacataaagc ttgaaaccac ataaaactgc   57360
atttgtattt gtgtagacat gcatggattg ttctttaggc cagtagattc agagacaaaa   57420
acaaacaaaa accatccccc agtgttacag atagttaggg ggactggact gtgtaacatc   57480
aatcccaaga ataccttaa gtaagtactc ccaggttctt tagaatgaaa aatctaggag    57540
gtgtcttagt tctattgctg agaagagaca ctataaccaa ggcaagtctt atttaaaaaa   57600
aaaaagcatt taattggggc tggctcacag tttcagaggt ttagtccatc cattatcatc   57660
atgacagaaa gcactcaggc agacacgata ctggagaagt aactcagagt tctacatcta   57720
gatcctgcat gcagcaggga gagagacaca ggacctggct tgggctttta aaacgccaaa   57780
ccacaccctc agtgattaat tttctccaac caggctatac ctactccaac caggccacac   57840
ctactccaac aaggccacac ctactccaac aaagccacat gtcctaatgc tactccctaa   57900
gcattcaagc atatgatcct atgggagatg ttcttatcca aaccatcaga gatggtatca   57960
gatgccctat aaaggagtag ggctttcagg ccaaacttac tttgaaaggt tctcaaatga   58020
ttatgagaca caacgggttt gggcaacata acaggttgt ttttataaat ttcaaccact    58080
ggcttgctat cttatcactc aacctttac caatgagcag atttcaacca aaacaacatt    58140 ttttttttgat tagttgagtg aaatctcaat tcattgcatc tcaatttatt gtcagacttt   58200
aaatcaagtg gcaattatt tattcccatc aaggcagcct tttgctatcc tgtagccaaa    58260
ataataaata ctggttgtta gttttatatt caaccttgtt cctcagtgtt ttaaattatt   58320
ctgatacagc tttggatgga gagtgaataa aaagaggcat ggtctctgga gccccagatc   58380
ttctcataaa gacccaagaa taaagtggtc taaacaaccc ttacacactt gctcactcac   58440
tcaacaactc tttggaaaac tcacccaatc ccagctccgt ctcttgattt actctttatt   58500
ctcatgactg aagaactcag ctgtttatgt tttaataaaa aatggtttaa aagaccaagc   58560
agaatccaat ggggactgtt tctgagatat ccagcttact ggcatattct aatgtctact   58620
tggcaataac tgaaagtgtg gcctttgtat tccaagtaac tctgtctttg agtagtttgc   58680
agatttatca cttgttggtc tacagccttt aagttaggga tcatatccaa agctgcctgg   58740
ttttatagga aaagcctagt tgtttccaaa agcaaggcca attaatagag cattcgagat   58800
atttgagatc tatttccatg gaggaaatga tcttaaagtg aagttaatta ggagtgcaga   58860
gagccagaga tgataaattc agaattgcat aatagatttg tatactaaag gggcctgtgt   58920
catctccagt cctaaagaga ccggctgctg aagaatgaga ctcagaaaaa tgggtgggtt   58980
atatcgcctc cagcttttcca tgtcacatgc acatgtcaca tggcctttca tgacctatat  59040
taaagttctc cagagaaaga gaaccagtgg gttattctgt aaatatgtgt gtaggtttat   59100
atatgcatgt atatataaat gaagggagat ttttttatgg caagggattg aagtgatgat   59160
attaagttta aattcaatct ggagacctag gaatgacaat gatgtaactc attctacatc   59220
tcaactgaga gattcctggt ggtataactt ttacttagag gccaaaacct aaggtacaga   59280
gtagagactg ggggagtcta gtgacctgaa aaccaagagc tctcatgtcc agagtcagga   59340
caaaatgaat ctcacatcca ccagactttt agttttctg ttctgactct taaggattg    59400 gatagtactc acctaaaaca acaacaaaaa agaaaaaaga agagaaaaga aaacaggaaa   59460
aaccattctc cttttgagtc aaactctatt ctccttccagt aatactgtca gagatacatc   59520
agaaatagta tcttaccagc tatcaaagta cctttaccc tagtcaagca gactaggcta    59580
cacaaaattg aagcctttat gtccctgtcc atagaagaca ggcttagctg gataatacccc  59640 aagtcctcta ttatagcatc ttgccagcta tcaaagtgcc tcttagccta tcaagcagtc   59700
```

```
tgggccatgc aaaaatcacg aagcctcagt atccccatct gcaggagaca ggcttagctg    59760
aataacacct aagttctcaa ttatatacca gtgctctatg aatgcaaaaa taaggcttgg    59820
aacactctgc cttgaccagt ttaagcatca acagaagctg atcgctggac atgccttcaa    59880
tcacaactta cacattaact tattaaattt actagctaat tccaatttgt tttctatttt    59940
gaatggcaaa attttcaac tgggtctcta cttgatttta tcaagaaatt gatggttctg     60000
tttggtataa aagtattttg gttcttttc cagaatatgg tcatcattac tagagatata     60060
aattgagcta ataggagta aagtatcatg tctgtgattt catttaaaaa taaagataaa     60120
ataaaatgtg gctagatcac ataagatgct gtttgggctg gcaacatttc tcattaaaaa    60180
ctatattctg aaaaaggta tcagggacct aggggagaca gatatgggta acattgactg     60240
ttctgggcgt ggaggttcaa tttatttatt tgccttttca ccctctgtag tgtgtgtgtg    60300
agtgagtgtg tgtgtgtgtg tgtgtgtgtg tgtgtgtgtg tgtgtgtgtg tgtgttagtg    60360
aagtggaatc aatttcctga agccttgaga gatttaaatc tcttcactga gagtgtctct    60420
tcaactgcat gcaagcatga atgaatatta agggtaaggt actatgactg ccctcttggt    60480 tcatcttcc attgctactg cacaagtccc agaattttga atatcgttgg gtcaccattt      60540
gtcctatagg cttctgtaac ctccttaatc atttgtatat aatctagtgt gtgttcatta    60600
cacagattca aagcttatgt tggagtgtat ctgtagatag attgggcttt ctcatattct    60660
tccctctacc ctccttgttt tatatcctca caacatcttt tcttttcctt ttttgtttg     60720 tttcttgttt gtacatatga atttaaaact gtgaattat ctgtctttct atatctggct     60780
tgttttgctt gacaccatga cctgtgtttc catccatttt cctgaaaatg ataatactta    60840
aatttttatg gctgaattaa actccattgt ggatttattc tatgcttta tcaatttacc     60900 tattgaaaag tactatact gcttttataa ctcggctatt ccttaatcat tttctaatt      60960 ctttctaata gacatcctat taaataaaac tgaacaaggt attgtaccaa tgaactcaga    61020
acacatttac tggctttaca tagaacatta caacttttcc tttggaagga aaatagatgc    61080
tgccctcgag tagggtgcac actatgttca tatcaattaa cattggtgaa aacattacaa    61140
ttcaattggt ccatcagtaa gtcagagttg tctatagaac acatgtttat aaccctatat    61200
cccgctctga tagaaataac cggttagctt cttaaggttg atatagtaaa gttgccacaa    61260
ttaggtggct taaaaaaaca gaaacttatt ttctccaggt tccagagtcg aacaacttag    61320
aatctaggtt tatttggtac tgtgctccaa ttgaaaccct agatagaacc cattcttgtt    61380
tctcctgaac ttttcatgag aaccaactgc cttgtcattt ctcagctgaa agctgcatcc    61440
tccaatcttc atcttcatat gtgatctctc ctgtgtctat gacttataag cacaccatga    61500
gattaagggc acaccctatt tcaggatgac ttcatctcta ctcattacac ttttccaaa     61560 caaggctgtg ttctgaacat agaagggctt caccatctct ttttggaaga agcaactcaa    61620
accacgaggc catccaaaca aatgacactg tgagatggat tccatttgaa tcttttatca    61680
tagctatagt tcctaatttt acaaaaatga agggctaaag tttacttcct gccatgcctg    61740
ggaaataata ttcagacaac atgttccagg acaatgtcta ggatctttag aaacacatac    61800
tctgtgctat atggctgttc tacagaagcc acctgagagt cacaaatagag acatcggatg   61860 taagcttctt ctgaaaagaa ttaatgatgc ttctatagct tgcccttgtt ataccacgcc    61920
cactcctacc taaagtccctt ccactccatc tgaatcactg aaagctttaa atctaactgt   61980
gttgatgctg cagcaggaaa gccacaaacc aaatcaggac aaaccaacaa cccaatcaga    62040
```

```
agtattttat acaattatta tgttggaggt tgtggtcttt tcttacttga gtttttctgc    62100
aatgagggag aaatagtgag gacctttgt atctctaggt aaatattaaa tctgccagaa    62160
gagccagtta cccaacaggt agtcagctca caggtcagtg ctcattggaa gatgttcaga    62220
gccagaaacc aatcccagca gggatcctat gcaaatctag caagaccttg gctttcatct    62280
tctatttcct gaaacaagca cccaagtgtt aactggcttg tgaaatacct tgggtaagtc    62340
tcttgtgtgt ttaagattct ggctgattta catctgccaa aaaggggtat ttgttatttc    62400
ttgatgaggc ccaggccctc tgcactaaca tgtatgtttt cgattttcat tcccaacctg    62460
atgcttgaca ctctacatgc tttctagggt gaatgaaaga aactgagaat caggtttctc    62520
tgtcattagc acagaatcag ctaagaaaga actaggataa agatggaaga aggggaaatg    62580
aatatcataa gactaaggaa aaacctttaa tatgaattac aatgattaag gattagcatt    62640
agaaagtatg tgggtttgac aaagctactg gaatcttttt agactttaga gctctcacct    62700
ttcttgaagt cacttgagtt tgccatcttg agatcttgac tattatgtaa aacctctaac    62760
tgtgttaggt caaacaagag tgtaagaggt gtgagaaggt tgcatgattg cttgtgactc    62820
ttttgttgcc agctaatgta tgagtgtgga accagagcag agaatagaat gaatggaaca    62880
atcaccatat ttgctgaata aatgtctttg tccattttt gttgccattc ctgtacttta    62940
tgaagcaaat tagttcactt cctacaagtc tggacatggg aagtccaaag ctgaaaggca    63000
gcatatggtg agaactatcc cactagtaaa gatgccctga gaaccccaa gccccaagtc    63060 agcacaggac agcatatgtc agaacaacca cgctgacttg tgtgtctctt cctcagatta    63120
cgaatccact actcattatg cagacatccc tctcatacct catcgactct taattattcc    63180
caaaggtcca agctccaatc aacactaaca ggtggtttgt gggttatgag aggacaaaca    63240
cgggaagaac ctagtgaggc atttcaaccc caaggatgaa gttggccatc accctggttt    63300
cttcaataaa ctgagcaaat gagtaacagt aagaaaggaa tagtaccctg atgcctaaag    63360
tctcaacacc agcatctaga aaggagtgca cacgacccca ccccttatct tccttgccag    63420
tttctgcttt ttattcagta accattgacc ctgccaccat tcatcaccag aagtcacaga    63480
gttgcaaggt tatgtcctca gtcaactcag ctttgatttg tccccttggg tcctcactta    63540
gtaaagaaaa gagaacaagg caatactggt aataaccaaa actgaggcag atatggtttg    63600
gcttgagagg tggacttgat aagaggagaa ccatttatca cttggatgcc aacttctcat    63660
ttgtcaaatg tttgatgggt ttagtcatga agtctccagg ccaggaggac tacatgttaa    63720
atagcttctt acttattgtc atctattcaa aacaggtcgg ctaagcatgg acaatgggtg    63780
ttacgatatc ttcaagtaag ctgtagactg acaggctagt tcatttttta ctatctattg    63840
ttataaattc atggattttt gggggacat tctcattgtg cccatcaaat gccttgatcc    63900
cactcatgct catgctactc tgctacccac cgcagcctct tttcttggtc tgtattgtct    63960
tccctaatgc agccttttag aaaataccttt cattgtgata aagtgtacat gcttaaagct    64020
catgtttaaa atgtatactt cagtgggttt tatgtagata cagagttata aaactgtcat    64080
aacaatctaa ttttagcaca tatcaccaag ttaaaatgtg tatgttagca ggcatagctc    64140
atccccctac tctctccact cccgttagca tacaatactc agtctgtggc aatctctaag    64200
tcactttgct ttgctattgc aattttttca taagttccta ccactgccta gatcataaaa    64260
tatttcccct atattttttct acagtaaatt gaacattgaa gttacatatt aaagtcttga    64320
tccattttga attgattttt ttttttttttc gagacagggt ttctctctgt agccctggct    64380
gtcctggaac tcactctgta gaccaggctg gccttgaaat ccgcctgcct ctgcctccca    64440
```

```
agtgctggga ttaaaggcat gcgccaccac tgccctgttt tgaattgatt ttttgcaaaa   64500
tgggagatac agatttaatt tcattcttca caatgtaaat accagttttg ccagcacaat   64560
ttattaggaa ggctgtcttt ttattgccag ctttgtcaaa gattagatga ctggagctgt   64620
gtgggttgat ctcaggtcct taatttcact ggtctatagg cttgttcagt actttgctat   64680
gatatcaata gcaaaagtaa attctattag tgtttatgaa gagtgagtgt ttatgaagag   64740
tgagtgtttg caatattcct taatggtaac agcatgaata agattccgat gtctatatct   64800
gtggttttca actatcttaa tcgacggcac ttaaatgatc ctttgcttcc cattgtaata   64860
aaacatatct aaaatgtaca gatgagtttg gttttgttta tgtgggatcc aactcctgac   64920
tttgtgtgct cagctgacgt gtctgtaacg gaatgttctg ccagtctcca gtgctgtcta   64980
ccaggaccag ctagccacct aatgctgtct gtaattttaa cttcatcttc tcacaggctg   65040
agtataaatg aggagacaca gtaggagata tacggagcaa agaggctttt aaaggtctta   65100
ggattcttcc agaatcacta ttcaggatgg tcttccttaa gaatggcaaa accctgcatg   65160
tttatcattt gtatgtggac agttcaaagt tcaggaggcc tcttgtggat gtttcttgtc   65220
ttcggagtat taaataatac ttaactgtct tctgttctca tcatcgaatg aatatgactt   65280
tgttcttatt tcctaggact atgctgtcag tgattatgaa taagatcatt aatgtgtatt   65340
cgttacttca gtttcttgtg tattgtgtac caaaaagaaa gaacaacaac ccaaaaagtt   65400
ggttagaatt agagactact gccttgtcat aaagatgtac atgctatatt tatacaactt   65460
tcagatggag cccctctgtt ggcccatgct gactacatat aacacatcag gttcgtcagc   65520
atcttattcc tgggatacaa ctacaacaac atgctcaaag aaaaagaaac cttggttttt   65580
ttgttttttg ggtttctttc tttttttcat aaaagtgatt gagtgagttg tatcattaag   65640
caatgatgtc actagaactc ataaggggaa atcagaaagg cgaacctgga aacgtctcga   65700
agtaaaaacc aggaaccccc agcacagtga gtgcacggac tcattgctgt cagctgagga   65760
attgctcttg tgtccctgct actggagctc tgacttggtg atgtaagatg gccatccccc   65820
tcaccactca tccatcagca gcactttttaa atttaccttg gaaacaaaag agcaaactga   65880
agtacagtgc gtgtcatatg atgagttcaa ctacctcttc gaaaggcaac atcagagagt   65940
gagatcaaca actagactaa gaaggagaag tcactgttgt tgacacaagc tattaattta   66000
ctgctctgaa atgatcgtta actgttttgc tccaagagag agaaatctgt tcaagggaca   66060
gagagaaata ttgtttagat ggtccctaat gagacagaag tagtagggaa atagaaatgg   66120
atttccccac tagcactgct ccctaaacag gctcccttat taaccagcat aaaggatgga   66180
aacattttgg ctacataacc ctacataatc ctaacccttg gatactaaga cgagaaagta   66240
tttactctct gatacttcca ggtaaagagg ggatgttctc agttcagatc accagaacca   66300
taacggttct cttagttaat tagaagagta tgttctctcc tggtgtacgg catttagtga   66360
cttccaactt ttaaaaatgt aacttttttat aaacctcctc gcgaggattt aaagaacagg   66420
acacaggtga catttaagaa tgattttaat actgcaatca atgaggaatt aattttcttc   66480
gaggtgagag tttcctgcgt ctggaaacgg aatctagtcc ttcacaccca ctaagcttgc   66540
actggagcac agacctgtag tctcagcctc acatatttaa aaaaaaaaaa aaacaattcc   66600 ggatttatg tggaggtcct tgatccactt ggacttaagc tttgtacaaa gaaataagaa    66660
tggattgatt tgcattcttc tacatgctaa ccaccagttg aaaatgctat ctttttttcc   66720
actggatagt tttagcttct ttgtcaaaga tcacgtgacc aaagtgtgtg ggttcatttt   66780
```

```
ggggtcttca attctattcc attgatctac ctgcctatct ctgcaccagt accatgcagt    66840
ttttatcact attgctctgt aatacagctt aaggtcaggg atggtgattc cccagaagtt    66900
tttttattgt tgagaatagt ttttgctatc ctgggttttt tgttattcca attaatttgc    66960
aaattgctct gtctaactct atgaagaatt gagttagaat tttaatgtgt gagtctcagc    67020
ctcacaaatt tttaaaaaa caattcctag agttttctag aatatatata tatatattta    67080
tcacttagat gctaggtttt tttctttttt tttctttttt ttattagata tttatttcat    67140
ttacatttcc aatgctatcc caaaagtccc ccacccgctc ccccacccac ccacttccac    67200
ttcttggccc tggcaagtct gttttgttct ttctggtttt tctgctctct tcatattagt    67260
agcatggccc tggtttgcga atgctccaca cttgacctga aagtggact tacactggtc    67320
tcttagctaa aataaacaga aagccattcc gttcgggtcc actgctggtg gtcacctcat    67380
taccatgccc aaaccatggc cactccagtt aagatgatca ctggccaact tccaaagaac    67440
cacatttgtg ctgcagttat tcattggact ggaacaacct cctccccgcc ccaccccac    67500
ccccacctct ctctctctct ctctctctct acctctctct ctctctctct gattttaaat    67560
tgtttgtata gctactttct tgcttacaaa atccaactct gaattgtaat attccatgtt    67620
ggtcaatcaa ggctccctgt tttgtttgtt tgtttgtttg ttttatatca tcagtagtac    67680
tctctattta ttttatatca ttctcaaaaa tatttaaagt aactcgcttc caatatgtct    67740
gtaataacca ataccagaac tgtaaatagg ttatgacaat aagaaaacat ataacccttt    67800
tggtatttcc ctgttacaga gcacatacat ccctccatta gagtcactac cctttgagaa    67860
taccaacctt tctagatgct cctggtaaag ctagcatgtg ggaaacattg ctcaaaaatg    67920
ccagggtacc tctgataaaa cacaggctgg taagactttc ttgagtagca gtgtgatagt    67980
ctacctgtgt tctcaacttt ggtttccaaa gaaattccca tcataatcta gtgaaactcc    68040
tagcagtgga gggtatggag cctgaagttg cctcttcctc tagccaggta gaactcccag    68100
tgaagggatt aggataaccc acccacaaaa ccttgggccc aaaatttatc ctgcctataa    68160
gaagtgcagg gacaaagatg gagcagagac tgagggaatt ctcaaccaac gactggctgg    68220
cttgaaatcc attccgtggg caaaaaccaa tccctgatac tactaatggt cagaacctgt    68280
tatgcttgca gacaggaacc tagcatggct gtcctctgaa aggctccacc tagtgctgac    68340
tgaaacggat gcagagaccc agagccaaaa gttagaactg aggaatctta tggaagagtt    68400
gggggagaaa ctaagggcct cgaagggaat aggaactcca caggaagaca acagagtcaa    68460
ctaacctgga ccctcagggg ctcccagaga attaatcacc aaccaatgag caagcttggg    68520
ttgcacctag gtcccctgaa catccttagc aggtgtgcag cttggtcttc atgagagtct    68580
tccatcaact aaaacagggg ctgtcttgt ctctgttgcc tatctgttga tcctgtttcc    68640
ctagctggct gccttgtatg gcctcattgg aggagagaat gtgccttgtc ctgaaatggt    68700
ttgatgtgtc agtgggcct cactgttctc agaggagaag gggacagagg aaggagggga    68760
ggagctgtgt gaggaaggtc agggagaaag ggctgggatc agaatgtaaa gggaataaat    68820
aaataaatta gtggaaaaat gtttatcaag aatagtgtac acagccacaa ttaaaaaaaa    68880
aaagagccat gaatttaaaa aagcaatggg gttatgtgat agggattgaa ggaaggaaaa    68940
gggaggaaga aatgtaatca tagtataatt ataaaatgct ctaaaattta tttaaatgta    69000
aaaaaaacag tagggaaat caaaagtgtc aaaagcagaa ggagagatgg gcatgttgtc    69060
atgaatccat acaagaata ggagacatat gaattcaaga atttaggttg gatgtgagta    69120
gttggaaaga accatgaatt ttccccagca gattattgca aaaatatcca aacattggag    69180
```

```
caaaagttct aagtgcagat taaattgtaa gtttctccaa tattctagaa ccagagtatt   69240
ccaaatactg ccttcttatg agttctgttt atccaaccca agtaagatcc gtgcatcttt   69300
gcaaagttct tgtcacatct atagtgacaa tgagcatact tttatcagaa tggcccttat   69360
cttcctgggt tgccataatg attagaaagt tattctgctc agttaaaaat ttattctagt   69420
tctggccagt aacagaaaag tagaaagtcc agcaagatgt tcattaaag tttactcaac    69480 ccaagttggc tgccacataa tttccactgg tttgagaaga cagtaatttg ggtggatcct   69540
tgaaagctca aattttggat aattaattct cagggtgtct gtgttggaaa gcaaagggta   69600
gagtctaaca agaagcaact aggtcatcac tcatgaaagc tttcttagaa aagcaagttc   69660
tgcctgcatt attgtccact ctctggtgtg agccctctcc tctttcttgt tttctctgat   69720
atgcagtaag ttgaacttcc tctttctacc tttgggtgat aaagccatag ggctctcacc   69780
agctgtgaga aagagtattt tatccttgga cttcccagtc tctagaacta taaaatataa   69840
ggcagggggt ccactctgtt ctctcaggcc tttgaatata ttttcttggt ggccatggcc   69900
attttgaatg aactcaggac aacacataga gttcttgaga agaacatgtt gtcttcctac   69960
ctttggctcc cccttgtctt ctatgttttc ttcatctttt cctttcctc tgacaagttg    70020 catctagctc tcataattct ttaatataac attttaattt taaaaactgt ttggaagaac   70080
tcatacatta gtcctgtatt tacatctcct ttctctccct caatccttcc tccatctgag   70140
gtccattacc tcttcttcta taattatagt tacacaaaat tgtgtttgta tacaacctcc   70200
tgagttcgtt tagtgtttct tttatgtaca tatgtttagg tcttggtagt tgggattgga   70260
taacctatta cagaacacct tgctggggaa gtctgacttt ccctacacag ccattgactg   70320
tgtatagttc ttcatctaga gatggagcct tgtgaaattt ttcctaccca cattggcatg   70380
tagactgacc ttgtcattat ctagaccta tttagatagc cacactgttg atgtttcatg     70440
agagcagcat ccctggcatg tctagaagat actatctagc agcaggtatt ttggtcttct   70500
ggctcataca atcattccat ctcatctgca ataatcaaac ctcaggtcta aagattgtat   70560
tgtagatgtg ccagttgggg ctgaacacct cacagtcact catcactgaa ttttgaccaa   70620
ctgtggatcc ctgtaatagc ctcttggatg gcatctttga tgagggttga gagctagcta   70680
cacttgtctg tgagtataaa acaacacaaa ccattgtcat gacccttggt tgccttgatt   70740
gcctccaaga acttgaaggt aagaccctac ttcttaagtc caaacatact tcagatgagg   70800
atatggtggc atcaagctgg gactgacctg aatgccccat ttctgaggac aaactctcat   70860
agtactagaa gtaatatgca aattgctaag gaagaaaaga aataaatatt ccttcccagc   70920
tagaaggcct ataaaccaca gcaatgacca gcctgccaag ggacctacag tggggtaata   70980
gtgaaactat tatcttggag tcatcaacag ccatctaatt agacttaaag tccacttact   71040
agaaggaaac tcatacctga tactggaagc ctaatgaaca catggctaga cctcataaga   71100
gaacctacta tgattttttt tctaaatcaa taaattatat aattattttc taagtgaata   71160
attactttat tagttcttta agaatatcaa acatgcacac catatatcat gtcattcctc   71220
cctcttcccc ttaacactgt ggttctcaac ctgagggtca aatgactctt tcaaaggggt   71280
cacctaagac cactggaaaa tgtgactatt tactgtatga accataacag aagcaaaatt   71340
acaattgtta agtaacaaca gaaataactt tatgattggg ggtcacaaca acaggaggaa   71400
ttgttttaag gttcacagca ttaggaaggt tgagacccac tgtcttaacc ctcacagttc   71460
tactcatcca ctccccatcc actttcaact tcaagttcac cttttacttt tataacccaa   71520
```

```
ctaatgcaat ttctgccgcc catgtactca aggggagaga ccatacactg aagcatgctc   71580
cacctatcaa aggccacacc tttaataaaa accggctgtc cttgacccccg cagccagaaa   71640 ctatgaatag ctcttcaggc tgtgatggga gttcatgaac cctgctcttt gctggaatgc   71700
tgaccagctg gatcttaaag cacatctctg agctgctggg agctcaggag tggggtggtc   71760
atgtcttctc cagaaggcac tgttttctc tggtcttcct tgacctctgg cccttacaat   71820
ccttctttgc tggttcctgg aactgggaga agcatatagc tgctgctttt aaaactctaa   71880
aaggcaagaa aattcagtta aaacaatgg agaactttgg ttgaagccag gataggttta   71940
tttctgcctc tacagaatca taaaacatca tacacctgac aggagtggga atgtgtaatt   72000
gaagacggcg agtaactatt tatcataagc taaaatttaa tataaagcta ctcaatgctt   72060
taatatccca tcctaaaggg ctaagcacta tgtagtgcta gatccttgag tagagaacaa   72120
taaacagaga agacagttga cgtacatgag aatcctcaga tattacccaa atacgtttca   72180
gataatcaat aactgttggc tgagtgaata tgtacatgaa caaatgagca acctactaga   72240
gctcattttc catgatgact ttttacagtt tttctccaat atgttacgta cattttaatc   72300
attttttaaa attaactctc tattaagaag cttggtactt atgaagatta gacaaaatcg   72360
tgtgttcaag tgctcatgct cagaaatagc gtctggcagt caacaaatgt taactagtga   72420
ttttcttctt ttttctagtt attctttaaa aataggatta tgctgatgcc ctcaggctca   72480
ctaatctcaa agtcatttcc ctaatccact aatgaaaaga gatctggagt tgcaatcagt   72540
tcctactctg tgcctttaac taggccaccc acaccaaccc cttggtgctg gcaccaataa   72600
aatatatgca aaatcctaaa tattttttca cttcttcctc tgtactgttt agttagcccc   72660
aaactttggg ccaaatctac catgtccagt cagcacttgt ctactccctg ttggacctga   72720
tgtctgaact gaatttacct catttgattc tgttcttct ccttctctct taatcagccc   72780
agtgaaggtt ttgtaatttc cttttggttc caacaaggct cactccatta acccaagttt   72840
tgggatttgc ctctgccaca tatggatcaa aatttccaaa ctgcagttgg catgagtgtt   72900
gaaacttatc cctcaaaact aggagatagg tctgatgttc tttgtgtttc tgtatttcag   72960
gaacagaagg ggggaaaaag aatttcacca agctcagatt tccttctttt atttctctgt   73020
tagtgctcta tgtgactggc tgccccactg aatctgttgg ctctgcctca gtctgtggtt   73080
ctcagaccca gctactcacc aagattatgc cacaaatgat ttcttggatg catgtatgtg   73140 ttcttcctt aagggcttgt gttttcaggt tgctatgagt gactagacct gttgccagaa   73200
tgcatgaatc ctctctgatt ttctgagtat atccgaaaat ttattgagct aatatcaata   73260
gataaggcac agctttggta aattcatcag ttacaatgac accagcagct ctggatagac   73320
aagaaatact tgctgtcttt ttcacctctg actagtggga gcttgccatg cagaatctcg   73380
tctgttagtt acataaagac caaaactgtg agctctgtgc tcctgaaaag ataaaattct   73440
ggacttgctt gcttcatgac acactatgca gaccgtgtct ccttttatat tgagaggcaa   73500
aatattgaac ataggactcc atgtggaacc taataaaggc actaacaaaa ttacactttc   73560
cactctgtgt tttatgccat actcctaaca ttgtggccaa actggtcttc aacgctttta   73620
ctcaatttac tcaagtgtgt gggtgggggt gggggggtc attgtttcct gaatggttga   73680
attttaaaaa caaatttact caatgtattt tatcatattt ctccctcccc attcctccca   73740
ataaccctct ttcctaacca acctacttca ctttttctt gcttaaaaaa aaaaaaaaa   73800 aggtacattt tgtgtggtcc acctcttcct gagcatgggg ccttccctgg actgtggtcg   73860
atatgcccag tgtcattgca ttcatcgaaa agaagtgatg tttcctttcc ctcaatgact   73920
```

```
gtcatttgca aatattgttt tcgtgtgggt ggtacactgt acccatttt ctttccccat    73980
acactgattt tgtcctgttc gaacttgagg tcttgtgcgt gctagcacca tctctgtgaa    74040
tagccatgag catcagtcct gttatgtctg agaaacgctg tttccttgaa gtcgcccacc    74100
acctctggct tttaaattct gcctctacat caattcctga gccttgagga gagaggtgtt    74160
atgcagagat tccatttagg actgagtgct ttaatatttc tcactttctg caggttgtcc    74220
acttgcgggt ctctgagtta attgccatct actgaaagaa gttctctgat gagagttctg    74280
taatacagtg agctgtggat ataacagtca tttattttgt tagaggagtt attctgttgc    74340
tatgttcatt taggctttcc cctaggccca tcatctagtc acagcttttg aacctcatta    74400
acagtgctga catgtgttcc atctcataga gtaacccaga aaccttacca aacgagtagt    74460
tggttacgcc aatagcacct atgctactat tgcatcactg agtgtatctt gaagacagat    74520
tgctactaca gctctcaggg aacatagctg gatgagactt aaaactgctt ttcttctcca    74580
gtagcttgta ttatatcatc acccagcacg atgaatgcta gtcgtaatag gtcaaacttc    74640
tagttgagta ccaggttggt ttctccatgt tcaataccat aagtgtgtgg tgtcttcagt    74700
aataatctct tagcatcata ttgtggtagg tactcaatat cattggcaat actttgtaat    74760
atttaagggt ggtctgtgga actgtttttg ccaatgactc aaaagatat aaccactccc    74820
aggtataggt tttatggtaa catatgatgt ccagttgaga cattgtctcc cccatcctat    74880
gataactcca tttaaattcc atttatatac gcatatattt taggaagcat ctacaggaat    74940
aggcttctgt atggcttttc aaaagacctt tagggtaagt tgtcccttcc catggtccct    75000
tctctactct gtccacctat caccctctcc atttaatcct cctattctaa tttcccttt    75060
attgtgtggt aacaatatag ttatttccca ttcatggtcc ctagaagatc acctcctcct    75120
tcatcctagc tctctacttt ctgttttaacc ttggttattc tgatattgaa acacatatat    75180
ctaaaagcta acactggcat atgagggaaa acattcaata tttgtctttc tgagtctcag    75240
ttccatcact ctgggtgatt gtttctaggg ccatccattt gcctgcagat ttaataattt    75300
catttttctt gaaagccaga taaaatttta ttgtataaat gtacctcatt tacattatcc    75360
aatttaccag acgtagact tcaaggcctt ttccaatttc tggccattat gaatagaaca    75420
gctatgagca gggggcccctt ttgtatatga acaagagttt tatagatgga tcttgagata    75480
gatcaatttt tggcttttga aggaacttcc gtactgactt ccatggtggc tatataaatt    75540
tgcactcctt ccacaatgaa taagtgttct tctttctcca catccttgcc agcatctgct    75600
gccgtttgtt ttatttatct tgcccatctt gactggaata agatgaattc tcaaagtagt    75660
ttttatctgc atttctctag tgattaaata tattggaaaa tcttgtttct cactcagttg    75720
tgtattatct tttgagaact ctacttctgt atcccatgtt ttaattggga tatttgcttt    75780
attaatgttg agggtttttt ttttttact tctttgtata ttgtagatac ttatcctctg    75840
taagatagat aattagtaaa gatttttttcc tattctgtag ctgatgcttt actcaaataa    75900
tgttgtctag catgtagaaa cttttttaact tcatgaggtt ccacctatta actgttggtt    75960
ttaaaccttg tgctatccag atccagggcc agaaagtctt ttcctgtgtc aatgagttca    76020
agcctattcc ttaagttctc ttctgtcatt ttcactgtat tttgtcttat gttgacgcct    76080
ttggtccatt tggagctgag ttttgtgcag agcaatagat atagatatag gtctgttttt    76140
ttttcttcag catgtagttt gtatgcagtt tgactagatg ctgtcttttt ccagtgtgtg    76200
tttttaggct tctttgtaaa aaaaaaaaaa taagaagaaa gagggaaaag aaaaagaaaa    76260
```

```
gcttttcatg gtgtgtatat ttattcgtgc attttcaatg tctctgattt tatgccaatg    76320
ctatgctatt tttattgctg tagttctgta attaatatga aatctagaga acctacaaaa    76380
aatgaacata tatgtgcatg acataccaaa cttaaatcaa gattaataaa acaacttaaa    76440
cagactcata acccttagtg aaatgcaaga gtaattaaaa atctcccacg taaatgaact    76500
ccaatgccaa atggattcag tgtagaattc taccagacct tcaatgaaga actaacacca    76560
atactcctca aattattcca tgaaacagaa actgagggaa atttctcaat gctgtttcta    76620
tcaggatcat acagtcacag ataagcttgt cttttaagag agagcaatga atgagactat    76680
gcagtgttat tgtgggcagg gctgagaaat aagaaatctg tcacaactca tcaacgtgaa    76740
aaagaaatga acaagaatga atttctctgg ggctcagtga aaggctgaac catggaggaa    76800
taatatggct ggagagacag accaccacta aaactaagtc acaggaaagg tagttgtgga    76860
aggaaagagg gcccttgcat gcccatttcc cattctctac ctcatgcccc atgcctctac    76920
ctctgcctcc atctccagaa ggttgattct tccagaagtc actcttctga aaggcaagag    76980
agcctagcag tcagaaccat caaacccaga acagaaaaag aataagcatg gaatcaagga    77040
ttgaccggga ttaagtggca tgccagtcat ctgatacata ttgaatgaat aatagaggtg    77100
caaatgatga gagcccaaga cccagcatgc agtaaaggct ttagcggctg ctgaaactac    77160
aattcccttg ctgtctctgt gctccgagtc tctcgtcagt actgtgtggt atttcagact    77220
gtccacttca gtgcagcctc tgacctgtgt cttgttgcct ctgtgacttt ctccacccctc   77280
agctaatacc tcttcatttc caacaagaat agagagtgtt gatgggaaca gggaggagca    77340
tgggttgttc cgaacagagt taggacatta tcaaagagag ctcaaataat ttccagaacc    77400
taaaacacat tctagaatat ttaagagatt cttttttcttt atcttttttc ttttttaaag   77460
aaaatttggt gccactgcac cctatggaga aaatttggtg acttacttct aggaagcttg    77520
ccccagacat ctgtgtcata agctgtgagt tcaccagacg cctcgttacc aaacgtcttg    77580
tggatgaaca tcttttctat tcaaatagct ttcatcctat tatgggcttt gattgaagac    77640
acaatccagc tatctagtca gagcagcaat gttgacactg cagtgactgt gcatgagtgt    77700
ttcagagtta tgaggacact ggtggccacc atgggcctcc tgctggtcac cttctcctcc    77760
ttagctgcat tagcaagaac atccagcact agcttcctca agggatcatt cctagtactc    77820
tggaatctga atgctaagaa attatttgaa agccttttttg gctggttcca ctagccagtt   77880
ggctctcaga tggaattgtg aaactaaatt ggacaatagc tatgaattta tgttcataaa    77940
taaaagacat tttaggggag gggatgtctt gcttcctttt ttgcgtgtgt atgtgatcca    78000
tgtgcatata tgtgtatatg gcccttgttt atgcatgtag aggctaaaga ttnnnnnnnn    78060
nnnnnnnnnn nntttaagta aatcctccta atctagctat atttggctgg cctaggtggc    78120
cagcttgcta cagggggtcct gtctctacag cccatgtttg ctgggatctg ggatcatagg    78180
taggccacca tggttcccca ggatgtacat gagtgctgga gatctgaaat ccagtctcac    78240
agtcacatgg caggtgcttt atccactaaa cagtcatcct agccctaaaa accaggttta    78300
taaggcagtt tatgccatat agacacctgg tttgcattca aatgttgaaa gagttccttt    78360
ctatctaaga tcagcatctc caactcttat ctactttgca tctcttaaac cctaaccaat    78420
gggaaacaag agtctggaat ttcatccaaa agcctagagt cagaaatgct agatgggata    78480
agattgaggc tgtgacacct ggtgtaagta catcccagaa gacaaaagcc ctcatccgac    78540
attttactga gtcttccact tctcactcta aaaagccttc tcctgccaaa ggatgtttga    78600
accactgatg aaggatctaa cttgagcttc acataaaagt gagtctcact cagacaagtt    78660
```

```
catatctgta ttcctcagta aatcccacct agggcctcca atatattcct tatactttaa    78720
ttccagttgg gacagctggt gaaagtgatc tatgcactat agattagata ctgaattaat    78780
attaatttca tgacacacac acatatatac atatatatat tacatatata tgtcaatggt    78840
tttgtataca cacacacaaa cacacacaca cacacacaca catatatatg atgaatgccc    78900
cattcttagg agaataaact caaataatta gggacaaaaa agaggcatcg taactatgac    78960
ttactctctg atgacctggg gaaaatgtaa ttttttgttac ataaaagata taggatggtg    79020
aataacatat taataattcg tgtgtttgtg tgcaatacgt gggatttatt tttacaactt    79080
ttttttccaa gattgacatg acttcataat gaagttgcaa aaacaagtaa gtccagcttt    79140
tctaatgctc atctatgctc tgcaacacag gaagctagaa atgctctctc ctgatttgtc    79200
ctgtttgagt taaaatgagt catcttctct ttcagctaaa gaacgcttct ctgtggaggt    79260
gagcatcgca gatgttttgc acatgaaccc tgaaggtaag gagggtttta ccgagtgccc    79320
acataattgc ctcccattgt ccctctcata cagacaaggg cagggacgtg gctatcttga    79380
ttctcaaaga gcatcatctc aaaccatcaa tactcacaca gagcagtcca ctatcctcaa    79440 aaggggggggg gggatcttca atctctgttt cagaaaacct gatgctcgtc tccttttctt    79500 gttttttctca aaagcttttc atggttgaaa tcccctagct gtgcaattag atttttattt    79560
cctctttata cttgtctgta cttgggagga ttttttttgac aatgtctggg ttacttttat    79620
aatcagaaag agaaagattg catcttcttt tattttttca accagctcaa taccaattct    79680
gctatcactt cctgagacat ctctcggcct ctttaatatt gtcactactt gggcctgatc    79740
cgtgccagcc tatatgacaa tacttatatg tggtgggctc tcagttttcc tcacctacta    79800
ataccaaggg agccctggga gccagaacct gccagcaaat aggtcatgga gaaatcaccc    79860
acacaaagat tgcctctgca tataccacag tcaaagatct aggctactta agaagatagc    79920
agattgcttt tggtctttga gacctttcct tcctgctctt caagagaaag tgaaaaactc    79980
attaagatag aaaactgact attattatta gctgaagaaa aatctaagtg aaacgttcct    80040
aagatttctt tgagccacct tgtgatggat gaatagtgat tctcctttaa gggccatctt    80100
tcactccagt gaaggctggc ctgtcccatg gatcaaagat gctcaaagat tgtcaagacc    80160
ttctgagtca aagatctttt tgtcacaaag actgctctct ggtagtatat tcagcaacat    80220
tggaatagaa taccactcca aacccagctt caacaaccaa cagtgtctag atgttgctta    80280
aggtcctggg aaggacaaaa ccacccaccc tgggtagtga cagtaatgtg ttcagacact    80340
gcctgatgtc tcctaagtga aacaaaaatc ccttctatca aaaaagcact tctctaagtt    80400
acctaagccc tgccaagacc ttctgttttt ttcatttaag tggattgaaa ttcatagtgt    80460
acagagtgga aacaggaaat gtctacaaaa agaatgccat aaacactttg ggtataagaa    80520
atctctgtgg cattaatgtc atttttctaga caatccatta acataaggac tggtgcgtca    80580
atccagcaag agttctatgc atttcttcct actttcttgg cttctaaccc ttgagttcac    80640
atggtacttg aaggatagag acagattgag agtcaaaaca ttatgctaag ttctttagta    80700
atcttttgcc atgtggatta ggaagcatag acaactggag tctgaactat gttgcaaaca    80760
caagagaaat ttgcctgcaa attacttttt tttttacttt tatgtgtact tatttattaa    80820
ccacatgttt gtgtaaaaac gttacctctg actgactttt caaatctttt aaacatcgag    80880
gcatagatcc ttaactaaaa ttcatctttt ccactccaaa cagtacacag caggtgaagt    80940
tttggtaaca gagagatgtt ccagtggttg gaacaggaga ttgaggctcc aatatcacat    81000
```

```
cccagtacac acacatagat atctactgtg cttgctcatc tctaagtacc cttggggcct    81060
ttcatccctc tggttgacct tcttccctag catctaccct agtctcatgt cctccaccct    81120
ttacccaacc tgggatgtgg tatgcaaaga ttatactcat gccagtggat atctgtgaaa    81180
acacaggcag aaacttgaag gcagttaaga caagtcaaga cacacagcaa cacagctctt    81240
cttcaacatg agaagaacat ctagaaacaa atgttnnnnn nnnnnnnnnn nnnnnnnnnn    81300
nnnnnnnnnn nnnnnnnnnn nnnnnnnnnn nnnnnnnnnn nnnnnnnnnn nnnnnnnnnn    81360
nnnnnnnnnn nnnnnnnnnn nnnnnnnnnn nnctccagct tttcaattat gatccactag    81420
ttgtaatcac ttcagagcat ggcaaagcaa agcaccgccc tacctggcac catacatcct    81480
tttacaagaa ctctggcatc gtccaggctc tgcccattcc atgtcttctg cagctcctgt    81540
ccatacactt gtgactttaa atcttgacag atctgtgaga tataaagaca cagaataatc    81600
caagagcact gtggaggagt tgtcattcac taggtgtctt ttgatgctca tctaaaggtc    81660
ttcacccatt atctttgtat acatcacatg tttctgccac catccaattc ttgccacttg    81720
ggcttctact ttgactaaaa tatggtatca ttcaaaatct gtgtgctaat cttggcatat    81780
agacatgtag ctcgctgata catttcttgc ttagtatgtg tgatactctg ggctcactct    81840
ccaacagaag acagaacaga aagacttgga gtgttgccta tgagggttaa taccttagct    81900
tatgcatcat atttgcttat gagttggact ttccttgtcca cctgggaaga ctttgaactt    81960
ggaactcaat ggagacttag ttttgttttt gttttgtttt tgttttgttt tgttttgtag    82020
tagagaagct gagtgcactg accctcattc actatgccac tagccccaaa taccaattta    82080
aatataagcc tgttgaaatt aaatattaaa aattcagttc ctcacttata ttgaatccac    82140
tcccaatgtt ctatagctgc acatgcttag tggtcatgtt attgggcagg gaatatcaag    82200
aatacttcca ttacaacata agtttctata agaacaagct gaccatccca gtgaggagct    82260
ctggaaagt gataaagctc aaacagacag gctcagcagt gagggagaga gatgacagaa    82320
caggattcta aaaagaaagt gaaaggacca gtcaacgtac ttcaactagg tcaacaatta    82380
tatcactgat acccaaccat gaacaaatgt acaactactc taccacaaaa cactaggaaa    82440
caaagaagta accatctttg agatggtctt tgagacccat tttctcccct gtctagtctt    82500
tggagtctgt gaactcattg tgaaacaaga aactttttctt ctgaatccag aggcaagaag    82560
atcctaagct gtgctcacac attgaagcca atgaactccc agtcaatcga gaaagcaaca    82620
ctctggtagc catatacaaa agcctatttta gagctaggat tattcaaacc aaagaaaaca    82680
atacaaggca aaggtaccat ctctctgggg acttttgact ctataacaag tccaaggaac    82740
acagggtttt ccaggacaat tattgtccct gtaatggagc agatagtgtg gtcatggcct    82800
cctgctgaca gcagtggctt atccttacct agcacattgt caacaaatag attacttcca    82860
caaagtcact catcttagtc tctcctcaca gagtcaccga gggaagaaga gcagatgtgg    82920
ccctctgtac tttacataca aaagagtgaa ggcacagaaa gagaatgaga caagccatag    82980
ttagcaaggt tggtgaaatt caggaccaac aatagaaaac agccacctaa cctgtctgca    83040
gttcacaact cctctctctg gagatacaag tcacttagca cctgttcagg tccctaagtc    83100
tgtcatctcc aaggctatga cctcctcata gataatgctg caaactcagc ttgtcactcc    83160
atccctgtac agagtcccca gcaagctcac tgatggtacc tcatctactc aaactgctgt    83220
aagagggggac agaagcaatt gttactaatt ctgttgctgc ccttctcaga agacccccttc    83280
tttcaagcaa aaacatacct agtaattgca gaaaaaaatc agtgtttgtc tcagtgtata    83340
cactaggtct accgtctatc ttcctggcaa aagtcaggtg gaaaatgcta ccccccaaaa    83400
```

```
tactctgtct gccttgagat actcttaatc atggcagatt ttatttctct agaaaactga    83460
gttagaatgt ttccattcat atgactttca atagcctgta accaaatatg atatattctc    83520
acacttgaat gaactcatca ttcatgatgt ctaatagtca tttgcattct tggctacatg    83580
aaagattgga ttcgatattt tcctttagca tgcaaagata tgcagagtag atatagcctt    83640
tatgtctgat aaactgtaaa cacaaaatcc accactgact aaaacagtga agaggaagta    83700
agatctaagg ctgtttagat aaaataatat tgaagatggc aacaaaaatt aaaatgctca    83760
ctttaaatgt ttcccaacta gctgacacat ccagcattgt ttggcttgga aacttgacaa    83820
agagcaaaga gtgaacgaat aaagggcaga tacacataca gaaaagccaa gttagccagg    83880
ctatgcacac tctaaaagaa cagcactgta ctggctggtt ttatgtgtca acttgacagc    83940
tggagttatc acagagaaag gagcttcagt agaggaactg cctccatgag atccaactgt    84000
aaggcatttt agtgatcaag ggggaaaggc cccttgtggg tgggaccatc tctgggcttg    84060
ttagttttgg gtagtcttgg ttctataaga gagcaggctg agcaagccag taatgaacac    84120
ccctccatgg cctctgcatc agctcctgct tcctgacctg cttgagttcc agccctgact    84180
tccttggtga caaacagcag tatggaagtg taagccgaat aaacccttc ctccccaact    84240
tgcttcttgg tcatgatatt tgtgcaggaa tagaaaccct gactaagaca ggcaccaact    84300
ccacagcacc ctggaacctc agcgtgttga ctctgtagag cacaggaggg agaatgtgcc    84360
taatctcagt aggaagtctt actagctatg caatctcagg gcaaaaactt ccaggaggag    84420
aaattgtgtt gctagttttt gcccacactg gtcagttgga ctgcttgaac acactttcaa    84480
catttgcatt tgaaccagag gaaagcttta ccatccctct aaggctccaa ctaggcgtgc    84540
aatctttgcc attcccatgc atctgaggag ttggtctttg acatggctgt aaacatgtca    84600
aacaatacat attcactcag aatttcatct gttcttgaca cactcaagac ttacgtgtgg    84660
ctcttcatac ctagcaatgc accccttgcc ttccattaca gcagaacccc agtgtttctc    84720
agtcggcatc aacctttctc ttcatctaag ccattacacg ttacagttag actactgagc    84780
tagctatgtc aagttttgct atctgcccaa ggcaaatggg ccacgctctg gagattctac    84840
ttcctcccag ggctgagtaa gtccagactc taagcttctt ctgcatcttt ttgtggcatg    84900
accccagaga ggatacttgg agcagcaagc catagcatgc ctggctaaag gtggattaaa    84960
cactgggcat gtagcacttt cctaagaaat tctgggaaaa tcagttttag gtttgattta    85020
gcaggtcatg ataacttcaa ggaaccagcg tcaggatgaa cggtagaagg ggggctcctc    85080
tccctctttc tttcagcaga gagggaattt tctgctatgc cttcatcact agaatttagt    85140
gggatggcca ttcctaaggc tgcagtctgg acaaaaaaaa aaaaaagatt acaatggccc    85200
tgattagcat agcctgttac ttcctcatcc cctggggctg gatgcctgat gcctgactgg    85260
actctgcata aaaacaaagg gagaagtagt tgttggagaa gaaacttatg gtatctgcca    85320
ggctcattgg gtggatagga ctgtgtcaaa gacaagacaa ggacgtttgt tctcaccaga    85380
gaggcaccct ccacagggaa gcagcgtcat ctcctcaaca aggtcagatc atttatgaca    85440
ataggcatga cacctacaga gcattttttt cctacacttg tcatttatgt gctttactgg    85500
agactctttg agagatggta tgtgtacact aaaggagttc tttctgacaa aatttatttt    85560
atgtcctgtt cttacatcta actatacata gctagatgaa aagatgggtg gatgaatgca    85620
tggatggatg agtgagtggg tgannnnnnn nnnnnnnnnn nnnnnnnnnn nnnnnnnnnn    85680
nnnnnnnnnn nnnnnnnnnn nnnnnnnnnn nnnnnnnnnn nnnnnnnnnn nnnnnnnnnn    85740
```

```
nnnnnnnnnn nnnnnnnnnn nnnnnnnnnn nnnnnnnnat ggatggatgg atggttgggt    85800
ggatgggtgg gtggatgggt ggatggatgg gtggatggct ggctgggtgg atggctgggt    85860
ggatggctgg gtgaatggct gggtggatgg ctgggtggat gagttgatga gtagatgggt    85920
ggttggatgg gtgtatggat gggtggatgg atggatggat gactggatgg gtggattgat    85980
gggtgtgtgg atgggtaggt ggatggatga atagttgaac atttaaatca ctaacatggg    86040
tcaatctacc tgttttctaa cctgccccac tacactcaca gctggatctt tatatattca    86100
ctcctttcca ttcccaccca acaagtctac aatgaaagta ttcactctat tccctgaact    86160
agccttgggt ctggttgtta cctctctgac tggttggtac cttttctgcc cagaaggttg    86220
cttctgaaga agaacaagat ggaaaaggga aaggggaaa gcaagtaatt atcttggtag     86280
atatagttgc ccagatgttt gaatgcagaa gtaagtctga agaacatct tgttcatgag     86340
tgataaagtg tgactcagaa aagtagagac aggttgtgct cctaagggga gcacagagag    86400
gagggttgac tttgggactg gttctgagca ttatgaggtg ggagagatgt gtaggctttc    86460
tgtgttcctg gcccagtctg tgaacctaca attactacta tcctttagac ttccagctcc    86520
tagtgctttg tattacaagt ctgttgagcc agaggaaaat ttacacagag aatctcacac    86580
caggagccct gctgaagttt cttctgaata agatggcctg gtccttctcg ggcccctga    86640
agaagatatt ttctgcaaaa ctgccattca cctacttgtc agaagctgaa tgcaaataa     86700
tgggttcctg gatgttttaa atgcactcag acacagtaat gcaattaggg aaagtaggag    86760
gaagtctcga aaacaactga gcagccagtg ggcatgagag ctgttgaaat ccttcactct    86820
agcttgagag ataggtacat gttcagctac aaaaatggtt catggaggtt ggttctcagc    86880
cactgcttta ctcattgcca gagacacaga ggtccgatac tctatggtag cctctgttca    86940
caccactgaa tgtcaggttt ccttagcga gctggttttg ttgcattaat gatggtgttc     87000
aaatctgcct cctcagttgc aatagcagtc acttttatt tcgttacatt agaaaagtag    87060
tcattaccca ctttagaata atattccctc ccagagggat tcaccatttc gtgttagca    87120
tgaatctgtt tcgtatccac tgtctgagca cccgtgcaaa gacatttgtg agacattagg    87180
atcaggcatg tctacttcct gtatctaatt attcctgcac ttcacctctg gaagtcattg    87240
aaattttaat cacattatgt caaggcttaa ataatattcc actgttgtct atgctatgat    87300
ctggttaagc agcccttag gatctggtgt ttagattgtt ttctaataat ttgggcttta    87360
taaataacac tacagaggtg gactctcttt attctaatgt tttgtgcacc taggttcact    87420
caggttaaag ttctgaagtg tattttctga ttcaatgtgt atccgtattc ttgagactta    87480
acatatgaga aaagttaaac caatgtcac tcaaaccaca aatccaaatg tatttataca     87540
ctcagtaata ccattctgaa acctccaggg ttgaaaaaaa aaaaaaaaa aaaaaaaaa     87600
gagtaaaaat aaaatatttt atatgaaat attttgaaaa ttaaattcc attaaaataa     87660
acattgtcat actatctatt tttaaatgac acaagtagaa gatgtcagct tctttgatga    87720
aatattgtgg tgttaatagc ctttttaaag tcccaaatcc ttgctaactt acctctctac    87780
attcggcaga cactcagaca ctcaacacag gttatttcct cagaaccatt tactgaatac    87840
ccatagagta tagagctttg ttttaaattt gaggattaac acacacatac acaaagaatt    87900
aatcaatgag cttctagtct agcctgaaga gctactagag tggggaattg cataaagata    87960
agtcaaaatc attatcagga ctaccctgta caacagcttt gtgagaccta agtgtctgc     88020
tggatgggag atgggacaga gaatcaggag gtatctggtc tttccattgg atgaccatga    88080
acctatcttt gctgcttcta aaaatactca tattttctag tagccagagt tctggatgga    88140
```

-continued

```
aagagagaca tcattttggg caaagactta ttttaacagt ctatatggta ggattaataa    88200
gatcccaatg ttaagtatca tctaccattg ctctagaaat caatagagct ttgtggtgaa    88260
ttaaatacaa aaggaggggc tgactataca actgtttgga accatagtag dacgcagaga    88320
ttttagggaa gtgtgaggga aaataaggag ggggggggc gcaaatattg ccactgttgg    88380
aagaacaaga caaggaattt tgccaagtat ctaacgtgtg gtggccagag aacccttcag    88440
ctttgtcaaa ctacaaaatc cttgctcttt ttaatgcttg gagtgacaag ggtctgagtg    88500
tagtttccag atgggtgcct ggtgagaacg aaggccacct actggaagct gtgacacttc    88560
aatactcacc cttcattctg ttcatgtgta agctctacca tggactcaga acagtggtgc    88620
tgaagctgga aacccttccc ttgaactgtg cagggtataa actgcccatg acctgcttct    88680
cttctcattt taatctgatg gatacccagg ttcccatgtg cttggcacat gagcctacag    88740
ttttaaagaa caagtgggga gtgtaatgcc atcttttaga ccataaaggg catgcagagg    88800
ttttttccca aacacccagg tatgtgtgag ccctgccact aaggacacc taagaaaagc    88860
atctcaggct attatagttt caaataaatt gaccattgat agaactaaga gtatcatcaa    88920
agcgaccaat ttttctccca aatcacattg gtttgataat attaaatcaa tttctgtttc    88980
taaaactcag ctgacagcct ttggactaca ctggtgcctg ccaggctatg gactgaaatc    89040
cttatgggtg attcccaagt agagtctttg tggaaaacag gaaaattgaa ctaacctttg    89100
agtattgaca tcccaaacta ttatcccttt catagtttca gagagtagtc gttataaggc    89160
atggtgctga ttagatgtta tggaaacagg cagtcatttt attcttataa agcaaagagt    89220
aacaatgatt tgctggggat tgcctggtca ttgttatggt agaaaagtgt gtagatgttt    89280
acctaggcct gttctacttc attgacctgg gaaaactact agtcaaatgg aaagtggggc    89340
cccgatttgc ttgataaata gcagtgtaat ggaggaccta agaaatacag agatacagag    89400
aagtattcct tccataactt agagccacac ttgagtttta cgacattaag catgctctgt    89460
ttttttcta attgatagtt tcttttgaca tgttttatt tactctttga atttttcata    89520
taatatattt tgatcacatt ccctctccca tatcctccca accaatctat ctatctatat    89580
atctatctat ctatctacct atctacctat ctacctatct atccatctat ccatctatct    89640
ctatctctat ctctatctct atctctctca aaataaaaaa taaaaaaaca aaaatcaaat    89700
ccagttttcc ttggccaaca actctttgac aggggacctg ttttgttgct tttaccttac    89760
accactactt aaagctcagc taagcagctc aactctctgg aacacaaatg agatccagaa    89820
agcaaaccaa atagacattt tgatgaagta catgtaatga aagccattta tctataagac    89880
aggtggaaaa ttcctttggt cctccctcac aacttattgt catcatttaa atgacttcaa    89940
ctttctaaat ttttattttc atgttagctt tccaactttg cagatcaaaa gcagcgatgg    90000
aatgaaatgg atctgtttag gcctactaga agagagttag tagcaaaaac agctattaac    90060
tattaaatta aaatttttag ggagcaaaaa caatgaagga tagaaaggtc gggagaagaa    90120
aaaaagacag ctaacaagaa aatagctagg cactgaggat ccttgtgtcc taggtatctg    90180
atttaagggt ctttggtctg tatttactct cggtatagca tcctgtgacc atgccactca    90240
ctataactga tatgttcaca aatgatatca gtgttctgat taagaagtca tagaagtaaa    90300
taatatttac atttgtatcc aattcattaa aatatttttt atctgagaac atgctttaca    90360
tagctagata catagctacc ctgtgatgtg ttttcattga aaaatacaca tttttaaaa    90420
atcatttat ttcatttgaa gattgtacac tcgaagtttt gtttgctgct gaaattccac    90480
```

```
acattccttc aattttcaat aattatattt cttatgtaat ttggctatta gccagatgcc   90540
ctggagccaa atctcattgt atgttttagt acatctgttg gcgccaaatc tcattgtatg   90600
ttttagtaca tttgttgctg agttcagttt aatgcacatg aaatggtatt ggaggaatgc   90660
acaagacctt agtcacttga agtgcatctt aataggaaga aagaattccc tgattcaagg   90720
gtacatgtta ttgctcctct ccttaccccc gtggatctga gactgtgaga aggggtgaaa   90780
atattatgtt ctttatggtt ttctataagt gagtcagtcc gagtttgtaa cttagtggta   90840
gattgctcac ttcaaaatcc tgacgctcta ggttcaaacc ctggcactac aaagaaggga   90900
gaaaatggta aagcaaccag tcattcagca agtgttactg caccggtgaa tgtgtgcaaa   90960
gtgacaacgc gaatggtata gaagctgaac aaaatgactt tgataatagt gttcacagtg   91020
acactgaatc agcacaccag acatcaaagg tttacttact cataggtact acttgattga   91080
atactgtagt tatcacccaa agtaagcagt aatagccagc catttccaga ttattcatag   91140
attagtcagg ctaagtaaaa ccaagcattt ccgatactca gtctctagct acaaagctta   91200
ctaactggat tgttacttct cagccctata aagttcagta ggttctgagt ggaattctag   91260
agcttccctt ctgttccatg atctcttggg tccacaaact actacaggcc aggagagaga   91320
aaggaatgtg cagacaagga tgtggagggg cagagtgtat ttatggaaag agctttaaag   91380
gtcaagacta gaccaaaaaa aaaaaaaaaa atgtagcctt tctccccatt ctccaatgcc   91440
acagctcaat catctgaccc catgtaacca taaaaggaac agttagaaga actttagctg   91500
tagagagaaa ggaagaatag acccaaactg tggcaggttc tggatccttt tccttctctt   91560
gtgagggact ctcaatatcc tcactgaagt ggtaaagaaa agtacaactt agaaagaaga   91620
gataattttg acatattctt ggggtgaatt tcttgttgga cttactagtt ttctcagatg   91680
taggtacagc tcatcctcag tgctctaaag atattcccat cagacacctg gctatttttcc   91740
cattgatgct caaaggaggc catgggttac tcaaggccac acagtcactg tgaaaaggga   91800
agaactggac ctccctcaca ctcctcaggc ttagagatga acctggacca gatttttctca   91860
agtctttggt ttcctttcag tgcatttttgg agtttttgga ttcaaaaact ccaaaaatct   91920
caaacaggca gccagggagt cagtaaaccg ataattaatc ttttttattt tcgttttcaa   91980
ttttccattt acttccaagc ttgtttcaag aaattaagaa acacacaaaa atagataagc   92040
ttgttaccaa cagtaatttg tgtgtgctca tgttttaaaa ggaatctaag gttctttttct   92100
gtttaattaa accgcatgca cacatacaca tacagctctg taaaacagaa tttttcttcta   92160
acaatctggc aaaacatatg tctcctccta ctacagtggc ctcttggtag tgacagcttg   92220
ccatagaaac aaactacagt gagatttctg tgacttgaaa caacattcat ttttttaaaa   92280
aaactctttt tataagaggc agcaggctga ctctggtgct gctgagatta tctgggctcc   92340
tctgggctct ggagaacttt ttgccttctt gttttgccac ccaattgagg atttattatc   92400
ttatactaaa tagctcccata acttagaaaa gaaaacctca gccacgtcct gtgactgttt   92460
ctggatggat ggatgcagcc aaagtatcac ccagtcacca ccacctttca aatggatgag   92520
tctaaagtaa ctggattgca gtgtgttccc tttccaacat aatgactcag tatgccttat   92580
aattatacat gcttccccat gactcggaat aagaaaatat ttggggacaa taatccactt   92640
agcctgtccc accaccacct gaccttcatt catcgaagtc tcaaatgtgg catttctcag   92700
agaaagcagc ctctctttct cttttttctct gtttacctct aaatggagct ctctaaattc   92760
agctccaatg tcagtcacag aattacattt ttcaaatgtc ccttcctggg ccctacatcc   92820
agagacatat gacattagga gatagtgtat acagaaaagt ctctaaagac aaggcccagg   92880
```

```
gaatgtctac tactataaaa gaagaactac tattggcctc acacagtacc cagcattaga   92940
gccacctttg ggaagttggt ttgagcatag agacccttat caaaacaagg gaaaacagcc   93000
ttggagaagt cacagtctgt ggtagcaagg tcaccttacc tgttccctgc tctcatacca   93060
ggtacatttt gtatgtctaa gatggggctc cttaaaggta ggatcagtgg tcctctgtag   93120
atatataaag tagaaagcat gcgataaata tacaaattct ggtgttcaac tcctaagatc   93180
ttcttcaccc actagctatg tgatcttggg cagttcatag aacatgtctg agctgcagca   93240
cccttatctg tgagatgaga ataataaggg agataggggtc ctagtggcct ttaattaata   93300
aagatactga ggaagccata taaagcacaa agattacaag ttcaaagctt gccttggaca   93360
cagggtaagt tggagatcaa catagtcaac ttggcaggac tatctcaaat atagttggaa   93420
agtggagtgg agttatacct agtaataaag ggctttctta gcatgtgaag ccctaggtta   93480
aaaccttact accaggggga ggaggaagag aaaaagaaga aggggaaggt aggggaagag   93540
gtatagggag agagaggagg agcagaaaaa agaagaggaa gagacagaaa aggaggaagg   93600
tagggttggg ttcagactca accccactct tgtatattat gtatacataa cctatacaca   93660
tcttcctgta cactttaaat cattccaaga ttatttatga tgcctaatat aagctaaatg   93720
atacattcag ttatcatact accctattta gagaatgaca aagagtcata tttggttaca   93780
atgcaaatgc tttccaaatg cattcagtct ggagttgatg aaactacaga tgcagaagct   93840
gtggatgtgg agcgcccaac catcttccga agctcagggg acacagtata ggaatggaaa   93900
ctctcccaca ctgggagtgt gaatcgtggt ttgaaagcca ctgcagcctg tggagctagc   93960
tgtgaaacat tctatccaaa acatgttgcc tttgcactgt tatttattga tggatgatct   94020
catgagtaac tggttcctct ggacctcagg ccaacatgga ttttctaaca tctgtccaaa   94080
ctctgccctg acagggagaa attaacattt acccaattcc tattctttcc tttaagccaa   94140
aaaaaaaaag ctgattaaaa acaaagctct gcagtaaaaa gaggcagcag ggactctaag   94200
ttgagtgagt tagtgtaata ggagatgggt gtgatgcctc cacctttggg taagcatcta   94260
catgttaaaa tcaccctagt gcagaagtga atacagcact gaactgtaat ttgctacatc   94320
tagctttgaa gatagaactc cctgggacac tactctgatg ttggaccaac ctgtgccagc   94380
tcccatttgg accgcactgt ctctgctagt taactctaca tcttacagaa tgcagctgtc   94440
tgcatacaca gcacatggcc gtacacagca cagcttcctc tcaggaacct cttcagtttt   94500
tgaaacagga agagaatggg gtatgcaaac tcagaagtga atgttttaaa gtgtctccat   94560
agctattgct agtagctttc acacaaccat gatgatctag ctaaaccact gagcagttat   94620
ccaaatggca gccaacttag gatggtgcac agggaggaca gatcttctgg aaattttaat   94680
tgaggataaa ttaccaccct gtggtgtaag catctttgcg ctagattcat tttaataaaa   94740
gaaatgcaga tccttattc ctagctggag ttattgctct gaaagccaac gtacaacaat   94800
cttaatcttc agcatggtgt gaaacagcta atcccttctg ttcttctctt cccctgggga   94860
agattatgtc ttttgttttc aaaattaaat gctagcattc tgtattggaa agaaaagtca   94920
gactcctgag aatcaagggg cacatgtgag gttcttaccc agttatttca ccctctggcc   94980
atttagtact gggggcaatt gaggtgatcc agtgagcaga ggagcccaaa ggatgtacct   95040
agcagtgcat aacacttaat agataaattt atttaatatt agtttacaaa ttatggaggc   95100
tttttttacat ttgggagaca gaaatgttag aaatggattt aggttagtgg aagaatgtat   95160
ggctggcagt acactcagtg cttatagtaa agaaccattg ttggtgagct ttatgtgtgc   95220
```

| | | | | |
|---|---|---|---|---|
| agggctttct | tatgagggtc | ttgagtgcta | ccagagggag | agtctggttt ttaccctgat 95280 |
| aagttctctg | ttctctgcca | cattgcccta | caacgttaaa | tgtacaggta gcaagcgcta 95340 |
| agtggattca | gtgagtttgg | tttggtttgg | tttggtttgg | tttggtttgg tttggtttgg 95400 |
| tttggtttgg | tttggtttgg | tttggtttgg | tttttaaaaa | agcacatgaa ttgaaaggaa 95460 |
| tagtgttagg | gagggttggt | gataaattgg | tggggaggaa | aagggggcat ctttgatcaa 95520 |
| aatgtattgt | atatgtatat | gaaattctca | aacagctttt | aaagttgtcc aaaaaccaaa 95580 |
| aacaaccta | acagtagaat | taatgtagaa | attacagtat | cacattcagc aaaatataaa 95640 |
| tgaaataaaa | caaaaataaa | ttatgtgaaa | ctacatacaa | caaccagaat gtatcataca 95700 |
| acaaggtaga | atgacagaaa | ctggatacgc | acattcatta | aatgcttatg atgcgattct 95760 |
| attacaggaa | gttgggaagt | actgttgggc | atggggtaga | gatcaggagg aggcactggt 95820 |
| tggatttctg | ggctactctt | tgtgatcttt | tgcaacttag | gtggaagcat agagctattc 95880 |
| acttgatgat | aacttattgc | aaaataccta | agatttattc | ttcttcaagt aagtcttaaa 95940 |
| ttgtctttgt | ccatcaaaga | caaggtttat | aagagctaaa | aagatcctta gacattctgc 96000 |
| cgagcttact | gggaacaatt | ctaggttaa | ggagactgag | tcaaatagag agaccacagt 96060 |
| gacaaaagaa | aaaaaaaagc | agcatggaga | agaaaactgg | aagtatctcc tagcaccaaa 96120 |
| ggatggaaac | aaatcccaca | tcatgggaga | gttaagcctt | ccttcagact tttataattg 96180 |
| ataatctcag | tggtgggtgg | gccaaagcat | gcagagaagt | ataagcagaa aggactacat 96240 |
| cagaaaagct | aacatcaggc | agtgatctgg | tgagagttca | gatctgtcct atttacctct 96300 |
| tgaaggtaat | actgtctcct | attatttggg | atgctttcca | caatgtggat gggagggaat 96360 |
| actgtaggcc | attggaccct | gcctagtttt | ccatctagga | aggagtcatt ctaggttccc 96420 |
| aaaagaatga | gccggactat | agattgcaaa | ctcagctgtt | gacctcaatg gaagagggtt 96480 |
| ggtttaatgg | aggacagcaa | taagagggg | cttctggaag | gagtgggtct aagtaggacc 96540 |
| actgttgatg | cacaaggcat | acctagggga | aaatggttag | ttttcttggc at          96592 |

<210> SEQ ID NO 2
<211> LENGTH: 1831
<212> TYPE: DNA
<213> ORGANISM: Mus Musculus

<400> SEQUENCE: 2

| | | | | |
|---|---|---|---|---|
| atgtcatctg | cacttgctta | catgctgctt | gtcctcagca | tcagcctcct gaatggacag    60 |
| tcaccacctg | gaaaacctga | aatccacaaa | tgtcgttccc | ctgacaagga aacattcacc   120 |
| tgctggtgga | atcctgggtc | agatggagga | ctccccacca | attattcatt gacatacagc   180 |
| aaagaaggag | agaaaaacac | ctatgaatgt | ccagactaca | aaaccagtgg ccccaattcc   240 |
| tgtttctta | gcaagcagta | cacttccata | tggaaaatat | acatcatcac agtaaatgcc   300 |
| acgaacgaaa | tggaagcag | tacctcggat | ccacttatg | tggatgtgac ttacattgtt   360 |
| gaaccagagc | ctcctcggaa | cctgactta | gaagtgaaac | aactaaaaga caaaaaaaca   420 |
| tatctgtggg | taaatggtt | gccacctacc | ataactgatg | taaaaactgg ttggtttaca   480 |
| atggaatatg | aaattcgatt | aaagtctgaa | gaagcagatg | agtgggagat ccacttcaca   540 |
| ggtcatcaaa | cacaatttaa | ggtttttgac | ttatatccag | acaaaagta tcttgtccag   600 |
| actcgctgca | agccagacca | tggatactgg | agtagatggg | gccaggagaa atctattgaa   660 |
| ataccaaatg | acttcacctt | gaaagacaca | actgtgtgga | tcattgtggc cgttctctct   720 |
| gctgtcatct | gtttgattat | ggtctgggca | gtggctttga | agggttatag catgatgacc   780 |

```
tgcatctttc caccagttcc ggggccaaaa ataaaaggat tgatactca tctgctagag      840 aagggcaagt ctgaagaact gctgagtgcc ttggggtgcc aagactttcc ccccacttct      900
gactgtgagg acttgctggt ggagttcttg gaagtggatg acaatgagga cgagcggcta      960
atgccatccc attccaaaga gtatccgggt caaggtgtta aacccacaca cctagatcct     1020
gacagtgact ctggtcatgg aagctatgac agccattctc ttttgtctga aaagtgtgag     1080
gagccccagg cctacccccc tgcgttccac atccctgaga tcactgagaa gccagagaat     1140
cctgaggcaa atattcctcc cacccccaaat ccccaaaata caccccccaa ttgtcataca     1200
gatacatcca aatctacaac atggccttta ccacctggcc aacacacgcg cagatctcct     1260
taccacagca ttgccgatgt gtgcaagcta gctggaagtc ctggagatac actggactct     1320
ttcttggaca aagcagagga aaatgttcta agttgtctg aagatgctgg agaggaagaa      1380
gtggctgtgc aagaagggc caaaagcttc ccttctgaca aacaaacac atcttggcca      1440 ccactccagg agaaaggccc cattgtctat gctaaacccc cagattacgt ggagattcac     1500
aaagtcaaca agacggagt gctatcatta ctccccaagc agagagaaaa ccaccagaca     1560
gaaaaccctg gggttcctga aaccagtaag gagtatgcca aggtatctgg ggtcacggat     1620
aacaacatcc tggtgttagt gccagactca cgagcccaga acacagcgtt gttcgaggaa     1680
tcagccaaga aggttccacc atcgcttgaa cagaaccaat ctgagaaaga tctggccagc     1740
tttactgcaa cctcaagcaa ctgcagactc caactgggca ggctggatta cctggatcct     1800
acgtgcttca tgcactcctt tcactgagag c                                    1831

<210> SEQ ID NO 3
<211> LENGTH: 1827
<212> TYPE: DNA
<213> ORGANISM: Mus Musculus

<400> SEQUENCE: 3
atgtcatctg cacttgctta catgctgctt gtcctcagca tcagcctcct gaatggacag       60
tcaccacctg gaaaacctga atccacaaaa tgtcgttccc ctgacaagga acattcacc      120 tgctggtgga atcctgggtc agatggagga ctccccacca attattcatt gacatacagc      180
aaagaaggag agaaaacac ctatgaatgt ccagactaca aaccagtgg ccccaattcc       240 tgtttcttta gcaagcagta cacttccata tggaaaatat acatcatcac agtaaatgcc      300
acgaacgaaa tgggaagcag tacctcggat ccacttatg tggatgtgac ttacattgtt      360
gaaccagagc ctcctcggaa cctgactta gaagtgaaac aactaaaaga caaaaaaaca      420
tatctgtggg taaaatggtt gccacctacc ataactgatg taaaaactgg ttggtttaca      480
atggaatatg aaattcgatt aaagtctgaa gaagcagatg agtgggagat ccacttcaca      540
ggtcatcaaa cacaatttaa ggttttttgac ttatatccag acaaaagta tcttgtccag     600 actcgctgca agccagacca tggatactgg agtagatggg gccaggagaa atctattgaa      660
ataccaaatg acttcacctt gaaagacaca actgtgtgga tcattgtggc cgttctctct     720
gctgtcatct gtttgattat ggtctgggca gtggctttga agggttataag catgatgacc     780 tgcatctttc caccagttcc ggggccaaaa ataaaaggat tgatactca tctgctagag      840 aagggcaagt ctgaagaact gctgagtgcc ttggggtgcc aagactttcc ccccacttct      900
gactgtgagg acttgctggt ggagttcttg gaagtggatg acaatgagga cgagcggcta      960
atgccatccc attccaaaga gtatccgggt caaggtgtta aacccacaca cctagatcct     1020
```

```
gacagtgact ctggtcatgg aagctatgac agccattctc ttttgtctga aaagtgtgag    1080
gagccccagg cctaccccc tgcgttccac atccctgaga tcactgagaa gccagagaat     1140
cctgaggcaa atattcctcc cacccaaat ccccaaaata acaccccaa ttgtcataca      1200 gatacatcca aatctacaac atggccttta ccacctggcc aacacacgcg cagatctcct    1260
taccacagca ttgccgatgt gtgcaagcta gctggaagtc ctggagatac actggactct    1320
ttcttggaca aagcagagga aaatgttcta aagttgtctg aagatgctgg agaggaagaa    1380
gtggctgtgc aagaagggc caaaagcttc ccttctgaca aacaaaacac atcttggcca     1440
ccactccagg agaaaggccc cattgtctat gctaaacccc cagattacgt ggagattcac    1500
aaagtcaaca agacggagt gctatcatta ctccccaagc agagagaaaa ccaccagaca     1560
gaaaaccctg ggttcctga accagtaag gagtatgcca aggtatctgg ggtcacggat      1620
aacaacatcc tggtgttagt gccagactca cgagcccaga acacagcgtt gttcgaggaa    1680
tcagccaaga aggttccacc atcgcttgaa cagaaccaat ctgagaaaga tctggccagc    1740
tttactgcaa cctcaagcaa ctgcagactc caactgggca ggctggatta cctggatcct    1800
acgtgcttca tgcactcctt tcactga                                        1827

<210> SEQ ID NO 4
<211> LENGTH: 96599
<212> TYPE: DNA
<213> ORGANISM: Homo Sapiens

<400> SEQUENCE: 4
cttccccagg gacacatatt gaataggcct gcaatggggc cttggaattt gcattttaat    60
ggccacctca tgttattctg atgcacagct atgtttgaga attatggctc taaagcaaag    120
ctctccaaga aagaagtaca tacctaggta tacaagatga tccagtgagt tgaagtatga    180
aaataatata gtagttattt ggggtatttt ttctaagaaa gaaactaatc tttactggta    240
tttagattga caatagtgcc ttcactgagt tctcaaatta gctcaacaca agttctggaa    300
actacacaag ataatctcca gaatcaaaaa gagttcagca acacacggg ggttgccatg     360 gtacctccac tgcttgattg ccatttatgt gctacaggtt ttcatcaatg cagtttattt    420
tataaaagca agacctttag aatatgcaac ttgacaaaat agggagtgag tatgaaaatg    480
tctggtacca cacagaagtt tcttgtttaa ttcatgacga agtagtaaaa aagttgttgg    540
atttaaaaat gagttgtcca tttccttta caaaacgata attgttccca aagtgtaaat     600
ctcaaatgca tgatgctgag tgaaagaatg ctacatactg tacaattcta cttcatggc    660 agcctggaaa agggaaacta taaggataga gaacagatta atggttgcca ggggacaggg   720
tagggacagg gtttggctac gcagaagcat gagcgtattt tgagggcccg ggctgcgggg    780
cggtggggtg tgcgggagta atgaaaccat tctacatcta cattgtgatg gttatgtgac    840
tttttgcatt tgtcaaagct cctagagata tacactaatg agtatgaatt ttatagcaag    900
ttacacccta aaaacattca cttaaaaaaa agtaagtttt gctgaacaaa agaaaatttt    960
ctaccacctt tcatgcagta tattttcag ccataatagg tgtaaaacta aaactgaaa     1020 ataaactaaa cttagaacca gatctgcata tcactgtgtc tcaaagtgtt aagccaacat   1080
cttttttttt taaaaaaagc atacttaatc acattattct cattaaaatt ttgataatta   1140
ataatttcag aactaaatgg tttataccat taaaaataaa attatttatt tattatttta   1200
aataattttg acttttattt tagattcggg agtacgtgtg caggtttgtt acatggatgt   1260
attgcatgac actgaggttt ggggtatgaa tgatcacgtc atccaatgag cgcagtaccg   1320
```

-continued

```
aataggtagt tttcagtcct tgccccgctc cttcccttcc cttctagaat tcctcattgt    1380
ctattgttcc tatctttacg tccatgcata ctcaaagttt agctcccact tataatagag    1440
aacatgaggt atttggtttt ctgttcctgc attaatttgc ttaggataat ggcctccagc    1500
tgcatccatc ttactgccaa gtacatgatt tggggttttt atggctgtgt agtattccat    1560
ggtcaaattt ttgtttcatc ttatttcatt cttttaaaat ttctactttc attcatttat    1620
aatacagtag tacatatata taatttatga ctaaaaatac atatgtattt ggaaaggcat    1680
gctaaaaatg atttactgc taagatgata aacagaaaac tttggaggtc acttctctag     1740
aaaataactc ttcaaaattt aatgtacgta ggaactacct agggatcttg ttaaaatata    1800
aagtctgatg cagcaggaag tctctcacca gatcaaatgc tggcaccttg atcttggact    1860
tcccagtctc caggactgtg agaaataaat ttatgttctt tataaattaa agaaaaaata    1920
caaagtctga ttcacaaagt agggatgggg tctgagatct tgcatttcta ataagattat    1980
gattaatcta ataagttgaa atcatttgtt ttggtttaaa ctaattacca agtcaattca    2040
ttctaatacc ttccgggttc actcatagac taggcctagg gttaaaatga taattagtat    2100
gatgccagtg cacctggccc taagactata ctttgaatag caggactcag accacagtag    2160
cccgaagaca tctatgcagc tattatagag actaacaact gctgcatttg attcagcaga    2220
ctcagttttc cctctttggg tttgggagac atgaattctt atcagtcaat aggccagctc    2280
tcttagcatc ttcccatgga gcaaatgatt cccattccca tgctcataaa agctgatttt    2340
acttaggtca ctgcttatcc accagcgtgg gtttccttag aaggaaggac acattgtcta    2400
ataatagcag tgccttatat ttacacatgg tttataatta accaaatgtc aactcatatc    2460
agcctcacaa tgacctttgg aggtagaaca aagcagatgt attataaacc catttgcaag    2520
tgctacatga cagaagcaag cacagtgctt tctttcagag ttggagtgat caggcaaagc    2580
tttaagaaga aagtaccatg gagtctgaag atcaagaatg ggtaaggttt ttagatgaag    2640
ggtgggaaat aacattccaa gaagagagga tggattcaaa cacactgtag atatgtattg    2700
agctactact actctaaagc ccaatgaaat cagcaggagt aaagatgttc taactttatt    2760
ctgtgggaag tagatgccat taaaaatttt taattcaggg actaatgtaa tcaagtttac    2820
catgaaagca tttgagtttg atgtaggcaa gactggtgaa gatgagtcca gccagggggg    2880
ctattgaaga ggaagaagta aaaaatgatg aaggcacaaa ttgaggcaat aacagtggaa    2940
gggacaaaaa tatttaagga cttcattcct tttttttttt tttattatac tttaagtttt    3000
agggtacatg tgcacattgt gcaggttagt tacatatgta tacatgtgcc atgctggtgc    3060
gctgcaccca ctaactcgtc atctagcatt aagtatatct cccgatgcta tccctccccc    3120
ctcccccac cccacaacag tccccagagt gtgatattcc ccttcctgtg tccatgtgat     3180
ctcattgttc agttcccacc tatgagtgag aatatgcggt gtttggtttt tgttcttgc     3240
gatagtttac tgagaatgat gatttccaat ttcatccatg tccctacaaa ggacatgaac    3300
tcatcatttt ttatggctgc atagtattcc atggtgtata tgtgccacat tttcttaatc    3360
cagaaggact tcattcctaa ttggatgtag agtgtaacag agagaacact gacagttgaa    3420
gccataaaaa aaaataata agcttttata tctcaaggcc cataaacaag tgcatgccct    3480
ttgacctagt tgggcctcac ctggtgtttt agacaaagga aattaattcc caaaggcaac    3540
tttttttct acacttccca taagtatgtt tattacagca ttatttataa gagtaaaaat     3600
ttgggaacaa tctaaatgtt cataaatatag aatgattaca taaattattg tgcaaaaaga   3660
```

```
ttataatgat aagattacat taaaaaattg aaggatactt ttaaaaagat ataaatagat    3720
atatttcctg gatgggaaga attaatgccc taacaatatc aattttttctc aaattaatat    3780 ataaatgtaa tgtaatgcca aaaaaagatt ttgaattgaa caaattgacc ctaaaatttt    3840
atgaaaaaat aaatatagtg gacttatcaa gacaatttca aaaggaaagt gacagtgtgc    3900
tttgcactaa caggtattgt actgttttta cagttacagt aaacaaaagt ctatattttt    3960
ggcatataaa taggcatctc aaagaaacag agtagtgtcc cgaattcata taaatatata    4020
tcaaaatgta acacatgata tgtgacacta gaaatcagtg gagaaattat gaattttttct    4080 ataagggta aaattaaaaa taaaattcag gagaaaatta actgtctacc ttatgtaata    4140
gttaaagatc tattaaaaaa aaacaatttt aacagagtta attgcaaaga agcaatacaa    4200
aaaacccaaa agctgtaaca gaaaataatt gacagatttg agtacatgaa aattaaaaac    4260
ttttgtgcaa tgaaacagtc cataaacaat atcaaaggaa gcctgacagg cacaaatgtt    4320
tgctatacat tgaacaaagt gttagtatgt ttaataataa aagagatgcc aaaaattaat    4380
tttaaaaaat atggaggcca ggcacggtgg ctcacgcctg taatcccagc actttgggag    4440
gctgaggttg gtggatcatg aggtcaggag attgagacca tcctggctaa cacggtgaaa    4500
ccccgtctct actaaaaata caaaaaatta gccgggtgtg gtggcaggcg cctgtagtcc    4560
cagctactca ggaggctgag gcaggagaat agcgtgaacc tgggaggcag agcttgcagt    4620
gagccgagat tgcaccactg cactccagcc tgggcaacag tgcaagattc catctgagaa    4680
aaaaaatata tatatatacg ggccaggtgt ggtggctcac aactgtaatc ccagcacttt    4740
gggaggccga ggtgggcgaa tcaggaggtc aggagttcaa gaccagccag gccaacatgt    4800
gaaaccctgt ctctattaaa aacagaaaga aatgctggtc gtggtggtgg gcacctgtaa    4860
tcccagctgc tcaggaggct gaggcaggaa aattgcttga acctggaaag tggagattgc    4920
agtgaaccga gatcatgcca ctgcactcca gcccaggtga cagtgcaaga ctccatctca    4980
aaagaaaaac aggcataaga ttgaacagcc acaacataag agaaaaagtc aaaatataat    5040
aagcacatga actcaacctt gaaggcaatc agaacactgt gaattagaac aacaatgagc    5100
tatcatattt tgcttatcag actagcaaga taagattgat aaagtccagt gctagcaaaa    5160
atgtgagtaa acatccttgg taagagtgga cactgaaaca tttgtggata aaaattggag    5220
gtatatatga aaatttaaaa tgttcctacc ctgtggctca gtaatctcat ttctagggct    5280
ttctccaaca acatatttgg agagcaattt ggtagctatc aaaattttaa tgttcattct    5340
ctttgagcca accaagtcat ttatttttta ttttatttat ttatttattt atctatttat    5400 tttttgaga cacagtctca atctgttgcc catgctggag tgccatggca ctatctcggc    5460
tccctgcaac ctctgcctcc caggttcaag cgatcctctg gcctcagcct ccctagcagc    5520
tgggactaca ggcgtgcacc accactcctg gctaattttt gtattttag tagagagagg    5580 gtttcaccat gttgggcaag ctggtgtgga actcctgacc tcaggtgatc tgcctgcctt    5640
ggccttccaa agtgttggga ttacaggcag acgcgagcca acctgcctgc caatcaggcc    5700
attctaagta tctatcctaa agtccatgca aagacaatcc tagcagcact tcttaaaata    5760
aaaagctgga attactaaag acctaacaat ggaagaatgg tagaatatat tacaaactat    5820
gtaaccatta aaaaaaaatg gagtaaatct atacatagtt acctggaata tgtgatttca    5880
ttaagtttaa aaaagaaaag tcacagaaat tattgcattt tgaatttttta aaatatttgc    5940 atgtgcatac agagacatga ctatatacac atgtaaaaaa ggaggcaacc accaatacgt    6000
caatggtggt tacctctgag acaggattag atgaaggaag gaggatgtgt gatttggaag    6060
```

```
tactatattt tactgtatag ataaagatgt agatttcttt ttaacagtgc taggatttgg    6120
ggtagttttt taatctttgg atatttttag cagttttcta tttttttttct aaagaaagaa    6180 acatagttct cccacatatg gacatgccat tcttctgagg atgcttaagt tgaccccagg    6240
aggagcccta gctgctgttc cccattagag gcccctttc agcaggaagt agccagaaag    6300
agtccttgcc caaaacccc taacagcagt tagtgtgata tcgccacagg gaggaatgtg    6360
gcatgagtta tcaagaaatt attttaggca gatagagagt aaaaggggtc cttgggaagt    6420
tttcattttt taaagtatct ccagaaaagt ttcttgtaaa accccggctt ttagagccag    6480
gcgggcaacc tttgatatgc aaacctaggc cattagaaac tgggttcacc caaacatgcc    6540
gattccaggg accttcttgc ccttgcccca catgttcctg gcaacatggc cgcccccaca    6600
tatccctatt tgtgtagaac atcatggcgc cccgcatttg catattaaaa ggctagagtg    6660
ggagggccag ctctttcatg ggctacgtga attacgtgcc tagtcaaacc aatcccctga    6720
gccctaggca aatcaaacac cgcctcctcc agcctctgct tatatacctg gctggtatcc    6780
gcagcaagtg gggacttact cttttggctt tggagcgccc ccctccctct gtctctgtac    6840
agggaagctt cttctttctt ccttctccct ttccttcttg ccttcttg cctattaacc    6900 tctccactcc ttaaaaccaa aaaaaaaaaa aaaaaaaga aatgtggttc tcaaagaaga    6960
caaatgaagt agcaatgata aaactccttc cctatttgag aaggaggaga gagaaaagga    7020
gccacggcag aaaccaacag aggaatgcca cagacagagg ggaggctccc gccagaggat    7080
ggcagaggcc tggaagccaa ggcgtgagaa cttcaagagg aggaagtgaa ccgaagccca    7140
gtgctgcaga gaggcctgga gggccctccc agagagcagc cagtgagtgg tagtgatgaa    7200
agccaggtgc aaagaattca agggagccat ttccaccct gcctgtgcat ttttgtaaaa    7260
acagagaagt cagagcccca ttctaaacct cctgcattag aagctctgca agtgacaccc    7320
agacacagta cattttaaac actcaggtga ttccttgttca cagccaaggt tgagaaccag    7380
tgagttaagg cactgagagg gaagtaagta aggaaagctg gtgtgcgtaa gtcattcttt    7440
cactaagttt ggcaggtaaa gaaatgagtg aattaaactg taaagccatc aaaagggtca    7500
aagaagatgt agaagttgta ggttgagata agaagcctta tgggcagaa aagattaaat    7560 atgcaagaaa ggtagaggaa aggggaagga aagaaaggaa cttgatgttt ctagactttg    7620
ttagatggca cacattttac atatgccatc accattatta ttcatttgac tggattttg    7680 aggcacatgc tactgtgtcc aatttacagt gagaaaccaa gaatagcaag gacctaaccc    7740
agtgccagtg ctgggctctt cctctgcatc aggctgagaa gcaaggtctt ggaggaagta    7800
aacggatatg gagtccagga ctcaggtagg gagtcagctt gcaaaggacg aacacgtccg    7860
ctaagacaga gatgcagaaa tgaactagag gaggacatca gtaaagaagc tgtgaagctg    7920
gagcacatca gtgcatagag agaaggagat agtcaaagaa ccactgtggg gcagaaaagg    7980
aaaatatagt ggctcactgc ggatttcatc atctcaggaa agctggggca aggtaactca    8040
ctgacaatga gtaccgtgg ctttgtgaca gtgcctgtgt gctacacaac agagcagaaa    8100
gccagccctg ccccttcttac cagtgaggta tggattagcc acgcaacgac cagtctgtaa    8160
gccaggagta cagacgagcc aagctgcctg cagctgagtg ggaaccacaa ggaggaaaag    8220
ccaagtccct gccttctaag agctgacagt ctggagttac ccagagtgat cttctatttc    8280
actaactgtt aaaatagtct gattagaaca actattgtag aattgagtga ccctttgctt    8340
tgcaaaggtc atatagaaat attctgccac tgaggatctc atgtcgccca gtggttctga    8400
```

```
aaataaatag aagttgcgta ccttcatgga cacccatgaa tgaaagtaaa tatacccctaa    8460 tcatcacagg aagcatgtgc ggtctgcacg tgaaagatgc atctcccatc agctaacaga    8520
accaggtgga gtctatgttt taataaggac gtgttattga tcgggaagta ttaggttatt    8580
atgcctaggt agttgcttct gggattccag tccaaaagga tcaccaaagc atcatgggat    8640
tttcaatggc ttcctgtggc ttggcaaatg ctcactgcta actgtgattt cccagttatc    8700
cagagtagca gtcaaatcaa aggggaaagc ctcatgtttc aataacttaa aacaaaacaa    8760
aaaaaaaaac ggccaggcgc agtggctcac gcctgtaatc ccagcacttc aggaggccaa    8820
ggtgggtgga tcatgaggtc aggaaatcaa gaccatcctg gctaacaggg tgaaacctca    8880
tctctactaa aaatacaaaa aactagccgg acatggtggc acgcgcctgt agtcccacct    8940
actcgggagg ctgaagcagg acaattgctt gaatccagga ggcagaggtt ccagtgagcc    9000
gagatggggt cactgcaatc cagcctgagc gacagagcga gactctgtct caaaaaaaca    9060
aacaaaaaca aacaaaaaaa aaaactcagt aaccttggtt taaagtattt ccttggtggc    9120
cctctgggtt gtgtaacaat cggatgcatt aattattatg gcatcaaatg acaccagcaa    9180
catacatagt cagaaataac tatttgattc aggcaggtgc tattatttgt ttcagcactg    9240
ttaaatgtgg ggttttttgtt tttgcaagag aaaaggcggt tgtgtgtggt ttcaagaaga    9300
agaaaagtca gaacaacatg cagcccatta gaaaagataa attctttatt tgtggaaaac    9360
aacagaagtg gggctattta ggcaccgcca atgtttatta tattcatatg gcagagaata    9420
aacacagcac actagaagtt tgcgctttgg gtattaaaaa aaaaaaaaag caaaaccttc    9480
ttaggtcact gactatcttc ttttgctcct ttctatctga ctcctcaggc aaggtgcaat    9540
tcaaatccct ggagaacctc tcaaatatag ctgctgttca atgttactca gaaataagga    9600
aagaaatttg acacggagac actccacatc ttggctgcct ggaaaaatat catctttgag    9660
gtcattcaac tcactaagtc attttttatta ttgttttgtc tgtctatttt ctggtacagt    9720
ctcaatgaaa gatatgtggc cctaatcatg caaaaccgat ctgggggggaa tcagttgttt    9780 cttcaggtct tcgcaggatt ccagctcccc caactacctc cgtcgccttc taaaactggc    9840
aggctctgga cgttttgcat gctgaagaaa atcactgttt tgcctccagc aaggaacata    9900
aatgttgcaa cactgactcc tcctctcatg aagaaagagt gaacaagtgc accgagttga    9960
gcttcttctc acagagccac cgggctgggg accggggagc ggaggctgaa atccccagac   10020
gccggttttc tgggctgggc tttctgcctt actcactcct tctccctctt tctggatttt   10080
accgaccgtt cgcgaaacag cttttccacac aatggagctt catgtcctcg tgcaggaagt   10140
actcatcgac tgatgtggca gactttgctc cctggcaaaa gtgagtaccc atggcgagct   10200
gaggccgcct ccgacggcgc gcggcagggg ctgcgcgggc ggccgctctc cgggatgcgg   10260
gttcgaggcc cgcgtgctga aggggagagc ggggccaccg gcgcgggctc ctggagagaa   10320
cgccagccag gagccagagt cggcagccgg cggggaagcc cggatccgc ccgcctcccg   10380 cccggatgtc ccttctcaga ggggctaaaa aatactctta aggtgctttg cctccaccac   10440
tgcccccaac cccagctttt acaaactgca ctcggctcgc attcgccttt gtcaaaggca   10500
tcttcacctg tatccttgag catgagtttc ggcgttgatt gtgggattct cagaatgcaa   10560
attatttgcg tcaaaataaa aagaaaagaa aaaagagcg gggaggggga aggggcgcag   10620
acaggtgatg tgatgaaagc cggactcgag actctcccat cagcagcagc cgccgccgca   10680
gcagcctcgc gggcatccgg cggggaaagt ttagggttag caatgctgac ctgaaaggtg   10740
ttgctcctcc caaaagtcag cgggggtagg ggcagatgag cagcctccgg gccagaagcc   10800
```

```
ggagctggac ggaggcacct aggcagagga attgcagccc gggaggaagc tggaaggaga    10860
gcccgctgga gaagggagga gggaagggaa gaggagttgg ttaaagtcag gcaaactcag    10920
gtaactggag ggccggcccg agtgctacgg caggggaagg caagggctgg agttctggct    10980
ctttgagtag aaaactatcc ttttagtgac ctctacctgt atcctgggga agcaacccac    11040
actgccctga aaacaagcaa cgtagggat tctatgactg gacttgaaaa tggttgcaaa     11100
acattattat tagtctggag ggatcacttt gtcttcattt gtcaagttga ccgggcaaga    11160
tttcccacct gaaatcgtgc ttcacttgac cagggaagtg ctgctaatcc caatcctgac    11220
catcagctgt gcaaacttgg gcaagaaact taccctctct gggcttcgat tttttttctg    11280
caaagtttag ggaattaatt aattatatat atatattata gaaatatata taatatatat    11340
ataaatgttt aatgaggtgg aagtgctgaa tagtgcaaga gaggagcaga tgaaaatatt    11400
aatttcagtg gttcttaaaa attaggggtg ataggtcctt ttgagaatta gctgtgagtc    11460
ctcttcctgg gggaaaatgc atatggcatg tacataaaat tttacatgca atccctgagg    11520
gtttgtggat actccctgaa agccatgcct gaatcccagg tgacaatccc ttattcctcc    11580
tcctgtatca agaccaccca gccaactcct tgctgctggt tgggctgact gtgggagtaa    11640
tccacagcct tcttgggggt ctggagtcag ccacgctgct gaaggagaca gctcccctgt    11700
catgggtgag ctccccacat gctctctcca gagctctacc agcctctgac tccaggggac    11760
ccctcctcac aacccttttt aatgactctc ctaaggcgac agtccttacc cctagaattt    11820
tcagtcccac caaccctgga gagccatcta agaggatcg ctgtctgaat cagagtgctc     11880
ttcaggtcac ctagctggat ggcagggagg ccaaggcttt gtttggaaat gaagcagtct    11940
ttgctccctg aggcatagta tgagtaggca gccatattct tttgaacctc tgtactttgc    12000
ctttagagga ctaaggactc acatctctgg ggaccctggg tgttccacta gcagtgccag    12060
caaggcacat cagaaaacac acagggcttt ggagctcaac agactgggct tcagatcttg    12120
actcccacac tgagcaagcc tctgagtttt cctgagcttc acttttcctg tcagcacaat    12180
gaaaataatg ctgcttttt ttttttttt ttgcatggtt gttgggagaa tggaaatact       12240
atgaatcatg cctagcccat agtcaatgat aaacttttc ttaatattaa tgtggcacca     12300
taaataagtg ttcaatagtc tcatgctttt aagaacagct tactctctct ctcctatggg    12360
gcttacatta gtagaagaat gagtaaaatt agttctggtc tagttatgca caaaaggag     12420 tggtggcctc agaatacaga gtcagactgg ctgttcgaat tgtgcagtgt caaggagagc    12480
actatgtatt gccggcaagt aaagtatgtc cagaccggcg tggatacttg acctgtctct    12540
cagttctctt ttgacccata atcttgagta caaaacagct agtgctgtgc ctgcagctaa    12600
aaacagccag gcatggaaag aagtgttgtg gctgggtcca tcttcagaaa ctgtagagag    12660
aaatatctcc attgtcatct ttcacagttt ggcacagatg tagccaactc agcatgtact    12720
ctctctccat ggggtcctgg tgcctccatt gcaagtggtc agatgatgta gcaatgaaag    12780
aaggaaacat cggaaactta aaaggaaatt ggatatccac agagtagcca agatctatc     12840 agtatacttt ggtgaggtat tcctgcatgc aaagatagca atattcatgc ctactattta    12900
ctgagccttt aagatgtgct aagcactttc acacattgcc tcaattaatt ctcatagcaa    12960
gattgcagag tatgagttat catttaaagc tttaccagta aagaaactga aacatggaaa    13020
tgtacataca ccccccaacc ccacacccca catccgccta gctcaggaaa ggcagaacca    13080
ggatccaagc ccaggtctgt ctgactttgg cacccactct ttttccacta cccagtgctc    13140
```

```
ccaagctccc caatatcagg cacttgcatc agccaaccgg attaagattc ttctaaaagg    13200
caggaatagc caaatctagt gggtgctttt aagtggtgtg aacatgtgct tggcttgtga    13260
tacatattaa cgggtagcaa caacaagatc acctatggga ggataatatt cctgaccctt    13320
cccaagccca gccattagac tcaagattgg caatatccaa cattagcagg tgaggctggc    13380
gctctgtcac tgacttcctt ggtaatcctt ttagttaaac agagctctgg aatgttcatt    13440
ctctaccacc tttagaatca gaacaccact taccttacc tccctgtgct gagcacgttt    13500
tcattcattt attcgacaag catttgctga gctctgtttt gtgctgggca cttgatgaca    13560
cagtggggaa tgagacacac aggatcccag cccttgtgga gcttctatgc cagagagagt    13620
gacagaaaac agtcgggtga acaaatacat aaataaaatc atttcagata ctgataaatg    13680
ctatgaagaa aatagaggct gaaggctaca gagggacagg gcgtgggagc aactttcaac    13740
agggaagtca gagaagactg ccatacaaag gatacccttg aacttaaacc cgcattttca    13800
aaaagggagc cagccctgtg aaagtctagg gaaagggcta ccttagcaga actctcaaga    13860
gaaagttctt aaattggagt aaatgaagca gtaaagctta aagtctgaag atgggccctt    13920
tagaagttga cttgtatata gggggaatta ttatttgaat gcctactata ctattctaag    13980
ctgtgctgta tactctgttt atcttcccaa tgatctggtg agttagctat ttttgttttt    14040
attttacagt tgaagaaacc aagagtcatc aaggttaagg agctagtcca aggttatgga    14100
gctagtccaa ggttatgaag ctggtatttg aatcccttag tctatttcac tccaaagccc    14160
acaactactt gctaacacag catgtgggct ttgagataat gtcttttgga gaaagtaagg    14220
aagccgatag aaggagaata tcaaaagtaa attaagtagc tgaatgctga caacgatttg    14280
tatttgatgt cccaaattcc agttagtgca cctacaactg aactgtccaa tacagtagcc    14340
actagccaca tgtgcctatt gagcacttga aatgtggcta tttcatattg agatgtactg    14400
taaatgtaca acgcacccca gattttaag acctagtatt ccccaaaaa agtaaactgt    14460 cttggccagg tgtggtggct catgcctgta atccaagcac tttaggaggc caaggcgggt    14520
ggattgcctg agctcaggaa ttcgagacca gcctggggaa cacggtgaaa ccccgtctct    14580
attaaaaatg caaaaattag gcaggcatgg tggtgggtgc ctgcaatccc agctacttgg    14640
gaggctgagg caggaaagtc tcttgaaccc gggaggcgga ggttgcagtg agccaagatt    14700
gcgccattgc actccagcct gggtgaaaga gtgagactcc gtctcaaaca aaacaaaaa    14760 caaaagtaaa ctgtctcaat tttatattg attgtgtgtt gaaatgataa tattttaggt    14820
atactagttt aaataaaata tattaaaatt aatttaacct ttttccttta atgtggctta    14880
atagaaatgt ttaaattaca tatgtgactc acatgatatt tccgttgaac agcactgatc    14940
tagactaata agttgacaaa tacatgatag gacctttttc ccccttcttc caaacgtgac    15000
ttcttcctct gttcttgtgt caggctcctt ctcatctgcc cccatattca gttatttggt    15060
gaagcacgag agaaaagagg tccctcttcc ttctccccca ccctcatgct gctggttagc    15120
aggtgatcat ttgaagtcca ctataccatg tcactttggg atctgataaa atagactcag    15180
tgattatatt catcaccaag accaatcctc tcactcaggt aaatctcaag aggctttcaa    15240
acgtcctaca atgaaagggt cattttaaat ctggatttaa agttttacct ttaaatcact    15300
tcctagtaca ttgtctttgt agttttgggc actttgtaaa atcagacgag gagacaacta    15360
gagcttcatg tttttgtgca aagctcatta aataagtaat ctcatgcagt aataaatgtt    15420
tctccctgtc ctcttgctta aaacagcatg aacaaaaagt agtcccagtt gccagaaggg    15480
ctactccagg ggcatcacaa aagaccacct ttggtttctt tcttttgtcc actagctaaa    15540
```

```
gtggccctca aatatgtcaa tgaaataaag atatatttt tttcctgcag tttcatttat    15600
ttcaaaaaaa agagcagtca gattctggta ttgctggaga aagcctctga agagcaaaga    15660
cctggattct gcttttgtgt actctactgg tttgcatgtt accctctctc tcccttttt    15720 cccccaactt tctcccttac ttcctgtagt aagtttggtg ttgatgagat aatgccacaa    15780
aaaatgctaa tggtgaaatg tgctgtacaa attggccatg ttatgattg ataacctgaa    15840 tacaaatggc atctctagac atgtgcctgc agggaggagt tgcctttatg tagctggagc    15900
aaaacattat gtaagattct cttggaataa catttgttca tttccacttg aaatccaaat    15960
ctgggggaaa tggcagtaaa gaagctgaca agaatgaatc ttagtgtatc tgtcactggt    16020
agactgagtt ctttctctag tctgtatagg ttccagagag agaacaccca attgaaaaag    16080
gacaagctgg ttttattcac tggccagaaa tggaaaatga gagacctctt gctctaaaaa    16140
gtcaccttct ccctagctgt gggaagctgc aggattgtga tgagttagat gtggggcggg    16200
gagctatgta aacacatgca gggagaaagt acagaggcac agacacagat aaacatgttt    16260
ctccatgcgt cctatggaga gaaaatggcg gcagttttct tctagggatg gggagcccag    16320
cattgtaacg ctatgttaat gacctaaacg gaacaagggg tagccagttc tggtttgcac    16380
tggtttcctg caggcctctt gtatttggca aaggatcacc aagctcctgc gacatcccag    16440
gccatctgga gttctttaag caagagtatc tatagataaa gaaactaggg aagataacaa    16500
tttaagaaaa taatgagctt tcccagctat ttctctaggg ctgccctggt aatatttcta    16560
catcaacagc aacacatatt tttcagcatt gtgtaagcca ggaaatctat gctagactcc    16620
acggggaaaa tagaagaata aaacatggtt cttgctctgg aggagcatag ttcctagttg    16680
ggaaggtgga cagaaacata aaagaccagt agcatgtaaa gaacattttc taagtgttac    16740
ataaatgatg caaacaaagt tttgcaattc tggagggcag catgcccata acctctaagg    16800
tatattaaga aagacaaagt agaaaatggg cattgagggc tggaagccta aagacacaag    16860
gagagaagga gagagccacc tcacataaga aaaatgcac agtggtgtgg cagtggaaat    16920
gtacatgggt tcgggggtgc gtgatgtgga aagaacagt tggcttaatc cagtggctcc    16980
agatctgagc tttacatcag aatcacctga gaagctttta aaaattacaa atgcctcagc    17040
cccactccag agcttccatt taattagttt aagactgggg actggtctca gtggtgtttc    17100
tgattgattt tgttttgttt ttgtttctgt ctcaatttcc cagaatattc taatgtgaag    17160
tcagagttga gaatcactga gcaaaaacca agatttttat atcatagtca tgggacataa    17220
aatgaaagaa gtaatctttt aaaggagatt aaatggacaa ccaagagtgt gacctttaat    17280
ttgtagaaac tgtatataca tgcacatttg tatgtagtct tttaaattca cagataattc    17340
ctcgtggtga ttctgtctac ttggatgatg tggctgaaag cctttgtaac cagctgccta    17400
ctcttgtcct ctgtgtactt tggggggtgtc ctatagtgga tcctagctaa gtggggcaca    17460
atgggcatct cacaggagct tgtttctacc aggctttttg taatcattgc caagggcttt    17520
attatcatgc ctaatagtgc ccacagtagc tattttataa gcatctgcaa tcttccctca    17580
cctctccaac tttacaaatt gagaaatgga gtttaattac ttgccttggg ccaggagact    17640
agctggtgat gaaggtgaaa tgagaattct caggaggtg aaattagaat ttccagctac    17700
tgaattccac ataccttatt aaactcccaa agtgagtcta cccactctcc tgttggtgtt    17760
agaatgttat ttcttacatg aatgaatcag tgtcacagat cagtaggtga agatgactgg    17820
tttccctaag ctgccaacac tgtgattatc tgagtgtcaa tgacccatag gcagtcacag    17880
```

```
tggtcccgag agccccgtcc ctgatgcctg ggagctctca gtctagtgaa gtttggcctt   17940
gcatatttat agtttatcca ctctaacatc tgggaagtga agactctggt tgctattcca   18000
ctgctcctag ccccacactt tacggctgtt ctgatttccc ttctctgaag ctcttgttca   18060
ctgaaaggat atcagctttt tgctacaccc ctgaaaaaaa gaggagaaag cccagcattt   18120
taaacagctg cttttttttt tcttttggat ggagtcttgc tctgtctcca ggctggagtg   18180
cagtggcgcg atctcggctc accgcaacct ctgcctcccg ggttcaagct agtctcctgc   18240
ctcagcctcc cgagtagctg ggactacagg cacgcgccac caagcccggc taatttttgt   18300 attttagta gagatggggt ttcaccatgt tggccaggat ggtctcgatc tcttgacctc   18360
ctgatctgcc cgccttggcc tcccaaagtg ctgggattac aggcatgagc cattgcaccc   18420
ggccaacagc tacattttaa agaatccttt atatgtgttg ggagcttctg ggttcactgc   18480
ccacggtgag actaggggtg gggacggagg ttcttctgaa ggacagtgcg gggaaaaagc   18540
cagagtcttg gcaatacagc ctctttagac aaaaagatag gtcaatttgt accattccca   18600
aatggttggg ttttcttttc tctgtctcaa aatccattac tgatttaaaa caatttccaa   18660 aagcttagc aatagcaaaa agcaagcctc ttaaacagtg ttgctccaca ctgattgcac   18720
gtgagaatca cctagggagc tttagaaaca actatagact cactgaatca atattctggg   18780
aaggggcctg gacattcgta tttatttaca gttctccagg tttataatgt gcatccaggg   18840
ctaagagcta ctactggtca gctatgatcc aaatcttaat tacttatttg tatttcttct   18900
tttgccttgt tttagagtct catggcccag aaaaccatca aactatattt ttgttgagta   18960
gcaatttcat cattctgttc tttaaaaaac atgatttga gcataattta agtttgctac   19020
ttctatagag agacctcaca ctcagtagcc tcatcactaa aattttctgt gtgcaattta   19080
gaaatcacat tgccagaagc ttgctaatta attatgagac tgaaagataa aggttaagct   19140
ttcctgccac ctatatatta gatttcccaa ttgctatgtt aatctttagt taaccaagac   19200
ttgctttctt gtctcagcca ttttaaagcc aattaactct gttcctgttc acacccttat   19260
taaaaatata attacagcag tagtctccag ggactgtcat tgggtaggct ttaccaaggt   19320
aaattagcca agaaataact aggctgtgta acaccctctc agaccctgga aatcattttg   19380
gttgcagaag ctacttagta tcagagtagg ctggggtact cataaatttg gatttggaaa   19440
aagccaattc caagtcatcc taaatgtgga agaatctgtg attttgagaa tgattctgga   19500
atcagttatc cagggtccag ccaagtctga tacaccgatc ctcagaaggt tgtattaata   19560
acaaaaagaa accaggtttt tgtattagat ttgatggaag aggctggggg acagaaggtg   19620
atgtagcatt tgttttctg gggtgctgag attgtgggat taggagaaaa taagaaaaaa   19680
gattgcaggg gagaacgatg gacagaggcc tcctgttagt caactatcat gggcatcaga   19740
atttctttat tcactcaact aatgtttatg gaggttctgc tttgttccaa ggacccatta   19800
taggagctgg agatagaagg atgaagttcc tactctagtg tagtttagat tccagtaaga   19860
ggaaacagat atccacacta aaaacaaaca ataaataaaa cccaataaat tagtcagtac   19920
tatgaaaaaa atgcaatgaa ctgaagggaa tagagtttgc tgaaggctgc tttcaatagc   19980
ttgtacaagt tgcactgtct gaggaggtgc ccttcaagct agcacatcaa tactaaaaag   20040 aaagcatgc cgagagctgg cagaaagaag gcttcaggca gaaagaacaa cagcaaaagt   20100
cctaagactg gaaaaggtct gagttgttca ggaaacagaa aggagaccat tgtggctgga   20160
cccgaggtaa aagcaatga gggaaaggtg ggaaaagagc aaggagggcc cgaggtcatg   20220
ggatggagtt aggctgttaa gtgctttgag agcctaacat cctaactcat tgggaggttt   20280
```

```
tcagcagggt aggaacatgg ttggcattgc ctttgagagc tcttcccagc ttctgtgtgg   20340
agaatggctt gaagactgaa agcagagggt ttgtaggagg ctgatcggaa gtacaagcaa   20400
gaggggaggg tggatcatgc caaggtgaca gcaagcaagg tggaagaggt gttggattca   20460
ggatggaatt tggaggtatg gccagcatgg ctttcagatg gaggggacca gcgaaagtgc   20520
tggaaaacct agtcctgctc aagatgattg ttcctgccct acccttgttt tagaccctt    20580 gttttgaact aaaacagaat aatatctagt gctatttaaa aacattagga attttaacct   20640
taacttgttt aagcagaaca aaacaaatcc ctgcctgggg agaaacttct gtttgctgct   20700
tttgcctctt aaccataaaa atttcatcct gtctcgtaag actattctga tggcttttgt   20760 tgttttgat tactgtgctt ttcgtaagtg ctggaaaggt cacattcgca ttactagttt    20820
atctcttttc tgagtgtttt gacactttgg ctgtgtttac caaggccttc ctgctgtcag   20880
acatttacat ggggctttct acagttgatc agtttctcca tataagtgct aatataatcg   20940
caagcattta gtgggcactg actgtatgca aggccttgtt ttaagaattt catgttttaa   21000
ctcatttagt ccttccagcc acccttata ataaaaagtg tgtactctta ttatcatttt    21060
atagatgagg aaactgaggc aaaaaaagag gttaagtcat atgcccaaga tcatacagct   21120
ggtaagtagt aaagccaggt tttgaactga atccatctgt acagtctggg ttcctagta    21180 actatgttgt gccactttc tatgtaattg aagctgccac cttcagaagt agacttgttt    21240
ctcctgcaaa accccaagg taccactagg agacactaaa actgggccgg gcttccggga    21300
gttggactgg tggggagatg gcataatcta gaggctgaat gatccaaccc ccctccagga   21360
aggcctcaca tctaaaccac ctgccatctg ccaaggtggg aggataaacc acccccacc    21420 ccgccgccaa cagggcactg gctggtgaaa gttgccaata ccagaggagt cttgatgaaa   21480
tgccctctct tttcctcaaa ctctttctgc ctactattca tagtatctgt gttgtaccca   21540
cccacctgcc acttatcaaa gactgaagaa accaaagtta ttcaacaagc catgaagcaa   21600
attctaattg ctccccacgg ccatctgagg ctggcctttg gaaacttaaa aaaaaaaaat   21660 taaaaaaga gagtcatatt aatttatttg ttaccacatt atttgcttta aaattctggt   21720
ggcttctttc cagtgtttta ttagtagaag cgaaataagc ctaggaaaca caatatttca   21780
ttctgtcttc tctgcttttc actgcatatc taccttcaaa aatgtcttct ctcaagttac   21840
ttggtttctc aataactagc gtgaaagtaa cagaccttcc ttccttccta atgatagtaa   21900
caacaaggga tttacagaat tgaagtttat ataaggaaat gcattaagat tttaacttaa   21960
gtaagtgaac tattcagcaa tggctataaa gacagtaatt gtgatgattt gtcttctata   22020
ttatatgttt aaactagtta tatattttaa ttatataaga tgcaatttt ttgctccagt    22080 ttccataggg taattttcaa cagagattaa catgcgttca ttggaagtgt gaatttacc    22140 taatcaaatc atcaatttgt ttattcaact ttaatttca aaaaatgtt attttaaaat     22200 attatatgat atgtgtcagg tatttcttac ggttgacttc caaatttaaa actgcaaaga   22260
aaacagaaat ccatacatat agttgcagta aactatactc aattttggaa gattgcagtg   22320
gcaacatcag tgaattaaag tttgaaagct atttcaaatc tttgcatatt ctccaaataa   22380
ctcagaatcc tacaaaaagc taaatattta aaaaattta tcttcaaacc aataatgtaa    22440
gtttcttctt tattgggatg attttggtta aatatttagc agaaagtaag ggtgaatata   22500
tatttgatat aggtatgtcc taagctaaaa tcaagtcatt taaagatcag agcaattaat   22560
ggcagttatg tgatcacagg aatcagtcta tctcctccct cagggtttga ttcaatgagt   22620
```

```
tttattttc  tcttagcaac  ttttcttatt  ttacttttca  aaggacatca  ttgaaaccat  22680
aatagtgttc  atatctgtga  ctttaaatt  tttatttatt  tttatgcatg  gtttaaaatt  22740
catttagttc  atttaaaatt  caaagatata  aaagagcatt  cataaaaatg  tccccctctc  22800
ctgtcctcca  gcctttacaa  aaatatacca  tatatattaa  tatgggctaa  atacccttt   22860 aaagttatct  cacacgcaag  atgctatgac  tgtgtgaagc  cggagcctac  agactattgc  22920
tgatccccca  gtagtagtag  cagtgactct  ttagtggccc  tggagcttcc  tttctaaact  22980
caagtgtata  tttaatgtgg  ctatttaggg  atgaacagca  gtattttcag  agaaaagtat  23040
agaagaacag  atgaaatcac  acaagatgca  cacatctggg  tattggtggg  catgtacttt  23100
cagcagtgag  tttacaaata  atctagacag  agttaagtat  caggtttaag  agtcctagga  23160
tctaagcctg  cacgggttca  gtcttctgca  ggaacttggg  aatgttgggg  ttcacttagg  23220
cccccagtgt  tggcatgtac  acccactttc  aggaggctgg  aggtataagt  tcctctctgc  23280
atttgtctca  ggtcatcaca  ggcctcagaa  gtttctcaac  agaaaaggat  tgcatgggtt  23340
ggatgtccag  aaggatacgt  ggagttaaac  atcagtcagt  ggagctagag  gcttgctaag  23400
acttgggaag  aggatgaggg  aaggcaaaac  ctgtcaccta  aagggaatt   ctagaatgta  23460 cttactacac  tcatgacatt  accctaccac  cttcatttat  cacctgtgt  caaacataga  23520 cttcttggtc  aagaccacta  tgctgtaagc  tacctgaggg  caggactatg  acttattctc  23580
ctttgtttac  cctgccccag  tgcctaacag  tgtctttgga  attggaatgt  tcaataagtg  23640
ggttaaactt  ttgaaactga  atatttcaaa  taatcacaga  taacagatgg  ttaaaaacca  23700
agtccttctc  agcctaacta  gtgccaaacc  aaatcattgt  ccatgtctcc  taaagaaatg  23760 aaagtttct   aattacctat  ataggtctgg  actcaaaact  ataaggcagc  acactgtctt  23820
tggtgttgac  ctatgtccca  ggttgtccat  ggtcatcaca  cactaatgac  cacttgtatg  23880
tatttcatct  agaggatcac  acagagtggt  atgctaggcc  caaggaataa  gtttacctgc  23940
ttatttcact  tctccactgt  catcctactg  tgtttcagga  agaatttctt  ttacctctgc  24000
ttactctact  aagatgcccc  acataagccc  ccaactcctt  ttcttgtccc  ctcccactt   24060 tgttgtctat  tttcttctgt  cagaccccttt  cctcctccaa  actgaacctt  cctgagaata  24120
taccaaagaa  ctcaataaac  cattcagccc  actatagttc  aataaatgag  cacttccaga  24180
atttgcattt  taatagtggt  tcaacctcaa  gtctctgttg  gtggaaatgt  cactgtgatc  24240
taggtgaggg  aaacattttg  agagcctgtg  ggaacctcca  atagcacctt  atagtagctt  24300
cttctggtgc  ctgtgtaata  ctacaatttc  cagaagcctt  gttgatatcc  agctaagtga  24360
aaagaaagtc  ctcagttcca  gagttcttac  ttctattct   ttttttttc   ttttccctt   24420 tgtttttttt  tgagacagag  tcttttttctg  tcacccaggc  tgcagtgcag  tggcgcaatc  24480
tcggctcact  gcaacctctg  cctcctgcgt  tcaagcgatt  ctcttgcctc  agcctcctga  24540
gtagctggaa  cagatgtgcg  tcaccaagcc  cagctaattt  tttttttttt  tttttttttt  24600
ttagtagaga  caggatttca  ccatgttgac  caagctggtc  tcgaactcct  gcctatccac  24660
ctgcctcagc  ctcccaaagt  gctgcaatta  caggcatgcg  ccaccgtgcc  cggccttac   24720 ttctatttct  aaatagcaat  ggattccact  cttccaagga  cccagaactt  gccctagggg  24780
tgagggtctt  ttgtacatct  tgcaactgag  aactttgct   agaatcagac  agacaacata  24840
gatctcagct  ctaattttcc  aggagtgaag  ctgtggagca  agtgagttac  ctctctgtct  24900
cactttttca  tctgtacaat  gaggctacta  aaacatacat  tccagggttg  ctgggagaaa  24960
aagacaagac  aaggtatgta  caacacttgg  caccaaggaa  gcacacaatt  catgggagta  25020
```

```
attactatca tcctcaccaa gagttcatga tttactgggg gacaccaaca catgtacagt   25080
caacagggta aaatgctaag ggtgtggggc aagtgttgag tctgagctca gtagaaattt   25140
atgagcctca aaggccctaa aacatccttg accactcagt tctatttcac acccttcttg   25200
tacttcacca acaaaccagc aacatgcttc tggttggcag cccttataaa agaatttacc   25260
ttctatagtc aagtccaaag ctcttaactg cttaccacat gacagccaat aagacaagat   25320
attgggcaa ggaagatgac ttttttttcag ggagccagca atcctagaag atggcagact   25380
gatgtactaa agaaccatct taagttgata gattgttagg ctcctttat gttaggggaa    25440
gggggaatag gtagggggtt aaggtccaca gttgactggt gaccacaggc atctgggcat   25500
cagcagggat ctaggaggtt gcaaaacttc tttgttcatg gtcaactatt ttccagattg   25560
accttgtttc tataaatttt taagatggca ttgttatttg tgtgcatact ttctaatctc   25620
ctcaggggtc tgtttcaaaa gagagatggt cattagttct gaagttaaac tataatctaa   25680
attctttcca tcattagctt ggcctatgta taggaatgag caaaggcagt tagcctgtga   25740
ggttagaagc aagatggagt cagctatgtg atatttctcc cactgttaca catctctgaa   25800
tacaagagga atacatttct tcttttttgct gtgtttgctt caagcctgta ccactgagaa   25860
attgggtgat ccagggaagt tttacttctc ttgaacctca ggctctatct ttgtaacaat   25920
ggagaaatca atgcctgcat tctaggccct tttgagggtg gaggaagaca atggttgaga   25980
aacttctcat ctatagttga tcctcaatgc gtttgccccct tttcctgtgg cactgctttg   26040
tatttggatg gttcgagcag tgcgtcacac atggaggaaa ggcaatggaa tgatgacaaa   26100
tagtttgttg atttggtgct ttgtacattc acccacaaat ggcacagttt cagggccact   26160
gtccttgcca aatactatct gaagagctag gttatgagcc tttggaaccc agatctgata   26220
agcatggagg aaaactcctc aagggagatg aagctaggag attagcagaa tatactttct   26280
ccatttgtcc cacatttgat gccagcaggc aaaccagagc cagctgggca gtgtacaatt   26340
cccagaaata aggaagggt agaagcacct gttttttcctc tagcaaaacc aaggcaaatg   26400
gaaaagctca gaaatatatc agcaccatta gcaagaggca caacgggaa ggctggaaat    26460
gtgctgagga aaatcacatt gccggtcaac gcatagctac ctgctggaga agagagtctg   26520
cagacacacc tcagcctgga caaaggcctc caggaccggg agctgtgctc tgcaggaact   26580
gggcccccagg cactgaggac tgaaaaccag cccaacaaag catacctgtt tccatttgtg   26640
agagatgaaa tgatatgggt tttgtgactc actaaaccac ttggaaggcc aaacaattac   26700
aaaagcaaga tgcctggctt cttctagcca catggagggg ccctcagact tgagtagctg   26760
tgtgccactt gtctggggtg gctgcaccaa aaggaacagt gaggtttaga tgcttgttat   26820
tgttcattgt tcagttttgg ttctgtctat ttacttctaa ttcctcaaat attattgtga   26880
ttagtggtat agaaaggaaa cgttcatttg tgagcaaagt gtgtaataag aatttaataa   26940
tgaaattccc agaaaaaaaa actcagatag ctaaagaaac agcagtaaca tgagctccaa   27000
atatcttgag ttgtattgtt aaggtgagaa tccataatgt aaaggaaata atgtaaaggg   27060
aatgctttga aatcaaaggc ataatccaag tgtgataacc taaaaggttg tggatttctt   27120
ttaaagtaga aattacatgt ggctttggga aatcatcagc tgaagcataa gctatgctta   27180
tggattctcg ctgtgttgtc actaagaccg attatataaa gacttggcaa atccatgtac   27240
aaatgtaaaa cttcccacaa tggtatttca tggggatctc ctttttacaaa gtggtcgttg   27300
atcaggacat ttttcactga tatattcctt tggaagcaat gaattttaga taggatatga   27360
```

```
ttattgtaca atgtgatagg tagctctgat tattcaagca gctagggcat tattcagtgg    27420
caaagcatta agctactctg gaatctttct tctgtgtaag caggcagctg ctgttgagac    27480
tttctctttg tgggtgaatt tgcccaacca atggcaagca ttcattggga gtagggaat    27540 gacgctgatc actgttaatg acagttgaaa atgaaatgct ttaatgaatc tcatacttgg    27600
acttggctgc tgagccagag ccctgtactt gaagagctta attatgatgc ctcaaaattt    27660
agatcttgac cctgaactgc tatgacttcc tcccaccctc agttttgaga gaaactttaa    27720
attcgctagg ggattcaatg ttttacatgc ttggttatgc aaaatgggaa cagtagtgtc    27780
caaacaatgg aataggcttc tatattatta ttttcattta ggcagtataa ctgacatgat    27840
taccaaagtc atgttatagt acatgtatac aaattaattt cataccgggg gacttcactg    27900
gggggaaaaa agggaagtcc ctatttgtga aaactatgat tttggtttct ttctgagtaa    27960
agcactgcta atctctttgg tgtacaggaa agtatggtat tatgttctaa aaatcagaag    28020
ccccagacct taatttcaac taatctgatg acatcatttt gtactcagag tttcatttcc    28080
caacaatttc atgtttctta gtaggtgggg aacccagaat tgaaaggcat caaaaacagc    28140
taaatataac caaaaacctg ctaactcacc agctttctaa aattcaggaa gtatctttaa    28200
cttgattgct gaatctccaa agacatgatg atcagatgac tggttaatgg gtatttttc    28260 agactctaca tgattatcag aaatggctgc cctggccaat tgtataccta cgaagaggta    28320
ttatgtagaa gaacttatat tcatctactt aatgtggacc tcaaatatta aggatgttcc    28380
taatgtgttc tagaccggag tcagcaatac ttttcataaa gagccagata gtaaatattt    28440
ctaggctttt tgggccatat agcctctgtc acaattcctc aactctgctc ttgtcacaca    28500
aaagcagcca tagacaatgc ataggtgaat gaatgtggct gtgtttcaat aaaactagac    28560
tctcttaatg ccaagtattt gctggaataa cacaaattaa tttatcctca aatctgttta    28620
acctattaat atgtcagtca atattacatt aatattttat gaatctggta tcatattata    28680
catgaattta tctgaacatt tggttaattc atgaatattt actcaatatt aatactacat    28740
catgaatctg ttatcaagtc atatacagat ttcttaaaaa atttccctta tttagcatac    28800
ttgtgaataa catcaataag caagtatctt aagttaacta tcaggttata tagcagatcc    28860 tctcccccctt ttgtaactct ttctgttaca agggattta cattattatg gtattgggaa    28920
gtaagtctat ttatcctgtc cctatctgtc ttcgtattaa ccatattctg ttatagcttt    28980
tatctttgca gacagaatag ttcaaatctt catgatttgt ccttaaacaa cccccacttc    29040
ctcatcctct tgaacatttt atgcctccat cactgtctct tcaggtcttg tgagtccttg    29100
aagtgcagtg actaggctgg aacatggtgt tccaggttgg tcacatcacc tcttcctaat    29160
gatgccccat tgtacctttt gactatagca aggaataaac aaagtcagaa gtgtgaaagt    29220
gggggagaaa ttgagaaagt gcaggggatt taggggagag aaaaatggac tacaggaaaa    29280
gaaaacattg acttttgcaa agtgctctaa actggctaca aatgcattcc gtaattcttt    29340
aaaccttaat tgtaaccgca gttaagcttt ccggtgtgtt ggaataagaa caaaactaaa    29400
atccttcttt gtatagaaat tatcctgcag taacttagag ccaatatctc tagttaggat    29460
gagcgcagtg gctcatgcct gtagtcccag cactttggga ggctgaggca ggtggattgc    29520
ttgcacccaa gtagtttgag accagcctgg gcaacatagc gaaatgctgt ctctacaaaa    29580
aaattaaaaa attagacgag catggtgtca cgcacctgtt gtcctagcta cttggggca    29640 ctgaggggag agaatcactt gaacctgtaa ggtcaaggct gcagtgagtc ataatcacgc    29700
cactgcactc cagcctggat aacagagtta gacctgtctc aaaaaaaaag aggaagagat    29760
```

```
ctctggttag agtttgtctc tgatggatac taaccatgca agtagtttac acaaaccaca   29820
ttctttctgt agaatgagaa atcttggat ataatttagc ataatgagct aaataactct    29880
agactgagct tcgctgccca gacaggactc tacttgtgat ctgggaagat ctacccttgc   29940
actgaattct ctcctcttct ctcctgactc tgtgagaaaa gtttgcatga atttactgag   30000
attagttata gaaggaactg tgtgtcattg aaagtcttgt acagaagttc acattaaaat   30060
atatcatagt catctttggg aatgattctg caaaattcat aaaacaaaga tctctgaaac   30120
cctaaggcac actgtgctgg aggctaaggg aataatagtg agctgagtgg tttctgccta   30180
cacagagctt ctaatatatt gaggaaagag atctcaatca aattcaattg catttataag   30240
tatggtaagg acaacaaagg agagagacat tattctgtag gagaataacc ctgtcaaagt   30300
gatgactgat ttaagatcaa aatgggaagg taaaattttc tcagtacctg caaaggcact   30360
gaggtgggag ggagcatgcc aatgtaggga aatgaagaaa cccagtgtgt atgagccaag   30420
ctgaataaaa catgagaaga agctggagaa tgagagagac cagtccccaa gctctcaagg   30480
agcaagagga agccttttcg gcatttgaag tggagggatg gcatgatctc gtgcgtagtt   30540
tttaaaagaa ccactcaggc tactcttttg agaatattgt gggaggccag agtagatgcc   30600
tatagactta tacagaggtt aaggcagttg ataagagtat aaacaatgat ggtagcttac   30660
ctcacatgct ttttagatta taggctagaa ggtggcccaa gcccatatac catcatggca   30720
cagtgaatac gtttccttc tggatcgtgg aaatgaatat tgtgccacac agcttgattg   30780
acactcccca atgactttta atactgtggg atctctggca catacttcag aagatgagaa   30840
aggagtttta attaacctct gtttaggaat tccatagaca taattttcat taacatctac   30900
ttggtatttc atctccatga attctttcca gtgataaagc tagttggttt atcctccagg   30960
actgctcagt tctgaacagt gggtcttaag tactctttgg atttctttga aggctttttt   31020 ttattttgt tgactacctc tctactcatt ttgccccaga aaaatgtag tcatttcttt     31080 gataagtgaa atctaagaaa ggcttatttc atttggtaca ttaaagagat ggaagaaagt   31140
aactttacat aagaatataa atgccagctg tccagcatat tacagaatag atttctaaat   31200
ttgctgaaag gttaggaaaa tggattctta tataggctta aaattttat aattttttg     31260 gcattctaga atgaaataaa gaaaatcggt atcatcttga tctcatcacc cagaagaaaa   31320 aaaaacact gatacatggt gaaatatttt cctctctcat ttttaaaaag aatcaggaat    31380
agattgtata catattttc aaattctttc tacttagtgt tatatgatag tcaataatat    31440
atgtgtatgt aagtagcaat aaatcattcc tgaaaacttg ttttttaagc ttgtataaca  31500
ttccgtcata tggatgtact gattttgcta atttgttaag tttaaaataa tattcattt    31560 catttctttg actactaggt ataattaatt ttttcataca ctcactaccc ttcatacttc   31620
ttttattgat ttccttttta tgttaattat taagatttct atttgactct caacattttc   31680 ttaattttt tatcattaat agatgtaaaa aaattcttaa ttttaaaaa ataacccctt    31740 ttcatcttaa agatagcaat ctattttcca taatacttgt tataaatatt tccccagttt   31800
gatgttggtc ttttaatttt gtttaaagta ttttgacaa ataaataagt ttttgtggct   31860
tgaagtttgt tcattttttt catttgtgat tacagtttag ttgttgattc aacacatcct   31920
tattgagtgt tttgtgttca gcactaagcg agacacaaga ggtaagacag aaaaacaagg   31980
tgcaggtggt tttgccactt agagattaca atttaatgag gggatagaca aacaaaacca   32040
ggtcattata aaatagtata ctacaagcta tgcaagagga aatacaggtg ggaagaagta   32100
```

-continued

```
cctgatctgg acctgggga taagggaagg cttctggaag gaaacaacct tctagctgag   32160
aatgaaggaa aatggcaaca tgaatttaga gagaggaaac agtatgtgtg aaagtgttgt   32220
tcagtgtcct aaatgttaaa ggtcctcttt ccccagaaca tggagtgtgt gtgtgtgtgt   32280
gtgtgtgtgt gcgcgcgcgt gggtgtgtga aggagcaggg caggtggtg gtcaagtgtg   32340
agcaggaggc cactggggag gctgcggcag tccgagagaa agacaatgat gttgggcaga   32400
ggatgtgttg aataactcat ccctttcac tggacaagca atgcttcagt gtatattaag   32460
ttcttattca tagcataccg tctattccag aataatctaa ttagttttat tgctatatca   32520
attcttgggc caacaccaca ctggttttga gtttaatgaa acgtctaaac tggtaatgca   32580
tgcatcctct catcactttt cattttcaaa attgatttac ctattcttgc caatgcgtcc   32640
tcccaagtaa actctaaaat aatttcaaaa gtcacaaaag catacgtgtg tgtatatgca   32700
tgtgtgtaaa tacatgtata tatgtgtatg tgtgtttctt ccaaccattt ttcagttttt   32760
ggagaataag atgttttat tcaagttgct gtcagtaaat attttatatt acatgacttc   32820
tctatacaca cacacacaca cacacacaat ctcccattgg taatttgatt   32880
gggaatgtgt taaatcagga gaacagacat tcttttaat attgagtcag cccatcaaga   32940
agcattgaat gttttcccac ttactcaatt cttttatact tcttttaag cctttatagt   33000
cttactcata taggtcctgc atattattg acggggtatt ctttttctt ttataatttt   33060
agcttttaat tatgaatgga ttttcttcc attatctcct ctctggtatt actggactac   33120
aggataaata ttaatgatgt atattacttt ttatctgat tatttaactg attataatta   33180
attataagtg ttcatagtta attataaaag tttataatca tggtgtcttt aaataatgat   33240
aattgttctc cttccaaaaa ttgcatctaa ttttattg tgtcttaca gcattgatcg   33300
taacttctaa tactaaataa caatgataat agtgagcgtc ctgtcttaat atcaattcca   33360
agaagaacac ctcttacata acattttaa aagtgtgtta tgtggaagct aataaaataa   33420
acttgggaaa tgcgacaaat gaaaattctc tctcccaggc attcttaatt catattaaca   33480
tattaagatg agatctgcaa caaagagatg agttcaactg agtttaaccc agtatttcta   33540
aaatgtatt gactatggaa gtatttttcc ctcatttaga attttacatc agttatgaca   33600
gtcaaaatta tattaattg atcttctttc ttttttaga aaataattt tcatactttc   33660
ttgtctttc tgtttgatct ctcttttgcc atatggacta tgatttgggt ttactttaa   33720
tttttttcaa taattgagaa gctcgtcacc cttctttta tttctacaag tggttacact   33780
taaagtttcc aagacatttc tatccatatc ttatacttag caaagtcaaa gacatgacca   33840
tacagttttc taatcaactt caaaatgaaa tgttatcttt gaataacccc atcaaaagaa   33900
atttaatcca tttttacttc cttccaacct ttcctcagta ttggtaagaa taatttaaca   33960
tttttattc atgttactgt cagtaaatat tttatattat atgacttctc ttttgtgaat   34020
tatgtgatct gttcagcaac ataatccttt acaatacatt cctgagcagt tctatggtta   34080
tctgatttct gtgtccataa ctattgtctt tttataccat aaatttctca tttttttact   34140
ttttaatttt aatatcttaa gattcgccac ctttatccc atttatcctt ttagggtgta   34200
taatgtaggt catctacatt ttgagaagtg cctgattctg tttactatag tgtcagtttt   34260
accccttact gccttcagtg gacaaattag tactattatt tcattctgg ctcctctaca   34320
accccttta atctaaccca gcactctttt ccttccttac ttttatctca taatggctac   34380
ctgtccgttt tccacagtat tttctatttc agttgaagat gataaacagt tttctgacat   34440
tgacattaag atgatgtttc agtttctcttg ttagacaatt ttgttcactg tctaagctac   34500
```

```
ttatttttca tgattactcg tctaggaata aaaatcaatc tacttagacc caatatttt    34560 gaacactgag catatgtaat gtgttcttaa acctgttcaa tatgtactgg gctctaaatg   34620
tcctggccta cagctggagg gcagaatgac atgtcctagt tcaatatcag cctctaacag   34680
gaatgctact gatgtagttt tctgcactga gataggatct tctttttcttc cattgcctat  34740 tctcctggag gcaaaataga aacataaaa agtcatcatc tttggtatgt tcttctttag    34800 gggcttttc tttctcccag cccaaccccc atagtcctta cttgctagat gtgtgttcca    34860
ggattcagtt caccactgcc cagtcttcta acatccaatt tcattgtttt ctgagagttg   34920
agaattttca tacagatata aagggatgc tgtgcttgtt tgaaatggtt ctatttggca    34980
gaggatagcc gaacagtttt taggcaaaga atgaactgtc tacttacttt ctttgaagaa   35040
gccaacaatt tggttttgtt gccaacagca ataatatat tggctaataa ttgtggttta    35100
cagtgacatg ggtaatgtta gtcataacat gtcttccaag tttctggcta tggactaact   35160
gtaggtcttg gagtttggta ttatctagaa ttttccttct ccctcctccc ccacctctta   35220
tcttttagca tagttgaaga ttggaacttc ttcccagaaa tctagcatct tcataagtcc   35280
tttccggttt taagatttt atcttatat ttatatatat attacatata tttcctgtga    35340
atcttggctg aatttctcat ttaataaagt ccaagttagt atgaataaat aacatgtttc   35400
ccgattttac acacatacag aaattcaaac acataatgaa ctctctggca gcctttagca   35460
tttgtaagtg ctctctcacc aggaaaatcc tttaatagat aaccaagtgt cctggggaag   35520
aagggtgtca ggaaacttat tatatttgtg tcactttctt caaagggtga ttaagtatat   35580
gtctccaaag atgtgatgtt atcatctttg agtatcactt gaattcaagt caatatttat   35640
tgagacccca tgttgtatca ggtgcctac tagaaagtcg acatatagag atgcataaga    35700
catgatcttt ttcagtgggt aatttaaggt cttctctta ctgctagcat tgtcatgtgt    35760
aaggctggtg ggttgagtct ttggaatttg tgaagattct tccaggttgt ttaaaaaatc   35820
ttttgattct cacaaatgta tttttcctat ttcttagaat tatgttcttt atggctacca   35880
ggaaatcctt tgaaactgga attagattgc attattccac tggggtaata ggattggtaa   35940
ggtaggagtg tctttgaaga ataatgctaa ataacccaga cactaaggct gaatcttcag   36000
cacagctctt aaggcatcct gtaagtaccc tctgctgctt attagaaatc ccaaagccct   36060
gctcccttag gaaagcggcc catccccatc ctcatcataa gatgcaaggc atagctaaac   36120
atctcaactt ctcacttgag tattatatac tctcaggcca ggatactttc caactcaaga   36180
gtaagataac attacattct gatcttcttg tgtgtgtttt tatgttttt tttcattttt    36240 atttattatt ttttttttg agacagaaat tttactcttg tcacccaggc tggaatacaa    36300
cggcgcaaca ttctgatctt cttttgagag aaaagtttca cacaattagc ctttgaaata   36360
cacattcctt taagtaccat gaaaacattg tcccatacaa caatatttct aagaaacaca   36420
catgtccctc ccacaatgat ttttttcttgt taccaccaat aaaaattaga gctgtgttgt   36480
ttttgttgtt gggtttgttt ttgttttttgt tttttggtga ctactgtgac cctcaaaaaa   36540
tcaatccgac tttctcgatc ttgatttgca acaccaaggt taccaaacaa agagaatggt   36600
tcaatgaggg aaagctcaac tacctgccct aaatatttag tatagcaatg ctgagctttt   36660
ggtaatggct caaaattctc atgctttccc actaaatgaa aaggggagct ttgctactag   36720
taaaccatat tcaagaaata attcttatta atacttgct tctttcctat gaattattgc    36780
tttgtaatgg atgtttgaca agttactagc aaagcagtct tcgatgagca cagagaccca   36840
```

```
tcagatctgt attaacacct ccaaccactg gagtttcatt aagtaggttt ctctacccct   36900
ctccttcagg ccacagatag gaagaatgac attgggtcca aagttctggc acaaagaatg   36960
atgtctgcct tcctgtgatg atttcaaatt cagggtaata attccaacta tctttccctg   37020
gccatgatag aaagctcaag aaatcttggt tccttgtctc ttttcttcca tccagttggt   37080
ctttctaatt acacactcaa cacaatgttc tgctgagcaa gacatctgct gtagccacta   37140
tcacccttgg cataaccaga tatttaaagg tacctaaagg agtttagcta tattttgcca   37200
agatcctaag ttctatggca taagaatcca tccacttctc tattgcctat agaaaaggac   37260
agctcagtct ttctgaaaga attgttctca aacaagaaag catttgaggt aacatgtcaa   37320
caaggtggac tggtaattgg tgttcctttc agagccagtt ggaggaaatg ccagctcag   37380 acattctctt ctccccagtg tcctatggga acaagattta cccagacaca gctgactatg   37440
agaagtcttc agggatttac aacctgtcta agaacaaggc caatggggga ctcactttgc   37500
aacacgtccc tatttgattg tcagaggaca gatactctat taacaaagga atttgcactg   37560
gtattttcag ggacacatca agtaattgcc acttgaacgt ttttccaggc tttcaaagga   37620
atgtaagaat ggcctaaggc taaattacat tcatgtcttt agtgagtcat tatattactg   37680
gcaataaagt atattattac tttactttca gatgccctca catatttttt taaagtagaa   37740
aggagacata ttatggtcac cattcttaag agacttaact aaaagacact aatttaatct   37800
tttagttact taaaaatagc tgttgctcac ccactatgtg ccaggctcta taccaggcac   37860
caatatgaaa aggtgagtat tctctggtct ccctaagcac agtctagtgg aggagacaga   37920
caaaatgcag ccatggccag aaggggagc agttaatgaa caagtaggca gagagtaggg   37980 agggattct gagagacagt acggacggac tgagggtaag ttgtacatcc ctgatatttt   38040
gggcaattgc aaatagtttg atgaccaaat cacaaggaga agaagtgaca gcaagcatgg   38100
ctgaaaatgt aggttggtgt caaattgtaa aaagccttga atactgtgct gaacggtttg   38160
atccgtgaat caggtagagg acttgactca ggtctcttga ctcaaaggtc atgttttttc   38220
tctgctagat tgcacttatc cttccaaatg ctagtggaca ccacactgaa tttgatcaaa   38280
gatctctcaa tggaaatatg taaatttcct gtaagaagca attggtaggt tctcttatta   38340
tcatctccat ctcacagata aggaaactga agtataaaga acttgagtaa cttgtccaag   38400
gtcacacagc tagttaggtg atcccagaca atttggctcc agagtcacta gtcctaacta   38460
caacaattta gcctctcttt atctagaggt ctttatgcat ttgtctgcat tctacttacg   38520
ttggtattgg tgagtaaaga ttcccttcca gaataggttt gataaattgc caagtctgaa   38580
actgaaaaat taatatccat gataacagag gttttggggt caaggagtga aaggaattca   38640
tcccatcctg tctctaaata cttttttctt taccaattta tgggaatttg agaccagata   38700
tctggaacca agcagcctca ccctattaag ggaaagaaaa agaacagaag aaaagaggag   38760
aggagaagag aagagaagag aactaaaagt atctgcaaaa atattaaagg atttgaccga   38820
gatctctgag atgctccaaa gattgcaatt gtgcttacta tccaagttaa tggctgtaaa   38880
tctaagagaa ttatgatgtg cctggtaaat attggttgtt ttgttttaag tcttcatgga   38940
gaaaatggaa aagacattgg catgtaggat gaagtcacag caggacagac aggtcctgca   39000
agtgtttctt tagatgcatt gatattcata acatccaaac aggccttaag gctgtcttct   39060
tactttacac ttaccaaagg ggtaaaatat cattttcctt ggacacacaa ataataaacg   39120
tactctcaca acatcacttg aatgttgtgg ttttgcaaat atactatgtt ttaaaagcta   39180
tagccctcaa atcccttact agacatcaat atttgttgga atttcaacat caaagattta   39240
```

```
ttgtgaaggg ggaggggggag gagttactcc aaaggctaga accagtgcat ataccataat    39300
aacaactctg catgcattat tgcttctaat cttcataatt ttgagtacta tctttattgt    39360
caccatttaa tgaagatgtt aaggttctgg gggcttaagt gacttgccca aagttacaca    39420
gcttggtaga aacagaattt accacagaac ttgtgtgtta agccaaataa ttttctagtt    39480
ccatacaact aaaaattgga aggaaaaagt agagccttat gaatagagtc ctgagcaaga    39540
aggatgaaca atctgcagat gaagtactct gtaaaggaaa gatctgggtt tgaattctaa    39600
ccctgcctcc gttcatctgt gtgatcttcg caaagtctgt taactcttta aactgttgga    39660
tatttataaa atgggactgg tgctatttgg cctgatatct tacaggggaa gattcagtca    39720
ggccaggcgt atgtagggtc tctctgacct ggaaagccct atataaagac atggtaccat    39780
tcttagtgtt aggactgaaa ctacatccct agtgtcctga cacctcatac caatacccag    39840
aaaccctagg ctcttccttc aatcccatac tccttcctca gctgccagga cagcttggtt    39900
aagaaaagcc ttgttcttgg ggagtatatc catgaaagta tctctatttc gttgcagttt    39960
cacattaagt aaaattagag tgcccttcac gaagaatata taattgaaag ccctcccact    40020
gactgctgga caaagcactt gtcagtcaac aaaccaggta gattgagtct gccctcagag    40080
tttttgtatt ctgagagtga ctagcaactt tctctcatcc tagagcaaca gggctttcag    40140
aggacaggtt ctggggcagc gtgtagccac gatagaattg gtttgctttt gtgtccaaag    40200
tcatgattat caggagagct gccatttatc aaccacctct ttgatacttg gtgtatagga    40260
caggcgtgtt aactatatta tttctaaacc acaagataag tctgtgaagt attttttatcc    40320 ctggtttaca aaggaagaaa tgaggctctg cgagacatgc cagaaagaac atgctctaca    40380
caaccaactg gttacaatgt gcggctttgt ccagcactac ctcttctttc ttggcaatca    40440
tcagagccac tcaaggcttg gaggactgtg ctggcaaaaa agaaatcttg tattttctaa    40500
aactcacacc cacactttgg aggggacaag attgagatca accccatttc ctactctttt    40560
ctttatgaca gtttatcaga gcattttttc cttatattca ctcagtcctg agtttctatt    40620
tagttgtgat aatagataca tttttgaatt tttaatacct tcgggtgcaa atttggaatc    40680
tatggaggat aagggagtaa caaaatgtta tggaaattga aatatataaa ttattaattt    40740
tccctctcct ctacagattt acaatcactt tatttgggga tatcaagtag gttatgtggt    40800
tactgtagta ctcatttaat aatcagattt tatttagaga actataaaag gtacaactta    40860 aggggaaat atattttaga tgatgttttt ttttcaattt ccaattttg aagaatgacg    40920 tgttttaaa aacttttaaa gaatttctcc cacatttcac tcccttttaag gtaaattgat    40980 agctgtgaaa atggcacctt ggaaacattt ctgtcataat cataggagag agtgagaatt    41040
attaatattc tcagccatgt agcatcataa agtagatcac agctgtttct ttcagaaaat    41100
gtcatttgat tttcgatcag atgtatggtc catctcacaa tctaaccgct tccacatctg    41160
gaatatctta actgaaaatg tccacagcat tacacggcct ggctcagggg gagaaaagaa    41220
ctagggcctg catcgaattc tgtctctcac tcagctgatc tgcattcctc ctatagcatt    41280
tccttataat taagaagagc tcatagattt gggaactgca tgagcctctg taaccttctg    41340
gtgagggtga aagctcaga actgcatttc tatgcatttt tccctagtct ttcctgcttc    41400
ggaggagaag ccctgcaaga gcttcctgcc aagggaccct gctttctcag cagccggatc    41460
cggagagcca gaaatccatc ttcagctcct ttgaacttgg ctgttgttaa tcatgctgtg    41520
gttgtccttt aagagcaaag gcttcacgga gagcagatca gctggctgta gggagggttt    41580
```

```
cagcttctca ttgtaggcag atcatctgct aacagcttac tgagagaaag ttgaggacat   41640
gtggctgaaa cactgtcaga gctgctgtga acacagtcca agtgagcaat tttatgaccc   41700
aaaccaagca gacactaagt gctttctagt ggtggaaaag gagcagagag aaaaagaaca   41760
aagaccaagt ggtggaaaca aaaaaaatat atatttcttt cagcagctaa catatttttc   41820
tgtttagaag attggtatct cctacttaac cacaaactac aacacataag atcaaataag   41880
attaaatgtc cggtttgcta aatagcagag cgaagaaact aaggtcaaga tttcagactc   41940
ttacatctga ggaaagagag aggcaaagag aagatactgg aaatgccaat atccagtcaa   42000
tgaaataaac agaggctact gtaggcatcc ccagaagctt gccttttgtc cagtgccatg   42060
ggaaccacag aaggcactca gctttgcagc ttcactcaga attggggcaa tgctccacag   42120
agtcaagggc atgttattat aaagtgctcc atttgtttac tttggcaagt ggaagatgac   42180
tttgctaagc gatactctgc tggggctcag ggccagcact gctggagtag aaaagggag   42240 acttcctggg gcaaggcttc tcaatcttcc tgccagcagc attgcagtcg gagcggcact   42300
gaggtgtcaa caaaggatg atgaactgtg tcagcagtgt tagcaaatgg ctgaagtaga   42360
acggagctgc ccaggatgct gccctgtcgc tggggaatct gagggaggct gaaagatatt   42420
gtaaaagaga ttgaagggct ggactggctg gaggaatggt gccatcggca tccatgccac   42480
aatactccag gactgccctg cctttgtcag gacagccatc agaggcggtt ttccctctaa   42540
ccaggatggg catcactcct tgggcttgcc agtcttacct ctcctcatgc aattgcatgt   42600
ccaaggcatg ccctcagggg atggtgctga tccagggtgg caaacccaag tggggagaaa   42660
atgctgaatc tcatcctctc agagatctgc tgcagtcagc gactatactg aggtgcatga   42720
tctgagcagc agtcgctggt tggggaggct tctttgtgga gtgggtctca gccacagcct   42780
gagggtcctc tcttggggat gctaccagtt aattgggtca tcttcagcct ccacccaaac   42840
ttaggcctgt aggtccatca attactatat cagcctcaag gactgaacag gtgggaggaa   42900
ggactagtgt gagtgatgga agcagctgag ctgaggagtg ctggcacctg tgcaaatcca   42960
gcaagaatga catctggctg agcttcagtc attcacctaa gcaccaatcg ggggtcactc   43020
ccagatctga gcaatgaggg aaacttccca gggggaaccc cgcacttggg tagacctggg   43080
ggagcagcca gaaggaaagg ggttgaacct gtagttgatt aagattcaga gaaagaaaaa   43140
acaaaaacag aaaacgatca tagtttcaga cactcccaat gagcctgtga cctccccaaa   43200
atcctatagc caaacacacg ggtggatctg gcctcacttt cccattctcc cacttgtgac   43260
ttttgattcc acatcatagc taaggtcctc ggcaaattgg attaaacttt ggatttaaaa   43320
ataaaataga attaaaataa aataaaaaag ttggggacag gagaaagtgg tttccaagaa   43380
cctacacctc tctaccctga aatgactgaa tattgtgttc ccctcaaaat tcatatgttg   43440
aaatcctaac ccccaatata atggagcctt tgggaggctt catgaatgag attagtgcgc   43500
ttacaaaagg gtcccagaga gctctctcac ctttttccac catgtgaggt tacaacagga   43560
agtcagcagt gtgcagtcca gaaaagagcc ctaaccagaa cctgaccatg ctggcaacct   43620
gatctcagac ttcagcctc cagaactgtg agaaattaag ttatgtggtt tataagccac   43680
tccgtctaaa gcactttatt atagcagcct gaactgatta agacactcct gagaacgatt   43740
ccttcgggga aggtcttgat tagccttcac ctagcccagt ttgcaaacac actggagtgt   43800
cctgcccatg gcaatgttca tgtagcagcc tgggagacag aggaggggga ttcctgcagg   43860
agcaatcttc ccaaggaggc agttcctact agctaacttt cttgtcctgc ttgtgctcat   43920
tgaaggtcca aacctgtccc ctgccctatg tttgttttcc tcctaatccc ctggctgatg   43980
```

```
gagtcaggct tggagaatt cctttaagag tcttagttgg ccttatggat cccaaaacac    44040
acccttctct attgatgcca gattctgagc aggctgacag tgcatgcatg agaaccttc    44100
ataaaatagg actattttt attcccttg cttttctt gtgttattc ccctcttcac        44160
tccctgtcct tttaccttac catatacatt tgtcacctcc ttgcctggaa agcctagtgt   44220
cacctccctg ccttttcaca gcctatagga ttgagtccaa acttgccagc ttggcctttc   44280
atggagtgca ggtttagtac aggactgcta aacacagttt cagaatgaac cattctcctg   44340
gcctttatca ttgccaatat ttctctttat tttatttat tttatttat ttagggagag    44400
ccgatatttc ataagagttg atggactgct ttgcctggaa acttgagaat tcatatttt   44460
attcaaaatc gttttcattt tttgcttag agcctgttaa agactgaggc cctctctctg    44520
tcccttctac tcccagccaa acccaataga cacatgtgag caagttgtca cctgacccga   44580
agctccagcc cctggaacca actgaaacaa aatgtatcct tgcattttcc agcaaggaat   44640
tgccttgcct acaaaaatac tctgtacttt aatatgcaga tcaattatta acagtaggct   44700
gtacctttca ccaggttgta aaaggatgac tgcgtagagc cacagcattc tccttgtcag   44760
tgtaggaaat gcagaggagg atgttacctc cggcacttgc ctctaagaca cctaataaag   44820
atgaggaagg ctccagcctg aagcgtgggt gaggtgtcca gctgcccaaa ggcgacaggt   44880
gagatactca ggtccccttc ctcttttgc tgtcagttct gattctctcc tttcaatctt   44940
tctcatctgt gattgggaat ggcaggggtg gggtgtgttt ggggcatcag tggtggtaaa   45000
aatggtctta tgggcagggc catgttgaat aagagatgag catggagaca gcgtattaac   45060
ttaaaaggcc aacaccgagg ctcatttgag accgtaggaa ttccagggag acagtgttgt   45120
tcaggcatgg gatcgaagat caggaggggcg gctcaataac acgctggccc ggtcacatga   45180
cagaccagtc cttggagtga actgggagac aaggaggctg ctttggcatg gagctgagaa   45240
catctctaga tcgcactgga aggcagagag aggccagaca gggaactctg aagagctgcc   45300
acagcctgtg ccagggtgac atcagggtga gttgagatga tttttttaac aaacttcatt   45360
ttttgcagca gtcttaggct tacagaaaaa ttgaacagaa agtacagaca gttcccacat   45420
acccgttttc ccccacagag tttcttctat taataacatc ttatgttcgt gtggtatgtt   45480
tatcatgatg aaccgatgtt gatatatcat tattaactaa caagtccaga gtttacatta   45540
gggtttactt tttgggtcgt atggttctat gagttttaac aaatgtataa tgacctgtat   45600
ctatcattac agtatcatac agaatagttt cacttcccta aaaatcaccc tcccttcctt   45660
cctgcaaatc tctgacaact gctgatcttt ttactgtctc tatacttgtg tcttttctga   45720
aatgtcatgt agtcagaatc atgcagaatg tagtcttttc tgactgcttc tttcacttag   45780
caatatgctt ttaagcttcc tccatgtttt tccagggctt ggtagcttct ctccgtttta   45840
gcactgagtg atactccatt gtatggatgt actgtagtct gtttatccat ttgggcagac   45900
tttccagcaa gatagaaggc agaagcaatg gaaagggtgg atgaagggaa aactgcaagg   45960
aacacaggac aagatagaag caagagcagg aaggttttgg agaagtggaa aaacaagcta   46020
gagagatagg cacagaggcc taacctgggg taaggcaggg ccttgtaacc aacgctcagt   46080
gagagaggca gccctcact gacctgcacc aggcctttcc tgattttata gacagagtgt    46140
catgaggtca tgagggcagg aaccatgtca gcttcatcct gagagcccag cactttgtag   46200
gcatctaata aatatttatt acaccaatga aaccttcaaa gtctcttcta aaaaagcaag   46260
ttctcccaga caccagaaga caaatggcct agcagcccct gagccagtca tctcgggcag   46320
```

```
ttgtgagctg gttgcttatt tgaaccctcc atgccacggg gcagcatcaa gcttgcctga    46380
cacacacctc ctgagccagg aattcaccac tttgccacca tctctgcctg gcttgggaga    46440
tgctccgtgg acagaaccag agccgtgctg cagggaagca gaaaaaccaa aggagatgca    46500
tgccaatcta acatgccagt ttaaaaaaag gcattcttgc ctcagagtaa gaatccagct    46560
ctccatgcac tcgtctttca acccaatcac aaggcatcag aattagccca tatgacctct    46620
atgggacaag aagagcaagc agggtgattt gggtgctaag aaatagctgt gagaggatga    46680
tgcggcagct gtgccctcca gatgttcgga gagaacatct gtgcaacaat agcagtagct    46740
cccatgcact gatgtgagaa cccagcctaa ggggtacagc aatctgggtg gtaggggta    46800 gctctcagag ggtctgacaa ttcacctaaa gattgcagga ccaataggaa cctgccagtc    46860
agaatttcct agctcagtgg tgccctccaa gcaagagagc ttatcagcca gacctgtgtc    46920
ttggtgcaac atcactgctt aaaatcaagt cctcccaagg catggtgtcc atttactttt    46980
ctctggatga aatgaagaca gagaatgaac ccagtaagat gatagagtgc tttgctttgg    47040
atctgttcat atcttacccg tgtttgtgct cacatgagtt acacagtcag tacaagggta    47100
gagagctctt gagaatttct tacctaaggg aaagaacttg ggggctgctt tgctcaaagg    47160 ctattttca gtgtggggct tatctagaga catatatttt gctccttgtc cccactgctg    47220
ttgcataact acgggagttg agggtcacta tacacagaca cagatggtag agatgggggc    47280
agtggttggg caaggaatag ctgccttgcc acttcgaagt ctcctaaatg gcatctctga    47340
agaagaagga tatgtccaca gggagaaggg ccccatggtg actctgttgc tcctaatgtg    47400
ccaggctcag actcttcaaa ccacaagaag tggcccagcg agttccatgt aactgcaaat    47460
gcaagcagga aaaaccaca ctcagatctc agcacagcat cagtcttggg acagctggc    47520 cttttcctaat gcagcagcat ctggctgctt ctgctgtacc tggatgtctt cagggcagtt    47580
cttccacaca gaggacccca aataaaagca gaattcctac cattaagctt tccgtatcca    47640
aaactttcta tgtgaaagat acagcatctg tgtctcacaa gaatctgttt tcttgggca    47700 tctgctattt ggcagctaac caaaacagaa ttcccatctt attttcttgt tcatttgtgc    47760
tacatggaag ggactggtcc tgaatattca gggcaacatc cagcatttgg tagtagtgga    47820
gagaaagaga agagaaagct ctggactgtg ttcctctgtc tgggaatgtg actctcacac    47880
ctcccaaatc ctcccattca cacttttct ccctgacttt ccagaaccct ttttaggctt    47940 agctccttt atcttaccct acacgctttc tttctaccca cactggtggg tacttttcag    48000
ccatagacat tggagcacat ttaaatatgc tggagtcctt agagaattaa gaggtggggg    48060
agagaggagg gcacagagct gaggatggca ctagctcatt cacaaggagc cctgaatttc    48120
cagggacatt aaagaacaga tgctcatgac agagcataga gctctgccct aattgttgt    48180 aatgttgaac tatgtgtcat tcgttcactc atatattctc tcaacattgg aattgagcac    48240
caattatgta acagagtagg tcttggcaat acaaagatga atgaaacata ccccttgtcc    48300
ccaagaagta tgtggacacg acaggcacat ggaccaatga tggtcatgtc aagcgtgatg    48360
aagtccatgg tcctgaggga cacttggacc acggcctgca tgagggcc tggaacccaa    48420 ctgggcggat ctagaaagaa ttcctctgga cttgattcct gaacttgaag gtagagatgg    48480
aaggagaaga gttctgggta gcatgttcct ggcagaagaa gcccactgca agagcaaagg    48540
cactgaggaa gcctggtggt cactggaaaa ctgggattca agtagctgaa atcgtaaggg    48600
tgcagcctag ggagaagtga gacccgtggt gggggggcaga gccaaatctc tgtatccaaa    48660
cctttctata tgaaagatac agtgtctgtg tctcacaaga atctgttttc ttcgggtgtc    48720
```

```
tgttatttga gtgctaacca gaacagaatt tctaaagatg gtctttgagg ccaggtaaca    48780
aggctgaggc taagaagaac tatggaaggt ctgttggcag gagagatgta tgattagatc    48840
tgcattagca gaaggaaagt tctggctgaa atctgcagag cagtttggag gggacaagac    48900
agatgacatg gagaacactt aggacgctgt tataataaaa taggctagaa atgatgttcc    48960
tcagaagtcc ctttctccct gcacacctgg ccacctcaga cttcctgttc aaggggaagg    49020
caggctgggg agagaggttt cttgaaaata acacatctgg gccgggcgcg gtggctcacg    49080
cctgtaatcc cagcactttg ggaggccgag gcgggcggat cacgaggtca ggagatcgag    49140
accatcccgg ctaaaacggt gaaacccgt ctctactaaa aatacaaaaa attagccggg    49200
cgtagtggcg ggcgcctgta gtcccagcta cttgggaggc tgaggcagga gaatggcgtg    49260
aacccgggag gcggagcttg cagtgagccg agattgcgcc actgcactcc agcctgggcg    49320
acagagcgag actccgtctc aaaaaaaaaa aaaaaaaaa aaaaaaaaa aaaaaaaag    49380 aaaataacac atctgttaat tggatcattt ctgtgtggtc aatgtctgta ggggctttgt    49440
tttggtcatc atagtataaa atccccatta tgtaatattt cctcctgata aaagctcact    49500
gtgtgtctat accctaccag cttccttata gtatttgctc attaccaggt tcaaggacct    49560
gtctgtgtgg ctcttcccca gagcctctgt tggaaagaag atttgtcttt ggttataagt    49620
agatacacag tggtcaagat gctctagcac agtgcagcag aataagatgg gctcagtagg    49680
gaaagatcat tcacccctaa agtgtacact tattcttttc tgattatgat aggattatgt    49740
tgaaattaaa aattgtttca acgaaaaagc aactgattgc ttaggccaaa gcagaacttt    49800
tttttttttt cctgaggcaa agtctcagtc tgtcacccat gctggagtgc agtggcacaa    49860
tctcacaatc tcggctcact gcaacctcca tctcccagt tctagcgatt ctcctgcctc    49920
agacttccga gtagctagga ttacaggcac ctgccactat gcccagctaa ttttgtatt    49980 tttagtagag acagggtttt gccacgttgg ccaggctggt cttgaactcc tgacctcaag    50040
cgatccactc gcatcagcct tccgaagtgc tgggattaca ggtgtgagcc accatgccca    50100
gccagaatta ttttttagtac tgtagttaag agggcacatt ctggagcaaa ctgcctgcta    50160
agtgttcgct gtgggcatt gggaagaac ttaatctctt tgtgccttgg tttccacatg    50220
taaaatggga taattatatt gtcccctgt actggtttgc tggggctgcc ataacaaagt    50280
accacaactg ggtggcttaa acaacagaaa tgtgttgtct catagtgctg gaagccgact    50340
cacctcagaa gcatggactc ccttacctcc aagtccaagg caatgggct ctctcctct    50400 tgcctcttga attcctgcat ctcatttcac tgggtaaaca gggaggctcc tgtgctccag    50460
caggaaaacc ctggactggg aagcaggatg tctactctga tcctgctgcc ccaaagctgt    50520
gcggctttag acaagtggtt tgacctttct gggctcagtt tccttgattt tcactattat    50580
ttgaagggct tggggtcatg gaaatcatga actcttcaca ctgagaggaa tcttcataat    50640
ccattttgta gataacgaac ctaaggctga agaggtcagg ggcttgcacc cagtcataga    50700
gctaaatgag gtgcaaagaa cctagaactc cggcgtcttg actcccacct gggacacatt    50760
ttatcagtaa tagtgaactc tcatctgttg atagtgttag aattctcaca tttactcccc    50820
ataacaactt tctttttttt tttttaaacg gagtttctct ctgtcaccca ggctggagtg    50880
cagtggcacg atctcagctc actacaacct ctgcctcccg ggttcaagct attcttcagc    50940
ctcagcctcc ctagtagctg ggaatacagg catgcaccat ggcgcctggt taattttgt    51000 atttttagta aggatggggt tttgccatgt tggccagact ggtctcaaac tcctgacctc    51060
```

```
aagtggtcca cctgcctcaa cctcccaaag tgctgggatc acaggtgtaa gccaccatgc    51120
ctgaccagca cccttctgaa gtaggtgctt tcagaaatct gaaagcatag tgtcggttag    51180
cagggttgga tctcttctgg tactgtgagg aagaatctgt gccatggctg tctgctagct    51240
tctggtggtg tgctggtcat ccttagtgtt acttggcttg cagaagcacc atcgatctct    51300
gctttcatcg tcgtgtggtg ctgcccctgc atgcatgtat ctgtgtccaa atttccccct    51360
tttataagag caccaatcat attgaaatag ggctcaccct cataatctca tctcaactaa    51420
ttatatctgc aataaccctc cttccaaaaa acaccacgtt ctgaggtcct gggtgttggg    51480
atttcaacgt atgaatttgg ggtgggaggg cacaattcaa cccaaacatt acctaataaa    51540
gttttcaaca gtaagtaaat gagttaactc ctggaaagca tttaaaacag tgtctgacat    51600
tcagaaagct ctcagtaaac gttacattat gctgggtata aataaaaagc tcccaggaca    51660
gtggacggca ttgagattcc accggtttgt attagtgtgg cctcgccagt aatttacatc    51720
ttctatcttt tttggttggt cagggcttaa gccataccag gtaaatattt tgaataatac    51780
tcctagctaa aaggtgcaag gagtagatac tgtgggttct gattttttctt tcccgttctc    51840 caagctgtgt acacagaacc atgcaagtcg ccccaaccag ggaaaaacaa ctgccatttc    51900
ttttaaaggg gaaccaatga aggtcttgtc ctgatgagct cacaaaagca aacttctcca    51960
tgtctgtcgc tcactcagtg ggctgaagca gagccttcac gctaagcttt ggagacaaag    52020
cttcttagag aatgtgcaac gtgggctgat cccaggctgc ccaaggagca gctgacgagt    52080
gtaaaagtgt ttgctcaccg attagaatca gtcctttaaa aaataaataa ggtatgttga    52140
tcttttatgt gatgattaaa caaatcagat ggcccaaaat gaattccagg taaagaggaa    52200
taaaatatca gaaggcaagc tgctgaaatt agcaagagct gaactcgaaa agcccgactt    52260
tccaggcacg gctagtttct tcctagcaag ttcctgacgg agctgggtgg ctgccccagg    52320
tgactgcagt agcaggagat taaggagaca gcacctgcct gacaaaaaag gttgctgaca    52380
caataggcca aagttaaatt gagctgccaa gggaaaatga ttggggatat gcagttaaca    52440
gttgagggag ataccagaag aatttgtgtc cacagagaga ttttgatggg gctgactttg    52500
ccgctgaccg actcacctca gaagcatgga ctcccttacc tccaagtcca aggcaatggg    52560
gctctctccc tcttgcctct tgaattcctg catctcattt cactgggtaa acagggaggc    52620
tcctgtgctc cagcaggaaa accctggact gggaagcagg atgtctactc tgatcctgct    52680
gccccaaagc tatgcggctt cagacaagtg gtttgacctt tctggctcca gtttccttga    52740
ttttcactat tatttgaagg gcttggggtc atggaaatca tgaactcttc acactgagag    52800
gaatcttcat aatccatttt gtagataagg aacctaaggc tgaagaggtc aggggcttgc    52860
acccagccat agagctaaat gaggggcaaa gaacctagaa ctctggcgtc ttgactccca    52920
cctgggacac attttatcag taatagtgag ctctcatctg ttgatagtgt tagaattctc    52980
acatttactc cccataacaa ccttcttctt cttttttttt tttttaaacg gagtttctct    53040
ctgtcaccca ggctggagtg cagtggcgtg atctcggctc accgcaacct ctgcctccag    53100
ggttcaagct attcttcagc ctcagcctcc ctagtagccg ggaatacagg catgcaccat    53160
ggcgcctggt taattttttgt attttttagta aagatggggt ttcaccatgt tggccagact    53220
ggtctcaaac tcctgacctc aagtggtcca cgtgcctcaa cctcccaaag tgctgggatc    53280
acaggtgtaa gccaccatgc ctgaccagca cccttctgaa gtaggcactc ttatacccat    53340
tttactgatc aggagaccgg cttgcccagg atcctgcagc tactgaatag aggggccaga    53400
actttgctgg tttggtgcgc ttcctggtac acaccagctg cctccaatct cccttttgata    53460
```

| | | | | |
|---|---|---|---|---|
| atcctagcca | catgccaccg | cgggtgctct | agtgtaggct | ggcaccaacc ccacccagca 53520 |
| agagccagga | tctgcttctt | gagggcaggc | aggtttatca | cacagcgggg tgcagaagag 53580 |
| tagtattcat | cttcctagtg | taaccactta | taactacttt | tcagtgaatc aaatagattt 53640 |
| ttaagcaaga | acattgtaaa | aatctgctta | atcaaggggtg | gagcaaaatg agttagccag 53700 |
| ggccaccctta | gctcagatgg | ggtggtagct | gcctctgctc | cacaatgagg tatttacact 53760 |
| tgctccccac | cctctccttt | gccccattat | cttttagtta | aagggccagg tgcaccagaa 53820 |
| cacaggtgcc | ttgagtagca | ccagcacctc | tcagggtcat | agggaagagc tgtttcctct 53880 |
| gggtaaactg | aggcctcaat | aaggcataaa | tgccttctct | gggtgaagaa gatatgccct 53940 |
| ctaagatctc | tccagggtga | atctagaata | agttgtagtc | tagatggctt ggcagcacta 54000 |
| gccagtgtga | cagtaagtct | tgatgaacat | cagtcagcgt | catgctgagg gacaacctcg 54060 |
| aggagaggga | atgtgtactt | gttacaacag | cacacccaat | agaaatagca tgtaagctac 54120 |
| aaatgtaact | ttatatttttc | tagcaaaaaa | aaaattttt | aaagaaacca gtgcaattca 54180 |
| ttttaataga | tcttatttgt | ttcaatatat | cccaaatatt | gtcctttcaa tgtgtgataa 54240 |
| tatagttatt | agtgagatat | tttccattcc | cttttttcata | caaagtcttt gatactcagt 54300 |
| gtgtatttca | ctctgacagt | gcacctcaat | gtggtgcaat | aggcgagggt ctatgtggta 54360 |
| catcccgtgc | ccagtgtgca | cttaaaggct | gtagatccat | atatggcgac tgtctcctag 54420 |
| atagatgagc | ccagcaaggc | tcagtgggtg | ttttgaggtc | catggtctct caggtcccgt 54480 |
| tccaccccga | cattcgacga | atcagagaac | actaatatgg | ttgggaacac ttttatcttg 54540 |
| ctccccatag | tctgaacaga | aagagacgcc | acagaataca | atcacgactc tctccctcct 54600 |
| acggactccc | tccccacaag | caatcaatgg | gctggtctca | gacaaagaca cctagtcaag 54660 |
| gctggtgaaa | cctgctctat | ttcctagtag | gcctccacct | gtaattctca gcagtttgtg 54720 |
| tgtatagata | gaattcctgc | cttctactaa | tgtgactgtt | cctgctcaga gatctagagt 54780 |
| taattattag | caaattcaca | gtgaaccaga | gctaggtctt | gctgtaaggc tcctgtgttt 54840 |
| tttagaagta | cgttgccatg | gggattttttg | tccccactgg | gttcctcctc aggacccccag 54900 |
| acagatagat | acacaaaccc | tgggcccata | attttagtta | gaaaaggccc aagcctagaa 54960 |
| cctcagggaa | ctcatttgga | agctttttttt | ttttaggaaa | cttacctttc ctatttgaca 55020 |
| tctcaatcaa | acaggtgttt | ggggagaata | aaagcatact | accttagaag ggactggggt 55080 |
| catctggcca | gacttgtgga | ataaagagaa | tttcattcct | tgtataaaat aactctaaat 55140 |
| aatggtaagc | tcttaggaga | cttgatctac | tggctacata | tacccactat gaaattaaca 55200 |
| cattctggaa | tttagatgga | agaatatgga | aattggtcct | tctcagtgta tggacgaagc 55260 |
| atcagaaatg | aagagaaggg | ccaagcctag | agagcaaaac | taaagactca ctggtctgtg 55320 |
| ggcttcctgc | ccaaggagag | ctgaaagcta | aaggatgctt | cacaatgtcc tacaagttgt 55380 |
| ttttctaaag | tccttccagc | ggttgaaact | gtgtttatgc | aaaacaaaac tttcctttgt 55440 |
| tgctataatc | tagaggtgga | ctttggctta | agtcatgcca | aaatattatc attctaaacc 55500 |
| agtaacacct | atatttgttg | agcatttact | atatgtgtgg | cactatgcta aacttaacta 55560 |
| cccctttttcc | tcatgtgtaa | cagtcaggtg | acttcacagc | tgccttgtgg atacttgtgt 55620 |
| tatttgaaag | attgcataaa | cacatgtaaa | atgcttagaa | gtctaccacc tcatcttacc 55680 |
| tacagctttg | gtgagtccct | gctttggcca | agtagaatca | ttccctgtga ggaggggaag 55740 |
| aggataagaa | acaggcagag | ttgaccttac | aggtagacac | aacaggcgag ggtccatgtg 55800 |

```
gtgcaatgga tcccatgcac atgcctgatt cagtcattct agttgagtag gattgtctgg    55860
ttggttgtta ttattttgtt ttttgtttgt ttctttcttt tgtttataa gatggagtct     55920 cactctgtcg cctaggctgg agtgcagtgg ctcaatctcg gctcactgct gcaacctctt    55980
cctcccggga tcaagcaatt ctcctgcctc agcctaccga gtagctgggg ctacaggggc    56040
atgccaccac acctggctaa tgttttgtat tttagtagaa atggggtttc accgtgttgc    56100
ccaggctggt ctcaaactcc tgagctcagg caatcctccc acctcagcct cccagagtgc    56160
taggattaca cacgtgagcc accgtgcctg gccagttttt atcttgaaag cttaagggtc    56220
tcccacttaa attcaaatac tcttctgagg ataacctttt aatcagccaa ctatcatgaa    56280
tctcaattat caggaattcc agttattcca attatcagga attctttata tcatcccagg    56340
aatctaaaag agcaaggtct tataggtaag ggcaaacttt ctgatgcctt ggaattcaga    56400
ccctaagtag agatggtcat ttgacatcta gtctgatcga ctgtagagtt acttctatac    56460
aaataaattc aagttatcac agggtttctt tcagttgggg acaatacttt gaaaactttt    56520
aggctctgaa tgaataactt ggcaaaagaa atgttaggg tccttcaaat accatacttg     56580
ttgtggtttt ctcacagata caccagtcta taaccctgag gttcaacac tccactcagt     56640 tgtgggcttt ttatctaaat caaaactatc acatgcccac atgtgcatct gcagccaacc    56700
acaaatgatc taacaggacc agatttcact ggagctctgt gacccttctc ccagtgtgaa    56760
ctgaagggaa aaaaacctgg agcctaaggg actccctttt ccgtgtcctg aagaccactg    56820
gctttggtta agccaatatg atgggctcat tgagagagag actcaggacc tcggatcatg    56880
ccacactctc tggccccaga aggcatacca caggctgcca gctttgttgg agaacctgag    56940
acttaaggcc aggatatatc aagagccctg tacccagttc tgtgatgtct taataccttt    57000
gacaagagac attggcaact cactgggtgt ccattggggg gcgacaagga aacagactga    57060
tgaaaccaga gaatgtgaca actaattaca tgttgtttcc tgtagaagag aaattctcag    57120
aggaacgtgg tgactgtctg ttcttaatg gactgtcata tgaaagcagg agaaggagat     57180
tcttccttac tccaaatgac aaaactagga gcagtgaaat gagcttataa ggtggccggg    57240 ttttctagc aattggagct ctctgcagtg agtggacact tggcagggta gtgcctactc     57300
cgcatttgat gtgttcacac cacggctaga agtaggtgtc gcaacttcca gttgaagagg    57360
gaattctttt ccttgggtgg gagaggggct agagaacgtc tcaggttgtt gctaactatg    57420
agcatggttt tataattgtt taaagtggg taaacaagaa gagtgtgttt atggtgtctg     57480
tattccacaa actattattt cccacattaa ctgtttcata tatggaaaat ctgagaaaca    57540
ggaatgctaa caaggttgca gtataattta aaaatacttc tgagagatca ttgtatccca    57600
aaggcagtgc ccagtgaggt taagagcgtg gtttgtggaa tctgagccca caggggttta    57660
aatcctgcct ctgcccttct tagattctgt gaacttggac agattccctc acttatttaa    57720
gacttcactt ttcagccctt gagatcccac ctgctcaatt atctaaatga aatctatcac    57780
tgtggaaaga gcaaaggcct cctgctgttg agcaaaatgt tttccagtcc tttgtttctg    57840
tgtgaaataa agcagctcca tcccagtgct aaatgatcaa ctgcatatga cagaatgagc    57900
ttatttcatg ctcccagtaa atacaagacc atagactact ctggatggta gtttaagttt    57960
aagatgaaat tgcttcttct gattgccttc ttctttattg cttctttctc tgttgttcct    58020
tccttctctt gtttataaca ctaacagtca aatctatctg tgtggaaatc tatctactat    58080
atagaacgct acatcacaat ttacagaggg gaaaatattt ttgtcggcag taacatttca    58140
ctggaagagg cactatttgg ccacctaact ctgggattta ggctcaggta gaatcagtgc    58200
```

```
ctcagtttct ttaggtcagc cattatgagt tgttccttat ttgacctagc acatatatag   58260
atggtggtta aatttagcaa aattctcttc acaaaggttt catttgtctg gaagactcta   58320
agtactgatc tggtcagagt accatcaaag ccccttgttt gtcatgagac cgtggaccaa   58380
catgttagtc tttctcatgt aaaaaaaaaa atcatcaaca aatgcagtgg gagttggtag   58440
tcatgagttt gaggtagtac aatatcctta aagtacacac tcaatcatgt gtgataattg   58500
gccaactcta cctaacaaca gttgaagacc tccaaacagc tatcaggact actggaatca   58560
tgtctccaga agaacctgga gaaacattca catttgtgtg gaccaaggag gaaagcaacc   58620
cagacgactt ctacttagaa gcacaggcac atagagcctg tgttattggc acaggtattt   58680
ctctcctaag agccttttct gcttaagaag gcttgaggat ctattcccat taatcataaa   58740
aaagggattt gctgggctaa attatttag cctcctcttt atgccttact tcacaaagaa   58800
ttgcagttaa tctgtaaatg agttctgatg ttatgaaaat tggatatggc aaattgtgtt   58860
attaagtcta ttaagggatg aagaaggact cttctaaaag aataacgtag tctgagtggc   58920
agctctcact taatagacat ctacctagaa atgtttctga acttaatgga cacatgatat   58980
aattcaaaat taatataagc acacagcacc tctccccata accttattga aattaagggt   59040
tccaaatcat tcttctctcc cttttacttc acctgcaaca tgtggctcac ccttctttag   59100
actaagagct aaactctaat gcctagttaa tgtaaaacaa tgccaggatt attaagcatg   59160
attctgataa gttttaaccc ctaatgagat tatccttggt taaataaatt gaatggctag   59220
tggaattcca atgtaaagtc agcagaggtt agctggttgc tagatattta actatacata   59280
ccaggaagct atgaggacaa atttccattt gcacagagcc ttgagaattg gccattttag   59340
gactaaatgt gctgctcatt acttttactc aaggacatac taatgaccaa tatatgttta   59400
aatacctact atgtacaact gctttcaaaa acactttcaa tcttgaattg agaaggtagg   59460
agatccatac ctgtattagg ccatcctcac agtgctataa agaaatatct gagactgggt   59520
aatttattaa aaaaagaggt ggatgaagct ggaaaccatc attctgagca aactatcaca   59580
aggacagaac accgcatgtt ctcactcata ggtgcgaatt gaacaatgag aacacttgga   59640
cacagggtgg ggaacctcac acaccagggc ctgtcatggg gtggggagag tggggaggga   59700
tagcattagg agatatacct aatgtaaatg acaagttaat gggtgcagca caccaacatg   59760
gcacatgtat acacgtgtaa caaacctgca cgttgtgcag atgtacccta gaatttaaag   59820
tataataaaa aaaaagtgg ggaaaagaaa agaaagagg tttaattggc tcacggttct   59880
gcaggctata caggaagcat gatactggca tctgttcagc ttctgtggag gcctcgggaa   59940
acttacaatc atggcagaag gcaaaggggc aacaggtatg tcacatggcc aaagcaggag   60000
tgagagagag aacaaggtgc cacacacttt taaacaacta catctcatga gaagtcactc   60060
actatcacga agagagcacc aagggaatgg tgctaaacca aggtcccaa ccccaggcc     60120 acggatcagt attggtccat ggcctgttag aaaccaggcc acacagcagg aggtgagtgg   60180
cgggcaagca agcaaagttt catttgtatt tacagctgct ccccatcgct cattactgcc   60240
tgagctcagc ctcctgtcag atcagcagca gcattagatt tcataggag tgcaaacgct   60300 attgtgaact gcacatgtga gggatctagg ttgcacactc cttatgagac tataatgcgt   60360
ggtgatcggt cattgtctcc cgtcactccc aaatgggacc gcctagttgc aggaaagcaa   60420
gctcaggact cccactgatt ttacattatg gtgagttgta taattatttc attaaatatt   60480
acaaggtaat aataatagaa ataaagtgca caataaatgt aatgtgcttg aatcatccca   60540
```

```
aaaccacccc ctctctgccc cgtcccagtc catggaaaaa ttgtcttcca caaaaccaat    60600
ccctggtgcc aaaaactttg ggaactgttg tgctaaacca ctcataagaa atccaaaccc    60660
atgatccagt cacctcccac caggccccac ctccaacact ggggattata atccaacatg    60720
aaatttgggt ggggacacac atccaaacta tatcaatacc ttcataaaag caattaaata    60780
actgtacagt gtgataggca ataaatgtca aatgtcatat gtatgaggaa catagagagg    60840
tgctgttatc aagtcactgt gtgacccact gagcactcgc aatgaggcac aggtagtaat    60900
gtacctgctc acttgcttat tgttgtccca ccacgctgaa ttgggagctt catgagagca    60960
gggcccatgt cgcatctatt accacaactg ccttattcgc gtggcctgta gctagcaatc    61020
agtaaaaaat tacagcatgg atgaagctac agaagaaag taaatactga caggtgggca    61080 aaattttag atatggatat ttaatgatgg gatgaacaga tgaatcaaga caggaaacaa    61140
ggcttcgcgt ggcaaatata tcctttcatt tgcccagcaa acatttgcag atccctcact    61200
atgtgctaga cactgtgggc acatttctgt gtggattggt gttttctct ctcaaaactg     61260 gagagatttt gagatcagcc tgtatgtagt gagatgaaga ggtatgtggt tgagatcagg    61320
agtagttggg attctgtgag ggataggget ccttaggtgt agagagcctt gagacctttg    61380
ttgtgaggat agtgaaaatc aacaaagaa tttatgttaa ggaaggttaa aaagtcactc     61440
taaaggtctc agaagtgcct atgacatcat gaggagatgt ccattcctga aaactttagc    61500
caggttacaa acactttaag aaatcctatc tcaaaacttc aagaaaagtg agatctgtat    61560
ttacacagat agaatttcca ggactggatt atatttgcac ttttttgtta aattttact     61620 taactagtat attaatattg atagtacttt gtgactttt tcataaatat aacttttaaa    61680
aaatatggta tttctaaaaa ggtttggtgc attgttaaaa tgtggttttg atttattcac    61740
agacagaaat cttctctaac agactatact tccatttcat aattcagtga ggtaatggga    61800
ctcagttata ctaaatttat catagagcaa actttgctag ttttcatctg ttcattacat    61860
tttatgtaat ggcagacagt gtaataacta ataccgttaa cccaaccatc tcttccctat    61920
aatgttctta taggaacata cagtgtacat tttgcagttc tctacacgca gacaaattct    61980
accagtgtgt attctgatta caagctagtt gcttcatagg ccatatgtct atcttcagtc    62040
cctatgaatc atgtaaatta cagagcaaac tgccgatact cagtatatgt atatgacaca    62100
taagagtcaa gtatactcag ctcctaagag caagtgagaa gacaaagaag atctactgtg    62160
tgtagaaata cttcttaaat catctttcct gaaggcctag tttgcaactg agtcgcaaaa    62220
atttggtttc aaaaagttaa gcttgcaata ataaaaagat aacccagttt aacaatgggc    62280
aaagtgatct gaacagacat ttctcaaaaa atgatataga aatggccagt aagcacaaga    62340
aaagatactc atcatcatta ctaattaggg aaatgcaaat cagaacgaca atgagtcacc    62400
tcttcacagt cactaggatg gctatgatta aaaaaaaaaa agacaggcaa taaccagtgt    62460
tggcaaggat gtggacaatt tagaaccctc atacactatt ggtagacatg cgaaatgaaa    62520
tagtcatttc agaaaacatt ctggcagttc ctcaaaaggt tgaacataaa gttactaggt    62580
gaaccaacaa ttccactact agctatatat ccgccaaact gaaaacagat actcaagcaa    62640
atacttgtac atgaatgttt atagcagccc tattcacact gtccacatac ttgaaaacaa    62700
ttcaaatatc catcaatgga taaatagata acaaaacgt ggtaatttgt acaatcgagg     62760
attcagccat agaaaagagt gaagtactga tacatactag aacatagatg aacctcaaaa    62820
atgttatggt aagtaaagga aaccagtcaa aaaagaccac atactttatg attccatgtg    62880
tatgatatgt ccagaatagg gaattccata cagacaaaaa gtagatgagt gtttgccagg    62940
```

```
ggctggggag aggtggggat ggggaatgac tggctgatgg ttagtttcct taggtggtga    63000
aaaaaatgtt ttaaaattga ttgtagtaat ggatccacag ccttgtgaat ataccaaaaa    63060
ccactgaact gtgtagggt gggttgcccc tccacacctg tgggtgtttc tcgtaaggtg    63120
gaacgagaga cttaggaaag aaaaagacac agagacaaag tatagagaaa gaataagg    63180 gacccgggga accagcgttc agcatatgga ggatcccgcc agcctctgag ttcccttagt    63240
atttattgat cattcgtggg tgtttctcga agaggggag gtgtcagggt cacaagacaa    63300
ttgtggggag agggtcagca gacaaacacg tgaacaaagg tctttgcatc atagacactg    63360
taaaggatta agtgctgtgc ttttagatat gcatacacat aaacatctca atgctttaca    63420
aagcagtatt gctgcccgca ggtcccacct ccagccctaa ggcagttttt ccctatctca    63480
gtagatggag catacaatcg ggttttatac caagacattc cattgcccag ggacaggcag    63540
gagacagatg ccttcctctt gtctcaactg caagaggcat gccttcctct tatactaatc    63600
ctcctcagca cagacccttt acgggtgtcg ggctgggga cggtcaggtc tttcccttcc    63660
cacgaggccg tatttcagac tatcacatgg ggagaaacct tggacaatac ctggcttcc    63720 taggcagagg tccctgcggc cttccgcagt ttttgtgtcc ctgggtactt gagattaggg    63780
agtggtgatg actcttaagg agcgtgctgc cttcaagcat ctgtttaaca aagcacatct    63840
tgcaccgccc ttaatccatt taactctgag tttgacacag cacatgtttc agagagcacg    63900
gggttggggg taaggttata gattaacaga atctcaaggc agaagaattt ttcttagtac    63960
agaacaaaat ggagtctcct atgtctactt ctttctacac agacacagta acaatctgat    64020
ctctcttgct tttccccaca gaactgtaca ctgtaaaagg gtgagtttgt ggtatgtaaa    64080
tttatctgaa ttttaaaat aaaaaagaaa gttaaaaat gttaaacttg gaattaatga    64140
tggttttttt gaagcagatt agtaactact gaaattagtc cttgattttt ggaaaagcct    64200 ttaaaaatg gtaagtggga gaagttataa acaaagagat gaatgagtca cagaaaattg    64260
ggagacaaat agatgataac aagggacagt acagaaagac tcaactgagt tttatcaaat    64320
cactcaggca gataaacatg ggggctgcat gtgcatccgt atgtgtgtat atgtttattt    64380
acatctaata tacacacatg atattacatg aaatattata acatataata aatatatatt    64440
catactggaa aaattctcaa agaatatacc accaaatgtt aacaatagct gtccctgttt    64500
agtgggattt caggtgactt agatcctttc ccccttggc ctctcagtat cttataactt    64560
tgtgtgctaa gatcattgat agttgaacaa taagaagaag aaagtgagtg tggaaggatg    64620
ttgctagaga aagtgtattc ttgattatat ggaggaagtg ggggcagttt gtgaagtctt    64680
ccttacgaat agcatcctat ttgagaagac cagtcttcac actggaaaaa atgcatagag    64740
caaggtgggc atcacttgca gaacagtttg gcacaggact acctctgaaa tattaaggct    64800
taggagactt gttcttagaa acttcttcagg caaagtttac aaaaggcctt ttcctccttg    64860
cttagcagat tctcccaagg catccacatc tacactctcc gtaagtcact atatactgga    64920
cctagcacac atctgtctac ccatcattgt attagtctgt cctcacgctg cttataaaga    64980
catacctgag actgggcaat ttacaaaaga aacaggtgta atggacttac agttccatat    65040
ggctggggaa gcctcacaat cgtggtggaa gacaaggagg agcaagttgt gtcttacatg    65100 aatgcagca ggcaaagaga gagagcttgt gcagggaaac tcctgctttc aaaactatca    65160
gatcttgtga gaattattca ctattatgag aacagcatgg gaaatacccg ccccatttat    65220
ttaattattt cccaccaggt ccctcccaca acacgtgcgc attatggggg ctacaagatg    65280
```

```
agatttgggt ggggacacag agccaaacca tatcaactat ctatctatct atccatccat    65340
ctgtccatcc atttatcttt aattgggata cgtctacaag acaactgata cctaaaagta    65400
tgggaatttc atttgctaag tcacaaaata acttttaaac catccttata ttatacctaa    65460
catgatctga gcacataata ttgtctaagt cagacccatt cttgcctctc tgagcttaca    65520
ctcttgtcaa gtgtgagcca gaaggagttg gtccaagtag agcaagtctc acaggctttg    65580
tggtactcag ggtgggggtc ttacccaaca tttcctccca gaagctgaaa ggcagagaca    65640
agaaattcat cctgaaagag ttcacaaggg taaagtcaag gtggctggtc cccagacagg    65700
tcataggaat aaggttctgg tcatacaaca ggaggcaagg agcccaagta gagggacttg    65760
ggtgtggggc aagtgggagg gtttcattga aaaactaggt agaagacagg gagtaatggt    65820
ggataaggca aaggacagca tctaattcag gcctgtcatc aagctagaga atgttcacag    65880
cagtgttgtt tgaaagagaa aggcatggaa acactttgt tgtctatcag caggtgtgaa     65940
taatttaatt gtggtgtttt caaatagtga gatttccagc agaggaaatt aataaaccag    66000
agctgcatgt gtcgatgtag aaaaaaaccc aaagtgtcca gacatggtgg ctcacgcctg    66060
taatcctagc actttgggag gccgaggcgg gtggattgcc tgagctcagg agttcgagac    66120
cagcctgggc aacatggtga aactccgtct ccactaaaat acaaaaaatt agccgggcgt    66180
ggcggcctac gcctgtagtc ccagctactt gggaggctga ggcaggagaa ttgctagaac    66240
ctgggaggca gaggttgcag tgagccgaga tcgcgccact gcattctagc ttgggtgaca    66300
gagtgagact ccgtctctta gcaaaaaaaa aaaaaaaccg aacacccagt gttctcactc    66360
ataggtggga attgaacaat gagaacactt ggacacagga aggggaacat cacacaccgg    66420
ggcctgttgt ggggtggggg gaaggaggag ggatagcatt aggagatata cctaatgtaa    66480
atgatgagtt aatggatgca gcacaccaac atggcacatt catacatatg taataaacat    66540
gcacgttgtg cacacgtacc ctagaactta agtataata aaaaaagtaa aagaaaaga     66600
aagaaacaa caacaaaaaa aaactaccct ttaaaggaat gcatataaac aataatttat     66660
ttctttcaca ttcatttcac agtttgctta ctgaagcatc agtgtgtctt tcaattggat    66720
gtgatgtgtt ttgaagacat aagaggcagg aaagttttgg ttgccaaaaa taagagaaa     66780
cagggaagaa tttagcttct gaactggatg gtcactcttg ccagaggcct tggaggaggg    66840
caaggttttg cattttgttt gccaattttt tccttaaata aagtgccctg gacttcaggt    66900
cagtcttgcc ccttgagctg ctaaatgatt ctgccagatt cttcagctg agctgtgcgg     66960
ggtcctgaag acctgctttg acttcctctg caccaaactg actcactccc cagggaacaa    67020
gatcaaggct gaggaagaga aaaagcaggg catgaatgga ccctatcccc aaaatagtaa    67080
ttccattttc tccacctgcc attctaccat cacagtgaag cttttctaaa ttgtaagagg    67140
ctcttgtaaa aatgaagcca ctcctgggag atgttgaatt ttatcagcca acatgtatgt    67200
gggtgtccga ggaaaacaag accttggcaa attataccac aaatgggctg gggcaagtgg    67260
gaggagagtg ataggagaac gtttgaatca ggacaaaacg agtgaacaat gtggaggcaa    67320
agggtgggaa caagatgtgc tttgccaacc agacaagttt ttcaaggcta atttttctag    67380
agaccatctt aagaacaatt gcaacactag acaaaaagca cacaaaccaa aaaaagaaaa    67440
aaatctaaac ccaacagcct aagtatcaga aaccatcttc ttatccatat ggttaaaaag    67500
tcaaaatgaa tttattacat tttcacagaa ccatttcctg ggccggaact catttctcct    67560
taaataaata ctataaaatt ttcctcagaa caaatcaagt cccctctata accccagaag    67620
acaaagtaca tcggcagtaa aaacagacac aaagtctcca ctgttgtcag aggtagcatg    67680
```

```
gcctggtggg aggacaggga gctcatgctg ccgcatcagt cgggaggagg gatttgtctt   67740
ctccacaggg caggatccct acaggaaaca ggacaaactg agaagggctt gacaatggaa   67800
ctctttacaa aggtgtcagc agagtattca aaaccacagg agaattgagt gtcagggcta   67860
gcaactgtac ggttccagag ccaacccatg tcggaagggt cagagggtgg gacagtcacc   67920
acaaccccag aagggagagt tctgtagaaa gggccatctg gagggaagca gtgaccttca   67980
gtcagcccaa ggtgacagcc aggcagcaag gagatgagta ccctcagcct cactccttcc   68040
cttcctccaa cctcctacca agcctccctg tgggtcaagc tcatcctggg agtcagaagg   68100
caagagagcc cctagatgca gtccacatag ttcagagcag gttgcaggtc aggaagggtg   68160
aagacaggag aggcaaaggg aagacattgg gcaggtcttc cagctcacgg ccctgtcatg   68220
cctgcagtca ctgtagtaca gactgaatgt tcactgtgtc ctgctttcag catttaagat   68280
gcctctgaga taaagagcct gccttgagtc tcacgggaca tgctcacatt ttctgaaacc   68340
atgtagcttg cactgttaac ctcttcctcg gtttagaggt tttaggggct cgtttcacaa   68400
agctgcccca gcccctcatg ttaaacaacc tgagggctgt gactgggcaa aaaataaata   68460
aatacatttg cattcaacat tgacaaaata cacacttaag tgagacttttt ttgcatcaca   68520
aaaaaataag ttttttacttt tttcaaaaag taaaggttct ttaaaagata tcatctagag   68580
tagaattaag ggctattatt agaaaatcac agtggtccct aggcaagaca ttttgaggga   68640
tgaacttaag caggccccag actcacgtct tccatgtcct acaacccagg cataccccat   68700
catcccatac cttcaatttta tccaaatact tcctgtttca gttggcaaat tccactgccc   68760
caagcttcca aatgtcttcc actgctggct tagccttctt cctaaatccc ctccccatag   68820
tgtcctggac cccattaaaa tgccagcaat gaaagcatct cctttcccct gtctagcaca   68880
gccaggtaca tctgttctga gtggtcagtg cccaaaacag cccagttgct aaacagtttg   68940
accatcacct atgctcacac aggagttact gagatgatgg tcctcaactg caaataaaaa   69000
aacacaggcc actctgtagg agccattagc tcacaacttg ctgggcaggc tcaagttttta   69060
ggactcagca tgctgaataa cacctctatc caatggtaaa tttctctgga aatgaatcca   69120
aaaacctctc agatgacaga tcctgggact ttcaagttgt tacatagcag caagggttgc   69180
tgtcatgatt tgtttactct ttgattccct gctgtggctc atttgagatc ttggagtgtt   69240
tgctgcagta attatggcag gattttttcca gagtggtttt agcatcagtg aaagaattag   69300
tgttcattac tccttaattc tatcactcaa caaattatag gggtaaaatt agatcctatt   69360
aaaaaaaaaa aaaacaggg aaaaacagca aacagaaaca agccggaaaa gaggaaacta   69420
aattcaccct ctaatactga taagcaattc ttccctacca ctaaattta aaccttcatc   69480
agagacagta ctttgtccgt ttgttcaata ctttattctt agtgcctatt acagtgcctg   69540
gtacatagtt ggccctcaat atatgtttat ttaatgaact gattaaataa actagactca   69600
ggctctgacc cttgtgctaa atctgtgctc acaatagatg ttttagggca tattaaattt   69660
tgaagtcagt tcatctctat ggaatttata ggcaaagggg cttttctttt ttagaggtag   69720
gttcttgttc tgtcacccag actagagtgc attttgcatt ttgagtgcag tggtgtctgc   69780
cagtcagact agagtgcagt ggtgtgatca tagctgactg cagcctcaaa cttctcggct   69840
caaacaatcc tcccacctca gcttcctcac tagcagacta caggcacatg ccattgcacc   69900
tggctaattt tttaattttta ttttttttatt tttgtagaga cagagttttg ccacattgcc   69960
caggctggtc taaaactcct gggctcaagc tatcctcctg cctttatttc tattttgaag   70020
```

```
caaacaaaat gatgcaaatg aataaagagt cctaggaaga agtgtcctct gctcttgact    70080
gtccactaac tccagacttc atagtggccc cctttgctta aggcatatga taaacttcta    70140
atgatgcttg aattatattt ccaccagcag gatcagttat tttcctcaga ctcaaatttt    70200
gcaatcaaaa tgcacagtgt acacacggct gcttatattg cagcacatag catctatttt    70260
accatttcaa tttgtgtgat ttcttacatg atggattgtg ggatgacaat aatgtgttct    70320
cagtgaagcc tcttgactaa accaaaattt gcatttttat aaacctccat gaaacagctt    70380
tacttagtaa gattctataa tgctatacta aagaaaatta cgtggtagct tctaaaagaa    70440
atactccctc catcacagag accgagcctc atatgaaaac agtaagcagc acacaggaaa    70500
ctcatgctgt agatgaattt ggagagccac ctcaggttat ttgcattata gaatgctaaa    70560
cgcagactat gcaagaaacc agccacctag agagatctat atagaagtag agaaacttcc    70620
ataccaccag caattttggc tttccaataa atattgagtg atgtccaaaa gtcgtataat    70680
tcaaaaagtc tagggtaagg aacaagataa aagctaaccc ttgtgggtgt tggtaaatca    70740
ataattaatt ggagatcttc catgatattt cctcataaga atcattgcta aaattgttgt    70800
aatgactaca cagactccca agattgcaat agtcaaacaa cacaaactgt tgaagtcatg    70860
aagggatatg caacatggct ccttggttaa ccttttggta gggatccagt ttccaccatc    70920
atgaagtcct gttttcaata ttaatttaca tcattagaat gcctgctgtt ccatcagcat    70980
tttcttgaga tttcctgggc cattctcaga aaccagagtt agaatgcaga aattaatcat    71040
atttcatttt gacctaacta ttatacccag atatttataa gcctgaagta tattttgcc     71100 ttactgataa accaataaga aagaacttga atatctcata aaataaggtc tttccgcaag    71160
ccacacatat ctagatatgg ataatagagc taaataatca ggtgtcgagt ccaatacact    71220
gtcaatctat gtttgacaag catccagttc cttgccttga gtcattcagt tcttcgttgt    71280
tcttgctgga atgaaagcct atacaaaacc tagcattaat gaagttaata tgaaactaat    71340
tagctgcaat gctactgcgg gaaaacggcc aatcatcatt taatgaatga ttctcagtta    71400
agcacttcag aaaagtattt cctctgcccc ataatcaccc agcttcatga agatcctgct    71460
ttccaggttt gaggtgtggg atccagattc acttataacc taatcaggaa atgaacagga    71520
tgatcttgta ctgaagtcct atattagtaa tatatcaaat gaataaagaa aaatgtaaat    71580
aaagttagaa cttgtagtat cgtttttatca actcgcagta tgtgaaatcc atgatgtacc    71640
tgcaccataa ataaaacaag atcttcaaac ttcccagggc tatttaattc ttccatgatt    71700
tttgttcaca aagaacaatc attgctcagc ctattcattg ctcctttttgg aatgaaatac    71760 ttttattact attcacttca aaatattttt aaatttctgt tgtgattgct ccttagaccc    71820
acgggtttat taaagtgtata ttgcttattt ttaaatattt agggatattt tagttacttg    71880
tctgatattg attcctaatt cagtttctct gtggtcagaa tgcatgttct gtatgacttc    71940 aacccttttga aatttgctga aacaatgtta tgattcagga tatggccttg gtgaatattc    72000
catgagtact taaaaggaac atacattcta cagttgttgg ctgtagtgtt ttattatata    72060
aacgtcaatt aagtcatttc ttaatcatgt tgagaaatca tctatgccct tactaatttt    72120
ttattttcat gtttaatcag atatgagaat ggtgcgttaa catcttctat gattgtgtat    72180
ttgtctattt ctgcttttag tcttggaagt ttttgctttg tatattttgg gtctatgtaa    72240
ttagatgaat gtagatcttt attttcctga tgaattgacc ctttttatcat tatgacatgt    72300 cactttttat atttaatagt atttcttgca ttaagttttta atttatctga tattatgtat    72360
aactctacca actttcttca gattagtgtt atgatggtct ttttttccca tatctttatt    72420
```

```
ttcaaccttc ttggtcctta ttagagtatt taatccattt acatttagtg taattactgg   72480
attatttgaa tttaaaccta ccatcttagt atttcttttt ctgttgtctc acctattctt   72540
tgtttctatt ttaatccctg cttgccttta taaaaatttt aaacaatgac aattttttaaa  72600 atattttcat ttatcttctt tgttaccttta ttaattaggc ctctgttgta attcacctag  72660
tgctaaccca gggattatag catccatctt tcactcatta cagtctactt aagttaactt   72720
agtcctttag ttagcatcat ttctgtcttc catactactg tatgcgtttt aattctacat   72780
atattattaa aattataaga cattttttatt gttgttttaa atagtcagtt taaaaaatgt  72840
accctatatt tactgttttc aatgaacttt cttttttccc acattacata cttccatgaa   72900
cacctccttt tggcctatag aactcctatt aatatttctt ttagttcaga gctgctggta   72960
tgtattttct cagttttagt ctgggctcac tttctgtgat tctctcatcc ctggattatt   73020
gactttcaaa actcagtcat attggcagcc cctagcccag tgacactgtc tcaaatccca   73080
gaacaattta tttaatgcca catctattct tgctccaaaa attggcaaat gcctcaagaa   73140
gaaatgaaga gaagccagta tgagactcgc ctcaatctac ttccctttttc tgtgggatct   73200 tggatccctc tcattgacca atatctttaa agagttagat gatagataga tagatagata   73260
gatagataga tagatagata gatgatgat agacaaacag attgatgtta ttttttagcag 73320 cagcattagt gtgaataagc tactccattt tagctagagg tagaagtaat ttcttcttag   73380
agaaaaagtt tgtatagaat tgaatttacc atcatagcca ttcttgaatg tcaggccaat   73440
tgaactccta agactctagc atatacaaaa aacagaaacc actatttctt atcatatgtt   73500
taagggtgtg tatttggaac caatttagcc acaaacttcc agatgatgct gacataccaa   73560
taattactat taaaaagcaa tataatacac agggaaagca aatatagtca attgatatat   73620
gagctgttgc tcttattgca aggattgtaa gagttctgca gtgtggccat tatatgtgtg   73680
cctcacaact tgtattcatt gtaagcttcc tttgagaatt tttatctaag aataagtcta   73740
ccctcatttt ttgtggagta tcagagcttc ttctcctatt tgtcttcaag attgaaagga   73800
gaatattgaa tgctgattct ctgaacatct gcaataatgt attccaagat attggcaaaa   73860
tcagtccaaa ggctcaacca tcccagctaa ttaaattacc tggttaactc tgtggactac   73920
caaatctaaa tggatgtaag agaggaagaa atttgaaaaa aataaagatt acacagttga   73980
aaaaacaaga tattctccag ttatgaattc ttttccccaa gagtgtcttt tgtgtacatt   74040
gttattacaa aatccagttg tcacattaaa caagccatgc tatccaaagc agagttgatt   74100
gtggctggaa atttattcca atattgaaaa gatgtgaaag ggctataaca cgtatcagac   74160
aatctagaat tgaccactag gggacatgac catgaagcct tagacaataa ttcatattta   74220
gtttgaagta ctattctgag gcaaaacaaa caaaaaagaa tgattatgga ggactcaatc   74280
ttaaagtgtc tccaagcatg tcttgttctg tctcaaacct tggcctcaac aatcaaagct   74340
ctgtatcatt atttgcaaca catgaatgct aaatggtatc atttctgact atggacctat   74400
gtgtagttaa gttgtgtgta ggaatatgag gatagaaact attactatca accaaatggt   74460
aatattggac atgtttcaaa gattgtctga aagagcttgt ccatggagac taacccttaa   74520
caagtcccag gttctcctc tcctagaatg tgaattccac gttcaccagc agaattcagt    74580
tctgctgaaa tagtcatgga acagtattgt tttaatttct caaactttttc aaccatatgt  74640 ttataaaggt ttataagaca aataagacta tccctggcat ataattcttt cagtaaatac   74700
ttcacatatt cttccataag aattagcctc ttctgtaaac tctggagcta ccccaaggta   74760
```

```
agatcgtact actgtaaata agcccgaatc actagattcc aaaggccaat ggttacccag   74820
gcattatttg tttatgacct aagaaaataa gtccatagaa ataaattggc ttgaacagaa   74880
ccatcaaaaa ccccttttcaa tagacatctc aaatgaaata ggtggttcta cttcctgaga   74940
acacctaaag aacctttgtg taaaagaaga aatcattatt tccattcagt agcaattttt   75000
gaatggtgta acttgctatc tccttgccta ttggtacaat gcagagaaac tgttcaaagg   75060
tgagccattc ggtaaagaac gatagagtta atcagagagt ctctgttatg cagctacatg   75120
gaatgcaggt gttcattgct ggtgttttta cccgctttga gttcttgttt gtttttgttc   75180
ctatagtagg atgctgcact gatttgggca gggcaaagtg gtggttgatg gaagagcaga   75240
acacctggga aagtcatcca gagtaatttt tgatcccaag aaaagatcag cagaattctc   75300
cttgagtctc taagtcttca cattgtagaa ctgcttaggt aaaaactaat tcaggaaatg   75360
tgcagttata aactttaat aagtcaccca ttaactgaca ttttaaatgt aaatgtacta    75420
aggggactct ttatttccct ctcattcgta agtggaccat cctcaacaca gagacccaaa   75480
ccagaaactt aggaatcatc tttgattact ctctttcaat cttatcaaat cttattagca   75540
aatcttatcc ctgaaatctt tgtccctgaa atatatctca agtcttacct gtcctcacca   75600
gttccaccgc taccatccta atcctggcat caactctgaa ctggactgag tcctccagca   75660
gcctggttcc actgcttcta ttttttttcc attgtctctc tccatttcat tgtacacaca   75720
gttgccaaaa taatatttta aaatctgtat cactaattta aacgcttgtg cttttcagt    75780
gtacttagaa gaaaatccac acttgtagac cctgatgcat tcagcccta cctgcctccc    75840
cagtcttata ccagactcca tttctcatat attgcagcca tgcttgcctt ttcaacatct   75900
caagcaatcg aagtgctttc tcgatttgag acttttgtg cttgctattt tcattgcccg    75960
gaatgccttt tctgagaatc tcaagcagtt gactcctctg catttttat gtataagctt    76020
tacatggttc atattcagag atcccttccc tgagcaccct tagtaaactg ttcttggctt   76080
tgttgggtat tattggaact taccactgcc tataattatt atgtttgtca tcaggtttac   76140
ttgtttcttg cctgtgtcct ccactagatt gtaagcccca gatatcagct aattggttgt   76200
ataagtttcc attcttatta tagtctttga atagtaatca tgtacttagt aaagccacta   76260
aggcaagtgg ccaaggagac gtggacagtt atttatatct aatccaatct gaagaattat   76320
tccaagcaaa aatgacgtga ctgacggctt aaaatagcta aaaacttatt tagttctatc   76380
tcaaacctca gcttcaataa gcaggctttc agccacatgt tttcagtata tgaattgcca   76440
gagcttccta ccaactagtc atatagtgtg tctaccttaa cctggtacct ttacttgggt   76500
tgcatttcat cagcagccaa gtccatctat ttgtcacagt gtctctagta cactgcttct   76560
acatagtcag caatcagtga atacttgatg cctgcatgca tgaataaatg aacttctcag   76620
gaatgctagg gccagagaaa gttgatgttt aaaaagttag aaaatgtagg cacttgagaa   76680
ggattaagaa attaacataa gccttctttg aatttatcat tgaaatctat tattcaattt   76740
acatgtacaa tttcagcaat acatatactt cctttagtca aatacatctc cctgtagcac   76800
ttaccatgtc tctgaccctt tgccttgcaa attccactct gataatacca gcagtgaata   76860
gaaatttaaa aagccactgt cctcactcct tccactcatg ttctaatgta agcctttctt   76920
ttatgcagcc tgaatgcaca attcacttgt cattatctcg catcctagct gctcctcatg   76980
aaatggcatt cctctggatt tgctgagtcc taatgttcag gcaaagtaaa tcccacatca   77040
ttctggcagg ctttcaggaa gacttaggga ctcgttgtct gctagtgcaa ataacagcaa   77100
agtgtggtag gacttcctcc ttagttcagc gaagagccag gtccttgtcg cacggccatg   77160
```

```
aaaaattagg ctcacagacg atttcgaggg ggagaaaaat gaaatttatt gggcaaaaat   77220
ggggaaatta gaaacagggg ccctctccaa agccagagtc cctgctagag tacttcccac   77280
ctcacaggtt gaatcccagg tgccacccag gaagaggagg ggccagactc ctcccctctg   77340
ccagcagagc aaacttctgt ggctccaccc cagtgtgtat tcctcccagt gcgcaagtcg   77400
gttggagttt tctgggaacc gccttcccac ctggctgtct caaaaggact cccagttgca   77460
gaggtatgtg tgattcaaca agatccactg gcagaaaata gaggcaaatt aactcaagga   77520
gtccattgga atatatcaac gtactcccct tccactcaca aggcaatgat ttctaaaaca   77580
gtgaatcatt ttacttacaa ggggtcacaa tggagacagg atagaggaaa ctgcccggga   77640
gacacaggga cgaggcatgt ggagaggtag accttggatc cagttctgca gccagtgagc   77700
tgctcactca gacctgttgc tcccctccag agcctcccctt tcttcatctg gggtatgaaa   77760
caactggacc agcttatctc tgagatcccg ctcagctctg accctcctgt tggagaaggc   77820
ttgcattctg agactgcagt cccaagtagc aatctcttcg gagggcatgt atgtgattac   77880
gtacttagtg tgctcacata gtttcataag aatccggtaa aattcattct tatgctactt   77940
ttgtattccc acttattttg aatggaaaat ccttgtacat atttcctcaa attatggata   78000
aaaagtatac aaaatacacc ctagaggcca agaagctcct tttggtagaa agaatgttga   78060
gccctatgaa tttgagctac tcaaactttg tggtttgttt tgggagccaa tcttgaatat   78120
aaaatatttt ttgatccagc agaaaggtga aatcacattg aagttacaa aatagtaatg   78180 ctaagataga tagattttct tgtgtgccac acttatgttg taaccagaac ttaattcacc   78240
ataatcattg acaagtcttt tgttactgga aaggataagg gttggcaggt cttgtgacaa   78300
atgttagaat ttaatgccca ggattttct tgatgcacag gactcattgg aaaagcggca   78360
gctatttatt gtgactatga atcacgtcca cagatgaata tgattaagtg ctaaatccat   78420
agcagctcaa gttttttaaa gccttggaaa attggcttta aaaatatca cctgacaaac   78480 ctcaagcttt ttctgtctca caagactttt ggaaaagaac taggatcgac agtgttttaa   78540
ggctcacaag gaaaagaatc taacacttgt aaaattatct tctgtgcaag ttttattttc   78600
caacgtgaat ctgggctgcc aagcatactg gctctagcca gatcttcatt agccgatcca   78660
aaaagacagt cggggcattt atccagataa tgcaagccaa cactaccctc tgagaaaaca   78720
aaaagtaact tgcctgatga agcaaggaac ctcaccgatt attccagatt aatgcatctc   78780
cttttactgg caccatgatc agatattttc aagacaaagt acttggcaag ttggaatcca   78840
gctgggtcct ttgattttg aattcacttt gcttctgtga ttatggccac agttttgaaa   78900
ataaagtcat gtggatagag ttgtgatttt tagggatcag gatgcctcat aaaacaacaa   78960
tgctgtattc ttttgtagaa caagatcctg cctaggcctc tttcctagta ttaatctttg   79020
gtcatgatga atgtgctccc aaccatccaa cctatccctt tgcaaccagg cttttgtgag   79080
atcaaataat ttttagagtt gaaatgaagt tattaccagc tctaaaataa ggtactacag   79140
gagggaagta aggaccgaca agagttaaat cactttctag ggttgcgcag gtaactggga   79200
atgaagccag gatgacaact ctacttgctc tttcattgta tcttatgctt ctctgatgtc   79260
ttccaaggga tagcaatata atcaatagtc ttgaaagaaa gatctttgta gagaaagggt   79320
cagcagatta tgtttgtaat tgactagata gaagtagttt tgcttttgca ggttaaatgg   79380
cctctataaa atgtaattac ccaatggggtt cttcctgccc actacacaaa gaccacagct   79440
ctgcagtaaa gagtttaact gacacaaggc cggccacgcc atgtgagaga cagagttatt   79500
```

```
actcaagtca gtcttatcga aggcttgtgg gctagtggtt tttcaaagac agtttagggg    79560
aagaggtggg ggtggctagg aaatgggtgc tttccactga ttggttgaag cggagaagaa    79620
atcgtaaggg gtcaaagctg tcctcttgag ctgattcact tataggtggg gccctaaggg    79680
tgatttggca ggtccgggtg aagccatctg gtacaagtgg agccaaccat gtcagacatg    79740
caaaaaacct gaaaacatat ctcaaaaggc caatctgcaa tagtgatgtt atctgcagga    79800
gtaattgggg aatttgcata tcttgtgacc agcctacacc ttagcagaat tcaggctcct    79860
ctcctcccca tagactgggg ctctctcatg gctttacaaa ggtggttgac ttttggggag    79920
gggctattat catttaaacc ataacctaaa agtcttccaa agttatcttg gcctcagccc    79980
aggagtaatt aaggcagctt gaccactaaa ggtaagagca gagatggcta aatcagatct    80040
ccttcactgc cataattttc tcactgatac aattttttgca aaggcatttt cacccactac    80100
ccaactgtgt cattgtagca tgaaggcagc catagaaagg aataggcatg actgttccag    80160
tggaacttta tgaattaaca ctgaaatgga aatgtcatac aattgtgaca tgtcacagaa    80220
tatttcattt ttaattgttt tcaactattc aaaaatgtca aaatcatttt tagcttggtg    80280
gtggactgga tttggtccag agcagtagtt tgcctgcctc tgttatagag taacacatct    80340
gagcccatga gagaattgat cctgtacctt gggtaatgct cttcctctct ggctcctttc    80400
tacacctcag tcacttttcc cctgcaagag tgttgtcaca ttagactgta aaattggatc    80460
acttttatat ttcatctcta acatgcctta tttaataaaa gtcattctag gtatgactaa    80520
agttccaggg ctaacttaga aaaggactga agagaagaat tccttctgac aaatgcggac    80580
ccagccacaa atgccagtga tattgtccca agtattggtg gcttgggttg cacttgataa    80640
cagagggcaa aagaaagtat aaattttgct tgttaacata gctttagtgg aaaatacaga    80700
aaatgccccc aaactccatg ctaagatcat gaactaaact gttacaatga aaggaattac    80760
ttgggtttct ataaaaacag ctgcctcaag gaatttgcca cattccttgg gtctgcctga    80820
gctctggtgg cccactgctt ggataggcct ggtttgtttg ctaacttaac atgcttgctt    80880
aacggccaaa cattcccttg aaattcaagg actttctgtc ccgctgacac tgtttatttg    80940
tatcagtaga gtggagggct ctctggtgac actctagttt tttctgggtt ataagcagat    81000
gcaggtctgt agttttttctg acttggatgg ggccaatggg tctaagccaa gaggaaaatg    81060 ctttttttctt tttcgtgttt atttccttt ttttttttt cctatcttga ttggagtacc    81120
cttagaagga aaaggagagc cataatcgtt ctctggaggc caaaagaagg ccgaaggatg    81180
ccaaaaattg tcacagtggt gacttttggc tggagccagt gcagaatgag gggctatgag    81240
tgtgtcacta gaactgtaat ccagatctct tccatgaggt caggaaccct gattcgtatt    81300 gcttttttcca tgctgtagaa catgacaccc cactcaatca cttgtgctgg ttcattgtta    81360
cttgttatag tagtcattgt tatcaagact ttttggttgt aagtgtcaga aacctaactc    81420
aaacagagct aagcaaaaat aaatctataa ataaatataa ttagctcaaa agtctgaact    81480
cactggattg atcttcagac ataattgcat gcagtgttca agcagcagct accatctctc    81540
cttcccttcc tctctcttat ctctgctttc ctctgtgtta acatcctgct ctgataagct    81600
ttctccatgt ggaatgaaag acgggctcca gcctttccag gctcctaagt tccttgcagc    81660
tcacggtccc agaaggaaag agattgtctc ccagcatctg tctccataaa aagaagccac    81720
cgtccttgct tgagtcatgt tctcactctt ggacttagca gagtccagag gggcttggat    81780
actctcactt ggatactctc aatacgtgcc agcaaggggc acatattcac ccttcattgg    81840
gcaaggtaag cctgttaaca gtcccactcg aatcatgggg agtaagcaaa aggaagttct    81900
```

```
gaaaatgaaa gaatgtggga cagacataaa actcaaagct gtgcactatg ctagtaaatt   81960
attcttgtgt acttaatatg aatatggctt ttataaacag taagcaaatc agaagccacc   82020
ctgtgaatca tcagttatct ctagacattt ctggattcct tctttattcc ctgataatct   82080
tctttccttc ctttcactgc gttgtaagtg gaaataacac aagccaaaaa gaccctctcc   82140
tgctctcaat acacacatgg tctagttcag gaagacaaca tataaacagc aggcatacga   82200
gcaatttcag tagactgtga tgcctgccca gggtgctcgt ggtctaccct tcatggacca   82260
aagacaacag gaataagagc attcatcttc ctctgctatt gtgagaatat agacagtgca   82320
aagacttgga tgccagtgct aacatccctg cctgacctga ctttgagaaa aggaccgcca   82380
ttttcagcac aacccacagg ttctctaaat actcaaagtg tgaggctagc agataaattt   82440
ggcttataga gggagcttca taccatggtt agaacacagc aagaaaggaa caaattttta   82500
atgtattaat tgaaaatcag atttctcagc tgggaagaag atattagctg aacacacac    82560 aaaaaagtat ttttaaaggt gcccttttaa aggctgccaa aactcaccca agtagtatt    82620 caaatatgaa gacagatgtc ttttcaagac gggaaatttt agttccgagt atgaaagaga   82680 attttatttta tttgttttttt cccttgcctt ttcaggcttt tcactgactt cgaggggatg   82740
agggtatgtg tgcttaaagt agatgccaga gtgtcttctt ggaacttcag gtttccatga   82800
gtagaaggaa gtgttgaatg aatgaggacc cacggccctg tccagtgtgg acatgccata   82860
accctgtgct gagcttcctc atctgtgttc tgggcttaca ttgaatatgg cataagcaac   82920
cccgaagagc cacaaaactc tgctctgtta agggaggagg gcaagtcctc cctggaaggg   82980
gttgtctcat caaccaggaa atggtggtca ggatggatac agtagcatct atacctcagc   83040 cccttgaag tatcctgatg tccactcccc acaaaatcta ggccttccat aggaagtcaa    83100
gaggatattg tgctgatata aatttggacc accagtgagt ttgccctcag acctggtaag   83160
aagtgcatat ttcagatata agatattgct ctggcctcag ctacatacag tttccataaa   83220
ggaaaacttt gaaggactgc ctgcaggaaa agaatagcct cgtgttgatg tatctaggga   83280
cagaactctc aggcaggaca acagcttcct caagtcttgt gactcactc ttttttcccaa   83340 gatatctcat tgcatcttta atttagctcc taattcaaag ccaagctcat ggactgtttc   83400
aagctctgga ccatgagctt agctctgaat taggagctaa attaaggatg caacgagaca   83460
tcctgggaga aatagtatag tcacaagact tgaggaagct ttagtgaaaa gcagacccac   83520
ccagcatgtg taattcttcc atgaggtttc atctcacagt ctgcatgtct tgcaagtggg   83580
cttagggcca caggggcagg agctcttggt actcagaatg ttgtctagaa gtttggagga   83640
gagagatccc ttccaaccta ggtcaaaagg cagaactggt aaaggacttg cagacatgat   83700
aactttgagc acaatatctg agagagcaat ccatggaagt catttgagga agagcattgt   83760
agacaacagg aatagcaagt tcataagccc tgacctcagg aacctgcccg gtacattcag   83820
gagcatcaag gagaccatac tggccaaatg gcacaagtgt gaggaaagtg ttggtaggag   83880
gtgatttcag agggatgcct ggaggccaga tcctggagag tcttgtaggt cattgtataa   83940
ctttgacttt tactttgaat gagatggtaa gcacttatga gcagaaaagt gtatgattta   84000
acttacgttc taaagaagt attctggctc ctgtattaaa aataaactga agggcaagga    84060
gagaggtgga gagacccatt gggaggctaa cgcagacatt tatccaggca aatatcactt   84120
agacctcggt ggtgcaagta aggaaaatga gaggaaattg catttataaa aatctccattt   84180 aaagatagag tcaacaggat tcatcattgg attggattgg agtaaatgag agagagaggg   84240
```

```
aaatcaagga tgattcaaag ttggttttgt tttttttttt gtttttttttt tttatcttga    84300 gcaactggag agatggagac aacattttaa attactttgt tctttggtaa catggcagta    84360
aacacactta taaactgtat tacaggtggc aatcaaaata agcacctggc tgatttgaaa    84420
tatggtttaa aaaaaattac aaagtaagga agatgaactt gtattgttct gcccatgcaa    84480
acaatctgta aaactgtgtg catttatata tttttcagtc attaatattt acagcgggag    84540
agaactgttt gtgaaatcat gaattatctt ttgtttgaat tttattttat taatgagtta    84600
gaagtacctt tgtaagccat tgtaccttt  tctaaaggt gagagcctaa aactaccatg     84660
ttgcaatgga ataagccctg ttctagctt  cacgccctgg gagtgacttc tattagcttt    84720
ggaatctccg gtaactcctt taatcctttg aattctcact ttctatgtct taaaggtgat    84780
ggctgcccat ttcatcaact gtgaaatggc atccaagtcc caggtatcgt taagaaccaa    84840
cggcttccat tttaaacaga agttttgtta aacaaatatt tggttttaca agggtattat    84900
aattcatacc cttattcatt gttcttcctt gctcccaata gtcgatgggt tttttttta    84960 gctgtggctt atgtgatcaa agaggtgaaa caagttagct caattggtta tattctgaaa    85020
ttaataaggt gttcttttg  catgtgtata caaattaact tccctctgtt tcttggccac    85080
acacctcacc tcagcttcac aaatgagtag aattgattac aacatgaatc agacaagaga    85140
gtgtagatct atcactgtta ttgagaaagc agttcaaaaa acaagcattc ccgcatgtta    85200
gtaacatgtt tttataaaag ctgtaaatgt atatttattc atatgattta atatttttta    85260
tcttcagttt ttattttaag ttcaggggta catgtacagg atgtgcaggt tagttacaca    85320
ggtaaacatg tgccgtggtg gtttgctgca cagatcctcc catcatgtag gtattaagcc    85380
cagcatccat tagctattct tcctggtgcc caccctcccc tgaaccccct ccctgacag    85440 gctccagtgt gtgttggtcc ctgcaatgtg tccacgcgtt ctcatcattc agctcccact    85500
aataagtgaa aacatgtagt gtttggtttt ctgttcctgc attaattcgc tggggataat    85560
ggctttcagc tccatccatg tccctgaaga agacatgatc tcgttttttt atggctgcat    85620
agtattccat ggtgtatacg taccacattt tctttatcca gtctattatt aatgggcatt    85680
tggcttgatt ccatgtattt gctattgtga atagtgctgc aataaacata tgtgtgcatg    85740
tatctttata atagaatggt ttatattcct ttgggtatat actcggtaag ggaattgctg    85800
ggtcaagtgg tatttctgcc tctgggtctt tgaggaattg ccacactgtc ttccatagtg    85860
gttgaactaa tttacactcc caccaacagc ataaaagcct tccttttttct ctgcaacctc    85920 actagagtca gtaatatttc ttcaaatatg aaggacttga cctcagatcc tttatgatga    85980
tcataaatac ataaatagat aagttaaaaa ataggaagga cagtgtgata ctaaataact    86040
acaaaattag agatgtatca aaaagtattt aggcactaaa atagttgaga gatcattttc    86100
agagcctcca agagtttcta tgccttgaat tatttgagca tccagtgcaa gctttcagag    86160
tccttgcttc cttaaatata aaacaagaag tcagatacct ttgcctctga cttctcagag    86220
gtctttgagc ttgacagttc tataattcta tgagttttct acctagaaac tattccttcc    86280
attcagttag gaaatatatt caagtatatt ttatttaatc ttaaactttg gaatcccatt    86340
ttggtaagct gctgttattt gaaggtgttg acgtatcctc tgggatctga gaaaattatt    86400
atcaaaacca attaaaggaa tcatctattt tgtgcgattg gttttgaaat ctgtccagtg    86460
ggctctttct ggaggcaagg atcctggtta ccaagagact tgctgcaaa  taaggcaaac    86520 tgggatgaca tttggggttg ggatccttct caggaccaaa tgggcaccca tcatctttgg    86580
gtctagaaga ctgcactggc ataaagcagc tgacttcctg tagccttgca gaataacaa    86640
```

```
tggggtgtgt gtgtgtgtgt gtagtgtgtg tagtgtgtgc agtgtgtgtg tgtgtgtgtg   86700
tgtacaatgg tggggaacag ttggcagagc aatgagcaag aaatgggaaa cgacactcag   86760
aaaagcagca acctaccctg agcaaatcaa agaatttctt agaatgcaac actagctgtg   86820
tgtatgaata attggcttgc aaatcacttc ctctatttgc ttgttatata ataccaatca   86880
tttcagtgtc actgacgaaa gcccagaagg gaattaccac ttaccagcca gttttacata   86940
tggcttttgt gaggaataag gccttgagga tgagggtcta aatctctggc ccacagatct   87000
ggacaggcag atttcaagct gatcattaca tatcttttga gagagacaat cccagacgaa   87060
ttggcctggg gggcaacatg agaaggcaag acaaaagaac attgtaaaga cttcacctag   87120
aatccaaatt gtagttctct cagcaagtta tcaagaagca aattaactgc tagattttgt   87180
aatccaaaga ttatttaatc tgtttagctt tgtgttggaa ggatcgctac taatcatctc   87240
ttttattaaa atatgataat gatagccatc ctttattaag tgcttatgat ataccaggca   87300
ctttgtatac atgatttgcc ttattcagaa taaccctgaa ggatcaatat tattgtctcc   87360
atatcaaaga gagggaaact aaggcataca aaagttattt gctcaaggtc aaacagcatg   87420
gtaagaggaa ctgcaattt c attccaggtc ttacggatac caagtccgat gcctgccagc   87480
ttgcacctgt taagtcatgt gatacttagg aaatgtacac atcacccag tgcagaggcc   87540 tttatccact tcccttcatt ttgcctggat tgttgctgtg agtgagaaat aaatgacatg   87600
aaatgatcat gtatatcact gtcttcagag gatggttagt tccttgctct ggattgtttt   87660
tctcttttgt tggatattta ttttgacttc tctgcaaact aaaaatatgc atgctctagt   87720
ttctcttggg tacataactc ccaatatatt gtgaagaatg aaactggcct acaaagttta   87780
attaagaagc agtgaactag agcttactta gacaatactt gtactagtgt gggttcatgt   87840
tgtccatttg tctttagagg tgtagaacct tgaaagtcag ctaattaatc actattactg   87900
ttgtgtacag tattggcaat ctcctatgct aaaattttt gtgatgattt gaaggtggga   87960
gggggcaata tttactaagt ctctcaacct acatggcaat atctgaaacc tgcttataat   88020
gtagtaatag cttaggcacc acctatttct gaaacataaa tcatcccaca atataagcct   88080 cccagttta ttcatgcgtc ttaccatgta taaatatctt ttaatatacc atttatttcc   88140
ttgagggaca gttatttgta gcataaatct gcctggataa aatagtaaaa attgctatgc   88200
cccagtgaat tcagtttaca aaagcttaca tacgtgaatg agacattgga aatgtggttt   88260
atagttaagg agaatggatc acacggatta tacctgtata acttccctag aaggttgata   88320
ccactaagat attaacacca aaaaactgaa aatagtattt ttcatcttac tttgttatgt   88380
accctttgtg aatttctgaa aaacaccttt ctattatgat gggataaatt acggtgtggt   88440
aacaaacaag cccaacctgt ttgttccggt caactagttg ctttataaca aaccacccca   88500
aaatttgttt aaaacagcta tcatttgatt gtgctcacaa gttctgtgag ttaggaaata   88560
agacacaaca cagtggtctt atgtctgttg tgtaatgtct gggttctcag ctgtgaacac   88620
tcaaatggct tggaaactga aatcagctgg aggcttcctt attcatatgt ttggtgcctg   88680
gctgggatga ctcagattag ttggggctct tgacaaaagc acctatacat gaaccctctc   88740
aggagccttg gctctatggt ggctggattc tgagagggag catgcagaga aaagaattcc   88800
aagacaatgg atgctctaag agaagctact tggccttttc tgatctagtc ttggtggtca   88860
tgcagcatca cttttgccac ccagatcaaa ggggaagagg agacagactc cacctgtgga   88920
tgggagagtg tcaaattcac acagaagttg tatgcaagct attcttggtc atcttgctca   88980
```

```
tctatgaaat ataccctcct ccatgcattg acttacaaca agggtttatt tcttgctcaa   89040
agtctgctgt gaatctaggc aattctccag agcagctgtt cttttgttgg cttagcaatc   89100
caagctgctg cttccatctt acagcttttc catatcaact catgattcca caaccattgc   89160
tacgaggcaa gagtagtatg gaggatcaca cactactctt agaaaccacc agctggaagg   89220
gacttatatc actcctgctt acatttgatg gctcacatag ccatgcccaa attcagtaga   89280
gcaagcatgg ccctcctgtg tacccagaaa ggaaggagag ctagaaatat tggtaaatag   89340
caatattgtt taccatagcc tcagagatat tgcctcgtgg tgaaacccta taattcccct   89400
caattctgat ttttgccctt tatcaaatca ttttattcat tccttcatcc atccaacaaa   89460
gatgttttat atgcctacta ttagcaacaa tcagtagctt gttcctggag ggaatgcagc   89520
tgctccccgc caaacacca  tataattcac tctagaaaac taaaatttca gatgctttgt   89580
cattgattat tgtggggaga aaatgtctct ttcagctccg actttgtcct gtctcctcta   89640
aggcatgtga aataagattt ttttttccta ttcttacctc ctatggtccc attttatggt   89700
tttcatgcac tactgtcagt caaatattta tcatatgtct ttcaatatct ttccaatatt   89760
tatcatatat ctttcccctt gtaggcctta actttatgac ccactattaa gcacgcagct   89820
gtatttccag aaaatgtaga tggtttaatt caatactgca tggcaattaa ctgtcttata   89880
aattaaatca ttttaatcca tcttagagtt atcatgcata attagtctga cagcacaatt   89940
ctgtttgttg ttgttttaaa ggaaatttag atatcaaggc tgcaaagaat gcgtaagtct   90000
aggcagaagg ctcttatttt ccaaaagcag agcccatcgt tgcatttcaa caatgaccgc   90060
aacaaaaacc atcaggagct gtttggggcc tgtttgtgct ttagtcttca attagaaaaa   90120
aatgtgtttc tgatggaaaa ccatagaaca atcctcactc tgtggtaaga aagaataaag   90180
agaaagaagt gggctctatg atagactgaa gcaagaatac tattttagac taggtagtgg   90240
ccgggcgtgg tggctcacgc ctgtaatcct agcactttga gaggccaagg tgggcgtatc   90300
acctgaggtt gggagttcga gaccagcctg accaacatgg agaaaccctg tctctactaa   90360
aaatacaaaa ttagctgggc gtcgtggcgc atgcctgtaa tcccagctac tcaggcgcac   90420
tggctcacgc ctgtacttgg gaggctgagg caggagaatc gcttgagccc aggaggcaga   90480
ggttgcagtg agctgagatt gcgccattgc actccagcct gggcaacaag agtgaaactc   90540
tgtctcagaa aaaaaaaaaa gactaggtag ttatcttcct gggtggtttt ggctatgtag   90600
aaaatcactc ttactctcga ttaatttatg taccaaatca tgctttgaaa tatcccactg   90660
aaaaggtcta aattattgat atcttgggtc aagttctgac ttgaaggcaa atagtaggaa   90720
atacaatggc atttattgga ggcacacact acaaatattg tagtatcttt aagatgtgtt   90780
taaataaaca agtagatgat aaaactataa attagagtca ctaagactct ctagcagaga   90840
cccttacctt ttgaagtgca ccttaaaatg gcaacaacac ttatcagaaa ttccataaga   90900
agcttagttg tctgctactc tattgcagta tcatatgtgt gagctgcatg aaaactggat   90960
attattatta tcaaaggtta ttatcaaatg gagcacaatt ttattaataa caatattatt   91020
attatcaaag gttttaattt gctaaaacta tacagcttcc ttaggtcttc caaactaggt   91080
cagccagtta accctcagat ctggagtacc acatttggct gagtcagaag aaataaagat   91140
gctctcaaaa ccacaaacaa aactgataat agacattctg ataactttaa ctcccacagt   91200
aataaatctt gggtctttta agttggtca  gatgtacaca gagctgctta ctaattatac   91260
taaaatagtt actaagcaac tcgacatttt gatttccaag aatttcagat aaagattatg   91320
aactttattt atttggtgct ttagagtcca aggcactatt ttacagccta aagctgtatt   91380
```

```
tctcaaggcc atcttcttgc attcttctaa aacttaagag ggatcatctg tcctcaaaaa   91440
tataagaaat tctgtaaatg tgtatttttg tgtatatata tatttgatat ttaaaattct   91500
gtatctatat atacttccaa gaccccttag aacttacacg gtacctgtaa tttgtttctt   91560
ttttatactt aagtacaagt aatgttagtg atacatttaa aactaggaat taccttgttt   91620
gcaatatcaa atttttgtaa aatattgagt taaaaaagtc tcctaaaatt aagatttgaa   91680
ctattataaa tggcttcaaa gatcctttcg tttctaagag aaggaaggaa ttaggattta   91740
ttgtgcatgt atttcatacc aggtgctcat ctacagttat tgaatccttg caacaatcgt   91800
atcaggtaaa cgctgttatt cttctcttac agatgaaaaa tctaaacctt ctaaaatgaa   91860
agtttgtcca agtaacatg accaattagg agagcttgga ttccaaccca aatctgttca   91920
gtatcaaagc tcactctctt ccatccttgc cccttctcag ctcacatagt agctttcaga   91980
aaacagtagc tatctacccc agataaaatt aagccttttt ttccttagga gaggctagaa   92040
actgaatctt ctaccccctt tattggcatc acacaggcac aaaaatcacc aattctcaaa   92100
aaccctatac tcccaagttc aacccaaatt gaatggttgg aatattgttg gtttgtatgg   92160
aataattaac ccacatctaa aaattaatta tacaaagtga agtggagatt gaagcagttt   92220
tctagataat taaggcaaaa ataactgcaa ttttttaaa agacagtttg aaatatttag   92280
aagggtagat tgcaaaatta tccaacttaa ggtagtcata ttcagggagt ttagccaaaa   92340
cacctctgaa gttcattgcc ttacaaatga gtataaaact taaacctatg attaattccc   92400
tgttgttttt ctatctgtat tatacatata aatatatttt atatattgtc ctcctgagat   92460
ttcaagagca attttcttct aattcttcta atttcttcta tggattcacc atagtgaatc   92520
caccgacacg tctaccctgt gacaatcttg ttctccattt gattgcatga aaaataccat   92580
atgaatttga caaatcattg gttttttgt ttgttttct cttttgctgc atatcattgc   92640
ctatgcttct tgagcactag aatatatttg tgcatgtata aaccaaggcc tttcttctga   92700
aaattaatag tactttgaat ctcttctata ttctggttct tttaaactgt ggttgtttta   92760
agtttgcctc tcttgtttta ggatttattc tttattttga ggccctgatt tttcacaaaa   92820
catttttctc aacgaatcct gagaacactg gacaatcata gcttttagct atcatgagtc   92880
ccattaccct ttggcctcca gttaagctct gtcctgcaag acataaattg tctgattatc   92940
aactcctact ttgagtgaaa aatggttgaa tgaaatgaat atgcagttca tttcaacaaa   93000
gcaagaaatt tgctgtttaa aattgtgttt ttataattct tgagatggaa atatagcaga   93060
cctctgtgaa tctgagaagg catttcatgc ttccagaaat gagggagaa gtggcaatga   93120 tattgctcat gaacaattgg aagcaatgat actagagtat gcagcaaatc tcagggagat   93180
ttcagtggta cagtaactgg cctcacaaaa gtgggattta ttgcattaaa tctttgctgt   93240
cctttctggc tggtttgata tttaagaaat tattaaacat aaaattgtat gagcagttac   93300
ctatggtagg acaaaatgga ctgacctcta atggcttggt agatgggata attttgggaa   93360
gagagagtgg agctcagttc agcatcctac tctcctcctc aacatcattt cccattcttg   93420
gcccttgagt ttagatagga gttgggcatg tgtgtgtgtg tatgtgtgtg tgtggtgaag   93480
tgggtagatt cctgttccca acccaattag ataactccac ttccatctat cttccttgca   93540
tcttctccag ctcatttgca aaagaatgaa agaagccttg cttcaaaaag gtttagaggg   93600
ctaaataaga gcacaaactg gattttctga aaactgacct gattgcctgg gtaattaaac   93660
tgtcactcca gcaaaagcat ttgtctccaa aaagtactga ggttgtcttt catcactcta   93720
```

```
agtctagaca ttctgaaacc tccatcctct cctgcagaga gaggaattaa gtctccacat   93780
ttctaaacca ttgacagtct gtggggtgcc ccattgtgtt cctgacttcc tattctcaga   93840
aggagttata acgatgacaa tgatgcatgc atgagacata gaggtcctcc ccagccctcg   93900
gttaggaagt aaggcagcca cccatgtact gaacacaata gtgctttgga aagagctctg   93960
ttaaaagtga gtctcaaaaa tgtaaaggcc tttacgagag gaacttaatc tccagtgtga   94020
taaaacgatg cacacattac aaggagatgg atgttatgaa aacataagt acacccaaga    94080
gtacacgtac aaatctgcat tgcaattgat ttatttggat gcctgtttct tcctacacta   94140
tgagctcctt ggggccatga aattcatttg ttttatctat atatactctc tttgatatcc   94200
cccaccctga cagctagtgc agtcctttct aaatagttgt tactaaatat gtcaaatcaa   94260
atgcctacaa ggactggttg gtagaaccag attctggaag tgaccaagca ggtctagctt   94320
cataagaatg ccatcatcgt agatttgagg gtcatgatga agttgtacta ggatttatgg   94380
aggttctttg tcaaccagtt cacaccacca gtgacttaag gaaactatat gtcgtctatt   94440
gggaacagtc ctgcttaaag caattagcag ggacaattaa tttggaggga agtctctctc   94500
cactcaacag cattcaaata ccctctgcat tagccatgtt ttgaaaaact ccaattgcct   94560
gagtcactga tagacaaaca gaaatgcaga ctattttgta tgcagttta taagaagtt    94620
tctaaccaga gaagaaaggt gttatttga aatattaagc tcttagttgt tctttcattt    94680
cagtgaacat ttgttgaggg cctgacatga gctaggcaca tggcaaagtt ttagagatgc   94740
aaaggtaaat taagacccct gtgttaattc tcatgcgggc aaagcaagca catttttaa    94800
gttgcaataa tgcaacaatg gtggtgtgta catagtaggg caaaagcata gagaaagcca   94860
tggaaatcct caagccaagt tcaaagagtc ctctaatgta tggcatacca caacaaggac   94920
cttcaagggg tgcatttggt aagaaaaggc aacctccaaa gattcatcca atcctaaggt   94980
ttcatagagt agggacttct tcccttagct ggaaaggaaa gaagtcattt ggtgtgcagt   95040
agacataaat tagggggccgt ccactttttc ttgcaatgat tcatctaatg gaggagcaga  95100
ccctggagag aaacatatct cttcttgtct tcattttgtt cttcttttat taaatcaccc   95160
gcaggacaac cggatgctcc agcaatagat tatagaaaaa acagatgggt atttctgtgc   95220
agtcagaagg ctcctgtgcc cttttccagc ataaaacgtt tatgaaaatc aattttcagt   95280
gcctgctgaa ccaggctgat gtgagaacta gctttccaca gttcataata ttcactccgg   95340
gatgatttga cagggctgat attttatcac gaatacaaag gagatgagca ccattctcct   95400
aatatattca ttacttgtct caccaccctg gtaaataata tgcatatggt aatttgagag   95460
acacagtgtt cccattgctc ttttttattc ccagaactct ggctgtcttt tctaaatgct   95520
gcaaatcaaa ggcaaagtta cctcacgcac ctgtagtccc agctactcaa gagacagagg   95580
ctctagacca ggacttgaag ttcagcctgg gcaacacagt gagaccctat gtctttaaaa   95640
aaaattgcct aaaaatttgg ccaggtgcgg tggcccatgc ctgtaattgg aggaactttg   95700
ggaggccaag gtgggcagat cacttgaggc caggagtttg agaccatcct ggccaacatg   95760
gctaaaccct gtctctacta aaaatacaaa aaaaaaaaa aattagccag gcatggtggt    95820
gtgcacctgt aatcccagct acttgggagg ctgaggcata agaatcactt gaacctggga   95880
ggcagaggtt gcagtgagcc gagattgtgc cactgctgta ttccagtctg ggtgatagag   95940
cgagactctg cctcaaaaaa attaaattaa aatttaaaat aaaaaattac ttaaaaattt   96000
gattttacat tcctcctatt ctcactttct ggtgcccata caacacataa attacattct   96060
tctctatgtt tacctgcatc tctagggaac aaagcccctt tcacttgttc tgttactata   96120
```

| | |
|---|---|
| gaatgttcta caataccoca ataaagattc attcatttgt tcatttacaa atatctatta | 96180 |
| agcacctact gtgtgtcaag cagtatgcta aatcttaagc atgaaacaaa agaaagataa | 96240 |
| aagtatctga ttcagggact ggttgttctg ttgttctggg tttttttttt tttttttttgg | 96300 |
| aagcttgttg aaaatctgtg gcatcataca aaacaaaaaa gaatgcaaaa ctggtgcctt | 96360 |
| aaatagaaat gtattaataa tgagtgttag agctaagaga aggcaaaatg tctacagaac | 96420 |
| acatgatttc aattaacaac agtgagtaaa cgaatgatct ggaaaaaaat tatgatcggg | 96480 |
| cccatgattt tttttttgtcg tttttttaaaa attttgtttg tttttctcat actcatatta | 96540 |
| ttctaaggcc cattgatttt agaaagaaaa tctgtttat aaacttagca tattaaaag | 96599 |

```
<210> SEQ ID NO 5
<211> LENGTH: 2723
<212> TYPE: DNA
<213> ORGANISM: Homo Sapiens

<400> SEQUENCE: 5
```

| | |
|---|---|
| ggaggctgaa atccccagac gccggttttc tgggctgggc tttctgctta ctcactcctt | 60 |
| ctccctcttt ctggatttta ccgaccgttc gcgaaacagc tttccacaca atggagcttc | 120 |
| atgtcctcgt gcaggaagta ctcatcgact gatgtggcag actttgctcc ctgacaaaac | 180 |
| taaagaactc tcctattcat ggaggcgaac actgaggatg ctttccacat gaaccctgaa | 240 |
| gtgaacttct gatacatttc ctgcagcaag agaaggcagc caacatgaag gaaaatgtgg | 300 |
| catctgcaac cgttttcact ctgctacttt ttctcaacac ctgccttctg aatggacagt | 360 |
| tacctcctgg aaaacctgag atcttaaaat gtcgttctcc caataaggaa acattcacct | 420 |
| gctggtggag gcctgggaca gatggaggac ttcctaccaa ttattcactg acttaccaca | 480 |
| gggaaggaga gacactcatg catgaatgtc cagactacat aaccggtggc cccaactcct | 540 |
| gccactttgg caagcagtac acctccatgt ggaggacata catcatgatg gtcaatgcca | 600 |
| ctaaccagat gggaagcagt ttctcggatg aactttatgt ggacgtgact tacatagttc | 660 |
| agccagaccc tccttggag ctggctgtgg aagtaaaaca gccagaagac agaaaaccct | 720 |
| acctgtggat taaatggtct ccacctaccc tgattgactt aaaaactggt tggttcacgc | 780 |
| tcctgtatga aattcgatta aaacccgaga agcagctga gtgggagatc cattttgctg | 840 |
| ggcagcaaac agagtttaag attctcagcc tacatccagg acagaaatac cttgtccagg | 900 |
| ttcgctgcaa accagaccat ggatactgga gtgcatggag tccagcgacc ttcattcaga | 960 |
| tacctagtga cttcaccatg aatgatacaa ccgtgtggat ctctgtggct gtcctttctg | 1020 |
| ctgtcatctg tttgattatt gtctgggcag tggctttgaa gggctatagc atggtgacct | 1080 |
| gcatctttcc gccagttcct gggccaaaaa taaaaggatt tgatgctcat ctgttggaga | 1140 |
| agggcaagtc tgaagaacta ctgagtgcct tgggatgcca agactttcct cccacttctg | 1200 |
| actatgagga cttgctggtg gagtatttag aagtagatga tagtgaggac cagcatctaa | 1260 |
| tgtcagtcca ttcaaaagaa cacccaagtc aaggtatgaa acccacatac ctggatcctg | 1320 |
| acactgactc aggccggggg agctgtgaca gcccttccct tttgtctgaa aagtgtgagg | 1380 |
| aaccccaggc caatccctcc acattctatg atcctgaggt cattgagaag ccagagaatc | 1440 |
| ctgaaacaac ccacacctgg gacccccagt gcataagcat ggaaggcaaa atcccctatt | 1500 |
| ttcatgctgg tggatccaaa tgttcaacat ggccttacc acagcccagc cagcacaacc | 1560 |
| ccagatcctc ttaccacaat attactgatg tgtgtgagct ggctgtgggc cctgcaggtg | 1620 |

```
caccggccac tctgttgaat gaagcaggta aagatgcttt aaaatcctct caaaccatta    1680
agtctagaga agagggaaag gcaacccagc agagggaggt agaaagcttc cattctgaga    1740
ctgaccagga tacgccctgg ctgctgcccc aggagaaaac ccccttttggc tccgctaaac    1800 ccttggatta tgtggagatt cacaaggtca acaaagatgg tgcattatca ttgctaccaa    1860
aacagagaga gaacagcggc aagcccaaga agcccgggac tcctgagaac aataaggagt    1920
atgccaaggt gtccgggtc atggataaca acatcctggt gttggtgcca gatccacatg     1980
ctaaaaacgt ggcttgcttt gaagaatcag ccaaagaggc cccaccatca cttgaacaga    2040
atcaagctga gaaagccctg gccaacttca ctgcaacatc aagcaagtgc aggctccagc    2100
tgggtggttt ggattacctg gatcccgcat gttttacaca ctccttttcac tgatagcttg    2160 actaatggaa tgattggtta aaatgtgatt tttcttcagg taacactaca gagtacgtga    2220
aatgctcaag aatgtagtca gactgacact actaaagctc ccagctcctt tcatgctcca    2280
tttttaacca cttgcctctt tctccagcag ctgattccag aacaaatcat tatgtttcct    2340
aactgtgatt tgtagattta cttttttgctg ttagttataa aactatgtgt tcaatgaaat    2400
aaaagcacac tgcttagtat tcttgaggga caatgccaat aggtatatcc tctggaaaag    2460
gctttcatga tttggcatgg gacagacgga aatgaaattg tcaaaattgt ttaccataga    2520
aagatgacaa aagaaaattt tccacatagg aaaatgccat gaaaattgct tttgaaaaac    2580
aactgcataa cctttacact cctcgtccat tttattagga ttacccaaat ataaccattt    2640
aaagaaagaa tgcattccag aacaaattgt ttacataagt tcctatacct tactgacaca    2700
ttgctgatat gcaagtaaga aat                                            2723

<210> SEQ ID NO 6
<211> LENGTH: 1869
<212> TYPE: DNA
<213> ORGANISM: Homo Sapiens

<400> SEQUENCE: 6
atgaaggaaa atgtggcatc tgcaaccgtt tcactctgc tacttttttct caacacctgc    60 cttctgaatg gacagttacc tcctggaaaa cctgagatct ttaaatgtcg ttctcccaat    120
aaggaaacat tcacctgctg gtggaggcct gggacagatg gaggacttcc taccaattat    180
tcactgactt accacaggga aggagagaca ctcatgcatg aatgtccaga ctacataacc    240
ggtggcccca actcctgcca cttggcaag cagtacacct ccatgtggag gacatacatc    300
atgatggtca atgccactaa ccagatggga agcagtttct cggatgaact ttatgtggac    360
gtgacttaca tagttcagcc agaccctcct ttggagctgg ctgtggaagt aaaacagcca    420
gaagacagaa accctacct gtggattaaa tggtctccac ctaccctgat tgacttaaaa    480
actggttggt tcacgctcct gtatgaaatt cgattaaaac ccgagaaagc agctgagtgg    540
gagatccatt ttgctgggca gcaaacagag tttaagattc tcagcctaca tccaggacag    600 aaatacctg tccaggttcg ctgcaaacca gaccatggat actggagtgc atggagtcca    660
gcgaccttca ttcagatacc tagtgacttc accatgaatg atacaaccgt gtggatctct    720
gtggctgtcc tttctgctgt catctgtttg attattgtct gggcagtggc tttgaagggc    780
tatagcatgg tgacctgcat cttccgcca gttcctgggc caaaaataaa aggatttgat    840
gctcatctgt tggagaaggg caagtctgaa gaactactga gtgccttggg atgccaagac    900
tttcctccca cttctgacta tgaggacttg ctggtggagt atttagaagt agatgatagt    960
gaggaccagc atctaatgtc agtccattca aaagaacacc caagtcaagg tatgaaaccc    1020
```

```
-continued acatacctgg atcctgacac tgactcaggc cggggagct gtgacagccc ttcccttttg    1080
tctgaaaagt gtgaggaacc ccaggccaat ccctccacat tctatgatcc tgaggtcatt    1140
gagaagccag agaatcctga aacaacccac acctgggacc cccagtgcat aagcatggaa    1200
ggcaaaatcc cctattttca tgctggtgga tccaaatgtt caacatggcc cttaccacag    1260
cccagccagc acaaccccag atcctcttac cacaatatta ctgatgtgtg tgagctggct    1320
gtgggccctg caggtgcacc ggccactctg ttgaatgaag caggtaaaga tgctttaaaa    1380
tcctctcaaa ccattaagtc tagagaagag ggaaaggcaa cccagcagag ggaggtagaa    1440
agcttccatt ctgagactga ccaggatacg ccctggctgc tgcccagga gaaaaccccc     1500 tttggctccg ctaaaccctt ggattatgtg gagattcaca aggtcaacaa agatggtgca    1560
ttatcattgc taccaaaaca gagagagaac agcggcaagc ccaagaagcc cgggactcct    1620
gagaacaata aggagtatgc caaggtgtcc ggggtcatgg ataacaacat cctggtgttg    1680
gtgccagatc cacatgctaa aaacgtggct tgctttgaag aatcagccaa agaggcccca    1740
ccatcacttg aacagaatca agctgagaaa gccctggcca acttcactgc aacatcaagc    1800
aagtgcaggc tccagctggg tggtttggat tacctggatc ccgcatgttt tacacactcc    1860
tttcactga                                                             1869

<210> SEQ ID NO 7
<211> LENGTH: 5
<212> TYPE: PRT
<213> ORGANISM: Unknown
<220> FEATURE:
<223> OTHER INFORMATION: Cytokine receptor extracellular motif found in
      many species
<221> NAME/KEY: VARIANT
<222> LOCATION: 3
<223> OTHER INFORMATION: Xaa = Any Amino Acid

<400> SEQUENCE: 7

Trp Ser Xaa Trp Ser
1               5
```